US009856216B2

(12) United States Patent
Choi et al.

(10) Patent No.: US 9,856,216 B2
(45) Date of Patent: Jan. 2, 2018

(54) COMPOUNDS AS TNIK, IKKε AND TBK1 INHIBITORS AND PHARMACEUTICAL COMPOSITION COMPRISING SAME

(71) Applicant: GREEN CROSS CORPORATION, Yongin-si, Gyeonggi-do (KR)

(72) Inventors: Soongyu Choi, Yongin-si (KR); Eun-Jung Park, Yongin-si (KR); Hee Jeong Seo, Yongin-si (KR); Younggyu Kong, Yongin-si (KR); Ickhwan Son, Yongin-si (KR); Sang-ho Ma, Yongin-si (KR); Man-Young Cha, Yongin-si (KR); Mi-Soon Kim, Yongin-si (KR); Kisoo Park, Yongin-si (KR)

(73) Assignee: GREEN CROSS CORPORATION, Yongin-si (KR)

( * ) Notice: Subject to any disclaimer, the term of this patent is extended or adjusted under 35 U.S.C. 154(b) by 0 days.

(21) Appl. No.: 15/134,987

(22) Filed: Apr. 21, 2016

(65) Prior Publication Data
US 2016/0311772 A1 Oct. 27, 2016

(30) Foreign Application Priority Data

Apr. 27, 2015 (KR) .................. 10-2015-0059158

(51) Int. Cl.
| | | |
|---|---|---|
| *C07D 209/14* | (2006.01) | |
| *C07D 209/48* | (2006.01) | |
| *C07D 209/46* | (2006.01) | |
| *C07D 417/04* | (2006.01) | |
| *C07D 403/04* | (2006.01) | |
| *C07D 401/04* | (2006.01) | |
| *C07D 403/14* | (2006.01) | |
| *C07D 409/12* | (2006.01) | |
| *C07D 405/12* | (2006.01) | |
| *C07D 409/04* | (2006.01) | |
| *C07D 413/04* | (2006.01) | |
| *C07D 409/14* | (2006.01) | |
| *C07D 403/12* | (2006.01) | |
| *C07D 405/06* | (2006.01) | |
| *C07D 409/06* | (2006.01) | |
| *C07D 471/04* | (2006.01) | |
| *C07D 217/24* | (2006.01) | |
| *C07D 401/12* | (2006.01) | |

(52) U.S. Cl.
CPC ......... *C07D 209/46* (2013.01); *C07D 217/24* (2013.01); *C07D 401/04* (2013.01); *C07D 401/12* (2013.01); *C07D 403/04* (2013.01); *C07D 403/12* (2013.01); *C07D 403/14* (2013.01); *C07D 405/06* (2013.01); *C07D 405/12* (2013.01); *C07D 409/04* (2013.01); *C07D 409/06* (2013.01); *C07D 409/12* (2013.01); *C07D 409/14* (2013.01); *C07D 413/04* (2013.01); *C07D 417/04* (2013.01); *C07D 471/04* (2013.01)

(58) Field of Classification Search
CPC ........................... C07D 209/14; C07D 209/48
See application file for complete search history.

(56) References Cited

U.S. PATENT DOCUMENTS

| | | | |
|---|---|---|---|
| 2005/0026976 A1* | 2/2005 | Curtin | .................. C07D 209/46 514/379 |
| 2007/0161648 A1* | 7/2007 | Hughes | ................ C07D 209/46 514/254.06 |

FOREIGN PATENT DOCUMENTS

| | | |
|---|---|---|
| JP | 2002220338 A | 8/2002 |
| KR | 1020080011199 A | 1/2008 |
| WO | 2006112479 A1 | 10/2006 |
| WO | 2007139464 A1 | 12/2007 |

OTHER PUBLICATIONS

Krivec et al. (Journal of Organic Chemistry (2012), 77(6), 2857-2864).*
CAS Registry Nos. 1283087-14-8; Mar. 26, 2017 (31 pages).
Korean Intellectual Property Office; Communication dated Mar. 28, 2017 in counterpart application No. 10-2015-0059158.
Pubchem; U.S. National Library of Medicine at https://pubchem.ncbi.nlm.nih.gov/compound/91363192, visited Mar. 18, 2017 (8 pages total).

* cited by examiner

*Primary Examiner* — Bruck Kifle
(74) *Attorney, Agent, or Firm* — Sughrue Mion, PLLC

(57) ABSTRACT

Provided is a compound of formula (I) as a TNIK (Traf2- and NCK-interacting kinase), IKKε (I-kappa-B kinase epsilon) and TBK1 (TANK-binding kinase 1) inhibitor; the compound according to the present invention effectively inhibits TNIK, IKKε and TBK1, and thus is useful not only as an anticancer agent for the treatment of various cancers including colorectal cancer, breast cancer, CNS cancer, colon cancer, non-small cell lung cancer, kidney cancer, prostate cancer, ovarian cancer, uterus cancer, stomach cancer, liver cancer, skin cancer, lung cancer, brain cancer, bladder cancer, esophageal cancer, pancreatic cancer, thyroid cancer, head and neck cancer, squamous cell carcinoma, osteosarcoma, B-cell or T-cell lymphoma, acute or chronic leukemia and multiple myeloma, but as a therapeutic agent for chronic inflammation.

14 Claims, No Drawings

COMPOUNDS AS TNIK, IKKε AND TBK1 INHIBITORS AND PHARMACEUTICAL COMPOSITION COMPRISING SAME

CROSS REFERENCE TO RELATED APPLICATIONS

This is a non-provisional application claiming priority based on Korean Patent Application No. 10-2015-0059158 filed on Apr. 27, 2015, the contents of all of which are incorporated herein by reference in their entirety.

FIELD OF THE INVENTION

The present invention relates to novel compounds as TNIK (Traf2- and NCK-interacting kinase), IKKε (I-kappa-B kinase epsilon) and TBK1 (TANK-binding kinase 1) inhibitors and a pharmaceutical composition comprising same for the prevention or treatment of cancer.

BACKGROUND OF THE INVENTION

Cancer, a genetic disorder caused by mutations of genes such as oncogene and tumor suppressor gene, is a serious life-threatening disease which is considered as $1^{st}$ or $2^{nd}$ ranked leading cause of death in humans. Although various techniques have been developed for the treatment of cancer including surgical treatment, radiation therapy, immunotherapy, etc., problems related with inhibition and recurrence of malignant tumor still remain unresolved.

Protein kinase is a family of enzymes which plays an important role in signal transduction for various cellular activities including cellular proliferation, carcinogenesis, apoptosis, and cytodifferentiation, and it has been known that inhibitors thereof are useful in the treatment and prevention of proliferative diseases such as cancer (see Plowman, G. D, et al., *Drug Discovery Today*, 334-339 (1994)). In this regard, attempts have been made to treat proliferative diseases such as cancer by inhibiting protein kinase which is closely related with various signal transductions and disease mechanisms in cells.

IKKε and TBK1 are homoglous Ser/Thr kinases which play an essential role in the innate immune responses derived by induction of Type I interferon and other cytokines, and are activated by viral and bacterial infection. The immune responses triggered by viral and bacterial infection include binding between Toll-like receptor and an antigen, e.g., lipopolysaccharide (LPS) or viral double-stranded RNA (dsRNA), followed by the activation of IKKε and/or TBK1 pathway. The activation of TBK1 and/or IKKε leads to phosphorylation of IFN regulatory factor 7 (IRF7) and/or IFN regulatory factor 3 (IRF3), which triggers dimerization and nuclear translocalization of interferon regulatory transcription factors, inducing signaling cascade that ultimately leads to the production of interferon (see Y.-H. Ou et al., *Molecular Cell* 41, 458-470, 2011 and D. A. Barbie et al., *Nature*, 1-5, 2009).

Recently, a study revealed that TNIK, IKKε and TBK1 are over-activated in patients with colon cancer, breast cancer, brain tumor, gastric cancer, hepatic cancer, ovarian cancer, and the like (see J. S. Boehm et al., *Cell* 129, 1065-1079, 2007). Medications exhibiting inhibitory actions on TNIK, IKKε and TBK1 block signal transduction pathways of TNIK, IKKε and TBK1 by inhibiting phosphorylation of IRF3 and/or IRF7, which leads to the inhibition of angiogenesis, proliferation and survival of cancer, etc. Thus, it is expected that such medications can be effectively used as therapeutic agents for the treatment of cancer (see WO2010-100431 and WO2009-030890).

Additionally, it is known that TNIK, IKKε and TBK1 play an important role not only in basic processes of memory and learning via cellular signaling pathways, but also in the regulation of learning ability and judgment (see Takaoka et al., *Drug Delivery Rev* 60, 847-857, 2008). It is also expected that TNIK, IKKε and TBK1 inhibitors can be useful in the treatment and prevention of a wide range of diseases including inflammatory diseases as well as cancer.

Conventionally, a number of TNIK, IKKε and TBK1 inhibitors have been developed, but such inhibitors have not yet been commercialized due to their poor effectiveness and deviations in therapeutic effects depending on the type of cancer. Thus, there is an increasing need for developing various compounds which are more effective in the treatment of cancer.

SUMMARY OF THE INVENTION

Therefore, it is an object of the present invention to provide compounds as TNIK, IKKε and TBK1 inhibitors.

Also, it is another object of the present invention to provide a pharmaceutical composition comprising the compound for the prevention or treatment of cancer.

In accordance with one object, the present invention provides a compound of formula (I), a pharmaceutically acceptable salt, a hydrate, and a solvate thereof:

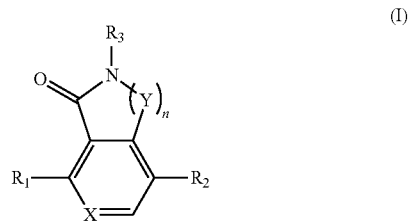

(I)

wherein,
X is CH or N;
Y is $CH_2$ or C(=O);
n is 1 or 2;
$R_1$ is 5- to 10-membered heterocycloalkyl, —$NH_2$, —NH—C(=O)—$R_4$, —NH—C(=O)—NH—$R_5$, —NH—C(=O)—O—$R_6$, —NH—C(=S)—NH—$R_7$, —NH—S(=O)$_2$—$R_8$, —NH—$R_9$—$R_{10}$, or —N(—$R_{11}$)—$R_{12}$;
$R_2$ is H, halogen, cyano, hydroxy, benzyl, $C_{1-7}$ alkyl, substituted or unsubstituted $C_{6-14}$ aryl, substituted or unsubstituted 5- to 13-membered heteroaryl, substituted or unsubstituted $C_{3-10}$ cycloalkyl, —C(=O)—$R_{13}$, —C(=O)—NH—$R_{14}$, hydroxy-($C_{1-7}$ alkyl), —S—$R_{15}$, —S(=O)$_2$—$R_{16}$ or —NH—$R_{17}$; and
$R_3$ is H, $C_{1-7}$ alkyl, —C(=O)—$R_{18}$ or —C(=O)—NH—$R_{19}$;
wherein,
$R_4$ to $R_8$ are each independently $C_{1-7}$ alkyl, substituted or unsubstituted $C_{6-14}$ aryl, substituted or unsubstituted 5- to 13-membered heteroaryl, substituted or unsubstituted $C_{3-10}$ cycloalkyl or substituted or unsubstituted 5- to 10-membered heterocycloalkyl;
$R_9$ is $C_{1-7}$ alkyl;
$R_{10}$ is H, hydroxy, halogen, cyano, $C_{1-7}$ alkyl, ($C_{1-7}$ alkyl)amino, (di$C_{1-7}$ alkyl)amino, substituted or unsubstituted $C_{6-14}$ aryl, substituted or unsubstituted 5- to 13-membered heteroaryl or substituted or unsubstituted 5- to 10-membered heterocycloalkyl;

$R_{11}$ and $R_{12}$ are each independently $C_{1-7}$ alkyl;

$R_{13}$ and $R_{14}$ are each independently hydroxy, $C_{1-7}$ alkyl, or 5- to 10-membered heterocycloalkyl;

$R_{15}$ to $R_{17}$ are each independently substituted or unsubstituted $C_{6-14}$ aryl or substituted or unsubstituted 5- to 13-membered heteroaryl;

$R_{18}$ is 5- to 13-membered heteroaryl;

$R_{19}$ is $C_{3-10}$ cycloalkyl; and said cycloalkyl, heterocycloalkyl, aryl or heteroaryl is optionally substituted with one or more substituents selected from the group consisting of $C_{1-7}$ alkyl; —OCF$_3$;

$C_{1-7}$ alkoxy; ($C_{1-7}$ alkoxy)carbonyl; ($C_{1-7}$ alkyl)carbonyl; $C_{6-14}$ aryl; ($C_{1-7}$ alkyl)thio; halogen; ($C_{1-7}$ alkyl)sulfonyl; —NH—$R_{20}$—$R_{21}$; —N(CH$_3$)—$R_{20}$—$R_{21}$; 5- to 13-membered heteroaryl; 5- to 10-membered heterocycloalkyl unsubstituted or substituted with $C_{1-7}$ alkyl or amino; ($C_{1-7}$ alkylcarbonylamino)($C_{6-14}$ aryl); (5- to 10-membered heterocycloalkyl)-($C_{1-7}$ alkyl)-(5- to 13-membered heteroaryl);

—CF$_3$; cyano; ($C_{1-7}$ alkyl)amino; nitro; oxo; (5- to 10-membered heterocycloalkyl)-($C_{1-7}$ alkoxy); (di$C_{1-7}$ alkyl)amino; ($C_{1-7}$ alkyl)carbonylamino; hydroxy; (5- to 10-membered heterocycloalkyl)-($C_{1-7}$ alkyl); (tert-butoxycarbonyl)-(5- to 10-membered heterocycloalkyl)-($C_{1-7}$ alkyl); benzyl;

and amino, wherein $R_{20}$ is $C_{6-14}$ aryl, 5- to 13-membered heteroaryl or $C_{1-7}$ alkyl which is unsubstituted or substituted with hydroxy; and $R_{21}$ is 5- to 10-membered heteroaryl or 5- to 10-membered heterocycloalkyl which is unsubstituted or substituted with H, hydroxy, halogen, amino, $C_{1-7}$ alkyl, (di$C_{1-7}$ alkyl)amino, $C_{1-7}$ alkylcarbonylamino, $C_{1-7}$ alkoxy, methyl or oxo.

In accordance with another object, the present invention provides a pharmaceutical composition for the prevention or treatment of cancer, comprising the aforementioned compound and one or more pharmaceutically acceptable additives.

A compound in accordance with the present invention effectively inhibits TNIK, IKKε and TBK1, and thus is useful not only as an anticancer agent for the treatment of various cancers including colorectal cancer, breast cancer, CNS cancer, colon cancer, non-small cell lung cancer, kidney cancer, prostate cancer, ovarian cancer, uterus cancer, stomach cancer, liver cancer, skin cancer, lung cancer, brain cancer, bladder cancer, esophageal cancer, pancreatic cancer, thyroid cancer, head and neck cancer, squamous cell carcinoma, osteosarcoma, B-cell or T-cell lymphoma, acute or chronic leukemia and multiple myeloma, but as a therapeutic agent for chronic inflammation.

DETAILED DESCRIPTION OF THE INVENTION

The term "halogen" as used herein, refers to fluorine, chlorine, bromine or iodine, unless otherwise specified.

The term "alkyl" as used herein, refers to linear or branched hydrocarbon chain radicals having 1 to 7 carbon atoms. Particular examples thereof may include, but not limited to, methyl, ethyl, N-propyl, i-propyl, N-butyl, i-butyl, t-butyl, N-pentyl, N-hexyl, and the like.

Also, the term "cycloalkyl" refers to a saturated carbocyclic group having 3 to 10 carbon atoms which has a single ring (e.g., cyclohexyl) or a plurality of fused rings (e.g., norbornyl and adamantyl). Particular examples thereof may include, but not limited to, cyclopropyl, cyclopentyl, cyclohexyl, norbornyl, adamantyl, and the like.

Also, the term "aryl" refers to an organic radical derived from aromatic hydrocarbon by removing one hydrogen therefrom, which includes a substituted or unsubstituted single ring or a plurality of fused rings, wherein each ring has 6 to 20, preferably, 6 to 14, atoms; it also includes a plurality of aryls which are connected via single bonds. In the present invention, aryl also includes a fused bicyclic ring system, which comprises one benzene ring and one hetero ring containing nitrogen or oxygen atom. Particular examples thereof may include, but not limited to, phenyl, naphthyl, biphenyl, terphenyl, indenyl, isoindolinyl and the like. Preferably, the aryl group may be selected from phenyl, naphthyl, and the like.

Also, the term "heteroaryl" refers to a 5- to 13-membered aromatic radical having at least one, preferably, 1 to 4, hetero atom selected from O, N and S; the heteroaryl includes monocyclic heteroaryl with 5- to 6-membered ring and polycyclic heteroaryl group condensed with at least one benzene ring; and the heteroaryl may be partially saturated. Also, in the present invention, the heteroaryl also includes a plurality of heteroaryls which are connected via single bonds. The heteroaryl group also includes heteroaryl in which the hetero atom in the ring is oxidized or forms a quaternary salt. Particular examples may include, but not limited to, monocyclic heteroaryl such as furyl, thiophenyl, pyrrolyl, imidazolyl, pyrazolyl, thiazolyl, thiadiazolyl, isothiazolyl, isoxazolyl, oxazolyl, oxadizolyl, triazinyl, tetrazinyl, oxotriazolyl, tetrazolyl, furazanyl, pyridyl, pyrazinyl, pyrimidinyl, pyridazinyl, and the like; polycyclic heteroaryl such as benzofuranyl, benzothiophenyl, dibenzofuranyl, dibenzothiophenyl, isobenzofuranyl, benzoimidazolyl, benzothiazolyl, benzoisothiazolyl, benzoisoxazolyl, benzoxazolyl, benzodioxolyl, benzothiadiazolyl, dihydrobenzofuranyl, dihydrobenzoxazinyl, benzodioxinyl, dihydrobenzodioxinyl, thioxothiazolidinyl, isoindolyl, indolyl, indazolyl, quinolyl, isoquinolyl, cinnolinyl, quinazolinyl, quinoxalinyl, carbazolyl, phenanthridinyl, acridinyl, phenanthrolinyl, phenazinyl, phenothiazinyl, phenoxazinyl, and the like; N-oxides thereof (for example, pyridyl N-oxide and quinolyl N-oxide); and quaternary salts thereof. Preferably, the heteroaryl is selected from the group consisting of thiophenyl, imidazolyl, pyrazolyl, thiazolyl, oxotriazolyl, tetrazolyl, pyridyl, pyrimidinyl, pyridazinyl, benzothiophenyl, benzoimidazolyl, benzothiazolyl, benzothiadiazolyl, indolyl, indazolyl, quinolyl, isoquinolyl, benzodioxolyl, dihydrobenzofuranyl, dihydrobenzoxazinyl, benzodioxinyl, dihydrobenzodioxinyl, thioxothiazolidinyl, and the like.

Also, the term "heterocycloalkyl" refers to 5- to 10-membered mono- or poly-cyclic ring, excluding aromatic ring, having at least one, preferably, 1 to 4, hetero atom selected from O, N and S. Particular examples may include pyrrolidine, imidazoline, imidazolidine, pyrazoline, pyrazolidine, piperidine, morpholine, piperazine, tetrahydropyridinyl, and the like.

The present invention provides a compound selected from the group consisting of a compound of formula (I), a pharmaceutically acceptable salt, a hydrate, and a solvate thereof:

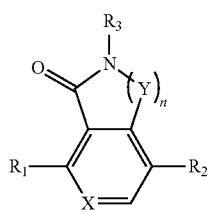

(I)

wherein,
X is CH or N;
Y is $CH_2$ or $C(=O)$;
n is 1 or 2;
$R_1$ is 5- to 10-membered heterocycloalkyl, $-NH_2$, $-NH-C(=O)-R_4$, $-NH-C(=O)-NH-R_5$, $-NH-C(=O)-O-R_6$, $-NH-C(=S)-NH-R_7$, $-NH-S(=O)_2-R_8$, $-NH-R_9-R_{10}$, or $-N(-R_{11})-R_{12}$;
$R_2$ is H, halogen, cyano, hydroxy, benzyl, $C_{1-7}$ alkyl, substituted or unsubstituted $C_{6-14}$ aryl, substituted or unsubstituted 5- to 13-membered heteroaryl, substituted or unsubstituted $C_{3-10}$ cycloalkyl, $-C(=O)-R_{13}$, $-C(=O)-NH-R_{14}$, hydroxy-($C_{1-7}$ alkyl), $-S-R_{15}$, $-S(=O)_2-R_{16}$ or $-NH-R_{17}$; and
$R_3$ is H, $C_{1-7}$ alkyl, $-C(=O)-R_{18}$ or $-C(=O)-NH-R_{19}$;
wherein,
$R_4$ to $R_8$ are each independently $C_{1-7}$ alkyl, substituted or unsubstituted $C_{6-14}$ aryl, substituted or unsubstituted 5- to 13-membered heteroaryl, substituted or unsubstituted $C_{3-10}$ cycloalkyl or substituted or unsubstituted 5- to 10-membered heterocycloalkyl;
$R_9$ is $C_{1-7}$ alkyl;
$R_{10}$ is H, hydroxy, halogen, cyano, $C_{1-7}$ alkyl, ($C_{1-7}$ alkyl)amino, (di$C_{1-7}$ alkyl)amino, substituted or unsubstituted $C_{6-14}$ aryl, substituted or unsubstituted 5- to 13-membered heteroaryl or substituted or unsubstituted 5- to 10-membered heterocycloalkyl;
$R_{11}$ and $R_{12}$ are each independently $C_{1-7}$ alkyl;
$R_{13}$ and $R_{14}$ are each independently hydroxy, $C_{1-7}$ alkyl, or 5- to 10-membered heterocycloalkyl;
$R_{15}$ to $R_{17}$ are each independently substituted or unsubstituted $C_{6-14}$ aryl or substituted or unsubstituted 5- to 13-membered heteroaryl;
$R_{18}$ is 5- to 13-membered heteroaryl;
$R_{19}$ is $C_{3-10}$ cycloalkyl; and said cycloalkyl, heterocycloalkyl, aryl or heteroaryl is optionally substituted with one or more substituents selected from the group consisting of $C_{1-7}$ alkyl; $-OCF_3$; $C_{1-7}$ alkoxy; ($C_{1-7}$ alkoxy)carbonyl; ($C_{1-7}$ alkyl)carbonyl; $C_{6-14}$ aryl; ($C_{1-7}$ alkyl)thio; halogen; ($C_{1-7}$ alkyl)sulfonyl; $-NH-R_{20}-R_{21}$; $-N(CH_3)-R_{20}-R_{21}$; 5- to 13-membered heteroaryl; 5- to 10-membered heterocycloalkyl unsubstituted or substituted with $C_{1-7}$ alkyl or amino; ($C_{1-7}$ alkylcarbonylamino)($C_{6-14}$ aryl); (5- to 10-membered heterocycloalkyl)-($C_{1-7}$ alkyl)-(5- to 13-membered heteroaryl);
$-CF_3$; cyano; ($C_{1-7}$ alkyl)amino; nitro; oxo; (5- to 10-membered heterocycloalkyl)-($C_{1-7}$ alkoxy); (di$C_{1-7}$ alkyl)amino; ($C_{1-7}$ alkyl)carbonylamino; hydroxy; (5- to 10-membered heterocycloalkyl)-($C_{1-7}$ alkyl); (tert-butoxycarbonyl)-(5- to 10-membered heterocycloalkyl)-($C_{1-7}$ alkyl); benzyl; and amino, wherein $R_{20}$ is $C_{6-14}$ aryl, 5- to 13-membered heteroaryl or $C_{1-7}$ alkyl which is unsubstituted or substituted with hydroxy; and $R_{21}$ is 5- to 10-membered heteroaryl or 5- to 10-membered heterocycloalkyl which is unsubstituted or substituted with H, hydroxy, halogen, amino, $C_{1-7}$ alkyl, (di$C_{1-7}$ alkyl)amino, $C_{1-7}$ alkylcarbonylamino, $C_{1-7}$ alkoxy, methyl or oxo.

In formula (I), a compound, in which X is CH, Y is $CH_2$, and n is 1, has an oxoisoindoline scaffold and, thus, can be referred to as an 'oxoisoindoline derivative'.

In formula (I), a compound, in which X is CH, Y is $CH_2$, and n is 2, has a 3,4-dihydroisoquinolin-1(2H)-one scaffold and, thus, can be referred to as a '3,4-dihydroisoquinolin-1 (2H)-one derivative'.

In formula (I), a compound, in which X is CH, Y is $C(=O)$, and n is 1, has a dioxoisoindoline scaffold and, thus, can be referred to as a 'dioxoisoindoline derivative'.

In formula (I), a compound, in which X is N, Y is $CH_2$, and n is 1, has a 1,2-dihydropyrrolo[3,4-c]pyridin-3-one scaffold and, thus, can be referred to as a '1,2-dihydropyrrolo[3,4-c]pyridin-3-one derivative'.

In formula (I), a compound, in which X is N, Y is $CH_2$, and n is 2, has a 3,4-dihydro-2,7-naphthyridin-1(2H)-one scaffold and, thus, can be referred to as a '3,4-dihydro-2,7-naphthyridin-1 (2H)-one derivative'.

In formula (I), a compound, in which X is N, Y is $C(=O)$, and n is 1, has a 2H-pyrrolo[3,4-c]pyridin-1,3-dione scaffold and, thus, can be referred to as a '2H-pyrrolo[3,4-c]pyridin-1,3-dione derivative'.

Preferably, the inventive compound may be an oxoisoindoline derivative having an oxoisoindoline scaffold.

According to one embodiment of the present invention, $R_1$ is pyrrolidine.

According to another embodiment of the present invention, $R_1$ is $-NH-C(=O)-R_4$, $R_4$ being $C_{1-4}$ alkyl, substituted or unsubstituted phenyl, substituted or unsubstituted thiophenyl, substituted or unsubstituted furanyl, substituted or unsubstituted pyridinyl or substituted or unsubstituted pyrrolidinyl; and said phenyl, thiophenyl, furanyl, pyridinyl or pyrrolidinyl is optionally substituted with one or more substituents selected from the group consisting of fluoro, chloro, bromo, nitro, cyano, amino, tertbutyloxycarbonyl, methyl, methylthio, methylsulfonyl, methoxy, acetamido, methylpiperazinyl, aminopiperidinyl, morpholino, morpholinoethoxy, methylamino, dimethylamino, dimethylaminoethylamino, dimethylaminopropylamino, aminoethylamino, hydroxyethylamino, hydroxypropylamino, hydroxybutylamino, methoxyethylamino, methoxypropylamino, methyl(2-(methylamino)ethyl)amino, acetamidoethylamino, pyrrolidinylethylamino, pyrrolidinylpropylamino, piperidinylethylamino, piperidinylpropylamino, azepanylethylamino, morpholinoethylamino, morpholinopropylamino, methylpiperazinylethylamino, methylpiperazinylpropylamino, thiophenylmethylamino, oxopyrrolidinylpropylamino, and (2-hydroxy-3-(piperidinyl)propyl)amino.

According to another embodiment of the present invention, $R_1$ is $-NH-C(=O)-NH-R_5$, $R_5$ being methyl, ethyl, butyl, isopropyl, cyclopentyl, cyclohexyl or substituted or unsubstituted phenyl; and said phenyl is optionally substituted with one or more substituents selected from the group consisting of fluoro, chloro, cyano, nitro, methyl, methylthio and methoxy.

According to another embodiment of the present invention, $R_1$ is $-NH-C(=O)-O-R_6$, $R_6$ being phenyl.

According to another embodiment of the present invention, $R_1$ is $-NH-C(=S)-NH-R_7$, $R_7$ being phenyl.

According to another embodiment of the present invention, $R_1$ is —NH—S(=O)$_2$—$R_8$, $R_8$ being phenyl, methyl, fluorophenyl or methoxyphenyl.

According to another embodiment of the present invention, $R_1$ is —NH—$R_9$—$R_{10}$, $R_9$ being methyl, ethyl, propyl or butyl, and $R_{10}$ being H, hydroxy, chloro, cyano, methylamino, dimethylamino, phenyl, isoindolindione, methylpiperazinyl, piperidinyl, morpholino or pyrrolidine.

According to another embodiment of the present invention, $R_1$ is —N(—$R_{11}$)—$R_{12}$, $R_{11}$ being methyl, and $R_{12}$ being methyl or butyl.

According to one embodiment of the present invention, $R_2$ is substituted or unsubstituted phenyl, thiazolyl, pyrazolyl, imidazolyl, triazolyl, pyridinyl, 1H-pyrrolo[2,3-b]pyridinyl, pyrimidinyl, thiophenyl, furanyl, benzo[d]oxazol-7-yl, quinolinyl, indolyl, benzo[d]imidazolyl or benzofuranyl.

According to another embodiment of the present invention, $R_2$ is selected from the group consisting of H; halogen; cyano; hydroxy; $C_{1-4}$ alkyl; $C_{3-5}$ cycloalkyl; phenyl unsubstituted or substituted with one or more substituents selected from the group consisting of hydroxy, cyano, amino, dimethylamino, ethyl, propyl, isopropyl, tertbutyl, acetyl, trifluoromethoxy, isopropoxy, methoxycarbonyl, methylthio, fluoro, methyl, chloro, methoxy, propoxy, butoxy, methylsulfonyl, —CF$_3$, —O—CF$_3$, and acetamido; thiazolyl; pyrazolyl; methylpyrazolyl; imidazolyl; methylimidazolyl; triazolyl; methyltriazolyl; pyridinyl; chloropyridinyl; fluoropyridinyl; methoxyphenylaminopyridinyl; methoxypyridinyl; phenyl-1H-pyrrolo[2,3-b]pyridinyl; 1H-pyrrolo[2,3-b]pyridinyl; acetamidophenyl-1H-pyrrolo[2,3-b]pyridinyl; morpholinomethylthiophenyl-1H-pyrrolo[2,3-b]pyridinyl; pyrimidinyl; dichloropyrimidinyl; methoxyphenylaminopyrimidinyl; methylpyrazolylaminopyrimidinyl; phenylaminopyrimidinyl; fluorophenylaminopyrimidinyl; acetamidophenylaminopyrimidinyl; methylpiperazinylpyrimidinyl; morpholinopyrimidinyl; tolylaminopyrimidinyl; chloropyrimidinyl; thiophenyl; pyrrolidinylmethylthiophenyl; piperidinylmethylthiophenyl; morpholinomethylthiophenyl; tertbutyloxycarbonylpiperazinylmethylthiophenyl; furanyl; benzo[d]oxazol-7-yl; methyl-benzo[d]oxazol-7-yl; quinolinyl; indolyl; benzo[d]imidazolyl; benzofuranyl; —C(=O)—$R_{13}$; —C(=O)—NH—$R_{14}$; hydroxy-($C_{1-7}$ alkyl); —S—$R_{15}$; —S(=O)$_2$—$R_{16}$; and —NH—$R_{17}$; $R_{13}$ being hydroxy, methoxy or pyrrolidinyl, $R_{14}$ being methyl, $R_{15}$ being phenyl, $R_{16}$ being phenyl, and $R_{17}$ being phenyl, methoxyphenyl, methylphenyl, fluorophenyl, chlorophenyl, dimethoxyphenyl, bis(trifluoromethyl)phenyl, dimethylphenyl, pyridinyl, pyrazinyl, methylpyrazolyl or pyrazolyl.

According to one embodiment of the present invention, $R_3$ is methyl, —C(=O)—$R_{18}$ or —C(=O)—NH—$R_{19}$, $R_{18}$ being furanyl or thiophenyl, and $R_{19}$ being cyclohexyl.

According to preferred embodiments of the present invention, the inventive compound is selected from the group consisting of:

(1) N-(7-(2-ethylphenyl)-3-oxoisoindolin-4-yl)benzamide;
(2) N-(7-(3-isopropylphenyl)-3-oxoisoindolin-4-yl)benzamide;
(3) N-(7-(4-(tert-butyl)phenyl)-3-oxoisoindolin-4-yl)benzamide;
(4) N-(3-oxo-7-(2-(trifluoromethoxy)phenyl)isoindolin-4-yl)benzamide;
(5) N-(3-oxo-7-(3-(trifluoromethoxy)phenyl)isoindolin-4-yl)benzamide;
(6) N-(7-(2-isopropoxyphenyl)-3-oxoisoindolin-4-yl)benzamide;
(7) N-(7-(3-isopropoxyphenyl)-3-oxoisoindolin-4-yl)benzamide;
(8) methyl 2-(7-benzamido-1-oxoisoindolin-4-yl)benzoate;
(9) methyl 3-(7-benzamido-1-oxoisoindolin-4-yl)benzoate;
(10) methyl 4-(7-benzamido-1-oxoisoindolin-4-yl)benzoate;
(11) N-(7-(2-acetylphenyl)-3-oxoisoindolin-4-yl)benzamide;
(12) N-(7-(3-acetylphenyl)-3-oxoisoindolin-4-yl)benzamide;
(13) N-(7-(4-acetylphenyl)-3-oxoisoindolin-4-yl)benzamide;
(14) N-(7-(2-(methylthio)phenyl)-3-oxoisoindolin-4-yl)benzamide;
(15) N-(7-(2,4-difluorophenyl)-3-oxoisoindolin-4-yl)benzamide;
(16) N-(7-(2,3-dimethylphenyl)-3-oxoisoindolin-4-yl)benzamide;
(17) N-(7-(2,3-dichlorophenyl)-3-oxoisoindolin-4-yl)benzamide;
(18) N-(7-(2,4-dichlorophenyl)-3-oxoisoindolin-4-yl)benzamide;
(19) N-(7-(2,5-dichlorophenyl)-3-oxoisoindolin-4-yl)benzamide;
(20) N-(7-(3,4-dichlorophenyl)-3-oxoisoindolin-4-yl)benzamide;
(21) N-(7-(3,5-dichlorophenyl)-3-oxoisoindolin-4-yl)benzamide;
(22) N-(7-(4-fluoro-2-methoxyphenyl)-3-oxoisoindolin-4-yl)benzamide;
(23) N-(7-(2-chloro-3-fluorophenyl)-3-oxoisoindolin-4-yl)benzamide;
(24) N-(7-(2-fluoro-3-methoxyphenyl)-3-oxoisoindolin-4-yl)benzamide;
(25) N-(3-oxo-7-(2,3,4-trimethoxyphenyl)isoindolin-4-yl)benzamide;
(26) N-(7-(3,4-dimethylphenyl)-3-oxoisoindolin-4-yl)benzamide;
(27) N-(7-(3,5-dimethylphenyl)-3-oxoisoindolin-4-yl)benzamide;
(28) N-(7-(2,6-dimethylphenyl)-3-oxoisoindolin-4-yl)benzamide;
(29) N-(7-ethyl-3-oxoisoindolin-4-yl)benzamide;
(30) N-(7-(3,5-difluorophenyl)-3-oxoisoindolin-4-yl)benzamide;
(31) N-(7-(2,5-dimethylphenyl)-3-oxoisoindolin-4-yl)benzamide;
(32) N-(7-(2,5-difluorophenyl)-3-oxoisoindolin-4-yl)benzamide;
(33) N-(7-(3,4-difluorophenyl)-3-oxoisoindolin-4-yl)benzamide;
(34) N-(7-(2,3-difluorophenyl)-3-oxoisoindolin-4-yl)benzamide;
(35) N-(7-butyl-3-oxoisoindolin-4-yl)benzamide;
(36) 4-fluoro-N-(3-oxo-7-propylisoindolin-4-yl)benzamide;
(37) N-(7-methyl-3-oxoisoindolin-4-yl)benzamide;
(38) N-(7-(2,4-dimethylphenyl)-3-oxoisoindolin-4-yl)benzamide;
(39) N-(7-(4-ethylphenyl)-3-oxoisoindolin-4-yl)benzamide;
(40) N-(7-(4-isopropoxyphenyl)-3-oxoisoindolin-4-yl)benzamide;
(41) N-(7-(4-(methylthio)phenyl)-3-oxoisoindolin-4-yl)benzamide;
(42) N-(7-(3-ethylphenyl)-3-oxoisoindolin-4-yl)benzamide;
(43) N-(3-oxo-7-(2-propoxyphenyl)isoindolin-4-yl)benzamide;
(44) N-(3-oxo-7-(3-propoxyphenyl)isoindolin-4-yl)benzamide;

(45) N-(7-(2-butoxyphenyl)-3-oxoisoindolin-4-yl)benzamide;
(46) N-(7-(3-butoxyphenyl)-3-oxoisoindolin-4-yl)benzamide;
(47) N-(7-(2-(methylsulfonyl)phenyl)-3-oxoisoindolin-4-yl)benzamide;
(48) N-(7-(3-fluoro-2-methoxyphenyl)-3-oxoisoindolin-4-yl)benzamide;
(49) N-(7-(4-chloro-2-methoxyphenyl)-3-oxoisoindolin-4-yl)benzamide;
(50) N-(7-(3-chloro-2-fluorophenyl)-3-oxoisoindolin-4-yl)benzamide;
(51) N-(3-oxo-7-(thiazol-5-yl)isoindolin-4-yl)benzamide;
(52) N-(3-oxo-7-(thiazol-4-yl)isoindolin-4-yl)benzamide;
(53) N-(3-oxo-7-(thiazol-2-yl)isoindolin-4-yl)benzamide;
(54) N-(7-(1H-imidazol-4-yl)-3-oxoisoindolin-4-yl)benzamide;
(55) N-(3-oxo-7-(1H-pyrazol-4-yl)isoindolin-4-yl)benzamide;
(56) N-(7-(1-methyl-1H-imidazol-5-yl)-3-oxoisoindolin-4-yl)benzamide;
(57) N-(7-(1-methyl-1H-pyrazol-4-yl)-3-oxoisoindolin-4-yl)benzamide;
(58) N-(3-oxo-7-(1H-1,2,4-triazol-5-yl)isoindolin-4-yl)benzamide;
(59) N-(7-(1-methyl-1H-1,2,4-triazol-5-yl)-3-oxoisoindolin-4-yl)benzamide;
(60) 7-amino-4-(4-methoxyphenyl)isoindolin-1-one;
(61) 7-amino-4-(4-fluorophenyl)isoindolin-1-one;
(62) 7-amino-4-(4-chlorophenyl)isoindolin-1-one;
(63) 7-amino-4-(p-tolyl)isoindolin-1-one;
(64) 4-(4-acetylphenyl)-7-aminoisoindolin-1-one;
(65) 7-amino-4-(pyridin-4-yl)isoindolin-1-one;
(66) 7-amino-4-(2,6-dichloropyrimidin-4-yl)isoindolin-1-one;
(67) 7-amino-4-(2-chloropyrimidin-4-yl)isoindolin-1-one;
(68) 7-amino-4-(2-((3-methoxyphenyl)amino)pyridin-4-yl)isoindolin-1-one;
(69) 7-amino-4-(4-((3-methoxyphenyl)amino)pyridin-2-yl)isoindolin-1-one;
(70) 7-amino-4-(2-((3-methoxyphenyl)amino)pyrimidin-4-yl)isoindolin-1-one;
(71) 7-amino-4-(2-((1-methyl-1H-pyrazol-4-yl)amino)pyrimidin-4-yl)isoindolin-1-one;
(72) 7-amino-4-(2-(phenylamino)pyrimidin-4-yl)isoindolin-1-one;
(73) 7-amino-4-(2-((3-fluorophenyl)amino)pyrimidin-4-yl)isoindolin-1-one;
(74) 7-amino-4-(2-((4-fluorophenyl)amino)pyrimidin-4-yl)isoindolin-1-one;
(75) 7-amino-4-(2-((4-methoxyphenyl)amino)pyrimidin-4-yl)isoindolin-1-one;
(76) N-(4-((4-(7-amino-1-oxoisoindolin-4-yl)pyrimidin-2-yl)amino)phenyl)acetamide;
(77) N-(3-((4-(7-amino-1-oxoisoindolin-4-yl)pyrimidin-2-yl)amino)phenyl)acetamide;
(78) 7-amino-4-(6-((3-methoxyphenyl)amino)pyrimidin-4-yl)isoindolin-1-one;
(79) 7-amino-4-(5-phenyl-1H-pyrrolo[2,3-b]pyridin-3-yl)isoindolin-1-one;
(80) 7-amino-4-(1H-pyrrolo[2,3-b]pyridin-4-yl)isoindolin-1-one;
(81) 7-amino-4-(2-(4-methylpiperazin-1-yl)pyrimidin-4-yl)isoindolin-1-one;
(82) 7-amino-4-(2-morpholinopyrimidin-4-yl)isoindolin-1-one;
(83) 7-amino-4-(2-(p-tolylamino)pyrimidin-4-yl)isoindolin-1-one;
(84) 7-amino-4-(2-(m-tolylamino)pyrimidin-4-yl)isoindolin-1-one;
(85) N-(4-(3-(7-amino-1-oxoisoindolin-4-yl)-1H-pyrrolo[2,3-b]pyridin-5-yl)phenyl)acetamide;
(86) 7-amino-4-(5-(5-(morpholinomethyl)thiophen-2-yl)-1H-pyrrolo[2,3-b]pyridin-3-yl)isoindolin-1-one;
(87) 2-methyl-N-(3-oxo-7-phenylisoindolin-4-yl)benzamide;
(88) 3-methyl-N-(3-oxo-7-phenylisoindolin-4-yl)benzamide;
(89) 4-methyl-N-(3-oxo-7-phenylisoindolin-4-yl)benzamide;
(90) 3-chloro-N-(3-oxo-7-phenylisoindolin-4-yl)benzamide;
(91) 2,4-difluoro-N-(3-oxo-7-phenylisoindolin-4-yl)benzamide;
(92) 3,4-difluoro-N-(3-oxo-7-phenylisoindolin-4-yl)benzamide;
(93) 3,4-dimethyl-N-(3-oxo-7-phenylisoindolin-4-yl)benzamide;
(94) 2-(dimethylamino)-N-(3-oxo-7-phenylisoindolin-4-yl)benzamide;
(95) 3-(dimethylamino)-N-(3-oxo-7-phenylisoindolin-4-yl)benzamide;
(96) 2-(methylthio)-N-(3-oxo-7-phenylisoindolin-4-yl)benzamide;
(97) 3-(methylthio)-N-(3-oxo-7-phenylisoindolin-4-yl)benzamide;
(98) 2-(methylsulfonyl)-N-(3-oxo-7-phenylisoindolin-4-yl)benzamide;
(99) 3-(methylsulfonyl)-N-(3-oxo-7-phenylisoindolin-4-yl)benzamide;
(100) 4-(methylsulfonyl)-N-(3-oxo-7-phenylisoindolin-4-yl)benzamide;
(101) 2,4-dimethoxy-N-(3-oxo-7-phenylisoindolin-4-yl)benzamide;
(102) 3,4-dimethoxy-N-(3-oxo-7-phenylisoindolin-4-yl)benzamide;
(103) 2,4-dichloro-N-(3-oxo-7-phenylisoindolin-4-yl)benzamide;
(104) 3,4-dichloro-N-(3-oxo-7-phenylisoindolin-4-yl)benzamide;
(105) 2,4-dimethyl-N-(3-oxo-7-phenylisoindolin-4-yl)benzamide;
(106) 2-acetamido-N-(3-oxo-7-phenylisoindolin-4-yl)benzamide;
(107) 3-acetamido-N-(3-oxo-7-phenylisoindolin-4-yl)benzamide;
(108) 4-(methylamino)-N-(3-oxo-7-phenylisoindolin-4-yl)benzamide;
(109) 3-methyl-N-(3-oxo-7-phenylisoindolin-4-yl)thiophene-2-carboxamide;
(110) 4-methyl-N-(3-oxo-7-phenylisoindolin-4-yl)thiophene-2-carboxamide;
(111) 5-methyl-N-(3-oxo-7-phenylisoindolin-4-yl)thiophene-2-carboxamide;
(112) N-(3-oxo-7-(o-tolyl)isoindolin-4-yl)benzamide;
(113) N-(3-oxo-7-(m-tolyl)isoindolin-4-yl)benzamide;
(114) N-(3-oxo-7-(2-(trifluoromethyl)phenyl)isoindolin-4-yl)benzamide;
(115) N-(3-oxo-7-(3-(trifluoromethyl)phenyl)isoindolin-4-yl)benzamide;
(116) 4-acetamido-N-(3-oxo-7-phenylisoindolin-4-yl)benzamide;
(117) N-(3-oxo-7-phenylisoindolin-4-yl)benzamide;

(118) N-(7-(4-methoxyphenyl)-3-oxoisoindolin-4-yl)benzamide;
(119) 4-nitro-N-(3-oxo-7-phenylisoindolin-4-yl)benzamide;
(120) 4-acetamido-N-(7-(4-methoxyphenyl)-3-oxoisoindolin-4-yl)benzamide;
(121) 4-methoxy-N-(3-oxo-7-phenylisoindolin-4-yl)benzamide;
(122) 4-fluoro-N-(3-oxo-7-phenylisoindolin-4-yl)benzamide;
(123) N-(7-(4-fluorophenyl)-3-oxoisoindolin-4-yl)-4-methoxybenzamide;
(124) 4-acetamido-N-(7-(4-fluorophenyl)-3-oxoisoindolin-4-yl)benzamide;
(125) N-(3-oxo-7-(thiophen-2-yl)isoindolin-4-yl)benzamide;
(126) N-(7-(furan-2-yl)-3-oxoisoindolin-4-yl)benzamide;
(127) N-(3-oxo-7-(pyridin-4-yl)isoindolin-4-yl)benzamide;
(128) N-(3-oxo-7-(pyridin-4-yl)isoindolin-4-yl)benzamide hydrochloride;
(129) 2-methoxy-N-(3-oxo-7-phenylisoindolin-4-yl)benzamide;
(130) 3-fluoro-N-(3-oxo-7-phenylisoindolin-4-yl)benzamide;
(131) 4-(methylthio)-N-(3-oxo-7-phenylisoindolin-4-yl)benzamide;
(132) N-(3-oxo-7-(4-propoxyphenyl)isoindolin-4-yl)benzamide;
(133) N-(7-(4-isopropylphenyl)-3-oxoisoindolin-4-yl)benzamide;
(134) N-(7-(2,3-dimethoxyphenyl)-3-oxoisoindolin-4-yl)furan-2-carboxamide;
(135) N-(7-(2,3-dimethoxyphenyl)-3-oxoisoindolin-4-yl)-4-fluorobenzamide;
(136) N-(7-(2,3-dimethoxyphenyl)-3-oxoisoindolin-4-yl)thiophene-2-carboxamide;
(137) 4-fluoro-2-methyl-N-(3-oxo-7-phenylisoindolin-4-yl)benzamide;
(138) 4-acetamido-N-(7-(2-methoxyphenyl)-3-oxoisoindolin-4-yl)benzamide;
(139) 4-(dimethylamino)-N-(3-oxo-7-phenylisoindolin-4-yl)benzamide;
(140) 4-acetamido-N-(7-(furan-2-yl)-3-oxoisoindolin-4-yl)benzamide;
(141) 4-fluoro-N-(7-(2-methoxyphenyl)-3-oxoisoindolin-4-yl)benzamide;
(142) 2-fluoro-N-(3-oxo-7-phenylisoindolin-4-yl)benzamide;
(143) 4-chloro-N-(3-oxo-7-phenylisoindolin-4-yl)benzamide;
(144) N-(7-(2-methoxyphenyl)-3-oxoisoindolin-4-yl)benzamide;
(145) N-(7-(3-methoxyphenyl)-3-oxoisoindolin-4-yl)benzamide;
(146) N-(3-oxo-7-(thiophen-3-yl)isoindolin-4-yl)benzamide;
(147) N-(7-(3-cyanophenyl)-3-oxoisoindolin-4-yl)benzamide;
(148) N-(7-(3-(dimethylamino)phenyl)-3-oxoisoindolin-4-yl)benzamide;
(149) N-(7-(2-fluorophenyl)-3-oxoisoindolin-4-yl)benzamide;
(150) N-(7-(furan-3-yl)-3-oxoisoindolin-4-yl)benzamide;
(151) N-(7-(3-fluorophenyl)-3-oxoisoindolin-4-yl)benzamide;
(152) N-(3-oxo-7-(pyridin-3-yl)isoindolin-4-yl)benzamide;
(153) N-(3-oxo-7-(pyridin-3-yl)isoindolin-4-yl)benzamide hydrochloride;
(154) N-(3-oxo-7-(pyrimidin-5-yl)isoindolin-4-yl)benzamide;
(155) 3-chloro-N-(3-oxo-7-phenylisoindolin-4-yl)thiophene-2-carboxamide;
(156) 5-bromo-N-(3-oxo-7-phenylisoindolin-4-yl)thiophene-2-carboxamide;
(157) 3-bromo-N-(3-oxo-7-phenylisoindolin-4-yl)thiophene-2-carboxamide;
(158) 4-fluoro-N-(7-(furan-2-yl)-3-oxoisoindolin-4-yl)benzamide;
(159) N-(3-oxo-7-phenylisoindolin-4-yl)pentanamide;
(160) N-(3-oxo-7-phenylisoindolin-4-yl)acetamide;
(161) N-(7-(2-chloropyrimidin-4-yl)-3-oxoisoindolin-4-yl)acetamide;
(162) N-(7-(2-((3-methoxyphenyl)amino)pyrimidin-4-yl)-3-oxoisoindolin-4-yl)acetamide;
(163) N-(7-(2-((3-fluorophenyl)amino)pyrimidin-4-yl)-3-oxoisoindolin-4-yl)acetamide;
(164) N-(3-oxo-7-(2-(m-tolylamino)pyrimidin-4-yl)isoindolin-4-yl)acetamide;
(165) N-(3-oxo-7-(2-(p-tolylamino)pyrimidin-4-yl)isoindolin-4-yl)acetamide;
(166) N-(7-(2-((3-methoxyphenyl)amino)pyrimidin-4-yl)-3-oxoisoindolin-4-yl)propionamide;
(167) N-(7-(4-(methylsulfonyl)phenyl)-3-oxoisoindolin-4-yl)benzamide;
(168) N-(7-(3-(methylsulfonyl)phenyl)-3-oxoisoindolin-4-yl)benzamide;
(169) N-(7-(3-acetamidophenyl)-3-oxoisoindolin-4-yl)benzamide;
(170) 5-chloro-N-(3-oxo-7-phenylisoindolin-4-yl)thiophene-2-carboxamide;
(171) N-(7-(2,3-dimethoxyphenyl)-3-oxoisoindolin-4-yl)benzamide;
(172) N-(7-(3,5-dimethoxyphenyl)-3-oxoisoindolin-4-yl)benzamide;
(173) N-(7-cyclopropyl-3-oxoisoindolin-4-yl)benzamide;
(174) N-(7-(2-chlorophenyl)-3-oxoisoindolin-4-yl)benzamide;
(175) N-(7-(2,4-dimethoxyphenyl)-3-oxoisoindolin-4-yl)benzamide;
(176) N-(7-(3,4-dimethoxyphenyl)-3-oxoisoindolin-4-yl)benzamide;
(177) N-(7-(3-ethoxyphenyl)-3-oxoisoindolin-4-yl)benzamide;
(178) N-(7-(2,5-dimethoxyphenyl)-3-oxoisoindolin-4-yl)benzamide;
(179) N-(7-(4-chlorophenyl)-3-oxoisoindolin-4-yl)benzamide;
(180) N-(7-(3-chlorophenyl)-3-oxoisoindolin-4-yl)benzamide;
(181) N-(7-(4-ethoxyphenyl)-3-oxoisoindolin-4-yl)benzamide;
(182) N-(7-(2-ethoxyphenyl)-3-oxoisoindolin-4-yl)benzamide;
(183) N-(7-(2-cyanophenyl)-3-oxoisoindolin-4-yl)benzamide;
(184) N-(7-(4-butoxyphenyl)-3-oxoisoindolin-4-yl)benzamide;
(185) N-(7-(2-(dimethylamino)phenyl)-3-oxoisoindolin-4-yl)benzamide;
(186) N-(3-oxo-7-(4-(trifluoromethoxy)phenyl)isoindolin-4-yl)benzamide;
(187) N-(7-(2,6-dimethoxyphenyl)-3-oxoisoindolin-4-yl)benzamide;
(188) N-(3-oxo-7-(4-propylphenyl)isoindolin-4-yl)benzamide;

(189) N-(7-(2,3-dihydroxyphenyl)-3-oxoisoindolin-4-yl)-4-fluorobenzamide;
(190) 4-fluoro-N-(7-(2-hydroxy-3-methoxyphenyl)-3-oxoisoindolin-4-yl)benzamide;
(191) 4-fluoro-N-(3-oxo-7-(thiophen-2-yl)isoindolin-4-yl)benzamide;
(192) 5-methyl-N-(3-oxo-7-phenylisoindolin-4-yl)furan-2-carboxamide;
(193) N-(7-(benzo[d]oxazol-7-yl)-3-oxoisoindolin-4-yl)-4-fluorobenzamide;
(194) 4-fluoro-N-(7-(2-methylbenzo[d]oxazol-7-yl)-3-oxoisoindolin-4-yl)benzamide;
(195) N-(3-oxo-7-(5-(pyrrolidin-1-ylmethyl)thiophen-2-yl)isoindolin-4-yl)benzamide;
(196) N-(3-oxo-7-(5-(piperidin-1-ylmethyl)thiophen-2-yl)isoindolin-4-yl)benzamide;
(197) N-(7-(5-(morpholinomethyl)thiophen-2-yl)-3-oxoisoindolin-4-yl)benzamide;
(198) tert-butyl 4-((5-(7-benzamido-1-oxoisoindolin-4-yl)thiophen-2-yl)methyl)piperazine-1-carboxylate;
(199) N-(7-(6-fluoropyridin-3-yl)-3-oxoisoindolin-4-yl)benzamide;
(200) N-(7-(6-methoxypyridin-3-yl)-3-oxoisoindolin-4-yl)benzamide;
(201) 2-chloro-N-(3-oxo-7-phenylisoindolin-4-yl)benzamide;
(202) 3-methoxy-N-(3-oxo-7-phenylisoindolin-4-yl)benzamide;
(203) N-(3-oxo-7-phenylisoindolin-4-yl)thiophene-2-carboxamide;
(204) N-(7-(4-acetylphenyl)-3-oxoisoindolin-4-yl)-4-methoxybenzamide;
(205) N-(7-(4-fluorophenyl)-3-oxoisoindolin-4-yl)benzamide;
(206) N-(7-(4-(dimethylamino)phenyl)-3-oxoisoindolin-4-yl)benzamide;
(207) N-(7-(4-cyanophenyl)-3-oxoisoindolin-4-yl)benzamide;
(208) 4-cyano-N-(3-oxo-7-phenylisoindolin-4-yl)benzamide;
(209) N-(3-oxo-7-(p-tolyl)isoindolin-4-yl)benzamide;
(210) N-(3-oxo-7-(4-(trifluoromethyl)phenyl)isoindolin-4-yl)benzamide;
(211) N-(3-oxo-7-phenylisoindolin-4-yl)isonicotinamide;
(212) N-(3-oxo-7-phenylisoindolin-4-yl)furan-2-carboxamide;
(213) N-(3-oxo-7-phenylisoindolin-4-yl)nicotinamide;
(214) 4-fluoro-N-(3-oxo-7-(quinolin-6-yl)isoindolin-4-yl)benzamide;
(215) 4-fluoro-N-(3-oxo-7-(quinolin-5-yl)isoindolin-4-yl)benzamide;
(216) 4-fluoro-N-(3-oxo-7-(quinolin-4-yl)isoindolin-4-yl)benzamide;
(217) N-(7-(1H-indol-7-yl)-3-oxoisoindolin-4-yl)-4-fluorobenzamide;
(218) N-(7-(1H-benzo[d]imidazol-4-yl)-3-oxoisoindolin-4-yl)-4-fluorobenzamide;
(219) N-(7-benzyl-3-oxoisoindolin-4-yl)-4-fluorobenzamide;
(220) (R)-tert-butyl 24-(3-oxo-7-phenylisoindolin-4-yl) carbamoyl)pyrrolidine-1-carboxylate;
(221) (R)—N-(3-oxo-7-phenylisoindolin-4-yl)pyrrolidine-2-carboxamide;
(222) 3-amino-N-(2-methyl-3-oxo-7-phenylisoindolin-4-yl)benzamide;
(223) 2-amino-N-(2-methyl-3-oxo-7-phenylisoindolin-4-yl)benzamide;
(224) N-(7-(2,3-dimethoxyphenyl)-2-(furan-2-carbonyl)-3-oxoisoindolin-4-yl) furan-2-carboxamide;
(225) N-(7-(2,3-dimethoxyphenyl)-3-oxo-2-(thiophene-2-carbonyl)isoindolin-4-yl)thiophene-2-carboxamide;
(226) 1-(4-fluorophenyl)-3-(3-oxo-7-phenylisoindolin-4-yl)urea;
(227) 1-(3-oxo-7-phenylisoindolin-4-yl)-3-phenylurea;
(228) 1-(4-cyanophenyl)-3-(3-oxo-7-phenylisoindolin-4-yl)urea;
(229) 1-butyl-3-(3-oxo-7-phenylisoindolin-4-yl)urea;
(230) 1-(4-methoxyphenyl)-3-(3-oxo-7-phenylisoindolin-4-yl)urea;
(231) 1-cyclohexyl-3-(3-oxo-7-phenylisoindolin-4-yl)urea;
(232) 1-(3-oxo-7-phenylisoindolin-4-yl)-3-(p-tolyl)urea;
(233) 1-(2-methoxyphenyl)-3-(3-oxo-7-phenylisoindolin-4-yl)urea;
(234) 1-isopropyl-3-(3-oxo-7-phenylisoindolin-4-yl)urea;
(235) 1-(4-nitrophenyl)-3-(3-oxo-7-phenylisoindolin-4-yl)urea;
(236) 1-ethyl-3-(3-oxo-7-phenylisoindolin-4-yl)urea;
(237) 1-(4-acetylphenyl)-3-(3-oxo-7-phenylisoindolin-4-yl)urea;
(238) 1-(3-oxo-7-phenylisoindolin-4-yl)-3-(o-tolyl)urea;
(239) 1-cyclopentyl-3-(3-oxo-7-phenylisoindolin-4-yl)urea;
(240) 1-(3-fluorophenyl)-3-(3-oxo-7-phenylisoindolin-4-yl)urea;
(241) 1-(3-(methylthio)phenyl)-3-(3-oxo-7-phenylisoindolin-4-yl)urea;
(242) 1-(2-fluorophenyl)-3-(3-oxo-7-phenylisoindolin-4-yl)urea;
(243) 1-(4-chlorophenyl)-3-(3-oxo-7-phenylisoindolin-4-yl)urea;
(244) 1-(7-(4-methoxyphenyl)-3-oxoisoindolin-4-yl)-3-phenylurea;
(245) 1-(7-(4-fluorophenyl)-3-oxoisoindolin-4-yl)-3-phenylurea;
(246) 7-amino-N-cyclohexyl-1-oxo-4-phenylisoindolin-2-carboxamide;
(247) 1-(3-oxo-7-phenylisoindolin-4-yl)-3-phenylthiourea;
(248) phenyl (3-oxo-7-phenylisoindolin-4-yl)carbamate;
(249) N-(3-oxo-7-phenylisoindolin-4-yl)benzenesulfonamide;
(250) N-(3-oxo-7-phenylisoindolin-4-yl)methanesulfonamide;
(251) 4-fluoro-N-(3-oxo-7-phenylisoindolin-4-yl)benzenesulfonamide;
(252) 4-methoxy-N-(3-oxo-7-phenylisoindolin-4-yl)benzenesulfonamide;
(253) 7-((2-chloroethyl)amino)-4-phenylisoindolin-1-one;
(254) 3-((3-oxo-7-phenylisoindolin-4-yl)amino)propanenitrile;
(255) 7-((2-(dimethylamino)ethyl)amino)-4-phenylisoindolin-1-one;
(256) 7-((2-hydroxyethyl)amino)-4-phenylisoindolin-1-one;
(257) 2-(2-((3-oxo-7-phenylisoindolin-4-yl)amino)ethyl)isoindolin-1,3-dione;
(258) 7-((2-(4-methylpiperazin-1-yl)ethyl)amino)-4-phenylisoindolin-1-one;
(259) 4-phenyl-7-((2-(piperidin-1-yl)ethyl)amino)isoindolin-1-one;
(260) 7-((2-morpholinoethyl)amino)-4-phenylisoindolin-1-one;
(261) 7-((2-(methylamino)ethyl)amino)-4-phenylisoindolin-1-one;
(262) 4-phenyl-7-((2-(pyrrolidin-1-yl)ethyl)amino)isoindolin-1-one;
(263) 7-(benzylamino)-4-phenylisoindolin-1-one;

(264) 2-(3-((3-oxo-7-phenylisoindolin-4-yl)amino)propyl) isoindolin-1,3-dione;
(265) 4-(pyridin-4-yl)-7-(pyrrolidin-1-yl)isoindolin-1-one;
(266) 7-(dimethylamino)-4-(2-((3-methoxyphenyl)amino) pyrimidin-4-yl) isoindolin-1-one;
(267) 7-(dimethylamino)-4-(2-((3-fluorophenyl)amino)pyrimidin-4-yl) isoindolin-1-one;
(268) 7-(butylamino)-4-(2-((3-methoxyphenyl)amino)pyrimidin-4-yl) isoindolin-1-one;
(269) 7-(butyl(methyl)amino)-4-(2-((3-methoxyphenyl)amino)pyrimidin-4-yl) isoindolin-1-one;
(270) 7-(butyl(methyl)amino)-4-(2-((3-methoxyphenyl)amino)pyrimidin-4-yl)-2-methylisoindolin-1-one;
(271) 4-amino-7-phenylisoindolin-1,3-dione;
(272) 4-amino-7-(2-methoxyphenyl)isoindolin-1,3-dione;
(273) 4-amino-7-(2,3-dimethoxyphenyl)isoindolin-1,3-dione;
(274) 4-amino-7-(furan-2-yl)isoindolin-1,3-dione;
(275) 4-amino-7-(thiophen-2-yl)isoindolin-1,3-dione;
(276) N-(1,3-dioxo-7-phenylisoindolin-4-yl)benzamide;
(277) N-(7-(2-methoxyphenyl)-1,3-dioxoisoindolin-4-yl) benzamide;
(278) N-(7-(2,3-dimethoxyphenyl)-1,3-dioxoisoindolin-4-yl)benzamide;
(279) 4-fluoro-N-(3-oxo-7-phenyl-2,3-dihydro-1H-pyrrolo [3,4-c]pyridin-4-yl) benzamide;
(280) N-(7-(2,3-dimethoxyphenyl)-3-oxoisoindolin-4-yl)-4-((3-(pyrrolidin-1-yl) propyl)amino)benzamide;
(281) N-(7-bromo-3-oxoisoindolin-4-yl)-4-((2-(dimethylamino)ethyl)amino) benzamide;
(282) N-(7-bromo-3-oxoisoindolin-4-yl)-4-((3-(piperidin-1-yl) propyl)amino) benzamide;
(283) N-(7-bromo-3-oxoisoindolin-4-yl)-4-((2-(pyrrolidin-1-yl)ethyl)amino) benzamide;
(284) N-(7-bromo-3-oxoisoindolin-4-yl)-4-((2-(piperidin-1-yl)ethyl)amino) benzamide;
(285) 4-((2-(azepan-1-yl)ethyl)amino)-N-(7-bromo-3-oxoisoindolin-4-yl) benzamide;
(286) N-(7-bromo-3-oxoisoindolin-4-yl)-4-((3-(dimethylamino)propyl)amino) benzamide;
(287) N-(7-(furan-2-yl)-3-oxoisoindolin-4-yl)-4-((2-(pyrrolidin-1-yl)ethyl) amino)benzamide;
(288) N-(7-(furan-2-yl)-3-oxoisoindolin-4-yl)-4-((2-methoxyethyl)amino)benzamide;
(289) N-(7-(furan-2-yl)-3-oxoisoindolin-4-yl)-4-((2-(piperidin-1-yl)ethyl)amino) benzamide;
(290) N-(7-(furan-2-yl)-3-oxoisoindolin-4-yl)-4-((2-morpholinoethyl)amino) benzamide;
(291) 4-((2-(dimethylamino)ethyl)amino)-N-(7-(furan-2-yl)-3-oxoisoindolin-4-yl)benzamide;
(292) N-(7-(furan-2-yl)-3-oxoisoindolin-4-yl)-4-((2-hydroxyethyl)amino) benzamide;
(293) 4-((2-(azepan-1-yl)ethyl)amino)-N-(7-(furan-2-yl)-3-oxoisoindolin-4-yl)benzamide;
(294) N-(7-(furan-2-yl)-3-oxoisoindolin-4-yl)-4-((2-(4-methylpiperazin-1-yl)ethyl)amino)benz amide;
(295) N-(7-(furan-2-yl)-3-oxoisoindolin-4-yl)-4-((3-(4-methylpiperazin-1-yl)propyl)amino)benzamide;
(296) N-(7-(2,3-dimethoxyphenyl)-3-oxoisoindolin-4-yl)-4-((3-morpholinopropyl)amino)benz amide;
(297) N-(7-(2,3-dimethoxyphenyl)-3-oxoisoindolin-4-yl)-4-((2-morpholinoethyl)amino)benzamide;
(298) N-(7-(2,3-dimethoxyphenyl)-3-oxoisoindolin-4-yl)-4-((2-(piperidin-1-yl)ethyl)amino)benzamide;
(299) N-(7-(2,3-dimethoxyphenyl)-3-oxoisoindolin-4-yl)-4-((2-(pyrrolidin-1-yl)ethyl)amino)benzamide;
(300) N-(7-(2,3-dimethoxyphenyl)-3-oxoisoindolin-4-yl)-4-((2-methoxyethyl)amino)benzamide;
(301) N-(7-(2,3-dimethoxyphenyl)-3-oxoisoindolin-4-yl)-4-((2-(dimethylamino)ethyl)amino)benzamide;
(302) N-(7-(2-methoxyphenyl)-3-oxoisoindolin-4-yl)-4-((3-(pyrrolidin-1-yl)propyl)amino)benzamide;
(303) N-(7-(2-methoxyphenyl)-3-oxoisoindolin-4-yl)-4-((2-(pyrrolidin-1-yl)ethyl)amino)benzamide hydrochloride;
(304) N-(7-(2,3-dimethoxyphenyl)-3-oxoisoindolin-4-yl)-4-((2-(pyrrolidin-1-yl)ethyl)amino)benzamide hydrochloride;
(305) 4-((2-(dimethylamino)ethyl)amino)-N-(7-(2-methoxyphenyl)-3-oxoisoindolin-4-yl)benzamide;
(306) N-(7-(2,3-dimethoxyphenyl)-3-oxoisoindolin-4-yl)-4-((3-(dimethylamino)propyl)amino) benzamide;
(307) N-(7-(2-methoxyphenyl)-3-oxoisoindolin-4-yl)-4-((3-(piperidin-1-yl)propyl)amino)benz amide;
(308) N-(7-(2,3-dimethoxyphenyl)-3-oxoisoindolin-4-yl)-4-((3-(piperidin-1-yl)propyl)amino)benzamide;
(309) 2-methyl-N-(3-oxo-7-phenylisoindolin-4-yl)-4-((2-(pyrrolidin-1-yl)ethyl)amino)benzamide;
(310) 4-((3-methoxypropyl)amino)-N-(7-(2-methoxypyridin-3-yl)-3-oxoisoindolin-4-yl)benzamide;
(311) N-(7-(2,3-dimethoxyphenyl)-3-oxoisoindolin-4-yl)-4-((2-hydroxyethyl)amino)benzamide;
(312) N-(7-(2,3-dimethoxyphenyl)-3-oxoisoindolin-4-yl)-4-morpholinobenzamide;
(313) N-(7-(3-fluoro-2-methoxyphenyl)-3-oxoisoindolin-4-yl)-4-((2-(pyrrolidin-1-yl)ethyl)amino)benzamide;
(314) N-(7-(2,3-dimethoxyphenyl)-3-oxoisoindolin-4-yl)-4-((2-(4-methylpiperazin-1-yl)ethyl) amino)benzamide;
(315) 4-((2-aminoethyl)amino)-N-(7-(2,3-dimethoxyphenyl)-3-oxoisoindolin-4-yl)benzamide;
(316) N-(7-(2,3-dimethoxyphenyl)-3-oxoisoindolin-4-yl)-4-((3-(4-methylpiperazin-1-yl)propyl)amino)benzamide;
(317) N-(3-oxo-7-phenylisoindolin-4-yl)-4-((2-(pyrrolidin-1-yl)ethyl)amino)benzamide;
(318) N-(7-(2-methoxyphenyl)-3-oxoisoindolin-4-yl)-4-((2-(pyrrolidin-1-yl)ethyl)amino)benzamide;
(319) 4-(4-methylpiperazin-1-yl)-N-(3-oxo-7-phenylisoindolin-4-yl)benzamide;
(320) 4-morpholino-N-(3-oxo-7-phenylisoindolin-4-yl)benzamide;
(321) 4-((2-methoxyethyl)amino)-N-(3-oxo-7-phenylisoindolin-4-yl)benzamide;
(322) 4-((2-morpholinoethyl)amino)-N-(3-oxo-7-phenylisoindolin-4-yl)benzamide;
(323) N-(7-(2-methoxyphenyl)-3-oxoisoindolin-4-yl)-4-morpholinobenzamide;
(324) 4-((2-methoxyethyl)amino)-N-(7-(2-methoxyphenyl)-3-oxoisoindolin-4-yl)benzamide;
(325) N-(7-(2-methoxyphenyl)-3-oxoisoindolin-4-yl)-4-(4-methylpiperazin-1-yl)benzamide;
(326) N-(7-(2-methoxyphenyl)-3-oxoisoindolin-4-yl)-4-((2-morpholinoethyl)amino)benzamide;
(327) 4-((3-morpholinopropyl)amino)-N-(3-oxo-7-phenylisoindolin-4-yl)benzamide;
(328) N-(7-(2-methoxyphenyl)-3-oxoisoindolin-4-yl)-4-((3-morpholinopropyl)amino)benzamide;
(329) 4-((3-(4-methylpiperazin-1-yl)propyl)amino)-N-(3-oxo-7-phenylisoindolin-4-yl)benzamide;
(330) N-(7-(2-methoxyphenyl)-3-oxoisoindolin-4-yl)-4-((3-(4-methylpiperazin-1-yl)propyl)amino)benzamide;
(331) 4-((3-methoxypropyl)amino)-N-(3-oxo-7-phenylisoindolin-4-yl)benzamide;
(332) N-(7-(2-methoxyphenyl)-3-oxoisoindolin-4-yl)-4-((3-methoxypropyl)amino)benzamide;

(333) N-(3-oxo-7-phenylisoindolin-4-yl)-4-((thiophen-2-ylmethyl)amino)benzamide;
(334) N-(7-(2-methoxyphenyl)-3-oxoisoindolin-4-yl)-4-((thiophen-2-ylmethyl)amino)benzamide;
(335) 4-((3-(dimethylamino)propyl)amino)-N-(7-(furan-2-yl)-3-oxoisoindolin-4-yl)benzamide
(336) N-(7-(furan-2-yl)-3-oxoisoindolin-4-yl)-4-((3-methoxypropyl)amino)benzamide;
(337) N-(7-(furan-2-yl)-3-oxoisoindolin-4-yl)-4-((3-morpholinopropyl)amino)benzamide;
(338) N-(7-(furan-2-yl)-3-oxoisoindolin-4-yl)-4-((3-(piperidin-1-yl)propyl)amino)benzamide;
(339) N-(7-(furan-2-yl)-3-oxoisoindolin-4-yl)-4-((3-(pyrrolidin-1-yl)propyl)amino)benzamide;
(340) 4-(4-aminopiperidin-1-yl)-N-(3-oxo-7-phenylisoindolin-4-yl)benzamide;
(341) N-(7-(benzo[d]oxazol-7-yl)-3-oxoisoindolin-4-yl)-4-((2-(dimethylamino)ethyl)amino)benzamide;
(342) N-(7-(benzo[d]oxazol-7-yl)-3-oxoisoindolin-4-yl)-4-((2-(piperidin-1-yl)ethyl)amino)benzamide;
(343) N-(7-(benzo[d]oxazol-7-yl)-3-oxoisoindolin-4-yl)-4-((3-(piperidin-1-yl)propyl)amino)benzamide;
(344) 4-((2-(azepan-1-yl)ethyl)amino)-N-(7-(benzo[d]oxazol-7-yl)-3-oxoisoindolin-4-yl)benzamide;
(345) 4-(2-morpholinoethoxy)-N-(3-oxo-7-phenylisoindolin-4-yl)benzamide;
(346) N-(3-oxoisoindolin-4-yl)-4-((2-(pyrrolidin-1-yl)ethyl)amino)benzamide;
(347) N-(7-(2,3-dimethoxyphenyl)-3-oxoisoindolin-4-yl)-4-(2-morpholinoethoxy)benzamide;
(348) N-(7-(3-amino-2-hydroxyphenyl)-3-oxoisoindolin-4-yl)-4-((2-morpholinoethyl)amino)benzamide;
(349) 4-((2-(azepan-1-yl)ethyl)amino)-N-(7-(2-methoxyphenyl)-3-oxoisoindolin-4-yl)benzamide;
(350) 4-((2-(azepan-1-yl)ethyl)amino)-N-(7-(2,3-dimethoxyphenyl)-3-oxoisoindolin-4-yl)benzamide;
(351) 4-((3-(dimethylamino)propyl)amino)-N-(7-(2-hydroxyphenyl)-3-oxoisoindolin-4-yl)benzamide;
(352) 4-((2-hydroxyethyl)amino)-N-(7-(2-methoxyphenyl)-3-oxoisoindolin-4-yl)benzamide;
(353) 4-((2-hydroxyethyl)amino)-N-(7-(2-hydroxyphenyl)-3-oxoisoindolin-4-yl)benzamide;
(354) 4-((3-hydroxypropyl)amino)-N-(7-(2-methoxyphenyl)-3-oxoisoindolin-4-yl)benzamide;
(355) N-(7-(2-hydroxyphenyl)-3-oxoisoindolin-4-yl)-4-((3-hydroxypropyl)amino)benzamide;
(356) 4-((4-hydroxybutyl)amino)-N-(7-(2-methoxyphenyl)-3-oxoisoindolin-4-yl)benzamide;
(357) 4-((4-hydroxybutyl)amino)-N-(7-(2-hydroxyphenyl)-3-oxoisoindolin-4-yl)benzamide;
(358) 4-(methyl(2-(methylamino)ethyl)amino)-N-(3-oxo-7-phenylisoindolin-4-yl)benzamide;
(359) N-(7-(2,3-difluorophenyl)-3-oxoisoindolin-4-yl)-4-((2-morpholinoethyl)amino)benzamide;
(360) N-(3-oxo-7-phenylisoindolin-4-yl)-4-((2-(piperidin-1-yl)ethyl)amino)benzamide;
(361) N-(7-(2-methoxyphenyl)-3-oxoisoindolin-4-yl)-4-((2-(piperidin-1-yl)ethyl)amino)benzamide;
(362) 4-((2-(dimethylamino)ethyl)amino)-N-(3-oxo-7-phenylisoindolin-4-yl)benzamide;
(363) N-(3-oxo-7-phenylisoindolin-4-yl)-4-((3-(pyrrolidin-1-yl)propyl)amino)benzamide;
(364) N-(7-(2,3-difluorophenyl)-3-oxoisoindolin-4-yl)-4-((2-(pyrrolidin-1-yl)ethyl)amino)benzamide;
(365) N-(7-(2,3-difluorophenyl)-3-oxoisoindolin-4-yl)-4-((2-(pyrrolidin-1-yl)ethyl)amino)benzamide hydrochloride;
(366) N-(7-(2,3-difluorophenyl)-3-oxoisoindolin-4-yl)-4-((3-(pyrrolidin-1-yl)propyl)amino)benzamide hydrochloride;
(367) N-(7-(2,3-difluorophenyl)-3-oxoisoindolin-4-yl)-4-((2-(dimethylamino)ethyl)amino)benzamide;
(368) N-(7-(2,3-difluorophenyl)-3-oxoisoindolin-4-yl)-4-((3-(dimethylamino)propyl)amino)benzamide;
(369) 4-((2-(azepan-1-yl)ethyl)amino)-N-(3-oxo-7-phenylisoindolin-4-yl)benzamide;
(370) N-(3-oxo-7-phenylisoindolin-4-yl)-4-((3-(piperidin-1-yl)propyl)amino)benzamide;
(371) 4-((2-hydroxyethyl)amino)-N-(3-oxo-7-(thiophen-2-yl)isoindolin-4-yl)benzamide;
(372) 4-((2-methoxyethyl)amino)-N-(3-oxo-7-(thiophen-2-yl)isoindolin-4-yl)benzamide;
(373) 4-((2-(dimethylamino)ethyl)amino)-N-(3-oxo-7-(thiophen-2-yl)isoindolin-4-yl)benzamide;
(374) N-(3-oxo-7-(thiophen-2-yl)isoindolin-4-yl)-4-((2-(piperidin-1-yl)ethyl)amino)benzamide;
(375) 4-((2-morpholinoethyl)amino)-N-(3-oxo-7-(thiophen-2-yl)isoindolin-4-yl)benzamide;
(376) N-(7-(benzo[d]oxazol-7-yl)-3-oxoisoindolin-4-yl)-4-((2-(pyrrolidin-1-yl)ethyl)amino)benzamide;
(377) N-(7-(2-methylbenzo[d]oxazol-7-yl)-3-oxoisoindolin-4-yl)-4-((2-(pyrrolidin-1-yl)ethyl) amino)benzamide;
(378) 4-((2-(4-methylpiperazin-1-yl)ethyl)amino)-N-(3-oxo-7-(thiophen-2-yl)isoindolin-4-yl)benzamide;
(379) 4-((2-(4-methylpiperazin-1-yl)ethyl)amino)-N-(3-oxo-7-phenylisoindolin-4-yl)benzamide;
(380) 4-((2-hydroxyethyl)amino)-N-(3-oxo-7-phenylisoindolin-4-yl)benzamide;
(381) 4-((3-(dimethylamino)propyl)amino)-N-(3-oxo-7-phenylisoindolin-4-yl)benzamide;
(382) 4-((3-hydroxypropyl)amino)-N-(3-oxo-7-phenylisoindolin-4-yl)benzamide;
(383) 4-((4-hydroxybutyl)amino)-N-(3-oxo-7-phenylisoindolin-4-yl)benzamide;
(384) N-(7-(benzofuran-2-yl)-3-oxoisoindolin-4-yl)-4-((2-(pyrrolidin-1-yl)ethyl)amino)benzamide;
(385) N-(3-oxo-7-(quinolin-6-yl)isoindolin-4-yl)-4-((2-(pyrrolidin-1-yl)ethyl)amino)benzamide;
(386) N-(3-oxo-7-(quinolin-5-yl)isoindolin-4-yl)-4-((2-(pyrrolidin-1-yl)ethyl)amino)benzamide;
(387) N-(3-oxo-7-(quinolin-4-yl)isoindolin-4-yl)-4-((2-(pyrrolidin-1-yl)ethyl)amino)benzamide;
(388) 7-(4-fluorobenzamido)-1-oxoisoindoline-4-carboxylic acid;
(389) 7-(4-fluorobenzamido)-N-methyl-1-oxoisoindoline-4-carboxamide;
(390) N-methyl-1-oxo-7-(4-((2-(pyrrolidin-1-yl)ethyl)amino)benzamido)isoindoline-4-carboxamide;
(391) 4-fluoro-N-(3-oxo-7-(pyrrolidine-1-carbonyl)isoindolin-4-yl)benzamide;
(392) N-(3-oxo-7-(pyrrolidine-1-carbonyl)isoindolin-4-yl)-4-((2-(pyrrolidin-1-yl)ethyl)amino) benzamide;
(393) 4-fluoro-N-(7-(2-hydroxypropan-2-yl)-3-oxoisoindolin-4-yl)benzamide;
(394) N-(7-(2-hydroxypropan-2-yl)-3-oxoisoindolin-4-yl)-4-((2-(pyrrolidin-1-yl)ethyl)amino) benzamide;
(395) N-(7-cyano-3-oxoisoindolin-4-yl)-4-fluorobenzamide;
(396) 4-fluoro-N-(7-hydroxy-3-oxoisoindolin-4-yl)benzamide;
(397) 4-acetamido-N-(1-oxo-5-phenyl-1,2,3,4-tetrahydroisoquinolin-8-yl)benzamide;
(398) N-(1-oxo-5-phenyl-1,2,3,4-tetrahydroisoquinolin-8-yl)benzamide;

(399) N-(1-oxo-5-phenyl-1,2,3,4-tetrahydroisoquinolin-8-yl)furan-2-carboxamide;
(400) N-(5-(2,3-dimethoxyphenyl)-1-oxo-1,2,3,4-tetrahydroisoquinolin-8-yl)-4-fluorobenzamide;
(401) N-(1-oxo-5-phenyl-1,2,3,4-tetrahydroisoquinolin-8-yl)-4-((2-(pyrrolidin-1-yl)ethyl)amino)benzamide;
(402) N-(5-(2-methoxyphenyl)-1-oxo-1,2,3,4-tetrahydroisoquinolin-8-yl)-4-((2-(pyrrolidin-1-yl)ethyl)amino)benzamide;
(403) N-(5-bromo-1-oxo-1,2,3,4-tetrahydroisoquinolin-8-yl)-4-((2-(pyrrolidin-1-yl)ethyl)amino)benzamide;
(404) 4-fluoro-N-(3-oxo-7-(phenylthio)isoindolin-4-yl)benzamide;
(405) N-(1-oxo-5-(phenylthio)-1,2,3,4-tetrahydroisoquinolin-8-yl)-4-((2-(pyrrolidin-1-yl)ethyl) amino)benzamide;
(406) N-(3-oxo-7-(phenylsulfonyl)isoindolin-4-yl)benzamide;
(407) N-(3-oxo-7-(phenylthio)isoindolin-4-yl)benzamide;
(408) 4-fluoro-N-(3-oxo-7-(phenylamino)isoindolin-4-yl)benzamide;
(409) N-(3-oxo-7-(phenylamino)isoindolin-4-yl)benzamide;
(410) N-(7-((2-methoxyphenyl)amino)-3-oxoisoindolin-4-yl)benzamide;
(411) N-(3-oxo-7-(o-tolylamino)isoindolin-4-yl)benzamide;
(412) N-(3-oxo-7-(p-tolylamino)isoindolin-4-yl)benzamide;
(413) N-(7-((2-fluorophenyl)amino)-3-oxoisoindolin-4-yl)benzamide;
(414) N-(7-((4-fluorophenyl)amino)-3-oxoisoindolin-4-yl)benzamide;
(415) N-(7-((3-fluorophenyl)amino)-3-oxoisoindolin-4-yl)benzamide;
(416) N-(7-((4-methoxyphenyl)amino)-3-oxoisoindolin-4-yl)benzamide;
(417) 4-methyl-N-(3-oxo-7-(phenylamino)isoindolin-4-yl)benzamide;
(418) N-(7-((3-chlorophenyl)amino)-3-oxoisoindolin-4-yl)-4-fluorobenzamide;
(419) N-(7-((2-chlorophenyl)amino)-3-oxoisoindolin-4-yl)-4-fluorobenzamide;
(420) 2-fluoro-N-(3-oxo-7-(phenylamino)isoindolin-4-yl)benzamide;
(421) 3-fluoro-N-(3-oxo-7-(phenylamino)isoindolin-4-yl)benzamide;
(422) N-(7-((2,3-dimethoxyphenyl)amino)-3-oxoisoindolin-4-yl)-4-fluorobenzamide;
(423) N-(7-((3,5-bis(trifluoromethyl)phenyl)amino)-3-oxoisoindolin-4-yl)-4-fluorobenzamide;
(424) N-(7-((2,3-dimethylphenyl)amino)-3-oxoisoindolin-4-yl)-4-fluorobenzamide;
(425) 4-fluoro-N-(7-((2-methoxyphenyl)amino)-3-oxoisoindolin-4-yl)benzamide;
(426) 4-fluoro-N-(3-oxo-7-(o-tolylamino)isoindolin-4-yl)benzamide;
(427) 4-fluoro-N-(3-oxo-7-(pyridin-3-ylamino)isoindolin-4-yl)benzamide;
(428) 4-fluoro-N-(3-oxo-7-(pyridin-2-ylamino)isoindolin-4-yl)benzamide;
(429) 4-fluoro-N-(3-oxo-7-(pyrazin-2-ylamino)isoindolin-4-yl)benzamide;
(430) 4-fluoro-N-(7-((1-methyl-1H-pyrazol-4-yl)amino)-3-oxoisoindolin-4-yl)benzamide;
(431) N-(7-((3-methoxyphenyl)amino)-3-oxoisoindolin-4-yl)benzamide;
(432) 2-methoxy-N-(3-oxo-7-(phenylamino)isoindolin-4-yl)benzamide;
(433) 4-methoxy-N-(3-oxo-7-(phenylamino)isoindolin-4-yl)benzamide;
(434) 3-methoxy-N-(3-oxo-7-(phenylamino)isoindolin-4-yl)benzamide;
(435) 4-acetamido-N-(3-oxo-7-(phenylamino)isoindolin-4-yl)benzamide;
(436) N-(3-oxo-7-(m-tolylamino)isoindolin-4-yl)benzamide;
(437) N-(7-((1H-pyrazol-3-yl)amino)-3-oxoisoindolin-4-yl)-4-fluorobenzamide;
(438) N-(3-oxo-7-(phenylamino)isoindolin-4-yl)-4-((2-(pyrrolidin-1-yl)ethyl)amino)benzamide;
(439) N-(3-oxo-7-(phenylamino)isoindolin-4-yl)-4-((2-(piperidin-1-yl)ethyl)amino)benzamide;
(440) N-(3-oxo-7-(phenylamino)isoindolin-4-yl)-4-((2-(piperidin-1-yl)ethyl)amino)benzamide hydrochloride;
(441) 4-((2-(dimethylamino)ethyl)amino)-N-(3-oxo-7-(phenylamino)isoindolin-4-yl)benzamide;
(442) 4-((2-morpholinoethyl)amino)-N-(3-oxo-7-(phenylamino)isoindolin-4-yl)benzamide;
(443) 4-((2-(4-methylpiperazin-1-yl)ethyl)amino)-N-(3-oxo-7-(phenylamino)isoindolin-4-yl)benzamide;
(444) 4-((2-methoxyethyl)amino)-N-(3-oxo-7-(phenylamino)isoindolin-4-yl)benzamide;
(445) N-(7-((3-methoxyphenyl)amino)-3-oxoisoindolin-4-yl)-4-((2-(pyrrolidin-1-yl)ethyl)amino)benzamide;
(446) N-(7-((3-methoxyphenyl)amino)-3-oxoisoindolin-4-yl)-4-((2-(piperidin-1-yl)ethyl)amino)benzamide;
(447) N-(7-((3-methoxyphenyl)amino)-3-oxoisoindolin-4-yl)-4-((3-(pyrrolidin-1-yl)propyl)amino)benzamide;
(448) N-(7-((3-methoxyphenyl)amino)-3-oxoisoindolin-4-yl)-4-((3-(piperidin-1-yl)propyl)amino)benzamide;
(449) N-(3-oxo-7-(m-tolylamino)isoindolin-4-yl)-4-((2-(pyrrolidin-1-yl)ethyl)amino)benzamide;
(450) N-(3-oxo-7-(m-tolylamino)isoindolin-4-yl)-4-((2-(piperidin-1-yl)ethyl)amino)benzamide;
(451) N-(3-oxo-7-(m-tolylamino)isoindolin-4-yl)-4-((3-(pyrrolidin-1-yl)propyl)amino)benzamide;
(452) N-(3-oxo-7-(m-tolylamino)isoindolin-4-yl)-4-((3-(piperidin-1-yl)propyl)amino)benzamide;
(453) N-(7-((2-chlorophenyl)amino)-3-oxoisoindolin-4-yl)-4-((2-(pyrrolidin-1-yl)ethyl)amino) benzamide;
(454) N-(7-((2-chlorophenyl)amino)-3-oxoisoindolin-4-yl)-4-((2-(piperidin-1-yl)ethyl)amino) benzamide;
(455) N-(7-((3-chlorophenyl)amino)-3-oxoisoindolin-4-yl)-4-((2-(pyrrolidin-1-yl)ethyl)amino) benzamide;
(456) N-(7-((3-chlorophenyl)amino)-3-oxoisoindolin-4-yl)-4-((2-(piperidin-1-yl)ethyl)amino) benzamide;
(457) N-(7-((3-chlorophenyl)amino)-3-oxoisoindolin-4-yl)-4-((3-(pyrrolidin-1-yl)propyl)amino)benzamide;
(458) N-(7-((3-chlorophenyl)amino)-3-oxoisoindolin-4-yl)-4-((3-(piperidin-1-yl)propyl)amino)benzamide;
(459) N-(3-oxo-7-(phenylamino)isoindolin-4-yl)-4-((3-(2-oxopyrrolidin-1-yl)propyl)amino)benzamide;
(460) 4-((3-(dimethylamino)propyl)amino)-N-(3-oxo-7-(phenylamino)isoindolin-4-yl)benzamide;
(461) 4-((3-morpholinopropyl)amino)-N-(3-oxo-7-(phenylamino)isoindolin-4-yl)benzamide;
(462) N-(3-oxo-7-(phenylamino)isoindolin-4-yl)-4-((3-(pyrrolidin-1-yl)propyl)amino)benzamide;
(463) 4-((3-(4-methylpiperazin-1-yl)propyl)amino)-N-(3-oxo-7-(phenylamino)isoindolin-4-yl) benzamide;
(464) 4-((3-hydroxypropyl)amino)-N-(3-oxo-7-(phenylamino)isoindolin-4-yl)benzamide;
(465) N-(7-((3,5-bis(trifluoromethyl)phenyl)amino)-3-oxoisoindolin-4-yl)-4-((2-(pyrrolidin-1-yl)ethyl)amino)benzamide;

(466) N-(7-((3,5-bis(trifluoromethyl)phenyl)amino)-3-oxoisoindolin-4-yl)-4-((3-(pyrrolidin-1-yl)propyl)amino)benzamide;
(467) N-(7-((3,5-bis(trifluoromethyl)phenyl)amino)-3-oxoisoindolin-4-yl)-4-((2-(piperidin-1-yl)ethyl)amino)benzamide;
(468) N-(7-((3,5-bis(trifluoromethyl)phenyl)amino)-3-oxoisoindolin-4-yl)-4-((3-(piperidin-1-yl)propyl)amino)benzamide;
(469) N-(7-((2,3-dimethylphenyl)amino)-3-oxoisoindolin-4-yl)-4-((2-(pyrrolidin-1-yl)ethyl)amino)benzamide;
(470) N-(7-((2,3-dimethylphenyl)amino)-3-oxoisoindolin-4-yl)-4-((3-(pyrrolidin-1-yl)propyl)amino)benzamide;
(471) N-(7-((2,3-dimethylphenyl)amino)-3-oxoisoindolin-4-yl)-4-((2-(piperidin-1-yl)ethyl)amino)benzamide;
(472) N-(7-((2,3-dimethylphenyl)amino)-3-oxoisoindolin-4-yl)-4-((3-(piperidin-1-yl)propyl)amino)benzamide;
(473) N-(3-oxo-7-(o-tolylamino)isoindolin-4-yl)-4-((2-(pyrrolidin-1-yl)ethyl)amino)benzamide;
(474) N-(7-((2-methoxyphenyl)amino)-3-oxoisoindolin-4-yl)-4-((2-(pyrrolidin-1-yl)ethyl)amino)benzamide;
(475) N-(7-((2-methoxyphenyl)amino)-3-oxoisoindolin-4-yl)-4-((3-(pyrrolidin-1-yl)propyl)amino)benzamide;
(476) N-(3-oxo-7-(o-tolylamino)isoindolin-4-yl)-4-((3-(pyrrolidin-1-yl)propyl)amino)benzamide;
(477) N-(7-((2-methoxyphenyl)amino)-3-oxoisoindolin-4-yl)-4-((2-(piperidin-1-yl)ethyl)amino)benzamide;
(478) N-(7-((2-methoxyphenyl)amino)-3-oxoisoindolin-4-yl)-4-((3-(piperidin-1-yl)propyl)amino)benzamide;
(479) N-(3-oxo-7-(phenylamino)isoindolin-4-yl)-4-((3-(piperidin-1-yl)propyl)amino)benzamide;
(480) N-(3-oxo-7-(phenylamino)isoindolin-4-yl)-4-((3-(piperidin-1-yl)propyl)amino)benzamide hydrochloride;
(481) 4-((2-aminoethyl)amino)-N-(3-oxo-7-(phenylamino)isoindolin-4-yl)benzamide;
(482) N-(3-oxo-7-(o-tolylamino)isoindolin-4-yl)-4-((2-(piperidin-1-yl)ethyl) amino)benzamide;
(483) N-(3-oxo-7-(o-tolylamino)isoindolin-4-yl)-4-((3-(piperidin-1-yl)propyl) amino)benzamide;
(484) 4-((4-hydroxybutyl)amino)-N-(3-oxo-7-(phenylamino)isoindolin-4-yl)benzamide;
(485) 4-((2-acetamidoethyl)amino)-N-(3-oxo-7-(phenylamino)isoindolin-4-yl)benzamide;
(486) 4-((3-aminopropyl)amino)-N-(3-oxo-7-(phenylamino)isoindolin-4-yl)benzamide;
(487) 4-((2-hydroxyethyl)amino)-N-(3-oxo-7-(phenylamino)isoindolin-4-yl)benzamide;
(488) 4-((2-hydroxy-3-(piperidin-1-yl)propyl)amino)-N-(3-oxo-7-(phenylamino)isoindolin-4-yl)benzamide;
(489) (S)-4-((2-hydroxy-3-(piperidin-1-yl)propyl)amino)-N-(3-oxo-7-(phenylamino)isoindolin-4-yl)benzamide;
(490) (R)-4-((2-hydroxy-3-(piperidin-1-yl)propyl)amino)-N-(3-oxo-7-(phenylamino)isoindolin-4-yl)benzamide;
(491) 4-(4-aminopiperidin-1-yl)-N-(3-oxo-7-(phenylamino)isoindolin-4-yl)benzamide; and
(492) 4-((2-(azepan-1-yl)ethyl)amino)-N-(3-oxo-7-(phenylamino)isoindolin-4-yl)benzamide.

The compound according to the present invention may exist as a pharmaceutically acceptable salt. Preferably, the pharmaceutically acceptable salt of the inventive compound is a salt formed with an inorganic or organic acid. Examples of the inorganic acid include hydrochloric acid, sulfuric acid, nitric acid, phosphoric acid, perchloric acid, bromic acid, and the like. Also, examples of the organic acid include acetic acid, methanesulfonic acid, ethanesulfonic acid, p-toluenesulfonic acid, fumaric acid, maleic acid, malonic acid, phthalic acid, succinic acid, lactic acid, citric acid, gluconic acid, tartaric acid, salicylic acid, malic acid, oxalic acid, benzoic acid, embonic acid, aspartic acid, glutamic acid, and the like. Examples of organic bases which can be used for preparing an organic base addition salt include tris(hydroxymethyl)methylamine, dicyclohexylamine, and the like. Examples of amino acids which can be used for preparing an amino acid addition salt include natural amino acids such as alanine, glycine, and the like.

Said salts may be prepared by conventional methods known in the art, e.g., dissolving the compound of formula (I) in a water-miscible solvent such as methanol, ethanol, acetone, 1,4-dioxane, adding a free acid or free base thereto, and subjecting the mixture to crystallization.

Also, the compounds of the present invention may have asymmetric carbon centers and, thus, may exist as R- or S-isomer, racemic mixtures, individual enantiomers or mixtures thereof, and individual diastereomers or mixtures thereof. Such stereoisomers and mixtures thereof are all included within the scope of the present invention.

Additionally, solvates and hydrates of the compound of formula (I) are also included within the scope of the present invention. Such solvates and hydrate may be prepared by conventional methods known in the art. Preferably, the solvates and hydrates are non-toxic and water-soluble, and form 1 to 5 bonds with water or alcohol-based solvent (particularly, ethanol and the like).

Meanwhile, the present invention provides a pharmaceutical composition for the prevention or treatment of cancer, comprising a compound selected from the group consisting of the compound of formula (I), and a pharmaceutically acceptable salt, a hydrate and a solvate thereof.

Examples of said cancer include colorectal cancer, breast cancer, CNS cancer, colon cancer, non-small cell lung cancer, kidney cancer, prostate cancer, ovarian cancer, uterus cancer, stomach cancer, liver cancer, skin cancer, lung cancer, brain cancer, bladder cancer, esophageal cancer, pancreatic cancer, thyroid cancer, head and neck cancer, squamous cell carcinoma, osteosarcoma, B-cell or T-cell lymphoma, acute or chronic leukemia and multiple myeloma.

In addition, since the inventive compound of formula (I) can inhibit TNIK, IKKε and TBK1, it can also be used for the prevention or treatment of diseases associated with TNIK, IKKε and TB protein activation, e.g., chronic inflammation, and the like.

A pharmaceutical composition of the present invention may comprise one or more conventional non-toxic pharmaceutically acceptable additives as effective components, in addition to the compound of formula (I) or a pharmaceutically acceptable salt, a hydrate or a solvate thereof.

Examples of acceptable additives for the pharmaceutical composition of the present invention include sweeteners, binders, solubilizing agents, dissolution aids, wetting agents, emulsifiers, isotonic agents, adsorbents, disintegrants, antioxidants, preservatives, lubricants, fillers, fragrances, and the like, e.g., lactose, dextrose, sucrose, mannitol, sorbitol, cellulose, glycine, silica, talc, stearic acid, stearin, magnesium stearate, magnesium aluminum silicate, starch, gelatin, tragacanth gum, alginic acid, sodium alginate, methylcellulose, sodium carboxymethyl cellulose, agar, water, ethanol, polyethylene glycol, polyvinyl pyrrolidone, sodium chloride, calcium chloride, orange essence, strawberry essence, vanilla flavor, etc.

A pharmaceutical composition of the present invention may be prepared as an oral dosage form such as a tablet, a pill, powders, a capsule, a syrup or an emulsion or a parenteral dosage form for intramuscular, intravenous or subcutaneous administration. Preferably, the pharmaceutical composition is prepared in an oral dosage form.

In the case where the pharmaceutical composition of the present invention is prepared as an oral dosage form, the inventive pharmaceutical composition may contain additives such as cellulose, calcium silicate, corn starch, lactose, sucrose, dextrose, calcium phosphate, stearic acid, magnesium stearate, calcium stearate, gelatin, talc, a surfactant, a suspension agent, an emulsifier, a diluent, etc.

Also, in the case where the pharmaceutical composition of the present invention is prepared as an injectable dosage form, the inventive pharmaceutical composition may contain additives such as water, brine, a glucose aqueous solution, an analog glucose aqueous solution, alcohol, glycol, ether, oil, a fatty acid, a fatty acid ester, a glyceride, a surfactant, a suspension agent, an emulsifier, etc.

Preferably, a proposed daily dose of the compound in accordance with the present invention for an adult patient (of approximately 70 kg body weight) may be in the range of 0.1 to 2,000 mg/day. The compound in accordance with the present invention may be administered in a single dose or in divided doses per day. It is understood that the daily dose should be determined in light of various relevant factors including health status, age, weight and sex of a subject to be treated, administration route and disease severity. Thus, the amount of proposed daily dose is not limited to the above-described range.

Hereinafter, the present invention is described in detail with reference to the following examples. However, these examples are merely presented to exemplify the present invention, and the scope of the present invention is not limited thereto.

The symbols and conventions used for describing the processes, schemes and examples of the present invention are consistent with those used in contemporary scientific literatures, for example, the *Journal of the American Chemical Society* or the *Journal of Biological Chemistry*. Unless otherwise noted, all starting materials were obtained from commercial suppliers and used without further purification.

The following are definitions of abbreviations that are used in the examples.

Hz (Hertz)
TLC (thin layer chromatography)
$T_r$ (retention time)
RP (reverse phase)
MeOH (methanol)
i-PrOH (isopropanol)
TFA (trifluoroacetic acid)
TEA (triethylamine)
EtOH (ethanol)
THF (tetrahydrofuran)
DMSO (dimethylsulfoxide)
EtOAc (ethyl acetate)
DCM (dichloromethane)
HOAc (acetic acid)
DMF (N,N-dimethylformamide)
Ac (acetyl)
HOBt (1-hydroxybenzotriazole)
Bn (benzyl)
Boc (tert-butyloxycarbonyl)
mCPBA (meta-chloroperbenzoic acid)
FMOC (9-fluorenylmethoxycarbonyl)
DCC (dicyclohexylcarbodiimide)
Cbz (benzyloxycarbonyl)
NMM (N-methyl morpholine)
HOAt (1-hydroxy-7-azabenzotriazole)
TBAF (tetra-n-butylammonium fluoride)
THP (tetrahydro-2H-pyran-2-yl)
DMAP (4-dimethylaminopyridine)
HPLC (high pressure liquid chromatography)
BOP (bis(2-oxo-3-oxazolidinyl)phosphinic chloride);
EDCI (1-ethyl-3-[3-dimethylaminopropyl]carbodiimide hydrochloride)
HBTU (0-Benzotriazole-1-yl-N,N,N',N'-tetramethyluronium hexafluorophosphate)
AIBN (2,2'-azobis(2-methylpropionitrile))
MeI (iodomethane)
DIPEA (diisopropylethylamine)
NaSMe (sodium thiomethoxide)
DAST (diethylaminosulfur trifluoride)
DMAc (dimethylacetamide)
NBS (N-bromosuccinimide)
BPO (benzoyl peroxide)
MTBE (tert-butyl methyl ether)
DME (dimethoxyethane)
LiHMDS (lithium bis(trimethylsilyl)amide
TMS (trimethylsilyl)
S-Phos (2-dicyclohexylphosphino-2',6'-dimethoxybiphenyl)
RBF (round-bottom flask)
mCPBA (3-chloroperbenzoic acid)
Pd2dba3 (tris(dibenzylideneacetone)dipalladium(0))
Xphos (2-dicyclohexylphosphino-2',4',6'-triisopropylbiphenyl)
BrettPhos (2-(dicyclohexylphosphino)3,6-dimethoxy-2',4',6'-triisopropyl-1,1'-biphenyl)

While the present invention has been described with respect to specific embodiments, it should be recognized that various modifications and changes may be made to the invention by those skilled in the art which also fall within the scope of the invention as defined by the appended claims.

All references to ether are to diethyl ether; brine refers to a saturated aqueous solution of NaCl. Unless otherwise indicated, all temperatures are expressed in ° C. (degrees Centigrade). All reactions were conducted under an inert atmosphere at room temperature unless otherwise noted, and all solvents are of the highest available purity unless otherwise indicated.

Microwave reaction was conducted with a Biotage Initiator™ microwave synthesizer.

$^1$H NMR spectra were recorded on Bruker Ultrashield 400 plus spectrometer. Chemical shifts were expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet) or br (broad).

Mass spectra were obtained with either Quattro LC Triple Quadruple Tandem Mass Spectrometer (ESI; Micromass) or 1200LC/MSD (ESI; Agilent).

For preparative HPLC, ca 100 mg of a product was injected into 1 mL of DMSO onto a SunFire™ Prep C18 OBD 5 μm 19×100 mm Column with a 10 min gradient from 10% CH$_3$CN to 90% CH$_3$CN in H$_2$O (purification systems from Gilson, Inc). Flash chromatography was carried out using Merck silica gel 60 (230-400 mesh). Biotage SP1™ FLASH Purification System and Biotage Isolera™ FLASH Purification System were used for normal phase column chromatography with ethyl acetate and hexane. Most of the reactions were monitored by thin-layer chromatography on 0.25 mm E. Merck silica gel plates (60F-254), visualized with UV light using a 5% ethanolic phosphomolybdic acid or p-anisaldehyde solution.

The following synthetic schemes are merely illustrative of the methods by which the compounds of the invention may

Preparation Example 1: Preparation of 1H-isoindolinone

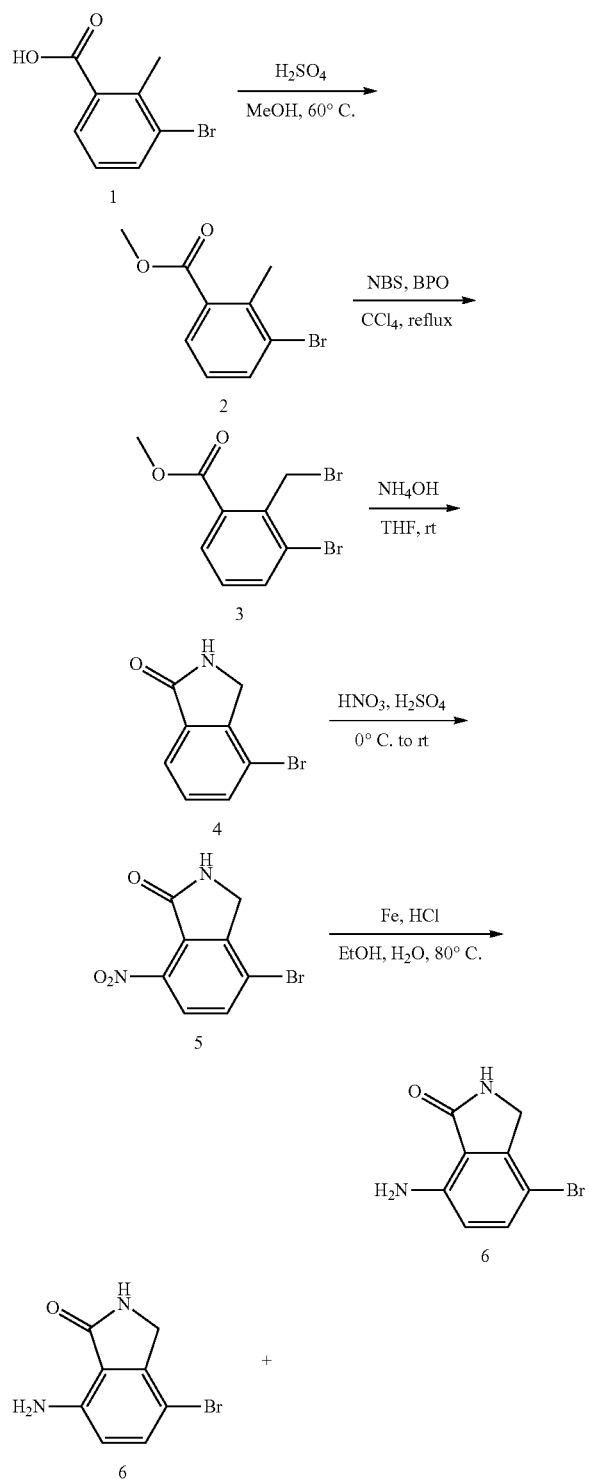

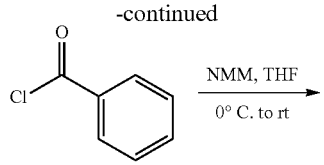

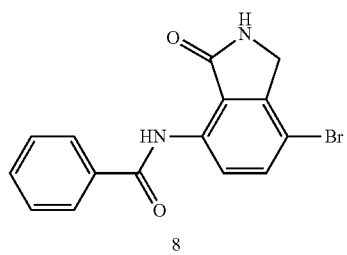

Step 1: Preparation of methyl 3-bromo-2-methylbenzoate (2)

To a solution of 3-bromo-2-methylbenzoic acid 1 (10.8 g, 0.05 mol) in MeOH (92 mL) was added conc. $H_2SO_4$ (17.6 mL, 0.32 mol) dropwise at room temperature. The resulting mixture was then stirred at 60° C. for 1.5 hours, then poured into saturated $NaHCO_3$ (500 mL) slowly, extracted with EtOAc (3×300 mL), dried over anhydrous $Na_2SO_4$, filtered, and concentrated in vacuo to give the title product 2 (10.9 g) as a pale brown oil.

$^1$H NMR (400 MHz, $CDCl_3$) δ 7.71 -7.68 (m, 2H), 7.11-7.07 (t, J=7.1 Hz, 1H), 3.90 (s, 3H), 2.63 (s, 3H). [M+H]$^+$: 229.

Step 2: Preparation of methyl 3-bromo-2-(bromomethyl)benzoate (3)

To a solution of methyl 3-bromo-2-methylbenzoate 2 (10.9 g, 47.6 mmol) in $CCl_4$ (138 mL) at refluxing was added the mixture of NBS (9.74 g, 54.7 mmol) and BPO (0.58 g, 2.38 mmol) as three portions. Then, the resulting mixture was stirred at refluxing for 3.5 hours, then cooled to room temperature, and filtered. The filtrate was concentrated to give the crude product 3 (15.0 g) as an oil, which was directly used in the next step without further purification.

$^1$H NMR (400 MHz, $CDCl_3$) δ 7.89-7.87 (d, J=7.6 Hz, 1H), 7.77-7.75 (d, J=8.0 Hz, 1H), 7.26-7.21 (t, J=8.0 Hz, 1H), 5.13 (s, 2H), 3.95 (s, 3H).

Step 3: Preparation of 4-bromoisoindolin-1-one (4)

To a solution of methyl 3-bromo-2-(bromomethyl)benzoate 3 (8.3 g, 26.9 mmol) in THF (100 mL) was added concentrated $NH_4OH$ (9 mL) dropwise. After stirring them at room temperature overnight, the mixture was concentrated in vacuo to give the residue, which was then washed with water and MTBE, and dried to give the title product 4 (4.14 g).

1H NMR (400 Hz, $CDCl_3$) δ 7.85-7.83 (d, J=7.5 Hz, 1H), 7.72-7.70 (d, J=7.9 Hz, 1H), 7.42-7.38 (t, J=7.7 Hz, 1H), 6.81 (s, 1H), 4.39 (s, 2H).

Step 4: Preparation of 4-bromo-7-nitroisoindolin-1-one (5)

To a solution of 4-bromoisoindolin-1-one 4 (3.0 g, 14.1 mmol) in conc. $H_2SO_4$ (6 mL) at 0° C. was added dropwise a solution of conc. HNO₃ (1 mL) in conc. H₂SO₄ (6 mL) The resulting mixture was then stirred at room temperature overnight, then poured over ice, and filtered. The filter cake was washed with water, MTBE, dried in vacuo to give the title product 5 (3.0 g).

¹H NMR (400 MHz, DMSO-d₆) δ 9.17 (s, 1H), 8.06-8.04 (d, J=8.4 Hz, 1H), 7.89-7.87 (d, J=8.4 Hz, 1H), 4.39 (s, 2H).

Step 5: Preparation of 7-amino-4-bromoisoindolin-1-one (6)

To a suspension solution of Fe (54.6 g, 0.975 mol) in H₂O (500 mL) and EtOH (750 mL) was added HCl (5 mL), and the mixture was stirred for 0.5 hour at 50° C., then 4-bromo-7-nitroisoindolin-1-one 5 (50.0 g, 0.195 mol) was added as portions at refluxing. After stirred at refluxing for 1 hour, the reaction mixture was filtered through a Celite pad when it was hot, and the filter cake was washed with THF (2 L). And then the filtrate was concentrated in vacuo to give the title product 6 (40 g).

¹H NMR (400 MHz, DMSO-d₆) δ 8.35 (s, 1H), 7.33-7.31 (d, J=8.6 Hz, 1H), 6.56-6.54 (d, J=8.6 Hz, 1H), 6.18 (s, 2H), 4.13 (s, 2H). [M+H]⁺: 227.

Step 6: Preparation of N-(7-bromo-3-oxoisoindolin-4-yl)benzamide (8)

To a suspension solution of 7-amino-4-bromoisoindolin-1-one 6 (40.0 g, 0.176 mol) in THF (1.9 L) was added NMM (54.3 g, 0.528 mol) at 0° C., then benzoyl chloride 7 (49.5 g, 0.352 mol) was added dropwise over 20 min. The resulting reaction mixture was then stirred at room temperature overnight, poured into water (400 mL), concentrated in vacuo to remove THF. Then the residue was washed with EtOAc (3×300 mL), and filtered to give the title product 8 (56 g).

¹H NMR (400 Hz, DMSO-d₆) δ 11.41 (s, 1H), 9.17 (s, 1H), 8.43-8.41 (d, J=8.6 Hz, 1H), 7.96-7.94 (d, J=7.4 Hz, 2H), 7.80-7.78 (d, J=8.6 Hz, 1H), 7.67-7.59 (m, 3H), 4.36 (s, 2H). [M+H]⁺: 331.

Example 1: N-(7-(2-ethylphenyl)-3-oxoisoindolin-4-yl)benzamide

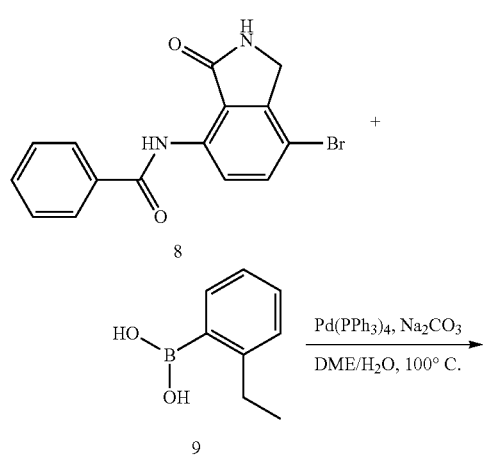

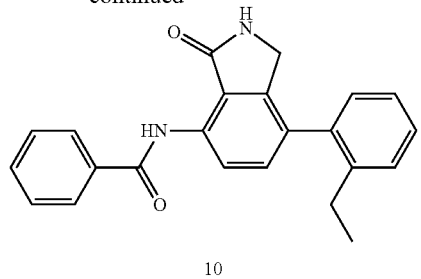

To a suspension solution of the intermediate 8 (200 mg, 0.604 mmol), (2-ethylphenyl)boronic acid (181 mg, 1.208 mmol), Na₂CO₃ (256 mg, 2.416 mmol) in DME (7 mL) and H₂O (1.7 mL) was added Pd(PPh₃)₄ (69 mg, 0.060 mmol), then the mixture was purged with nitrogen, and stirred at 100° C. for 5 hours. The reaction mixture was then cooled to room temperature, diluted with EtOAc (50 mL) and water (50 mL), and filtered. The filtrate was washed with brine, and the organic phase was concentrated in vacuo and purified by chromatography to give the title compound 10 (77 mg).

¹H NMR (400 MHz, DMSO-d₆) δ 11.60 (s, 1H), 8.97 (s, 1H), 8.54-8.52 (d, J=8.32 Hz, 1H), 8.00-7.98 (m, 2H), 7.70-7.61 (m, 3H), 7.48-7.45 (d, J=8.24 Hz, 1H), 7.40-7.34 (m, 2H), 7.29-7.24 (m, 2H), 4.17 (s, 2H) 2.47-2.43 (m, 2H), 1.01-0.97 (m, 3H). [M+H]⁺ 357.

The following compounds of Examples 2 to 41 were obtained by using corresponding starting materials and repeating the procedure of Example 1.

Example 2: N-(7-(3-isopropylphenyl)-3-oxoisoindolin-4-yl)benzamide

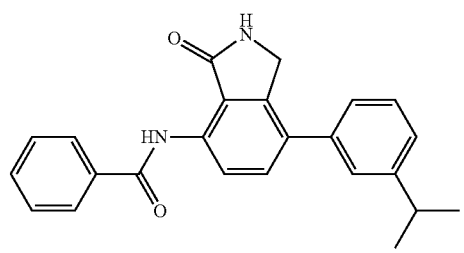 [SMILES: CC(C)c1cccc(-c2ccc(NC(=O)c3ccccc3)c3c2CNC3=O)c1]

¹H NMR (400 MHz, DMSO-d₆) δ 11.74 (s, 1H), 9.06 (s, 1H), 8.59-8.57 (d, J=8.40 Hz, 1H), 8.00-7.98 (m, 2H), 7.73-7.61 (m, 4H), 7.48 (s, 1H), 7.42-7.40 (m, 2H), 7.29-7.27 (d, J=6.24 Hz, 1H), 4.61 (s, 2H), 3.02-2.95 (m, 1H) 1.27-1.26 (m, 6H). [M+H]⁺: 371.

Example 3: N-(7-(4-(tert-butyl)phenyl)-3-oxoisoindolin-4-yl)benzamide

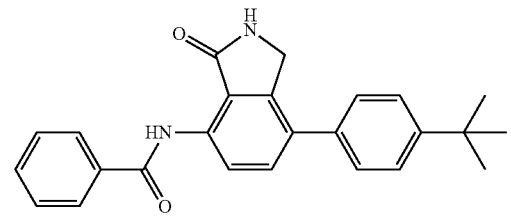 [SMILES: CC(C)(C)c1ccc(-c2ccc(NC(=O)c3ccccc3)c3c2CNC3=O)cc1]

¹H NMR (400 MHz, DMSO-d₆) δ 11.74 (s, 1H), 9.08 (s, 1H), 8.58-8.56 (d, J=8.44 Hz, 1H), 8.00-7.98 (m, 2H), 7.72-7.61 (m, 4H), 7.57-7.55 (m, 2H), 7.52-7.50 (m, 2H), 4.62 (s, 2H), 1.33-1.29 (s, 9H). [M+H]⁺: 385.

Example 4: N-(3-oxo-7-(2-(trifluoromethoxy)phenyl)isoindolin-4-yl) benzamide

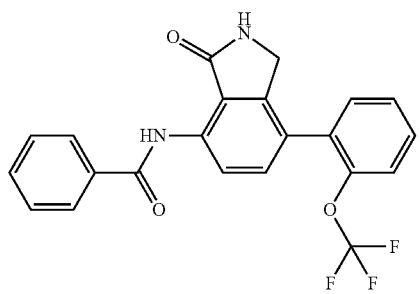 [SMILES: O=C(Nc1ccc(-c2ccccc2OC(F)(F)F)c2c1C(=O)NC2)c1ccccc1]

¹H NMR (400 MHz, DMSO-d₆) δ 11.65 (s, 1H), 9.04 (s, 1H), 8.58-8.56 (d, J=8.44 Hz, 1H), 8.00-7.98 (m, 2H), 7.70-7.51 (m, 8H), 4.31 (s, 2H). [M+H]⁺: 413.

Example 5: N-(3-oxo-7-(3-(trifluoromethoxy)phenyl)isoindolin-4-yl) benzamide

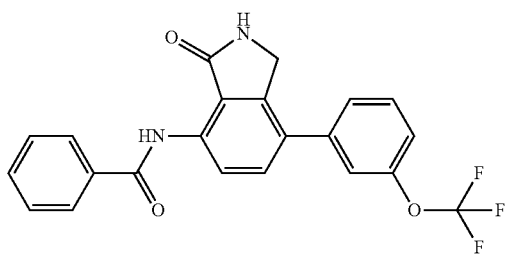 [SMILES: O=C(Nc1ccc(-c2cccc(OC(F)(F)F)c2)c2c1C(=O)NC2)c1ccccc1]

¹H NMR (400 MHz, DMSO-d₆) δ 11.76 (s, 1H), 9.11 (s, 1H), 8.61-8.59 (d, J=8.40 Hz, 1H), 8.00-7.99 (m, 2H), 7.79-7.77 (d, J=8.44 Hz, 1H), 7.70-7.61 (m, 6H), 7.42-7.40 (d, J=8.20 Hz, 1H), 4.64 (s, 2H). [M+H]⁺: 413.

Example 6: N-(7-(2-isopropoxyphenyl)-3-oxoisoindolin-4-yl)benzamide

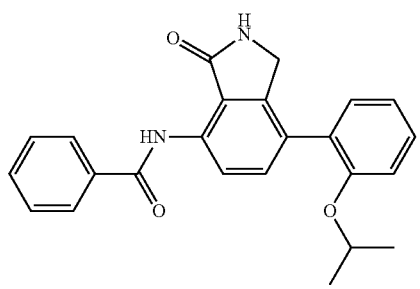 [SMILES: CC(C)Oc1ccccc1-c1ccc(NC(=O)c2ccccc2)c2c1CNC2=O]

¹H NMR (400 MHz, DMSO-d₆) δ 11.66 (s, 1H), 8.93 (s, 1H), 8.53-8.51 (d, J=8.36 Hz, 1H), 8.00-7.98 (m, 2H), 7.68-7.61 (m, 3H), 7.56-7.54 (d, J=8.36 Hz, 1H), 7.39-7.33 (m, 2H), 7.16-7.14 (d, J=8.20 Hz, 1H), 7.05-7.01 (m, 1H), 4.58-4.52 (m, 1H), 4.34 (s, 2H), 1.16-1.15 (m, 6H). [M+H]⁺: 387.

Example 7: N-(7-(3-isopropoxyphenyl)-3-oxoisoindolin-4-yl)benzamide

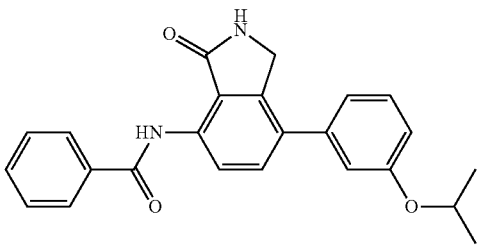 [SMILES: CC(C)Oc1cccc(-c2ccc(NC(=O)c3ccccc3)c3c2CNC3=O)c1]

¹H NMR (400 MHz, DMSO-d₆) δ 11.74 (s, 1H), 9.07 (s, 1H), 8.58-8.56 (d, J=8.44 Hz, 1H), 8.00-7.89 (m, 2H), 7.73-7.61 (m, 4H), 7.40-7.36 (m, 1H), 7.15-7.11 (m, 2H), 6.96-6.93 (d, J=8.20 Hz, 1H), 4.75-4.69 (m, 1H), 4.61 (s, 2H), 1.31-1.29 (m, 6H). [M+H]⁺: 397.

Example 8: Methyl 2-(7-benzamido-1-oxoisoindolin-4-yl)benzoate

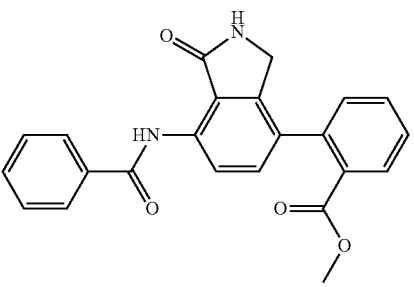 [SMILES: COC(=O)c1ccccc1-c1ccc(NC(=O)c2ccccc2)c2c1CNC2=O]

¹H NMR (400 MHz, DMSO-d₆) δ 11.61 (s, 1H), 8.96 (s, 1H), 8.51-8.49 (d, J=8.28 Hz, 1H), 8.00-7.98 (m, 2H), 7.92-7.90 (d, J=7.88 Hz, 1H), 7.70-7.61 (m, 4H), 7.58-7.56 (m, 1H), 7.51-7.49 (d, J=7.48 Hz, 1H), 7.38-7.36 (d, J=8.28 Hz, 1H), 4.20 (s, 2H), 3.60 (s, 3H). [M+H]⁺: 387.

Example 9: Methyl 3-(7-benzamido-1-oxoisoindolin-4-yl)benzoate

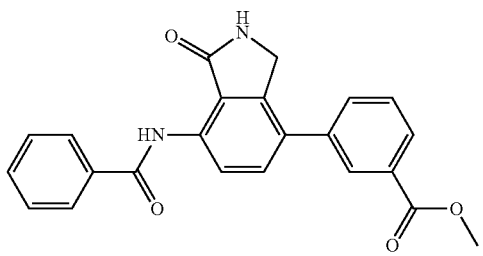 [SMILES: COC(=O)c1cccc(-c2ccc(NC(=O)c3ccccc3)c3c2CNC3=O)c1]

¹H NMR (400 MHz, DMSO-d₆) δ 11.75 (s, 1H), 9.11 (s, 1H), 8.62-8.60 (d, J=8.44 Hz, 1H), 8.12 (s, 1H), 8.01-7.99

(m, 3H), 7.95-7.93 (d, J=7.64 Hz, 1H), 7.79-7.77 (d, J=8.44 Hz, 1H), 7.70-7.62 (m, 4H), 4.61 (s, 2H), 3.90 (s, 3H). [M+H]⁺: 387.

Example 10: Methyl 4-(7-benzamido-1-oxoisoindolin-4-yl)benzoate

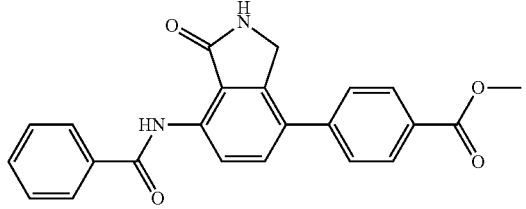 [SMILES: COC(=O)c1ccc(-c2ccc(NC(=O)c3ccccc3)c3c2CNC3=O)cc1]

¹H NMR (400 MHz, DMSO-d₆) δ 11.77 (s, 1H), 9.13 (s, 1H), 8.62-8.60 (d, J=8.5 Hz, 1H), 8.07-8.05 (d, J=8.4 Hz, 2H), 7.99-7.98 (d, J=7.0 Hz, 2H), 7.82-7.78 (m, 3H), 7.70-7.61 (m, 3H), 4.64 (s, 2H), 3.89 (s, 3H). [M+H]⁺: 387.

Example 11: N-(7-(2-acetylphenyl)-3-oxoisoindolin-4-yl)benzamide

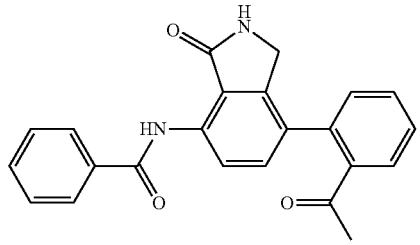 [SMILES: CC(=O)c1ccccc1-c1ccc(NC(=O)c2ccccc2)c2c1CNC2=O]

¹H NMR (400 MHz, DMSO-d₆) δ 11.62 (s, 1H), 9.00 (s, 1H), 8.51-8.49 (d, J=8.28 Hz, 1H), 8.01-7.99 (m, 2H), 7.80-7.78 (d, J=7.56 Hz, 1H), 7.69-7.61 (m, 4H), 7.58-7.50 (m, 2H), 7.37-7.35 (d, J=8.32 Hz, 1H), 4.27 (s, 2H), 2.33 (s, 3H). [M+H]⁺: 371.

Example 12: N-(7-(3-acetylphenyl)-3-oxoisoindolin-4-yl)benzamide

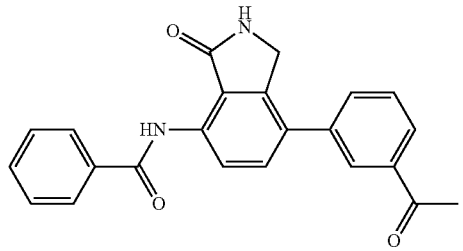 [SMILES: CC(=O)c1cccc(-c2ccc(NC(=O)c3ccccc3)c3c2CNC3=O)c1]

¹H NMR (400 MHz, DMSO-d₆) δ 11.76 (s, 1H), 9.12 (s, 1H), 8.62-8.60 (d, J=8.40 Hz, 1H), 8.13 (s, 1H), 8.01-7.97 (m, 3H), 7.92-7.90 (d, J=7.76 Hz, 1H), 7.81-7.79 (d, J=8.44 Hz, 1H), 7.71-7.62 (m, 4H), 4.63 (s, 2H), 2.66 (s, 3H). [M+H]⁺: 371.

Example 13: N-(7-(4-acetylphenyl)-3-oxoisoindolin-4-yl)benzamide

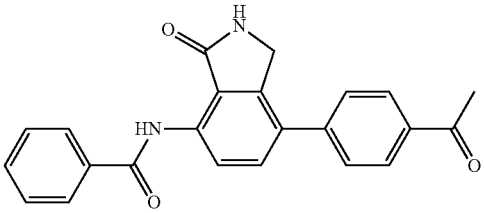 [SMILES: CC(=O)c1ccc(-c2ccc(NC(=O)c3ccccc3)c3c2CNC3=O)cc1]

¹H NMR (400 MHz, DMSO-d₆) δ 11.78 (s, 1H), 9.13 (s, 1H), 8.62-8.60 (d, J=8.44 Hz, 1H), 8.07-8.05 (m, 2H), 8.01-7.99 (m, 2H), 7.82-7.78 (m, 3H), 7.69-7.61 (m, 3H), 4.65 (s, 2H), 2.63 (s, 3H). [M+H]⁺: 371.

Example 14: N-(7-(2-(methylthio)phenyl)-3-oxoisoindolin-4-yl)benzamide

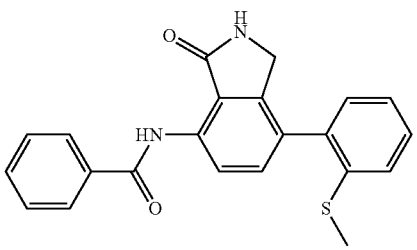 [SMILES: CSc1ccccc1-c1ccc(NC(=O)c2ccccc2)c2c1CNC2=O]

¹H NMR (400 MHz, DMSO-d₆) δ 11.60 (s, 1H), 8.95 (s, 1H), 8.53-8.51 (d, J=8.28 Hz, 1H), 8.00-7.98 (m, 2H), 7.68-7.61 (m, 3H), 7.50-7.37 (m, 3H), 7.29-7.25 (m, 2H), 4.24 (s, 2H), 2.38 (s, 3H). [M+H]⁺: 375.

Example 15: N-(7-(2,4-difluorophenyl)-3-oxoisoindolin-4-yl)benzamide

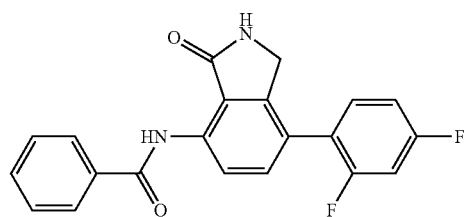 [SMILES: O=C(Nc1ccc(-c2ccc(F)cc2F)c2c1C(=O)NC2)c1ccccc1]

¹H NMR (400 MHz, DMSO-d₆) δ 11.69 (s, 1H), 9.05 (s, 1H), 8.58-8.56 (d, J=8.40 Hz, 1H), 8.00-7.98 (m, 2H), 7.68-7.61 (m, 5H), 7.45-7.39 (m, 1H), 7.24-7.20 (t, J=8.36 Hz, 1H), 4.39 (s, 2H). [M+H]⁺: 365.

Example 16: N-(7-(2,3-dimethylphenyl)-3-oxoisoindolin-4-yl)benzamide

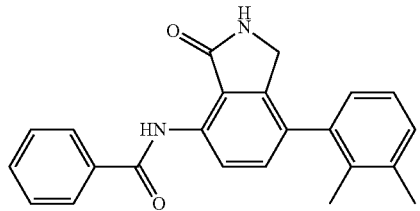 [SMILES: Cc1cccc(-c2ccc(NC(=O)c3ccccc3)c3c2CNC3=O)c1C]

¹H NMR (400 MHz, DMSO-d₆) δ 11.61 (s, 1H), 8.96 (s, 1H), 8.54-8.52 (d, J=8.24 Hz, 1H), 8.00-7.98 (m, 2H), 7.70-7.61 (m, 3H), 7.43-7.41 (d, J=8.28 Hz, 1H), 7.23-7.21 (d, J=7.44 Hz, 1H), 7.18-7.14 (m, 1H), 7.11-7.09 (d, J=7.36 Hz, 1H), 4.17-4.16 (s, 2H), 2.31 (s, 3H), 2.03 (s, 3H). [M+H]⁺: 357.

Example 17: N-(7-(2,3-dichlorophenyl)-3-oxoisoindolin-4-yl)benzamide

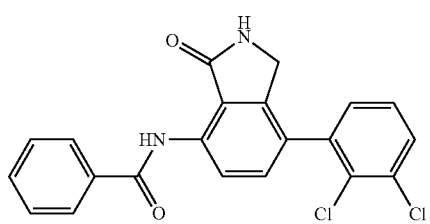 [SMILES: O=C(Nc1ccc(-c2cccc(Cl)c2Cl)c2c1C(=O)NC2)c1ccccc1]

¹H NMR (400 MHz, DMSO-d₆) δ 11.63 (s, 1H), 9.03 (s, 1H), 8.57-8.55 (d, J=8.40 Hz, 1H), 8.00-7.98 (m, 2H), 7.74-7.61 (m, 4H), 7.58-7.56 (d, J=8.36 Hz, 1H), 7.51-7.45 (m, 2H), 4.28 (s, 2H). [M+H]⁺: 397.

Example 18: N-(7-(2,4-dichlorophenyl)-3-oxoisoindolin-4-yl)benzamide

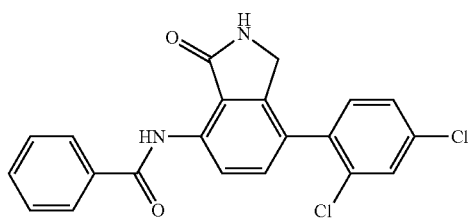 [SMILES: O=C(Nc1ccc(-c2ccc(Cl)cc2Cl)c2c1C(=O)NC2)c1ccccc1]

¹H NMR (400 MHz, DMSO-d₆) δ 11.63 (s, 1H), 9.02 (s, 1H), 8.57-8.55 (d, J=8.40 Hz, 1H), 8.00-7.98 (m, 2H), 7.80 (s, 1H), 7.70-7.61 (m, 3H), 7.56-7.52 (m, 3H), 4.29 (s, 2H). [M+H]⁺: 397.

Example 19: N-(7-(2,5-dichlorophenyl)-3-oxoisoindolin-4-yl)benzamide

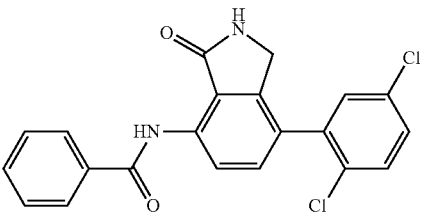 [SMILES: O=C(Nc1ccc(-c2cc(Cl)ccc2Cl)c2c1C(=O)NC2)c1ccccc1]

¹H NMR (400 MHz, DMSO-d₆) δ 11.64 (s, 1H), 9.04 (s, 1H), 8.57-8.55 (d, J=8.36 Hz, 1H), 8.00-7.99 (m, 2H), 7.69-7.61 (m, 5H), 7.58-7.53 (m, 2H), 4.32 (s, 2H). [M+H]⁺: 397.

Example 20: N-(7-(3,4-dichlorophenyl)-3-oxoisoindolin-4-yl)benzamide

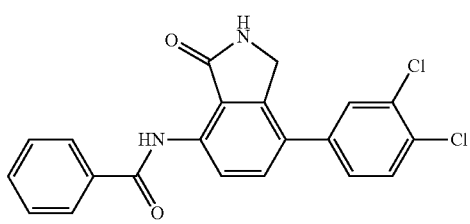 [SMILES: O=C(Nc1ccc(-c2ccc(Cl)c(Cl)c2)c2c1C(=O)NC2)c1ccccc1]

¹H NMR (400 MHz, DMSO-d₆) δ 11.74 (s, 1H), 9.11 (s, 1H), 8.59-8.57 (d, J=8.48 Hz, 1H), 8.00-7.98 (m, 2H), 7.90 (s, 1H), 7.77-7.72 (m, 2H), 7.68-7.66 (m, 1H), 7.64-7.61 (m, 3H), 4.63 (s, 2H). [M+H]⁺: 397.

Example 21: N-(7-(3,5-dichlorophenyl)-3-oxoisoindolin-4-yl)benzamide

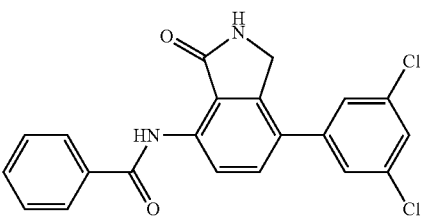 [SMILES: O=C(Nc1ccc(-c2cc(Cl)cc(Cl)c2)c2c1C(=O)NC2)c1ccccc1]

¹H NMR (400 MHz, DMSO-d₆) δ 11.75 (s, 1H), 9.11 (s, 1H), 8.59-8.57 (d, J=8.48 Hz, 1H), 8.00-7.98 (m, 2H), 7.79-7.77 (d, J=8.48 Hz, 1H), 7.69-7.61 (m, 6H), 4.64 (s, 2H). [M+H]⁺: 397.

Example 22: N-(7-(4-fluoro-2-methoxyphenyl)-3-oxoisoindolin-4-yl) benzamide

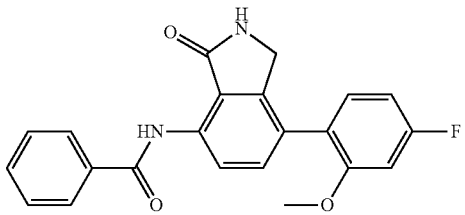 [SMILES: COc1cc(F)ccc1-c1ccc(NC(=O)c2ccccc2)c2c1CNC2=O]

¹H NMR (400 MHz, DMSO-d₆) δ 11.65 (s, 1H), 8.96 (s, 1H), 8.52-8.50 (d, J=8.44 Hz, 1H), 8.00-7.98 (m, 2H), 7.68-7.63 (m, 3H), 7.52-7.50 (d, J=8.36 Hz, 1H), 7.37-7.34 (m, 1H), 7.08-7.04 (dd, J=11.44 Hz, 1H), 6.88-6.87 (t, J=6.52 Hz, 1H), 4.26 (s, 2H), 3.79 (s, 3H). [M+H]⁺: 377.

Example 23: N-(7-(2-chloro-3-fluorophenyl)-3-oxoisoindolin-4-yl)benzamide

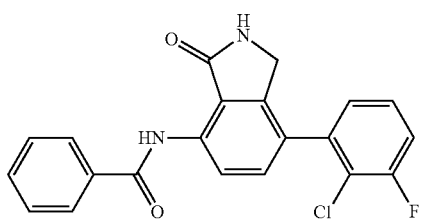 [SMILES: O=C(Nc1ccc(-c2cccc(F)c2Cl)c2c1C(=O)NC2)c1ccccc1]

¹H NMR (400 MHz, DMSO-d₆) δ 11.70 (s, 1H), 9.06 (s, 1H), 8.59-8.57 (d, J=8.28 Hz, 1H), 8.01-7.99 (m, 2H), 7.68-7.61 (m, 5H), 7.57-7.56 (m, 1H), 7.37-7.35 (m, 1H), 4.41 (s, 2H). [M+H]⁺: 381.

Example 24: N-(7-(2-fluoro-3-methoxyphenyl)-3-oxoisoindolin-4-yl) benzamide

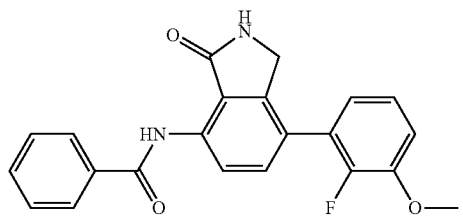 [SMILES: COc1cccc(-c2ccc(NC(=O)c3ccccc3)c3c2CNC3=O)c1F]

¹H NMR (400 MHz, DMSO-d₆) δ 11.68 (s, 1H), 9.01 (s, 1H), 8.58-8.56 (d, J=8.36 Hz, 1H), 8.00-7.98 (m, 2H), 7.70-7.61 (m, 4H), 7.25-7.21 (m, 2H), 7.10-7.07 (m, 1H), 4.37 (s, 2H), 3.90 (s, 3H). [M+H]⁺: 377.

Example 25: N-(3-oxo-7-(2,3,4-trimethoxyphenyl) isoindolin-4-yl)benzamide

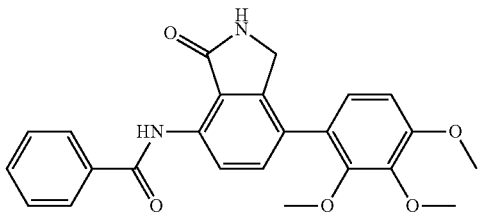 [SMILES: COc1ccc(-c2ccc(NC(=O)c3ccccc3)c3c2CNC3=O)c(OC)c1OC]

¹H NMR (400 MHz, DMSO-d₆) δ 11.65 (s, 1H), 8.95 (s, 1H), 8.53-8.51 (d, J=8.44 Hz, 1H), 8.00-7.98 (m, 2H), 7.68-7.61 (m, 3H), 7.55-7.52 (d, J=8.40 Hz, 1H), 7.09-7.07 (d, J=8.56 Hz, 1H), 6.91-6.89 (d, J=8.72 Hz, 1H), 4.33 (s, 2H), 3.85 (s, 3H), 3.51 (s, 3H), 3.81 (s, 3H). [M+H]⁺: 419.

Example 26: N-(7-(3,4-dimethylphenyl)-3-oxoisoindolin-4-yl)benzamide

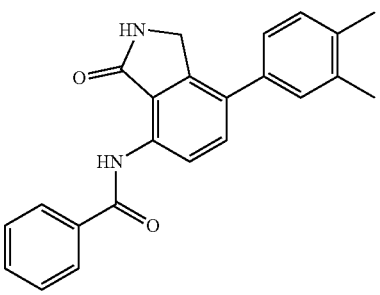 [SMILES: Cc1ccc(-c2ccc(NC(=O)c3ccccc3)c3c2CNC3=O)cc1C]

¹HNMR (400 MHz, DMSO-d₆) δ 11.74 (s, 1H), 9.08 (s, 1H), 8.57 (d, J=8.6 Hz, 1H), 8.00 (d, J=8.6 Hz, 2H), 7.72-7.59 (m, 4H), 7.40 (s, 1H), 7.34 (d, J=7.8 Hz, 1H), 7.25 (d, J=7.8 Hz, 1H), 4.60 (s, 2H), 2.30 (d, J=10.9 Hz, 1H); MS (ESI) m/z 357 (M+H)⁺.

Example 27: N-(7-(3,5-dimethylphenyl)-3-oxoisoindolin-4-yl)benzamide

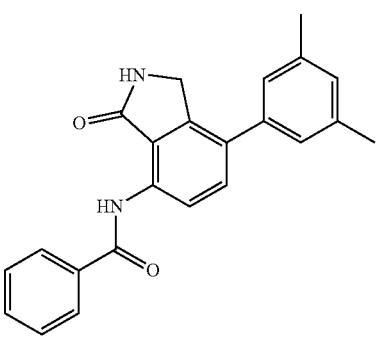 [SMILES: Cc1cc(C)cc(-c2ccc(NC(=O)c3ccccc3)c3c2CNC3=O)c1]

¹H NMR (400 MHz, DMSO-d₆) δ 11.75 (s, 1H), 9.08 (s, 1H), 8.57 (d, J=8.6 Hz, 1H), 8.00 (d, J=8.4 Hz, 2H), 7.71-7.58 (m, 4H), 7.23 (s, 2H), 7.05 (s, 1H), 4.60 (s, 2H), 2.36 (s, 6H); MS (ESI) m/z 357 (M+H)⁺.

Example 28: N-(7-(2,6-dimethylphenyl)-3-oxoisoindolin-4-yl)benzamide

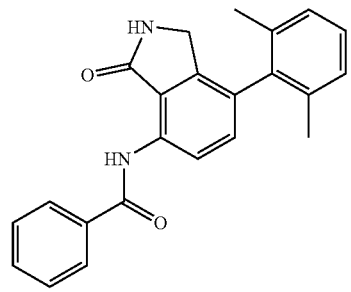 [SMILES: Cc1cccc(C)c1-c1ccc(NC(=O)c2ccccc2)c2c1CNC2=O]

¹H NMR (400 MHz, DMSO-d₆) δ 11.58 (s, 1H), 8.96 (s, 1H), 8.57 (d, J=8.3 Hz, 1H), 8.01 (d, J=7.3 Hz, 2H), 7.72-7.59 (m, 3H), 7.35 (d, J=8.2 Hz, 1H), 7.23-7.14 (m, 3H), 4.03 (s, 2H), 1.97 (s, 6H); MS (ESI) m/z 357 (M+H)⁺.

Example 29: N-(7-ethyl-3-oxoisoindolin-4-yl)benzamide

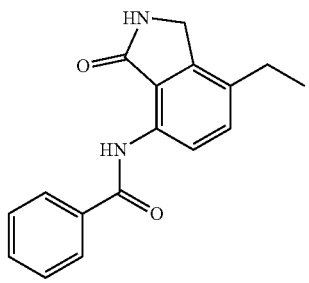 [SMILES: CCc1ccc(NC(=O)c2ccccc2)c2c1CNC2=O]

¹H NMR (400 MHz, DMSO-d₆) δ 11.49 (s, 1H), 8.95 (s, 1H), 8.42 (d, J=8.3 Hz, 1H), 7.97 (d, J=7.0 Hz, 2H), 7.72-7.58 (m, 4H), 7.46 (d, J=8.3 Hz, 1H), 4.45 (s, 2H), 2.64 (q, J=7.6 Hz, 2H), 1.23 (t, J=7.6 Hz, 3H); MS (ESI) m/z 281 (M+H)⁺.

Example 30: N-(7-(3,5-difluorophenyl)-3-oxoisoindolin-4-yl)benzamide

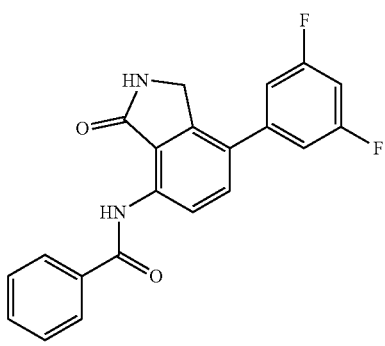 [SMILES: O=C(Nc1ccc(-c2cc(F)cc(F)c2)c2c1C(=O)NC2)c1ccccc1]

¹H NMR (400 MHz, DMSO-d₆) δ 11.79 (s, 1H), 9.16 (s, 1H), 8.60 (d, J=8.4 Hz, 1H), 8.00 (d, J=7.2 Hz, 2H), 7.81 (d, J=8.5 Hz, 1H), 7.70-7.61 (m, 3H), 7.41 (d, J=7.0 Hz, 1H), 7.30 (t, J=9.3 Hz, 1H), 4.68 (s, 2H); MS (ESI) m/z 365 (M+H)⁺.

Example 31: N-(7-(2,5-dimethylphenyl)-3-oxoisoindolin-4-yl)benzamide

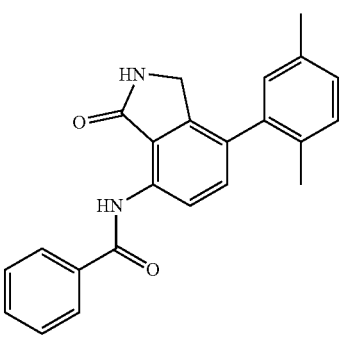 [SMILES: Cc1ccc(C)c(-c2ccc(NC(=O)c3ccccc3)c3c2CNC3=O)c1]

¹H NMR (400 MHz, DMSO-d₆) δ 11.63 (s, 1H), 8.99 (s, 1H), 8.54 (d, J=8.3 Hz, 1H), 8.01 (d, J=7.2 Hz, 2H), 7.70-7.61 (m, 3H), 7.46 (d, J=8.3 Hz, 1H), 7.24 (d, J=7.7 Hz, 1H), 7.15-7.10 (m, 2H), 4.22 (s, 2H), 2.32 (s, 3H), 2.10 (s, 3H); MS (ESI) m/z 357 (M+H)⁺.

Example 32: N-(7-(2,5-difluorophenyl)-3-oxoisoindolin-4-yl)benzamide

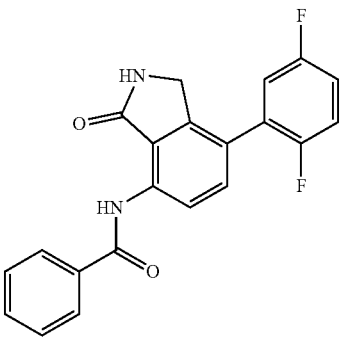 [SMILES: O=C(Nc1ccc(-c2cc(F)ccc2F)c2c1C(=O)NC2)c1ccccc1]

¹H NMR (400 MHz, DMSO-d₆) δ 11.72 (s, 1H), 9.08 (s, 1H), 8.60 (d, J=8.4 Hz, 1H), 8.01 (d, J=7.1 Hz, 2H), 7.73-7.61 (m, 4H), 7.55-7.31 (m, 3H), 4.46 (s, 2H); MS (ESI) m/z 365 (M+H)⁺.

Example 33: N-(7-(3,4-difluorophenyl)-3-oxoisoindolin-4-yl)benzamide

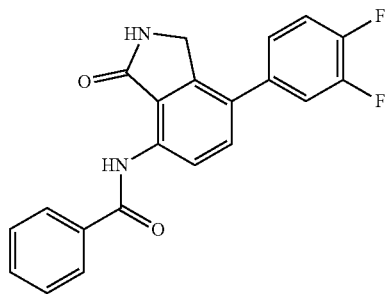 [SMILES: O=C(Nc1ccc(-c2ccc(F)c(F)c2)c2c1C(=O)NC2)c1ccccc1]

¹H NMR (400 MHz, DMSO-d₆) δ 11.76 (s, 1H), 9.13 (s, 1H), 8.59 (d, J=8.5 Hz, 1H), 8.01 (d, J=7.1 Hz, 2H), 7.81-7.49 (m, 7H), 4.64 (s, 2H); MS (ESI) m/z 365 (M+H)⁺.

Example 34: N-(7-(2,3-difluorophenyl)-3-oxoisoindolin-4-yl)benzamide

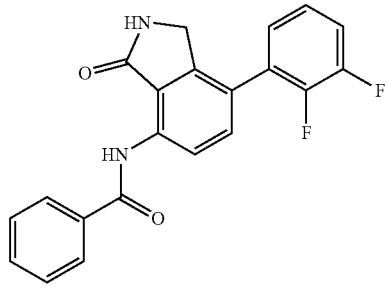 [SMILES: O=C(Nc1ccc(-c2cccc(F)c2F)c2c1C(=O)NC2)c1ccccc1]

¹H NMR (400 MHz, DMSO-d₆) δ 11.72 (s, 1H), 9.09 (s, 1H), 8.61 (d, J=8.4 Hz, 1H), 8.01 (d, J=7.3 Hz, 2H), 7.73-7.61 (m, 4H), 7.57-7.31 (m, 3H), 4.44 (s, 2H); MS (ESI) m/z 365 (M+H)⁺.

Example 35: N-(7-butyl-3-oxoisoindolin-4-yl)benzamide

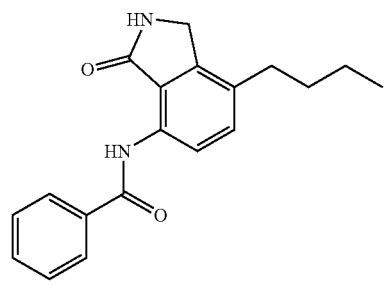 [SMILES: CCCCc1ccc(NC(=O)c2ccccc2)c2c1CNC2=O]

¹H NMR (400 MHz, DMSO-d₆) δ 11.49 (s, 1H), 8.94 (s, 1H), 8.40 (d, J=8.2 Hz, 1H), 7.97 (d, J=7.2 Hz, 2H), 7.71-7.59 (m, 3H), 7.42 (d, J=8.3 Hz, 1H), 4.43 (s, 2H), 2.61 (t, J=7.6 Hz, 2H), 1.65-1.1.53 (m, 2H), 1.39-1.29 (m, 2H), 0.93 (t, J=7.3 Hz, 2H); MS (ESI) m/z 309 (M+H)⁺.

Example 36: 4-Fluoro-N-(3-oxo-7-propylisoindolin-4-yl)benzamide

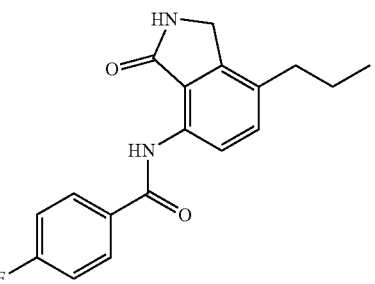

MS (ESI) m/z 313 (M+H)⁺.

Example 37: N-(7-methyl-3-oxoisoindolin-4-yl)benzamide

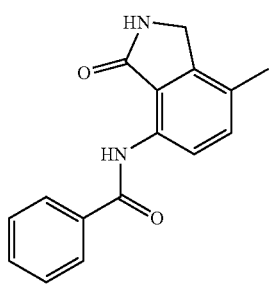 [SMILES: Cc1ccc(NC(=O)c2ccccc2)c2c1CNC2=O]

¹H NMR (400 MHz, DMSO-d₆) δ 11.43 (s, 1H), 8.93 (s, 1H), 8.36 (d, J=8.2 Hz, 1H), 7.95 (d, J=7.2 Hz, 2H), 7.71-7.57 (m, 3H), 7.40 (d, J=8.2 Hz, 1H), 4.38 (s, 2H), 2.28 (s, 3H); MS (ESI) m/z 267 (M+H)⁺.

Example 38: N-(7-(2,4-dimethylphenyl)-3-oxoisoindolin-4-yl)benzamide

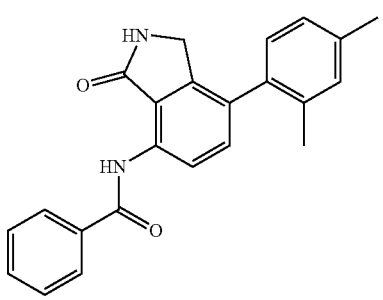 [SMILES: Cc1ccc(-c2ccc(NC(=O)c3ccccc3)c3c2CNC3=O)c(C)c1]

¹H NMR (400 MHz, DMSO-d₆) δ 11.63 (s, 1H), 8.95 (s, 1H), 8.53 (d, J=8.3 Hz, 1H), 8.00 (d, J=7.2 Hz, 2H), 7.70-7.61 (m, 3H), 7.46 (d, J=8.3 Hz, 1H), 7.19-7.07 (m, 32H), 4.20 (s, 2H), 2.34 (s, 3H), 2.11 (s, 3H); MS (ESI) m/z 357 (M+H)⁺.

Example 39: N-(7-(4-ethylphenyl)-3-oxoisoindolin-4-yl)benzamide

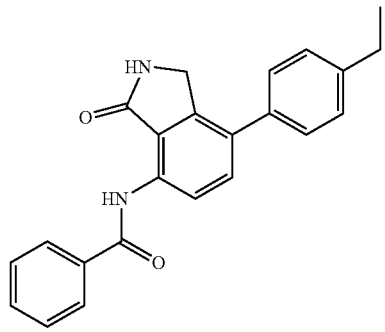 [SMILES: CCc1ccc(-c2ccc(NC(=O)c3ccccc3)c3c2CNC3=O)cc1]

$^1$H NMR (400 MHz, DMSO-d$_6$) δ 11.75 (s, 1H), 9.09 (s, 1H), 8.58 (d, J=8.4 Hz, 1H), 8.00 (d, J=7.0 Hz, 2H), 7.74-7.59 (m, 4H), 7.55 (d, J=8.1 Hz, 2H), 7.34 (d, J=8.0 Hz, 2H), 4.62 (s, 2H), 2.68 (q, J=7.6 Hz, 2H), 1.25 (t, J=7.6 Hz, 3H); MS (ESI) m/z 357 (M+H)$^+$.

Example 40: N-(7-(4-isopropoxyphenyl)-3-oxoisoindolin-4-yl)benzamide

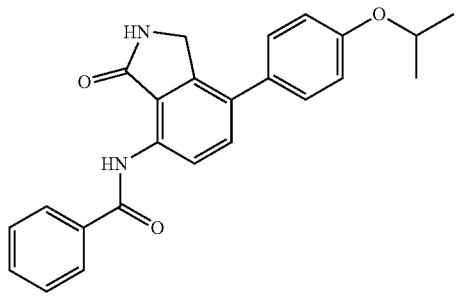 [SMILES: CC(C)Oc1ccc(-c2ccc(NC(=O)c3ccccc3)c3c2CNC3=O)cc1]

$^1$H NMR (400 MHz, DMSO-d$_6$) δ 11.74 (s, 1H), 9.08 (s, 1H), 8.57 (d, J=8.4 Hz, 1H), 8.00 (d, J=7.1 Hz, 2H), 7.70-7.61 (m, 4H), 7.55 (d, J=8.6 Hz, 2H), 7.02 (d, J=8.6 Hz, 2H), 4.71-4.65 (m, 1H), 4.60 (s, 2H), 1.32 (d, J=6.0 Hz, 6H); MS (ESI) m/z 387 (M+H)$^+$.

Example 41: N-(7-(4-(methylthio)phenyl)-3-oxoisoindolin-4-yl)benzamide

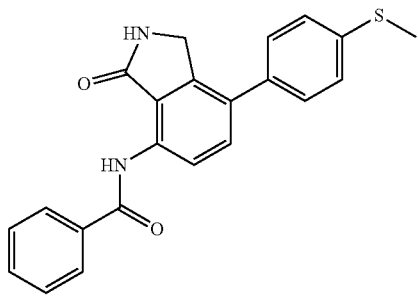 [SMILES: CSc1ccc(-c2ccc(NC(=O)c3ccccc3)c3c2CNC3=O)cc1]

$^1$H NMR (400 MHz, DMSO-d$_6$) δ 11.76 (s, 1H), 9.10 (s, 1H), 8.59 (d, J=8.4 Hz, 1H), 8.01 (d, J=7.1 Hz, 2H), 7.75-7.55 (m, 6H), 7.38 (d, J=8.3 Hz, 2H), 4.62 (s, 2H), 2.52 (s, 3H); MS (ESI) m/z 375 (M+H)$^+$.

Example 42: N-(7-(3-ethylphenyl)-3-oxoisoindolin-4-yl)benzamide

Step 1: Preparation of N-(3-oxo-7-(4,4,5,5-tetramethyl-1,3,2-dioxaborolan-2-yl) isoindolin-4-yl)benzamide

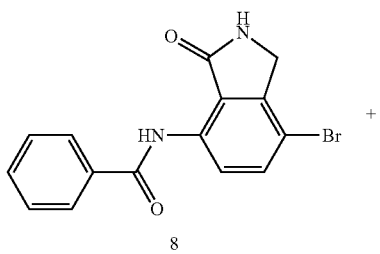

8

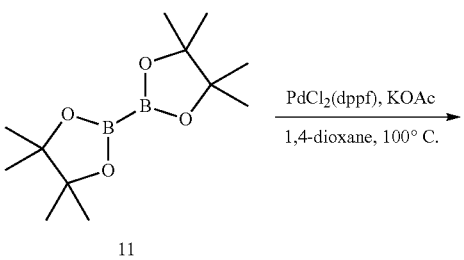

11

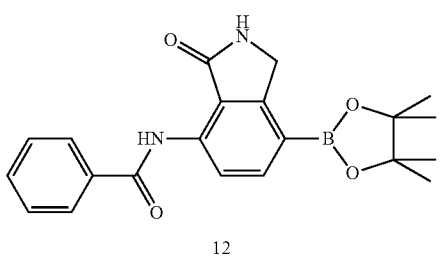

12

A suspension solution of N-(7-bromo-3-oxoisoindolin-4-yl)benzamide (3.0 g, 9.06 mmol), 4,4,4',4',5,5,5',5'-octamethyl-2,2'-bi(1,3,2-dioxaborolane) (6.9 g, 27.18 mmol), KOAc (3.1 g, 31.71 mmol), and PdCl$_2$(dppf) (0.33 g, 0.45 mmol) in 1,4-dioxane (120 mL) was purged with nitrogen, and then stirred at 95° C. overnight. The reaction mixture was then cooled to room temperature, concentrated in vacuo, and washed with water to give the crude product, which was purified by column chromatography to give the intermediate 12 (1.9 g).

$^1$H NMR (400 MHz, DMSO-d$_6$) δ 11.70 (s, 1H), 8.97 (s, 1H), 8.48-8.46 (d, J=8.1 Hz, 1H), 7.98-7.97 (d, J=7.2 Hz, 2H), 7.89-7.87 (d, J=8.2 Hz, 1H), 7.70-7.61 (m, 3H), 4.46 (s, 2H), 1.32 (s, 12H).

Step 2: Preparation of N-(7-(3-ethylphenyl)-3-ox-oisoindolin-4-yl)benzamide

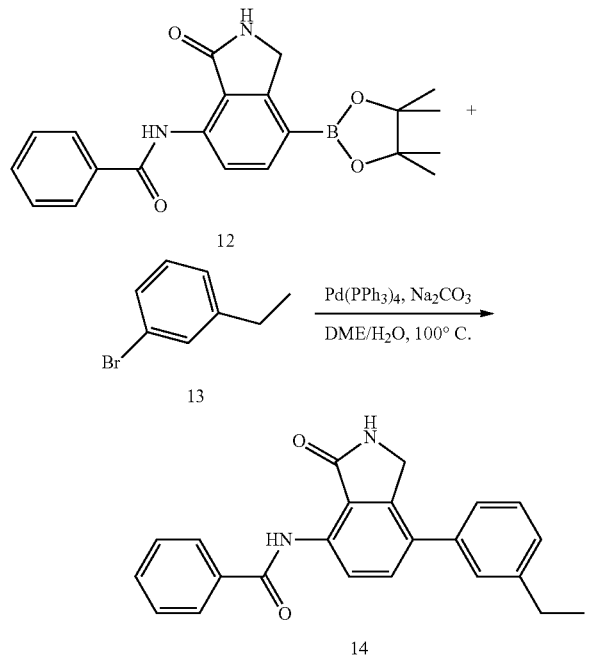

To a suspension solution of 1-bromo-3-ethylbenzene (400 mg, 2.161 mol), the intermediate 12 (1.062 g, 2.809 mol) and Na$_2$CO$_3$ (458 mg, 4.322 mol) in DME (12 mL) and H$_2$O (3 mL) was added Pd(PPh$_3$)$_4$ (250 mg, 0.216 mol), and the mixture was purged with nitrogen, and stirred at 100° C. for 5 hours. The reaction mixture was then cooled to room temperature, diluted with EtOAc (100 mL) and water (100 mL), filtered; the filtrate was washed with brine (200 mL); and the organic phase was concentrated in vacuo and purified by column chromatography to give the title product 14.

$^1$H NMR (400 MHz, DMSO-d$_6$) δ 11.74 (s, 1H), 9.06 (s, 1H), 8.59-8.58 (d, J=8.4 Hz, 1H), 8.00-7.98 (d, J=7.0 Hz, 2H), 7.22-7.61 (m, 4H), 7.45-7.38 (m, 3H), 7.26-7.24 (d, J=7.0 Hz, 1H), 4.61 (s, 2H), 2.72-2.66 (q, J=7.5 Hz, 2H), 1.26-1.22 (t, J=7.6 Hz, 3H).

The following compounds of Examples 43 to 59 were obtained by using corresponding starting materials and repeating the procedure of Example 42.

Example 43: N-(3-oxo-7-(2-propoxyphenyl)isoindolin-4-yl)benzamide

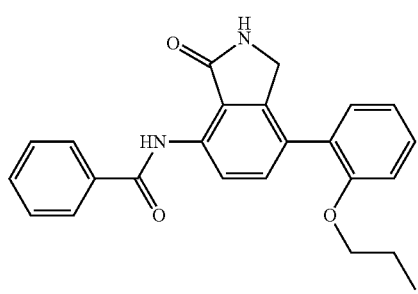 [SMILES: CCCOc1ccccc1-c1ccc(NC(=O)c2ccccc2)c2c1CNC2=O]

$^1$H NMR (400 MHz, DMSO-d$_6$) δ 11.66 (s, 1H), 8.96 (s, 1H), 8.53-8.51 (d, J=8.36 Hz, 1H), 8.00-7.98 (m, 2H), 7.68-7.61 (m, 3H), 7.56-7.54 (d, J=8.36 Hz, 1H), 7.40-7.33 (m, 2H), 7.15-7.13 (d, J=8.20 Hz, 1H), 7.06-7.02 (m, 1H), 4.32 (s, 2H), 3.96-3.93 (m, 2H), 1.60-1.59 (m, 2H), 0.84-0.81 (m, 3H). [M+Na]$^+$409.3

Example 44: N-(3-oxo-7-(3-propoxyphenyl)isoindolin-4-yl)benzamide

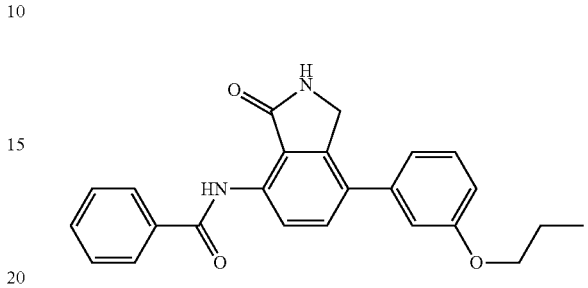

$^1$H NMR (400 MHz, DMSO-d$_6$) δ 11.74 (s, 1H), 9.07 (s, 1H), 8.58-8.56 (d, J=8.4 Hz, 1H), 8.00-7.98 (d, J=7.0 Hz, 2H), 7.74-7.71 (d, J=8.4 Hz, 1H), 7.68-7.61 (m, 3H), 7.40-7.36 (t, J=15.8 Hz, 1H), 7.17-7.13 (m, 2H), 6.97-6.95 (dd, J=6.1 Hz, J=10.3 Hz, 1H), 4.60 (s, 2H), 4.02-2.99 (t, J=6.5 Hz, 2H), 1.78-1.73 (m, 2H), 1.02-0.98 (t, J=7.4 Hz, 3H). [M+Na]$^+$409.2.

Example 45: N-(7-(2-butoxyphenyl)-3-oxoisoindolin-4-yl)benzamide

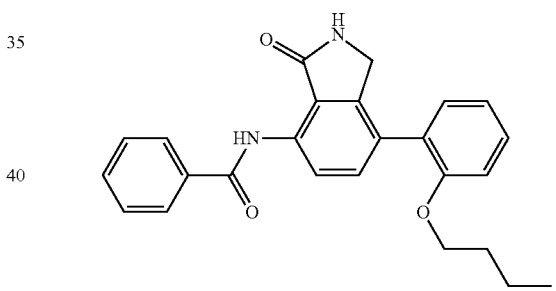

$^1$H NMR (400 MHz, DMSO-d$_6$) δ 11.65 (s, 1H), 8.94 (s, 1H), 8.52-8.50 (d, J=8.36 Hz, 1H), 8.00-7.98 (m, 2H), 7.70-7.61 (m, 3H), 7.55-7.53 (d, J=8.36 Hz, 1H), 7.40-7.32 (m, 2H), 7.15-7.13 (d, J=8.16 Hz, 1H), 7.06-7.02 (m, 1H), 4.31 (s, 2H), 3.97-3.98 (m, 2H), 1.60-1.53 (m, 2H), 1.27-1.24 (m, 2H), 0.84-0.80 (m, 3H). [M+H]$^+$: 401.4.

Example 46: N-(7-(3-butoxyphenyl)-3-oxoisoindolin-4-yl)benzamide

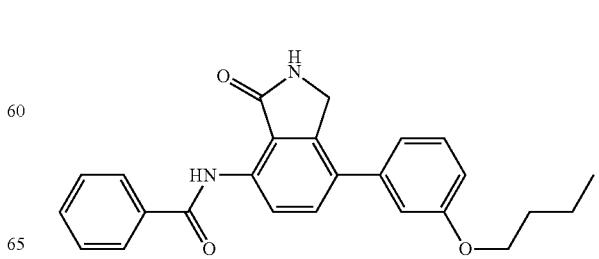

¹H NMR (400 MHz, DMSO-d₆) δ 11.74 (s, 1H), 9.07 (s, 1H), 8.58-8.56 (d, J=8.44 Hz, 1H), 8.00-7.98 (m, 2H), 7.74-7.72 (d, J=8.44 Hz, 1H), 7.68-7.61 (m, 3H), 7.40-7.36 (m, 1H), 7.17-7.13 (m, 2H), 6.97-6.95 (d, J=8.16 Hz, 1H), 4.60 (s, 2H), 4.04-4.03 (m, 2H), 1.71-1.72 (m, 2H), 1.47-1.45 (m, 2H), 0.97-0.93 (m, 3H). [M+H]⁺: 401.2.

Example 47: N-(7-(2-(methylsulfonyl)phenyl)-3-oxoisoindolin-4-yl) benzamide

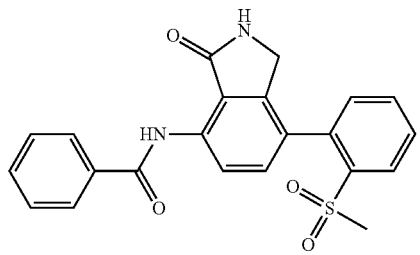 [SMILES: CS(=O)(=O)c1ccccc1-c1ccc(NC(=O)c2ccccc2)c2c1CNC2=O]

¹H NMR (400 MHz, DMSO-d₆) δ 11.60 (s, 1H), 8.96 (s, 1H), 8.54-8.52 (d, J=8.3 Hz, 1H), 8.15-8.13 (d, J=7.6 Hz, 1H), 8.00-7.99 (d, J=7.2 Hz, 2H), 7.81-7.79 (t, J=6.6 Hz, 1H), 7.76-7.58 (m, 5H), 7.54-7.52 (d, J=7.2 Hz, 1H), 7.19-4.15 (d, J=16.4 Hz, 1H), 2.90 (s, 3H). [M+H]⁺: 407.3.

Example 48: N-(7-(3-fluoro-2-methoxyphenyl)-3-oxoisoindolin-4-yl) benzamide

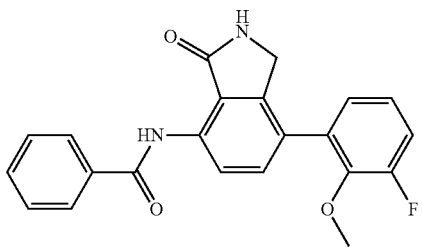 [SMILES: COc1c(F)cccc1-c1ccc(NC(=O)c2ccccc2)c2c1CNC2=O]

¹H NMR (400 MHz, DMSO-d₆) δ 11.67 (s, 1H), 9.00 (s, 1H), 8.57-8.55 (d, J=8.4 Hz, 1H), 8.00-7.98 (d, J=6.9 Hz, 2H), 7.70-7.59 (m, 4H), 7.37-7.32 (m, 1H), 7.25-7.18 (m, 2H), 4.34 (s, 2H), 3.62 (s, 3H). [M+Na]⁺: 399.3

Example 49: N-(7-(4-chloro-2-methoxyphenyl)-3-oxoisoindolin-4-yl) benzamide

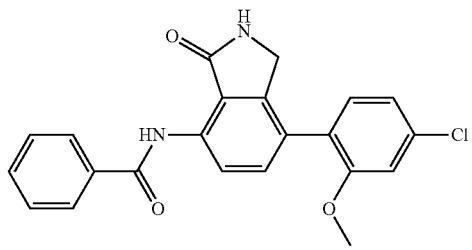 [SMILES: COc1cc(Cl)ccc1-c1ccc(NC(=O)c2ccccc2)c2c1CNC2=O]

¹H NMR (400 MHz, DMSO-d₆) δ 11.66 (s, 1H), 8.98 (s, 1H), 8.53-8.51 (d, J=8.4 Hz, 1H), 8.00-7.98 (d, J=7.0 Hz, 2H), 7.68-7.61 (m, 3H), 7.53-7.51 (d, J=8.3 Hz, 1H), 7.36-7.34 (d, J=8.1 Hz, 1H), 7.23-7.22 (d, J=1.8 Hz, 1H), 7.12-7.10 (dd, J=1.8 Hz, J=10.0 Hz, 1H), 4.27 (s, 2H), 3.80 (s, 3H). [M+Na]⁺: 415.2

Example 50: N-(7-(3-chloro-2-fluorophenyl)-3-oxoisoindolin-4-yl)benzamide

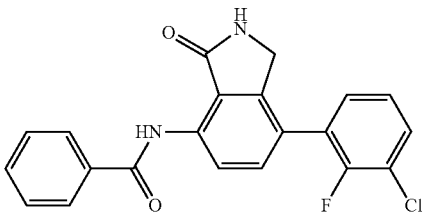 [SMILES: O=C(Nc1ccc(-c2cccc(Cl)c2F)c2c1C(=O)NC2)c1ccccc1]

¹H NMR (400 MHz, DMSO-d₆) δ 11.70 (s, 1H), 9.07 (s, 1H), 8.59-8.57 (d, J=8.4 Hz, 1H), 8.00-7.99 (d, J=7.0 Hz, 2H), 7.69-7.61 (m, 5H), 7.59-7.56 (t, J=7.9 Hz, 1H), 7.37-7.33 (t, J=8.0 Hz, 1H), 4.42 (s, 2H). [M+H]⁺: 381.3.

Example 51: N-(3-oxo-7-(thiazol-5-yl)isoindolin-4-yl)benzamide

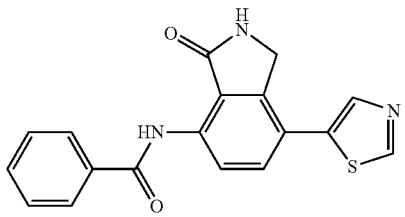 [SMILES: O=C(Nc1ccc(-c2cncs2)c2c1C(=O)NC2)c1ccccc1]

¹H NMR (400 MHz, DMSO-d₆) δ 11.74 (s, 1H), 9.24 (s, 1H), 9.19 (s, 1H), 8.58-8.55 (d, J=8.4 Hz, 1H), 8.29 (s, 1H), 7.99-7.98 (d, J=8.0 Hz, 2H), 7.94-7.92 (d, J=8.4 Hz, 1H), 7.68-7.61 (m, 3H), 4.68 (s, 2H). [M+H]⁺: 336.0.

Example 52: N-(3-oxo-7-(thiazol-4-yl)isoindolin-4-yl)benzamide

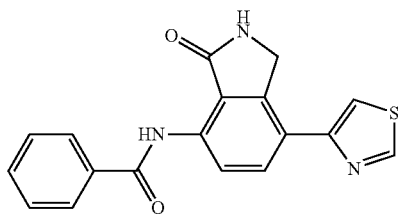 [SMILES: O=C(Nc1ccc(-c2cscn2)c2c1C(=O)NC2)c1ccccc1]

¹H NMR (400 MHz, DMSO-d₆) δ 11.79 (s, 1H), 9.28 (s, 1H), 9.16 (s, 1H), 8.59-8.57 (d, J=8.6 Hz, 1H), 8.26-8.24 (d, J=8.5 Hz, 1H), 8.17 (s, 1H), 8.00-7.98 (d, J=7.6 Hz, 2H), 7.68-7.63 (m, 3H), 4.76 (s, 2H). [M+H]⁺: 336.1.

Example 53: N-(3-oxo-7-(thiazol-2-yl)isoindolin-4-yl)benzamide

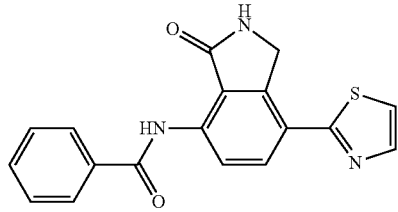 [SMILES: O=C(Nc1ccc(-c2nccs2)c2c1C(=O)NC2)c1ccccc1]

$^1$H NMR (400 MHz, DMSO-d$_6$) δ 11.81 (s, 1H), 9.22 (s, 1H), 8.62-8.60 (d, J=8.5 Hz, 1H), 8.21-8.19 (d, J=8.6 Hz, 1H), 8.01-7.99 (m, 3H), 7.86-7.85 (d, J=3.2 Hz, 1H), 7.69-7.62 (m, 3H), 4.77 (s, 2H). [M+H]$^+$: 336.1

Example 54: N-(7-(1H-imidazol-4-yl)-3-oxoisoindolin-4-yl)benzamide

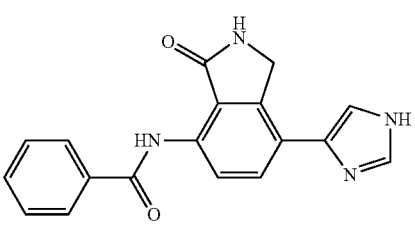 [SMILES: O=C(Nc1ccc(-c2c[nH]cn2)c2c1C(=O)NC2)c1ccccc1]

$^1$H NMR (400 MHz, DMSO-d$_6$) δ 11.75 (s, 1H), 8.91 (s, 1H), 8.44-8.42 (d, J=8.0 Hz, 1H), 8.20 (s, 1H), 8.04-7.97 (m, 3H), 7.66-7.62 (m, 4H), 4.51 (s, 2H). [M+H]$^+$: 319.0.

Example 55: N-(3-oxo-7-(1H-pyrazol-4-yl)isoindolin-4-yl)benzamide

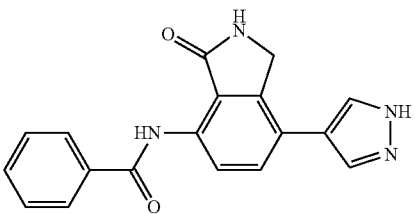 [SMILES: O=C(Nc1ccc(-c2cn[nH]c2)c2c1C(=O)NC2)c1ccccc1]

$^1$H NMR (400 MHz, DMSO-d$_6$) δ 11.75 (s, 1H), 8.91 (s, 1H), 8.43-8.41 (d, J=8.0 Hz, 1H), 8.22 (s, 2H), 8.03-7.97 (m, 3H), 7.68-7.60 (m, 4H), 4.51 (s, 2H). [M+H]$^+$: 319.2.

Example 56: N-(7-(1-methyl-1H-imidazol-5-yl)-3-oxoisoindolin-4-yl) benzamide

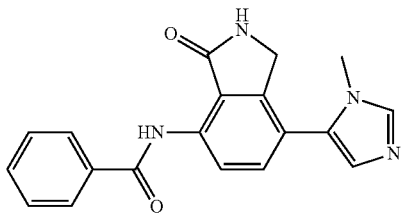 [SMILES: Cn1cncc1-c1ccc(NC(=O)c2ccccc2)c2c1CNC2=O]

$^1$H NMR (400 MHz, DMSO-d$_6$) δ 11.66 (s, 1H), 9.09 (s, 1H), 8.58-8.56 (d, J=8.0 Hz, 1H), 8.01-7.98 (m, 2H), 7.77 (s, 1H), 7.71-7.61 (m, 4H), 7.21 (s, 1H), 4.48 (s, 2H), 3.65 (s, 2H). [M+H]$^+$: 333.1

Example 57: N-(7-(1-methyl-1H-pyrazol-4-yl)-3-oxoisoindolin-4-yl) benzamide

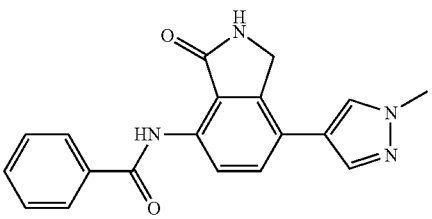 [SMILES: Cn1cc(-c2ccc(NC(=O)c3ccccc3)c3c2CNC3=O)cn1]

$^1$H NMR (400 MHz, DMSO-d$_6$) δ 11.74 (s, 1H), 8.88 (s, 1H), 8.44-8.41 (d, J=8.4 Hz, 1H), 8.18 (s, 2H), 8.04-7.97 (m, 3H), 7.68-7.60 (m, 3H), 4.51 (s, 2H). [M+H]$^+$: 333.1

Example 58: N-(3-oxo-7-(1H-1,2,4-triazol-5-yl)isoindolin-4-yl)benzamide

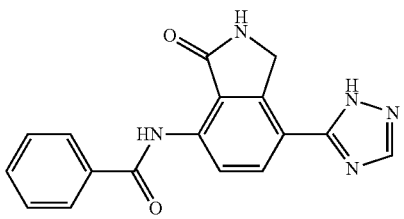 [SMILES: O=C(Nc1ccc(-c2ncn[nH]2)c2c1C(=O)NC2)c1ccccc1]

$^1$H NMR (400 MHz, DMSO-d$_6$) δ 11.4 (s, 1H), 8.90 (s, 1H), 8.44-8.42 (d, J=8.2 Hz, 1H), 8.21 (s, 2H), 8.04-8.02 (d, J=8.2 Hz, 1H), 7.99-7.97 (d, J=7.2 Hz, 1H), 7.70-7.60 (m, 3H), 4.52 (s, 2H). [M+H]$^+$: 319.0.

Example 59: N-(7-(1-methyl-1H-1,2,4-triazol-5-yl)-3-oxoisoindolin-4-yl) benzamide

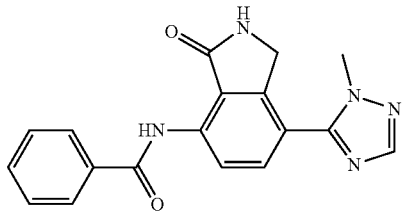 [SMILES: Cn1ncnc1-c1ccc(NC(=O)c2ccccc2)c2c1CNC2=O]

$^1$H NMR (400 MHz, DMSO-d$_6$) δ 11.75 (s, 1H), 9.14 (s, 1H), 8.65-8.63 (d, J=8.4 Hz, 1H), 8.08 (s, 1H), 8.03-7.99 (m, 3H), 7.71-7.62 (m, 3H), 4.58 (s, 2H), 4.02 (s, 3H). [M+H]$^+$: 334.0.

Preparation Example 2: Preparation of 7-amino-4-phenylisoindolin-1-one

Scheme 2. Total scheme for compound 16

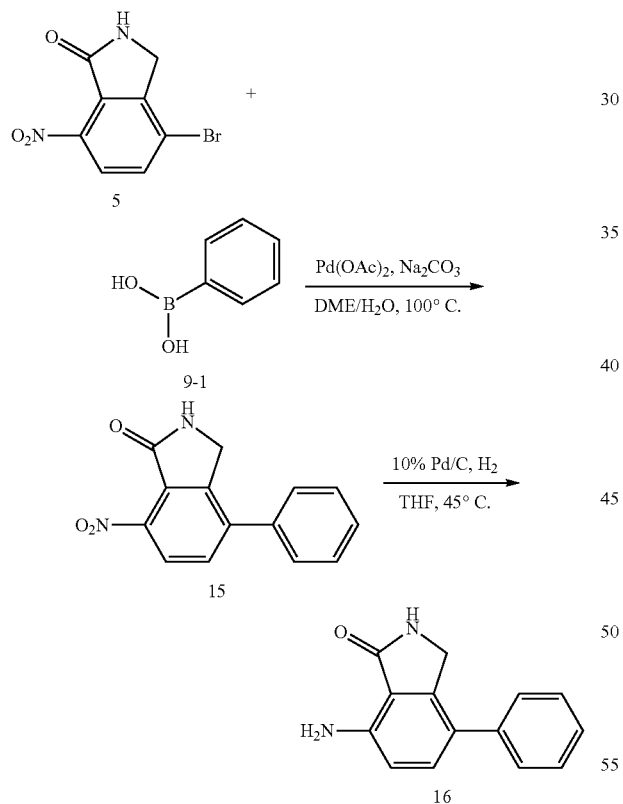

Step 1: Preparation of 7-nitro-4-phenylisoindolin-1-one (15)

To a stirred suspension solution of the key intermediate 5 (50.00 g, 194.5 mmol) in DME (1700 mL) was added phenylboronic acid (31.00 g, 254.2 mmol), Pd(OAc)$_2$ (4.38 g, 19.5 mmol), Na$_2$CO$_3$ (41.30 g, 389.6 mmol) and H$_2$O (425 mL). The mixture was degassed with N$_2$ for three times, then stirred at 75° C. under N$_2$ atmosphere for 3 hours; the reaction mixture was filtered through a Celite pad when it was hot; the precipitate was filtered to give the compound 15 (15.50 g) as a brown solid; and the filtrate was extracted with EtOAc (2×200 mL), washed with brine (300 mL), dried over anhydrous Na$_2$SO$_4$, and concentrated in vacuo to give the compound 15 (28 g, 110.1 mmol, 57%) as a yellow solid.

$^1$H NMR (400 MHz, DMSO-d$_6$) δ 9.06 (s, 1H), 7.97-7.95 (d, J=8.12 Hz, 1H), 7.83-7.81 (d, J=8.12 Hz, 1H), 7.67-7.65 (m, 2H), 7.56-7.47 (m, 3H), 4.57 (s, 2H). [M+H]$^+$; 255.

Step 2: Preparation of 7-amino-4-phenylisoindolin-1-one (16)

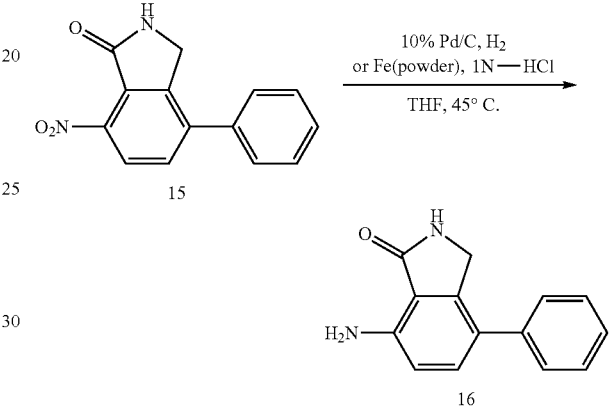

To a stirred suspension solution of the compound 15 (10.00 g, 39.3 mmol) in THF (500 mL) was added 10% Pd/C (1.50 g). The reaction mixture was degassed with H$_2$ three times, and then stirred at 45° C. under N$_2$ atmosphere overnight. After TLC showed the reaction was completed, the reaction mixture was cooled to room temperature, and filtered through a Celite pad. The filtrate was concentrated in vacuo to give the crude solid; then EtOAc (150 mL) was added thereto and the resulting mixture was stirred for 10 min, and filtered to give the pure title compound 16 (7.50 g, 33.4 mmol, 85%) as a light yellow solid.

$^1$H NMR (400 MHz, DMSO-d$_6$) δ 8.24 (s, 1H), 7.49-7.47 (m, 2H), 7.43-7.39 (m, 2H), 7.33-7.26 (m, 2H), 6.69-6.67 (d, J=8.32 Hz, 1H), 6.21 (s, 1H), 4.40 (s, 2H). [M+H]$^+$: 225.

The following compounds of Examples 60 to 86 were obtained by using corresponding starting materials and repeating the procedure of Preparation Example 2.

Example 60: 7-Amino-4-(4-methoxyphenyl)isoindolin-1-one

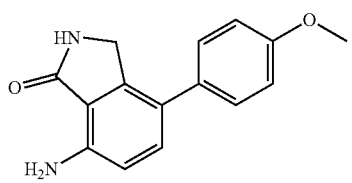 [SMILES: COc1ccc(-c2ccc(N)c3c2CNC3=O)cc1]

¹H NMR (400 MHz, DMSO-d₆) δ 8.23 (s, 1H), 7.40 (d, J=8.8 Hz, 2H), 7.26 (d, J=8.4 Hz, 1H), 6.97 (d, J=8.8 Hz, 2H), 6.65 (d, J=8.0 Hz, 1H), 6.15 (s, 2H), 4.37 (s, 2H), 3.78 (s, 3H). [M+H]⁺: 255.

Example 61:
7-Amino-4-(4-fluorophenyl)isoindolin-1-one

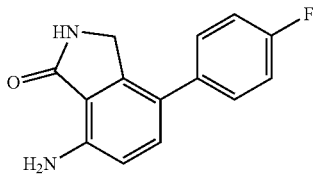 [SMILES: Nc1ccc(-c2ccc(F)cc2)c2c1C(=O)NC2]

¹H NMR (400 MHz, DMSO-d₆) δ 8.95 (d, J=2.0 Hz, 1H), 8.74 (s, 1H), 8.52 (s, 1H), 7.57 (dd, J=5.2, 8.8 Hz, 2H), 7.50 (d, J=8.0 Hz, 1H), 7.26 (t, J=8.8 Hz, 2H), 7.11 (d, J=8.4 Hz, 1H), 6.15 (s, 2H), 4.46 (s, 2H). [M+H]⁺: 243.

Example 62:
7-Amino-4-(4-chlorophenyl)isoindolin-1-one

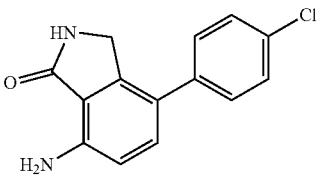 [SMILES: Nc1ccc(-c2ccc(Cl)cc2)c2c1C(=O)NC2]

¹H NMR (400 MHz, DMSO-d₆) δ 8.30 (s, 1H), 7.51 (d, J=8.4 Hz, 2H), 7.44 (d, J=8.4 Hz, 2H), 7.33 (d, J=8.4 Hz, 1H), 6.67 (d, J=8.4 Hz, 1H), 6.28 (s, 2H), 4.40 (s, 2H). [M+H]⁺: 259.

Example 63: 7-Amino-4-(p-tolyl)isoindolin-1-one

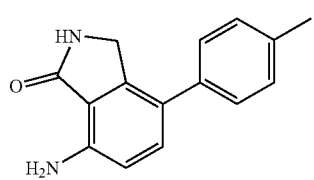 [SMILES: Cc1ccc(-c2ccc(N)c3c2CNC3=O)cc1]

¹H NMR (400 MHz, CDCl₃) δ 7.35-7.22 (m, 4H), 6.69 (d, J=7.6 Hz, 1H), 5.97 (d, J=7.6 Hz, 1H), 4.47 (s, 2H), 2.40 (s, 3H). [M+H]⁺: 239.

Example 64:
4-(4-Acetylphenyl)-7-aminoisoindolin-1-one

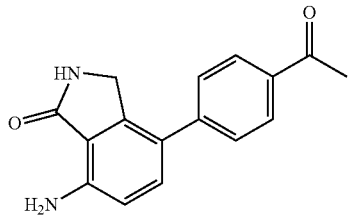 [SMILES: CC(=O)c1ccc(-c2ccc(N)c3c2CNC3=O)cc1]

¹H NMR (400 MHz, DMSO-d₆) δ 8.34 (s, 1H), 7.98 (d, J=8.4 Hz, 2H), 7.64 (d, J=8.4 Hz, 2H), 7.43 (d, J=8.4 Hz, 1H), 6.70 (d, J=8.0 Hz, 1H), 6.28 (s, 2H), 4.47 (s, 2H), 2.59 (s, 3H). [M+H]⁺: 267.

Example 65:
7-Amino-4-(pyridin-4-yl)isoindolin-1-one

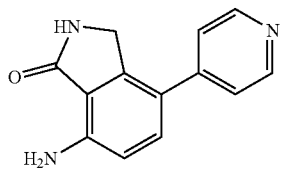 [SMILES: Nc1ccc(-c2ccncc2)c2c1C(=O)NC2]

¹H NMR (400 MHz, CDCl₃) δ 8.64 (d, J=6.0 Hz, 2H), 7.43 (d, J=8.4 Hz, 1H), 7.32 (d, J=6.0 Hz, 2H), 6.71 (d, J=8.4 Hz, 1H), 6.06 (s, 1H), 5.49 (s, 2H), 4.64 (s, 2H). [M+H]⁺: 226.

Example 66: 7-Amino-4-(2,6-dichloropyrimidin-4-yl)isoindolin-1-one

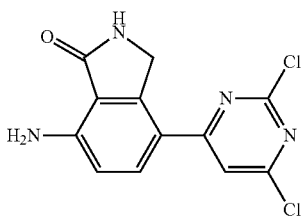 [SMILES: Nc1ccc(-c2cc(Cl)nc(Cl)n2)c2c1C(=O)NC2]

¹H NMR (400 MHz, DMSO-d₆) δ 8.46 (s, 1H), 8.13-8.11 (m, 2H), 7.03 (s, 2H), 6.71 (d, J=8.8 Hz, 1H), 4.65 (s, 2H). [M+H]⁺: 296.

Example 67:
7-Amino-4-(2-chloropyrimidin-4-yl)isoindolin-1-one

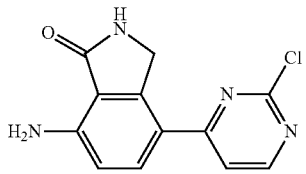 [SMILES: Nc1ccc(-c2ccnc(Cl)n2)c2c1C(=O)NC2]

¹H NMR (400 MHz, DMSO-d₆) δ 8.63 (d, J=5.6 Hz, 1H), 8.45 (s, 1H), 8.06 (d, J=8.8 Hz, 1H), 7.90 (d, J=5.6 Hz, 1H), 6.92 (s, 2H), 6.72 (d, J=8.8 Hz, 1H), 4.66 (s, 2H). [M+H]⁺: 261.

Example 68: 7-Amino-4-(2-((3-methoxyphenyl)amino)pyridin-4-yl) isoindolin-1-one

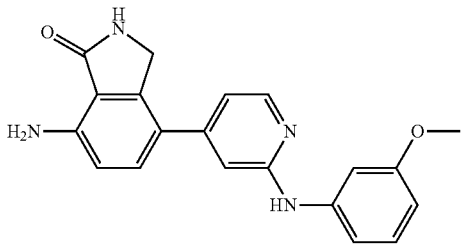 [SMILES: COc1cccc(Nc2cc(-c3ccc(N)c4c3CNC4=O)ccn2)c1]

¹H NMR (400 MHz, DMSO-d₆) δ 9.01 (s, 1H), 8.39 (s, 1H), 8.14 (d, J=5.2 Hz, 1H), 7.46-7.44 (m, 2H), 7.21-7.13 (m, 2H), 6.91-6.90 (m, 2H), 6.70 (d, J=8.4 Hz, 1H), 6.46 (d, J=6.8 Hz, 1H), 6.41 (s, 2H), 4.48 (s, 2H), 3.73 (s, 3H). [M+H]⁺: 347.

Example 69: 7-Amino-4-(4-((3-methoxyphenyl)amino)pyridin-2-yl) isoindolin-1-one

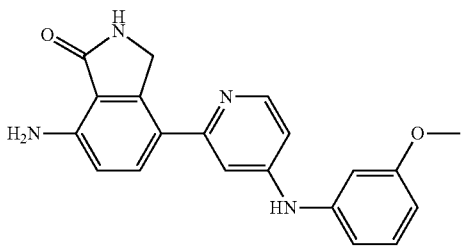 [SMILES: COc1cccc(Nc2ccnc(-c3ccc(N)c4c3CNC4=O)c2)c1]

¹H NMR (400 MHz, DMSO-d₆) δ 8.79 (s, 1H), 8.28 (s, 1H), 8.23 (d, J=5.6 Hz, 1H), 7.68 (d, J=8.4 Hz, 1H), 7.25 (t, J=8.0 Hz, 1H), 7.20 (d, J=2.4 Hz, 1H), 6.82-6.81 (m, 2H), 6.74 (t, J=2.0 Hz, 1H), 6.66 (d, J=8.8 Hz, 1H), 6.62-6.60 (m, 1H), 6.39 (s, 2H), 4.58 (s, 2H), 3.75 (s, 3H). [M+H]⁺: 347.

Example 70: 7-Amino-4-(2-((3-methoxyphenyl)amino)pyrimidin-4-yl) isoindolin-1-one

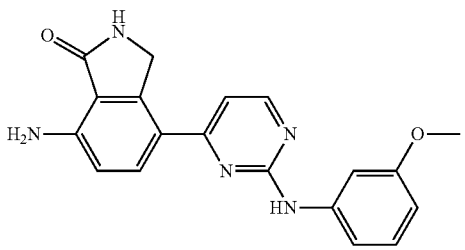 [SMILES: COc1cccc(Nc2nccc(-c3ccc(N)c4c3CNC4=O)n2)c1]

¹H NMR (400 MHz, DMSO-d₆) δ 9.36 (s, 1H), 8.46 (s, 1H), 8.42 (d, J=5.6 Hz, 1H), 7.94 (d, J=8.4 Hz, 1H), 7.45 (br.s, 1H), 7.32 (d, J=7.6 Hz, 1H), 7.19-7.17 (m, 2H), 6.70-6.68 (m, 3H), 6.55-6.52 (m, 1H), 4.72 (s, 2H), 3.74 (s, 3H). [M+H]⁺: 348.

Example 71: 7-Amino-4-(2-(1-methyl-1H-pyrazol-4-yl)amino)pyrimidin-4-yl) isoindolin-1-one

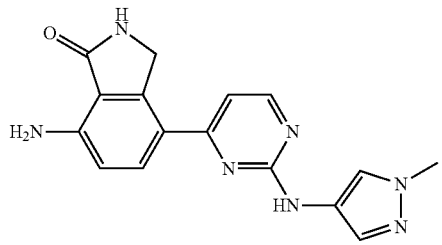 [SMILES: Cn1cc(Nc2nccc(-c3ccc(N)c4c3CNC4=O)n2)cn1]

¹H NMR (400 MHz, DMSO-d₆) δ 9.15 (s, 1H), 8.47 (s, 1H), 8.35 (d, J=5.2 Hz, 1H), 7.91 (d, J=8.4 Hz, 1H), 7.88 (br.s, 1H), 7.47 (s, 1H), 7.07 (d, J=5.6 Hz, 1H), 6.69-6.66 (m, 3H), 4.67 (s, 2H), 3.81 (s, 3H). [M+H]⁺: 322.

Example 72: 7-Amino-4-(2-(phenylamino)pyrimidin-4-yl)isoindolin-1-one

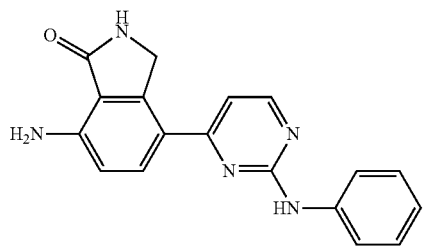 [SMILES: Nc1ccc(-c2ccnc(Nc3ccccc3)n2)c2c1C(=O)NC2]

¹H NMR (400 MHz, DMSO-d₆) δ 9.36 (s, 1H), 8.44 (s, 1H), 8.41 (d, J=5.2 Hz, 1H), 7.93 (d, J=8.8 Hz, 1H), 7.72 (d, J=8.0 Hz, 2H), 7.29 (t, J=8.0 Hz, 2H), 7.18 (d, J=5.2 Hz, 1H), 6.97-6.93 (m, 1H), 6.70-6.67 (m, 3H), 4.70 (s, 2H). [M+H]⁺: 318.

Example 73: 7-Amino-4-(2-((3-fluorophenyl)amino)pyrimidin-4-yl) isoindolin-1-one

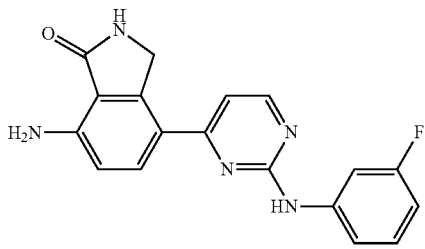 [SMILES: Nc1ccc(-c2ccnc(Nc3cccc(F)c3)n2)c2c1C(=O)NC2]

¹H NMR (400 MHz, DMSO-d₆) δ 9.59 (s, 1H), 8.48 (s, 1H), 8.46 (d, J=5.6 Hz, 1H), 7.95 (d, J=8.8 Hz, 1H), 7.79 (d, J=12.8 Hz, 1H), 7.51-7.48 (m, 1H), 7.31 (d, J=7.2 Hz, 1H), 7.24 (d, J=5.2 Hz, 1H), 6.75-6.74 (m, 1H), 6.71-6.68 (m, 3H), 4.73 (s, 2H). [M+H]⁺: 336.

Example 74: 7-Amino-4-(2-((4-fluorophenyl)amino) pyrimidin-4-yl) isoindolin-1-one

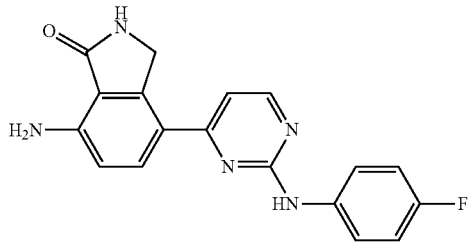 [SMILES: Nc1ccc(-c2ccnc(Nc3ccc(F)cc3)n2)c2c1C(=O)NC2]

$^1$H NMR (400 MHz, DMSO-d$_6$) δ 9.38 (s, 1H), 8.43 (s, 1H), 8.39 (d, J=5.2 Hz, 1H), 7.93 (d, J=8.8 Hz, 1H), 7.73-7.69 (m, 2H), 7.19-7.11 (m, 3H), 6.69-6.67 (m, 3H), 4.68 (s, 2H). [M+H]$^+$: 336.

Example 75: 7-Amino-4-(2-((4-methoxyphenyl) amino)pyrimidin-4-yl) isoindolin-1-one

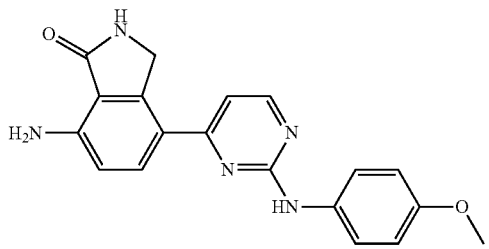 [SMILES: COc1ccc(Nc2nccc(-c3ccc(N)c4c3CNC4=O)n2)cc1]

$^1$H NMR (400 MHz, DMSO-d$_6$) δ 9.16 (s, 1H), 8.43 (s, 1H), 8.35 (d, J=5.2 Hz, 1H), 7.91 (d, J=8.8 Hz, 1H), 7.57 (d, J=8.8 Hz, 2H), 7.12 (d, J=5.6 Hz, 1H), 6.89 (d, J=9.2 Hz, 2H), 6.68 (d, J=8.4 Hz, 1H), 6.65 (s, 2H), 4.65 (s, 2H), 3.74 (s, 3H). [M+H]$^+$: 348.

Example 76: N-(4-((4-(7-amino-1-oxoisoindolin-4-yl)pyrimidin-2-yl)amino) phenyl)acetamide

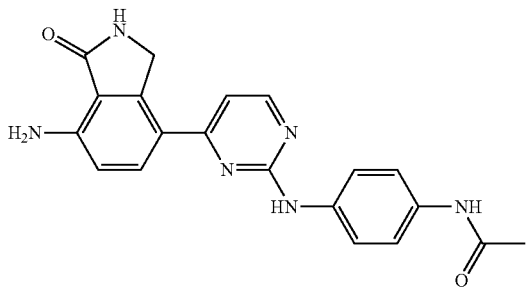 [SMILES: CC(=O)Nc1ccc(Nc2nccc(-c3ccc(N)c4c3CNC4=O)n2)cc1]

$^1$H NMR (400 MHz, DMSO-d$_6$) δ 9.82 (s, 1H), 9.28 (s, 1H), 8.44 (s, 1H), 8.38 (d, J=5.2 Hz, 1H), 7.92 (d, J=8.4 Hz, 1H), 7.61 (d, J=8.8 Hz, 2H), 7.48 (d, J=8.8 Hz, 2H), 7.15 (d, J=5.2 Hz, 1H), 6.69-6.67 (m, 3H), 4.68 (s, 2H), 2.01 (s, 3H). [M+H]$^+$: 375.

Example 77: N-(3-((4-(7-amino-1-oxoisoindolin-4-yl)pyrimidin-2-yl)amino) phenyl)acetamide

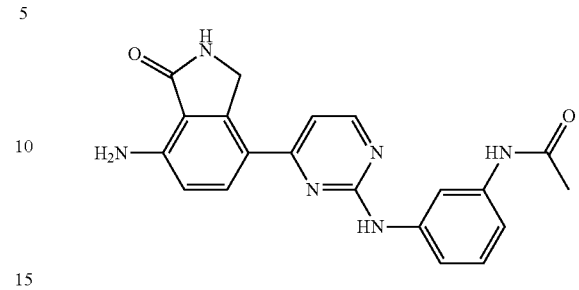

$^1$H NMR (400 MHz, DMSO-d$_6$) δ 9.87 (s, 1H), 9.38 (s, 1H), 8.44 (s, 1H), 8.39 (d, J=5.2 Hz, 1H), 797-7.94 (m, 2H), 7.38 (d, J=6.8 Hz, 1H), 7.19-7.16 (m, 3H), 6.69-6.67 (m, 3H), 4.70 (s, 2H), 2.03 (s, 3H). [M+H]$^+$: 375.

Example 78: 7-Amino-4-(6-((3-methoxyphenyl) amino)pyrimidin-4-yl) isoindolin-1-one

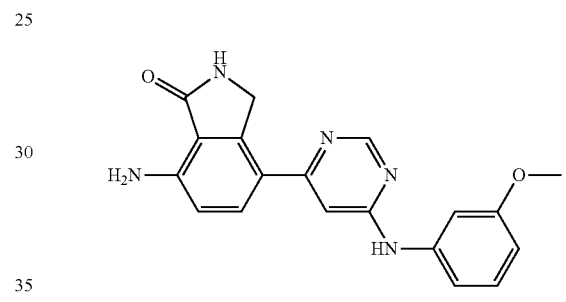

$^1$H NMR (400 MHz, DMSO-d$_6$) δ 9.53 (s, 1H), 8.63 (s, 1H), 8.41 (s, 1H), 7.84 (d, J=8.8 Hz, 1H), 7.41 (s, 1H), 7.23 (d, J=4.8 Hz, 2H), 7.01 (s, 1H), 6.70 (d, J=8.4 Hz, 1H), 6.62 (s, 2H), 6.60-6.57 (m, 1H), 4.64 (s, 2H), 3.75 (s, 3H). [M+H]$^+$: 348.

Example 79: 7-Amino-4-(5-phenyl-1H-pyrrolo[2,3-b]pyridin-3-yl) isoindolin-1-one

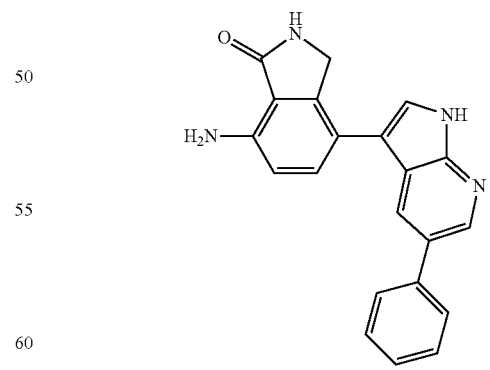

$^1$H NMR (400 MHz, DMSO-d$_6$) δ 11.90 (s, 1H), 8.54 (d, J=2.0 Hz, 1H), 8.26 (s, 1H), 8.20 (d, J=2.0 Hz, 1H), 7.74-7.71 (m, 3H), 7.59 (d, J=8.0 Hz, 1H), 7.47 (t, J=7.6 Hz, 2H), 7.35 (t, J=7.6 Hz, 1H), 6.71 (d, J=8.4 Hz, 1H), 6.12 (s, 2H), 4.42 (s, 2H) [M+H]$^+$: 341.

Example 80: 7-Amino-4-(1H-pyrrolo[2,3-b]pyridin-4-yl)isoindolin-1-one

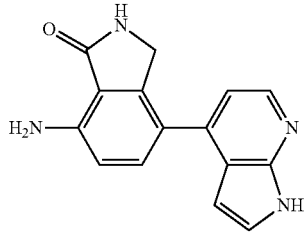 [SMILES: Nc1ccc(-c2ccnc3[nH]ccc23)c2c1C(=O)NC2]

$^1$H NMR (400 MHz, DMSO-d$_6$) δ 11.70 (s, 1H), 8.26 (s, 1H), 8.19 (d, J=4.8 Hz, 1H), 7.48 (d, J=8.4 Hz, 1H), 7.47-7.46 (m, 1H), 7.12 (d, J=5.2 Hz, 1H), 6.73 (d, J=8.4 Hz, 1H), 6.38 (d, J=3.2 Hz, 1H), 6.35 (s, 2H), 4.34 (s, 2H). [M+H]$^+$: 265.

Example 81: 7-Amino-4-(2-(4-methylpiperazin-1-yl)pyrimidin-4-yl) isoindolin-1-one

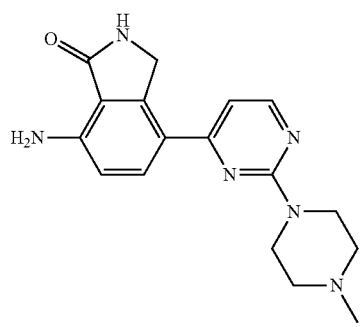 [SMILES: CN1CCN(c2nccc(-c3ccc(N)c4c3CNC4=O)n2)CC1]

$^1$H NMR (400 MHz, DMSO-d$_6$) δ 8.35 (s, 1H), 8.30 (d, J=5.6 Hz, 1H), 7.92 (d, J=8.4 Hz, 1H), 7.05 (d, J=5.6 Hz, 1H), 6.68-6.66 (m, 3H), 4.68 (s, 2H), 3.75 (t, J=4.8 Hz, 4H), 2.38 (t, J=4.8 Hz, 4H), 2.22 (s, 3H). [M+H]$^+$: 325.

Example 82: 7-Amino-4-(2-morpholinopyrimidin-4-yl)isoindolin-1-one

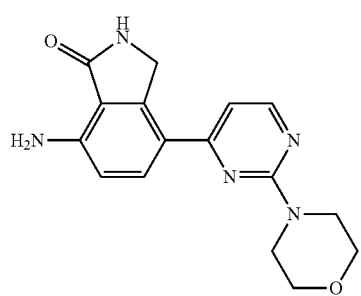 [SMILES: Nc1ccc(-c2ccnc(N3CCOCC3)n2)c2c1C(=O)NC2]

$^1$H NMR (400 MHz, DMSO-d$_6$) δ 8.35 (s, 1H), 8.33 (d, J=5.2 Hz, 1H), 7.94 (d, J=8.8 Hz, 1H), 7.10 (d, J=5.2 Hz, 1H), 6.68-6.66 (m, 3H), 4.69 (s, 2H), 3.72-3.70 (m, 8H). [M+H]$^+$: 312.

Example 83: 7-Amino-4-(2-(p-tolylamino)pyrimidin-4-yl)isoindolin-1-one

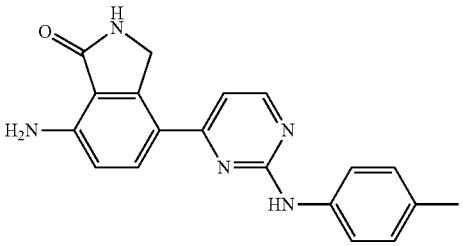 [SMILES: Cc1ccc(Nc2nccc(-c3ccc(N)c4c3CNC4=O)n2)cc1]

$^1$H NMR (400 MHz, DMSO-d$_6$) δ 9.25 (s, 1H), 8.43 (s, 1H), 8.38 (d, J=5.2 Hz, 1H), 7.92 (d, J=8.8 Hz, 1H), 7.58 (d, J=8.0 Hz, 2H), 7.15 (d, J=5.6 Hz, 1H), 7.10 (d, J=8.0 Hz, 2H), 6.68 (d, J=8.4 Hz, 1H), 6.66 (s, 2H), 4.68 (s, 2H), 2.26 (s, 3H). [M+H]$^+$: 332.

Example 84: 7-Amino-4-(2-(m-tolylamino)pyrimidin-4-yl)isoindolin-1-one

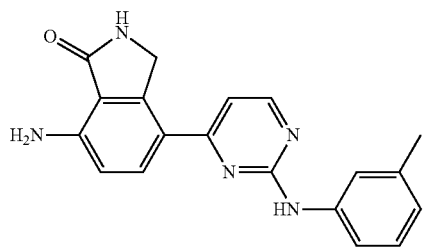 [SMILES: Cc1cccc(Nc2nccc(-c3ccc(N)c4c3CNC4=O)n2)c1]

$^1$H NMR (400 MHz, DMSO-d$_6$) δ 9.30 (s, 1H), 8.46 (s, 1H), 8.40 (d, J=5.2 Hz, 1H), 7.93 (d, J=8.8 Hz, 1H), 7.62-7.49 (m, 3H), 7.19-7.15 (m, 2H), 6.78 (d, J=8.0 Hz, 1H), 6.68 (d, J=8.0 Hz, 1H), 6.67 (s, 2H), 4.69 (s, 2H), 2.29 (s, 3H). [M+H]$^+$: 332.

Example 85: N-(4-(3-(7-amino-1-oxoisoindolin-4-yl)-1H-pyrrolo[2,3-b]pyridine-5-yl)phenyl)acetamide

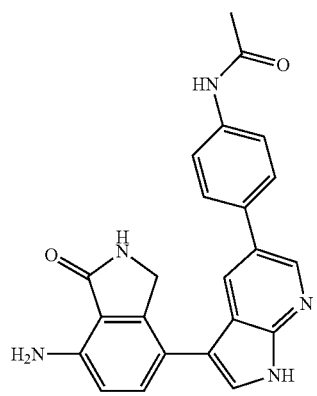 [SMILES: CC(=O)Nc1ccc(-c2cnc3[nH]cc(-c4ccc(N)c5c4CNC5=O)c3c2)cc1]

$^1$H NMR (400 MHz, DMSO-d$_6$) δ 11.86 (s, 1H), 10.02 (s, 1H), 8.52 (s, 1H), 8.26 (d, J=5.2 Hz, 1H), 8.17 (d, J=8.8 Hz,

1H), 7.67-7.65 (m, 3H), 7.57 (d, J=8.0 Hz, 1H), 6.72-6.70 (m, 2H), 6.12 (s, 2H), 4.41 (s, 2H), 2.06 (s, 3H). [M+H]$^+$: 398.

Example 86: 7-Amino-4-(5-(5-(morpholinomethyl)thiophen-2-yl)-1H-pyrrolo[2,3-b]pyridin-3-yl)isoindolin-1-one

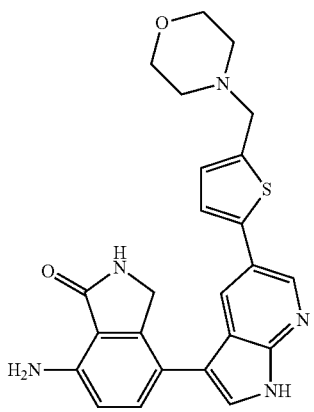 [SMILES: Nc1ccc(-c2c[nH]c3ncc(-c4ccc(CN5CCOCC5)s4)cc23)c2c1C(=O)NC2]

$^1$H NMR (400 MHz, DMSO-d$_6$) δ 11.93 (s, 1H), 8.54 (d, J=2.4 Hz, 1H), 8.27 (s, 1H), 8.13 (d, J=2.0 Hz, 1H), 7.70 (d, J=2.4 Hz, 1H), 7.53 (d, J=8.0 Hz, 1H), 7.37 (d, J=3.6 Hz, 1H), 6.97 (d, J=3.6 Hz, 1H), 6.73 (d, J=8.4 Hz, 1H), 6.13 (s, 2H), 4.40 (s, 2H), 3.67 (s, 2H), 3.58 (t, J=4.8 Hz, 4H), 2.42 (t, J=4.8 Hz, 4H). [M+H]$^+$: 446.

Example 87: 2-Methyl-N-(3-oxo-7-phenylisoindolin-4-yl)benzamide

Scheme 3. Preparation of compound of Example 87

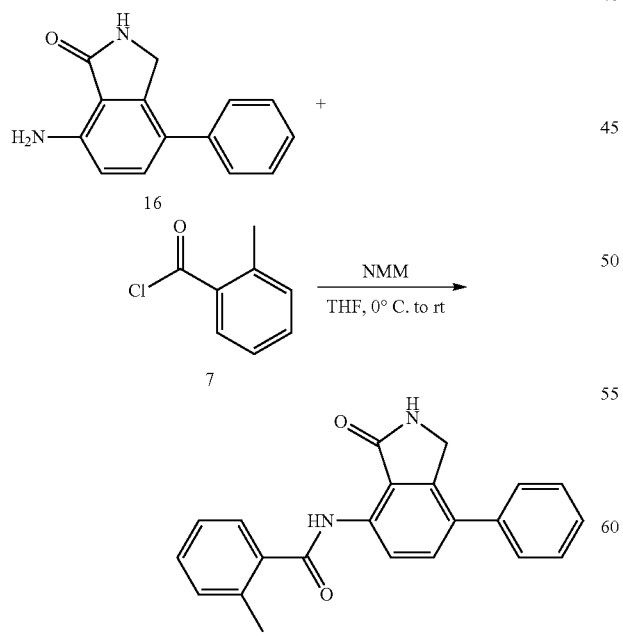

To a stirred solution of the compound 16 (200 mg, 0.89 mmol) in THF (30 mL) was added NMM (541 mg, 5.35 mmol) at 0° C., and the mixture was stirred for 10 min. Then, 2-Methylbenzoyl chloride (414 mg, 2.68 mmol) was added dropwise to the mixture, which was then stirred at room temperature for 2 hours. After TLC showed the reaction was completed, the reaction mixture was poured into water (50 mL), extracted with EtOAc (2×100 mL), washed with brine (200 mL), dried over anhydrous Na$_2$SO$_4$, and concentrated in vacuo to give the crude product, which was purified by column chromatography to give the compound 17 (205 mg, 0.60 mmol, 67%) as a white solid.

$^1$H NMR (400 MHz, DMSO-d$_6$) δ 11.10 (s, 1H), 9.00 (s, 1H), 8.58-8.56 (d, J=8.44 Hz, 1H), 7.72-7.70 (d, J=8.44 Hz, 1H), 7.63-7.61 (m, 3H), 7.52-7.45 (m, 3H), 7.42-7.35 (m, 3H), 4.57 (s, 2H), 2.51-2.49 (m, 3H). [M+H]$^+$: 343.

The following compounds of Examples 88 to 92 were obtained by using corresponding starting materials and repeating the procedure of Example 1.

Example 88: 3-Methyl-N-(3-oxo-7-phenylisoindolin-4-yl)benzamide

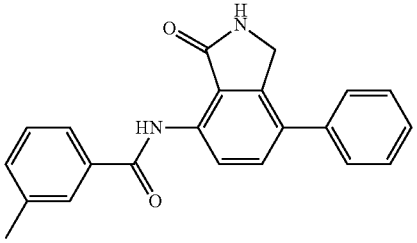

$^1$H NMR (400 MHz, DMSO-d$_6$) δ 11.71 (s, 1H), 9.06 (s, 1H), 8.59-8.57 (d, J=8.40 Hz, 1H), 7.81-7.77 (m, 2H), 7.72-7.70 (d, J=8.40 Hz, 1H), 7.63-7.61 (m, 2H), 7.53-7.48 (m, 4H), 7.42-7.39 (t, J=7.28 Hz, 1H), 4.60 (s, 1H), 2.43 (s, 3H). [M+H]$^+$: 343.

Example 89: 4-Methyl-N-(3-oxo-7-phenylisoindolin-4-yl)benzamide

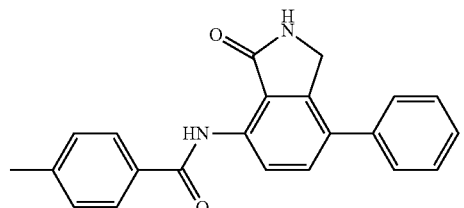

$^1$H NMR (400 MHz, DMSO-d$_6$) δ 11.69 (s, 1H), 9.06 (s, 1H), 8.58-8.56 (d, J=8.44 Hz, 1H), 7.89-7.87 (m, 2H), 7.71-7.69 (d, J=8.44 Hz, 1H), 7.63-7.61 (m, 2H), 7.51-7.47 (m, 2H), 7.43-7.38 (m, 3H), 4.60 (s, 2H), 2.42 (s, 2H). [M+H]$^+$: 343.

Example 90: 3-Chloro-N-(3-oxo-7-phenylisoindolin-4-yl)benzamide

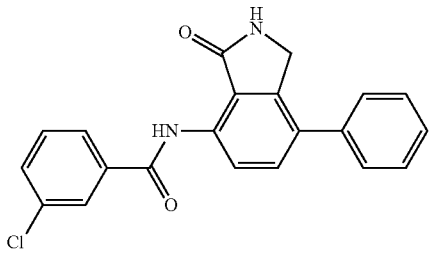 [SMILES: O=C(Nc1ccc(-c2ccccc2)c2c1C(=O)NC2)c1cccc(Cl)c1]

$^1$H NMR (400 MHz, DMSO-d$_6$) δ 11.74 (s, 1H), 9.10 (s, 1H), 8.54-8.52 (d, J=8.40 Hz, 1H), 7.97 (s, 1H), 7.94-7.92 (d, J=7.76 Hz, 1H), 7.77-7.72 (m, 2H), 7.52-7.48 (m, 2H), 7.43-7.41 (d, J=7.40 Hz, 1H), 4.61 (s, 1H). [M+H]$^+$: 363.

Example 91: 2,4-Difluoro-N-(3-oxo-7-phenylisoindolin-4-yl)benzamide

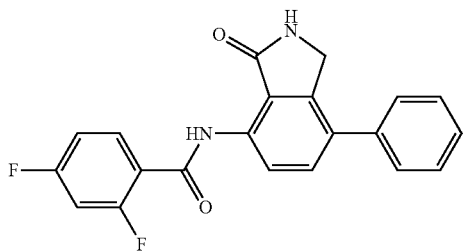 [SMILES: O=C(Nc1ccc(-c2ccccc2)c2c1C(=O)NC2)c1ccc(F)cc1F]

$^1$H NMR (400 MHz, DMSO-d$_6$) δ 11.55-11.53 (d, J=6.84 Hz, 1H), 8.99 (s, 1H), 8.63-8.61 (d, J=8.48 Hz, 1H), 8.10-8.03 (m, 1H), 7.72-7.70 (d, J=8.48 Hz, 1H), 7.63-7.61 (m, 2H), 7.56-7.48 (m, 3H), 7.43-7.39 (m, 1H), 7.34-7.30 (t, J=8.44 Hz, 1H), 4.57 (s, 2H). [M+H]$^+$: 365.

Example 92: 3,4-Difluoro-N-(3-oxo-7-phenylisoindolin-4-yl)benzamide

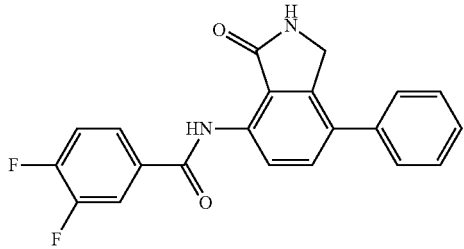 [SMILES: O=C(Nc1ccc(-c2ccccc2)c2c1C(=O)NC2)c1ccc(F)c(F)c1]

$^1$H NMR (400 MHz, DMSO-d$_6$) δ 11.72 (s, 1H), 9.11 (s, 1H), 8.52-8.50 (d, J=8.40 Hz, 1H), 7.98-7.93 (t, J=10.20 Hz, 1H), 7.83 (m, 1H), 7.76-7.69 (m, 2H), 7.63-7.61 (m, 2H), 7.51-7.48 (m, 2H), 7.43-7.39 (d, J=7.28 Hz, 1H), 4.61 (s, 2H). [M+H]$^+$: 365.

Example 93: 3,4-Dimethyl-N-(3-oxo-7-phenylisoindolin-4-yl)benzamide

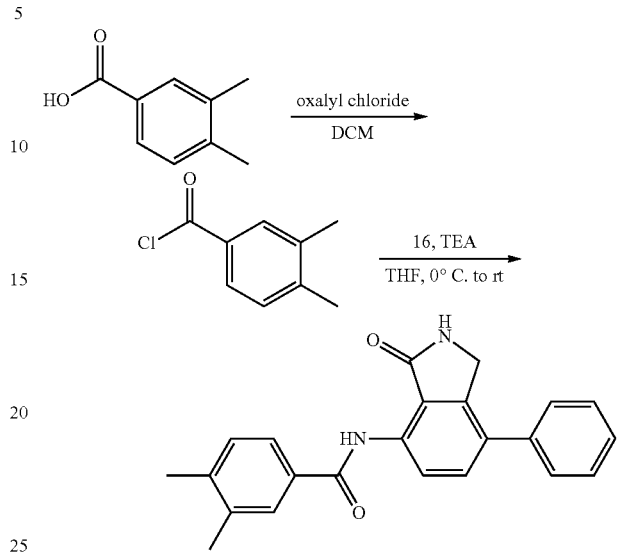

To a stirred solution of 3,4-dimethylbenzoic acid (502 mg, 3.34 mmol) in DCM (35 mL) was added oxalyl chloride (509 mg, 4.01 mmol) dropwise at 0° C. under N$_2$ atmosphere. After TLC showed the reaction was completed, the reaction mixture was added to a solution of 7-amino-4-phenylisoindolin-1-one 16 (250 mg, 1.11 mmol) in THF (25 mL) at 0° C. for 5 min, and then TEA (1354 mg, 13.38 mmol) was added dropwise over 5 min. The reaction mixture was then stirred at room temperature for 2 hours. After TLC showed the reaction was completed, the mixture was poured into water (50 mL), extracted with EtOAc (2×200 mL), washed with brine (200 mL), dried over anhydrous Na$_2$SO$_4$, and concentrated to give the crude residue, which was purified by column chromatography to give the title product (140 mg, 0.39 mmol, 35%) as a white solid.

$^1$H NMR (400 MHz, DMSO-d$_6$) δ 11.68 (s, 1H), 9.05 (s, 1H), 8.58-8.56 (d, J=8.40 Hz, 1H), 7.77 (s, 1H), 7.72-7.70 (m, 2H), 7.63-7.61 (m, 2H), 7.51-7.47 (m, 2H), 7.42-7.37 (m, 2H), 4.60 (s, 2H), 2.34-2.33 (m, 6H). [M+H]$^+$: 357.

The following compounds of Examples 94 to 105 were obtained by using corresponding starting materials and repeating the procedure of Example 93.

Example 94: 2-(Dimethylamino)-N-(3-oxo-7-phenylisoindolin-4-yl) benzamide

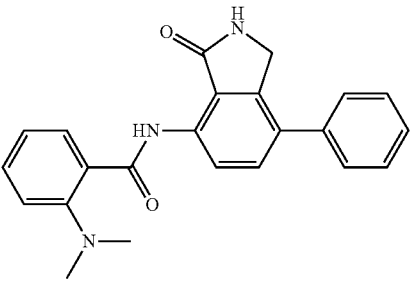 [SMILES: CN(C)c1ccccc1C(=O)Nc1ccc(-c2ccccc2)c2c1C(=O)NC2]

¹H NMR (400 MHz, DMSO-d₆) δ 12.58 (s, 1H), 8.81-8.78 (m, 2H), 7.87-7.85 (d, J=7.72 Hz, 1H), 7.67-7.65 (d, J=8.52 Hz, 1H), 7.61-7.60 (m, 2H), 7.52-7.47 (m, 3H), 7.42-7.38 (m, 1H), 7.28-7.26 (d, J=8.00 Hz, 1H), 7.16-7.12 (m, 1H), 4.53 (s, 2H), 2.77 (s, 6H). [M+H]⁺: 372.

Example 95: 3-(Dimethylamino)-N-(3-oxo-7-phenylisoindolin-4-yl) benzamide

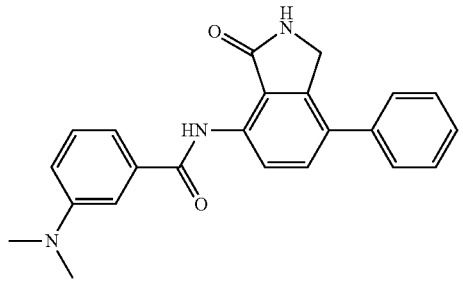 [SMILES: CN(C)c1cccc(C(=O)Nc2ccc(-c3ccccc3)c3c2C(=O)NC3)c1]

¹H NMR (400 MHz, DMSO-d₆) δ 11.72 (s, 1H), 9.06 (s, 1H), 8.58-8.56 (d, J=8.44 Hz, 1H), 7.72-7.70 (d, J=8.44 Hz, 1H), 7.63-7.61 (m, 2H), 7.51-7.48 (m, 2H), 7.42-7.40 (m, 2H), 7.30 (s, 1H), 7.25-7.23 (d, J=7.60 Hz, 1H), 7.01-6.99 (d, J=8.24 Hz, 1H), 4.60 (s, 2H), 3.00 (s, 6H). [M+H]⁺: 372.

Example 96: 2-(Methylthio)-N-(3-oxo-7-phenylisoindolin-4-yl)benzamide

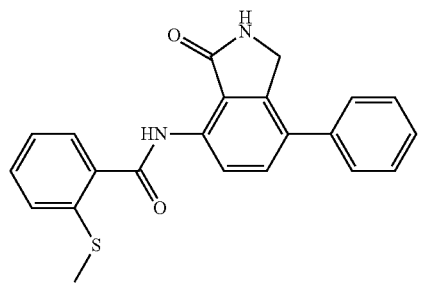 [SMILES: CSc1ccccc1C(=O)Nc1ccc(-c2ccccc2)c2c1C(=O)NC2]

¹H NMR (400 MHz, DMSO-d₆) δ 11.20 (s, 1H), 9.01 (s, 1H), 8.54-8.52 (d, J=8.40 Hz, 1H), 7.73-7.70 (d, J=8.44 Hz, 1H), 7.68-7.66 (d, J=7.56 Hz, 1H), 7.63-7.61 (m, 2H), 7.59-7.54 (m, 1H), 7.52-7.48 (m, 3H), 7.42-7.39 (m, 1H), 7.35-7.31 (m, 1H), 4.58 (s, 2H), 2.46 (s, 3H). [M+H]⁺: 375.

Example 97: 3-(Methylthio)-N-(3-oxo-7-phenylisoindolin-4-yl)benzamide

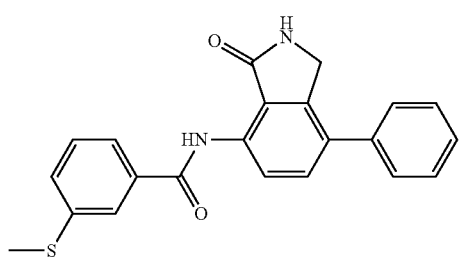

¹H NMR (400 MHz, DMSO-d₆) δ 11.76 (s, 1H), 9.10 (s, 1H), 8.56-8.54 (d, J=8.40 Hz, 1H), 7.83 (s, 1H), 7.74-7.71 (m, 2H), 7.63-7.62 (m, 2H), 7.56-7.55 (m, 2H), 7.52-7.48 (m, 2H), 7.42-7.39 (m, 1H), 4.61 (s, 2H), 2.58 (s, 3H). [M+H]⁺: 375.

Example 98: 2-(Methylsulfonyl)-N-(3-oxo-7-phenylisoindolin-4-yl) benzamide

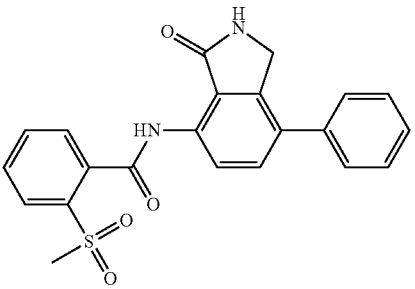 [SMILES: CS(=O)(=O)c1ccccc1C(=O)Nc1ccc(-c2ccccc2)c2c1C(=O)NC2]

¹H NMR (400 MHz, DMSO-d₆) δ 11.08 (s, 1H), 9.03 (s, 1H), 8.50-8.48 (d, J=8.40 Hz, 1H), 8.10-8.08 (d, J=7.80 Hz, 1H), 7.95-7.90 (m, 1H), 7.87-7.82 (m, 2H), 7.74-7.72 (d, J=8.40 Hz, 1H), 7.63-7.61 (m, 2H), 7.52-7.48 (m, 2H), 7.43-7.40 (m, 1H), 4.58 (s, 2H), 3.43 (s, 3H). [M+H]⁺: 407.

Example 99: 3-(Methylsulfonyl)-N-(3-oxo-7-phenylisoindolin-4-yl) benzamide

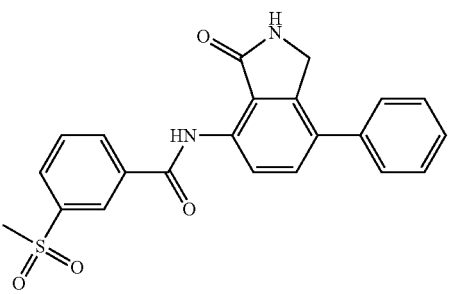 [SMILES: CS(=O)(=O)c1cccc(C(=O)Nc2ccc(-c3ccccc3)c3c2C(=O)NC3)c1]

¹H NMR (400 MHz, DMSO-d₆) δ 11.86 (s, 1H), 9.10 (s, 1H), 8.56-8.54 (d, J=8.40 Hz, 1H), 8.50 (s, 1H), 8.30-8.28 (d, J=7.96 Hz, 1H), 8.23-8.21 (d, J=8.40 Hz, 1H), 7.95-7.91 (m, 1H), 7.76-7.73 (d, J=8.40 Hz, 1H), 7.64-7.62 (m, 2H), 7.52-7.48 (m, 2H), 7.43-7.39 (m, 1H), 4.62 (s, 2H), 3.32 (S, 3H). [M+H]⁺: 407.

Example 100: 4-(Methylsulfonyl)-N-(3-oxo-7-phenylisoindolin-4-yl) benzamide

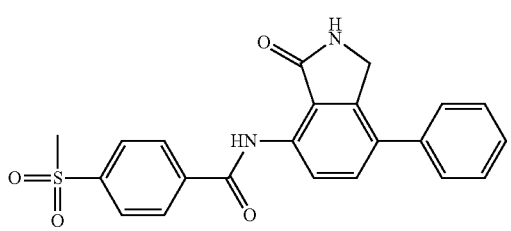 [SMILES: CS(=O)(=O)c1ccc(C(=O)Nc2ccc(-c3ccccc3)c3c2C(=O)NC3)cc1]

¹H NMR (400 MHz, DMSO-d₆) δ 11.81 (s, 1H), 9.10 (s, 1H), 8.56-8.54 (d, J=8.40 Hz, 1H), 8.21-8.04 (m, 5H), 7.75-7.73 (d, J=8.44 Hz, 1H), 7.64-7.62 (m, 2H), 7.52-7.48 (m, 2H), 7.43-7.39 (m, 1H), 4.61 (s, 2H). [M+H]⁺: 407.

Example 101: 2,4-Dimethoxy-N-(3-oxo-7-phenylisoindolin-4-yl)benzamide

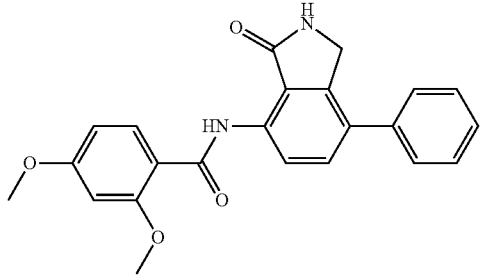 [SMILES: COc1ccc(C(=O)Nc2ccc(-c3ccccc3)c3c2C(=O)NC3)c(OC)c1]

¹H NMR (400 MHz, DMSO-d₆) δ 12.10 (s, 1H), 8.82-8.80 (m, 2H), 8.06-8.04 (d, J=8.52 Hz, 1H), 7.66-7.60 (m, 3H), 7.50-7.47 (m, 2H), 7.41-7.37 (m, 1H), 6.73-6.70 (m, 2H), 4.54 (s, 2H), 4.08 (s, 3H), 3.87 (s, 3H). [M+H]⁺: 389.

Example 102: 3,4-Dimethoxy-N-(3-oxo-7-phenylisoindolin-4-yl)benzamide

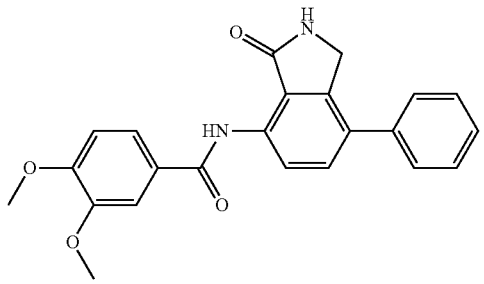 [SMILES: COc1ccc(C(=O)Nc2ccc(-c3ccccc3)c3c2C(=O)NC3)cc1OC]

¹H NMR (400 MHz, DMSO-d₆) δ 11.70 (s, 1H), 9.06 (s, 1H), 8.56-8.54 (d, J=8.40 Hz, 1H), 7.72-7.70 (d, J=8.44 Hz, 1H), 7.63-7.55 (m, 4H), 7.51-7.47 (m, 2H), 7.42-7.38 (m, 1H), 7.19-7.17 (d, J=8.44 Hz, 1H), 4.60 (s, 2H), 3.87 (s, 6H). [M+H]⁺: 389.

Example 103: 2,4-Dichloro-N-(3-oxo-7-phenylisoindolin-4-yl)benzamide

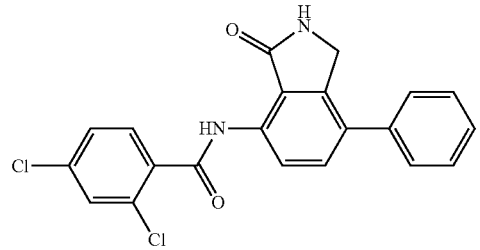 [SMILES: O=C(Nc1ccc(-c2ccccc2)c2c1C(=O)NC2)c1ccc(Cl)cc1Cl]

¹H NMR (400 MHz, DMSO-d₆) δ 11.14 (s, 1H), 9.03 (s, 1H), 8.52-8.50 (d, J=8.36 Hz, 1H), 7.84-7.84 (d, J=1.96 Hz, 1H), 7.80-7.78 (d, J=8.28 Hz, 1H), 7.74-7.72 (d, J=8.40 Hz, 1H), 7.65-7.61 (m, 3H), 7.52-7.48 (m, 2H), 7.43-7.41 (d, J=7.32 Hz, 1H), 4.58 (s, 2H). [M+H]⁺: 397.

Example 104: 3,4-Dichloro-N-(3-oxo-7-phenylisoindolin-4-yl)benzamide

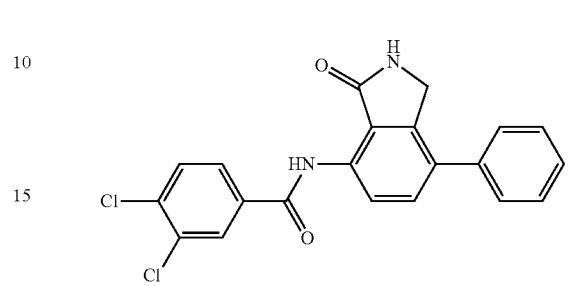

¹H NMR (400 MHz, DMSO-d₆) δ 11.74 (s, 1H), 9.10 (s, 1H), 8.51-8.49 (d, J=8.40 Hz, 1H), 8.14 (s, 1H), 7.92 (s, 2H), 7.74-7.72 (d, J=8.40 Hz, 1H), 7.63-7.61 (m, 2H), 7.52-7.48 (m, 2H), 7.43-7.39 (d, J=7.32 Hz, 1H), 4.61 (s, 2H). [M+H]⁺: 397.

Example 105: 2,4-Dimethyl-N-(3-oxo-7-phenylisoindolin-4-yl)benzamide

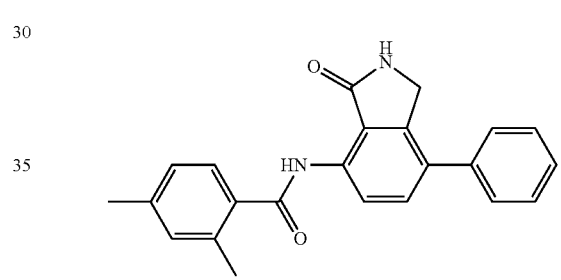

¹H NMR (400 MHz, DMSO-d₆) δ 11.09 (s, 1H), 8.99 (s, 1H), 8.58-8.55 (d, J=8.40 Hz, 1H), 7.71-7.69 (d, J=8.44 Hz, 1H), 7.62-7.60 (m, 2H), 7.54-7.47 (m, 3H), 7.42-7.38 (m, 1H), 7.19-7.17 (m, 1H), 4.57 (s, 2H), 2.47 (s, 3H), 2.35 (s, 3H). [M+H]⁺: 357.

Preparation Example 3: Preparation of 2-acetamido-N-(3-oxo-7-phenylisoindolin-4-yl)benzamide Scheme 4. Total scheme for compound 21

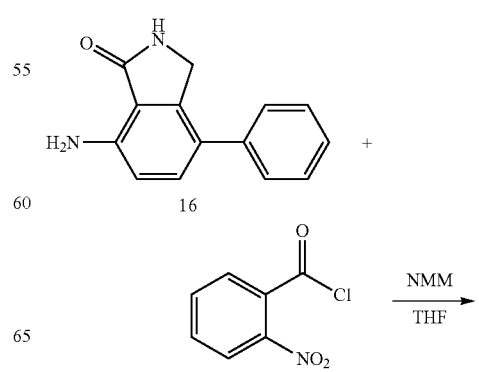

-continued

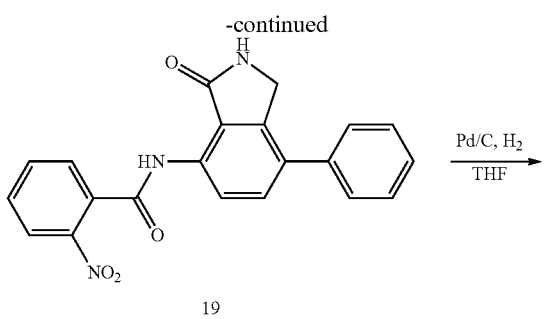
19

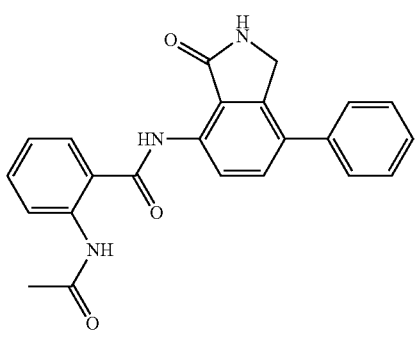
20

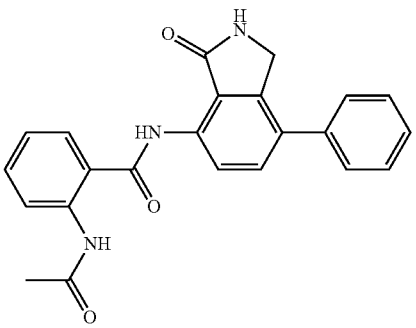
21

Step 1: Preparation of 2-nitro-N-(3-oxo-7-phenylisoindolin-4-yl)benzamide (19)

To a stirred solution of compound 16 (400 mg, 1.78 mmol) in THF (80 mL) was added NMM (1082 mg, 10.70 mmol) at 0° C., and the mixture was stirred for 10 min. Then, 2-nitrobenzoyl chloride (993 mg, 5.35 mmol) was added dropwise to the mixture, which was then stirred at room temperature for 2 hours. After TLC showed the reaction was completed, the reaction mixture was poured into water (30 mL), extracted with EtOAc (2×200 mL), washed with brine (300 mL), dried over anhydrous $Na_2SO_4$, and concentrated in vacuo to give the crude residue, which was purified by column chromatography to give the title compound 19 (450 mg, 1.21 mmol, 67%) as a light yellow solid.

$^1$H NMR (400 MHz, DMSO-$d_6$) δ 11.24 (s, 1H), 9.04 (s, 1H), 8.44-8.41 (d, J=8.36 Hz, 1H), 8.17-8.15 (d, J=8.04 Hz, 1H), 7.96-7.91 (m, 2H), 7.86-7.82 (m, 1H), 7.74-7.72 (d, J=8.40 Hz, 1H), 7.64-7.62 (m, 2H), 7.52-7.48 (m, 2H), 7.43-7.40 (m, 1H), 4.59 (s, 2H).

Step 2: Preparation of 2-amino-N-(3-oxo-7-phenylisoindolin-4-yl)benzamide (20)

To a stirred suspension solution of 2-nitro-N-(3-oxo-7-phenylisoindolin-4-yl)benzamide 19 (450 mg, 1.21 mmol) in THF (40 mL) was added 10% Pd/C (100 mg). The mixture was degassed with $H_2$ three times, and then heated at 40° C. overnight. After TLC showed the reaction was completed, the mixture was filtered through a Celite pad, and the filtrate was concentrated to give the title compound 20 (340 mg, 0.99 mmol, 82%) as a yellow solid.

$^1$H NMR (400 MHz, DMSO-$d_6$) δ 11.53 (s, 1H), 9.02 (s, 1H), 8.56-8.54 (d, J=8.48 Hz, 1H), 7.70-7.68 (d, J=8.44 Hz, 1H), 7.62-7.61 (m, 3H), 7.51-7.47 (m, 2H), 7.42-7.38 (m, 1H), 7.29-7.25 (m, 1H), 6.84-6.82 (d, J=8.04 Hz, 1H), 6.70 (s, 2H), 6.67-6.63 (m, 1H), 4.59 (s, 2H).

Step 3: Preparation of 2-acetamido-N-(3-oxo-7-phenylisoindolin-4-yl) benzamide (21)

To a stirred suspension solution of 2-amino-N-(3-oxo-7-phenylisoindolin-4-yl) benzamide 20 (150 mg, 0.44 mmol) in DCM (40 mL) was added TEA (89.1 mg, 0.88 mmol) at 0° C., and then acetyl chloride (51.9 mg, 0.66 mmol) was added dropwise to the mixture over 3 min. After TLC showed the reaction was completed, $H_2O$ (30 mL) was added, and the mixture was extracted with DCM (2×40 mL) The combined organic phase was washed with brine (100 mL), dried over $Na_2SO_4$, and concentrated in vacuo to give the crude residue, which was then purified by column chromatography to give the title compound 21 (90 mg, 0.23 mmol, 53%) as a yellow solid.

The following compounds of Examples 106 and 107 were obtained by using corresponding starting materials and repeating the procedure of Preparation Example 3.

Example 106: 2-Acetamido-N-(3-oxo-7-phenylisoindolin-4-yl)benzamide

21

$^1$H NMR (400 MHz, DMSO-$d_6$) δ 11.47 (s, 1H), 10.59 (s, 1H), 9.04 (s, 1H), 8.56-8.54 (d, J=8.44 Hz, 1H), 8.06-8.04 (d, J=8.20 Hz, 1H), 7.81-7.79 (m, 1H), 7.72-7.70 (d, J=8.40 Hz, 1H), 7.63-7.56 (m, 3H), 7.52-7.48 (m, 2H), 7.43-7.39 (m, 1H), 7.31-7.27 (m, 1H), 4.59 (s, 2H), 2.07 (s, 3H).

Example 107: 3-Acetamido-N-(3-oxo-7-phenylisoindolin-4-yl)benzamide

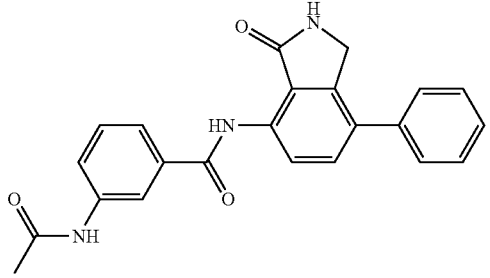 [SMILES: CC(=O)Nc1cccc(C(=O)Nc2ccc(-c3ccccc3)c3c2C(=O)NC3)c1]

¹H NMR (400 MHz, DMSO-d₆) δ 11.69 (s, 1H), 10.23 (s, 1H), 9.08 (s, 1H), 8.59-8.57 (d, J=8.44 Hz, 1H), 8.23 (s, 1H), 7.90-7.88 (d, J=7.96 Hz, 1H), 7.73-7.71 (d, J=8.44 Hz, 1H), 7.64-7.61 (m, 3H), 7.56-7.48 (m, 3H), 7.43-7.39 (m, 1H), 4.61 (s, 2H), 2.09 (s, 3H).

Example 108: 4-(Methylamino)-N-(3-oxo-7-phenylisoindolin-4-yl)benzamide

Scheme 5. Total scheme for compound of Example 108

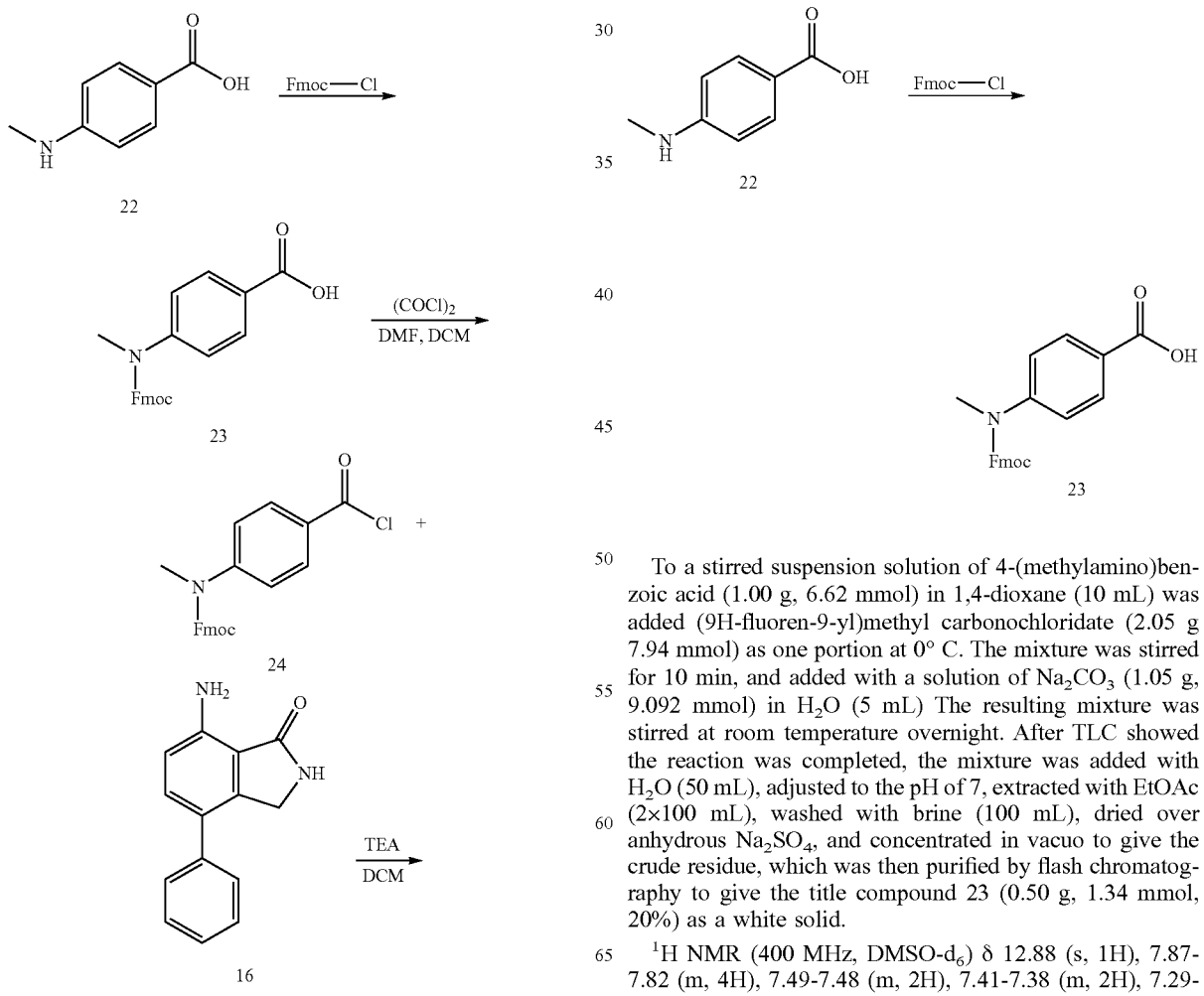

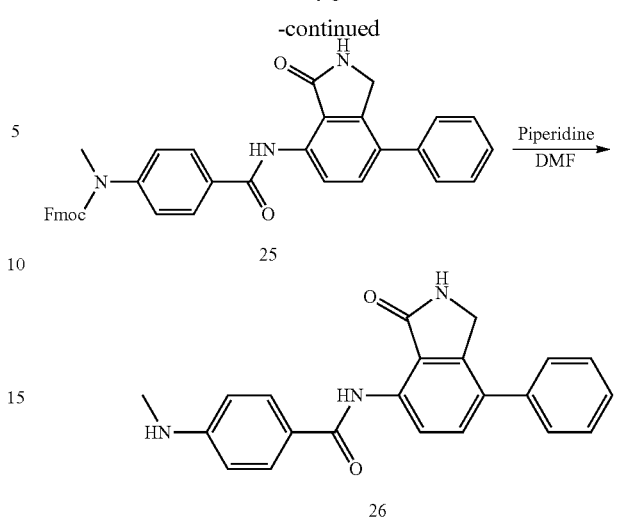

Step 1: Preparation of 4-((((9H-fluoren-9-yl)methoxy)carbonyl)(methyl) amino)benzoic acid (23)

To a stirred suspension solution of 4-(methylamino)benzoic acid (1.00 g, 6.62 mmol) in 1,4-dioxane (10 mL) was added (9H-fluoren-9-yl)methyl carbonochloridate (2.05 g 7.94 mmol) as one portion at 0° C. The mixture was stirred for 10 min, and added with a solution of Na₂CO₃ (1.05 g, 9.092 mmol) in H₂O (5 mL) The resulting mixture was stirred at room temperature overnight. After TLC showed the reaction was completed, the mixture was added with H₂O (50 mL), adjusted to the pH of 7, extracted with EtOAc (2×100 mL), washed with brine (100 mL), dried over anhydrous Na₂SO₄, and concentrated in vacuo to give the crude residue, which was then purified by flash chromatography to give the title compound 23 (0.50 g, 1.34 mmol, 20%) as a white solid.

¹H NMR (400 MHz, DMSO-d₆) δ 12.88 (s, 1H), 7.87-7.82 (m, 4H), 7.49-7.48 (m, 2H), 7.41-7.38 (m, 2H), 7.29-7.22 (m, 4H), 4.51-4.50 (m, 2H), 4.24 (m, 1H), 3.18 (s, 3H).

Step 2: Preparation of (9H-fluoren-9-yl)methylm-ethyl(4-((3-oxo-7-phenylisoindolin-4-yl)carbamoyl)phenyl)carbamate (25)

Step 3: Preparation of 4-(methylamino)-N-(3-oxo-7-phenylisoindolin-4-yl) benzamide (26)

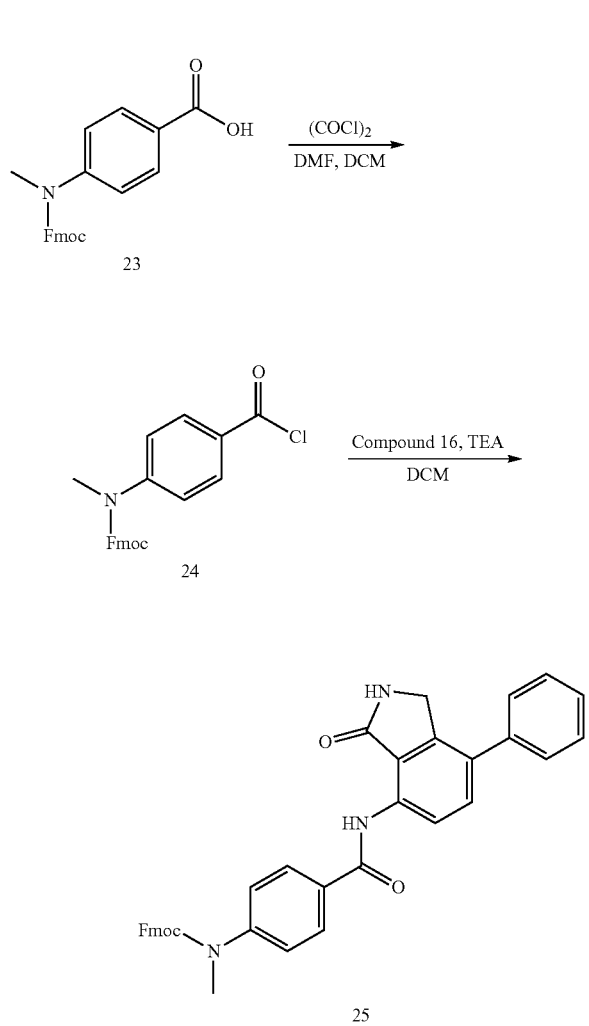

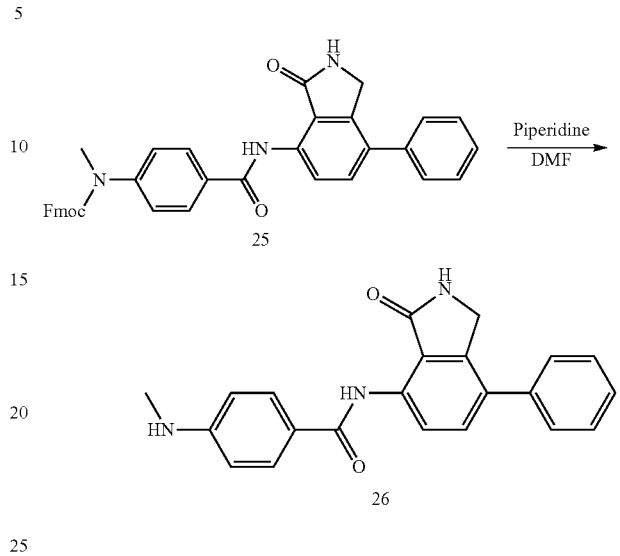

To a stirred solution of the compound 23 (500 mg, 1.34 mmol) in DCM (30 mL) was added DMF (0.1 mL) at 0° C. Then, (COCl)$_2$ (300 mg, 2.36 mmol) was added dropwise to the mixture over 5 min, and then the mixture was stirred at room temperature for 1 hour. After TLC showed the reaction was completed, the mixture was added dropwise to a suspension solution of 7-amino-4-phenylisoindolin-1-one 16 (208 mg, 0.93 mmol) in DCM (30 mL) at 0° C., followed by stirring them at room temperature overnight. After TLC showed the reaction was completed, H$_2$O (50 mL) was added, and the resulting mixture was extracted with DCM (2×50 mL), washed with brine (50 mL), dried over anhydrous Na$_2$SO$_4$, and concentrated in vacuo to give the crude residue, which was purified by column chromatography to give the title compound 25 (120 mg, 0.21 mmol, 22%) as a white solid.

$^1$H NMR (400 MHz, DMSO-d$_6$) δ 11.73 (s, 1H), 9.14 (s, 1H), 8.61-8.59 (d, J=8.44 Hz, 1H), 7.93-7.91 (m, 2H), 7.86-7.84 (m, 2H), 7.74-7.72 (d, J=8.44 Hz, 1H), 7.64-7.63 (m, 2H), 7.53-7.48 (m, 4H), 7.43-7.38 (m, 3H), 7.31-7.28 (m, 2H), 7.24-7.22 (m, 2H), 4.63 (s, 2H), 4.58-4.56 (m, 2H), 4.28-4.25 (m, 1H), 3.20 (s, 3H).

To a stirred solution of the compound 25 (120 mg, 0.21 mmol) in DMF (12 mL) was added piperidine (2.4 mL), and the mixture was stirred at room temperature overnight. After TLC showed the reaction was completed, the solution was concentrated in vacuo to give the crude residue, which was then purified by column chromatography to give the title compound 26 (50 mg, 0.14 mmol, 67%) as a white solid.

$^1$H NMR (400 MHz, DMSO-d$_6$) δ 11.48 (s, 1H), 9.00 (s, 1H), 8.58-8.56 (d, J=8.48 Hz, 1H), 7.77-7.75 (m, 2H), 7.68-7.66 (m, J=8.44 Hz, 1H), 7.62-7.60 (m, 2H), 7.50-7.47 (m, 2H), 7.41-7.37 (m, 1H), 6.67-6.65 (m, 2H), 6.52-6.49 (m, 1H), 4.58 (s, 2H), 2.77-2.76 (m, 3H).

The following compounds of Examples 109 to 225 were obtained by using corresponding starting materials and repeating the procedure of Example 108.

Example 109: 3-Methyl-N-(3-oxo-7-phenylisoindolin-4-yl)thiophene-2-carboxamide

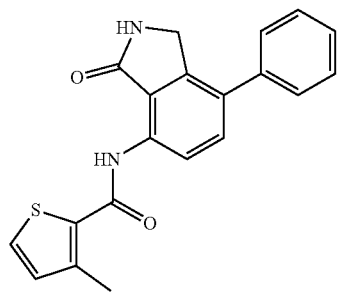 [SMILES: Cc1ccsc1C(=O)Nc1ccc(-c2ccccc2)c2c1C(=O)NC2]

$^1$H NMR (400 MHz, DMSO-d$_6$) δ 11.24 (s, 1H), 9.02 (s, 1H), 8.53 (d, J=8.5 Hz, 1H), 7.77 (d, J=5.0 Hz, 1H), 7.69 (d, J=8.4 Hz, 1H), 7.61 (d, J=7.3 Hz, 2H), 7.49 (t, J=7.5 Hz, 2H), 7.40 (t, J=7.6 Hz, 2H), 7.10 (d, J=5.0 Hz, 1H), 4.58 (s, 2H), 2.60 (s, 3H); MS (ESI) m/z 349 (M+H)$^+$.

Example 110: 4-Methyl-N-(3-oxo-7-phenylisoindolin-4-yl)thiophene-2-carboxamide

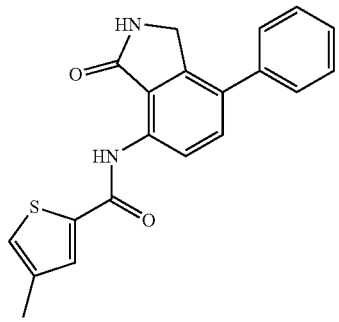 [SMILES: Cc1csc(C(=O)Nc2ccc(-c3ccccc3)c3c2C(=O)NC3)c1]

$^1$H NMR (400 MHz, DMSO-d$_6$) δ 11.58 (s, 1H), 9.07 (s, 1H), 8.45 (d, J=8.4 Hz, 1H), 7.61 (d, J=7.4 Hz, 2H), 7.56 (s, 2H), 7.49 (t, J=7.5 Hz, 2H), 7.41 (t, J=7.5 Hz, 1H), 4.60 (s, 2H), 2.30 (s, 3H); MS (ESI) m/z 349 (M+H)$^+$.

Example 111: 5-Methyl-N-(3-oxo-7-phenylisoindolin-4-yl)thiophene-2-carboxamide

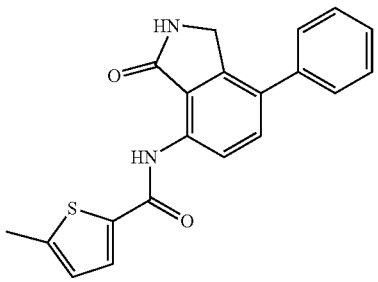 [SMILES: Cc1ccc(C(=O)Nc2ccc(-c3ccccc3)c3c2C(=O)NC3)s1]

$^1$H NMR (400 MHz, DMSO-d$_6$) δ 11.55 (s, 1H), 9.10 (s, 1H), 8.44 (d, J=8.4 Hz, 1H), 7.69 (d, J=8.4 Hz, 1H), 7.69 (d, J=8.4 Hz, 2H), 7.61 (d, J=7.3 Hz, 1H), 7.49 (t, J=7.5 Hz, 2H), 7.41 (t, J=7.5 Hz, 1H), 7.00 (dd, J=3.7, 0.94 Hz, 1H), 4.59 (s, 2H), 2.54 (s, 3H); MS (ESI) m/z 349 (M+H)$^+$.

Example 112: N-(3-oxo-7-(o-tolyl)isoindolin-4-yl)benzamide

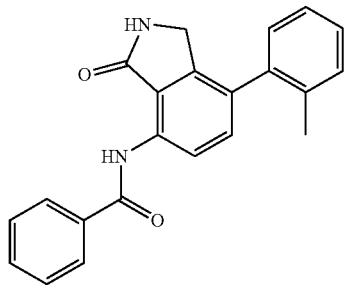 [SMILES: Cc1ccccc1-c1ccc(NC(=O)c2ccccc2)c2c1CNC2=O]

MS (ESI) m/z 343 (M+H)$^+$.
$^1$H NMR (400 MHz, DMSO-d$_6$) δ 11.63 (s, 1H), 8.98 (s, 1H), 8.55 (d, J=8.4 Hz, 1H), 8.02-7.99 (m, 2H), 7.70-7.62 (m, 3H), 7.49 (d, J=8.4 Hz, 1H), 7.38-7.27 (m, 4H), 4.22 (s, 2H), 2.16 (s, 3H); MS (ESI) m/z 343 (M+H)$^+$.

Example 113: N-(3-oxo-7-(m-tolyl)isoindolin-4-yl)benzamide

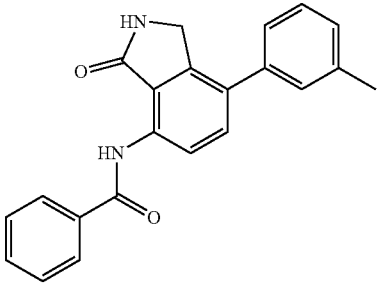 [SMILES: Cc1cccc(-c2ccc(NC(=O)c3ccccc3)c3c2CNC3=O)c1]

MS (ESI) m/z 343 (M+H)$^+$.
$^1$H NMR (400 MHz, DMSO-d$_6$) δ 11.77 (s, 1H), 9.12 (s, 1H), 8.62 (d, J=8.4 Hz, 1H), 8.02-7.95 (m, 4H), 7.83-7.74 (m, 3H), 7.70-7.62 (m, 3H), 4.65 (s, 2H), 2.45 (s, 3H); MS (ESI) m/z 343 (M+H)$^+$.

Example 114: N-(3-oxo-7-(2-(trifluoromethyl)phenyl)isoindolin-4-yl) benzamide

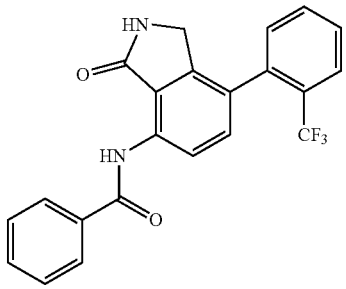 [SMILES: O=C(Nc1ccc(-c2ccccc2C(F)(F)F)c2c1C(=O)NC2)c1ccccc1]

MS (ESI) m/z 397 (M+H)$^+$.
$^1$H NMR (400 MHz, DMSO-d$_6$) δ 11.60 (s, 1H), 9.02 (s, 1H), 8.54 (d, J=8.4 Hz, 1H), 8.02-8.00 (m, 2H), 7.92-7.90 (m, 1H), 7.80-7.75 (m, 1H), 7.71-7.63 (m, 4H), 7.58-7.55 (m, 1H), 7.48 (d, J=8.4 Hz, 1H), 4.32-4.29 (m, 1H), 4.02-3.98 (m, 1H); MS (ESI) m/z 397 (M+H)$^+$.

Example 115: N-(3-oxo-7-(3-(trifluoromethyl)phenyl)isoindolin-4-yl) benzamide

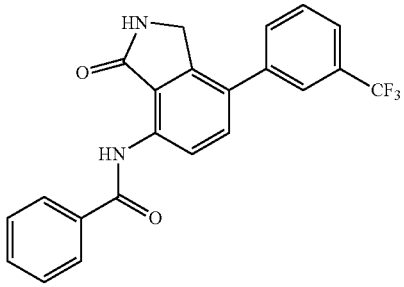 [SMILES: O=C(Nc1ccc(-c2cccc(C(F)(F)F)c2)c2c1C(=O)NC2)c1ccccc1]

MS (ESI) m/z 397 (M+H)$^+$.

$^1$H NMR (400 MHz, DMSO-d$_6$) δ 11.75 (s, 1H), 9.09 (s, 1H), 8.59 (d, J=8.4 Hz, 1H), 8.02-7.99 (m, 2H), 7.72-7.70 (m, 4H), 7.45-7.36 (m, 3H), 7.24-7.22 (m, 1H), 4.61 (s, 2H); MS (ESI) m/z 397 (M+H)$^+$.

Example 116: 4-Acetamido-N-(3-oxo-7-phenylisoindolin-4-yl)benzamide

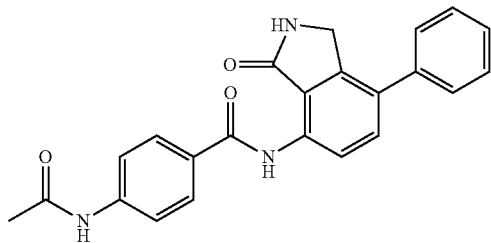 [SMILES: CC(=O)Nc1ccc(C(=O)Nc2ccc(-c3ccccc3)c3c2C(=O)NC3)cc1]

$^1$H NMR (400 MHz, DMSO-d$_6$) δ 10.84 (s, 1H), 10.38 (s, 1H), 8.76 (s, 1H), 8.06 (d, J=8.4 Hz, 2H), 7.80 (d, J=8.4 Hz, 2H), 7.58 (dd, J=8.4, 8.4 Hz, 3H), 7.47 (dd, J=7.6, 7.2 Hz, 2H), 7.44 (dd, J=7.2, 7.6 Hz, 1H), 7.25 (d, J=8.4 Hz, 1H), 4.55 (s, 2H), 2.11 (s, 3H). [M+H]$^+$: 386.

Example 117: N-(3-oxo-7-phenylisoindolin-4-yl)benzamide

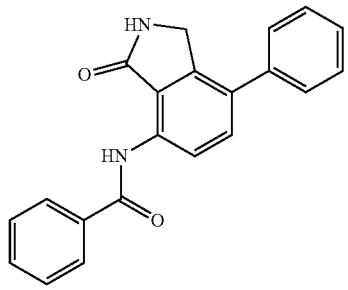 [SMILES: O=C(Nc1ccc(-c2ccccc2)c2c1C(=O)NC2)c1ccccc1]

$^1$H NMR (400 MHz, DMSO-d$_6$) δ 11.75 (s, 1H), 9.10 (s, 1H), 8.58 (d, J=8.4 Hz, 1H), 8.00 (d, J=6.8 Hz, 2H), 7.73 (d, J=8.4 Hz, 1H), 7.67 (d, J=6.8 Hz, 1H), 7.65-7.62 (m, 4H), 7.50 (dd, J=7.2, 8.0 Hz, 2H), 7.40 (dd, J=7.6, 7.2 Hz, 1H), 4.61 (s, 2H). [M+H]$^+$: 329.

Example 118: N-(7-(4-methoxyphenyl)-3-oxoisoindolin-4-yl)benzamide

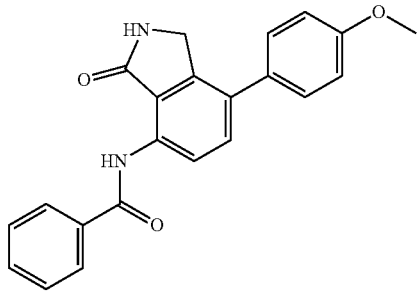 [SMILES: COc1ccc(-c2ccc(NC(=O)c3ccccc3)c3c2CNC3=O)cc1]

$^1$H NMR (400 MHz, DMSO-d$_6$) δ 11.73 (s, 1H), 9.09 (s, 1H), 8.55 (d, J=8.4 Hz, 1H), 7.99 (d, J=6.8 Hz, 2H), 7.69-7.61 (m, 4H), 7.56 (d, J=8.8 Hz, 2H), 7.05 (d, J=8.8 Hz, 2H), 4.59 (s, 2H), 3.81 (s, 3H). [M+H]$^+$: 359.

Example 119: 4-Nitro-N-(3-oxo-7-phenylisoindolin-4-yl)benzamide

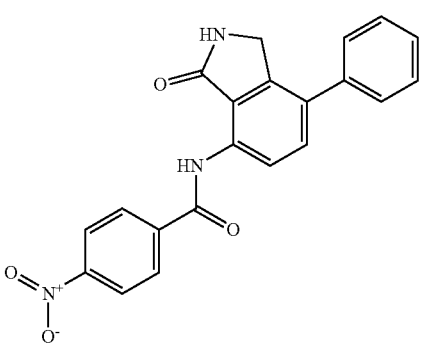 [SMILES: O=C(Nc1ccc(-c2ccccc2)c2c1C(=O)NC2)c1ccc([N+](=O)[O-])cc1]

$^1$H NMR (400 MHz, DMSO-d$_6$) δ 11.87 (s, 1H), 9.16 (s, 1H), 8.56 (d, J=8.4 Hz, 1H), 8.47 (d, J=8.8 Hz, 2H), 8.21 (d, J=8.8 Hz, 2H), 7.75 (d, J=8.4 Hz, 1H), 7.64 (d, J=7.2 Hz, 2H), 7.50 (t, J=7.6 Hz, 2H), 7.42 (dd, J=7.6, 6.8 Hz, 1H), 4.63 (s, 2H). [M+H]$^+$: 374.

Example 120: 4-Acetamido-N-(7-(4-methoxyphenyl)-3-oxoisoindolin-4-yl) benzamide

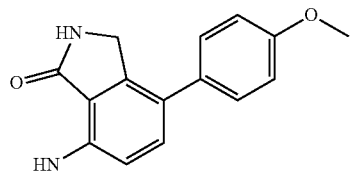

$^1$H NMR (400 MHz, DMSO-d$_6$) δ 11.65 (s, 1H), 10.32 (s, 1H), 9.09 (s, 1H), 8.54 (d, J=8.4 Hz, 1H), 7.92 (d, J=8.4 Hz, 2H), 7.80 (d, J=8.8 Hz, 2H), 7.66 (d, J=8.4 Hz, 1H), 7.56 (d, J=8.8 Hz, 2H), 7.04 (d, J=8.8 Hz, 2H), 4.59 (s, 2H), 3.81 (s, 3H). [M+H]$^+$: 416.

Example 121: 4-Methoxy-N-(3-oxo-7-phenylisoindolin-4-yl)benzamide

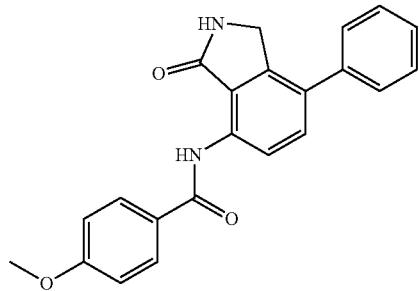 [SMILES: COc1ccc(C(=O)Nc2ccc(-c3ccccc3)c3c2C(=O)NC3)cc1]

$^1$H NMR (400 MHz, DMSO-d$_6$) δ 11.66 (s, 1H), 9.10 (s, 1H), 8.57 (d, J=8.4 Hz, 1H), 7.95 (d, J=8.4 Hz, 2H), 7.70-7.62 (m, 3H), 7.49-7.40 (m, 3H), 7.16 (d, J=8.8 Hz, 2H), 4.60 (s, 2H), 3.87 (s, 3H). [M+H]$^+$: 359.

Example 122: 4-Fluoro-N-(3-oxo-7-phenylisoindolin-4-yl)benzamide

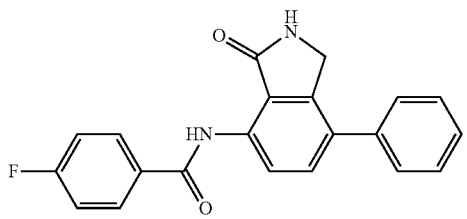 [SMILES: O=C(Nc1ccc(-c2ccccc2)c2c1C(=O)NC2)c1ccc(F)cc1]

$^1$H NMR (400 MHz, DMSO-d$_6$) δ 11.73 (s, 1H), 9.13 (s, 1H), 8.55 (d, J=8.4 Hz, 1H), 8.06-8.03 (m, 2H), 7.72 (d, J=8.4 Hz, 1H), 7.63 (d, J=8.4 Hz, 2H), 7.51-7.48 (m, 4H), 7.45-7.40 (m, 1H), 4.61 (s, 2H). [M+H]$^+$: 347.

Example 123: N-(7-(4-fluorophenyl)-3-oxoisoindolin-4-yl)-4-methoxy benzamide

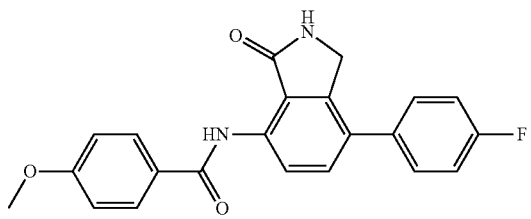 [SMILES: COc1ccc(C(=O)Nc2ccc(-c3ccc(F)cc3)c3c2C(=O)NC3)cc1]

$^1$H NMR (400 MHz, DMSO-d$_6$) δ 11.66 (s, 1H), 9.12 (s, 1H), 8.56 (d, J=8.4 Hz, 1H), 7.95 (d, J=8.4 Hz, 2H), 7.70-7.65 (m, 3H), 7.32 (t, J=8.4 Hz, 2H), 7.16 (t, J=8.8 Hz, 2H), 4.59 (s, 2H), 3.87 (m, 3H). [M+H]$^+$: 377.

Example 124: 4-Acetamido-N-(7-(4-fluorophenyl)-3-oxoisoindolin-4-yl) benzamide

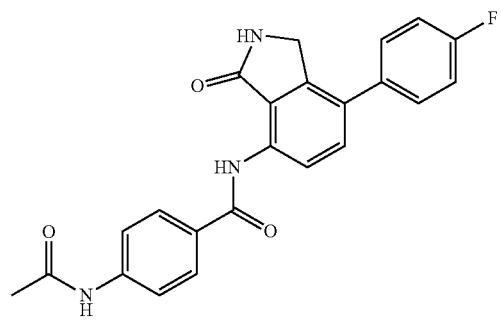 [SMILES: CC(=O)Nc1ccc(C(=O)Nc2ccc(-c3ccc(F)cc3)c3c2C(=O)NC3)cc1]

$^1$H NMR (400 MHz, DMSO-d$_6$) δ 10.82 (s, 1H), 10.39 (s, 1H), 8.78 (s, 1H), 8.06 (d, J=8.4 Hz, 2H), 7.79 (d, J=8.8 Hz, 2H), 7.61 (dd, J=8.6, 5.6 Hz, 2H), 7.56 (d, J=8.4 Hz, 1H), 7.29 (t, J=8.8 Hz, 2H), 7.24 (d, J=8.4 Hz, 1H), 4.54 (s, 2H), 2.10 (s, 3H). [M+H]$^+$: 404.

Example 125: N-(3-oxo-7-(thiophen-2-yl)isoindolin-4-yl)benzamide

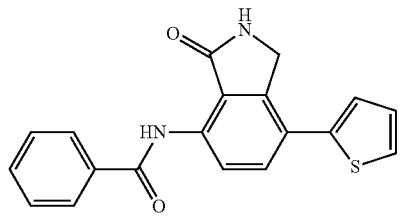 [SMILES: O=C(Nc1ccc(-c2cccs2)c2c1C(=O)NC2)c1ccccc1]

$^1$H NMR (400 MHz, DMSO-d$_6$) δ 11.74 (br s, 1H), 9.23 (br s, 1H), 8.55 (d, J=8.4 Hz, 1H), 7.98 (d, J=6.8 Hz, 2H), 7.92 (d, J=8.4 Hz, 1H), 7.68-7.61 (m, 4H), 7.49 (d, J=3.2 Hz, 1H), 7.23-7.21 (m, 1H), 4.68 (s, 2H); [M+H]$^+$: 335.

Example 126: N-(7-(furan-2-yl)-3-oxoisoindolin-4-yl)benzamide

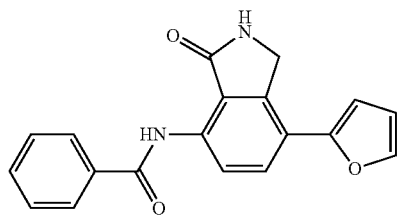 [SMILES: O=C(Nc1ccc(-c2ccco2)c2c1C(=O)NC2)c1ccccc1]

$^1$H NMR (400 MHz, DMSO-d$_6$) δ 11.71 (br s, 1H), 9.20 (br s, 1H), 8.55 (d, J=8.4 Hz, 1H), 8.00-7.97 (m, 3H), 7.84-7.83 (m, 1H), 7.68-7.60 (m, 3H), 6.89 (d, J=3.6 Hz, 1H), 6.68-6.66 (m, 1H), 4.66 (s, 2H); [M+H]$^+$: 319.

Example 127: N-(3-oxo-7-(pyridin-4-yl)isoindolin-4-yl)benzamide

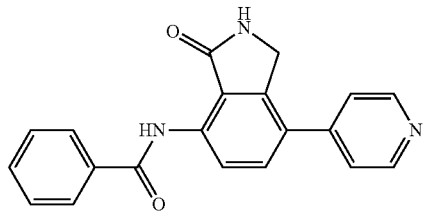 [SMILES: O=C(Nc1ccc(-c2ccncc2)c2c1C(=O)NC2)c1ccccc1]

¹H NMR (400 MHz, DMSO-d₆) δ 11.81 (br s, 1H), 9.21 (br s, 1H), 8.67 (d, J=6.0 Hz, 2H), 8.62 (d, J=8.4 Hz, 1H), 8.00 (d, J=6.8 Hz, 2H), 7.88 (d, J=8.4 Hz, 1H), 7.69-7.63 (m, 5H), 4.71 (s, 2H); [M+H]⁺: 330.

Example 128: N-(3-oxo-7-(pyridin-4-yl)isoindolin-4-yl)benzamide hydrochloride

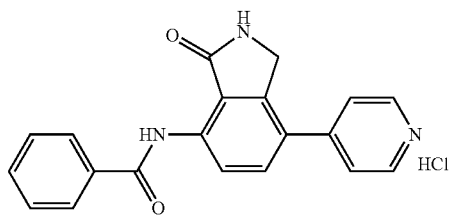 [SMILES: O=C(Nc1ccc(-c2ccncc2)c2c1C(=O)NC2)c1ccccc1 ; Cl]

¹H NMR (400 MHz, DMSO-d₆) δ 11.86 (br s, 1H), 9.26 (br s, 1H), 8.88 (d, J=6.0 Hz, 2H), 8.67 (d, J=8.4 Hz, 1H), 8.10 (d, J=5.6 Hz, 1H), 8.03-7.99 (m, 3H), 7.72-7.62 (m, 3H), 4.76 (s, 2H); [M+H]⁺: 330 (free form).

Example 129: 2-Methoxy-N-(3-oxo-7-phenylisoindolin-4-yl)benzamide

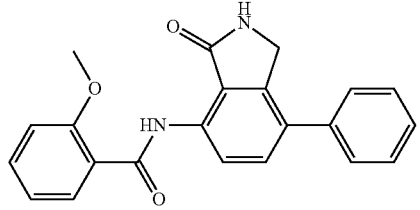 [SMILES: COc1ccccc1C(=O)Nc1ccc(-c2ccccc2)c2c1C(=O)NC2]

¹H NMR (400 MHz, DMSO-d₆) δ 12.16 (br s, 1H), 8.85 (br s, 1H), 8.80 (d, J=8.4 Hz, 1H), 8.07 (d, J=6.8 Hz, 1H), 7.67 (d, J=8.8 Hz, 1H), 7.62-7.58 (m, 3H), 7.49 (t, J=7.6 Hz, 2H), 7.40 (t, J=7.2 Hz, 1H), 7.26 (d, J=8.4 Hz, 1H), 7.13 (t, J=7.4 Hz, 1H), 4.55 (s, 2H), 4.07 (s, 3H); [M+H]⁺: 359.

Example 130: 3-fluoro-N-(3-oxo-7-phenylisoindolin-4-yl)benzamide

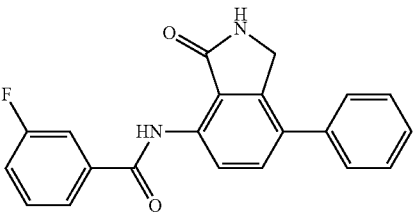 [SMILES: O=C(Nc1ccc(-c2ccccc2)c2c1C(=O)NC2)c1cccc(F)c1]

¹H NMR (400 MHz, DMSO-d₆) δ 11.75 (br s, 1H), 9.11 (br s, 1H), 8.54 (d, J=8.4 Hz, 1H), 7.82 (d, J=7.6 Hz, 1H), 7.74-7.67 (m, 3H), 7.63 (t, J=7.2 Hz, 2H), 7.57-7.47 (m, 3H), 7.40 (t, J=7.4 Hz, 1H), 4.61 (s, 2H); [M+H]⁺: 347.

Example 131: 4-(Methylthio)-N-(3-oxo-7-phenylisoindolin-4-yl)benzamide

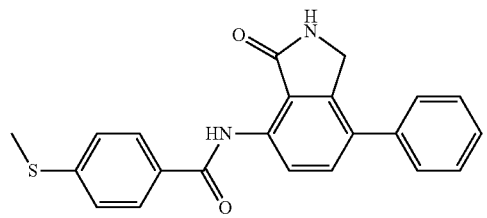 [SMILES: CSc1ccc(C(=O)Nc2ccc(-c3ccccc3)c3c2C(=O)NC3)cc1]

¹H NMR (400 MHz, DMSO-d₆) δ 11.70 (br s, 1H), 9.07 (br s, 1H), 8.56 (d, J=8.4 Hz, 1H), 7.91 (d, J=8.4 Hz, 2H), 7.71 (d, J=8.4 Hz, 1H), 7.62 (d, J=7.6 Hz, 2H), 7.51-7.46 (m, 4H), 7.40 (t, J=7.4 Hz, 1H), 4.60 (s, 2H), 2.56 (s, 3H); [M+H]⁺: 375.

Example 132: N-(3-oxo-7-(4-propoxyphenyl)isoindolin-4-yl)benzamide

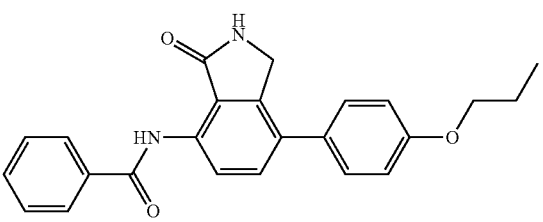 [SMILES: CCCOc1ccc(-c2ccc(NC(=O)c3ccccc3)c3c2CNC3=O)cc1]

¹H NMR (400 MHz, DMSO-d₆) δ 11.72 (br s, 1H), 9.06 (br s, 1H), 8.55 (d, J=8.4 Hz, 1H), 7.99 (d, J=6.8 Hz, 2H), 7.68-7.60 (m, 4H), 7.55-7.50 (m, 2H), 7.03 (d, J=8.8 Hz, 2H), 4.58 (s, 2H), 4.00-3.94 (m, 2H), 1.78-1.71 (m, 2H), 1.00 (t, J=7.2 Hz, 3H); [M+H]⁺: 387.

Example 133: N-(7-(4-isopropylphenyl)-3-oxoisoindolin-4-yl)benzamide

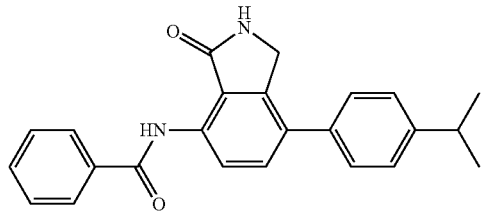

¹H NMR (400 MHz, DMSO-d₆) δ 11.73 (br s, 1H), 9.06 (br s, 1H), 8.56 (d, J=8.0 Hz, 1H), 7.99 (d, J=7.6 Hz, 2H), 7.71-7.60 (m, 4H), 7.55 (d, J=7.6 Hz, 2H), 7.36 (d, J=7.2 Hz, 2H), 4.61 (s, 2H), 1.25 (d, J=6.8 Hz, 6H); [M+H]⁺: 371.

Example 134: N-(7-(2,3-dimethoxyphenyl)-3-oxoisoindolin-4-yl)furan-2-carboxamide

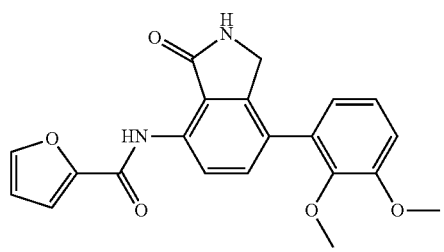 [SMILES: COc1cccc(-c2ccc(NC(=O)c3ccco3)c3c2CNC3=O)c1OC]

¹H NMR (400 MHz, DMSO-d₆) δ 9.92 (br s, 1H), 8.48 (d, J=8.4 Hz, 1H), 8.02 (d, J=1.2 Hz, 1H), 7.54 (d, J=8.4 Hz, 1H), 7.31 (d, J=3.2 Hz, 2H), 7.17-7.09 (m, 2H), 6.94 (dd, J=7.4, 1.8 Hz, 1H), 6.77 (dd, J=3.6, 1.6 Hz, 1H), 4.29 (s, 2H), 3.85 (s, 3H), 3.45 (s, 3H); [M+H]⁺: 379.

Example 135: N-(7-(2,3-dimethoxyphenyl)-3-oxoisoindolin-4-yl)-4-fluoro benzamide

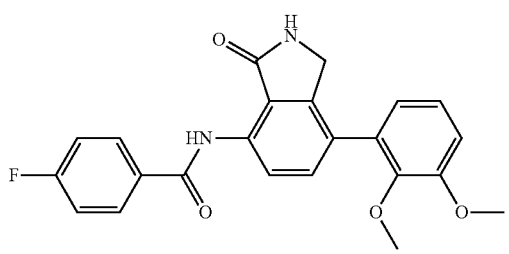 [SMILES: COc1cccc(-c2ccc(NC(=O)c3ccc(F)cc3)c3c2CNC3=O)c1OC]

¹H NMR (400 MHz, DMSO-d₆) δ 11.63 (br s, 1H), 8.98 (br s, 1H), 8.50 (d, J=8.4 Hz, 1H), 8.06-8.02 (m, 2H), 7.56 (d, J=8.4 Hz, 1H), 7.47 (t, J=8.8 Hz, 2H), 7.18-7.10 (m, 2H), 6.95 (dd, J=7.4, 1.8 Hz, 1H), 4.31 (s, 2H), 3.86 (s, 3H), 3.45 (s, 3H); [M+H]⁺: 407.

Example 136: N-(7-(2,3-dimethoxyphenyl)-3-oxoisoindolin-4-yl)thiophene-2-carboxamide

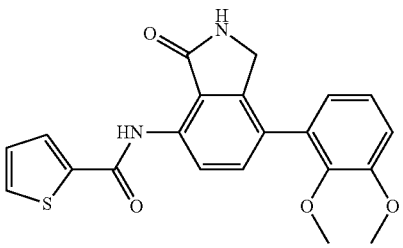 [SMILES: COc1cccc(-c2ccc(NC(=O)c3cccs3)c3c2CNC3=O)c1OC]

¹H NMR (400 MHz, DMSO-d₆) δ 11.60 (br s, 1H), 8.90 (br s, 1H), 8.40 (d, J=8.4 Hz, 1H), 7.97 (dd, J=5.0, 1.0 Hz, 1H), 7.76 (dd, J=3.6, 0.8 Hz, 1H), 7.54 (d, J=8.4 Hz, 1H), 7.32-7.29 (m, 1H), 7.18-7.10 (m, 2H), 6.95 (dd, J=7.4, 1.8 Hz, 1H), 4.31 (s, 2H), 3.86 (s, 3H), 3.45 (s, 3H); [M+H]⁺: 395.

Example 137: 4-Fluoro-2-methyl-N-(3-oxo-7-phenylisoindolin-4-yl) benzamide

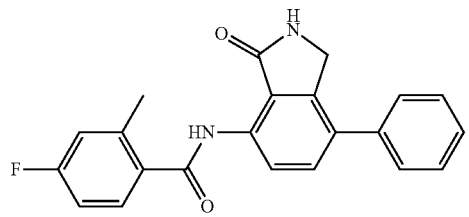 [SMILES: Cc1cc(F)ccc1C(=O)Nc1ccc(-c2ccccc2)c2c1C(=O)NC2]

¹H NMR (400 MHz, DMSO-d₆) δ 11.40 (br s, 1H), 8.91 (br s, 1H), 8.50 (d, J=8.4 Hz, 1H), 7.73 (d, J=8.4 Hz, 2H), 7.50 (d, J=8.4 Hz, 1H), 7.17-7.09 (m, 2H), 6.94 (d, J=6.4 Hz, 1H), 6.67 (d, J=8.4 Hz, 2H), 6.57 (t, J=5.2 Hz, 1H), 4.29 (s, 2H), 3.85 (s, 3H), 3.44 (s, 3H), 3.17-3.11 (m, 2H), 2.35-2.31 (m, 6H), 1.72-1.68 (m, 2H), 1.52-1.48 (m, 4H), 1.39-1.37 (m, 2H); [M+H]⁺: 529.

Example 138: 4-Acetamido-N-(7-(2-methoxyphenyl)-3-oxoisoindolin-4-yl) benzamide

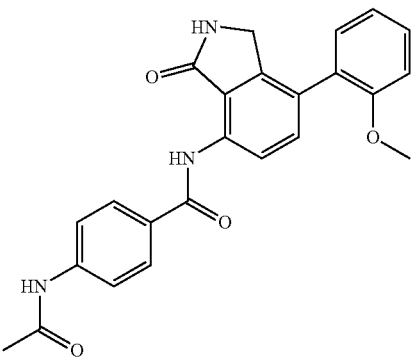 [SMILES: COc1ccccc1-c1ccc(NC(=O)c2ccc(NC(C)=O)cc2)c2c1CNC2=O]

¹H NMR (400 MHz, DMSO-d₆) δ 11.58 (s, 1H), 10.30 (s, 1H), 8.93 (s, 1H), 8.50 (d, J=8.4 Hz, 1H), 7.92 (d, J=8.5 Hz,

2H), 7.80 (d, J=8.4 Hz, 2H), 7.51 (d, J=8.3 Hz, 1H), 7.41 (s, 1H), 7.32 (d, J=7.6 Hz, 1H), 7.14 (d, J=8.4 Hz, 1H), 7.05 (t, J=7.4 Hz, 1H), 4.27 (s, 2H), 3.77 (s, 3H), 1.24 (s, 3H); [M+H]⁺: 416.

Example 139: 4-(Dimethylamino)-N-(3-oxo-7-phenylisoindolin-4-yl) benzamide

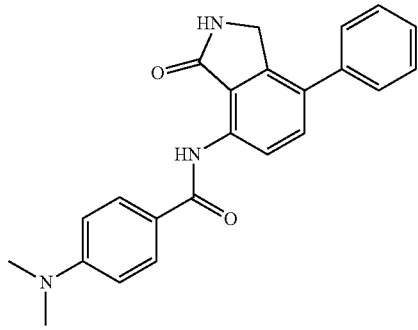 [SMILES: CN(C)c1ccc(C(=O)Nc2ccc(-c3ccccc3)c3c2C(=O)NC3)cc1]

¹H NMR (400 MHz, DMSO-d₆) δ 11.85 (br s, 1H), 8.57 (s, 1H), 8.48 (s, 1H), 7.84 (d, J=7.6 Hz, 2H), 7.79-7.77 (m, 1H), 7.65 (s, 1H), 7.53-7.48 (m, 3H), 7.19-7.16 (m, 1H), 6.35 (br s, 1H), 4.49-4.40 (m, 2H), 3.91-3.85 (m, 2H), 3.70-3.42 (m, 7H), 2.72-2.63 (m, 3H); [M+H]⁺: 372.

Example 140: 4-Acetamido-N-(7-(furan-2-yl)-3-oxoisoindolin-4-yl) benzamide

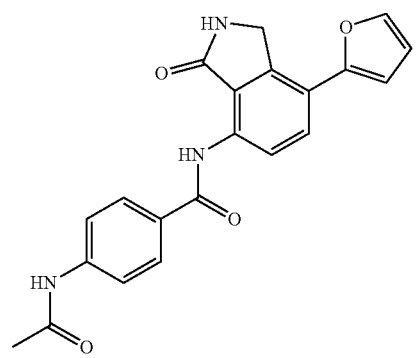 [SMILES: CC(=O)Nc1ccc(C(=O)Nc2ccc(-c3ccco3)c3c2C(=O)NC3)cc1]

¹H NMR (400 MHz, DMSO-d₆) δ 11.62 (s, 1H), 10.30 (s, 1H), 9.15 (s, 1H), 8.54 (d, J=8.6 Hz, 1H), 7.94 (dd, J=21.0, 8.6 Hz, 3H), 7.85-7.75 (m, 3H), 6.87 (d, J=3.5 Hz, 1H), 6.66 (dd, J=3.5, 1.8 Hz, 1H), 4.65 (s, 2H), 2.10 (s, 3H); [M+H]⁺: 376.

Example 141: 4-Fluoro-N-(7-(2-methoxyphenyl)-3-oxoisoindolin-4-yl) benzamide

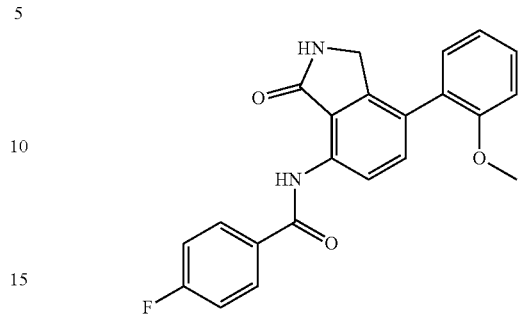

¹H NMR (400 MHz, DMSO-d₆) δ 11.63 (s, 1H), 8.95 (s, 1H), 8.48 (d, J=8.3 Hz, 1H), 8.09-7.99 (m, 2H), 7.52 (d, J=8.4 Hz, 1H), 7.46 (t, J=8.7 Hz, 2H), 7.43-7.38 (m, 1H), 7.31 (dd, J=7.5, 1.7 Hz, 1H), 7.14 (d, J=8.3 Hz, 1H), 7.05 (t, J=7.4 Hz, 1H), 4.27 (s, 2H), 3.77 (s, 3H); [M+H]⁺: 377.

Example 142: 2-Fluoro-N-(3-oxo-7-phenylisoindolin-4-yl)benzamide

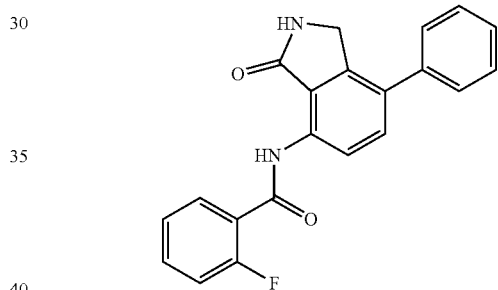

¹H NMR (400 MHz, DMSO-d₆) δ 11.54 (d, J=6.5 Hz, 1H), 8.98 (s, 1H), 8.64 (d, J=8.5 Hz, 1H), 7.97 (t, J=7.8 Hz, 1H), 7.70 (t, J=8.3 Hz, 2H), 7.62 (d, J=7.6 Hz, 2H), 7.50 (t, J=7.7 Hz, 2H), 7.46-7.37 (m, 3H), 4.57 (s, 2H); [M+H]⁺: 347.

Example 143: 4-Chloro-N-(3-oxo-7-phenylisoindolin-4-yl)benzamide

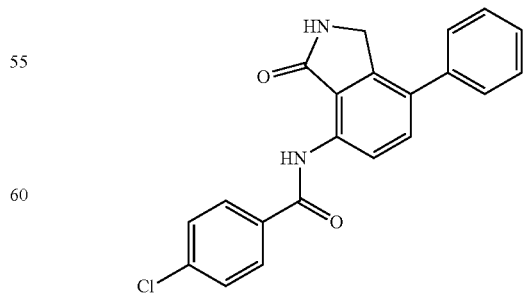

¹H NMR (400 MHz, DMSO-d₆) δ 11.74 (s, 1H), 9.09 (s, 1H), 8.55 (d, J=8.4 Hz, 1H), 7.99 (d, J=8.2 Hz, 2H), 7.72

(dd, J=8.3, 5.5 Hz, 3H), 7.62 (d, J=7.6 Hz, 2H), 7.50 (t, J=7.5 Hz, 2H), 7.41 (t, J=7.4 Hz, 1H), 4.61 (s, 2H); [M+H]⁺: 363.

Example 144: N-(7-(2-methoxyphenyl)-3-oxoisoindolin-4-yl)benzamide

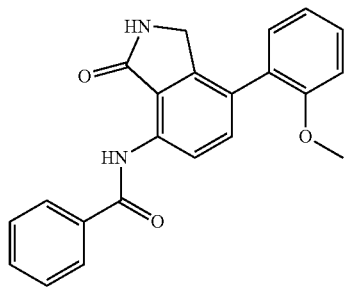 [SMILES: COc1ccccc1-c1ccc(NC(=O)c2ccccc2)c2c1CNC2=O]

¹H NMR (400 MHz, DMSO-d₆) δ 11.67 (s, 1H), 8.98 (s, 1H), 8.52 (d, J=8.4 Hz, 1H), 8.02-7.95 (m, 2H), 7.65 (dt, J=14.4, 6.9 Hz, 3H), 7.53 (d, J=8.4 Hz, 1H), 7.46-7.38 (m, 1H), 7.32 (dd, J=7.4, 1.7 Hz, 1H), 7.15 (d, J=8.2 Hz, 1H), 7.05 (dd, J=7.9, 6.8 Hz, 1H), 4.28 (s, 2H), 3.77 (s, 3H); [M+H]⁺: 359.

Example 145: N-(7-(3-methoxyphenyl)-3-oxoisoindolin-4-yl)benzamide

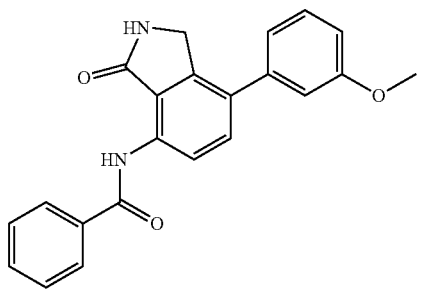 [SMILES: COc1cccc(-c2ccc(NC(=O)c3ccccc3)c3c2CNC3=O)c1]

¹H NMR (400 MHz, DMSO-d₆) δ 11.75 (s, 1H), 9.11 (s, 1H), 8.57 (d, J=8.4 Hz, 1H), 7.99 (dt, J=6.8, 1.5 Hz, 2H), 7.74 (d, J=8.5 Hz, 1H), 7.65 (ddd, J=14.3, 7.8, 6.1 Hz, 3H), 7.40 (t, J=7.9 Hz, 1H), 7.18 (d, J=8.0 Hz, 1H), 7.15 (t, J=2.1 Hz, 1H), 6.97 (dd, J=7.7, 2.4 Hz, 1H), 4.61 (s, 2H), 3.82 (s, 3H); [M+H]⁺: 359.

Example 146: N-(3-oxo-7-(thiophen-3-yl)isoindolin-4-yl)benzamide

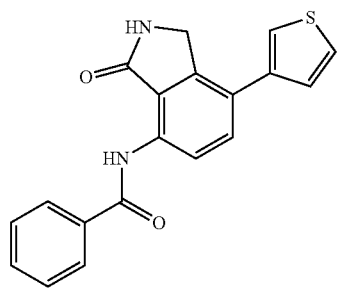

¹H NMR (400 MHz, DMSO-d₆) δ 11.74 (s, 1H), 9.19 (s, 1H), 8.54 (d, J=8.5 Hz, 1H), 7.98 (d, J=7.4 Hz, 2H), 7.91 (d, J=8.5 Hz, 1H), 7.84 (d, J=2.5 Hz, 1H), 7.75-7.55 (m, 5H), 4.68 (s, 2H); [M+H]⁺: 335.

Example 147: N-(7-(3-cyanophenyl)-3-oxoisoindolin-4-yl)benzamide

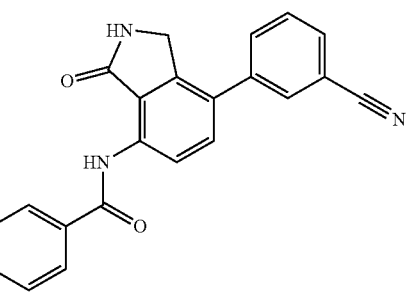

¹H NMR (400 MHz, DMSO-d₆) δ 11.77 (s, 1H), 9.17 (s, 1H), 8.60 (d, J=8.4 Hz, 1H), 8.13 (s, 1H), 8.03-7.94 (m, 3H), 7.88 (d, J=7.8 Hz, 1H), 7.80 (d, J=8.4 Hz, 1H), 7.74-7.60 (m, 4H), 4.66 (s, 2H); [M+H]⁺: 354.

Example 148: N-(7-(3-(dimethylamino)phenyl)-3-oxoisoindolin-4-yl) benzamide

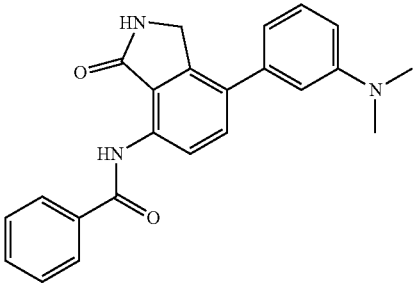 [SMILES: CN(C)c1cccc(-c2ccc(NC(=O)c3ccccc3)c3c2CNC3=O)c1]

¹H NMR (400 MHz, DMSO-d₆) δ 11.74 (s, 1H), 9.08 (s, 1H), 8.56 (d, J=8.4 Hz, 1H), 8.02-7.95 (m, 2H), 7.75-7.58 (m, 4H), 7.28 (t, J=8.0 Hz, 1H), 6.90-6.83 (m, 2H), 6.79-6.72 (m, 1H), 4.59 (s, 2H), 2.95 (s, 6H); [M+H]⁺: 372.

Example 149: N-(7-(2-fluorophenyl)-3-oxoisoindolin-4-yl)benzamide

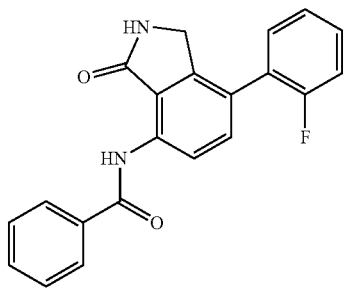

¹H NMR (400 MHz, DMSO-d₆) δ 11.71 (s, 1H), 9.08 (s, 1H), 8.58 (d, J=8.4 Hz, 1H), 7.99 (dt, J=6.9, 1.5 Hz, 2H), 7.72-7.55 (m, 5H), 7.54-7.44 (m, 1H), 7.42-7.28 (m, 2H), 4.40 (s, 2H); [M+H]⁺: 347.

Example 150: N-(7-(furan-3-yl)-3-oxoisoindolin-4-yl)benzamide

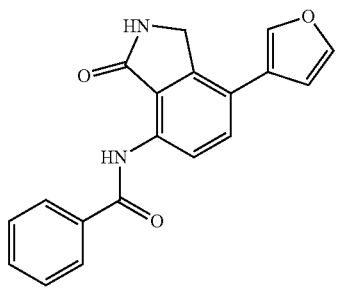 [SMILES: O=C(Nc1ccc(-c2ccoc2)c2c1C(=O)NC2)c1ccccc1]

¹H NMR (400 MHz, DMSO-d₆) δ 11.68 (s, 1H), 9.18 (s, 1H), 8.52 (d, J=8.5 Hz, 1H), 8.11 (s, 1H), 8.01-7.94 (m, 2H), 7.87 (d, J=8.5 Hz, 1H), 7.82 (t, J=1.7 Hz, 1H), 7.72-7.57 (m, 3H), 7.05 (d, J=1.8 Hz, 1H), 4.59 (s, 2H); [M+H]⁺: 319.

Example 151: N-(7-(3-fluorophenyl)-3-oxoisoindolin-4-yl)benzamide

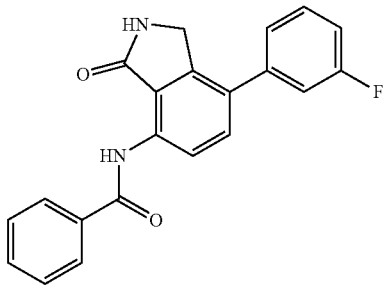 [SMILES: O=C(Nc1ccc(-c2cccc(F)c2)c2c1C(=O)NC2)c1ccccc1]

¹H NMR (400 MHz, DMSO-d₆) δ 11.76 (s, 1H), 9.14 (s, 1H), 8.59 (d, J=8.4 Hz, 1H), 7.99 (d, J=7.4 Hz, 2H), 7.76 (d, J=8.4 Hz, 1H), 7.69-7.59 (m, 3H), 7.50 (d, J=11.8 Hz, 3H), 7.24 (s, 1H), 4.64 (s, 2H); [M+H]⁺: 347.

Example 152: N-(3-oxo-7-(pyridin-3-yl)isoindolin-4-yl)benzamide

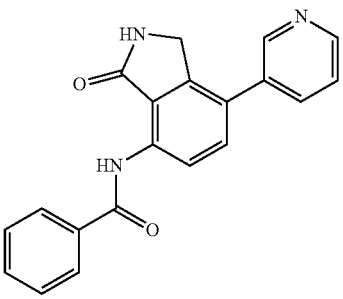 [SMILES: O=C(Nc1ccc(-c2cccnc2)c2c1C(=O)NC2)c1ccccc1]

¹H NMR (400 MHz, DMSO-d₆) δ 11.73 (s, 1H), 9.06 (s, 1H), 8.84 (d, J=2.4 Hz, 1H), 8.61 (d, J=7.1 Hz, 2H), 8.03 (dd, J=22.0, 7.5 Hz, 3H), 7.78 (d, J=8.4 Hz, 1H), 7.64 (dt, J=14.6, 7.2 Hz, 3H), 7.52 (dd, J=8.0, 4.8 Hz, 1H), 4.64 (s, 2H); [M+H]⁺: 330.

Example 153: N-(3-oxo-7-(pyridin-3-yl)isoindolin-4-yl)benzamide hydrochloride

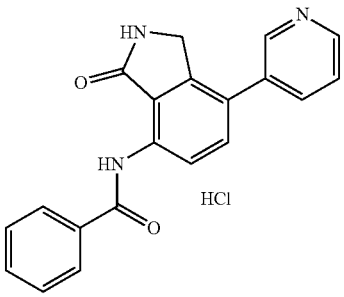 [SMILES: O=C(Nc1ccc(-c2cccnc2)c2c1C(=O)NC2)c1ccccc1 ; Cl]

¹H NMR (400 MHz, DMSO-d₆) δ 11.77 (s, 1H), 9.18 (s, 1H), 9.04 (s, 1H), 8.79 (d, J=5.2 Hz, 1H), 8.64 (d, J=8.4 Hz, 1H), 8.49 (d, J=8.0 Hz, 1H), 8.00 (d, J=7.2 Hz, 2H), 7.90-7.86 (m, 2H), 7.69-7.62 (m, 3H), 4.68 (s, 2H); [M+H]⁺: 330.

Example 154: N-(3-oxo-7-(pyrimidin-5-yl)isoindolin-4-yl)benzamide

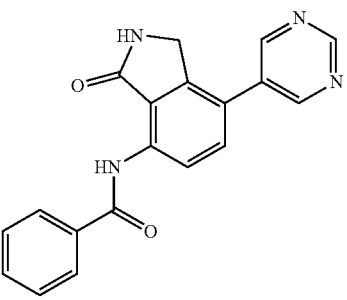 [SMILES: O=C(Nc1ccc(-c2cncnc2)c2c1C(=O)NC2)c1ccccc1]

¹H NMR (400 MHz, DMSO-d₆) δ 11.75 (s, 1H), 9.22 (s, 1H), 9.10 (s, 3H), 8.63 (d, J=8.3 Hz, 1H), 8.00 (d, J=7.4 Hz, 2H), 7.87 (d, J=8.5 Hz, 1H), 7.64 (s, 3H), 4.70 (s, 2H); [M+H]⁺: 331.

Example 155: 3-Chloro-N-(3-oxo-7-phenylisoindolin-4-yl)thiophene-2-carboxamide

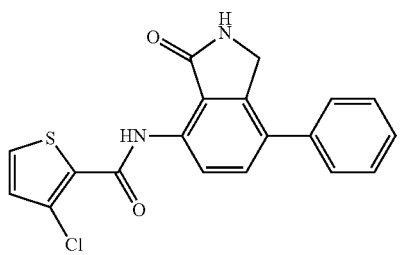

¹H NMR (400 MHz, DMSO-d₆) δ 11.56 (s, 1H), 8.98 (s, 1H), 8.48 (d, J=8.5 Hz, 1H), 8.03 (d, J=5.3 Hz, 1H), 7.70 (d, J=8.4 Hz, 1H), 7.62 (t, J=7.2 Hz, 2H), 7.49 (t, J=7.5 Hz, 2H), 7.41 (t, J=7.3 Hz, 1H), 7.28 (d, J=5.3 Hz, 1H), 4.58 (s, 2H); [M+H]⁺: 369.

Example 156: 5-Bromo-N-(3-oxo-7-phenylisoindolin-4-yl)thiophene-2-carboxamide

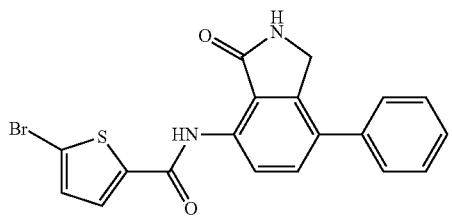

¹H NMR (400 MHz, DMSO-d₆) δ 11.63 (s, 1H), 9.14 (s, 1H), 8.39 (d, J=8.4 Hz, 1H), 7.71 (d, J=8.4 Hz, 1H), 7.62 (d, J=7.3 Hz, 2H), 7.56 (d, J=4.4 Hz, 1H), 7.51-7.45 (m, 3H), 7.40 (t, J=7.3 Hz, 1H), 4.60 (s, 2H); [M+H]⁺: 413.

Example 157: 3-Bromo-N-(3-oxo-7-phenylisoindolin-4-yl)thiophene-2-carboxamide

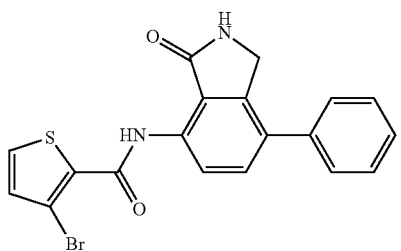 [SMILES: O=C(Nc1ccc(-c2ccccc2)c2c1C(=O)NC2)c1sccc1Cl]

¹H NMR (400 MHz, DMSO-d₆) δ 11.45 (s, 1H), 9.01 (s, 1H), 8.49 (d, J=8.4 Hz, 1H), 7.99 (d, J=5.2 Hz, 1H), 7.71 (d, J=8.4 Hz, 1H), 7.62 (d, J=7.4 Hz, 2H), 7.50 (t, J=7.6 Hz, 2H), 7.41 (t, J=7.2 Hz, 1H), 7.32 (d, J=5.2 Hz, 1H), 4.58 (s, 2H); [M+H]⁺: 413.

Example 158: 4-Fluoro-N-(7-(furan-2-yl)-3-oxoisoindolin-4-yl)benzamide

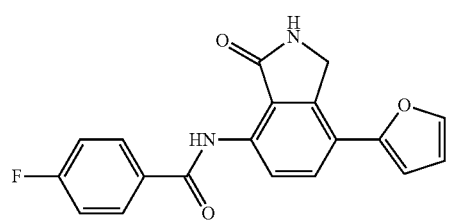 [SMILES: O=C(Nc1ccc(-c2ccco2)c2c1C(=O)NC2)c1ccc(F)cc1]

¹H NMR (400 MHz, DMSO-d₆) δ 11.68 (s, 1H), 9.19 (s, 1H), 8.52 (d, J=8.6 Hz, 1H), 8.03 (dd, J=8.8, 5.4 Hz, 2H), 7.88 (d, J=8.5 Hz, 1H), 7.83 (d, J=1.4 Hz, 1H), 7.47 (t, J=8.8 Hz, 2H), 6.88 (d, J=3.4 Hz, 1H), 6.67 (dd, J=3.4, 1.8 Hz, 1H), 4.66 (s, 2H); [M+H]⁺: 337.

Example 159: N-(3-oxo-7-phenylisoindolin-4-yl)pentanamide

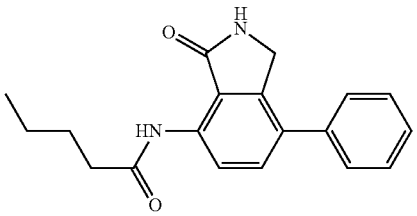 [SMILES: CCCCC(=O)Nc1ccc(-c2ccccc2)c2c1C(=O)NC2]

¹H NMR (400 MHz, DMSO-d₆) δ 10.66 (s, 1H), 8.98 (s, 1H), 8.42 (d, J=8.5 Hz, 1H), 7.63 (d, J=8.5 Hz, 1H), 7.59 (d, J=7.3 Hz, 2H), 7.48 (t, J=7.6 Hz, 2H), 7.39 (t, J=7.2 Hz, 1H), 4.55 (s, 2H), 2.42 (t, J=7.5 Hz, 2H), 1.63 (quint, J=7.3 Hz, 2H), 1.37 (quint, J=7.4 Hz, 2H), 0.91 (t, J=7.4 Hz, 3H); [M+H]⁺: 309.

Example 160: N-(3-oxo-7-phenylisoindolin-4-yl)acetamide

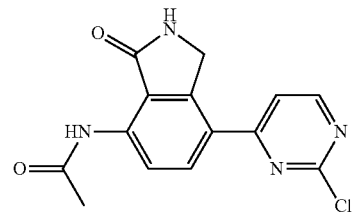 [SMILES: CC(=O)Nc1ccc(-c2ccnc(Cl)n2)c2c1C(=O)NC2]

¹H NMR (400 MHz, DMSO-d₆) δ 10.60 (s, 1H), 8.99 (s, 1H), 8.40 (d, J=8.4 Hz, 1H), 7.63 (d, J=8.4 Hz, 1H), 7.59 (d, J=7.1 Hz, 2H), 7.48 (t, J=7.5 Hz, 2H), 7.39 (t, J=7.3 Hz, 1H), 4.55 (s, 2H), 2.17 (s, 3H); [M+H]⁺: 267.

Example 161: N-(7-(2-chloropyrimidin-4-yl)-3-oxoisoindolin-4-yl)acetamide

¹H NMR (400 MHz, DMSO-d₆) δ 10.81 (s, 1H), 9.11 (s, 1H), 8.82 (d, J=5.2 Hz, 1H), 8.46 (d, J=8.8 Hz, 1H), 8.36 (d, J=8.8 Hz, 2H), 8.12 (d, J=5.6 Hz, 1H), 4.78 (s, 2H), 2.20 (s, 3H). [M+H]⁺: 303.

Example 162: N-(7-(2-((3-methoxyphenyl)amino)pyrimidin-4-yl)-3-oxoisoindolin-4-yl)acetamide

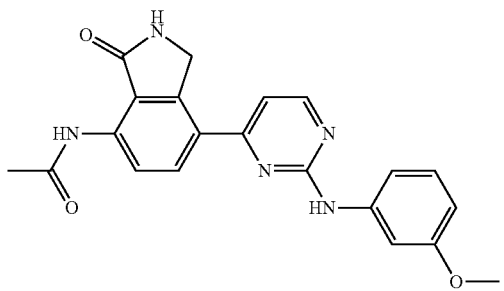 [SMILES: COc1cccc(Nc2nccc(-c3ccc(NC(C)=O)c4c3CNC4=O)n2)c1]

$^1$H NMR (400 MHz, DMSO-d$_6$) δ 10.78 (s, 1H), 9.55 (s, 1H), 9.14 (s, 1H), 8.56 (d, J=5.6 Hz, 1H), 8.44 (d, J=8.4 Hz, 1H), 8.22 (d, J=8.8 Hz, 1H), 7.43-7.44 (m, 1H), 7.35 (d, J=5.2 Hz, 1H), 7.33 (d, J=8.4 Hz, 1H), 7.21 (t, J=8.2 Hz, 1H), 6.56 (dd, J=8.2, 2.2 Hz, 1H), 4.84 (s, 2H), 3.74 (s, 3H), 2.19 (s, 3H). [M+H]$^+$: 390.

Example 163: N-(7-(2-((3-fluorophenyl)amino)pyrimidin-4-yl)-3-oxoisoindolin-4-yl) acetamide

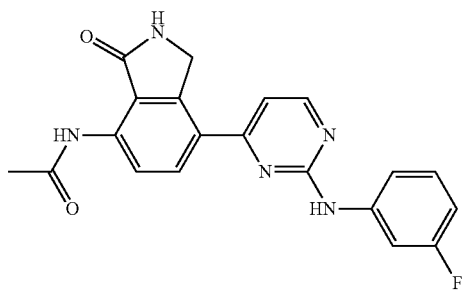 [SMILES: CC(=O)Nc1ccc(-c2ccnc(Nc3cccc(F)c3)n2)c2c1C(=O)NC2]

$^1$H NMR (400 MHz, DMSO-d$_6$) δ 10.78 (s, 1H), 9.79 (s, 1H), 9.16 (s, 1H), 8.60 (d, J=5.2 Hz, 1H), 8.45 (d, J=8.8 Hz, 1H), 8.24 (d, J=8.8 Hz, 1H), 7.78 (d, J=11.6 Hz, 1H), 7.50 (d, J=8.0 Hz, 1H), 7.42 (d, J=5.6 Hz, 1H), 7.36-7.30 (m, 1H), 6.78 (t, J=8.0 Hz, 1H), 4.85 (s, 2H), 2.19 (s, 3H). [M+H]$^+$: 378.

Example 164: N-(3-oxo-7-(2-(m-tolylamino)pyrimidin-4-yl)isoindolin-4-yl) acetamide

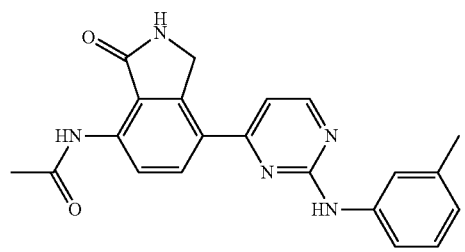 [SMILES: CC(=O)Nc1ccc(-c2ccnc(Nc3cccc(C)c3)n2)c2c1C(=O)NC2]

$^1$H NMR (400 MHz, DMSO-d$_6$) δ 10.78 (s, 1H), 9.49 (s, 1H), 9.14 (s, 1H), 8.54 (d, J=5.2 Hz, 1H), 8.44 (d, J=8.8 Hz, 1H), 8.22 (d, J=8.8 Hz, 1H), 7.55 (s, 1H), 7.51 (d, J=8.4 Hz, 1H), 7.34 (d, J=5.2 Hz, 1H), 7.19 (t, J=8.0 Hz, 1H), 6.81 (d, J=8.0 Hz, 1H), 4.82 (s, 2H), 2.30 (s, 3H), 2.19 (s, 3H). [M+H]$^+$: 374.

Example 165: N-(3-oxo-7-(2-(p-tolylamino)pyrimidin-4-yl)isoindolin-4-yl) acetamide

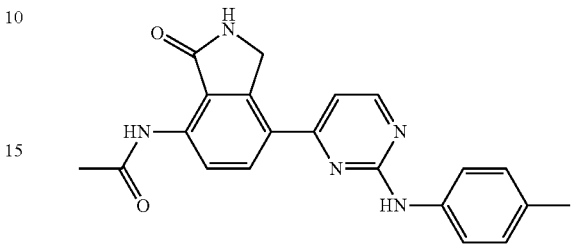

$^1$H NMR (400 MHz, DMSO-d$_6$) δ 10.78 (s, 1H), 9.46 (s, 1H), 9.12 (s, 1H), 8.52 (d, J=5.2 Hz, 1H), 8.44 (d, J=8.8 Hz, 1H), 8.21 (d, J=8.8 Hz, 1H), 7.59 (d, J=8.4 Hz, 2H), 7.32 (d, J=5.2 Hz, 1H), 7.12 (d, J=8.4 Hz, 2H), 4.80 (s, 2H), 2.27 (s, 3H), 2.19 (s, 3H). [M+H]$^+$: 374.

Example 166: N-(7-(2-((3-methoxyphenyl)amino)pyrimidin-4-yl)-3-oxoisoindolin-4-yl)propionamide

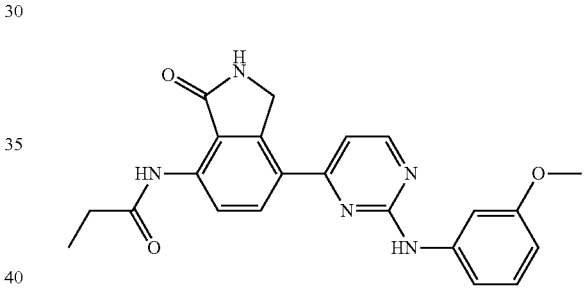

$^1$H NMR (400 MHz, DMSO-d$_6$) δ 10.84 (s, 1H), 9.56 (s, 1H), 9.14 (s, 1H), 8.55 (d, J=5.6 Hz, 1H), 8.46 (d, J=8.4 Hz, 1H), 8.23 (d, J=8.4 Hz, 1H), 7.44 (s, 1H), 7.36 (d, J=5.2 Hz, 1H), 7.33 (d, J=8.4 Hz, 1H), 7.21 (t, J=8.0 Hz, 2H), 6.56 (dd, J=8.2, 2.2 Hz, 1H), 4.84 (s, 2H), 3.74 (s, 3H), 2.49-2.46 (m, 2H), 1.15 (t, J=7.4 Hz, 3H). [M+H]$^+$: 404.

Example 167: N-(7-(4-(methylsulfonyl)phenyl)-3-oxoisoindolin-4-yl) benzamide

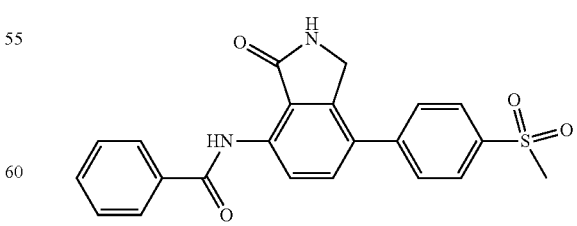

$^1$H NMR (400 MHz, DMSO-d$_6$) δ 11.78 (s, 1H), 9.14 (s, 1H), 8.62 (d, J=8.4 Hz, 1H), 8.05-7.99 (m, 5H), 7.91 (d, J=8.3 Hz, 2H), 7.81 (d, J=8.5 Hz, 1H), 7.69-7.61 (m, 3H), 4.66 (s, 2H), 3.28 (s, 3H); [M+H]$^+$: 407.

Example 168: N-(7-(3-(methylsulfonyl)phenyl)-3-oxoisoindolin-4-yl) benzamide

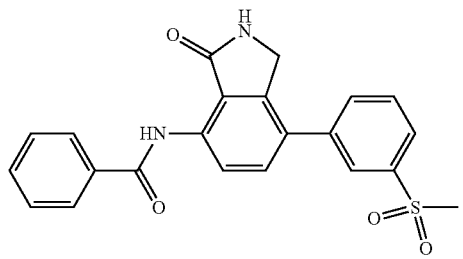 [SMILES: CS(=O)(=O)c1cccc(-c2ccc(NC(=O)c3ccccc3)c3c2CNC3=O)c1]

$^1$H NMR (400 MHz, DMSO-d$_6$) δ 11.77 (s, 1H), 9.13 (s, 1H), 8.63 (d, J=8.4 Hz, 1H), 8.11 (s, 1H), 8.02-8.01 (m, 3H), 7.98 (d, J=11.0 Hz, 1H), 7.84 (d, J=8.5 Hz, 1H), 7.78 (t, J=7.8 Hz, 1H), 7.71-7.62 (m, 3H), 4.64 (s, 2H), 3.31 (s, 3H); [M+H]$^+$: 407.

Example 169: N-(7-(3-acetamidophenyl)-3-oxoisoindolin-4-yl)benzamide

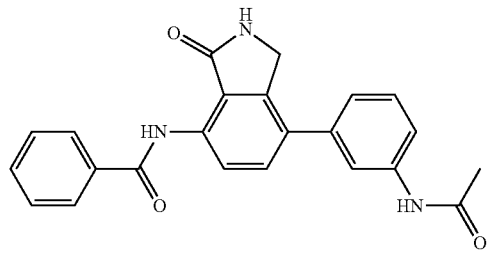 [SMILES: CC(=O)Nc1cccc(-c2ccc(NC(=O)c3ccccc3)c3c2CNC3=O)c1]

$^1$H NMR (400 MHz, DMSO-d$_6$) δ 11.74 (s, 1H), 10.04 (s, 1H), 9.10 (s, 1H), 8.59 (d, J=8.4 Hz, 1H), 7.99 (d, J=7.2 Hz, 2H), 7.83 (s, 1H), 7.71-7.58 (m, 5H), 7.41 (t, J=7.8 Hz, 1H), 7.30 (d, J=7.2 Hz, 1H), 4.58 (s, 2H), 2.07 (s, 3H); [M+H]$^+$: 386.

Example 170: 5-Chloro-N-(3-oxo-7-phenylisoindolin-4-yl)thiophene-2-carboxamide

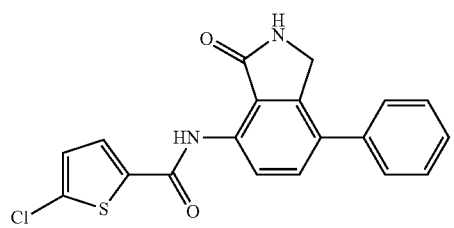 [SMILES: O=C(Nc1ccc(-c2ccccc2)c2c1C(=O)NC2)c1ccc(Cl)s1]

$^1$H NMR (400 MHz, DMSO-d$_6$) δ 11.64 (s, 1H), 9.14 (s, 1H), 8.39 (d, J=8.4 Hz, 1H), 7.71 (d, J=8.4 Hz, 1H), 7.63-7.61 (m, 2H), 7.49 (t, J=7.5 Hz, 3H), 7.41 (d, J=7.2 Hz, 2H), 7.36 (d, J=4.0 Hz, 1H), 4.61 (s, 2H); [M+H]$^+$: 369

Example 171: N-(7-(2,3-dimethoxyphenyl)-3-oxoisoindolin-4-yl)benzamide

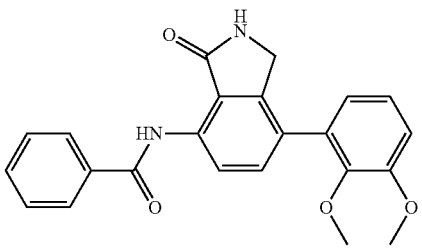 [SMILES: COc1cccc(-c2ccc(NC(=O)c3ccccc3)c3c2CNC3=O)c1OC]

$^1$H NMR (400 MHz, DMSO-d$_6$) δ 11.66 (s, 1H), 8.95 (s, 1H), 8.53 (d, J=8.4 Hz, 1H), 7.99 (d, J=7.1 Hz, 2H), 7.69-7.60 (m, 3H), 7.56 (d, J=8.3 Hz, 1H), 7.18-7.11 (m, 2H), 6.95 (d, J=7.5 Hz, 1H), 4.31 (s, 2H), 3.86 (s, 3H), 3.46 (s, 3H); [M+H]$^+$: 389.

Example 172: N-(7-(3,5-dimethoxyphenyl)-3-oxoisoindolin-4-yl)benzamide

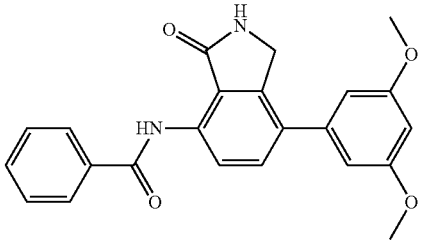 [SMILES: COc1cc(OC)cc(-c2ccc(NC(=O)c3ccccc3)c3c2CNC3=O)c1]

$^1$H NMR (400 MHz, DMSO-d$_6$) δ 11.74 (s, 1H), 9.07 (s, 1H), 8.56 (d, J=8.4 Hz, 1H), 7.99 (d, J=7.1 Hz, 1H), 7.73 (d, J=8.5 Hz, 2H), 7.68-7.61 (m, 3H), 6.73 (d, J=2.2 Hz, 2H), 6.54 (s, 1H), 4.61 (s, 2H), 3.81 (s, 6H); [M+H]$^+$: 389.

Example 173: N-(7-cyclopropyl-3-oxoisoindolin-4-yl)benzamide

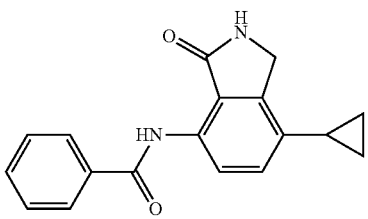 [SMILES: O=C(Nc1ccc(C2CC2)c2c1C(=O)NC2)c1ccccc1]

$^1$H NMR (400 MHz, DMSO-d$_6$) δ 11.44 (s, 1H), 8.95 (s, 1H), 8.36 (d, J=8.4 Hz, 1H), 7.95 (d, J=7.4 Hz, 2H), 7.66-7.58 (m, 4H), 7.17 (d, J=8.2 Hz, 1H), 4.50 (s, 2H), 1.89 (m, 1H), 0.96 (d, J=7.0 Hz, 2H), 0.75 (d, J=5.6 Hz, 2H); [M+H]$^+$: 293.

Example 174: N-(7-(2-chlorophenyl)-3-oxoisoindolin-4-yl)benzamide

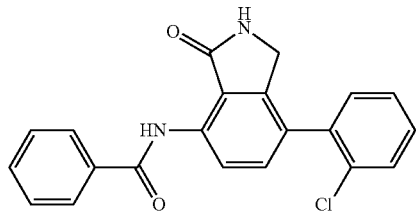 [SMILES: O=C(Nc1ccc(-c2ccccc2Cl)c2c1C(=O)NC2)c1ccccc1]

$^1$H NMR (400 MHz, DMSO-d$_6$) δ 11.63 (s, 1H), 9.01 (s, 1H), 8.56 (d, J=8.9 Hz, 1H), 7.99 (d, J=6.9 Hz, 2H), 7.69-7.61 (m, 3H), 7.56-7.45 (m, 4H), 4.29 (s, 2H); [M+H]$^+$: 363.

Example 175: N-(7-(2,4-dimethoxyphenyl)-3-oxoisoindolin-4-yl)benzamide

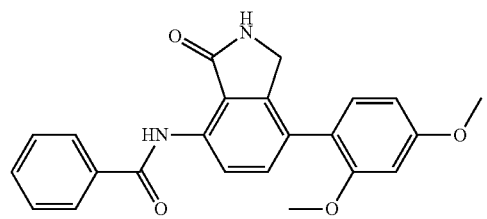 [SMILES: COc1ccc(-c2ccc(NC(=O)c3ccccc3)c3c2CNC3=O)c(OC)c1]

$^1$H NMR (400 MHz, DMSO-d$_6$) δ 11.64 (s, 1H), 8.92 (s, 1H), 8.49 (d, J=8.5 Hz, 1H), 7.99 (d, J=7.4 Hz, 2H), 7.69-7.60 (m, 3H), 7.48 (d, J=8.4 Hz, 1H), 7.23 (d, J=8.4 Hz, 1H), 6.69 (d, J=2.1 Hz, 1H), 6.63 (d, J=8.0 Hz, 1H), 4.26 (s, 2H), 3.82 (s, 3H), 3.76 (s, 3H); [M+H]$^+$: 389.

Example 176: N-(7-(3,4-dimethoxyphenyl)-3-oxoisoindolin-4-yl)benzamide

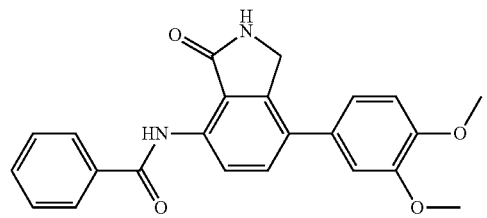 [SMILES: COc1ccc(-c2ccc(NC(=O)c3ccccc3)c3c2CNC3=O)cc1OC]

$^1$H NMR (400 MHz, DMSO-d$_6$) δ 11.73 (s, 1H), 9.06 (s, 1H), 8.56 (d, J=8.6 Hz, 1H), 7.99 (d, J=7.0 Hz, 2H), 7.71 (d, J=8.5 Hz, 1H), 7.68-7.61 (m, 3H), 7.17 (s, 1H), 7.14 (d, J=8.1 Hz, 1H), 7.05 (d, J=8.2 Hz, 1H), 4.61 (s, 2H), 3.83 (s, 3H), 3.81 (s, 3H); [M+H]$^+$: 389.

Example 177: N-(7-(3-ethoxyphenyl)-3-oxoisoindolin-4-yl)benzamide

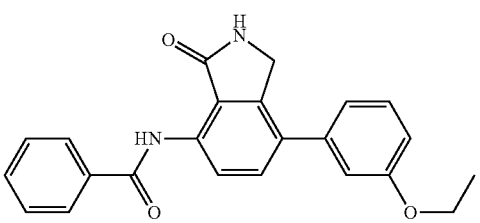 [SMILES: CCOc1cccc(-c2ccc(NC(=O)c3ccccc3)c3c2CNC3=O)c1]

$^1$H NMR (400 MHz, DMSO-d$_6$) δ 11.74 (s, 1H), 9.06 (s, 1H), 8.57 (d, J=8.6 Hz, 1H), 7.99 (d, J=7.2 Hz, 2H), 7.73 (d, J=8.4 Hz, 1H), 7.68-7.61 (m, 3H), 7.39 (t, J=7.9 Hz, 1H), 7.16 (d, J=7.7 Hz, 1H), 6.97 (s, 1H), 6.96 (d, J=6.0 Hz, 1H), 4.60 (s, 2H), 4.10 (q, J=6.9 Hz, 2H), 1.36 (t, J=6.9 Hz, 3H); [M+H]$^+$: 373.

Example 178: N-(7-(2,5-dimethoxyphenyl)-3-oxoisoindolin-4-yl)benzamide

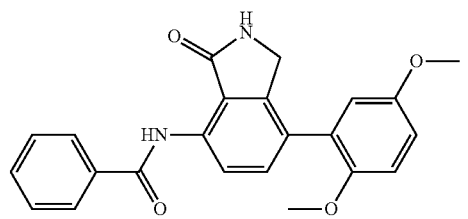 [SMILES: COc1ccc(OC)c(-c2ccc(NC(=O)c3ccccc3)c3c2CNC3=O)c1]

$^1$H NMR (400 MHz, DMSO-d$_6$) δ 11.65 (s, 1H), 8.94 (s, 1H), 8.51 (d, J=8.3 Hz, 1H), 7.99 (d, J=7.1 Hz, 2H), 7.68-7.61 (m, 3H), 7.54 (d, J=8.4 Hz, 1H), 7.07 (d, J=9.0 Hz, 1H), 6.97 (dd, J=8.9, 3.0 Hz, 1H), 6.90 (d, J=3.0 Hz, 1H), 4.29 (s, 2H), 3.75 (s, 3H), 3.70 (s, 3H); [M+H]$^+$: 389.

Example 179: N-(7-(4-chlorophenyl)-3-oxoisoindolin-4-yl)benzamide

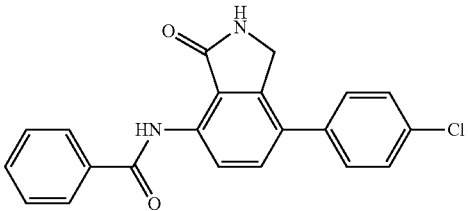

$^1$H NMR (400 MHz, DMSO-d$_6$) δ 11.74 (s, 1H), 9.10 (s, 1H), 8.58 (d, J=8.3 Hz, 1H), 7.99 (d, J=7.2 Hz, 2H), 7.73 (d, J=8.3 Hz, 1H), 7.68-7.63 (m, 5H), 7.54 (d, J=8.4 Hz, 1H), 4.60 (s, 2H); [M+H]$^+$: 363.

Example 180: N-(7-(3-chlorophenyl)-3-oxoisoindolin-4-yl)benzamide

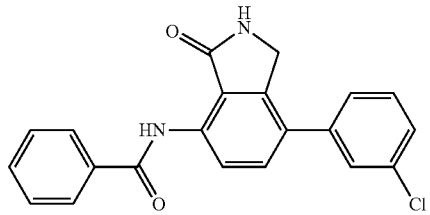 [SMILES: O=C(Nc1ccc(-c2cccc(Cl)c2)c2c1C(=O)NC2)c1ccccc1]

$^1$H NMR (400 MHz, DMSO-d$_6$) δ 11.75 (s, 1H), 9.10 (s, 1H), 8.58 (d, J=8.4 Hz, 1H), 7.99 (d, J=7.1 Hz, 2H), 7.75 (d, J=8.4 Hz, 1H), 7.69-7.59 (m, 5H), 7.54-7.46 (m, 2H), 4.62 (s, 2H); [M+H]$^+$: 363.

Example 181: N-(7-(4-ethoxyphenyl)-3-oxoisoindolin-4-yl)benzamide

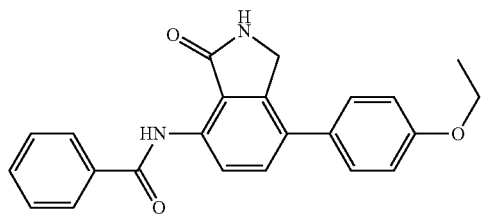 [SMILES: CCOc1ccc(-c2ccc(NC(=O)c3ccccc3)c3c2CNC3=O)cc1]

$^1$H NMR (400 MHz, DMSO-d$_6$) δ 11.72 (s, 1H), 9.06 (s, 1H), 8.55 (d, J=8.6 Hz, 1H), 7.99 (d, J=7.2 Hz, 2H), 7.68-7.62 (m, 3H), 7.54 (d, J=8.6 Hz, 2H), 7.02 (d, J=8.5 Hz, 2H), 4.58 (s, 2H), 4.09 (q, J=7.1 Hz, 2H), 1.36 (q, J=7.1 Hz, 3H); [M+H]$^+$: 373.

Example 182: N-(7-(2-ethoxyphenyl)-3-oxoisoindolin-4-yl)benzamide

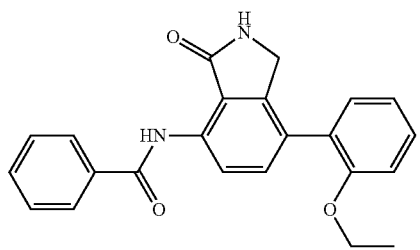 [SMILES: CCOc1ccccc1-c1ccc(NC(=O)c2ccccc2)c2c1CNC2=O]

$^1$H NMR (400 MHz, DMSO-d$_6$) δ 11.66 (s, 1H), 8.93 (s, 1H), 8.52 (d, J=8.4 Hz, 1H), 7.99 (d, J=7.0 Hz, 2H), 7.68-7.61 (m, 3H), 7.55 (d, J=8.4 Hz, 1H), 7.38 (t, J=7.8 Hz, 1H), 7.33 (d, J=7.4 Hz, 1H), 7.13 (d, J=8.2 Hz, 1H), 7.04 (d, J=7.3 Hz, 1H), 4.32 (s, 2H), 4.06 (q, J=6.9 Hz, 2H), 1.21 (q, J=7.0 Hz, 3H); [M+H]$^+$: 373.

Example 183: N-(7-(2-cyanophenyl)-3-oxoisoindolin-4-yl)benzamide

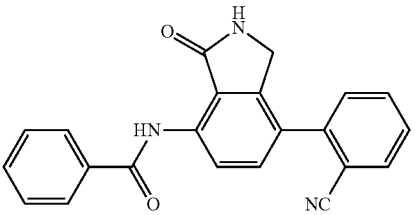

$^1$H NMR (400 MHz, DMSO-d$_6$) δ 11.69 (s, 1H), 9.09 (s, 1H), 8.61 (d, J=8.6 Hz, 1H), 8.00 (d, J=7.6 Hz, 2H), 7.82-7.76 (m, 2H), 7.72-7.62 (m, 6H), 4.44 (s, 2H); [M+H]$^+$: 354.

Example 184: N-(7-(4-butoxyphenyl)-3-oxoisoindolin-4-yl)benzamide

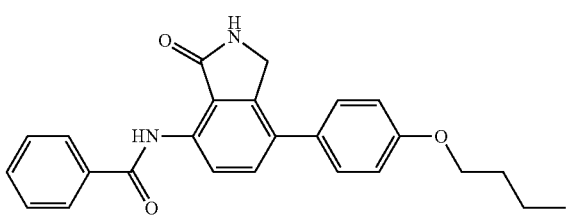 [SMILES: CCCCOc1ccc(-c2ccc(NC(=O)c3ccccc3)c3c2CNC3=O)cc1]

$^1$H NMR (400 MHz, DMSO-d$_6$) δ 11.72 (s, 1H), 9.06 (s, 1H), 8.55 (d, J=8.3 Hz, 1H), 7.99 (d, J=7.0 Hz, 2H), 7.68-7.61 (m, 4H), 7.54 (d, J=8.6 Hz, 2H), 7.03 (d, J=8.6 Hz, 2H), 4.58 (s, 2H), 4.03 (t, J=6.4 Hz, 2H), 1.73 (quint, 2H), 1.45 (quint, 2H), 0.95 (t, J=7.4 Hz, 3H); [M+H]$^+$: 401.

Example 185: N-(7-(2-(dimethylamino)phenyl)-3-oxoisoindolin-4-yl) benzamide

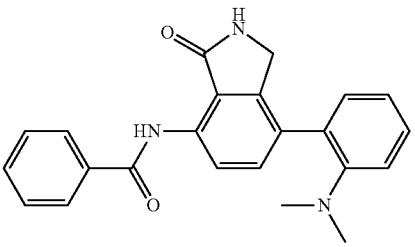

$^1$H NMR (400 MHz, DMSO-d$_6$) δ 11.65 (s, 1H), 8.92 (s, 1H), 8.55 (d, J=8.3 Hz, 1H), 7.99 (d, J=7.0 Hz, 2H), 7.70-7.59 (m, 4H), 7.33 (t, J=7.7 Hz, 1H), 7.23 (d, J=7.5 Hz, 1H), 7.12 (d, J=8.2 Hz, 1H), 7.02 (t, J=7.4 Hz, 1H), 4.29 (s, 2H); [M+H]$^+$: 372.

Example 186: N-(3-oxo-7-(4-(trifluoromethoxy)phenyl)isoindolin-4-yl) benzamide

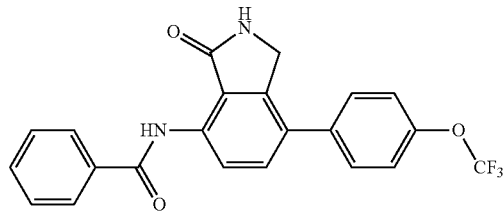 [SMILES: O=C(Nc1ccc(-c2ccc(OC(F)(F)F)cc2)c2c1C(=O)NC2)c1ccccc1]

$^{1}$H NMR (400 MHz, DMSO-d$_{6}$) δ 11.75 (s, 1H), 9.12 (s, 1H), 8.59 (d, J=8.4 Hz, 1H), 7.99 (d, J=7.2 Hz, 2H), 7.76 (t, J=7.8 Hz, 3H), 7.70-7.61 (m, 3H), 7.48 (d, J=8.4 Hz, 2H), 4.62 (s, 2H); [M+H]$^{+}$: 413.

Example 187: N-(7-(2,6-dimethoxyphenyl)-3-oxoisoindolin-4-yl)benzamide

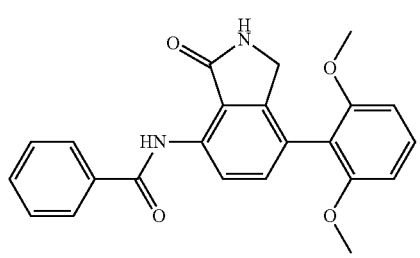 [SMILES: COc1cccc(OC)c1-c1ccc(NC(=O)c2ccccc2)c2c1CNC2=O]

$^{1}$H NMR (400 MHz, DMSO-d$_{6}$) δ 11.56 (s, 1H), 8.85 (s, 1H), 8.46 (d, J=8.4 Hz, 1H), 7.99 (d, J=6.9 Hz, 2H), 7.68-7.61 (m, 3H), 7.41-7.7.35 (m, 2H), 6.78 (d, J=8.4 Hz, 2H), 4.08 (s, 2H), 3.69 (s, 6H); [M+H]$^{+}$: 389.

Example 188: N-(3-oxo-7-(4-propylphenyl)isoindolin-4-yl)benzamide

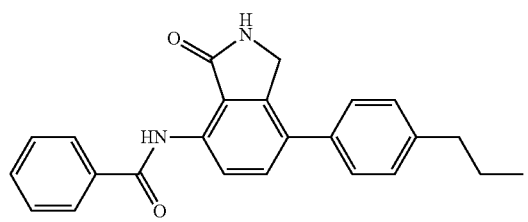 [SMILES: CCCc1ccc(-c2ccc(NC(=O)c3ccccc3)c3c2CNC3=O)cc1]

$^{1}$H NMR (400 MHz, DMSO-d$_{6}$) δ 11.74 (s, 1H), 9.07 (s, 1H), 8.57 (d, J=8.3 Hz, 1H), 7.99 (d, J=7.1 Hz, 2H), 7.72-7.61 (m, 4H), 7.53 (d, J=8.1 Hz, 2H), 7.31 (d, J=8.0 Hz, 2H), 4.60 (s, 2H), 2.61 (t, J=7.7 Hz, 2H), 1.64 (q, J=7.4 Hz, 2H), 0.94 (t, J=7.3 Hz, 3H); [M+H]$^{+}$: 371.

Example 189: N-(7-(2,3-dihydroxyphenyl)-3-oxoisoindolin-4-yl)-4-fluorobenzamide

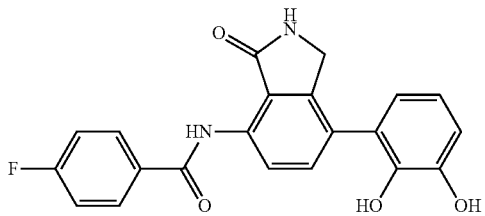 [SMILES: O=C(Nc1ccc(-c2cccc(O)c2O)c2c1C(=O)NC2)c1ccc(F)cc1]

$^{1}$H NMR (400 MHz, DMSO-d$_{6}$) δ 11.65 (s, 1H), 9.61 (s, 1H), 8.96 (s, 1H), 8.58 (s, 1H), 8.47 (d, J=8.4 Hz, 1H), 8.04 (dd, J=8.8, 5.2 Hz, 2H), 7.53 (d, J=8.4 Hz, 1H), 7.47 (t, J=8.8 Hz, 2H), 6.83 (dd, J=6.4, 3.2 Hz, 1H), 6.74-6.69 (m, 2H), 4.34 (s, 2H); [M+H]$^{+}$: 379.

Example 190: 4-Fluoro-N-(7-(2-hydroxy-3-methoxyphenyl)-3-oxoisoindolin-4-yl)benzamide

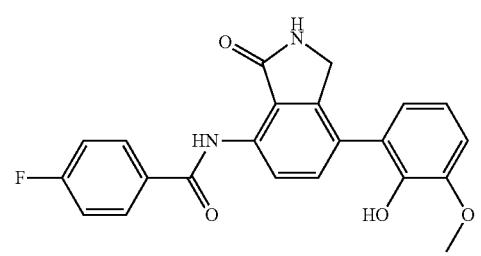 [SMILES: COc1cccc(-c2ccc(NC(=O)c3ccc(F)cc3)c3c2CNC3=O)c1O]

$^{1}$H NMR (400 MHz, DMSO-d$_{6}$) δ 11.65 (s, 1H), 8.98 (s, 1H), 8.88 (s, 1H), 8.48 (d, J=8.4 Hz, 1H), 8.04 (dd, J=8.8, 5.6 Hz, 2H), 7.53 (d, J=8.4 Hz, 1H), 7.47 (t, J=8.8 Hz, 2H), 7.01 (dd, J=5.6, 4.0 Hz, 1H), 6.87-6.85 (m, 2H), 4.34 (s, 2H), 3.85 (s, 3H). [M+H]$^{+}$: 393.

Example 191: 4-Fluoro-N-(3-oxo-7-(thiophen-2-yl)isoindolin-4-yl)benzamide

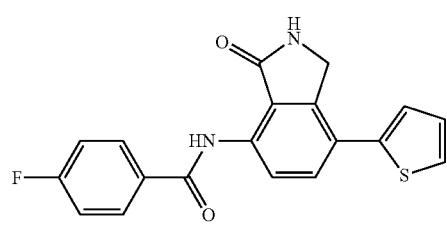 [SMILES: O=C(Nc1ccc(-c2cccs2)c2c1C(=O)NC2)c1ccc(F)cc1]

$^{1}$H NMR (400 MHz, DMSO-d$_{6}$) δ 11.71 (s, 1H), 9.23 (s, 1H), 8.51 (d, J=8.4 Hz, 1H), 8.05-8.01 (m, 2H), 7.91 (d, J=8.4 Hz, 1H), 7.66 (d, J=5.2 Hz, 1H), 7.49-7.44 (m, 3H), 7.21 (t, J=4.2 Hz, 1H), 4.67 (s, 2H). [M+H]$^{+}$: 353.

Example 192: 5-Methyl-N-(3-oxo-7-phenylisoindolin-4-yl)furan-2-carboxamide

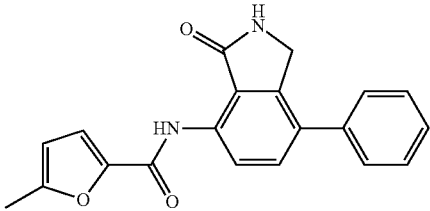 [SMILES: Cc1ccc(C(=O)Nc2ccc(-c3ccccc3)c3c2C(=O)NC3)o1]

¹H NMR (400 MHz, DMSO-d$_6$) δ 11.51 (s, 1H), 9.00 (s, 1H), 8.51 (d, J=8.8 Hz, 1H), 7.68 (d, J=8.4 Hz, 2H), 7.62-7.60 (m, 2H), 7.49 (d, J=7.6 Hz, 2H), 7.41-7.38 (m, 1H), 7.20 (d, J=3.2 Hz, 1H), 6.41 (dd, J=3.4, 1.0 Hz, 1H), 4.58 (s, 2H), 2.41 (s, 3H). [M+H]⁺: 333.

Example 193: N-(7-(benzo[d]oxazol-7-yl)-3-oxoisoindolin-4-yl)-4-fluorobenzamide

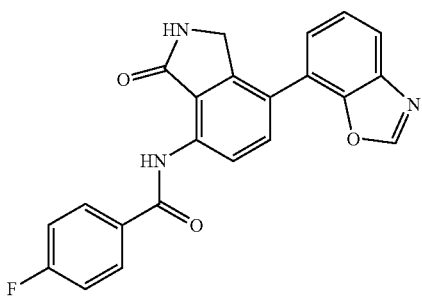 [SMILES: O=C(Nc1ccc(-c2cccc3ncoc23)c2c1C(=O)NC2)c1ccc(F)cc1]

¹H NMR (400 MHz, DMSO-d$_6$) δ 11.76 (s, 1H), 9.17 (s, 1H), 8.82 (s, 1H), 8.61 (d, J=8.4 Hz, 1H), 8.06 (dd, J=8.6, 5.4 Hz, 2H), 7.92 (d, J=8.4 Hz, 1H), 7.86 (d, J=7.6 Hz, 1H), 7.67 (d, J=7.2 Hz, 1H), 7.54-7.46 (m, 3H), 4.56 (s, 2H). [M+H]⁺: 388.

Example 194: 4-Fluoro-N-(7-(2-methylbenzo[d]oxazol-7-yl)-3-oxoisoindolin-4-yl)benzamide

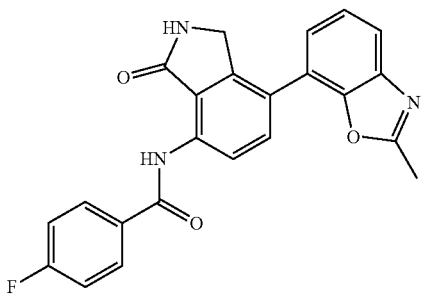 [SMILES: Cc1nc2cccc(-c3ccc(NC(=O)c4ccc(F)cc4)c4c3CNC4=O)c2o1]

¹H NMR (400 MHz, DMSO-d$_6$) δ 11.75 (s, 1H), 9.15 (s, 1H), 8.60 (d, J=8.8 Hz, 1H), 8.06 (dd, J=8.6, 5.4 Hz, 2H), 7.87 (d, J=8.4 Hz, 1H), 7.70 (d, J=7.2 Hz, 1H), 7.56-7.42 (m, 4H), 4.54 (s, 2H), 2.63 (s, 3H). [M+H]⁺: 402.

Example 195: N-(3-oxo-7-(5-(pyrrolidin-1-ylmethyl)thiophen-2-yl)isoindolin-4-yl)benzamide

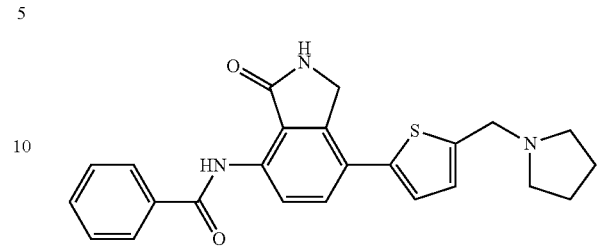

¹H NMR (400 MHz, DMSO-d$_6$) δ 11.73 (s, 1H), 9.17 (s, 1H), 8.53 (d, J=8.4 Hz, 1H), 7.98 (d, J=7.2 Hz, 2H), 7.86 (d, J=8.4 Hz, 1H), 7.67-7.60 (m, 3H), 7.28 (d, J=3.6 Hz, 1H), 7.01 (d, J=3.2 Hz, 1H), 4.65 (s, 2H), 3.80 (s, 2H), 2.58-2.50 (m, 4H), 1.74-1.70 (m, 4H). [M+H]⁺: 418.

Example 196: N-(3-oxo-7-(5-(piperidin-1-ylmethyl)thiophen-2-yl)isoindolin-4-yl)benzamide

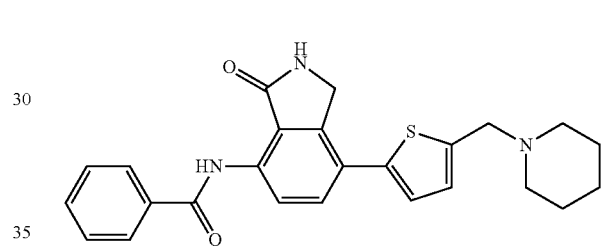

¹H NMR (400 MHz, DMSO-d$_6$) δ 11.73 (s, 1H), 9.17 (s, 1H), 8.53 (d, J=8.4 Hz, 1H), 7.98 (d, J=6.8 Hz, 2H), 7.86 (d, J=8.4 Hz, 1H), 7.67-7.60 (m, 3H), 7.28 (d, J=3.6 Hz, 1H), 7.01 (d, J=3.6 Hz, 1H), 4.65 (s, 2H), 3.66 (s, 2H), 2.42-2.38 (m, 4H), 1.54-1.48 (m, 4H), 1.40-1.36 (m, 2H). [M+H]⁺: 432.

Example 197: N-(7-(5-(morpholinomethyl)thiophen-2-yl)-3-oxoisoindolin-4-yl)benzamide

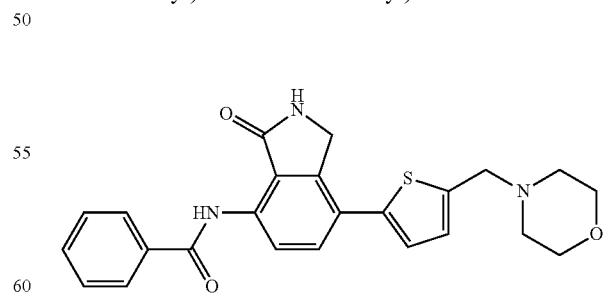

¹H NMR (400 MHz, DMSO-d$_6$) δ 11.73 (s, 1H), 9.17 (s, 1H), 8.53 (d, J=8.8 Hz, 1H), 7.98 (d, J=6.8 Hz, 2H), 7.86 (d, J=8.4 Hz, 1H), 7.67-7.62 (m, 3H), 7.29 (d, J=3.6 Hz, 1H), 7.04 (d, J=3.6 Hz, 1H), 4.65 (s, 2H), 3.71 (s, 2H), 3.62-3.56 (m, 4H), 2.48-2.42 (m, 4H). [M+H]⁺: 434.

Example 198: tert-Butyl 4-((5-(7-benzamido-1-ox-oisoindolin-4-yl)thiophen-2-yl) methyl)piperazine-1-carboxylate

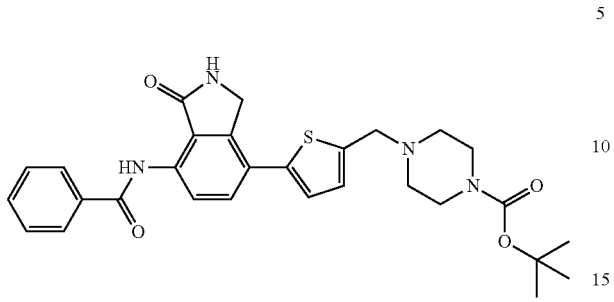

¹H NMR (400 MHz, DMSO-d₆) δ 11.73 (s, 1H), 9.17 (s, 1H), 8.53 (d, J=8.4 Hz, 1H), 7.98 (d, J=6.8 Hz, 2H), 7.86 (d, J=8.4 Hz, 1H), 7.67-7.62 (m, 3H), 7.30 (d, J=3.6 Hz, 1H), 7.04 (d, J=3.6 Hz, 1H), 4.66 (s, 2H), 3.73 (s, 2H), 3.35-3.30 (m, 4H), 2.42-2.38 (m, 4H), 1.39 (s, 9H). [M+H]⁺: 533.

Example 199: N-(7-(6-fluoropyridin-3-yl)-3-ox-oisoindolin-4-yl)benzamide

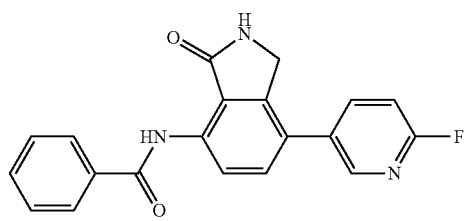 [SMILES: O=C(Nc1ccc(-c2ccc(F)nc2)c2c1C(=O)NC2)c1ccccc1]

¹H NMR (400 MHz, DMSO-d₆) δ 11.74 (s, 1H), 9.13 (s, 1H), 8.60 (d, J=8.0 Hz, 1H), 8.51 (s, 1H), 8.28-8.24 (m, 1H), 7.99 (d, J=6.4 Hz, 2H), 7.77 (d, J=8.4 Hz, 1H), 7.67-7.63 (m, 3H), 7.32 (d, J=6.8 Hz, 1H), 4.63 (s, 2H). [M+H]⁺: 348.

Example 200: N-(7-(6-methoxypyridin-3-yl)-3-ox-oisoindolin-4-yl)benzamide

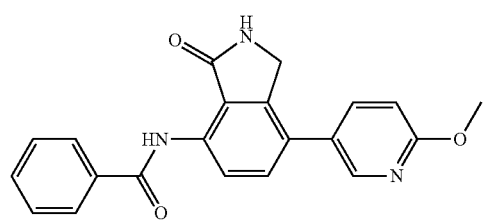 [SMILES: COc1ccc(-c2ccc(NC(=O)c3ccccc3)c3c2CNC3=O)cn1]

¹H NMR (400 MHz, DMSO-d₆) δ 11.72 (s, 1H), 9.09 (s, 1H), 8.57 (d, J=8.4 Hz, 1H), 8.43 (s, 1H), 7.99 (d, J=7.6 Hz, 3H), 7.73-7.62 (m, 3H), 6.94 (d, J=8.0 Hz, 1H), 4.61 (s, 2H), 3.91 (s, 3H). [M+H]⁺: 360.

Example 201: 2-Chloro-N-(3-oxo-7-phenylisoindo-lin-4-yl)benzamide

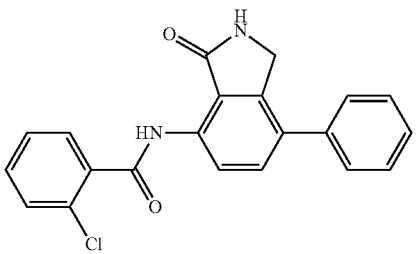 [SMILES: O=C(Nc1ccc(-c2ccccc2)c2c1C(=O)NC2)c1ccccc1Cl]

¹H NMR (400 MHz, DMSO-d₆) δ 11.12 (s, 1H), 9.02 (s, 1H), 8.54 (d, J=8.4 Hz, 1H), 7.74 (t, J=6.8 Hz, 2H), 7.65-7.59 (m, 4H), 7.57-7.48 (m, 3H), 7.43-7.39 (m, 1H), 4.58 (s, 2H). [M+H]⁺: 363.

Example 202: 3-Methoxy-N-(3-oxo-7-phenylisoin-dolin-4-yl)benzamide

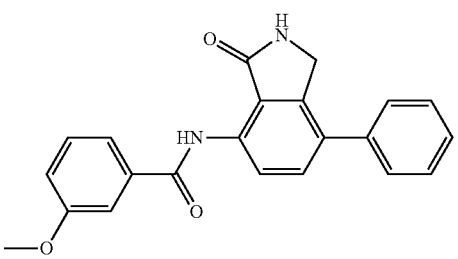 [SMILES: COc1cccc(C(=O)Nc2ccc(-c3ccccc3)c3c2C(=O)NC3)c1]

¹H NMR (400 MHz, DMSO-d₆) δ 11.73 (s, 1H), 9.08 (s, 1H), 8.56 (d, J=8.4 Hz, 1H), 7.72 (d, J=8.4 Hz, 1H), 7.62 (d, J=7.6 Hz, 2H), 7.55-7.49 (m, 5H), 7.47-7.41 (m, 1H), 7.26-7.23 (m, 1H), 4.60 (s, 2H), 3.87 (s, 3H). [M+H]⁺: 359.

Example 203: N-(3-oxo-7-phenylisoindolin-4-yl)thiophene-2-carboxamide

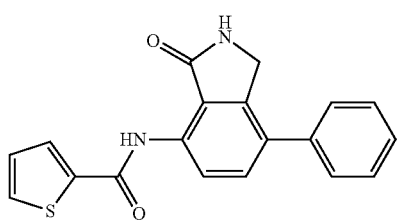 [SMILES: O=C(Nc1ccc(-c2ccccc2)c2c1C(=O)NC2)c1cccs1]

¹H NMR (400 MHz, DMSO-d₆) δ 11.64 (s, 1H), 9.09 (s, 1H), 8.44 (d, J=8.4 Hz, 1H), 7.97 (d, J=4.8 Hz, 1H), 7.76 (d, J=3.6 Hz, 1H), 7.70 (d, J=8.4 Hz, 1H), 7.62 (d, J=7.6 Hz, 2H), 7.49 (t, J=7.6 Hz, 2H), 7.40 (d, J=7.2 Hz, 1H), 7.31 (d, J=4.2 Hz, 1H), 4.60 (s, 2H). [M+H]⁺: 335.

Example 204: N-(7-(4-acetylphenyl)-3-oxoisoindolin-4-yl)-4-methoxy benzamide

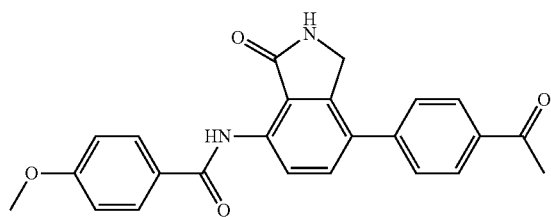 [SMILES: COc1ccc(C(=O)Nc2ccc(-c3ccc(C(C)=O)cc3)c3c2C(=O)NC3)cc1]

¹H NMR (400 MHz, DMSO-d₆) δ 11.70 (s, 1H), 9.15 (s, 1H), 8.60 (d, J=8.8 Hz, 1H), 8.06 (d, J=8.4 Hz, 2H), 7.96 (d, J=8.8 Hz, 2H), 7.79 (dd, J=8.6, 2.2 Hz, 2H), 7.16 (d, J=8.4 Hz, 2H), 4.65 (s, 2H), 3.87 (s, 3H), 2.63 (s, 3H). [M+H]⁺: 401.

Example 205: N-(7-(4-fluorophenyl)-3-oxoisoindolin-4-yl)benzamide

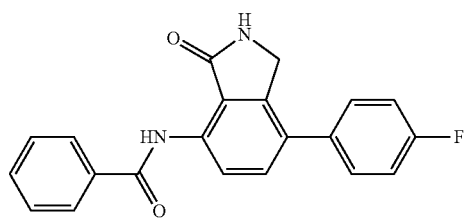 [SMILES: O=C(Nc1ccc(-c2ccc(F)cc2)c2c1C(=O)NC2)c1ccccc1]

¹H NMR (400 MHz, DMSO-d₆) δ 11.74 (s, 1H), 9.13 (s, 1H), 8.57 (d, J=8.4 Hz, 1H), 7.99 (d, J=8.4 Hz, 2H), 7.72-7.61 (m, 6H), 7.32 (t, J=8.8 Hz, 2H), 4.60 (s, 2H). [M+H]⁺: 347.

Example 206: N-(7-(4-(dimethylamino)phenyl)-3-oxoisoindolin-4-yl) benzamide

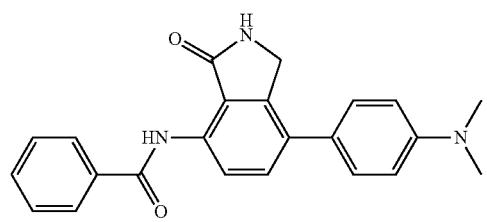 [SMILES: CN(C)c1ccc(-c2ccc(NC(=O)c3ccccc3)c3c2CNC3=O)cc1]

¹H NMR (400 MHz, DMSO-d₆) δ 11.72 (s, 1H), 9.08 (s, 1H), 8.53 (d, J=8.4 Hz, 1H), 7.98 (d, J=6.8 Hz, 2H), 7.67-7.60 (m, 4H), 7.46 (d, J=8.4 Hz, 2H), 6.82 (d, J=9.2 Hz, 2H), 4.59 (s, 2H), 2.95 (s, 6H). [M+H]⁺: 372.

Example 207: N-(7-(4-cyanophenyl)-3-oxoisoindolin-4-yl)benzamide

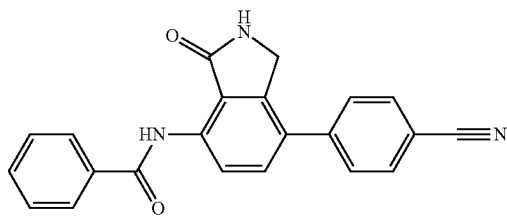 [SMILES: N#Cc1ccc(-c2ccc(NC(=O)c3ccccc3)c3c2CNC3=O)cc1]

¹H NMR (400 MHz, DMSO-d₆) δ 11.79 (s, 1H), 9.18 (s, 1H), 8.61 (d, J=8.4 Hz, 1H), 8.00-7.95 (m, 4H), 7.83 (dd, J=8.4, 14.4 Hz, 3H), 7.71-7.62 (m, 3H), 4.65 (s, 2H). [M+H]⁺: 354.

Example 208: 4-Cyano-N-(3-oxo-7-phenylisoindolin-4-yl)benzamide

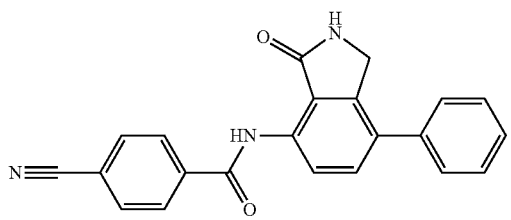 [SMILES: N#Cc1ccc(C(=O)Nc2ccc(-c3ccccc3)c3c2C(=O)NC3)cc1]

¹H NMR (400 MHz, DMSO-d₆) δ 11.82 (s, 1H), 9.16 (s, 1H), 8.54 (d, J=8.4 Hz, 1H), 8.12 (s, 4H), 7.74 (d, J=8.4 Hz, 1H), 7.63 (d, J=8.4 Hz, 2H), 7.50 (t, J=7.6 Hz, 2H), 7.41 (t, J=7.4 Hz, 1H), 4.62 (s, 2H). [M+H]⁺: 354.

Example 209: N-(3-oxo-7-(p-tolyl)isoindolin-4-yl) benzamide

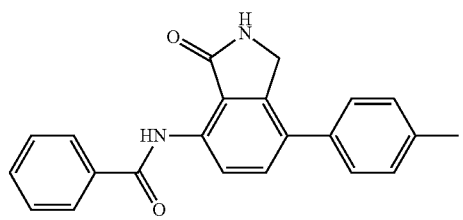 [SMILES: Cc1ccc(-c2ccc(NC(=O)c3ccccc3)c3c2CNC3=O)cc1]

¹H NMR (400 MHz, DMSO-d₆) δ 11.74 (s, 1H), 9.11 (s, 1H), 8.57 (d, J=8.0 Hz, 1H), 7.99 (d, J=7.2 Hz, 2H), 7.71-7.61 (m, 4H), 7.52 (d, J=8.0 Hz, 2H), 7.30 (d, J=8.0 Hz, 2H), 4.60 (s, 2H), 2.36 (s, 3H). [M+H]⁺: 343.

Example 210: N-(3-oxo-7-(4-(trifluoromethyl)phenyl)isoindolin-4-yl) benzamide

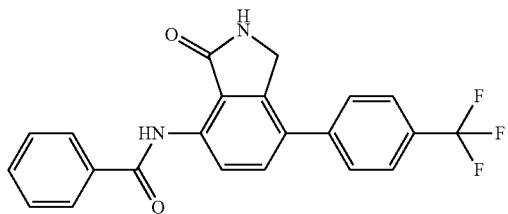 [SMILES: O=C(Nc1ccc(-c2ccc(C(F)(F)F)cc2)c2c1C(=O)NC2)c1ccccc1]

$^1$H NMR (400 MHz, DMSO-d$_6$) δ 11.78 (s, 1H), 9.17 (s, 1H), 8.61 (d, J=8.4 Hz, 1H), 7.99 (d, J=7.2 Hz, 2H), 7.88-7.79 (m, 5H), 7.69-7.62 (m, 3H), 4.65 (s, 2H). [M+H]$^+$: 397.

Example 211: N-(3-oxo-7-phenylisoindolin-4-yl)isonicotinamide

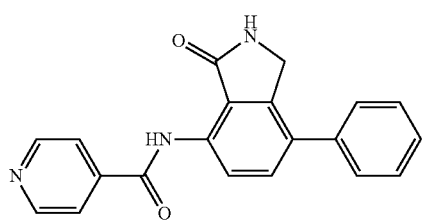 [SMILES: O=C(Nc1ccc(-c2ccccc2)c2c1C(=O)NC2)c1ccncc1]

$^1$H NMR (400 MHz, DMSO-d$_6$) δ 11.84 (s, 1H), 9.16 (s, 1H), 8.88 (d, J=5.6 Hz, 2H), 8.54 (d, J=8.4 Hz, 1H), 7.86 (d, J=6.0 Hz, 2H), 7.74 (d, J=8.8 Hz, 1H), 7.63 (d, J=7.2 Hz, 2H), 7.50 (t, J=7.4 Hz, 2H), 7.41 (d, J=7.4 Hz, 1H), 4.62 (s, 2H). [M+H]$^+$: 330.

Example 212: N-(3-oxo-7-phenylisoindolin-4-yl)furan-2-carboxamide

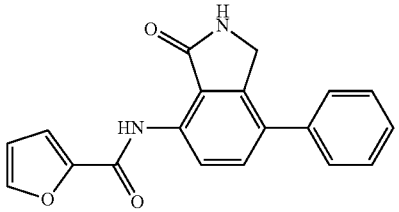

$^1$H NMR (400 MHz, DMSO-d$_6$) δ 11.59 (s, 1H), 9.05 (s, 1H), 8.53 (d, J=8.4 Hz, 1H), 8.03 (s, 1H), 7.70 (d, J=8.4 Hz, 1H), 7.62 (d, J=7.2 Hz, 2H), 7.49 (d, J=7.4 Hz, 2H), 7.42-7.40 (m, 1H), 7.31 (d, J=3.2 Hz, 1H), 6.78-6.77 (m, 1H), 4.59 (s, 2H). [M+H]$^+$: 319.

Example 213: N-(3-oxo-7-phenylisoindolin-4-yl)nicotinamide

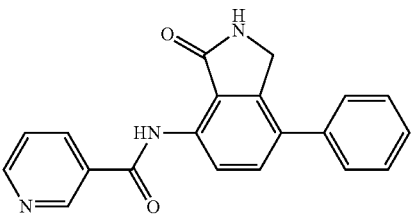 [SMILES: O=C(Nc1ccc(-c2ccccc2)c2c1C(=O)NC2)c1cccnc1]

$^1$H NMR (400 MHz, DMSO-d$_6$) δ 11.79 (s, 1H), 9.16 (s, 2H), 8.84 (dd, J=1.6, 4.8 Hz, 1H), 8.54 (d, J=8.4 Hz, 1H), 8.32 (d, J=8.0 Hz, 1H), 7.74 (d, J=8.4 Hz, 1H), 7.69-7.62 (m, 3H), 7.50 (t, J=7.6 Hz, 2H), 7.43-7.41 (m, 1H), 4.62 (s, 2H). [M+H]$^+$: 330.

Example 214: 4-Fluoro-N-(3-oxo-7-(quinolin-6-yl)isoindolin-4-yl)benzamide

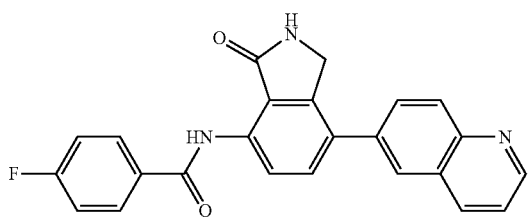 [SMILES: O=C(Nc1ccc(-c2ccc3ncccc3c2)c2c1C(=O)NC2)c1ccc(F)cc1]

$^1$H NMR (400 MHz, DMSO-d$_6$) δ 11.76 (s, 1H), 9.20 (s, 1H), 8.94 (d, J=4.2 Hz, 1H), 8.61 (d, J=8.4 Hz, 1H), 8.46 (d, J=8.3 Hz, 1H), 8.26 (d, J=2.0 Hz, 1H), 8.12 (d, J=8.7 Hz, 1H), 8.05 (dt, J=9.0, 4.5 Hz, 3H), 7.89 (d, J=8.5 Hz, 1H), 7.60 (dd, J=8.3, 4.4 Hz, 1H), 7.48 (t, J=8.6 Hz, 2H), 4.73 (s, 2H); [M+H]$^+$: 398.

Example 215: 4-Fluoro-N-(3-oxo-7-(quinolin-5-yl)isoindolin-4-yl)benzamide

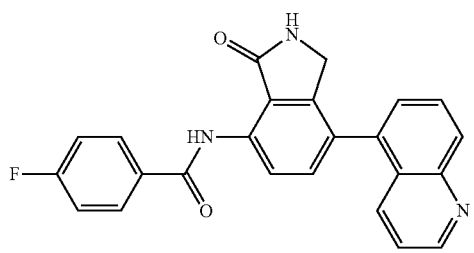 [SMILES: O=C(Nc1ccc(-c2cccc3ncccc23)c2c1C(=O)NC2)c1ccc(F)cc1]

$^1$H NMR (400 MHz, DMSO-d$_6$) δ 11.69 (s, 1H), 9.05 (s, 1H), 8.96 (dd, J=4.1, 1.6 Hz, 1H), 8.61 (d, J=8.3 Hz, 1H), 8.12 (dt, J=8.5, 1.1 Hz, 1H), 8.10-8.03 (m, 3H), 7.86 (dd, J=8.5, 7.1 Hz, 1H), 7.71 (dd, J=7.1, 1.2 Hz, 1H), 7.64 (d, J=8.3 Hz, 1H), 7.55-7.47 (m, 3H), 4.34 (s, 2H); [M+H]$^+$: 398.

Example 216: 4-Fluoro-N-(3-oxo-7-(quinolin-4-yl)isoindolin-4-yl)benzamide

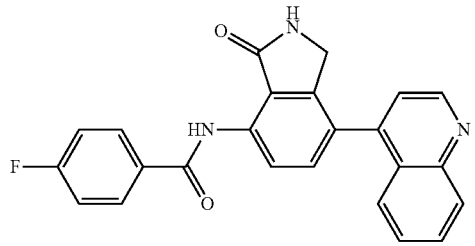 [SMILES: O=C(Nc1ccc(-c2ccnc3ccccc23)c2c1C(=O)NC2)c1ccc(F)cc1]

¹H NMR (400 MHz, DMSO-d₆) δ 11.71 (s, 1H), 9.09 (s, 1H), 8.99 (d, J=4.3 Hz, 1H), 8.64 (d, J=8.4 Hz, 1H), 8.14 (dd, J=8.6, 1.2 Hz, 1H), 8.10-8.05 (m, 2H), 7.83 (ddd, J=8.4, 6.8, 1.4 Hz, 1H), 7.74 (dd, J=8.5, 1.3 Hz, 1H), 7.71 (d, J=8.4 Hz, 1H), 7.64 (d, J=4.5 Hz, 1H), 7.62-7.58 (m, 1H), 7.53-7.46 (m, 2H), 4.30 (s, 2H); [M+H]⁺: 398.

Example 217: N-(7-(1H-indol-7-yl)-3-oxoisoindolin-4-yl)-4-fluorobenzamide

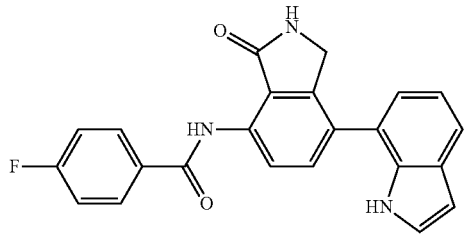 [SMILES: O=C(Nc1ccc(-c2cccc3cc[nH]c23)c2c1C(=O)NC2)c1ccc(F)cc1]

¹H NMR (400 MHz, DMSO-d₆) δ 11.73 (s, 1H), 10.95 (s, 1H), 9.04 (s, 1H), 8.60 (d, J=8.3 Hz, 1H), 8.08 (dd, J=8.5, 5.3 Hz, 2H), 7.73 (d, J=8.4 Hz, 1H), 7.61 (d, J=7.7 Hz, 1H), 7.50 (t, J=8.6 Hz, 2H), 7.33 (t, J=2.8 Hz, 1H), 7.14 (dd, J=20.1, 7.3 Hz, 2H), 6.54 (t, J=2.3 Hz, 1H), 4.33 (s, 2H); [M+H]⁺: 386.

Example 218: N-(7-(1H-benzo[d]imidazol-4-yl)-3-oxoisoindolin-4-yl)-4-fluorobenzamide

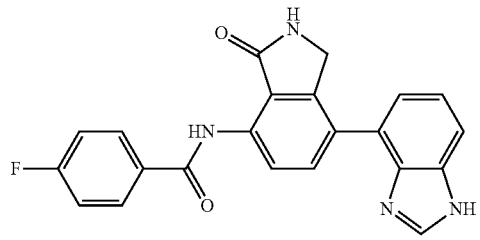 [SMILES: O=C(Nc1ccc(-c2cccc3[nH]cnc23)c2c1C(=O)NC2)c1ccc(F)cc1]

¹H NMR (400 MHz, DMSO-d₆) δ 12.65 (s, 1H), 11.74 (s, 1H), 9.03 (s, 1H), 8.57 (d, J=8.4 Hz, 1H), 8.28 (s, 1H), 8.10-8.03 (m, 2H), 7.85 (d, J=21.9 Hz, 1H), 7.62 (s, 1H), 7.53-7.44 (m, 2H), 7.33 (q, J=3.2, 2.5 Hz, 2H), 4.57 (s, 2H); [M+H]⁺: 387.

Example 219: N-(7-benzyl-3-oxoisoindolin-4-yl)-4-fluorobenzamide

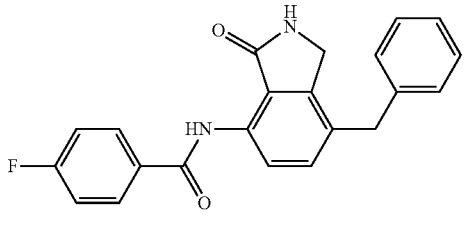 [SMILES: O=C(Nc1ccc(Cc2ccccc2)c2c1C(=O)NC2)c1ccc(F)cc1]

¹H NMR (400 MHz, DMSO-d₆) δ 11.44 (br s, 1H), 8.94 (br s, 1H), 8.37 (d, J=8.4 Hz, 1H), 8.02-7.98 (m, 2H), 7.47-7.42 (m, 3H), 7.32-7.28 (m, 2H), 7.25-7.19 (m, 3H), 4.29 (s, 2H), 4.00 (s, 2H); [M+H]⁺: 361.

Example 220: (R)-tert-butyl 2-((3-oxo-7-phenylisoindolin-4-yl)carbamoyl) pyrrolidine-1-carboxylate

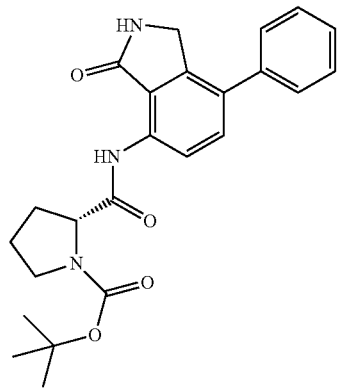 [SMILES: CC(C)(C)OC(=O)N1CCC[C@@H]1C(=O)Nc1ccc(-c2ccccc2)c2c1C(=O)NC2]

¹H NMR (400 MHz, DMSO-d₆) δ 10.89 (s, 1H), 10.77 (s, 1H), 9.03 (d, J=10.4 Hz, 2H), 8.29 (d, J=8.7 Hz, 2H), 7.74 (dd, J=8.7, 4.0 Hz, 2H), 4.32 (s, 2H), 4.21-4.15 (m, 2H), 3.56-3.54 (m, 1H), 3.52-3.46 (m, 1H), 3.43-3.39 (m, 2H), 1.97-1.94 (m, 2H), 1.23 (s, 9H); [M+H]⁺: 422.

Example 221: (R)—N-(3-oxo-7-phenylisoindolin-4-yl)pyrrolidine-2-carboxamide

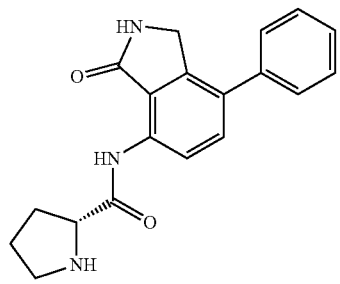 [SMILES: O=C1NCc2c(-c3ccccc3)ccc(NC(=O)[C@H]3CCCN3)c21]

¹H NMR (400 MHz, DMSO-d₆) δ 11.78 (s, 1H), 10.91 (s, 1H), 8.85 (s, 1H), 8.42 (d, J=8.7 Hz, 2H), 7.71 (dd, J=8.7, 5.4 Hz, 2H), 4.28 (s, 2H), 4.25-4.20 (m, 1H), 4.77 (dd, J=9.1, 5.0 Hz, 2H), 3.01-2.95 (m, 2H), 2.84-2.78 (m, 2H), 2.09-2.00 (m, 2H); [M+H]⁺: 322.

Example 222: 3-Amino-N-(2-methyl-3-oxo-7-phenylisoindolin-4-yl) benzamide

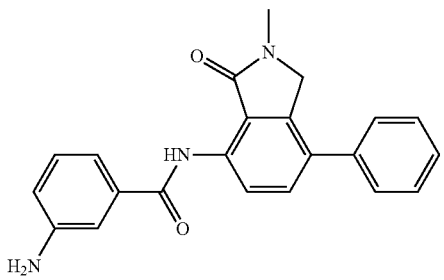 [SMILES: CN1Cc2c(-c3ccccc3)ccc(NC(=O)c3cccc(N)c3)c2C1=O]

[M+H]⁺: 358.
¹H NMR (400 MHz, DMSO-d₆) δ 11.49 (s, 1H), 8.58 (d, J=8.0 Hz, 1H), 7.69 (d, J=8.4 Hz, 1H), 7.61-7.59 (m, 2H), 7.52-7.48 (m, 2H), 7.43-7.39 (m, 1H), 7.25-7.20 (m, 2H), 7.11-7.09 (m, 1H), 6.83-6.80 (m, 1H), 5.45 (br s, 2H), 4.69 (s, 2H), 3.11 (s, 3H); MS (ESI) m/z 358 (M+H)⁺.

Example 223: 2-Amino-N-(2-methyl-3-oxo-7-phenylisoindolin-4-yl) benzamide

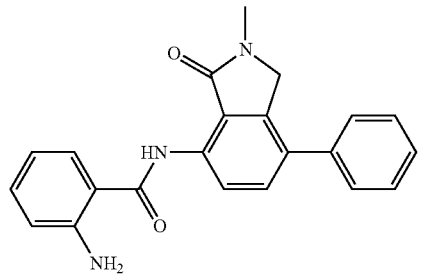 [SMILES: CN1Cc2c(-c3ccccc3)ccc(NC(=O)c3ccccc3N)c2C1=O]

[M+H]⁺: 358.
¹H NMR (400 MHz, DMSO-d₆) δ 11.48 (s, 1H), 8.55 (d, J=8.4 Hz, 1H), 7.68 (d, J=8.4 Hz, 1H), 7.65-7.59 (m, 3H), 7.52-7.48 (m, 2H), 7.43-7.39 (m, 1H), 7.29-7.25 (m, 1H), 6.83 (d, J=8.0 Hz, 1H), 6.72-6.64 (m, 3H), 4.69 (s, 2H), 3.11 (s, 3H); MS (ESI) m/z 358 (M+H)⁺.

Example 224: N-(7-(2,3-dimethoxyphenyl)-2-(furan-2-carbonyl)-3-oxoisoindolin-4-yl)furan-2-carboxamide

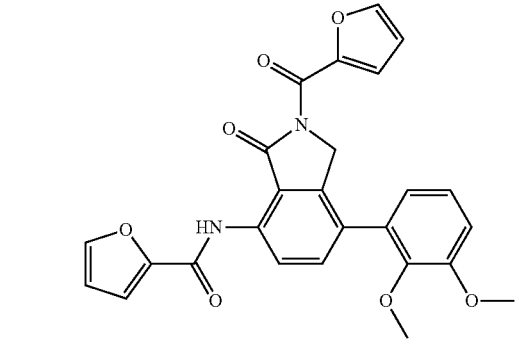 [SMILES: COc1cccc(-c2ccc(NC(=O)c3ccco3)c3c2CN(C(=O)c2ccco2)C3=O)c1OC]

¹H NMR (400 MHz, DMSO-d₆) δ 11.03 (br s, 1H), 8.59 (d, J=8.4 Hz, 1H), 8.07 (dd, J=3.6, 1.2 Hz, 1H), 7.72 (d, J=8.4 Hz, 1H), 7.64 (d, J=3.2 Hz, 1H), 7.37 (d, J=3.6 Hz, 1H), 7.22-7.14 (m, 2H), 6.97 (dd, J=7.2, 1.6 Hz, 1H), 6.79-6.77 (m, 2H), 4.89 (s, 2H), 3.87 (s, 3H), 3.49 (s, 3H); [M+H]⁺: 473.

Example 225: N-(7-(2,3-dimethoxyphenyl)-3-oxo-2-(thiophene-2-carbonyl) isoindolin-4-yl)thiophene-2-carboxamide

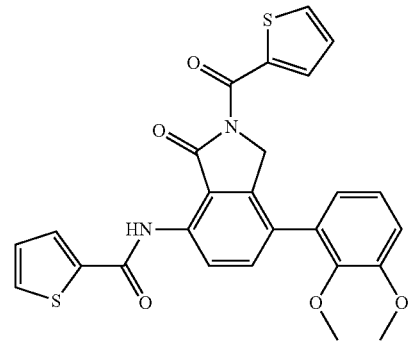 [SMILES: COc1cccc(-c2ccc(NC(=O)c3cccs3)c3c2CN(C(=O)c2cccs2)C3=O)c1OC]

¹H NMR (400 MHz, DMSO-d₆) δ 10.95 (br s, 1H), 8.48 (d, J=8.4 Hz, 1H), 8.13 (dd, J=3.8, 1.0 Hz, 1H), 8.04 (dd, J=5.0, 1.0 Hz, 1H), 7.99 (dd, J=5.0, 1.0 Hz, 1H), 7.79 (d, J=3.6 Hz, 1H), 7.73 (d, J=8.4 Hz, 1H), 7.32-7.29 (m, 1H), 7.28-7.25 (m, 1H), 7.23-7.15 (m, 2H), 6.97 (dd, J=7.4, 1.8 Hz, 1H), 4.90 (s, 2H), 3.88 (s, 3H), 3.50 (s, 3H); [M+H]⁺: 505.

Example 226: 1-(4-Fluorophenyl)-3-(3-oxo-7-phenylisoindolin-4-yl)urea

Scheme 6. Preparation of compound of Example 226

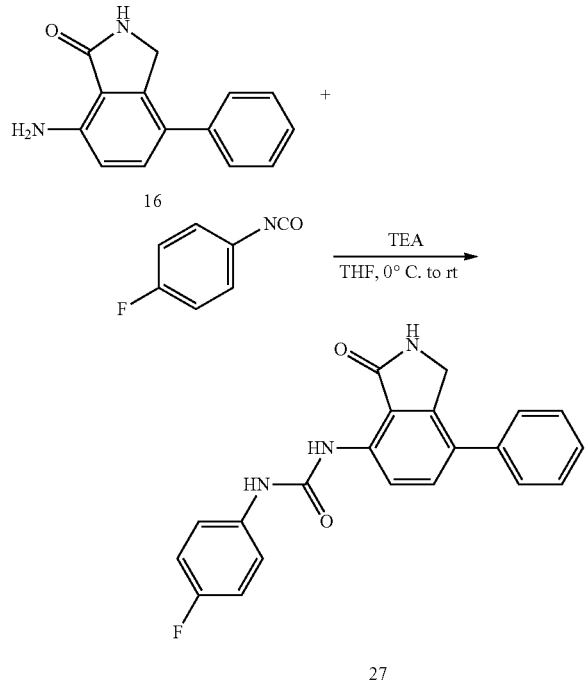

To a mixture of 7-amino-4-phenylisoindolin-1-one 16 (100 mg, 0.45 mmol) in THF (4 mL) was slowly added TEA (186 μL, 1.34 mmol) and 4-fluorophenyl isocyanate (61 μL, 0.54 mol) at 0° C. After warming the mixture to room temperature, the mixture was stirred for 12 hours. The solid thus obtained was washed with water to provide the title compound 27 (117 mg, 73%) as a white solid.

$^1$H NMR (400 MHz, DMSO-d$_6$) δ 9.53 (br s, 1H), 8.76 (br s, 1H), 8.30 (d, J=8.0 Hz, 1H), 7.57-7.51 (m, 4H), 7.45 (t, J=7.6 Hz, 2H), 7.35 (t, J=7.2 Hz, 1H), 4.49 (s, 2H), 3.08 (q, J=6.4 Hz, 2H), 1.43 (q, J=7.2 Hz, 2H), 1.35-1.29 (m, 2H), 0.90 (t, J=7.4 Hz, 3H); [M+H]$^+$: 324.

The following compounds of Examples 227 to 246 were obtained by using corresponding starting materials and repeating the procedure of Example 226.

Example 227: 1-(3-Oxo-7-phenylisoindolin-4-yl)-3-phenylurea

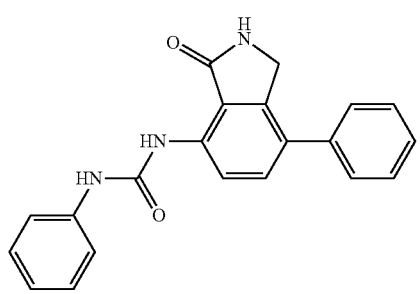 [SMILES: O=C(Nc1ccccc1)Nc1ccc(-c2ccccc2)c2c1C(=O)NC2]

$^1$H NMR (400 MHz, DMSO-d$_6$) δ 9.96 (br s, 1H), 9.86 (br s, 1H), 8.86 (s, 1H), 8.35 (d, J=8.4 Hz, 1H), 7.61-7.53 (m, 5H), 7.47 (t, J=7.8 Hz, 2H), 7.36-7.35 (m, 1H), 7.29 (t, J=7.8 Hz, 2H), 7.01-6.97 (m, 1H), 4.53 (s, 2H); [M+H]$^+$: 344.

Example 228: 1-(4-Cyanophenyl)-3-(3-oxo-7-phenylisoindolin-4-yl)urea

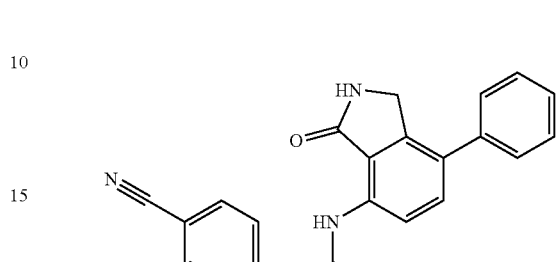

$^1$H NMR (400 MHz, DMSO-d$_6$) δ 10.48 (br s, 1H), 10.03 (br s, 1H), 8.92 (s, 1H), 8.35 (d, J=8.4 Hz, 1H), 7.75-7.74 (m, 4H), 7.64-7.58 (m, 3H), 7.49-7.45 (m, 2H), 7.40-7.38 (m, 1H), 4.55 (s, 2H); [M+H]$^+$: 369.

Example 229: 1-Butyl-3-(3-oxo-7-phenylisoindolin-4-yl)urea

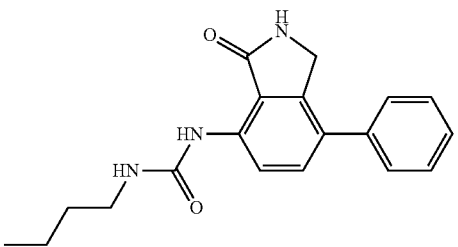 [SMILES: CCCCNC(=O)Nc1ccc(-c2ccccc2)c2c1C(=O)NC2]

$^1$H NMR (400 MHz, DMSO-d$_6$) δ 9.53 (br s, 1H), 8.76 (br s, 1H), 8.30 (d, J=8.0 Hz, 1H), 7.57-7.51 (m, 4H), 7.45 (t, J=7.6 Hz, 2H), 7.35 (t, J=7.2 Hz, 1H), 4.49 (s, 2H), 3.08 (q, J=6.4 Hz, 2H), 1.43 (q, J=7.2 Hz, 2H), 1.35-1.29 (m, 2H), 0.90 (t, J=7.4 Hz, 3H); [M+H]$^+$: 324.

Example 230: 1-(4-Methoxyphenyl)-3-(3-oxo-7-phenylisoindolin-4-yl)urea

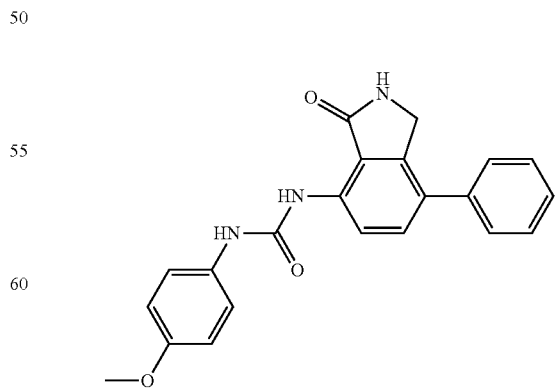

$^1$H NMR (400 MHz, DMSO-d$_6$) δ 9.80 (br s, 1H), 9.75 (br s, 1H), 8.83 (br s, 1H), 8.34 (d, J=8.4 Hz, 1H), 7.59-7.57 (m,

3H), 7.49-7.43 (m, 4H), 7.39-7.35 (m, 1H), 6.88 (d, J=9.2 Hz, 2H), 4.53 (s, 2H); [M+H]⁺: 374.

Example 231: 1-Cyclohexyl-3-(3-oxo-7-phenylisoindolin-4-yl)urea

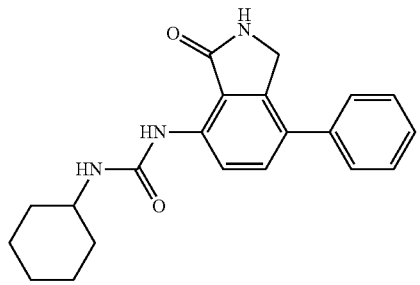 [SMILES: O=C(Nc1ccc(-c2ccccc2)c2c1C(=O)NC2)NC1CCCCC1]

¹H NMR (400 MHz, DMSO-d₆) δ 9.46 (br s, 1H), 8.75 (br s, 1H), 8.30 (d, J=8.8 Hz, 1H), 7.57-7.53 (m, 2H), 7.51-7.43 (m, 4H), 7.37-7.33 (m, 1H), 4.49 (s, 2H), 3.49-3.42 (m, 1H), 1.83-1.79 (m, 2H), 1.72-1.68 (m, 2H), 1.58-1.54 (m, 1H), 1.33-1.11 (m, 5H); [M+H]⁺: 350.

Example 232: 1-(3-Oxo-7-phenylisoindolin-4-yl)-3-(p-tolyl)urea

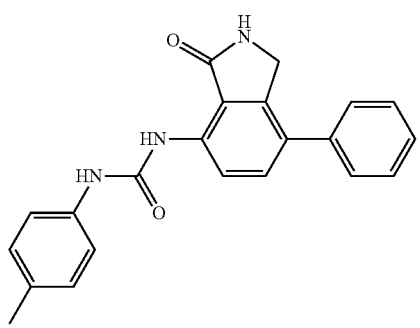 [SMILES: Cc1ccc(NC(=O)Nc2ccc(-c3ccccc3)c3c2C(=O)NC3)cc1]

¹H NMR (400 MHz, DMSO-d₆) δ 9.83-9.82 (m, 2H), 8.81 (br s, 1H), 8.35 (d, J=8.8 Hz, 1H), 7.59-7.57 (m, 3H), 7.49-7.37 (m, 5H), 7.10 (d, J=8.4 Hz, 2H), 4.52 (s, 2H), 2.25 (s, 3H); [M+H]⁺: 358.

Example 233: 1-(2-Methoxyphenyl)-3-(3-oxo-7-phenylisoindolin-4-yl)urea

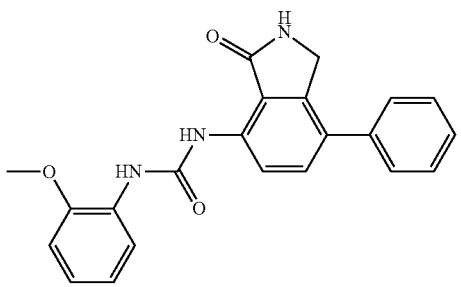 [SMILES: COc1ccccc1NC(=O)Nc1ccc(-c2ccccc2)c2c1C(=O)NC2]

¹H NMR (400 MHz, DMSO-d₆) δ 9.87 (br s, 1H), 9.22 (br s, 1H), 8.71 (br s, 1H), 8.27 (d, J=8.4 Hz, 1H), 7.85 (d, J=7.6 Hz, 1H), 7.59-7.55 (m, 3H), 7.47 (t, J=7.6 Hz, 2H), 7.37 (t, J=7.4 Hz, 1H), 7.04-7.03 (m, 2H), 6.93-6.88 (m, 1H), 4.50 (s, 2H), 3.85 (s, 3H); [M+H]⁺: 374.

Example 234: 1-Isopropyl-3-(3-oxo-7-phenylisoindolin-4-yl)urea

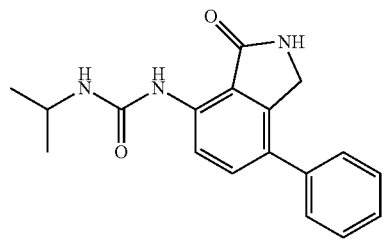 [SMILES: CC(C)NC(=O)Nc1ccc(-c2ccccc2)c2c1C(=O)NC2]

¹H NMR (400 MHz, DMSO-d₆) δ 9.46 (br s, 1H), 8.71 (br s, 1H), 8.30 (d, J=8.4 Hz, 1H), 7.56-7.51 (m, 3H), 7.47-7.43 (m, 3H), 7.37-7.34 (m, 1H), 4.48 (s, 2H), 3.81-3.76 (m, 1H), 1.11 (d, J=6.4 Hz, 6H); [M+H]⁺: 310.

Example 235: 1-(4-Nitrophenyl)-3-(3-oxo-7-phenylisoindolin-4-yl)urea

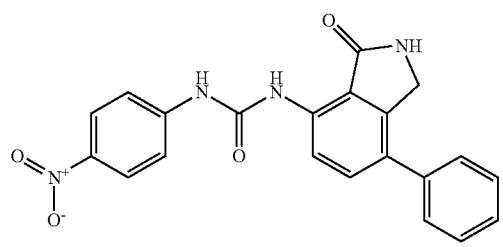 [SMILES: O=C(Nc1ccc([N+](=O)[O-])cc1)Nc1ccc(-c2ccccc2)c2c1C(=O)NC2]

¹H NMR (400 MHz, DMSO-d₆) δ 10.68 (br s, 1H), 10.08 (br s, 1H), 8.89 (br s, 1H), 8.36 (d, J=8.4 Hz, 1H), 8.21 (d, J=9.2 Hz, 2H), 7.80 (d, J=9.2 Hz, 2H), 7.63 (d, J=8.4 Hz, 1H), 8.36 (d, J=7.6 Hz, 2H), 7.48 (t, J=8.4 Hz, 2H), 8.36 (d, J=8.4 Hz, 1H), 7.38 (t, J=7.4 Hz, 1H), 4.54 (s, 2H); [M+H]⁺: 389.

Example 236: 1-Ethyl-3-(3-oxo-7-phenylisoindolin-4-yl)urea

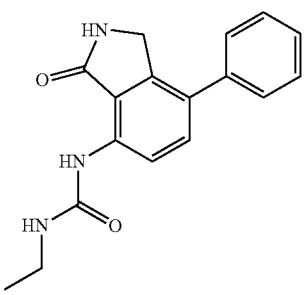 [SMILES: CCNC(=O)Nc1ccc(-c2ccccc2)c2c1C(=O)NC2]

¹H NMR (400 MHz, DMSO-d₆) δ 9.53 (s, 1H), 8.72 (s, 1H), 8.30 (d, J=8.5 Hz, 1H), 7.60-7.49 (m, 4H), 7.46 (t,

J=7.6 Hz, 2H), 7.36 (t, J=7.3 Hz, 1H), 4.49 (s, 2H), 3.17-3.05 (m, 2H), 1.07 (t, J=7.2 Hz, 3H); [M+H]⁺: 296.

Example 237: 1-(4-Acetylphenyl)-3-(3-oxo-7-phenylisoindolin-4-yl)urea

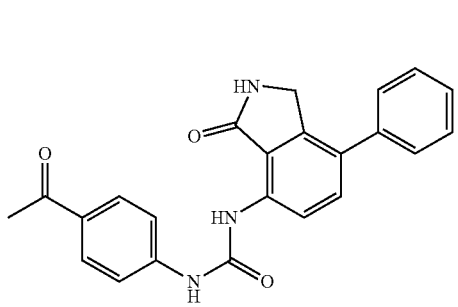 [SMILES: CC(=O)c1ccc(NC(=O)Nc2ccc(-c3ccccc3)c3c2C(=O)NC3)cc1]

¹H NMR (400 MHz, DMSO-d₆) δ 10.37 (s, 1H), 9.99 (s, 1H), 8.86 (s, 1H), 8.36 (d, J=8.5 Hz, 1H), 7.92 (d, J=8.4 Hz, 2H), 7.69 (d, J=8.4 Hz, 2H), 7.60 (dd, J=10.5, 7.8 Hz, 3H), 7.48 (t, J=7.5 Hz, 2H), 7.38 (t, J=7.3 Hz, 1H), 4.54 (s, 2H), 2.53 (s, 3H); [M+H]⁺: 386.

Example 238: 1-(3-Oxo-7-phenylisoindolin-4-yl)-3-(o-tolyl)urea

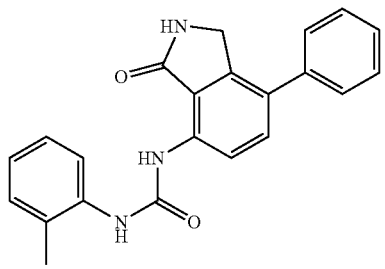 [SMILES: Cc1ccccc1NC(=O)Nc1ccc(-c2ccccc2)c2c1C(=O)NC2]

¹H NMR (400 MHz, DMSO-d₆) δ 9.86 (s, 1H), 9.16 (s, 1H), 8.76 (s, 1H), 8.32 (d, J=8.5 Hz, 1H), 7.61-7.54 (m, 3H), 7.46 (q, J=7.4 Hz, 3H), 7.37 (t, J=7.3 Hz, 1H), 7.25-7.12 (m, 2H), 7.06 (t, J=7.2 Hz, 1H), 4.51 (s, 2H), 2.26 (s, 3H); [M+H]⁺: 358.

Example 239: 1-Cyclopentyl-3-(3-oxo-7-phenylisoindolin-4-yl)urea

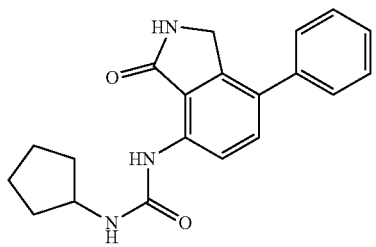 [SMILES: O=C(Nc1ccc(-c2ccccc2)c2c1C(=O)NC2)NC1CCCC1]

¹H NMR (400 MHz, DMSO-d₆) δ 9.47 (s, 1H), 8.71 (s, 1H), 8.31 (d, J=8.6 Hz, 1H), 7.59-7.49 (m, 4H), 7.45 (t, J=7.5 Hz, 2H), 7.35 (t, J=7.3 Hz, 1H), 4.48 (s, 2H), 3.96 (q, J=6.6 Hz, 1H), 1.87-1.79 (m, 2H), 1.66 (s, 2H), 1.52 (s, 2H), 1.48-1.38 (m, 2H); [M+H]⁺: 336.

Example 240: 1-(3-Fluorophenyl)-3-(3-oxo-7-phenylisoindolin-4-yl)urea

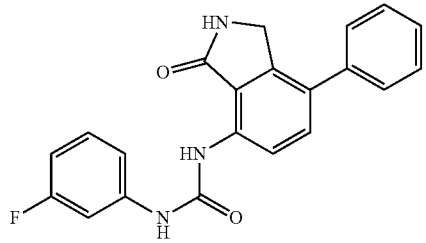 [SMILES: O=C(Nc1cccc(F)c1)Nc1ccc(-c2ccccc2)c2c1C(=O)NC2]

¹H NMR (400 MHz, DMSO-d₆) δ 10.17 (s, 1H), 9.92 (s, 1H), 8.85 (s, 1H), 8.35 (d, J=8.6 Hz, 1H), 7.64-7.43 (m, 6H), 7.38 (t, J=7.4 Hz, 1H), 7.37-7.22 (m, 2H), 6.81 (s, 1H), 4.53 (s, 2H); [M+H]⁺: 362.

Example 241: 1-(3-(Methylthio)phenyl)-3-(3-oxo-7-phenylisoindolin-4-yl) urea

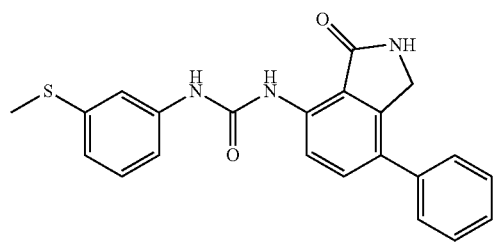 [SMILES: CSc1cccc(NC(=O)Nc2ccc(-c3ccccc3)c3c2C(=O)NC3)c1]

¹H NMR (400 MHz, DMSO-d₆) δ 9.98 (s, 1H), 9.88 (s, 1H), 8.83 (s, 1H), 8.35 (d, J=8.4 Hz, 1H), 7.69-7.58 (m, 3H), 7.53 (s, 1H), 7.47 (t, J=7.6 Hz, 2H), 7.37 (t, J=7.2 Hz, 1H), 7.30 (d, J=8.4 Hz, 1H), 7.22 (d, J=7.8 Hz, 1H), 6.88 (d, J=7.6 Hz, 1H), 4.53 (s, 2H), 2.46 (s, 3H). [M+H]⁺: 390.

Example 242: 1-(2-Fluorophenyl)-3-(3-oxo-7-phenylisoindolin-4-yl)urea

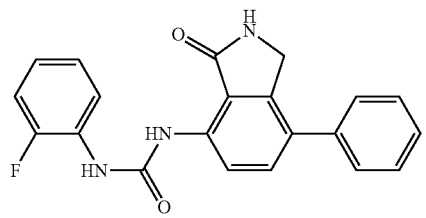 [SMILES: O=C(Nc1ccccc1F)Nc1ccc(-c2ccccc2)c2c1C(=O)NC2]

¹H NMR (400 MHz, DMSO-d₆) δ 9.96 (s, 1H), 9.80 (s, 1H), 8.78 (s, 1H), 8.30 (d, J=8.4 Hz, 1H), 7.91 (d, J=8.2 Hz, 1H), 7.59-7.57 (m, 3H), 7.49-7.45 (m, 2H), 7.39-7.35 (m, 1H), 7.26-7.09 (m, 3H), 4.52 (s, 2H). [M+H]⁺: 362.

Example 243: 1-(4-Chlorophenyl)-3-(3-oxo-7-phenylisoindolin-4-yl)urea

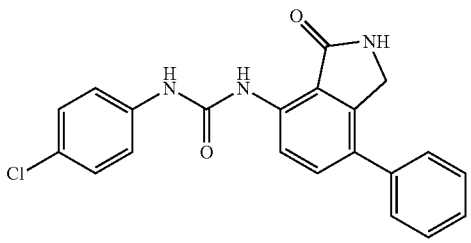 [SMILES: O=C(Nc1ccc(Cl)cc1)Nc1ccc(-c2ccccc2)c2c1C(=O)NC2]

¹H NMR (400 MHz, DMSO-d₆) δ 10.08 (s, 1H), 9.90 (s, 1H), 8.84 (s, 1H), 8.34 (d, J=8.4 Hz, 1H), 7.61-7.56 (m, 5H), 7.47 (t, J=7.6 Hz, 2H), 7.38 (d, J=7.2 Hz, 1H), 7.34 (d, J=8.8 Hz, 2H), 4.53 (s, 2H). [M+H]⁺: 378.

Example 244: 1-(7-(4-Methoxyphenyl)-3-oxoisoindolin-4-yl)-3-phenylurea

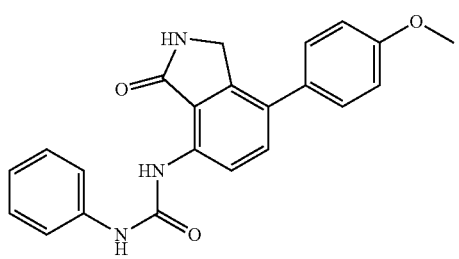 [SMILES: COc1ccc(-c2ccc(NC(=O)Nc3ccccc3)c3c2CNC3=O)cc1]

¹H NMR (400 MHz, DMSO-d₆) δ 9.93 (s, 1H), 9.83 (s, 1H), 8.84 (s, 1H), 8.32 (d, J=8.4 Hz, 1H), 7.56-7.51 (m, 5H), 7.29 (dd, J=8.0, 7.6 Hz, 2H), 7.04-7.01 (m, 3H), 4.51 (s, 2H), 3.80 (s, 3H). [M+H]⁺: 374.

Example 245: 1-(7-(4-Fluorophenyl)-3-oxoisoindolin-4-yl)-3-phenylurea

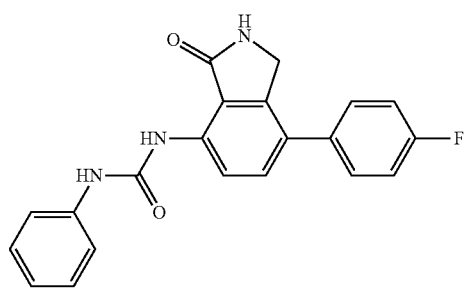 [SMILES: O=C(Nc1ccccc1)Nc1ccc(-c2ccc(F)cc2)c2c1C(=O)NC2]

¹H NMR (400 MHz, DMSO-d₆) δ 9.96 (s, 1H), 9.86 (s, 1H), 8.88 (s, 1H), 8.35 (d, J=8.4 Hz, 1H), 7.65-7.54 (m, 4H), 7.32-7.27 (m, 3H), 6.99 (t, J=7.2 Hz, 2H), 4.52 (s, 2H). [M+H]⁺: 362.

Example 246: 7-Amino-N-cyclohexyl-1-oxo-4-phenylisoindolin-2-carboxamide

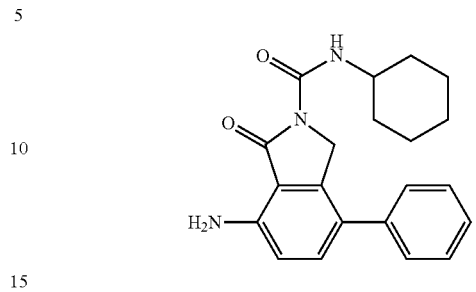

¹H NMR (400 MHz, DMSO-d₆) δ 8.44 (d, J=7.6 Hz, 1H), 7.51-7.49 (m, 2H), 7.46-7.42 (m, 3H), 7.34-7.30 (m, 1H), 6.77 (d, J=8.4 Hz, 1H), 6.48 (br s, 2H), 4.80 (s, 2H), 1.87-1.82 (m, 2H), 1.66-1.62 (m, 2H), 1.55-1.52 (m, 1H), 1.40-1.23 (m, 6H); [M+H]⁺: 350.

Example 247: 1-(3-Oxo-7-phenylisoindolin-4-yl)-3-phenylthiourea

Scheme 7. Preparation of compound of Example 247

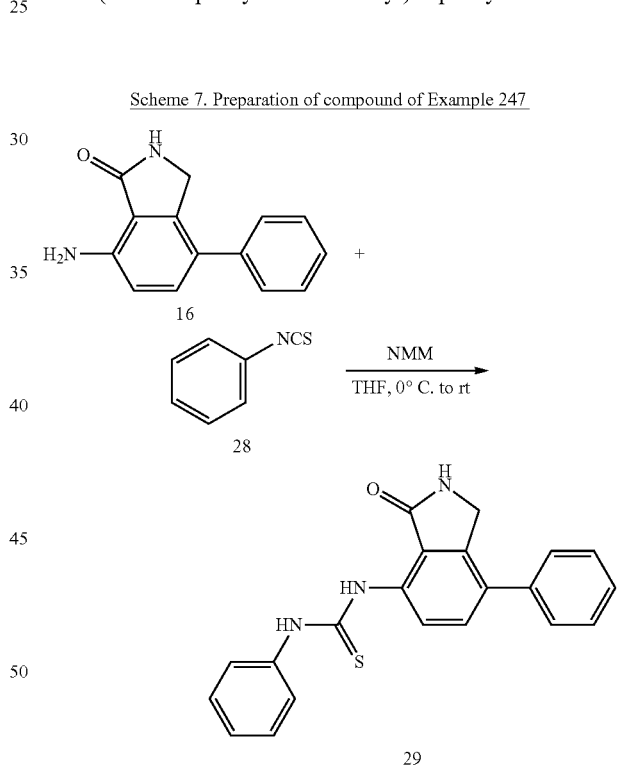

To a mixture of 7-amino-4-phenylisoindolin-1-one 16 (100 mg, 0.45 mmol) in THF (4 mL) was slowly added NMM (150 μL, 1.35 mmol) and phenyl isothiocyanate (61 μL, 0.54 mol) at 0° C. After warming the mixture to room temperature, the mixture was stirred for 12 hours. The solid thus obtained was washed with water to give the title compound 29 (41 mg, 25%) as a white solid.

¹H NMR (400 MHz, DMSO-d₆) δ 10.87 (br s, 1H), 10.67 (br s, 1H), 8.96 (d, J=8.4 Hz, 1H), 8.87 (br s, 1H), 7.63-7.58 (m, 3H), 7.50-7.46 (m, 4H), 7.23-7.19 (m, 3H), 7.21 (t, J=7.4 Hz, 1H), 4.53 (s, 2H); [M+H]⁺: 360.

Example 248: Phenyl (3-oxo-7-phenylisoindolin-4-yl)carbamate

Scheme 8. Total scheme for compound of Example 248

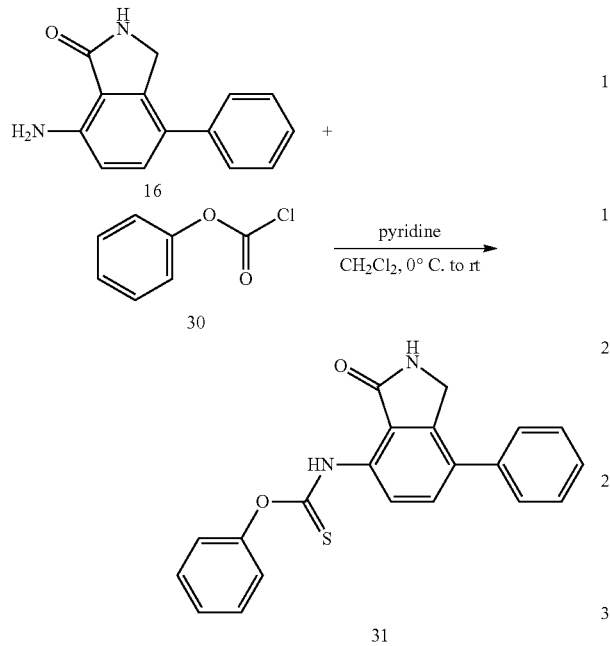

To a mixture of 7-amino-4-phenylisoindolin-1-one 16 (100 mg, 0.45 mmol) in CH$_2$Cl$_2$/pyridine (2/0.4 mL) was slowly added phenyl chloroformate (61 μL, 0.49 mmol) at 0° C. After warming the mixture to room temperature, the mixture was stirred for 1 hour. The solid thus obtained was washed with CH$_2$Cl$_2$ to provide the title compound 31 (45 mg, 29%) as a white solid.

$^1$H NMR (400 MHz, DMSO-d$_6$) δ 10.46 (br s, 1H), 9.07 (br s, 1H), 8.10 (d, J=8.4 Hz, 1H), 7.70 (d, J=8.8 Hz, 1H), 7.62-7.59 (m, 2H), 7.51-7.44 (m, 4H), 7.42-7.37 (m, 1H), 7.32-7.28 (m, 3H), 4.59 (s, 2H); [M+H]$^+$: 345.

Example 249: N-(3-oxo-7-phenylisoindolin-4-yl)benzenesulfonamide

Scheme 9. Preparation of compound of Example 249

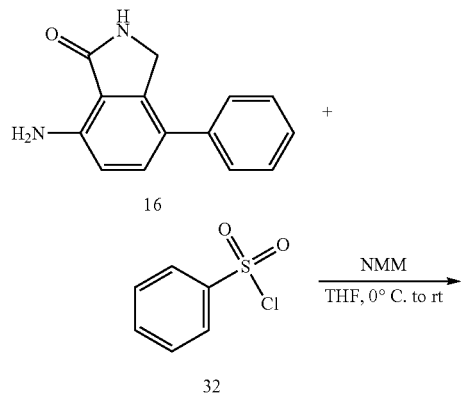

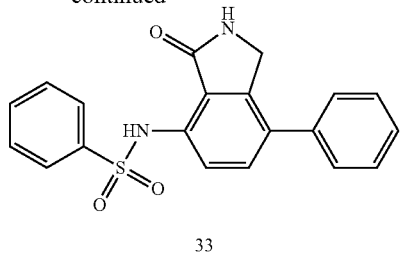

To a mixture of 7-amino-4-phenylisoindolin-1-one 16 (100 mg, 0.45 mmol) in THF (2.2 mL) was slowly added NMM (0.15 mL, 1.34 mmol) and benzenesulfonyl chloride (86 μL, 0.67 mol) at 0° C. The reaction mixture was stirred at room temperature for 12 hours, and then poured into water at 0° C. The solid thus obtained was washed with water to give N-(3-oxo-7-phenylisoindolin-4-yl)benzenesulfonamide 33 (150 mg, 94%) as a white solid.

$^1$H NMR (400 MHz, DMSO-d$_6$) δ 10.38 (s, 1H), 9.05 (s, 1H), 7.93 (d, J=7.6 Hz, 2H), 7.69-7.65 (m, 1H), 7.62-7.58 (m, 2H), 7.53-7.49 (m, 2H), 7.47-7.42 (m, 2H), 7.38-7.35 (m, 1H), 4.50 (s, 2H). [M+H]$^+$: 365.

The following compounds of Examples 250 to 252 were obtained by using corresponding starting materials and repeating the procedure of Example 249.

Example 250: N-(3-oxo-7-phenylisoindolin-4-yl)methanesulfonamide

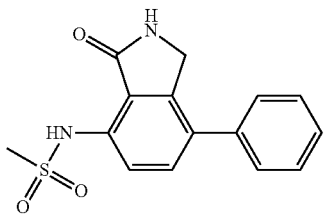 [SMILES: CS(=O)(=O)Nc1ccc(-c2ccccc2)c2c1C(=O)NC2]

$^1$H NMR (400 MHz, DMSO-d$_6$) δ 9.87 (s, 1H), 9.05 (s, 1H), 7.67 (d, J=8.4 Hz, 1H), 7.59 (d, J=7.6 Hz, 2H), 7.52-7.47 (m, 3H), 7.42-7.38 (m, 1H), 4.57 (s, 2H), 3.25 (s, 3H). [M+H]$^+$: 303.

Example 251: 4-Fluoro-N-(3-oxo-7-phenylisoindolin-4-yl)benzenesulfonamide

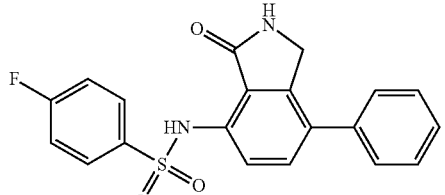

$^1$H NMR (400 MHz, DMSO-d$_6$) δ 10.38 (s, 1H), 9.06 (s, 1H), 8.02-7.99 (m, 2H), 7.61 (d, J=8.0 z, 1H), 7.54d, J=7.2 Hz, 2H), 7.49-7.42 (m, 5H), 7.39-7.35 (m, 3H), 4.51 (s, 2H). [M+H]$^+$: 383.

Example 252: 4-Methoxy-N-(3-oxo-7-phenylisoindolin-4-yl)benzene sulfonamide

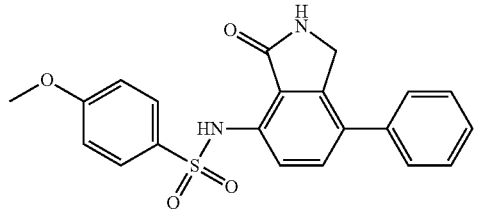 [SMILES: COc1ccc(S(=O)(=O)Nc2ccc(-c3ccccc3)c3c2C(=O)NC3)cc1]

$^1$H NMR (400 MHz, DMSO-d$_6$) δ 10.28 (s, 1H), 9.04 (s, 1H), 7.85 (d, J=8.8 Hz, 2H), 7.59 (d, J=8.4 Hz, 1H), 7.53 (d, J=7.2 Hz, 2H), 7.48-7.43 (m, 3H), 7.39-7.35 (m, 1H), 7.10 (d, J=9.2 Hz, 2H), 4.50 (s, 2H), 3.80 (s, 3H). [M+H]$^+$: 395.

Example 253: 7-((2-Chloroethyl)amino)-4-phenylisoindolin-1-one

Scheme 10. Preparation of compound of Example 253

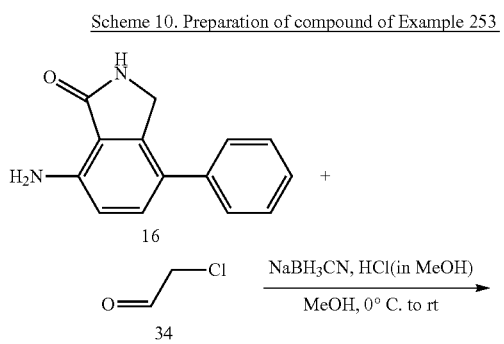

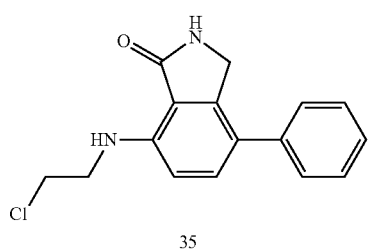

To a mixture of 7-amino-4-phenylisoindolin-1-one 16 (800 mg, 3.57 mmol) and NaBH$_3$CN (450 mg, 7.13 mmol) in methanol (18 mL) was added chloroacetaldehyde (0.7 mL, 5.35 mmol) and HCl (in methanol solution, 1.25M 5.7 mL) at 0° C. The reaction mixture was stirred at room temperature for 12 hours, and then poured to water at 0° C. The precipitate was washed with water to give the title compound (940 mg, 92%) as a white solid.

$^1$H NMR (400 MHz, DMSO-d$_6$) δ 8.42 (s, 1H), 7.54-7.49 (m, 2H), 7.44-7.40 (m, 3H), 7.30 (t, J=7.4 Hz, 1H), 7.20 (d, J=6.2 Hz, 1H), 6.78 (d, J=8.4 Hz, 1H), 4.43 (s, 2H), 3.81 (t, J=6.0 Hz, 2H), 3.62 (q, J=6.0 Hz, 2H). [M+H]$^+$: 287.

Example 254: 3-((3-Oxo-7-phenylisoindolin-4-yl)amino)propanenitrile

Scheme 11. Preparation of compound of Example 254

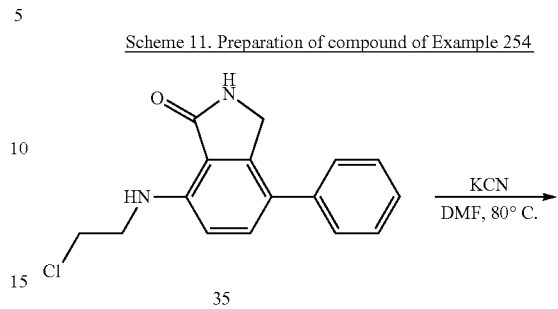

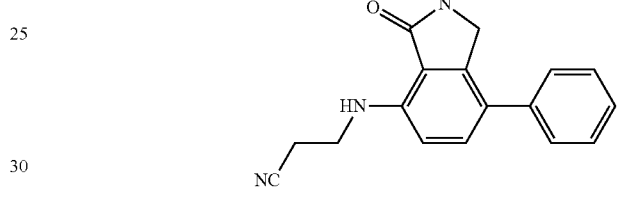

A mixture of 7-((2-chloroethyl)amino)-4-phenylisoindolin-1-one 35 (100 mg, 0.35 mmol) and KCN (34 mg, 0.52 mmol) in DMF (1.7 mL) was stirred at 80° C. for 12 hours. The reaction mixture was poured to ice water, filtered, washed with water, and dried to give the title compound 36 (89 mg, 92%).

$^1$H NMR (400 MHz, DMSO-d$_6$) δ 8.43 (s, 1H), 7.52-7.50 (m, 2H), 7.45-7.40 (m, 3H), 7.30 (t, J=7.4 Hz, 1H), 7.16 (t, J=6.6 Hz, 1H), 6.82 (d, J=8.4 Hz, 1H), 4.44 (s, 2H), 3.59 (q, J=6.4 Hz, 2H), 2.81 (t, J=6.4 Hz, 2H). [M+H]$^+$: 278.

The following compounds of Examples 255 to 270 were obtained by using corresponding starting materials and repeating the procedure of Example 254.

Example 255: 7-((2-(Dimethylamino)ethyl)amino)-4-phenylisoindolin-1-one

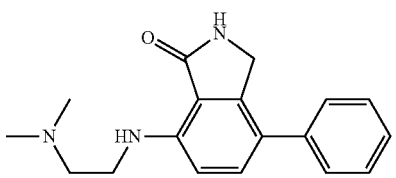 [SMILES: CN(C)CCNc1ccc(-c2ccccc2)c2c1C(=O)NC2]

$^1$H NMR (400 MHz, DMSO-d$_6$) δ 8.34 (s, 1H), 7.49 (d, J=7.2 Hz, 2H), 7.41 (t, J=8.0 Hz, 3H), 7.29 (t, J=7.2 Hz, 1H), 7.02 (t, J=5.4 Hz, 1H), 6.68 (d, J=8.4 Hz, 1H), 4.42 (s, 2H), 3.26 (q, J=6.0 Hz, 2H), 2.49 (t, J=6.0 Hz, 2H), 2.19 (s, 6H). [M+H]$^+$: 296.

Example 256: 7-((2-Hydroxyethyl)amino)-4-phenylisoindolin-1-one

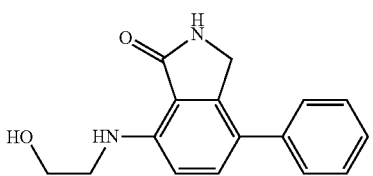 [SMILES: O=C1NCc2c(-c3ccccc3)ccc(NCCO)c21]

¹H NMR (400 MHz, DMSO-d₆) δ 8.36 (s, 1H), 7.49 (d, J=7.6 Hz, 2H), 7.43-7.39 (m, 3H), 7.49 (t, J=7.6 Hz, 1H), 7.06 (t, J=5.4 Hz, 1H), 6.70 (d, J=8.8 Hz, 1H), 4.86 (br, s, 1H), 4.42 (s, 2H), 3.61 (t, J=5.6 Hz, 2H), 3.27 (t, J=5.6 Hz, 2H), 2.19 (s, 6H). [M+H]⁺: 269.

Example 257: 2-(2-((3-Oxo-7-phenylisoindolin-4-yl)amino)ethyl)isoindolin-1,3-dione

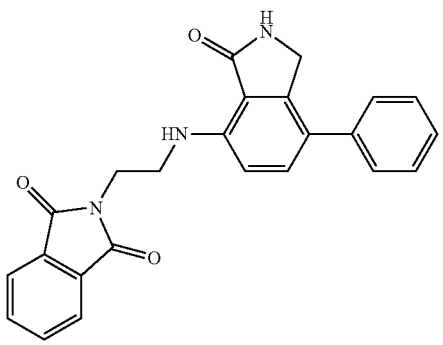 [SMILES: O=C1NCc2c(-c3ccccc3)ccc(NCCN3C(=O)c4ccccc4C3=O)c21]

¹H NMR (400 MHz, DMSO-d₆) δ 8.33 (s, 1H), 7.88-7.81 (m, 4H), 7.48-7.46 (m, 2H), 7.43-7.38 (m, 3H), 7.29 (t, J=7.2 Hz, 1H), 7.09 (t, J=6.6 Hz, 1H), 6.80 (d, J=8.8 Hz, 1H), 4.40 (s, 2H), 3.79 (t, J=6.2 Hz, 2H), 3.55 (q, J=6.4 Hz, 2H). [M+H]⁺: 398.

Example 258: 7-((2-(4-Methylpiperazin-1-yl)ethyl)amino)-4-phenylisoindolin-1-one

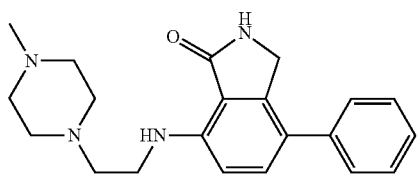 [SMILES: CN1CCN(CCNc2ccc(-c3ccccc3)c3c2C(=O)NC3)CC1]

¹H NMR (400 MHz, DMSO-d₆) δ 8.29 (s, 1H), 7.49 (d, J=6.8 Hz, 2H), 7.43-7.39 (m, 3H), 7.29 (t, J=7.2 Hz, 1H), 7.08 (t, J=5.2 Hz, 1H), 6.68 (d, J=8.8 Hz, 1H), 4.41 (s, 2H), 3.29 (q, J=5.6 Hz, 2H), 2.56 (t, J=6.4 Hz, 2H), 2.43 (br.s, 4H), 2.33 (br.s, 4H), 2.15 (s, 3H). [M+H]⁺: 351.

Example 259: 4-Phenyl-7-((2-(piperidin-1-yl)ethyl)amino)isoindolin-1-one

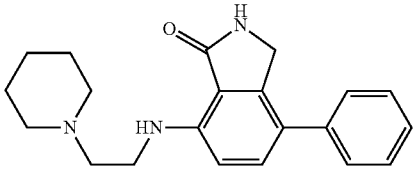 [SMILES: O=C1NCc2c(-c3ccccc3)ccc(NCCN3CCCCC3)c21]

¹H NMR (400 MHz, DMSO-d₆) δ 8.28 (s, 1H), 7.49 (d, J=7.2 Hz, 2H), 7.43-7.39 (m, 3H), 7.29 (t, J=7.4 Hz, 1H), 7.10 (t, J=5.4 Hz, 1H), 6.67 (d, J=8.4 Hz, 1H), 4.41 (s, 2H), 3.27 (q, J=6.0 Hz, 2H), 2.52 (t, J=6.4 Hz, 2H), 2.38 (br.s, 4H), 1.53-1.49 (m, 4H), 1.42-1.39 (m, 2H). [M+H]⁺: 336.

Example 260: 7-((2-Morpholinoethyl)amino)-4-phenylisoindolin-1-one

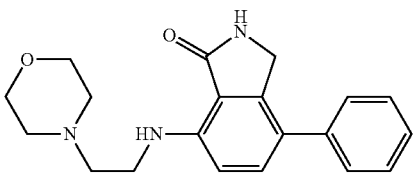 [SMILES: O=C1NCc2c(-c3ccccc3)ccc(NCCN3CCOCC3)c21]

¹H NMR (400 MHz, DMSO-d₆) δ 8.30 (s, 1H), 7.49 (d, J=7.2 Hz, 2H), 7.43-7.39 (m, 3H), 7.29 (t, J=7.4 Hz, 1H), 7.12 (t, J=5.2 Hz, 1H), 6.69 (d, J=8.4 Hz, 1H), 4.42 (s, 2H), 3.60 (t, J=4.4 Hz, 4H), 3.31 (q, J=5.6 Hz, 2H), 2.57 (t, J=6.4 Hz, 2H), 2.43 (br.s, 4H). [M+H]⁺: 338.

Example 261: 7-((2-(Methylamino)ethyl)amino)-4-phenylisoindolin-1-one

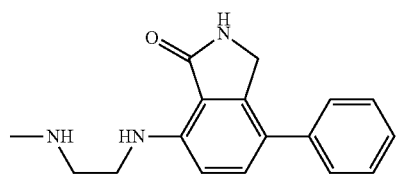 [SMILES: CNCCNc1ccc(-c2ccccc2)c2c1C(=O)NC2]

¹H NMR (400 MHz, DMSO-d₆) δ 8.33 (s, 1H), 7.50-7.48 (m, 2H), 7.43-7.39 (m, 3H), 7.30-7.27 (m, 1H), 7.05 (t, J=5.6 Hz, 1H), 6.69 (d, J=8.4 Hz, 1H), 4.41 (s, 2H), 3.26 (q, J=6.0 Hz, 2H), 2.71 (t, J=6.2 Hz, 2H), 2.31 (s, 3H). [M+H]⁺: 282.

Example 262: 4-Phenyl-7-((2-(pyrrolidin-1-yl)ethyl)amino)isoindolin-1-one

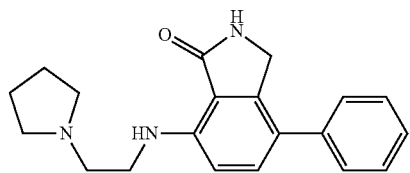 [SMILES: O=C1NCc2c(-c3ccccc3)ccc(NCCN3CCCC3)c21]

¹H NMR (400 MHz, DMSO-d₆) δ 8.31 (s, 1H), 7.50-7.48 (m, 2H), 7.43-7.39 (m, 3H), 7.31-7.27 (m, 1H), 7.04 (t, J=5.6 Hz, 1H), 6.68 (d, J=8.4 Hz, 1H), 4.42 (s, 2H), 3.31 (q, J=6.0 Hz, 4H), 2.67 (t, J=6.4 Hz, 2H), 1.72-1.68 (m, 4H). [M+H]⁺: 322.

Example 263:
7-(Benzylamino)-4-phenylisoindolin-1-one

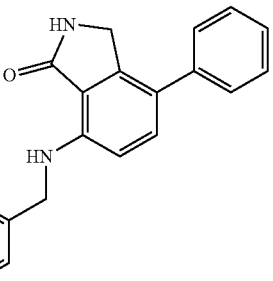

¹H NMR (400 MHz, DMSO-d₆) δ 8.41 (s, 1H), 7.50-7.46 (m, 2H), 7.45-7.32 (m, 8H), 7.32-7.22 (m, 2H), 6.62 (d, J=8.5 Hz, 1H), 4.50 (d, J=6.2 Hz, 2H), 4.42 (d, J=12.2 Hz, 2H); [M+H]⁺: 315.

Example 264: 2-(3-((3-Oxo-7-phenylisoindolin-4-yl)amino)propyl)isoindolin-1,3-dione

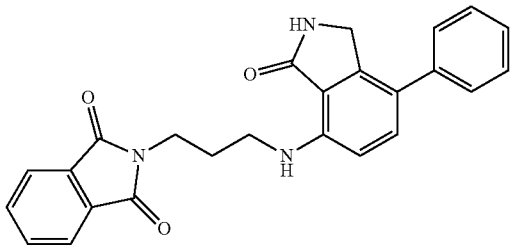 [SMILES: O=C1NCc2c(-c3ccccc3)ccc(NCCCN3C(=O)c4ccccc4C3=O)c21]

¹H NMR (400 MHz, CDCl₃) δ 7.85 (dd, J=5.4, 3.0 Hz, 2H), 7.71 (dd, J=5.5, 3.0 Hz, 2H), 7.44-7.36 (m, 5H), 7.33-7.27 (m, 1H), 7.00 (br s, 1H), 6.64 (d, J=8.4 Hz, 1H), 5.81 (s, 1H), 4.44 (s, 2H), 3.86 (t, J=6.8 Hz, 2H), 3.35 (t, J=7.0 Hz, 2H), 2.08 (p, J=6.9 Hz, 2H); [M+H]⁺: 412.

Example 265: 4-(Pyridin-4-yl)-7-(pyrrolidin-1-yl)isoindolin-1-one

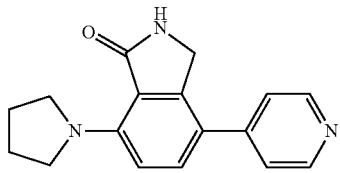 [SMILES: O=C1NCc2c(-c3ccncc3)ccc(N3CCCC3)c21]

¹H NMR (400 MHz, DMSO-d₆) δ 8.57 (s, 1H), 8.48 (dd, J=4.4, 1.6 Hz, 2H), 7.39 (dd, J=4.4, 1.6 Hz, 2H), 7.20 (d, J=8.4 Hz, 1H), 6.74 (d, J=8.4 Hz, 1H), 4.62 (s, 2H), 3.47 (t, J=6.4 Hz, 4H), 1.94 (t, J=6.4 Hz, 4H). [M+H]⁺: 280.

Example 266: 7-(Dimethylamino)-4-(2-((3-methoxyphenyl)amino)pyrimidin-4-yl)isoindolin-1-one

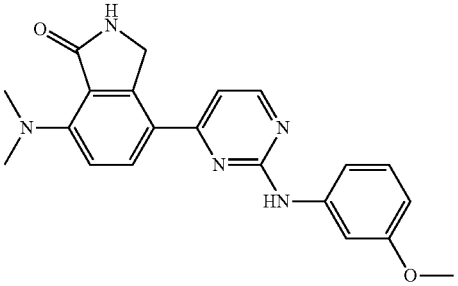

¹H NMR (400 MHz, DMSO-d₆) δ 9.47 (s, 1H), 8.48 (d, J=5.6 Hz, 1H), 8.42 (s, 1H), 8.03 (d, J=8.4 Hz, 1H), 7.45 (t, J=2.2 Hz, 1H), 7.34 (d, J=8.4 Hz, 1H), 7.25 (d, J=5.6 Hz, 1H), 7.19 (t, J=8.2 Hz, 1H), 6.95 (d, J=8.4 Hz, 1H), 6.55 (dd, J=8.4, 2.0 Hz, 1H), 4.71 (s, 2H), 3.74 (s, 3H), 3.01 (s, 6H). [M+H]⁺: 376.

Example 267: 7-(Dimethylamino)-4-(2-((3-fluorophenyl)amino)pyrimidin-4-yl)isoindolin-1-one

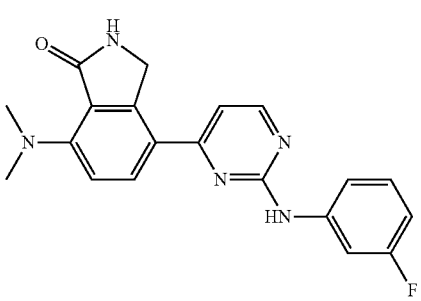 [SMILES: CN(C)c1ccc(-c2ccnc(Nc3cccc(F)c3)n2)c2c1C(=O)NC2]

¹H NMR (400 MHz, DMSO-d₆) δ 9.72 (s, 1H), 8.52 (d, J=5.2 Hz, 1H), 8.44 (s, 1H), 8.03 (d, J=8.8 Hz, 1H), 7.79 (d, J=12.8 Hz, 2H), 7.50 (d, J=8.0 Hz, 1H), 7.35-7.29 (m, 2H), 6.97 (d, J=8.8 Hz, 1H), 6.76 (t, J=8.8 Hz, 1H), 4.71 (s, 2H), 3.01 (s, 6H). [M+H]⁺: 364.

Example 268: 7-(Butylamino)-4-(2-((3-methoxyphenyl)amino)pyrimidin-4-yl)isoindolin-1-one

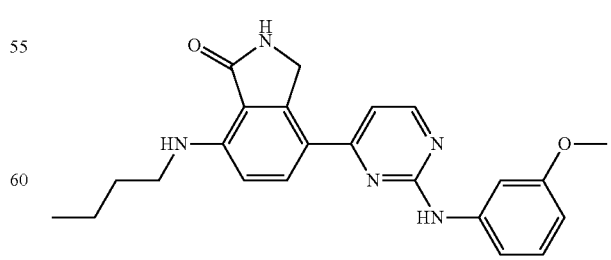

¹H NMR (400 MHz, DMSO-d₆) δ 9.37 (s, 1H), 8.57 (s, 1H), 8.42 (d, J=5.2 Hz, 1H), 8.04 (d, J=8.8 Hz, 1H), 7.45 (s, 1H), 7.32 (d, J=6.4 Hz, 2H), 7.20 (t, J=6.4 Hz, 1H), 6.72 (d,

J=8.8 Hz, 1H), 6.54 (dd, J=8.2, 1.2 Hz, 1H), 4.73 (s, 2H), 3.74 (s, 3H), 3.27 (q, J=6.4 Hz, 2H), 1.59 (qunt, J=7.4 Hz, 2H), 1.40 (sextet, J=7.4 Hz, 2H), 0.93 (t, J=7.2 Hz, 3H). [M+H]⁺: 403.

Example 269: 7-(Butyl(methyl)amino)-4-(2-((3-methoxyphenyl)amino) pyrimidin-4-yl)isoindolin-1-one

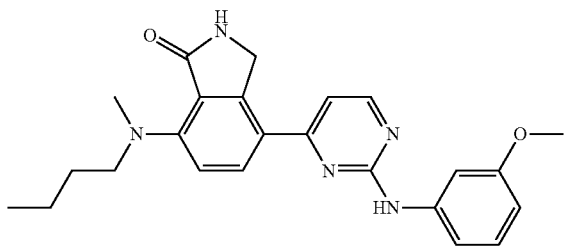 [SMILES: CCCCN(C)c1ccc(-c2ccnc(Nc3cccc(OC)c3)n2)c2c1C(=O)NC2]

¹H NMR (400 MHz, DMSO-d₆) δ 9.46 (s, 1H), 8.47 (d, J=5.6 Hz, 1H), 8.38 (s, 1H), 8.00 (d, J=8.4 Hz, 1H), 7.45 (s, 1H), 7.33 (d, J=8.0 Hz, 1H), 7.24-7.17 (m, 2H), 6.94 (d, J=9.2 Hz, 1H), 6.54 (d, J=8.0 Hz, 1H), 4.70 (s, 2H), 3.74 (s, 3H), 3.50 (t, J=7.6 Hz, 2H), 2.97 (s, 3H), 1.55-1.50 (m, 2H), 1.23-1.18 (m, 2H), 0.86-0.81 (m, 3H). [M+H]⁺: 418.

Example 270: 7-(Butyl(methyl)amino)-4-(2-((3-methoxyphenyl)amino) pyrimidin-4-yl)-2-methyl-isoindolin-1-one

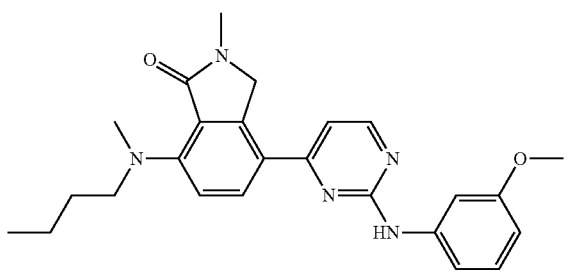 [SMILES: CCCCN(C)c1ccc(-c2ccnc(Nc3cccc(OC)c3)n2)c2c1C(=O)N(C)C2]

¹H NMR (400 MHz, DMSO-d₆) δ 9.42 (s, 1H), 8.48 (d, J=5.2 Hz, 1H), 8.01 (d, J=8.8 Hz, 1H), 7.42 (s, 1H), 7.31-7.20 (m, 3H), 6.96 (d, J=8.4 Hz, 1H), 6.58 (d, J=7.6 Hz, 1H), 4.76 (s, 2H), 3.75 (s, 3H), 3.48 (t, J=7.2 Hz, 2H), 3.02 (s, 3H), 2.96 (s, 3H), 1.55-1.50 (m, 2H), 1.23-1.18 (m, 2H), 0.86-0.82 (m, 3H). [M+H]⁺: 432.

Scheme 12. Total scheme for compound 40

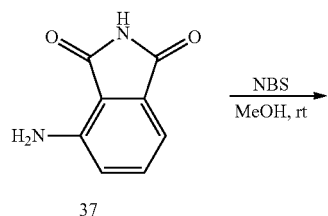

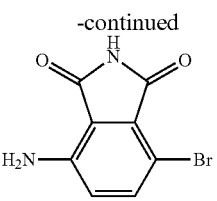

+

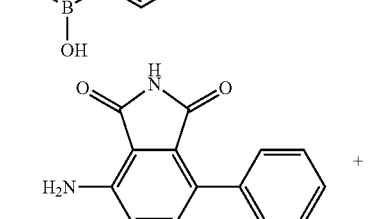

+

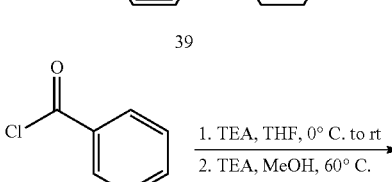

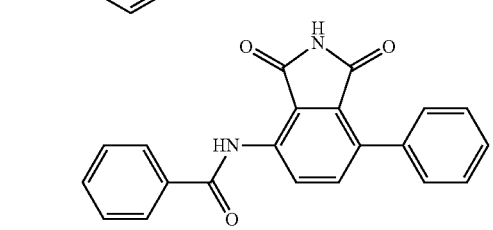

Example 271:
4-Amino-7-phenylisoindolin-1,3-dione

Step 1: Preparation of
4-amino-7-bromoisoindolin-1,3-dione (38)

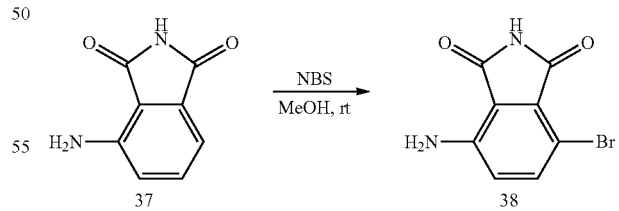

To a solution of 4-aminoisoindolin-1,3-dione (37) (0.5 g, 3.08 mmol) in MeOH (50 mL) was added a mixture of NBS (0.58 g, 3.24 mmol) as three portions at room temperature. Then, the mixture thus obtained was stirred at room temperature for 8 hours, and filtered. The filtrate was concentrated to give the crude product of 4-aminoisoindolin-1,3-dione 38 (0.42 g) as a solid, which was directly used in the next step without further purification.

Step 2: Preparation of 4-amino-7-phenylisoindolin-1,3-dione (39)

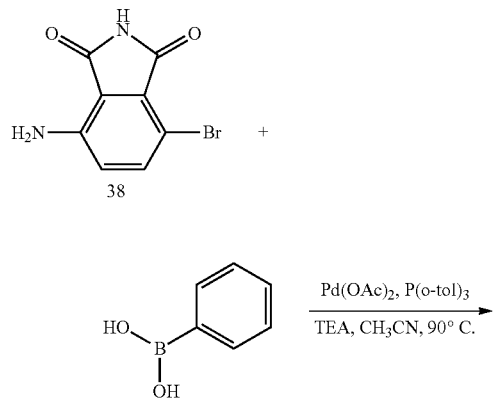

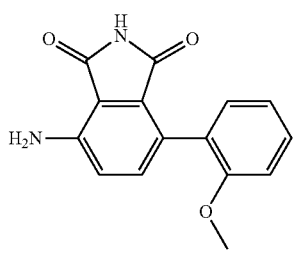 [SMILES: COc1ccccc1-c1ccc(N)c2c1C(=O)NC2=O]

To a stirred suspension solution of 4-amino-7-bromoisoindolin-1,3-dione 38 (200 mg, 0.83 mmol) in ACN (13.8 mL) was added phenylboronic acid (202 mg, 1.66 mmol), Pd(OAc)$_2$ (15 mg, 0.066 mmol), P(o-tol)$_3$ (40 mg, 0.13 mmol) and TEA (1.16 mL) The mixture was degassed with N$_2$ three times, stirred at 90° C. under N$_2$ atmosphere for 12 hours, and then filtered through a Celite pad. The reaction mixture was poured to methanol (15 mL), filtered, washed with water, and dried to give 4-amino-7-phenylisoindolin-1,3-dione 39 (120 mg, 61%).

The following compounds of Examples 272 to 275 were obtained by using corresponding starting materials and repeating the procedure of Example 271.

Example 272: 4-Amino-7-(2-methoxyphenyl)isoindolin-1,3-dione $^1$H NMR (400 MHz, DMSO-d$_6$) δ 10.75 (br.s, 1H), 7.31 (td, J=7.6, 1.6 Hz, 1H), 7.23 (d, J=8.4 Hz, 1H), 7.17 (dd, J=7.6, 1.6 Hz, 1H), 7.03 (d, J=8.0 Hz, 1H), 6.97-6.92 (m, 2H), 6.42 (s, 2H), 3.66 (s, 3H). [M+H]$^+$: 269.

Example 273: 4-Amino-7-(2,3-dimethoxyphenyl)isoindolin-1,3-dione

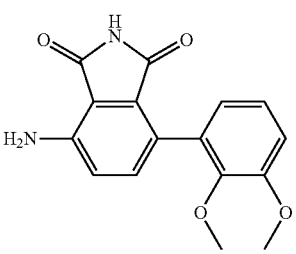 [SMILES: COc1cccc(-c2ccc(N)c3c2C(=O)NC3=O)c1OC]

$^1$H NMR (400 MHz, DMSO-d$_6$) δ 10.77 (br.s, 1H), 7.21 (d, J=8.4 Hz, 1H), 7.03 (d, J=4.8 Hz, 2H), 6.96 (d, J=8.4 Hz, 1H), 6.77 (d, J=4.6 Hz, 1H), 6.45 (s, 2H), 3.82 (s, 3H), 3.45 (s, 3H). [M+H]$^+$: 299.

Example 274: 4-Amino-7-(furan-2-yl)isoindolin-1,3-dione

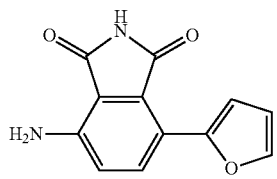 [SMILES: Nc1ccc(-c2ccco2)c2c1C(=O)NC2=O]

$^1$H NMR (400 MHz, DMSO-d$_6$) δ 11.02 (br.s, 1H), 7.84 (d, J=8.4 Hz, 1H), 7.75 (d, J=9.6 Hz, 1H), 7.57 (br.s, 1H), 7.06 (d, J=8.4 Hz, 1H), 6.64-6.61 (m, 3H). [M+H]$^+$: 229.

Example 275: 4-Amino-7-(thiophen-2-yl)isoindolin-1,3-dione

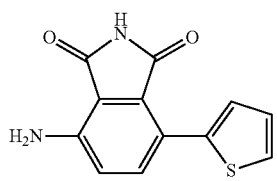 [SMILES: Nc1ccc(-c2cccs2)c2c1C(=O)NC2=O]

$^1$H NMR (400 MHz, DMSO-d$_6$) δ 10.97 (br.s, 1H), 7.67 (d, J=3.2 Hz, 1H), 7.56 (d, J=5.2 Hz, 1H), 7.54 (s, 1H), 7.10 (t, J=4.2 Hz, 1H), 7.02 (d, J=8.8 Hz, 1H), 6.60 (s, 2H). [M+H]$^+$: 245.

Example 276: N-(1,3-dioxo-7-phenylisoindolin-4-yl)benzamide

Scheme 13. Preparation of compound of Example 276

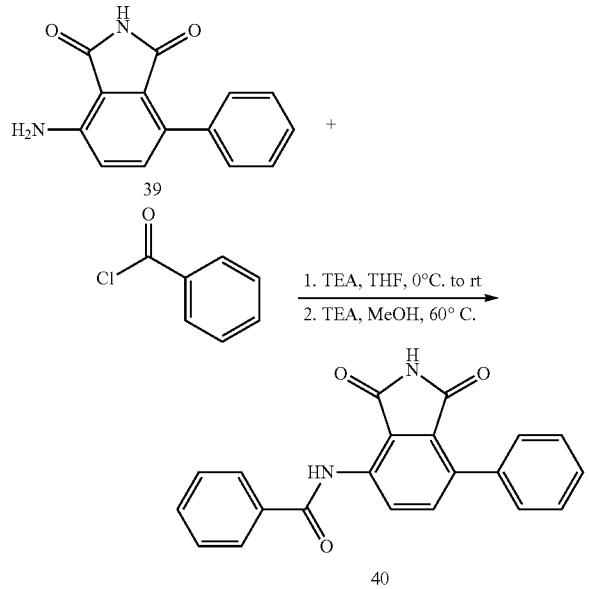

To a stirred solution of 4-amino-7-phenylisoindolin-1,3-dione 39 (50 mg, 0.21 mmol) in THF (2.1 mL) was added TEA (0.29 mL, 2.10 mmol) at 0° C., and the mixture was stirred for 10 min. Benzoyl chloride (0.12 mL, 1.05 mmol) was added dropwise to the mixture, which was then stirred at room temperature for 12 hours. TEA (0.29 mL) was added to the crude compound thus obtained in methanol (2.1 mL) The mixture was stirred at 60° C. under $N_2$ atmosphere for 12 hours, and the reaction mixture was filtered. The reaction mixture was poured to ACN (15 mL), filtered, washed with water, and dried to give the title compound 40 (7.3 mg, 10%).

$^1$H NMR (400 MHz, DMSO-$d_6$) δ 11.51 (s, 1H), 10.81 (s, 1H), 8.73 (d, J=8.8 Hz, 1H), 8.00 (d, J=6.8 Hz, 2H), 7.77 (d, J=8.8 Hz, 1H), 7.76-7.58 (m, 5H), 7.48-7.42 (m, 3H). [M+H]$^+$: 343.

The following compounds of Examples 277 and 278 were obtained by using corresponding starting materials and repeating the procedure of Example 276.

Example 277: N-(7-(2-methoxyphenyl)-1,3-dioxoisoindolin-4-yl)benzamide

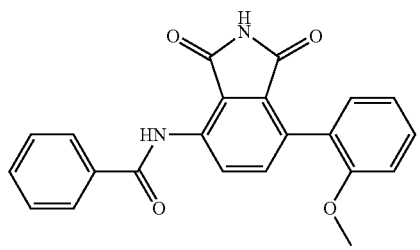 [SMILES: COc1ccccc1-c1ccc(NC(=O)c2ccccc2)c2c1C(=O)NC2=O]

$^1$H NMR (400 MHz, DMSO-$d_6$) δ 11.40 (s, 1H), 10.67 (s, 1H), 8.67 (d, J=8.4 Hz, 1H), 8.00 (d, J=8.4 Hz, 2H), 7.72-7.62 (m, 4H), 7.41 (t, J=7.8 Hz, 1H), 7.28 (dd, J=7.2, 1.6 Hz, 1H), 7.10 (d, J=8.0 Hz, 1H), 7.02 (d, J=7.4 Hz, 1H), 3.69 (s, 3H). [M+H]$^+$: 373.

Example 278: N-(7-(2,3-dimethoxyphenyl)-1,3-dioxoisoindolin-4-yl) benzamide

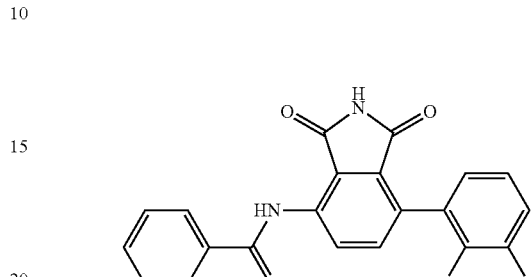

$^1$H NMR (400 MHz, DMSO-$d_6$) δ 11.45 (s, 1H), 10.68 (s, 1H), 8.67 (d, J=8.4 Hz, 1H), 8.00 (d, J=8.4 Hz, 2H), 7.70-7.62 (m, 4H), 7.12-7.10 (m, 2H), 6.85-6.87 (m, 1H), 3.86 (s, 3H), 3.50 (s, 3H). [M+H]$^+$: 403.

Example 279: 4-Fluoro-N-(3-oxo-7-phenyl-2,3-dihydro-1H-pyrrolo[3,4-c]pyridin-4-yl)benzamide Scheme 14. Total scheme for compound 50

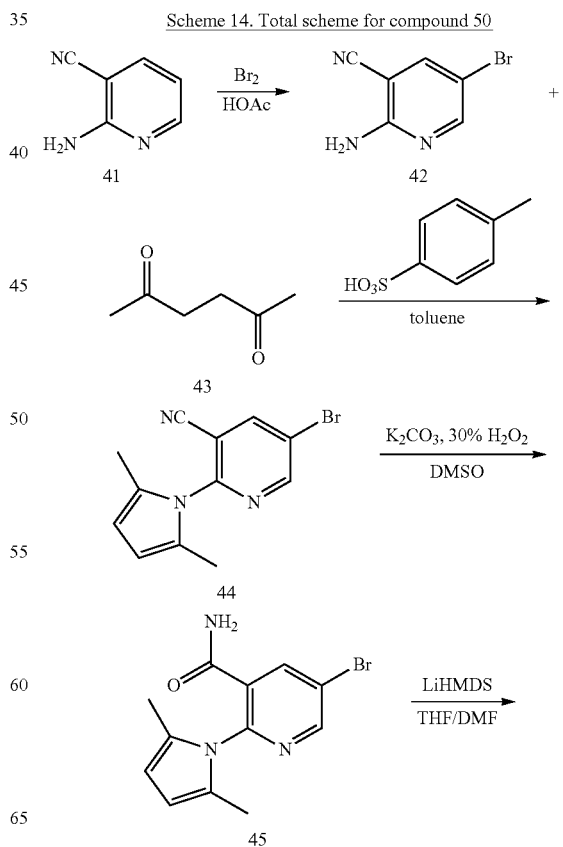

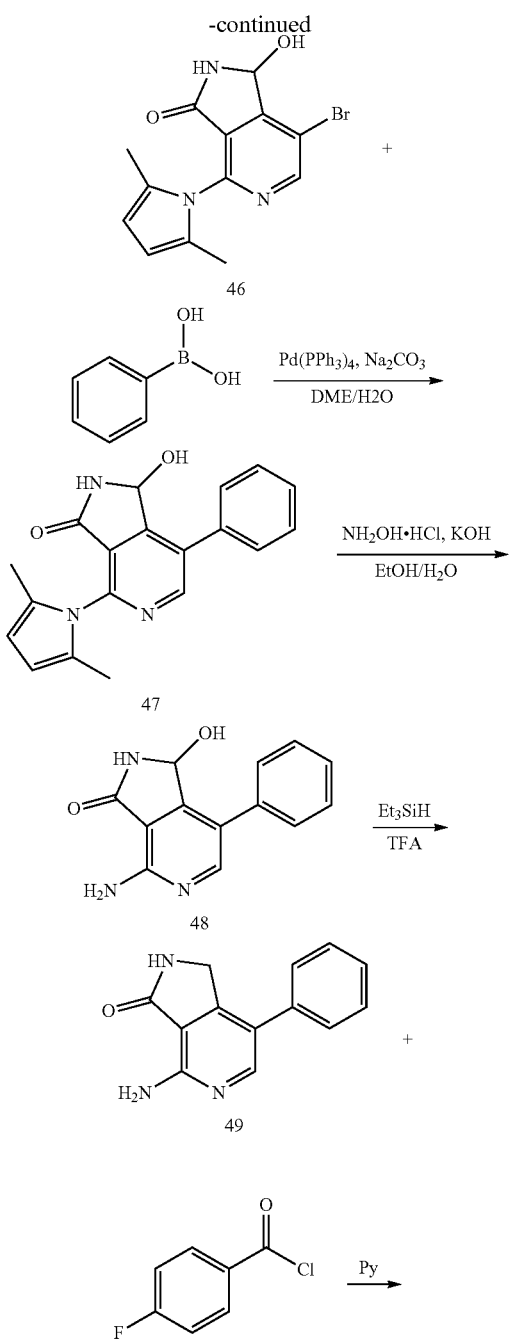

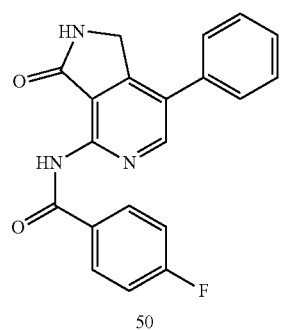

Step 1: Preparation of 2-amino-5-bromonicotinonitrile (42)

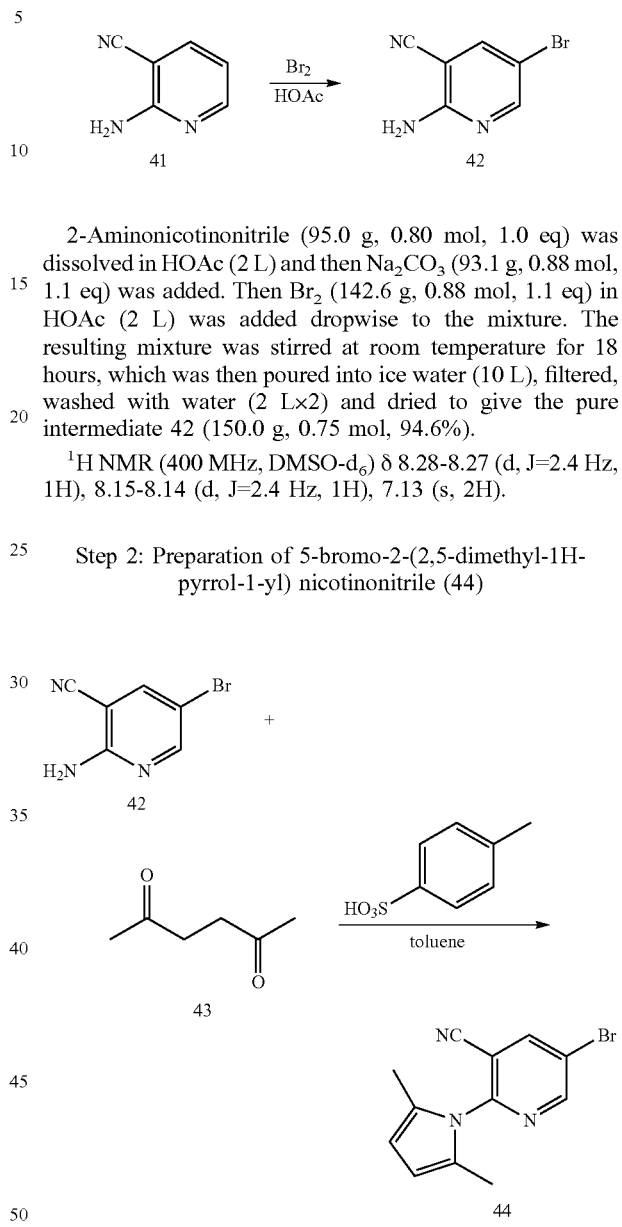

2-Aminonicotinonitrile (95.0 g, 0.80 mol, 1.0 eq) was dissolved in HOAc (2 L) and then $Na_2CO_3$ (93.1 g, 0.88 mol, 1.1 eq) was added. Then $Br_2$ (142.6 g, 0.88 mol, 1.1 eq) in HOAc (2 L) was added dropwise to the mixture. The resulting mixture was stirred at room temperature for 18 hours, which was then poured into ice water (10 L), filtered, washed with water (2 L×2) and dried to give the pure intermediate 42 (150.0 g, 0.75 mol, 94.6%).

$^1$H NMR (400 MHz, DMSO-$d_6$) δ 8.28-8.27 (d, J=2.4 Hz, 1H), 8.15-8.14 (d, J=2.4 Hz, 1H), 7.13 (s, 2H).

Step 2: Preparation of 5-bromo-2-(2,5-dimethyl-1H-pyrrol-1-yl) nicotinonitrile (44)

To a suspension solution of the intermediate 42 (90.0 g, 0.45 mol, 1.0 eq) in toluene (1.5 L) was added the compound 43 (78.2 g, 0.68 mol, 1.5 eq) and 4-methylbenzenesulfonic acid (2.5 g, 0.01 mol, 0.03 eq). The mixture was heated to 110° C. and stirred for 17 hours to remove water by Dean Stark trap. The mixture was cooled to room temperature, removed of toluene (about 1 L), and then added with EtOAc (2 L) and water (1 L). The mixture was filtered; the aqueous layer was extracted with EtOAc (2 L); the organic phase was washed with brine (3 L) and concentrated to give the crude product, which was purified by flash chromatography (EtOAc:Hexane=1:1) to give the intermediate 44 (110.0 g, 0.39 mol, 87.1%).

$^1$H NMR (400 MHz, DMSO-$d_6$) δ 9.07-9.06 (d, J=2.4 Hz, 1H), 8.96-8.95 (d, J=2.4 Hz, 1H), 5.88 (s, 2H), 2.01 (s, 6H).

Step 3: Preparation of 5-bromo-2-(2,5-dimethyl-1H-pyrrol-1-yl) nicotinamide (45)

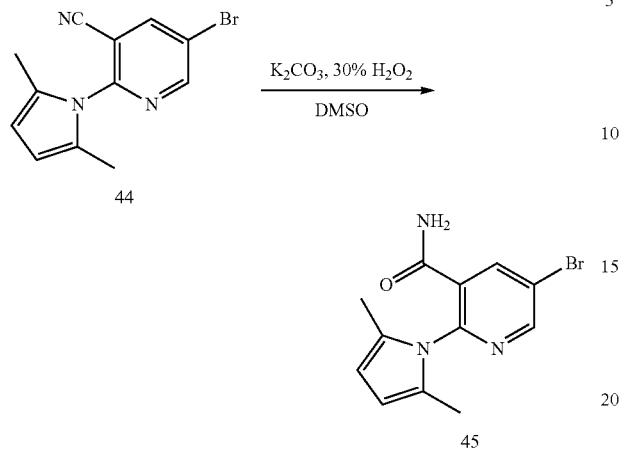

The intermediate 44 (45.0 g, 162.97 mmol, 1.0 eq) was dissolved in DMSO (300 mL) and K₂CO₃ (67.4 g, 488.90 mmol, 3.0 eq) was added. Then, 30% H₂O₂ (92.3 g, 814.83 mmol, 5.0 eq) was added thereto dropwise at 40° C., and the resulting mixture was stirred for 0.5 hour. The mixture was added with EtOAc (1 L) and water (2 L). The aqueous layer was extracted with EtOAc (1 L), washed with brine (2 L×2), dried over Na₂SO₄ and concentrated to give the intermediate 45 (43.2 g, 146.8 mmol, 90.1%).

$^1$H NMR (400 MHz, DMSO-$d_6$) δ 8.81-8.08 (d, J=2.4 Hz, 1H), 8.35-8.34 (d, J=2.4 Hz, 1H), 7.58 (s, 1H), 7.47 (s, 1H), 5.73 (s, 2H), 2.99 (s, 2H), 2.54 (s, 1H), 1.92 (s, 6H).

Step 4: Preparation of 7-bromo-4-(2,5-dimethyl-1H-pyrrol-1-yl)-1-hydroxy-1H-pyrrolo[3,4-c]pyridin-3(2H)-one (46)

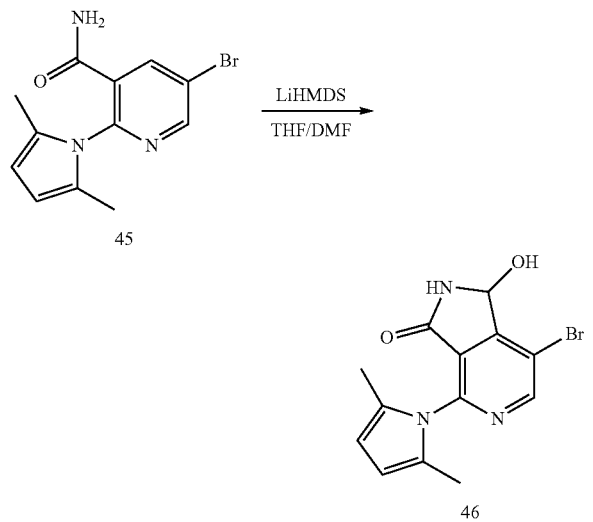

To a solution of LiHMDS (455 mL, 455.00 mmol, 4.0 eq) was added dropwise the intermediate 45 (34.0 g, 115.59 mmol, 1.0 eq) in THF (250 mL) at 0° C. The mixture was stirred for 0.5 hour at the above temperature, then was added with DMF (29.5 g, 404.56 mmol, 3.5 eq) dropwise at 0~5° C., then heated to room temperature, and stirred for 2 hours. A saturated solution of NH₄Cl (400 mL) and EtOAc (1 L) was added into the mixture, and then the aqueous layer was extracted with EtOAc (500 mL×2), washed with brine (1 L), dried over Na₂SO₄ and concentrated to give the residue, which was purified by chromatography (EtOAc:Hexane=1:1) to give the intermediate 46 (13.0 g, 40.3 mmol, 34.8%) as a yellow solid.

$^1$H NMR (400 MHz, DMSO-$d_6$) δ 9.31 (s, 1H), δ 8.89 (s, 1H), 6.70-6.67 (d, J=9.7 Hz, 1H), 5.91-5.90 (d, J=9.8 Hz, 1H), 5.77 (s, 2H), 1.95 (s, 3H), 1.90 (s, 3H).

Step 5: Preparation of 4-(2,5-dimethyl-1H-pyrrol-1-yl)-1-hydroxy-7-phenyl-1H-pyrrolo[3,4-c]pyridin-3(2H)-one (47)

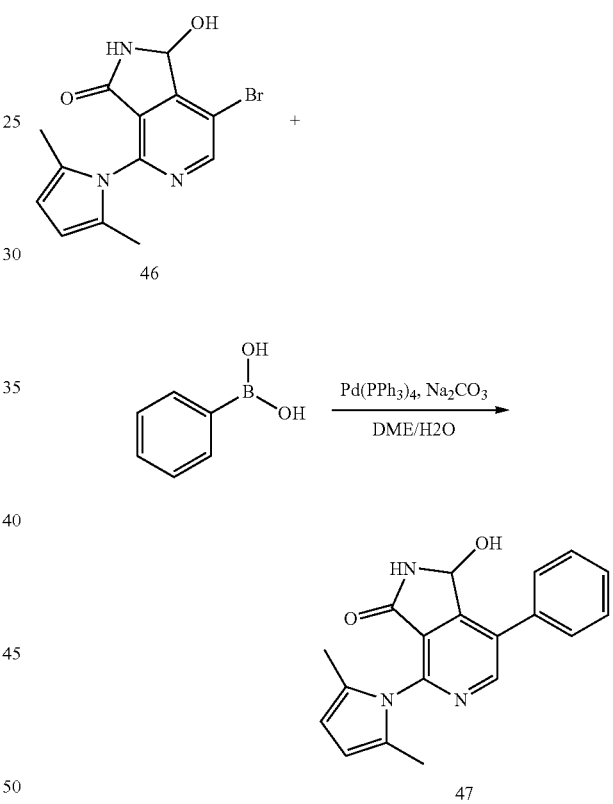

A suspension solution of intermediate 46 (14.2 g, 44.08 mmol, 1.0 eq), phenylboronic acid (8.06 g, 66.12 mmol, 1.5 eq), and Na₂CO₃ (9.34 g, 88.15 mmol, 2.0 eq) in DME (450 mL) and water (100 mL) was purged with nitrogen, treated with Pd(PPh₃)₄ (5.09 g, 4.41 mmol, 0.1 eq), then stirred at 70° C. for 15 hours. The resulting reaction mixture was cooled to room temperature, extracted with EtOAc (1 L×2), washed with brine, dried and concentrated to give the crude product, which was purified by chromatography (EtOAc:Hexane=1:1) to give the intermediate 47 (8.2 g, 25.6 mmol, 58.2%).

$^1$H NMR (400 MHz, DMSO-$d_6$) δ 9.17 (s, 1H), 8.78 (s, 1H), 7.81-7.79 (m, 2H), 7.55-7.45 (m, 3H), 6.39-6.32 (m, 2H), 5.78 (s, 2H), 2.00 (s, 3H), 1.94 (s, 3H).

Step 6: Preparation of 4-amino-1-hydroxy-7-phenyl-1H-pyrrolo[3,4-c]pyridin-3(2H)-one (48)

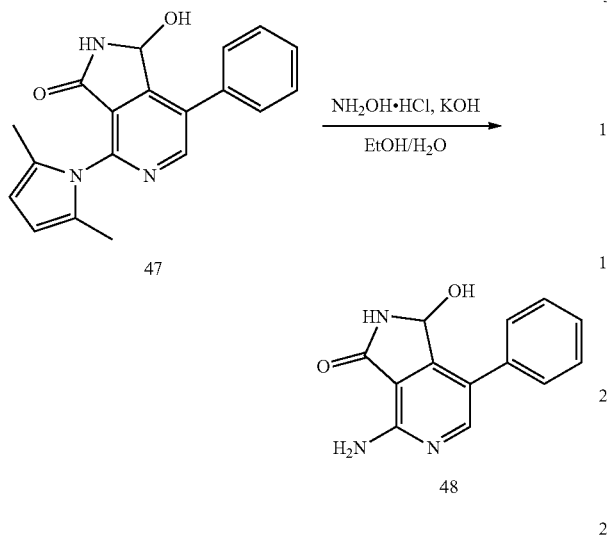

To a suspension solution of the intermediate 47 (11.5 g, 36.01 mmol, 1.0 eq) in EtOH (190 mL) was added a solution of NH$_2$OH.HCl (13.7 g, 198.05 mmol, 5.5 eq) and KOH (7.8 g, 126.03 mmol, 3.5 eq, in 70 mL water). The mixture was stirred at 80° C. for 20 hours. The resulting reaction mixture was cooled to room temperature, and added with Na$_2$CO$_3$ (pH about 7~8), and removed of EtOH. The mixture was then added with EtOAc (300 mL) and water (300 mL), filtered, and then the solid thus obtained was washed with EtOAc and dried to give the intermediate 48 (4.2 g, 17.4 mmol, 48.3%, HPLC: 90%).

$^1$H NMR (400 MHz, DMSO-d$_6$) δ 8.77 (s, 1H), 8.18 (s, 1H), 7.63-7.61 (d, J=7.3 Hz, 2H), 7.43-7.37 (t, J=7.4 Hz, 2H), 7.33-7.30 (m, 1H), 6.68 (s, 2H), 6.24-6.22 (m, 1H), 6.14-6.12 (m, 1H).

Step 7: Preparation of 4-amino-7-phenyl-1H-pyrrolo[3,4-c]pyridin-3(2H)-one (49)

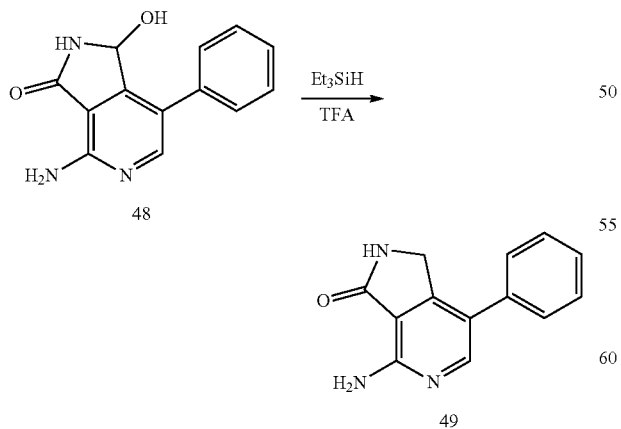

To a solution of intermediate 48 (4.9 g, 20.31 mmol, 1.0 eq) in TFA (90 mL) was added Et$_3$SiH (23.6 g, 203.11 mmol, 10 eq). The mixture was stirred at 50° C. for 17 hours. The reaction mixture was concentrated, added with DCM (150 mL) and water (150 mL), adjusted to the pH of about 7 with NaHCO$_3$, and filtered. The aqueous layer was extracted with DCM (200 mL×2), washed with brine, and then concentrated to give the crude product, which was purified by chromatography (DCM: MeOH=150:1) to give the pure compound 49 (1.37 g, 6.08 mmol, 29.9%) as a yellow solid.

$^1$H NMR (400 MHz, DMSO-d$_6$) δ 8.55 (s, 1H), 8.20 (s, 1H), 7.56-7.54 (d, J=7.3 Hz, 2H), 7.47-7.43 (t, J=7.4 Hz, 1H), 7.36-7.32 (t, J=7.3 Hz, 1H), 6.75 (s, 2H), 4.52 (s, 2H).

Step 8: Preparation of 4-fluoro-N-(3-oxo-7-phenyl-2,3-dihydro-1H-pyrrolo[3,4-c]pyridin-4-yl)benzamide (50)

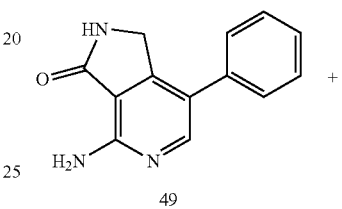

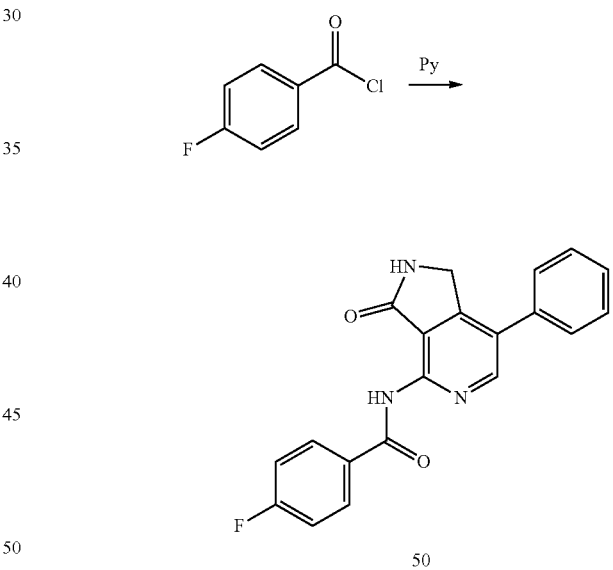

To a suspension solution of the compound 49 (800 mg, 3.55 mmol, 1.0 eq) in pyridine (20 mL) was added 4-fluorobenzoyl chloride (619 mg, 3.91 mmol, 1.1 eq).

The mixture was stirred at 100° C. for 2 hours. The reaction mixture was cooled to room temperature, added with EtOAc (50 mL) and water (50 mL), and filtered. The aqueous layer was extracted with EtOAc (50 mL×5), washed with brine, and concentrated to give the crude product, which was purified by chromatography (DCM: MeOH=50:1) to give the title compound 50 (42 mg, 0.12 mmol, 3.4%) as a yellow solid.

$^1$H NMR (400 MHz, DMSO-d$_6$) δ 8.36 (s, 1H), 7.73-7.70 (m, 2H), 7.59-7.58 (m, 2H), 7.53-7.49 (t, J=7.5 Hz, 2H), 7.41-7.38 (m, 1H), 7.30-7.28 (m, 2H), 5.08 (s, 2H).

Example 280: N-(7-(2,3-dimethoxyphenyl)-3-oxoisoindolin-4-yl)-4-((3-(pyrrolidin-1-yl)propyl)amino)benzamide

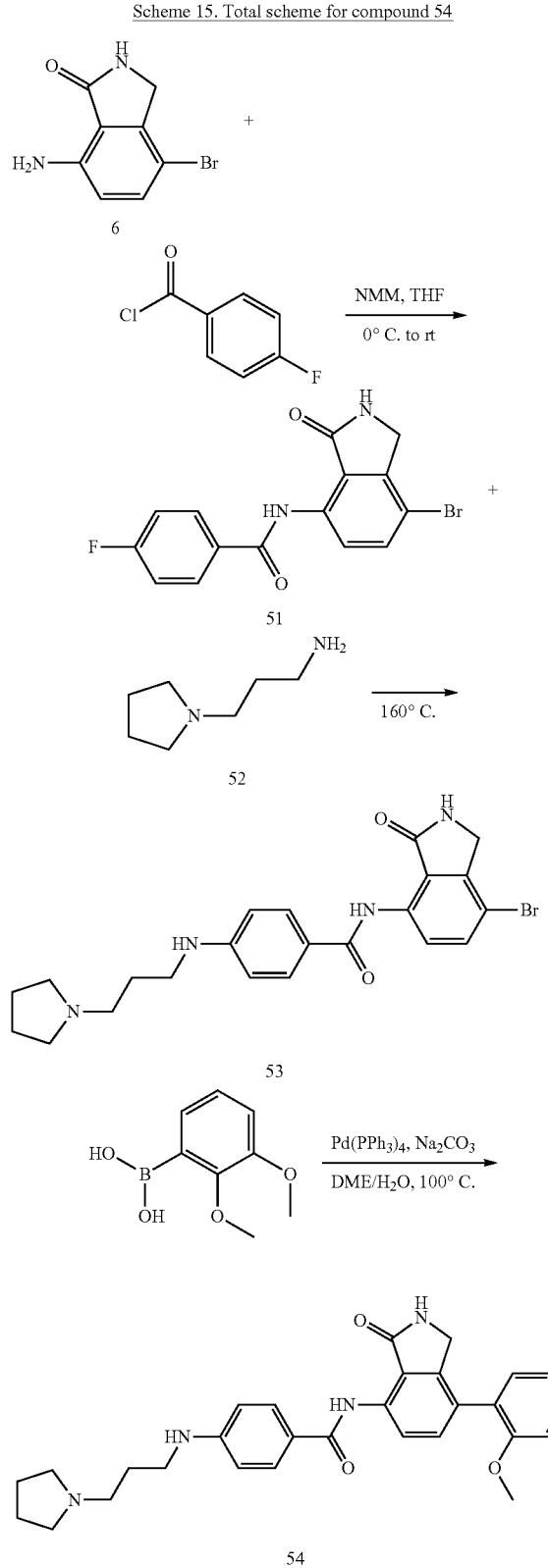

Scheme 15. Total scheme for compound 54

Step 1: Preparation of N-(7-bromo-3-oxoisoindolin-4-yl)-4-fluorobenzamide (51)

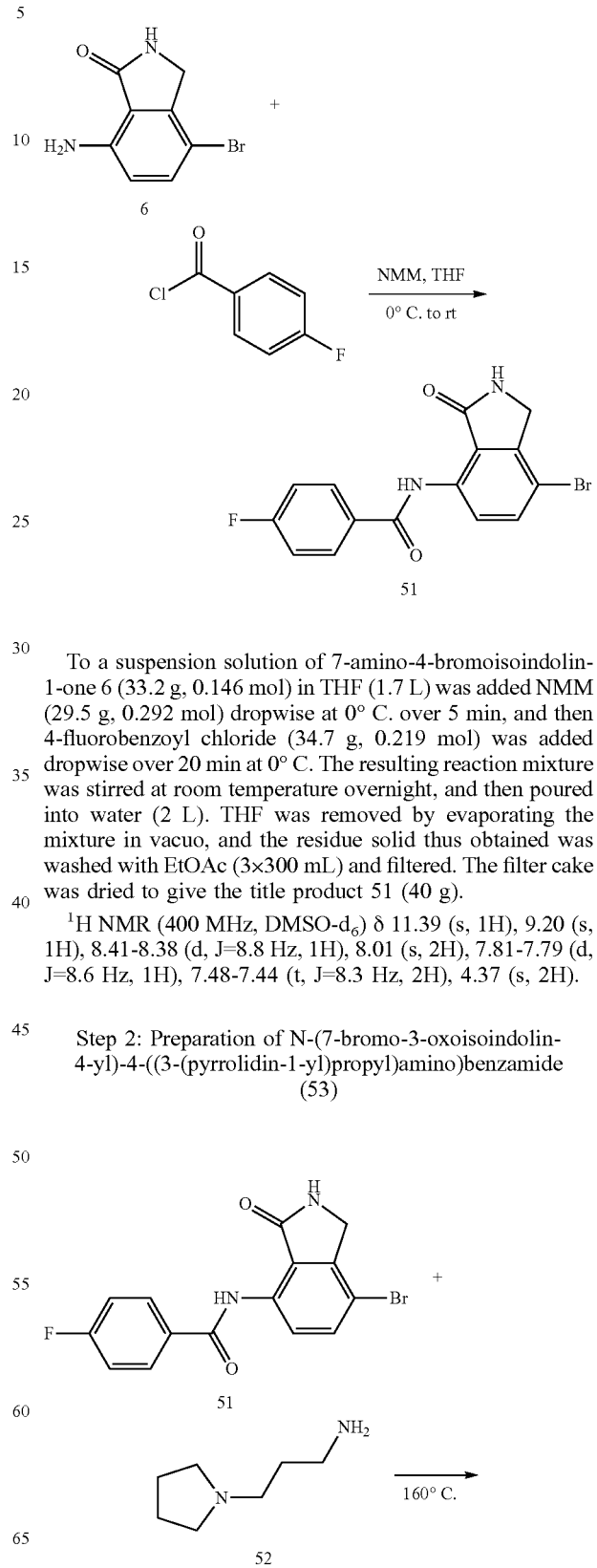

To a suspension solution of 7-amino-4-bromoisoindolin-1-one 6 (33.2 g, 0.146 mol) in THF (1.7 L) was added NMM (29.5 g, 0.292 mol) dropwise at 0° C. over 5 min, and then 4-fluorobenzoyl chloride (34.7 g, 0.219 mol) was added dropwise over 20 min at 0° C. The resulting reaction mixture was stirred at room temperature overnight, and then poured into water (2 L). THF was removed by evaporating the mixture in vacuo, and the residue solid thus obtained was washed with EtOAc (3×300 mL) and filtered. The filter cake was dried to give the title product 51 (40 g).

$^1$H NMR (400 MHz, DMSO-$d_6$) δ 11.39 (s, 1H), 9.20 (s, 1H), 8.41-8.38 (d, J=8.8 Hz, 1H), 8.01 (s, 2H), 7.81-7.79 (d, J=8.6 Hz, 1H), 7.48-7.44 (t, J=8.3 Hz, 2H), 4.37 (s, 2H).

Step 2: Preparation of N-(7-bromo-3-oxoisoindolin-4-yl)-4-((3-(pyrrolidin-1-yl)propyl)amino)benzamide (53)

-continued

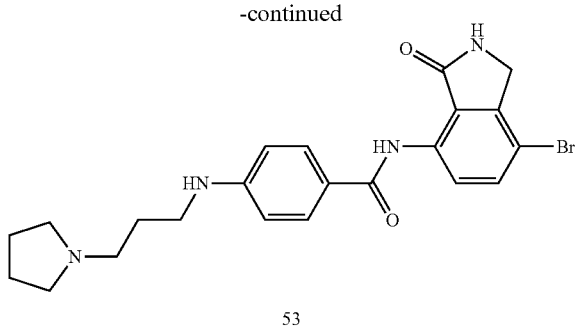

53

A mixture of N-(7-bromo-3-oxoisoindolin-4-yl)-4-fluorobenzamide (600 mg, 1.72 mmol) in 1-(3-aminopropyl)pyrrolidine (1.1 mL, 8.6 mmol) was stirred for 12 hours at 160° C., and then cooled to room temperature. After CH$_3$OH was poured into the mixture, the mixture was stirred for 1 hour. The obtained solid was washed with CH$_3$OH to give the title compound (380 mg, 48%) as a pale yellow solid.

$^1$H NMR (400 MHz, DMSO-d$_6$) δ 11.18 (br s, 1H), 9.13 (br s, 1H), 8.42 (d, J=8.8 Hz, 1H), 7.74 (d, J=8.8 Hz, 1H), 7.70 (d, J=8.8 Hz, 2H), 6.66 (d, J=8.8 Hz, 2H), 6.56 (t, J=5.4 Hz, 1H), 4.35 (s, 2H), 3.16-3.11 (m, 2H), 2.50-2.48 (m, 2H), 2.43-2.41 (m, 4H), 1.74-1.71 (m, 2H), 1.70-1.67 (m, 4H); [M+H]$^+$: 457.

Step 3: Preparation of N-(7-(2,3-dimethoxyphenyl)-3-oxoisoindolin-4-yl)-4-((3-(pyrrolidin-1-yl)propyl)amino)benzamide (54)

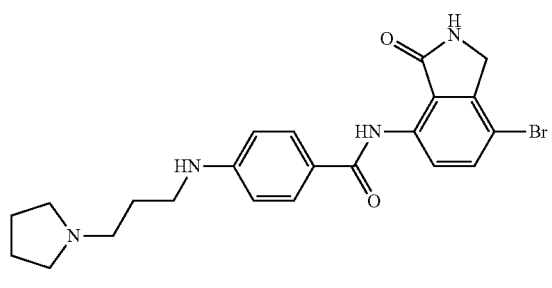

53

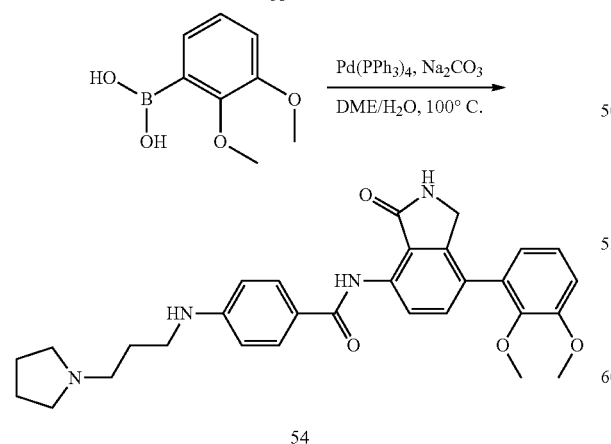

54

A mixture of the compound 53 (75 mg, 0.16 mmol), (2,3-dimethoxyphenyl)boronic acid (60 mg, 0.33 mmol), Pd(PPh3)$_4$ (19 mg, 0.02 mmol) and Na$_2$CO$_3$ (70 mg, 0.66 mmol) in DME/H$_2$O (2/0.5 mL) was stirred for 12 hours at 100° C. The resulting mixture was diluted with CH$_2$Cl$_2$ and washed with 1M Na$_2$CO$_3$ (aq.). The organic layer was dried over MgSO$_4$, filtered, and concentrated in vacuo. The crude product thus obtained was purified by silica-gel column chromatography (Biotage flash purification system, CH$_2$Cl$_2$/CH$_3$OH, KP-Sil) to provide the title compound 54 (9 mg, 11%) as a white solid.

$^1$H NMR (400 MHz, DMSO-d$_6$) δ 11.40 (br s, 1H), 8.92 (br s, 1H), 8.52 (d, J=8.4 Hz, 1H), 7.73 (d, J=8.8 Hz, 2H), 7.50 (d, J=8.4 Hz, 1H), 7.17-7.09 (m, 2H), 6.94 (dd, J=7.4, 1.8 Hz, 1H), 6.68 (d, J=8.8 Hz, 2H), 6.54 (t, J=5.0 Hz, 1H), 4.29 (s, 2H), 3.85 (s, 3H), 3.44 (s, 3H), 3.17-3.12 (m, 2H), 2.47-2.43 (m, 4H), 1.77-1.74 (m, 2H), 1.712-1.68 (m, 4H); [M+H]$^+$: 515.

The following compounds of Examples 281 to 387 were obtained by using corresponding starting materials and repeating the procedure of Example 280.

Example 281: N-(7-bromo-3-oxoisoindolin-4-yl)-4-((2-(dimethylamino)ethyl) amino)benzamide

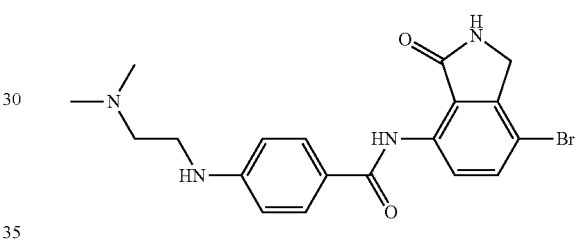

$^1$H NMR (400 MHz, DMSO-d$_6$) δ 11.19 (br s, 1H), 9.13 (br s, 1H), 8.42 (d, J=8.8 Hz, 1H), 7.74 (d, J=8.8 Hz, 1H), 7.70 (d, J=8.4 Hz, 2H), 6.71 (d, J=8.8 Hz, 2H), 6.35 (t, J=5.2 Hz, 1H), 4.35 (s, 2H), 3.20-3.16 (m, 2H), 2.48-2.44 (m, 2H), 2.20 (s, 6H); [M+H]$^+$: 417.

Example 282: N-(7-bromo-3-oxoisoindolin-4-yl)-4-((3-(piperidin-1-yl) propyl)amino)benzamide

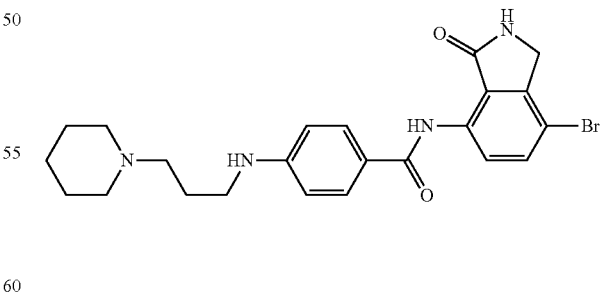

$^1$H NMR (400 MHz, DMSO-d$_6$) δ 11.18 (br s, 1H), 9.14 (br s, 1H), 8.42 (d, J=8.8 Hz, 1H), 7.74 (d, J=8.8 Hz, 1H), 7.70 (d, J=8.8 Hz, 2H), 6.66 (d, J=8.8 Hz, 2H), 6.60 (t, J=5.2 Hz, 1H), 4.34 (s, 2H), 3.14-3.09 (m, 2H), 2.34-2.30 (m, 6H), 1.73-1.65 (m, 2H), 1.53-1.47 (m, 4H), 1.39-1.37 (m, 2H); [M+H]$^+$: 471.

Example 283: N-(7-bromo-3-oxoisoindolin-4-yl)-4-((2-(pyrrolidin-1-yl)ethyl) amino)benzamide

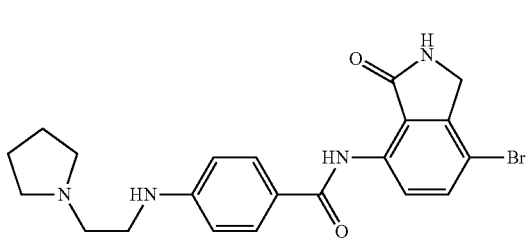 [SMILES: O=C(Nc1ccc(Br)c2c1C(=O)NC2)c1ccc(NCCN2CCCC2)cc1]

¹H NMR (400 MHz, DMSO-d₆) δ 11.19 (s, 1H), 9.15 (s, 1H), 8.42 (d, J=8.8 Hz, 1H), 7.74 (d, J=8.8 Hz, 1H), 7.69 (d, J=8.4 Hz, 2H), 6.69 (d, J=8.8 Hz, 2H), 6.45 (t, J=5.0 Hz, 1H), 4.35 (s, 2H), 3.21 (q, J=6.4 Hz, 2H), 2.61 (t, J=6.6 Hz, 2H), 2.49-2.45 (m, 4H), 1.72-1.68 (m, 4H). [M+H]⁺: 444.

Example 284: N-(7-bromo-3-oxoisoindolin-4-yl)-4-((2-(piperidin-1-yl)ethyl) amino)benzamide

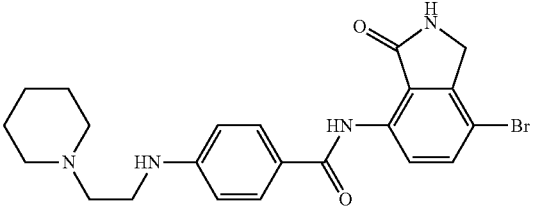 [SMILES: O=C(Nc1ccc(Br)c2c1C(=O)NC2)c1ccc(NCCN2CCCCC2)cc1]

¹H NMR (400 MHz, DMSO-d₆) δ 11.19 (s, 1H), 9.13 (s, 1H), 8.42 (d, J=8.8 Hz, 1H), 7.74 (d, J=8.8 Hz, 1H), 7.69 (d, J=8.8 Hz, 2H), 6.69 (d, J=8.8 Hz, 2H), 6.35 (t, J=5.4 Hz, 1H), 4.35 (s, 2H), 3.20 (q, J=6.0 Hz, 2H), 2.46 (t, J=5.8 Hz, 2H), 2.42-2.36 (m, 4H), 1.53-1.48 (m, 4H), 1.39-1.36 (m, 2H). [M+H]⁺: 458.

Example 285: 4-((2-(azepan-1-yl)ethyl)amino)-N-(7-bromo-3-oxoisoindolin-4-yl)benzamide

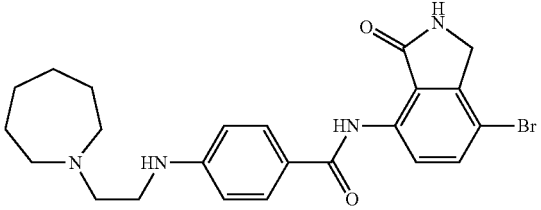 [SMILES: O=C(Nc1ccc(Br)c2c1C(=O)NC2)c1ccc(NCCN2CCCCCC2)cc1]

¹H NMR (400 MHz, DMSO-d₆) δ 11.19 (s, 1H), 9.13 (s, 1H), 8.42 (d, J=8.8 Hz, 1H), 7.74 (d, J=8.8 Hz, 1H), 7.70 (d, J=8.8 Hz, 2H), 6.69 (d, J=8.8 Hz, 2H), 6.31 (t, J=5.4 Hz, 1H), 4.35 (s, 2H), 3.17 (q, J=6.4 Hz, 2H), 2.68-2.63 (m, 6H), 1.59-1.53 (m, 8H). [M+H]⁺: 472.

Example 286: N-(7-bromo-3-oxoisoindolin-4-yl)-4-((3-(dimethylamino) propyl)amino)benzamide

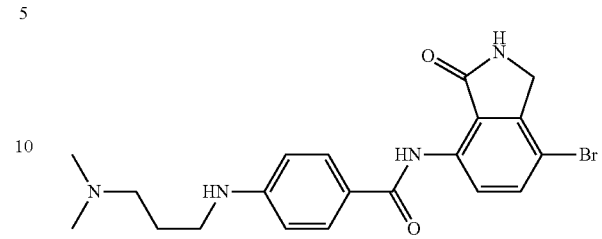

¹H NMR (400 MHz, DMSO-d₆) δ 11.18 (s, 1H), 9.13 (s, 1H), 8.42 (d, J=8.8 Hz, 1H), 7.74 (d, J=8.4 Hz, 1H), 7.69 (d, J=8.8 Hz, 2H), 6.66 (d, J=8.8 Hz, 2H), 6.54 (t, J=5.6 Hz, 1H), 4.35 (s, 2H), 3.11 (q, J=6.4 Hz, 2H), 2.30-2.27 (m, 2H), 2.14 (s, 6H), 1.68 (quint, J=6.8 Hz, 2H). [M+H]⁺: 432.

Example 287: N-(7-(furan-2-yl)-3-oxoisoindolin-4-yl)-4-((2-(pyrrolidin-1-yl) ethyl)amino)benzamide

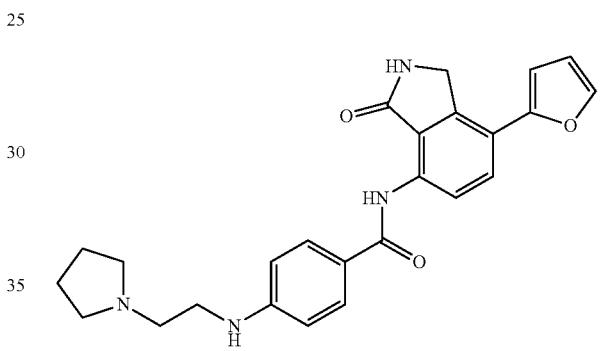

¹H NMR (400 MHz, DMSO-d₆) δ 11.48 (s, 1H), 9.14 (s, 1H), 8.54 (d, J=8.6 Hz, 1H), 7.94 (d, J=8.6 Hz, 1H), 7.82 (d, J=1.3 Hz, 1H), 7.75 (d, J=8.7 Hz, 2H), 6.85 (d, J=3.4 Hz, 1H), 6.76 (d, J=8.6 Hz, 2H), 6.66 (dd, J=3.3, 1.8 Hz, 2H), 4.63 (s, 2H), 3.46-3.35 (m, 3H), 1.92-1.83 (m, 5H); MS (ESI) m/z 431 (M+H)⁺.

Example 288: N-(7-(furan-2-yl)-3-oxoisoindolin-4-yl)-4-((2-methoxyethyl) amino)benzamide

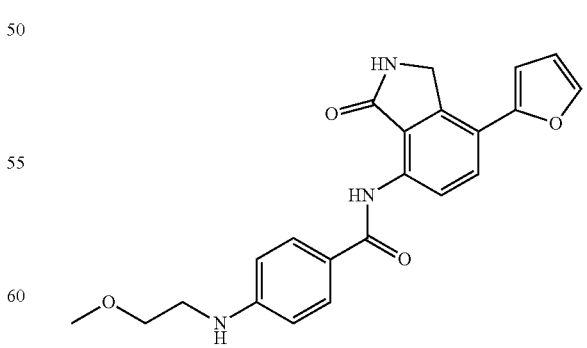

¹H NMR (400 MHz, DMSO-d₆) δ 11.45 (s, 1H), 9.13 (s, 1H), 8.54 (d, J=8.6 Hz, 1H), 7.93 (d, J=8.6 Hz, 1H), 7.81 (d, J=1.3 Hz, 1H), 7.72 (d, J=8.7 Hz, 2H), 6.85 (d, J=3.4 Hz, 1H), 6.72 (d, J=8.8 Hz, 2H), 6.66 (dd, J=3.4, 1.8 Hz, 1H), 6.55 (t, J=5.5 Hz, 1H), 4.63 (s, 2H), 3.51 (t, J=5.5 Hz, 2H), 3.32-3.25 (m, 5H); MS (ESI) m/z 392 (M+H)⁺.

Example 289: N-(7-(furan-2-yl)-3-oxoisoindolin-4-yl)-4-((2-(piperidin-1-yl) ethyl)amino)benzamide

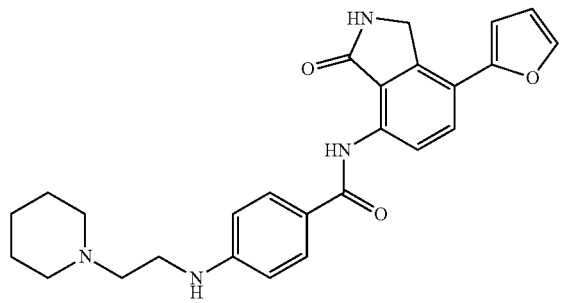 [SMILES: O=C(Nc1ccc(-c2ccco2)c2c1C(=O)NC2)c1ccc(NCCN2CCCCC2)cc1]

¹H NMR (400 MHz, DMSO-d₆) δ 11.48 (s, 1H), 9.13 (s, 1H), 8.54 (d, J=8.6 Hz, 1H), 7.94 (d, J=8.6 Hz, 1H), 7.82 (d, J=1.4 Hz, 1H), 7.77 (d, J=8.7 Hz, 2H), 6.85 (d, J=3.4 Hz, 1H), 6.76 (d, J=8.6 Hz, 2H), 6.67 (dd, J=3.4, 1.8 Hz, 1H), 6.58 (br s, 1H), 4.64 (s, 2H), 3.46-3.35 (m, 3H), 1.87-1.53 (m, 8H); MS (ESI) m/z 445 (M+H)⁺.

Example 290: N-(7-(furan-2-yl)-3-oxoisoindolin-4-yl)-4-((2-morpholinoethyl)amino)benzamide

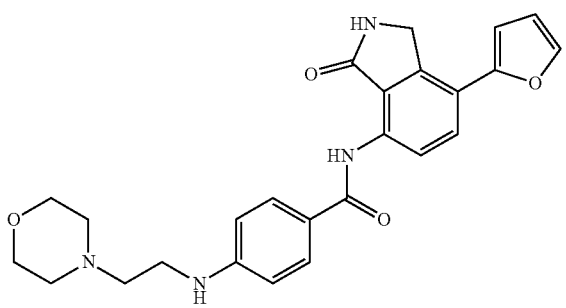 [SMILES: O=C(Nc1ccc(-c2ccco2)c2c1C(=O)NC2)c1ccc(NCCN2CCOCC2)cc1]

¹H NMR (400 MHz, DMSO-d₆) δ 11.46 (s, 1H), 9.12 (s, 1H), 8.54 (d, J=8.6 Hz, 1H), 7.94 (d, J=8.6 Hz, 1H), 7.82 (d, J=1.4 Hz, 1H), 7.73 (d, J=8.8 Hz, 2H), 6.85 (d, J=3.4 Hz, 1H), 6.71 (d, J=8.8 Hz, 2H), 6.66 (dd, J=3.3, 1.8 Hz, 1H), 6.38 (t, J=5.3 Hz, 1H), 4.63 (s, 2H), 3.59 (t, J=4.5 Hz, 4H), 3.27-3.21 (m, 2H), 2.51-2.30 (m, 6H); MS (ESI) m/z 447 (M+H)⁺.

Example 291: 4-((2-(Dimethylamino)ethyl)amino)-N-(7-(furan-2-yl)-3-oxoisoindolin-4-yl)benzamide

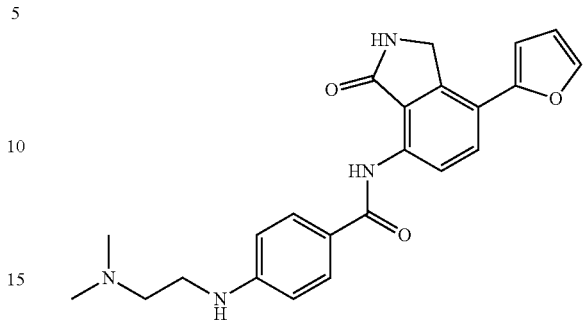

¹H NMR (400 MHz, DMSO-d₆) δ 11.48 (s, 1H), 9.13 (s, 1H), 8.54 (d, J=8.6 Hz, 1H), 7.94 (d, J=8.6 Hz, 1H), 7.82 (d, J=1.4 Hz, 1H), 7.73 (d, J=8.8 Hz, 2H), 6.85 (d, J=3.4 Hz, 1H), 6.71 (d, J=8.8 Hz, 2H), 6.66 (dd, J=3.3, 1.8 Hz, 1H), 6.38 (t, J=5.3 Hz, 1H), 4.63 (s, 2H), 3.41-3.30 (m, 2H), 2.97-2.85 (m, 2H), 2.56 (s, 6H); MS (ESI) m/z 405 (M+H)⁺.

Example 292: N-(7-(furan-2-yl)-3-oxoisoindolin-4-yl)-4-((2-hydroxyethyl) amino)benzamide

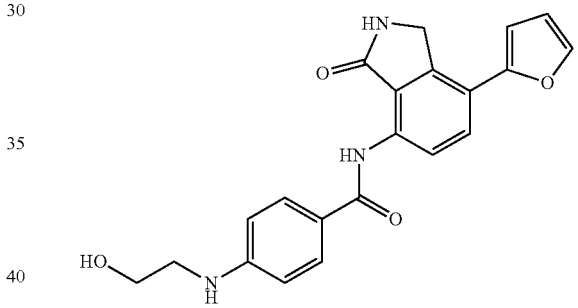

¹H NMR (400 MHz, DMSO-d₆) δ 11.45 (s, 1H), 9.12 (s, 1H), 8.54 (d, J=8.6 Hz, 1H), 7.93 (d, J=8.6 Hz, 1H), 7.81 (s, 1H), 7.72 (d, J=8.4 Hz, 2H), 6.84 (d, J=2.6 Hz, 1H), 6.71 (d, J=8.4 Hz, 2H), 6.66 (s, 1H), 6.49 (t, J=4.9 Hz, 1H), 4.77 (t, J=5.1 Hz, 1H), 4.63 (s, 2H), 3.61-3.50 (m, 2H), 3.19-3.13 (m, 2H); MS (ESI) m/z 378 (M+H)⁺.

Example 293: 4-((2-(Azepan-1-yl)ethyl)amino)-N-(7-(furan-2-yl)-3-oxoisoindolin-4-yl)benzamide

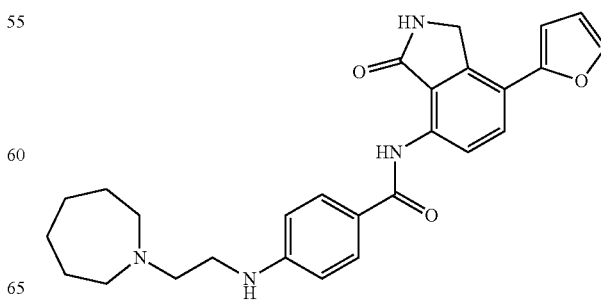

¹H NMR (400 MHz, DMSO-d₆) δ 11.45 (s, 1H), 9.13 (s, 1H), 8.54 (d, J=8.6 Hz, 1H), 7.93 (d, J=8.6 Hz, 1H), 7.82 (s, 1H), 7.72 (d, J=8.3 Hz, 2H), 6.84 (d, J=2.6 Hz, 1H), 6.70 (d, J=8.3 Hz, 2H), 6.66 (s, 1H), 6.31 (t, J=5.1 Hz, 1H), 4.63 (s, 2H), 3.23-3.13 (m, 2H), 2.71-2.60 (m, 6H), 1.71-1.45 (m, 9H); MS (ESI) m/z 459 (M+H)⁺.

Example 294: N-(7-(furan-2-yl)-3-oxoisoindolin-4-yl)-4-((2-(4-methylpiperazin-1-yl)ethyl)amino)benzamide

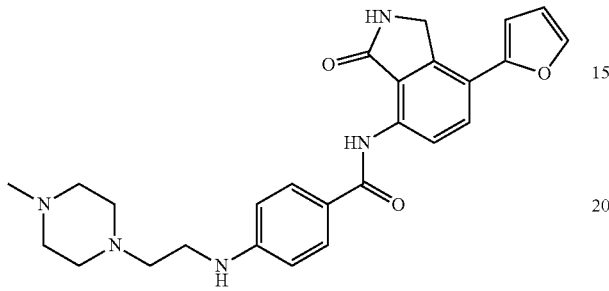

¹H NMR (400 MHz, DMSO-d₆) δ 11.44 (s, 1H), 9.12 (s, 1H), 8.53 (d, J=8.6 Hz, 1H), 7.92 (d, J=8.6 Hz, 1H), 7.81 (d, J=1.4 Hz, 1H), 7.71 (d, J=8.7 Hz, 2H), 6.83 (d, J=3.3 Hz, 1H), 6.69 (d, J=8.7 Hz, 2H), 6.65 (dd, J=3.2, 1.8 Hz, 1H), 6.39 (t, J=5.3 Hz, 1H), 4.62 (s, 2H), 3.20 (q, J=6.2 Hz, 2H), 2.49-2.07 (m, 10H), 2.13 (s, 3H); MS (ESI) m/z 460 (M+H)⁺.

Example 295: N-(7-(furan-2-yl)-3-oxoisoindolin-4-yl)-4-((3-(4-methyl piperazin-1-yl)propyl)amino) benzamide

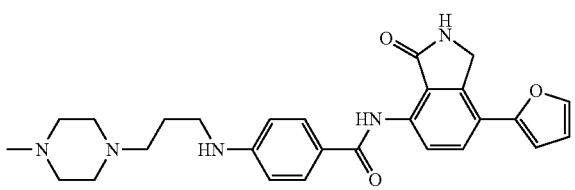 [SMILES: CN1CCN(CCCNc2ccc(C(=O)Nc3ccc(-c4ccco4)c4c3C(=O)NC4)cc2)CC1]

¹H NMR (400 MHz, DMSO-d₆) δ 11.45 (s, 1H), 9.12 (s, 1H), 8.54 (d, J=8.6 Hz, 1H), 7.93 (d, J=8.6 Hz, 1H), 7.82 (d, J=1.5 Hz, 1H), 7.72 (d, J=8.7 Hz, 2H), 6.84 (d, J=3.4 Hz, 1H), 6.68-6.66 (m, 3H), 6.56 (t, J=8.7 Hz, 1H), 4.63 (s, 2H), 3.12 (q, J=6.2 Hz, 2H), 2.38-2.34 (m, 7H), 2.15 (s, 4H), 1.70 (quint, J=6.9 Hz, 3H); [M+H]⁺: 459.

Example 296: N-(7-(2,3-dimethoxyphenyl)-3-oxoisoindolin-4-yl)-4-((3-morpholinopropyl)amino) benzamide

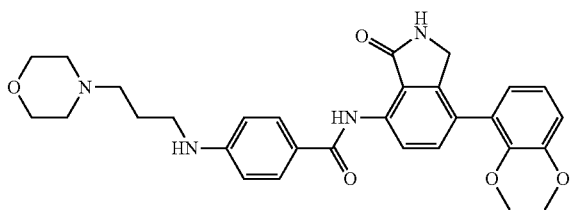 [SMILES: COc1cccc(-c2ccc(NC(=O)c3ccc(NCCCN4CCOCC4)cc3)c3c2CNC3=O)c1OC]

¹H NMR (400 MHz, DMSO-d₆) δ 11.40 (br s, 1H), 8.89 (br s, 1H), 8.52 (d, J=8.4 Hz, 1H), 7.73 (d, J=8.8 Hz, 2H), 7.50 (d, J=8.4 Hz, 1H), 7.17-7.09 (m, 2H), 6.94 (dd, J=7.4, 1.8 Hz, 1H), 6.68 (d, J=8.8 Hz, 2H), 6.53 (t, J=5.4 Hz, 1H), 4.29 (s, 2H), 3.85 (s, 3H), 3.59 (t, J=4.4 Hz, 2H), 3.44 (s, 3H), 3.17-3.12 (m, 2H), 2.50-2.48 (m, 2H), 2.39-2.35 (m, 6H), 1.72 (quint, J=6.8 Hz, 2H); [M+H]⁺: 531.

Example 297: N-(7-(2,3-dimethoxyphenyl)-3-oxoisoindolin-4-yl)-4-((2-morpholinoethyl)amino)benzamide

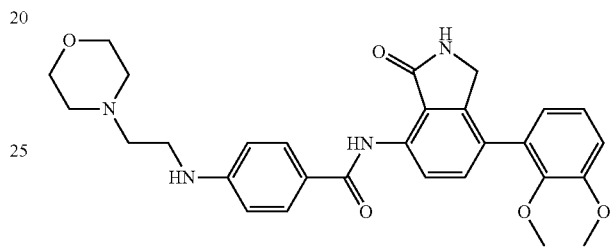

¹H NMR (400 MHz, DMSO-d₆) δ 11.41 (br s, 1H), 8.90 (br s, 1H), 8.52 (d, J=8.8 Hz, 1H), 7.74 (d, J=8.8 Hz, 2H), 7.50 (d, J=8.4 Hz, 1H), 7.17-7.09 (m, 2H), 6.94 (dd, J=7.4, 1.8 Hz, 1H), 6.72 (d, J=8.8 Hz, 2H), 6.36 (t, J=5.4 Hz, 1H), 4.29 (s, 2H), 3.85 (s, 3H), 3.60 (t, J=4.6 Hz, 4H), 3.44 (s, 3H), 3.24 (q, J=6.4 Hz, 2H), 2.50-2.48 (m, 2H), 2.44-2.43 (m, 4H); [M+H]⁺: 517.

Example 298: N-(7-(2,3-dimethoxyphenyl)-3-oxoisoindolin-4-yl)-4-((2-(piperidin-1-yl)ethyl)amino) benzamide

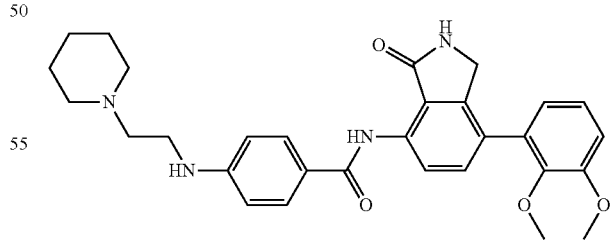

¹H NMR (400 MHz, DMSO-d₆) δ 11.41 (br s, 1H), 8.90 (br s, 1H), 8.52 (d, J=8.4 Hz, 1H), 7.73 (d, J=8.8 Hz, 2H), 7.50 (d, J=8.4 Hz, 1H), 7.17-7.09 (m, 2H), 6.94 (dd, J=7.2, 1.6 Hz, 1H), 6.71 (d, J=8.8 Hz, 2H), 6.32 (t, J=5.2 Hz, 1H), 4.29 (s, 2H), 3.85 (s, 3H), 3.44 (s, 3H), 3.21 (q, J=6.4 Hz, 2H), 2.50-2.48 (m, 2H), 2.42-2.40 (m, 4H), 1.55-1.48 (m, 4H), 1.41-1.39 (m, 2H); [M+H]⁺: 515.

Example 299: N-(7-(2,3-dimethoxyphenyl)-3-oxoisoindolin-4-yl)-4-((2-(pyrrolidin-1-yl)ethyl)amino)benzamide

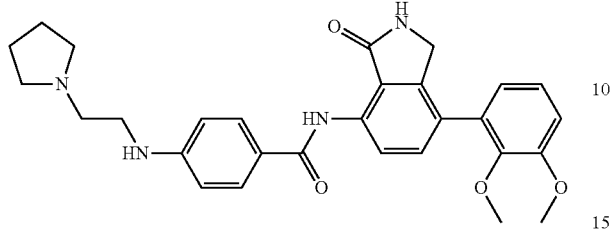

¹H NMR (400 MHz, DMSO-d₆) δ 11.40 (br s, 1H), 8.90 (br s, 1H), 8.52 (d, J=8.4 Hz, 1H), 7.73 (d, J=8.8 Hz, 2H), 7.50 (d, J=8.4 Hz, 1H), 7.17-7.09 (m, 2H), 6.94 (dd, J=7.4, 1.8 Hz, 1H), 6.71 (d, J=8.8 Hz, 2H), 6.40 (t, J=5.4 Hz, 1H), 4.29 (s, 2H), 3.85 (s, 3H), 3.44 (s, 3H), 3.22 (q, J=5.6 Hz, 2H), 2.63 (t, J=6.8 Hz, 2H), 2.50-2.48 (m, 4H), 1.71-1.68 (m, 4H); [M+H]⁺: 501.

Example 300: N-(7-(2,3-dimethoxyphenyl)-3-oxoisoindolin-4-yl)-4-((2-methoxyethyl)amino)benzamide

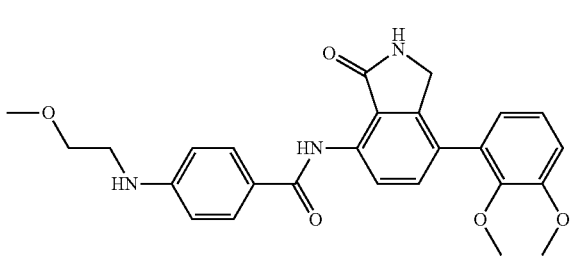 [SMILES: COCCNc1ccc(C(=O)Nc2ccc(-c3cccc(OC)c3OC)c3c2C(=O)NC3)cc1]

¹H NMR (400 MHz, DMSO-d₆) δ 11.41 (br s, 1H), 8.90 (br s, 1H), 8.52 (d, J=8.4 Hz, 1H), 7.73 (d, J=8.4 Hz, 2H), 7.50 (d, J=8.4 Hz, 1H), 7.17-7.09 (m, 2H), 6.94 (dd, J=7.2, 1.6 Hz, 1H), 6.73 (d, J=8.8 Hz, 2H), 6.53 (t, J=5.6 Hz, 1H), 4.29 (s, 2H), 3.85 (s, 3H), 3.52-3.49 (m, 2H), 3.44 (s, 3H), 3.30-3.28 (m, 2H), 3.29 (s, 3H); [M+H]⁺: 462.

Example 301: N-(7-(2,3-dimethoxyphenyl)-3-oxoisoindolin-4-yl)-4-((2-(dimethylamino)ethyl)amino)benzamide

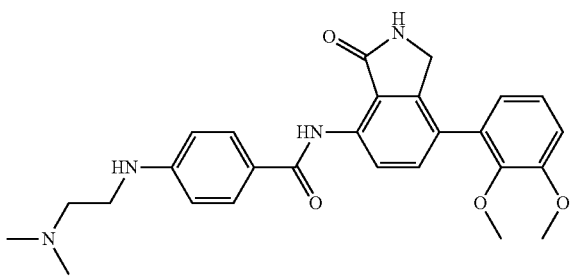 [SMILES: COc1cccc(-c2ccc(NC(=O)c3ccc(NCCN(C)C)cc3)c3c2CNC3=O)c1OC]

¹H NMR (400 MHz, DMSO-d₆) δ 11.41 (br s, 1H), 8.91 (br s, 1H), 8.52 (d, J=8.8 Hz, 1H), 7.73 (d, J=8.8 Hz, 2H), 7.50 (d, J=8.4 Hz, 1H), 7.17-7.09 (m, 2H), 6.94 (dd, J=7.4, 1.8 Hz, 1H), 6.72 (d, J=8.8 Hz, 2H), 6.33 (t, J=5.6 Hz, 1H), 4.29 (s, 2H), 3.85 (s, 3H), 3.44 (s, 3H), 3.22-3.17 (m, 2H), 2.50-2.48 (m, 2H), 2.21 (s, 6H); [M+H]⁺: 475.

Example 302: N-(7-(2-methoxyphenyl)-3-oxoisoindolin-4-yl)-4-((3-(pyrrolidin-1-yl)propyl)amino)benzamide

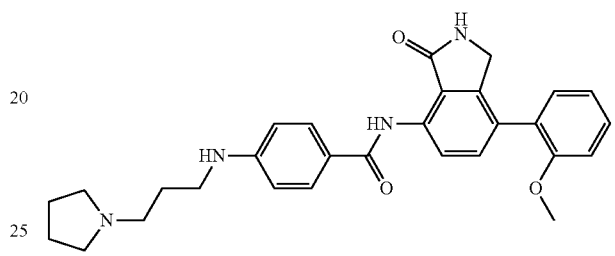

¹H NMR (400 MHz, DMSO-d₆) δ 11.40 (br s, 1H), 8.89 (br s, 1H), 8.50 (d, J=8.4 Hz, 1H), 7.73 (d, J=8.8 Hz, 2H), 7.47 (d, J=8.4 Hz, 1H), 7.42-7.37 (m, 1H), 7.30 (dd, J=7.2, 1.6 Hz, 1H), 7.13 (d, J=8.0 Hz, 1H), 7.04 (t, J=7.4 Hz, 1H), 6.68 (d, J=8.8 Hz, 2H), 6.53 (t, J=5.4 Hz, 1H), 4.24 (s, 2H), 3.76 (s, 3H), 3.14 (q, J=5.6 Hz, 2H), 2.50-2.48 (m, 2H), 2.47-2.43 (m, 4H), 1.75-1.69 (s, 6H); [M+H]⁺: 485.

Example 303: N-(7-(2-methoxyphenyl)-3-oxoisoindolin-4-yl)-4-((2-(pyrrolidin-1-yl)ethyl)amino)benzamide hydrochloride

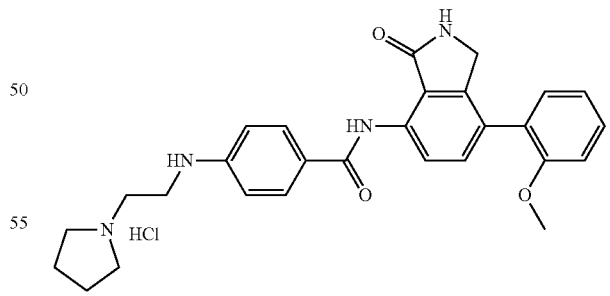

¹H NMR (400 MHz, DMSO-d₆) δ 11.45 (br s, 1H), 10.14 (br s, 1H), 8.92 (br s, 1H), 8.50 (d, J=8.4 Hz, 1H), 7.80 (d, J=8.8 Hz, 2H), 7.48 (d, J=8.4 Hz, 1H), 7.42-7.38 (m, 1H), 7.31 (dd, J=7.2, 1.6 Hz, 1H), 7.14 (d, J=8.0 Hz, 1H), 7.04 (t, J=7.4 Hz, 1H), 6.80 (d, J=8.8 Hz, 2H), 6.77-6.76 (m, 1H), 4.25 (s, 2H), 3.76 (s, 3H), 3.61-3.58 (m, 2H), 3.56-3.51 (m, 2H), 3.33-3.31 (m, 2H), 3.07-3.00 (m, 2H), 2.05-1.96 (m, 2H), 1.92-1.86 (m, 2H); [M+H]⁺: 471 (free form).

Example 304: N-(7-(2,3-dimethoxyphenyl)-3-ox-oisoindolin-4-yl)-4-((2-(pyrrolidin-1-yl)ethyl)amino)benzamide hydrochloride

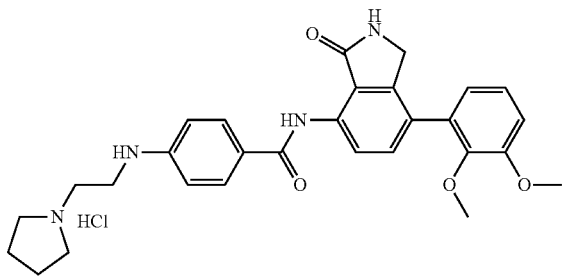 [SMILES: COc1cccc(-c2ccc(NC(=O)c3ccc(NCCN4CCCC4)cc3)c3c2CNC3=O)c1OC ; Cl]

$^1$H NMR (400 MHz, DMSO-d$_6$) δ 11.46 (br s, 1H), 10.29 (br s, 1H), 8.95 (br s, 1H), 8.51 (d, J=8.4 Hz, 1H), 7.79 (d, J=8.8 Hz, 2H), 7.51 (d, J=8.4 Hz, 1H), 7.17-7.09 (m, 2H), 6.94 (dd, J=7.4, 1.8 Hz, 1H), 6.81-6.76 (m, 3H), 4.29 (s, 2H), 3.85 (s, 3H), 3.62-3.58 (m, 2H), 3.56-3.52 (m, 2H), 3.33-3.32 (m, 2H), 3.05-3.03 (m, 2H), 2.02-2.00 (m, 2H), 1.88-1.87 (m, 2H); [M+H]$^+$: 501 (free form).

Example 305: 4-((2-(Dimethylamino)ethyl)amino)-N-(7-(2-methoxyphenyl)-3-oxoisoindolin-4-yl)benzamide

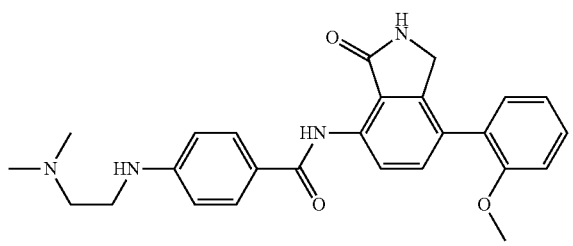 [SMILES: COc1ccccc1-c1ccc(NC(=O)c2ccc(NCCN(C)C)cc2)c2c1CNC2=O]

$^1$H NMR (400 MHz, DMSO-d$_6$) δ 11.41 (br s, 1H), 8.91 (br s, 1H), 8.50 (d, J=8.4 Hz, 1H), 7.73 (d, J=8.4 Hz, 2H), 7.47 (d, J=8.4 Hz, 1H), 7.42-7.39 (m, 1H), 7.38 (dd, J=7.2, 1.6 Hz, 1H), 7.31 (dd, J=7.4, 1.4 Hz, 1H), 7.14 (d, J=8.4 Hz, 1H), 7.04 (t, J=7.4 Hz, 1H), 6.72 (d, J=8.8 Hz, 2H), 6.34 (t, J=5.2 Hz, 1H), 4.25 (s, 2H), 3.76 (s, 3H), 3.19-3.18 (m, 2H), 2.48-2.45 (m, 2H), 2.20 (s, 6H); [M+H]$^+$: 445.

Example 306: N-(7-(2,3-dimethoxyphenyl)-3-ox-oisoindolin-4-yl)-4-((3-(dimethylamino)propyl)amino)benzamide

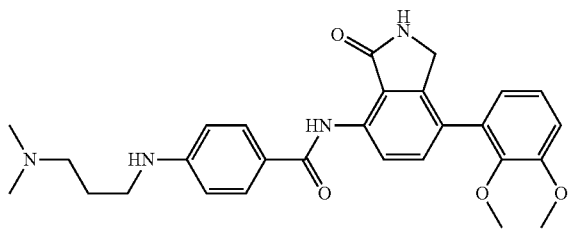 [SMILES: COc1cccc(-c2ccc(NC(=O)c3ccc(NCCCN(C)C)cc3)c3c2CNC3=O)c1OC]

$^1$H NMR (400 MHz, DMSO-d$_6$) δ 11.40 (br s, 1H), 8.92 (br s, 1H), 8.52 (d, J=8.4 Hz, 1H), 7.73 (d, J=8.8 Hz, 2H), 7.50 (d, J=8.4 Hz, 1H), 7.17-7.09 (m, 2H), 6.94 (dd, J=7.4, 1.8 Hz, 1H), 6.68 (d, J=8.8 Hz, 2H), 6.53 (t, J=5.6 Hz, 1H), 4.29 (s, 2H), 3.85 (s, 3H), 3.44 (s, 3H), 3.16-3.10 (m, 2H), 2.30-2.28 (m, 2H), 2.15 (s, 6H), 1.72-1.65 (m, 2H); [M+H]$^+$: 489.

Example 307: N-(7-(2-methoxyphenyl)-3-oxoisoindolin-4-yl)-4-((3-(piperidin-1-yl)propyl)amino)benzamide

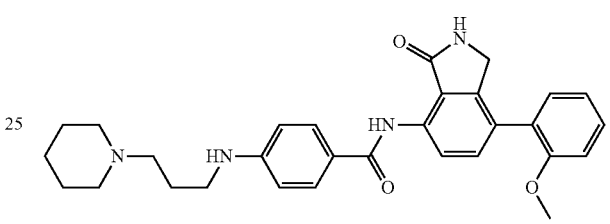

$^1$H NMR (400 MHz, DMSO-d$_6$) δ 11.40 (br s, 1H), 8.91 (br s, 1H), 8.50 (d, J=8.4 Hz, 1H), 7.73 (d, J=8.8 Hz, 2H), 7.47 (d, J=8.4 Hz, 1H), 7.42-7.37 (m, 1H), 7.31 (d, J=7.6 Hz, 1H), 7.13 (d, J=8.4 Hz, 1H), 7.04 (t, J=7.6 Hz, 1H), 6.68 (d, J=8.8 Hz, 2H), 6.58 (t, J=5.2 Hz, 1H), 4.25 (s, 2H), 3.76 (s, 3H), 3.16-3.12 (m, 2H), 2.35-2.31 (m, 6H), 1.72-1.68 (m, 2H), 1.52-1.49 (m, 4H), 1.39-1.37 (m, 2H); [M+H]$^+$: 499.

Example 308: N-(7-(2,3-dimethoxyphenyl)-3-ox-oisoindolin-4-yl)-4-((3-(piperidin-1-yl)propyl)amino)benzamide

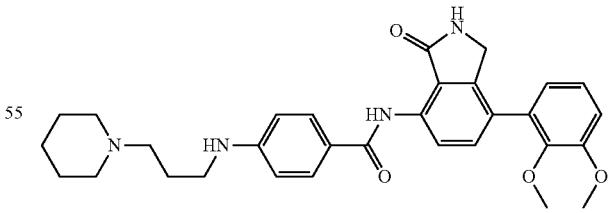

$^1$H NMR (400 MHz, DMSO-d$_6$) δ 11.40 (br s, 1H), 8.91 (br s, 1H), 8.50 (d, J=8.4 Hz, 1H), 7.73 (d, J=8.4 Hz, 2H), 7.50 (d, J=8.4 Hz, 1H), 7.17-7.09 (m, 2H), 6.94 (d, J=6.4 Hz, 1H), 6.67 (d, J=8.4 Hz, 2H), 6.57 (t, J=5.2 Hz, 1H), 4.29 (s, 2H), 3.85 (s, 3H), 3.44 (s, 3H), 3.17-3.11 (m, 2H), 2.35-2.31 (m, 6H), 1.72-1.68 (m, 2H), 1.52-1.48 (m, 4H), 1.39-1.37 (m, 2H); [M+H]$^+$: 529.

Example 309: 2-Methyl-N-(3-oxo-7-phenylisoindolin-4-yl)-4-((2-(pyrrolidin-1-yl)ethyl)amino)benzamide

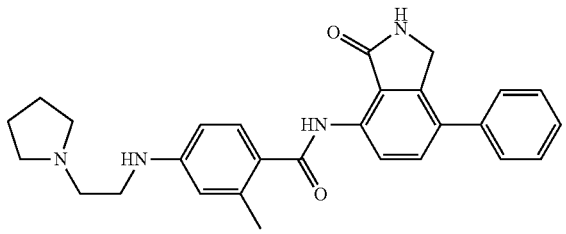 [SMILES: Cc1cc(NCCN2CCCC2)ccc1C(=O)Nc1ccc(-c2ccccc2)c2c1C(=O)NC2]

$^1$H NMR (400 MHz, DMSO-d$_6$) δ 11.05 (br s, 1H), 8.98 (br s, 1H), 8.55 (d, J=8.4 Hz, 1H), 7.66 (d, J=8.4 Hz, 1H), 7.61 (d, J=7.6 Hz, 2H), 7.50-7.44 (m, 3H), 7.41-7.39 (m, 1H), 6.53-6.49 (m, 2H), 6.13-6.11 (m, 1H), 4.57 (s, 2H), 3.20-3.18 (m, 2H), 2.61-2.59 (m, 2H), 2.50-2.49 (m, 4H), 2.44 (s, 3H), 1.70-1.68 (m, 4H); [M+H]$^+$: 455.

Example 310: 4-((3-Methoxypropyl)amino)-N-(7-(2-methoxypyridin-3-yl)-3-oxoisoindolin-4-yl)benzamide

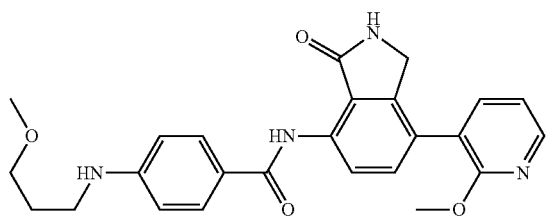 [SMILES: COCCCNc1ccc(C(=O)Nc2ccc(-c3cccnc3OC)c3c2C(=O)NC3)cc1]

$^1$H NMR (400 MHz, DMSO-d$_6$) δ 11.43 (br s, 1H), 8.95 (br s, 1H), 8.52 (d, J=8.4 Hz, 1H), 8.23 (dd, J=5.0, 1.8 Hz, 1H), 7.79 (dd, J=7.2, 1.6 Hz, 1H), 7.73 (d, J=8.8 Hz, 2H), 7.54 (d, J=8.4 Hz, 1H), 7.11 (m, 1H), 6.68 (d, J=8.8 Hz, 2H), 6.52 (t, J=5.2 Hz, 1H), 4.31 (s, 2H), 3.88 (s, 3H), 3.44-3.40 (m, 2H), 3.26 (s, 3H), 3.18-3.13 (m, 2H), 1.83-1.76 (m, 2H); [M+H]$^+$: 447.

Example 311: N-(7-(2,3-dimethoxyphenyl)-3-oxoisoindolin-4-yl)-4-((2-hydroxyethyl)amino)benzamide

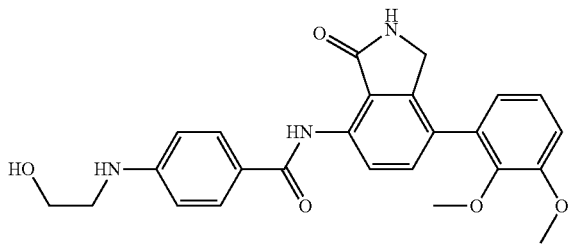 [SMILES: COc1cccc(-c2ccc(NC(=O)c3ccc(NCCO)cc3)c3c2CNC3=O)c1OC]

$^1$H NMR (400 MHz, DMSO-d$_6$) δ 11.41 (br s, 1H), 8.91 (br s, 1H), 8.52 (d, J=8.4 Hz, 1H), 7.73 (d, J=8.4 Hz, 2H), 7.50 (d, J=8.4 Hz, 1H), 7.17-7.09 (m, 2H), 6.94 (dd, J=7.2, 1.6 Hz, 1H), 6.71 (d, J=8.8 Hz, 2H), 6.48 (t, J=5.6 Hz, 1H), 4.77 (t, J=5.4 Hz, 1H), 4.29 (s, 2H), 3.85 (s, 3H), 3.59-3.57 (m, 2H), 3.44 (s, 3H), 3.20-3.18 (m, 2H); [M+H]$^+$: 448.

Example 312: N-(7-(2,3-dimethoxyphenyl)-3-oxoisoindolin-4-yl)-4-morpholinobenzamide

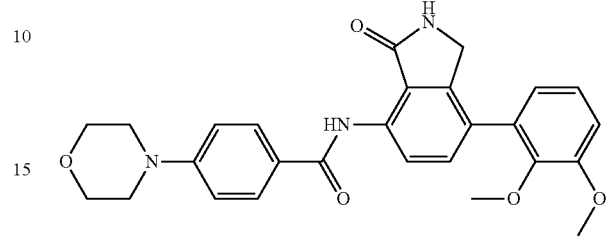

$^1$H NMR (400 MHz, DMSO-d$_6$) δ 11.52 (br s, 1H), 8.94 (br s, 1H), 8.52 (d, J=8.4 Hz, 1H), 7.85 (d, J=9.2 Hz, 2H), 7.52 (d, J=8.4 Hz, 1H), 7.17-7.09 (m, 4H), 6.94 (dd, J=7.4, 1.8 Hz, 1H), 4.30 (s, 2H), 3.85 (s, 3H), 3.77-3.74 (m, 4H), 3.45 (s, 3H), 3.33-3.28 (m, 2H); [M+H]$^+$: 474.

Example 313: N-(7-(3-fluoro-2-methoxyphenyl)-3-oxoisoindolin-4-yl)-4-((2-(pyrrolidin-1-yl)ethyl)amino)benzamide

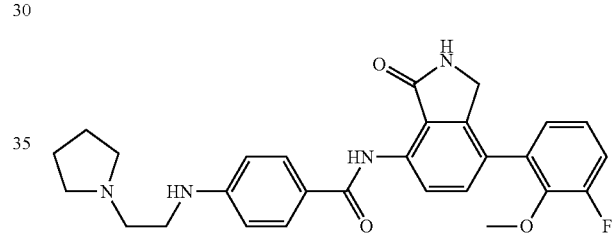

$^1$H NMR (400 MHz, DMSO-d$_6$) δ 11.42 (br s, 1H), 8.96 (br s, 1H), 8.52 (d, J=8.4 Hz, 1H), 7.74 (d, J=8.8 Hz, 2H), 7.54 (d, J=8.4 Hz, 1H), 7.36-7.30 (m, 1H), 7.24-7.16 (m, 2H), 6.71 (d, J=8.8 Hz, 2H), 6.42 (t, J=5.4 Hz, 1H), 4.32 (s, 2H), 3.60 (d, J=1.2 Hz, 3H), 3.25-3.20 (m, 2H), 2.65-2.60 (m, 2H), 2.51-2.50 (m, 2H), 1.72-1.69 (m, 4H); [M+H]$^+$: 489.

Example 314: N-(7-(2,3-dimethoxyphenyl)-3-oxoisoindolin-4-yl)-4-((2-(4-methylpiperazin-1-yl)ethyl)amino)benzamide

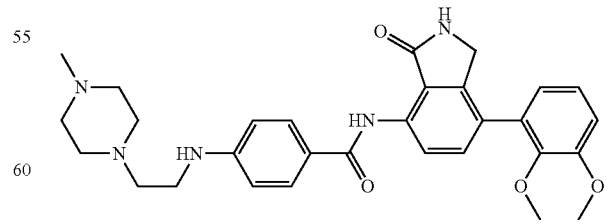

$^1$H NMR (400 MHz, DMSO-d$_6$) δ 11.41 (br s, 1H), 8.92 (br s, 1H), 8.52 (d, J=8.4 Hz, 1H), 7.73 (d, J=8.8 Hz, 2H), 7.50 (d, J=8.4 Hz, 1H), 7.17-7.09 (m, 2H), 6.94 (dd, J=7.4, 1.8 Hz, 1H), 6.71 (d, J=8.8 Hz, 2H), 6.34 (t, J=5.4 Hz, 1H), 4.29 (s, 2H), 3.85 (s, 3H), 3.44 (s, 3H), 3.22-3.19 (m, 2H), 2.50-2.48 (m, 4H), 2.35-2.27 (m, 6H), 2.15 (s, 3H); [M+H]⁺: 530.

Example 315: 4-((2-Aminoethyl)amino)-N-(7-(2,3-dimethoxyphenyl)-3-oxoisoindolin-4-yl)benzamide

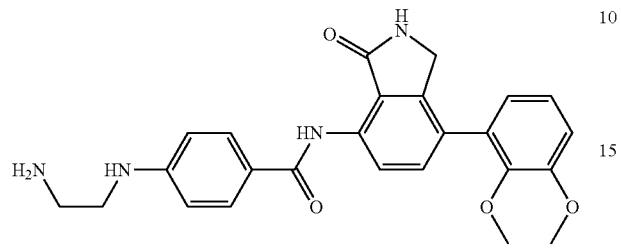

¹H NMR (400 MHz, DMSO-d₆) δ 11.41 (br s, 1H), 8.91 (br s, 1H), 8.52 (d, J=8.4 Hz, 1H), 7.73 (d, J=8.8 Hz, 2H), 7.50 (d, J=8.4 Hz, 1H), 7.17-7.09 (m, 2H), 6.94 (dd, J=7.4, 1.8 Hz, 1H), 6.70 (d, J=9.2 Hz, 2H), 6.49 (t, J=5.6 Hz, 1H), 4.29 (s, 2H), 3.85 (s, 3H), 3.44 (s, 3H), 3.12-3.07 (m, 2H), 2.75-2.72 (m, 2H); [M+H]⁺: 447.

Example 316: N-(7-(2,3-dimethoxyphenyl)-3-oxoisoindolin-4-yl)-4-((3-(4-methylpiperazin-1-yl)propyl)amino)benzamide

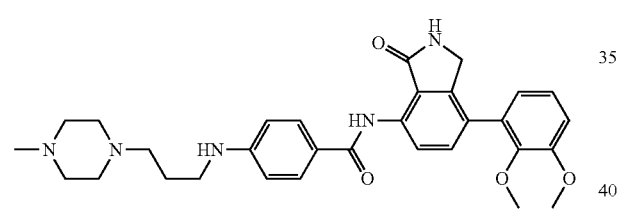

¹H NMR (400 MHz, DMSO-d₆) δ 11.40 (br s, 1H), 8.90 (br s, 1H), 8.52 (d, J=8.4 Hz, 1H), 7.73 (d, J=8.8 Hz, 2H), 7.50 (d, J=8.4 Hz, 1H), 7.17-7.09 (m, 2H), 6.94 (d, J=8.8 Hz, 1H), 6.71 (d, J=8.8 Hz, 2H), 6.54 (t, J=5.4 Hz, 1H), 4.29 (s, 2H), 3.85 (s, 3H), 3.44 (s, 3H), 3.15-3.10 (m, 2H), 2.40-2.32 (m, 10H), 2.16 (s, 3H), 1.74-1.66 (m, 2H); [M+H]⁺: 544.

Example 317: N-(3-oxo-7-phenylisoindolin-4-yl)-4-((2-(pyrrolidin-1-yl) ethyl)amino)benzamide

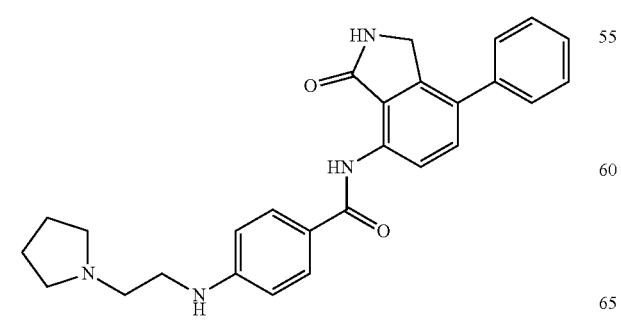

¹H NMR (400 MHz, DMSO-d₆) δ 11.48 (s, 1H), 9.00 (s, 1H), 8.57 (d, J=8.4 Hz, 1H), 7.74 (d, J=8.5 Hz, 2H), 7.67 (d, J=8.4 Hz, 1H), 7.61 (d, J=7.5 Hz, 2H), 7.49 (t, J=7.5 Hz, 2H), 7.39 (t, J=7.3 Hz, 1H), 6.71 (d, J=8.5 Hz, 2H), 6.38 (t, J=5.5 Hz, 1H), 4.58 (s, 2H), 3.23 (q, J=6.3 Hz, 4H), 2.63 (t, J=6.7 Hz, 2H), 1.70 (p, J=3.0 Hz, 4H); [M+H]⁺: 441.

Example 318: N-(7-(2-methoxyphenyl)-3-oxoisoindolin-4-yl)-4-((2-(pyrrolidin-1-yl)ethyl)amino)benzamide

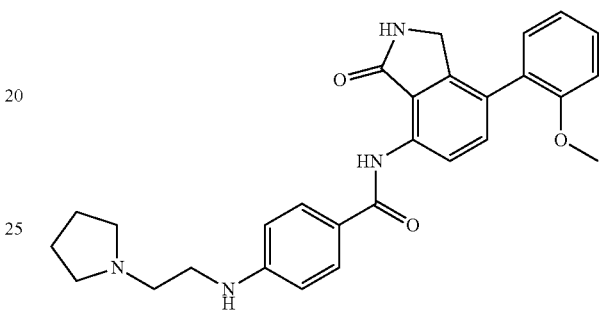

¹H NMR (400 MHz, DMSO-d₆) δ 11.40 (s, 1H), 8.86 (s, 1H), 8.50 (d, J=8.2 Hz, 1H), 7.74 (d, J=8.6 Hz, 2H), 7.47 (d, J=8.4 Hz, 1H), 7.40 (t, J=7.9 Hz, 1H), 7.31 (d, J=7.3 Hz, 1H), 7.14 (d, J=8.5 Hz, 1H), 7.04 (t, J=7.5 Hz, 1H), 6.71 (d, J=8.5 Hz, 2H), 6.37 (d, J=5.7 Hz, 1H), 4.25 (s, 2H), 3.77 (s, 3H), 3.23 (d, J=6.1 Hz, 4H), 2.63 (t, J=6.7 Hz, 2H), 1.70 (s, 4H); [M+H]⁺: 471.

Example 319: 4-(4-Methylpiperazin-1-yl)-N-(3-oxo-7-phenylisoindolin-4-yl)benzamide

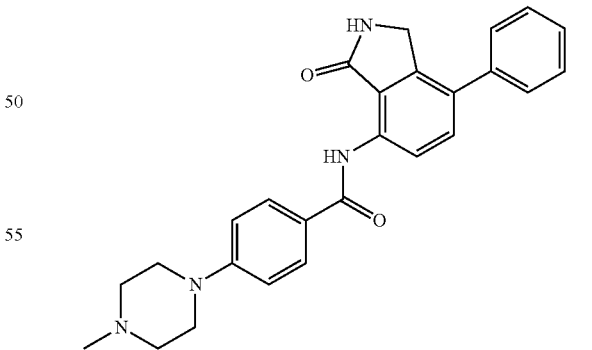

¹H NMR (400 MHz, DMSO-d₆) δ 11.62 (s, 1H), 10.13 (s, 1H), 9.07 (s, 1H), 8.57 (d, J=8.5 Hz, 1H), 7.89 (d, J=8.8 Hz, 2H), 7.70 (d, J=8.5 Hz, 1H), 7.66-7.58 (m, 2H), 7.49 (t, J=7.6 Hz, 2H), 7.40 (t, J=7.4 Hz, 1H), 7.19 (d, J=8.7 Hz, 2H), 4.60 (s, 2H), 4.09 (br s, 2H), 3.52 (br s, 2H), 3.17 (br s, 4H), 2.84 (s, 3H); [M+H]⁺: 427.

Example 320: 4-Morpholino-N-(3-oxo-7-phenylisoindolin-4-yl)benzamide

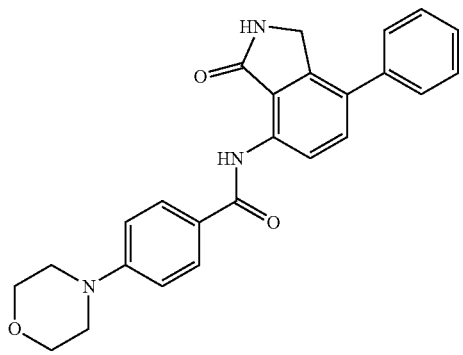 [SMILES: O=C(Nc1ccc(-c2ccccc2)c2c1C(=O)NC2)c1ccc(N2CCOCC2)cc1]

$^1$H NMR (400 MHz, DMSO-d$_6$) δ 11.59 (s, 1H), 9.03 (s, 1H), 8.57 (d, J=8.5 Hz, 1H), 7.86 (d, J=8.6 Hz, 2H), 7.69 (d, J=8.5 Hz, 1H), 7.65-7.58 (m, 2H), 7.49 (t, J=7.5 Hz, 2H), 7.40 (t, J=7.4 Hz, 1H), 7.10 (d, J=8.6 Hz, 2H), 4.59 (s, 2H), 3.76 (t, J=4.9 Hz, 4H); [M+H]$^+$: 414.

Example 321: 4-((2-Methoxyethyl)amino)-N-(3-oxo-7-phenylisoindolin-4-yl) benzamide

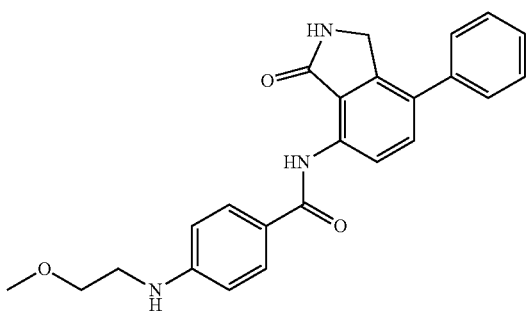 [SMILES: COCCNc1ccc(C(=O)Nc2ccc(-c3ccccc3)c3c2C(=O)NC3)cc1]

$^1$H NMR (400 MHz, DMSO-d$_6$) δ 11.48 (s, 1H), 9.00 (s, 1H), 8.57 (d, J=8.4 Hz, 1H), 7.74 (d, J=8.5 Hz, 2H), 7.67 (d, J=8.5 Hz, 1H), 7.61 (d, J=7.6 Hz, 2H), 7.48 (t, J=7.6 Hz, 2H), 7.39 (t, J=7.3 Hz, 1H), 6.73 (d, J=8.5 Hz, 2H), 6.50 (t, J=5.6 Hz, 1H), 4.58 (s, 2H), 3.52 (t, J=5.5 Hz, 2H); [M+H]$^+$: 402.

Example 322: 4-((2-Morpholinoethyl)amino)-N-(3-oxo-7-phenylisoindolin-4-yl)benzamide

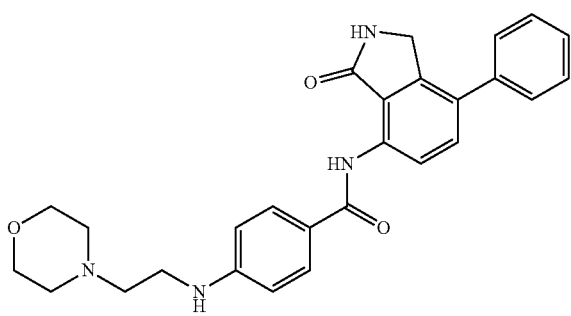 [SMILES: O=C(Nc1ccc(-c2ccccc2)c2c1C(=O)NC2)c1ccc(NCCN2CCOCC2)cc1]

$^1$H NMR (400 MHz, DMSO-d$_6$) δ 11.48 (s, 1H), 9.01 (s, 1H), 8.57 (d, J=8.4 Hz, 1H), 7.74 (d, J=8.3 Hz, 2H), 7.64 (dd, J=23.3, 8.0 Hz, 3H), 7.48 (t, J=7.5 Hz, 2H), 7.40 (d, J=7.5 Hz, 1H), 6.72 (d, J=8.5 Hz, 2H), 6.35 (s, 1H), 4.58 (s, 2H), 3.63-3.56 (m, 4H), 3.24 (s, 2H), 2.44 (s, 6H); [M+H]$^+$: 457.

Example 323: N-(7-(2-methoxyphenyl)-3-oxoisoindolin-4-yl)-4-morpholino benzamide

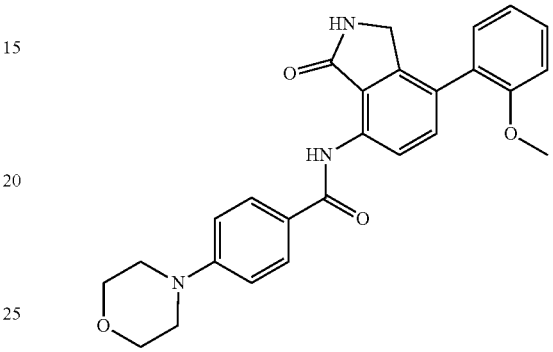

$^1$H NMR (400 MHz, DMSO-d$_6$) δ 11.51 (s, 1H), 8.89 (s, 1H), 8.51 (d, J=8.4 Hz, 1H), 7.86 (d, J=8.6 Hz, 2H), 7.49 (d, J=8.4 Hz, 1H), 7.40 (s, 1H), 7.31 (dd, J=7.5, 1.8 Hz, 1H), 7.14 (d, J=8.3 Hz, 1H), 7.10 (d, J=8.7 Hz, 2H), 7.04 (t, J=7.4 Hz, 1H), 4.26 (s, 2H), 3.76 (d, J=4.0 Hz, 8H), 2.08 (s, 3H); [M+H]$^+$: 444.

Example 324: 4-((2-Methoxyethyl)amino)-N-(7-(2-methoxyphenyl)-3-oxoisoindolin-4-yl)benzamide

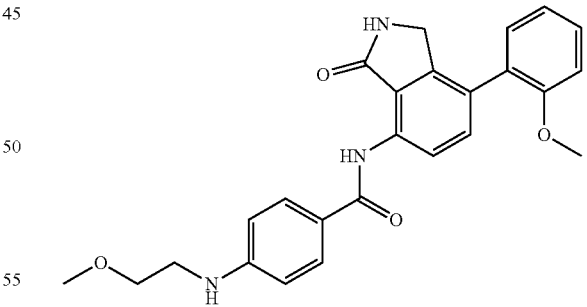

$^1$H NMR (400 MHz, DMSO-d$_6$) δ 11.40 (s, 1H), 8.86 (s, 1H), 8.50 (d, J=8.4 Hz, 1H), 7.77-7.69 (m, 2H), 7.46 (dd, J=8.5, 1.5 Hz, 1H), 7.39 (t, J=7.9 Hz, 1H), 7.34-7.27 (m, 1H), 7.13 (d, J=8.2 Hz, 1H), 7.04 (t, J=7.5 Hz, 1H), 6.76-6.69 (m, 2H), 6.49 (s, 1H), 4.25 (s, 2H), 3.76 (d, J=1.6 Hz, 3H), 3.51 (t, J=5.6 Hz, 2H); [M+H]$^+$: 432.

Example 325: N-(7-(2-methoxyphenyl)-3-oxoisoindolin-4-yl)-4-(4-methyl piperazin-1-yl)benzamide

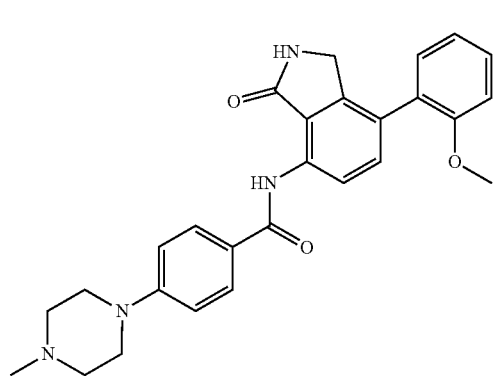

¹H NMR (400 MHz, DMSO-d₆) δ 11.49 (s, 1H), 8.89 (s, 1H), 8.50 (d, J=8.3 Hz, 1H), 7.83 (d, J=8.5 Hz, 2H), 7.48 (d, J=8.4 Hz, 1H), 7.40 (t, J=7.8 Hz, 1H), 7.35-7.28 (m, 1H), 7.14 (d, J=8.4 Hz, 1H), 7.11-7.02 (m, 3H), 4.25 (s, 2H), 3.77 (s, 3H), 3.33 (t, J=5.1 Hz, 4H), 2.46 (d, J=4.8 Hz, 4H), 2.23 (s, 3H); [M+H]⁺: 457.

Example 326: N-(7-(2-methoxyphenyl)-3-oxoisoindolin-4-yl)-4-(2-morpholinoethyl)amino)benzamide Example 327: 4-((3-Morpholinopropyl)amino)-N-(3-oxo-7-phenylisoindolin-4-yl)benzamide

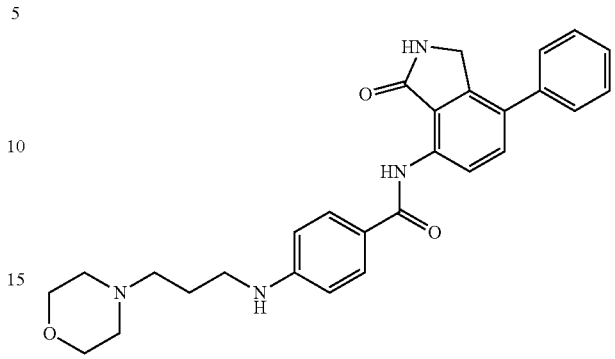

¹H NMR (400 MHz, DMSO-d₆) δ 11.47 (s, 1H), 9.00 (s, 1H), 8.57 (d, J=8.5 Hz, 1H), 7.74 (d, J=8.5 Hz, 2H), 7.67 (d, J=8.5 Hz, 1H), 7.61 (d, J=7.5 Hz, 2H), 7.48 (t, J=7.6 Hz, 2H), 7.39 (t, J=7.4 Hz, 1H), 6.69 (d, J=8.4 Hz, 2H), 6.51 (t, J=5.6 Hz, 1H), 4.58 (s, 2H), 3.59 (t, J=4.6 Hz, 4H), 3.15 (q, J=6.5 Hz, 2H), 2.43-2.33 (m, 4H), 1.72 (p, J=6.9 Hz, 2H); [M+H]⁺: 471.

Example 328: N-(7-(2-methoxyphenyl)-3-oxoisoindolin-4-yl)-4-(3-morpholinopropyl)amino)benzamide

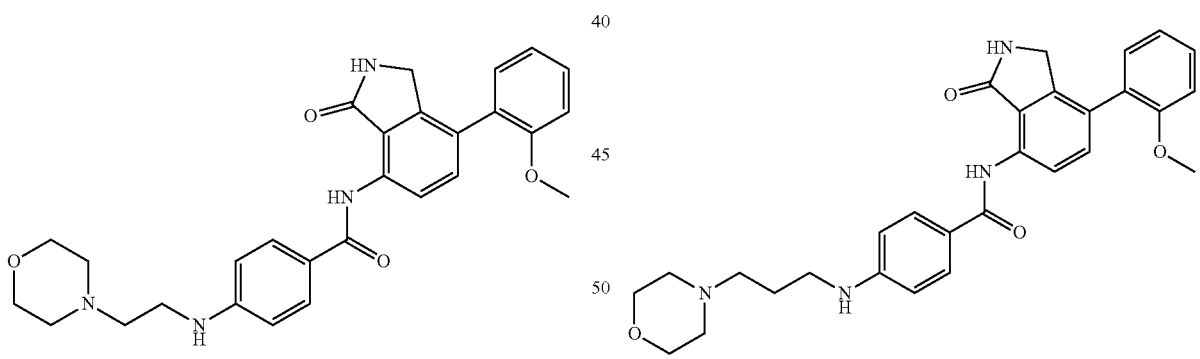

¹H NMR (400 MHz, DMSO-d₆) δ 11.40 (s, 1H), 8.85 (s, 1H), 8.50 (d, J=8.4 Hz, 1H), 7.74 (d, J=8.5 Hz, 2H), 7.47 (d, J=8.3 Hz, 1H), 7.43-7.37 (m, 1H), 7.30 (dd, J=7.4, 1.8 Hz, 1H), 7.14 (d, J=8.3 Hz, 1H), 7.04 (t, J=7.4 Hz, 1H), 6.72 (d, J=8.7 Hz, 2H), 6.32 (t, J=5.5 Hz, 1H), 4.25 (s, 2H), 3.77 (s, 3H), 3.60 (t, J=4.6 Hz, 4H), 3.24 (q, J=6.3 Hz, 2H), 2.53 (d, J=6.7 Hz, 2H), 2.44 (t, J=4.7 Hz, 4H); [M+H]⁺: 487.

¹H NMR (400 MHz, DMSO-d₆) δ 11.39 (s, 1H), 8.85 (s, 1H), 8.50 (d, J=8.3 Hz, 1H), 7.74 (d, J=8.4 Hz, 2H), 7.46 (d, J=8.4 Hz, 1H), 7.43-7.36 (m, 1H), 7.30 (dd, J=7.5, 1.7 Hz, 1H), 7.14 (d, J=8.3 Hz, 1H), 7.04 (t, J=7.4 Hz, 1H), 6.69 (d, J=8.5 Hz, 2H), 6.50 (t, J=5.5 Hz, 1H), 4.25 (s, 2H), 3.77 (s, 3H), 3.59 (t, J=4.6 Hz, 4H), 3.15 (q, J=6.5 Hz, 2H), 2.46-2.33 (m, 6H), 1.71 (q, J=7.0 Hz, 2H); [M+H]⁺: 501.

Example 329: 4-((3-(4-Methylpiperazin-1-yl)propyl)amino)-N-(3-oxo-7-phenylisoindolin-4-yl)benzamide

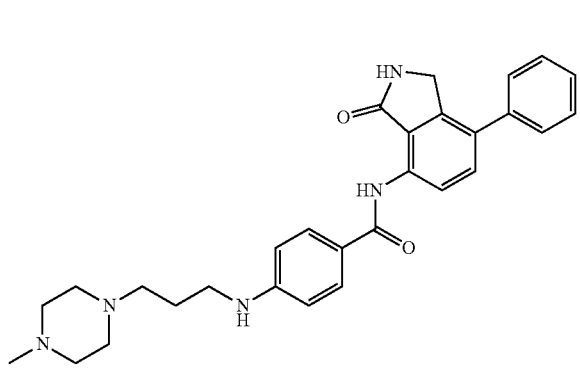 [SMILES: CN1CCN(CCCNc2ccc(C(=O)Nc3ccc(-c4ccccc4)c4c3C(=O)NC4)cc2)CC1]

$^{1}$H NMR (400 MHz, DMSO-d$_{6}$) δ 11.47 (s, 1H), 9.00 (s, 1H), 8.57 (d, J=8.5 Hz, 1H), 7.74 (d, J=8.4 Hz, 2H), 7.67 (d, J=8.4 Hz, 1H), 7.61 (d, J=7.6 Hz, 2H), 7.49 (t, J=7.6 Hz, 2H), 7.39 (t, J=7.4 Hz, 1H), 6.68 (d, J=8.5 Hz, 2H), 6.52 (t, J=5.4 Hz, 1H), 4.58 (s, 2H), 3.14 (t, J=6.3 Hz, 2H), 2.42-2.25 (m, 10H), 2.15 (s, 3H), 1.75-1.66 (m, 2H); [M+H]$^{+}$: 484.

Example 330: N-(7-(2-methoxyphenyl)-3-oxoisoindolin-4-yl)-4-((3-(4-methyl piperazin-1-yl)propyl)amino)benzamide

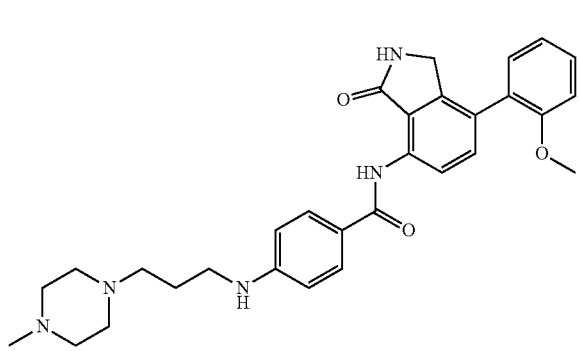

$^{1}$H NMR (400 MHz, DMSO-d$_{6}$) δ 11.39 (s, 1H), 8.85 (s, 1H), 8.50 (d, J=8.5 Hz, 1H), 7.73 (d, J=8.4 Hz, 2H), 7.46 (d, J=8.4 Hz, 1H), 7.40 (t, J=7.9 Hz, 1H), 7.30 (d, J=7.4 Hz, 1H), 7.14 (d, J=8.3 Hz, 1H), 7.04 (t, J=7.4 Hz, 1H), 6.68 (d, J=8.4 Hz, 2H), 6.50 (d, J=6.2 Hz, 1H), 4.25 (s, 2H), 3.77 (s, 3H), 3.17-3.08 (m, 2H), 2.43-2.25 (m, 10H), 2.15 (s, 3H), 1.75-1.66 (m, 2H); [M+H]$^{+}$: 514.

Example 331: 4-((3-Methoxypropyl)amino)-N-(3-oxo-7-phenylisoindolin-4-yl) benzamide

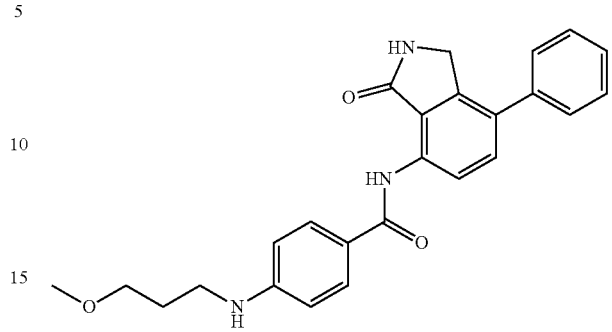

$^{1}$H NMR (400 MHz, DMSO-d$_{6}$) δ 11.48 (s, 1H), 9.00 (s, 1H), 8.57 (d, J=8.5 Hz, 1H), 7.74 (d, J=8.4 Hz, 2H), 7.67 (d, J=8.5 Hz, 1H), 7.61 (d, J=7.5 Hz, 2H), 7.48 (t, J=7.5 Hz, 2H), 7.39 (t, J=7.3 Hz, 1H), 6.68 (d, J=8.5 Hz, 2H), 6.48 (t, J=5.5 Hz, 1H), 4.58 (s, 2H), 3.43 (t, J=6.2 Hz, 2H), 3.26 (s, 3H), 3.16 (q, J=6.5 Hz, 2H), 1.80 (p, J=6.6 Hz, 2H); [M+H]$^{+}$: 416.

Example 332: N-(7-(2-methoxyphenyl)-3-oxoisoindolin-4-yl)-4-((3-methoxy propyl)amino)benzamide

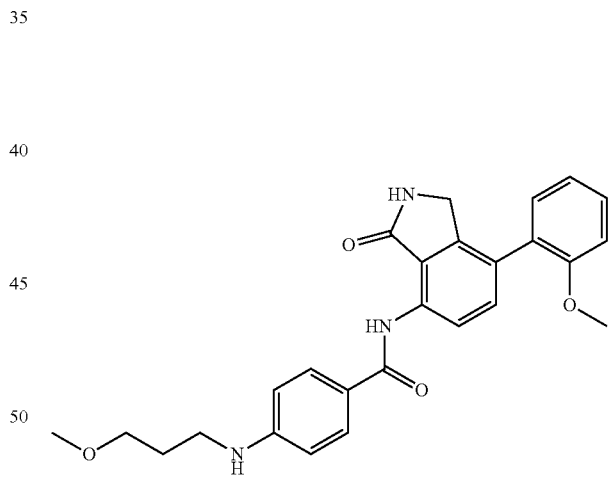

$^{1}$H NMR (400 MHz, DMSO-d$_{6}$) δ 11.39 (s, 1H), 8.86 (s, 1H), 8.50 (d, J=8.3 Hz, 1H), 7.74 (d, J=8.4 Hz, 2H), 7.46 (d, J=8.4 Hz, 1H), 7.43-7.36 (m, 1H), 7.30 (dd, J=7.4, 1.7 Hz, 1H), 7.14 (d, J=8.2 Hz, 1H), 7.04 (t, J=7.4 Hz, 1H), 6.68 (d, J=8.4 Hz, 2H), 6.47 (t, J=5.6 Hz, 1H), 4.25 (s, 2H), 3.77 (s, 3H), 3.43 (t, J=6.2 Hz, 2H), 3.26 (s, 3H), 3.16 (q, J=6.5 Hz, 2H), 1.80 (p, J=6.6 Hz, 2H); [M+H]$^{+}$: 446.

Example 333: N-(3-oxo-7-phenylisoindolin-4-yl)-4-((thiophen-2-ylmethyl) amino)benzamide

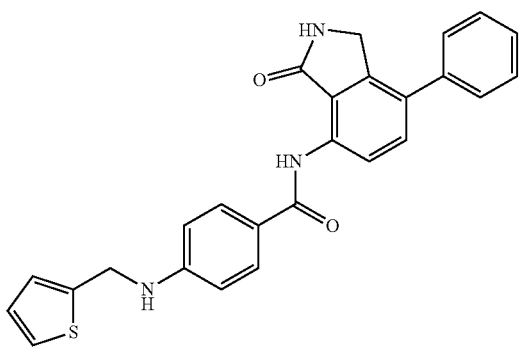 [SMILES: O=C(Nc1ccc(-c2ccccc2)c2c1C(=O)NC2)c1ccc(NCc2cccs2)cc1]

$^1$H NMR (400 MHz, DMSO-d$_6$) δ 11.48 (s, 1H), 9.00 (s, 1H), 8.56 (d, J=8.5 Hz, 1H), 7.73 (d, J=8.6 Hz, 2H), 7.67 (d, J=8.5 Hz, 1H), 7.61 (d, J=7.8 Hz, 1H), 7.48 (t, J=7.4 Hz, 2H), 7.43-7.35 (m, 2H), 7.10 (t, J=5.4 Hz, 1H), 6.99 (dd, J=5.1, 3.5 Hz, 1H), 6.78 (d, J=8.5 Hz, 2H), 4.63-4.53 (m, 4H); [M+H]$^+$: 440.

Example 334: N-(7-(2-methoxyphenyl)-3-oxoisoindolin-4-yl)-4-((thiophen-2-ylmethyl)amino)benzamide

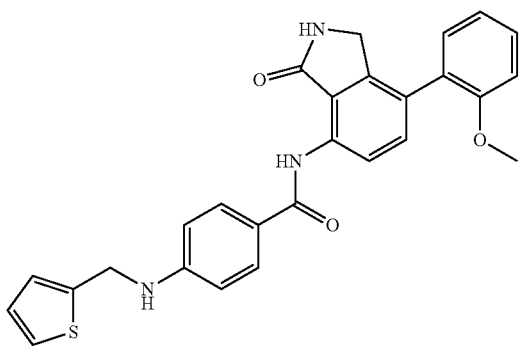 [SMILES: COc1ccccc1-c1ccc(NC(=O)c2ccc(NCc3cccs3)cc2)c2c1CNC2=O]

$^1$H NMR (400 MHz, DMSO-d$_6$) δ 11.40 (s, 1H), 8.86 (s, 1H), 8.49 (d, J=8.4 Hz, 1H), 7.73 (d, J=8.4 Hz, 2H), 7.46 (d, J=8.3 Hz, 1H), 7.39 (d, J=4.8 Hz, 2H), 7.30 (d, J=7.4 Hz, 1H), 7.17-7.07 (m, 3H), 7.04 (t, J=7.3 Hz, 1H), 6.99 (t, J=4.3 Hz, 1H), 6.78 (d, J=8.4 Hz, 2H), 4.56 (d, J=6.0 Hz, 2H), 4.24 (s, 2H), 3.76 (s, 3H); [M+H]$^+$: 470.

Example 335: 4-((3-(Dimethylamino)propyl) amino)-N-(7-(furan-2-yl)-3-oxoisoindolin-4-yl)benzamide

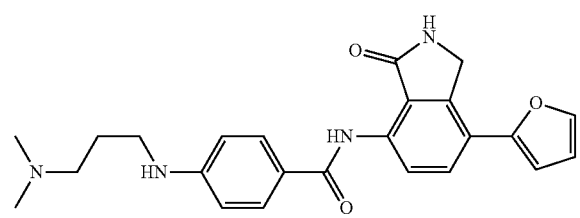 [SMILES: COCCCNc1ccc(C(=O)Nc2ccc(-c3ccco3)c3c2C(=O)NC3)cc1]

$^1$H NMR (400 MHz, DMSO-d$_6$) δ 11.45 (s, 1H), 9.13 (s, 1H), 8.54 (d, J=8.6 Hz, 1H), 7.93 (d, J=8.6 Hz, 1H), 7.82 (d, J=1.7 Hz, 1H), 7.72 (d, J=8.8 Hz, 2H), 6.84 (d, J=3.0 Hz, 1H), 6.68-6.65 (m, 3H), 6.55 (t, J=5.2 Hz, 1H), 4.63 (s, 2H), 3.12 (q, J=6.5 Hz, 2H), 2.29 (t, J=7.0 Hz, 2H), 2.14 (s, 6H), 1.69 (quint, J=6.9 Hz, 2H); [M+H]$^+$: 404.

Example 336: N-(7-(furan-2-yl)-3-oxoisoindolin-4-yl)-4-((3-methoxypropyl) amino)benzamide

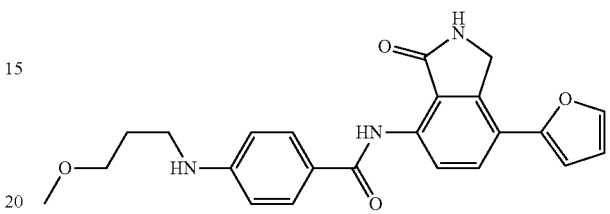

$^1$H NMR (400 MHz, DMSO-d$_6$) δ 11.45 (s, 1H), 9.12 (s, 1H), 8.54 (d, J=8.6 Hz, 1H), 7.93 (d, J=8.6 Hz, 1H), 7.82 (d, J=1.2 Hz, 1H), 7.72 (d, J=8.8 Hz, 2H), 6.84 (d, J=3.3 Hz, 1H), 6.68-6.65 (m, 3H), 6.53 (t, J=5.4 Hz, 1H), 4.63 (s, 2H), 3.42 (t, J=6.2 Hz, 2H), 3.25 (s, 3H), 3.15 (q, J=6.8 Hz, 2H), 1.79 (quint, J=6.6 Hz, 2H); [M+H]$^+$: 391.

Example 337: N-(7-(furan-2-yl)-3-oxoisoindolin-4-yl)-4-((3-morpholino propyl)amino)benzamide

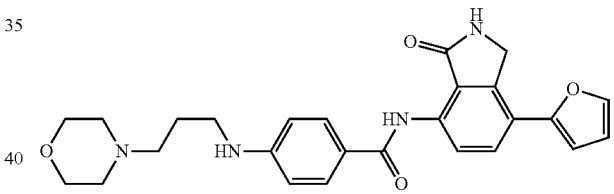

$^1$H NMR (400 MHz, DMSO-d$_6$) δ 11.45 (s, 1H), 9.13 (s, 1H), 8.54 (d, J=8.6 Hz, 1H), 7.93 (d, J=8.6 Hz, 1H), 7.82 (d, J=1.5 Hz, 1H), 7.72 (d, J=8.8 Hz, 2H), 6.84 (d, J=3.4 Hz, 1H), 6.69-6.65 (m, 3H), 6.56 (t, J=5.5 Hz, 1H), 4.63 (s, 2H), 3.58 (t, J=4.4 Hz, 5H), 3.14 (q, J=6.6 Hz, 2H), 2.36 (d, J=6.6 Hz, 5H), 1.71 (quint, J=6.8 Hz, 2H); [M+H]$^+$: 446.

Example 338: N-(7-(furan-2-yl)-3-oxoisoindolin-4-yl)-4-((3-(piperidin-1-yl) propyl)amino)benzamide

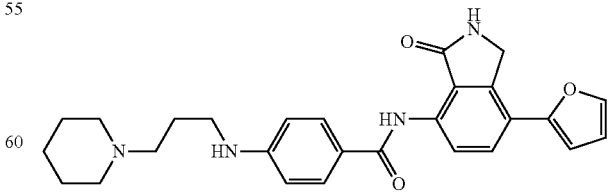

$^1$H NMR (400 MHz, DMSO-d$_6$) δ 11.45 (s, 1H), 9.13 (s, 1H), 8.54 (d, J=8.7 Hz, 1H), 7.93 (d, J=8.6 Hz, 1H), 7.82 (d, J=1.3 Hz, 1H), 7.72 (d, J=8.8 Hz, 2H), 6.84 (d, J=3.3 Hz, 1H), 6.68-6.65 (m, 3H), 6.59 (t, J=5.5 Hz, 1H), 4.63 (s, 2H), 3.12 (q, J=6.5 Hz, 2H), 2.34-2.31 (m, 5H), 1.70 (quint, J=6.8 Hz, 2H), 1.50 (quint, J=5.4 Hz, 5H), 1.39-1.38 (m, 2H); [M+H]$^+$: 444.

Example 339: N-(7-(furan-2-yl)-3-oxoisoindolin-4-yl)-4-((3-(pyrrolidin-1-yl) propyl)amino)benzamide

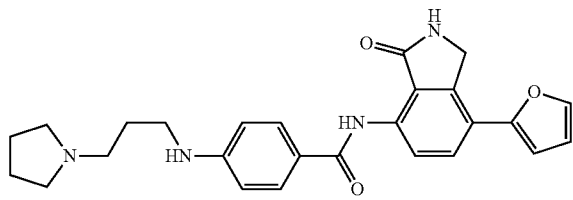 [SMILES: O=C(Nc1ccc(-c2ccco2)c2c1C(=O)NC2)c1ccc(NCCCN2CCCC2)cc1]

$^1$H NMR (400 MHz, DMSO-d$_6$) δ 11.45 (s, 1H), 9.13 (s, 1H), 8.54 (d, J=8.6 Hz, 1H), 7.93 (d, J=8.7 Hz, 1H), 7.82 (s, 1H), 7.72 (d, J=8.5 Hz, 2H), 6.84 (d, J=3.2 Hz, 1H), 6.68-6.66 (m, 3H), 6.56 (t, J=5.4 Hz, 1H), 4.63 (s, 2H), 3.15 (q, J=6.2 Hz, 2H), 2.47-2.42 (m, 5H), 1.74-1.68 (m, 7H); [M+H]$^+$: 430.

Example 340: 4-(4-Aminopiperidin-1-yl)-N-(3-oxo-7-phenylisoindolin-4-yl) benzamide

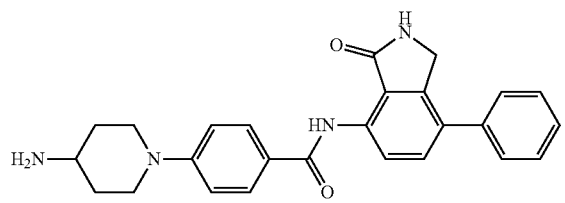 [SMILES: NC1CCN(c2ccc(C(=O)Nc3ccc(-c4ccccc4)c4c3C(=O)NC4)cc2)CC1]

$^1$H NMR (400 MHz, DMSO-d$_6$) δ 11.55 (s, 1H), 9.05 (s, 1H), 8.57 (d, J=8.4 Hz, 1H), 7.81 (d, J=8.8 Hz, 2H), 7.68 (d, J=8.4 Hz, 1H), 7.61 (d, J=7.2 Hz, 2H), 7.48 (t, J=7.6 Hz, 2H), 7.39 (t, J=7.2 Hz, 1H), 7.50 (d, J=8.8 Hz, 2H), 4.59 (s, 2H), 3.86 (d, J=12.8 Hz, 2H), 2.94-2.88 (m, 2H), 2.81-2.75 (m, 1H), 1.79-1.75 (m, 2H), 1.31-1.23 (m, 2H). [M+H]$^+$: 427.

Example 341: N-(7-(benzo[d]oxazol-7-yl)-3-oxoisoindolin-4-yl)-4-((2-(dimethylamino)ethyl)amino)benzamide

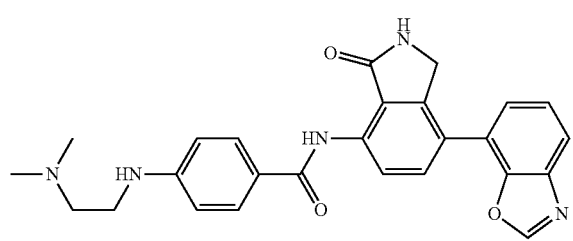 [SMILES: CN(C)CCNc1ccc(C(=O)Nc2ccc(-c3cccc4ncoc34)c3c2C(=O)NC3)cc1]

$^1$H NMR (400 MHz, DMSO-d$_6$) δ 11.53 (s, 1H), 9.08 (s, 1H), 8.81 (s, 1H), 8.63 (d, J=8.4 Hz, 1H), 7.85 (t, J=7.8 Hz, 2H), 7.76 (d, J=8.8 Hz, 2H), 7.65 (d, J=7.2 Hz, 1H), 7.51 (t, J=7.8 Hz, 1H), 6.74 (d, J=8.8 Hz, 2H), 6.41 (t, J=5.2 Hz, 1H), 4.53 (s, 2H), 3.24 (d, J=6.0 Hz, 2H), 2.62-2.56 (m, 2H), 2.29 (s, 6H). [M+H]$^+$: 456.

Example 342: N-(7-(benzo[d]oxazol-7-yl)-3-oxoisoindolin-4-yl)-4-((2-(piperidin-1-yl)ethyl)amino)benzamide

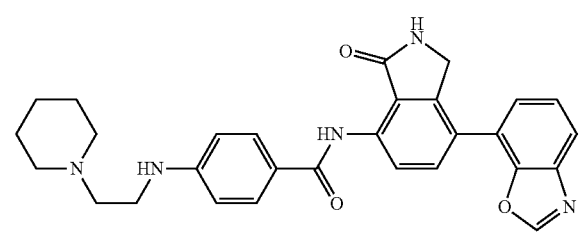 [SMILES: O=C(Nc1ccc(-c2cccc3ncoc23)c2c1C(=O)NC2)c1ccc(NCCN2CCCCC2)cc1]

$^1$H NMR (400 MHz, DMSO-d$_6$) δ 11.52 (s, 1H), 9.07 (s, 1H), 8.81 (s, 1H), 8.63 (d, J=8.4 Hz, 1H), 7.85 (t, J=7.6 Hz, 2H), 7.76 (d, J=8.8 Hz, 2H), 7.65 (d, J=7.2 Hz, 1H), 7.51 (t, J=7.8 Hz, 1H), 6.72 (d, J=8.8 Hz, 2H), 6.36 (t, J=5.2 Hz, 1H), 4.53 (s, 2H), 3.22 (d, J=6.0 Hz, 2H), 2.44-2.36 (m, 4H), 1.53-1.50 (m, 4H), 1.40-1.38 (m, 2H). [M+H]$^+$: 496.

Example 343: N-(7-(benzo[d]oxazol-7-yl)-3-oxoisoindolin-4-yl)-4-((3-(piperidin-1-yl)propyl)amino)benzamide

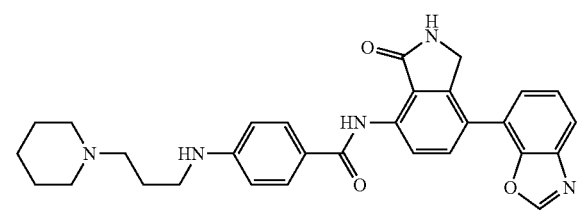 [SMILES: O=C(Nc1ccc(-c2cccc3ncoc23)c2c1C(=O)NC2)c1ccc(NCCCN2CCCCC2)cc1]

$^1$H NMR (400 MHz, DMSO-d$_6$) δ 11.52 (s, 1H), 9.07 (s, 1H), 8.81 (s, 1H), 8.62 (d, J=8.4 Hz, 1H), 7.85 (t, J=7.8 Hz, 2H), 7.75 (d, J=8.8 Hz, 2H), 7.65 (d, J=7.2 Hz, 1H), 7.51 (t, J=7.8 Hz, 1H), 6.74 (d, J=8.8 Hz, 2H), 6.60 (t, J=5.2 Hz, 1H), 4.53 (s, 2H), 3.14 (d, J=6.0 Hz, 2H), 2.46-2.30 (m, 6H), 1.73-1.69 (m, 2H), 1.53-1.49 (m, 4H), 1.40-1.36 (m, 2H). [M+H]$^+$: 510.

Example 344: 4-((2-(Azepan-1-yl)ethyl)amino)-N-(7-(benzo[d]oxazol-7-yl)-3-oxoisoindolin-4-yl)benzamide

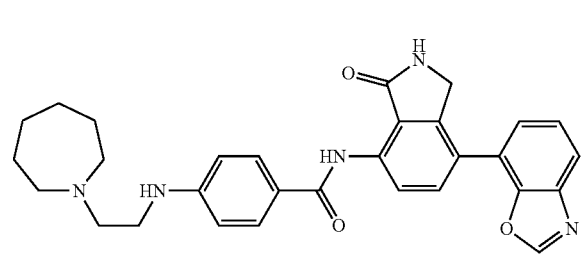 [SMILES: O=C(Nc1ccc(-c2cccc3ncoc23)c2c1C(=O)NC2)c1ccc(NCCN2CCCCCC2)cc1]

$^1$H NMR (400 MHz, DMSO-d$_6$) δ 11.52 (s, 1H), 9.07 (s, 1H), 8.81 (s, 1H), 8.63 (d, J=8.4 Hz, 1H), 7.85 (t, J=7.6 Hz,

2H), 7.75 (d, J=8.8 Hz, 2H), 7.65 (d, J=7.2 Hz, 1H), 7.51 (t, J=7.8 Hz, 1H), 6.72 (d, J=8.8 Hz, 2H), 6.32 (t, J=5.0 Hz, 1H), 4.53 (s, 2H), 3.20 (d, J=6.0 Hz, 2H), 2.69-2.65 (m, 6H), 1.60-1.54 (m, 8H). [M+H]⁺: 510.

Example 345: 4-(2-Morpholinoethoxy)-N-(3-oxo-7-phenylisoindolin-4-yl) benzamide

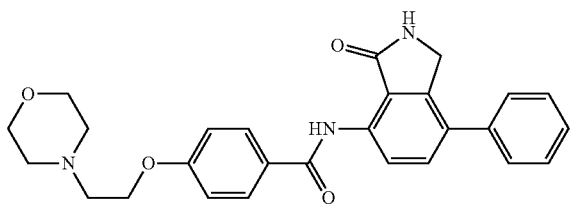 [SMILES: O=C(Nc1ccc(-c2ccccc2)c2c1C(=O)NC2)c1ccc(OCCN2CCOCC2)cc1]

¹H NMR (400 MHz, DMSO-d₆) δ 11.66 (s, 1H), 9.10 (s, 1H), 8.56 (d, J=8.4 Hz, 1H), 7.93 (d, J=8.8 Hz, 2H), 7.93 (d, J=8.8 Hz, 2H), 7.70 (d, J=8.4 Hz, 1H), 7.62 (d, J=7.2 Hz, 2H), 7.49 (t, J=7.4 Hz, 2H), 7.40 (t, J=7.4 Hz, 1H), 7.16 (d, J=8.8 Hz, 2H), 4.61 (s, 2H), 4.20 (t, J=5.6 Hz, 2H), 3.58 (t, J=4.6 Hz, 4H), 2.78 (t, J=5.8 Hz, 2H), 2.53-2.50 (m, 4H). [M+H]⁺: 458.

Example 346: N-(3-oxoisoindolin-4-yl)-4-((2-(pyrrolidin-1-yl)ethyl)amino) benzamide

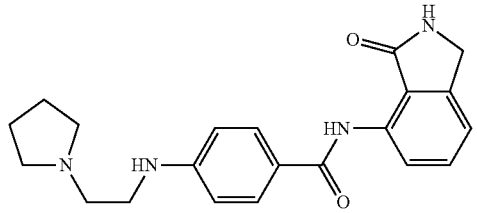 [SMILES: O=C(Nc1cccc2c1C(=O)NC2)c1ccc(NCCN2CCCC2)cc1]

¹H NMR (400 MHz, DMSO-d₆) δ 11.26 (s, 1H), 8.88 (s, 1H), 8.43 (d, J=8.0 Hz, 1H), 7.79 (d, J=9.2 Hz, 2H), 7.72 (t, J=9.2 Hz, 1H), 7.20 (d, J=7.2 Hz, 1H), 6.69 (d, J=8.8 Hz, 2H), 6.40 (t, J=6.0 Hz, 1H), 4.41 (s, 2H), 3.21 (q, J=6.0 Hz, 2H), 2.62 (t, J=6.6 Hz, 2H), 1.71-1.66 (m, 4H). [M+H]⁺: 365.

Example 347: N-(7-(2,3-dimethoxyphenyl)-3-oxoisoindolin-4-yl)-4-(2-morpholinoethoxy)benzamide

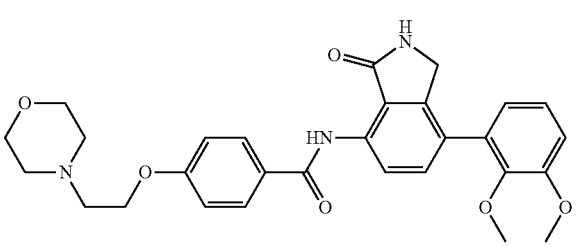

¹H NMR (400 MHz, DMSO-d₆) δ 11.57 (s, 1H), 8.97 (s, 1H), 8.51 (d, J=8.4 Hz, 1H), 7.93 (d, J=8.8 Hz, 2H), 7.53 (d, J=8.4 Hz, 1H), 7.17-7.10 (m, 4H), 6.95 (dd, J=7.2, 1.6 Hz, 1H), 4.30 (s, 2H), 4.20 (t, J=5.8 Hz, 2H), 3.85 (s, 3H), 3.58 (t, J=4.8 Hz, 4H), 3.45 (s, 3H), 2.73 (t, J=5.6 Hz, 2H), 2.53-2.50 (m, 4H). [M+H]⁺: 518.

Example 348: N-(7-(3-amino-2-hydroxyphenyl)-3-oxoisoindolin-4-yl)-4-((2-morpholinoethyl)amino) benzamide

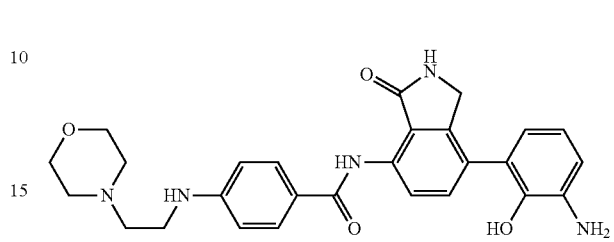

¹H NMR (400 MHz, DMSO-d₆) δ 11.41 (s, 1H), 8.87 (s, 1H), 8.49 (d, J=8.4 Hz, 1H), 7.73 (d, J=8.8 Hz, 2H), 7.45 (d, J=8.4 Hz, 1H), 6.71 (d, J=8.8 Hz, 2H), 6.68-6.66 (m, 2H), 6.44 (dd, J=6.2, 3.0 Hz, 1H), 6.37 (d, J=5.4 Hz, 1H), 4.28 (s, 2H), 3.59 (t, J=4.4 Hz, 4H), 3.23 (q, J=6.0 Hz, 2H), 2.53-2.50 (m, 2H), 2.46-2.40 (m, 4H). [M+H]⁺: 488.

Example 349: 4-((2-(Azepan-1-yl)ethyl)amino)-N-(7-(2-methoxyphenyl)-3-oxoisoindolin-4-yl)benzamide

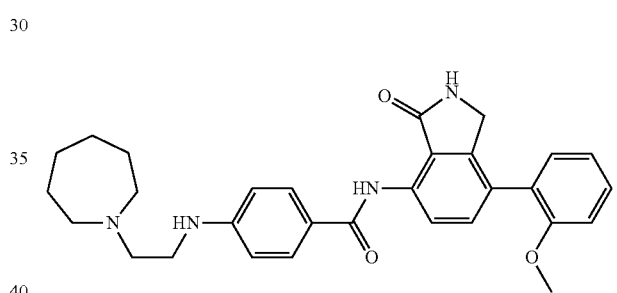

¹H NMR (400 MHz, DMSO-d₆) δ 11.40 (s, 1H), 8.90 (s, 1H), 8.49 (d, J=8.4 Hz, 1H), 7.73 (d, J=8.4 Hz, 2H), 7.46 (d, J=8.4 Hz, 1H), 7.39 (d, J=7.6 Hz, 1H), 7.30 (dd, J=7.4, 1.4 Hz, 1H), 7.13 (d, J=8.4 Hz, 1H), 7.04 (t, J=7.6 Hz, 1H), 6.71 (d, J=7.6 Hz, 2H), 6.29 (t, J=5.4 Hz, 1H), 4.25 (s, 2H), 3.76 (s, 3H), 3.18-3.15 (m, 2H), 2.68-2.64 (m, 6H), 1.58-1.55 (m, 8H). [M+H]⁺: 499.

Example 350: 4-((2-(Azepan-1-yl)ethyl)amino)-N-(7-(2,3-dimethoxyphenyl)-3-oxoisoindolin-4-yl) benzamide

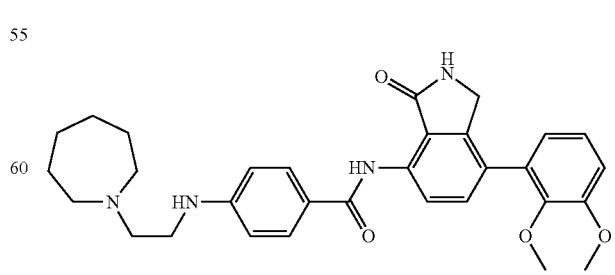

¹H NMR (400 MHz, DMSO-d₆) δ 11.40 (s, 1H), 8.92 (s, 1H), 8.51 (d, J=8.4 Hz, 1H), 7.73 (d, J=8.8 Hz, 2H), 7.50 (d,

J=8.4 Hz, 1H), 7.16-7.09 (m, 2H), 6.94 (dd, J=7.2, 1.6 Hz, 1H), 6.71 (d, J=8.8 Hz, 2H), 6.29 (t, J=5.4 Hz, 1H), 4.29 (s, 2H), 3.85 (s, 3H), 3.44 (s, 3H), 3.20-3.16 (m, 2H), 2.68-2.64 (m, 6H), 1.58-1.55 (m, 8H). [M+H]⁺: 529.

Example 351: 4-((3-(Dimethylamino)propyl) amino)-N-(7-(2-hydroxyphenyl)-3-oxoisoindolin-4-yl)benzamide

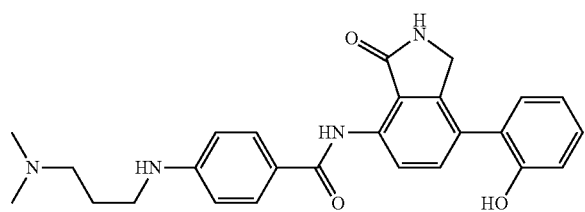 [SMILES: CN(C)CCCNc1ccc(C(=O)Nc2ccc(-c3ccccc3O)c3c2C(=O)NC3)cc1]

¹H NMR (400 MHz, DMSO-d₆) δ 11.40 (s, 1H), 8.85 (s, 1H), 8.49 (d, J=8.4 Hz, 1H), 7.73 (d, J=8.4 Hz, 2H), 7.48 (d, J=8.4 Hz, 1H), 7.23-7.17 (m, 2H), 6.94 (d, J=8.0 Hz, 1H), 6.84 (t, J=7.6 Hz, 1H), 6.67 (d, J=8.8 Hz, 2H), 6.49 (t, J=5.4 Hz, 1H), 4.34 (s, 2H), 3.12 (q, J=6.4 Hz, 2H), 2.30 (t, J=7.0 Hz, 2H), 2.14 (s, 6H), 1.69 (quint, J=7.0 Hz, 2H). [M+H]⁺: 445.

Example 352: 4-((2-Hydroxyethyl)amino)-N-(7-(2-methoxyphenyl)-3-oxoisoindolin-4-yl)benzamide

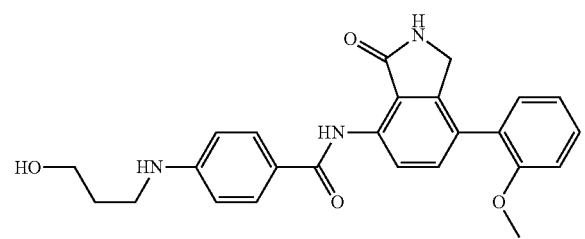 [SMILES: COc1ccccc1-c1ccc(NC(=O)c2ccc(NCCCO)cc2)c2c1CNC2=O]

¹H NMR (400 MHz, DMSO-d₆) δ 11.40 (s, 1H), 8.88 (s, 1H), 8.50 (d, J=8.0 Hz, 1H), 7.73 (d, J=8.8 Hz, 2H), 7.46 (d, J=8.4 Hz, 1H), 7.40 (td, J=7.8, 1.6 Hz, 1H), 7.31 (dd, J=7.4, 1.8 Hz, 1H), 7.13 (d, J=8.0 Hz, 1H), 7.03 (td, J=7.4, 0.8 Hz, 1H), 6.71 (d, J=8.8 Hz, 2H), 6.46 (t, J=5.6 Hz, 1H), 4.76 (t, J=5.0 Hz, 1H), 4.25 (s, 2H), 3.76 (s, 3H), 3.58 (q, J=5.2 Hz, 2H), 3.16 (q, J=5.6 Hz, 2H). [M+H]⁺: 418.

Example 353: 4-((2-Hydroxyethyl)amino)-N-(7-(2-hydroxyphenyl)-3-oxoisoindolin-4-yl)benzamide

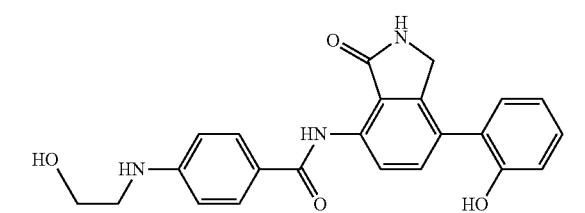

¹H NMR (400 MHz, DMSO-d₆) δ 11.40 (s, 1H), 9.65 (br.s, 1H), 8.85 (s, 1H), 8.50 (d, J=8.4 Hz, 1H), 7.73 (d, J=8.4 Hz, 2H), 7.49 (d, J=8.4 Hz, 1H), 7.21 (td, J=5.6, 1.6 Hz, 2H), 6.96 (d, J=8.0 Hz, 1H), 6.88 (t, J=7.4 Hz, 1H), 6.71 (d, J=8.8 Hz, 2H), 6.45 (t, J=5.6 Hz, 1H), 4.75 (t, J=5.4 Hz, 1H), 4.33 (s, 2H), 3.58 (q, J=5.6 Hz, 2H), 3.18 (q, J=5.6 Hz, 2H). [M+H]⁺: 404.

Example 354: 4-(3-Hydroxypropyl)amino)-N-(7-(2-methoxyphenyl)-3-oxoisoindolin-4-yl)benzamide

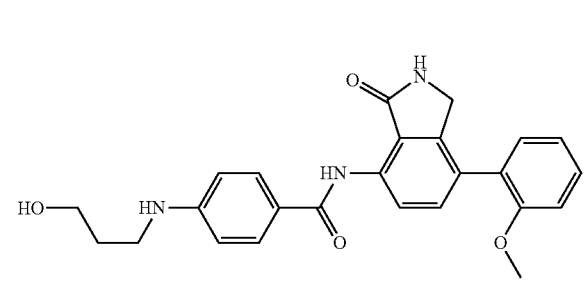 [SMILES: COc1ccccc1-c1ccc(NC(=O)c2ccc(NCCCO)cc2)c2c1CNC2=O]

¹H NMR (400 MHz, DMSO-d₆) δ 11.40 (s, 1H), 8.88 (s, 1H), 8.50 (d, J=8.4 Hz, 1H), 7.73 (d, J=8.8 Hz, 2H), 7.46 (d, J=8.4 Hz, 1H), 7.40 (td, J=7.8, 1.6 Hz, 1H), 7.31 (dd, J=7.2, 1.6 Hz, 1H), 7.13 (d, J=8.0 Hz, 1H), 7.04 (t, J=7.6 Hz, 1H), 6.68 (d, J=8.8 Hz, 2H), 6.47 (t, J=5.4 Hz, 1H), 4.52 (t, J=5.0 Hz, 1H), 4.25 (s, 2H), 3.76 (s, 3H), 3.51 (q, J=5.2 Hz, 2H), 3.16 (q, J=6.4 Hz, 2H), 1.72 (quint, J=6.6 Hz, 2H). [M+H]⁺: 432.

Example 355: N-(7-(2-hydroxyphenyl)-3-oxoisoindolin-4-yl)-4-(3-hydroxypropyl)amino)benzamide

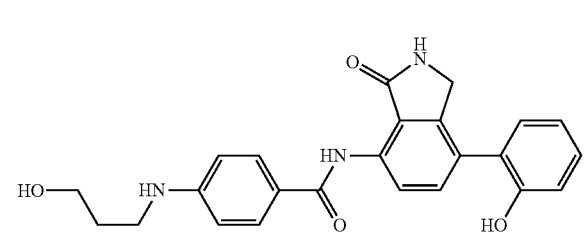

¹H NMR (400 MHz, DMSO-d₆) δ 11.40 (s, 1H), 9.77 (br.s, 1H), 8.85 (s, 1H), 8.49 (d, J=8.4 Hz, 1H), 7.73 (d, J=8.8 Hz, 2H), 7.48 (d, J=8.4 Hz, 1H), 7.24-7.18 (m, 2H), 6.96 (d, J=8.0 Hz, 1H), 6.87 (t, J=7.6 Hz, 1H), 7.13 (d, J=8.4 Hz, 2H), 6.46 (t, J=5.2 Hz, 1H), 4.52 (t, J=5.0 Hz, 1H), 4.33 (s, 2H), 3.52 (q, J=5.2 Hz, 2H), 3.16 (q, J=6.4 Hz, 2H), 1.72 (quint, J=6.4 Hz, 2H). [M+H]⁺: 418.

Example 356: 4-((4-Hydroxybutyl)amino)-N-(7-(2-methoxyphenyl)-3-oxoisoindolin-4-yl)benzamide

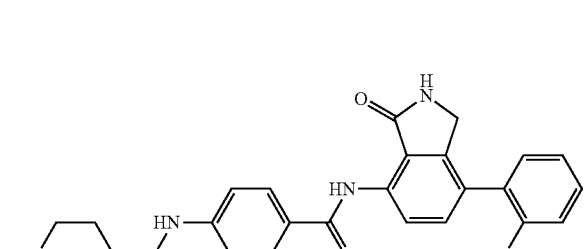

¹H NMR (400 MHz, DMSO-d₆) δ 11.39 (s, 1H), 8.88 (s, 1H), 8.50 (d, J=8.4 Hz, 1H), 7.73 (d, J=8.8 Hz, 2H), 7.46 (d, J=8.4 Hz, 1H), 7.40 (td, J=7.8, 1.6 Hz, 1H), 7.30 (dd, J=7.6, 1.6 Hz, 1H), 7.13 (d, J=8.0 Hz, 1H), 7.04 (t, J=7.4 Hz, 1H), 6.68 (d, J=8.4 Hz, 2H), 6.49 (t, J=5.4 Hz, 1H), 4.43 (t, J=4.8 Hz, 1H), 4.25 (s, 2H), 3.76 (s, 3H), 3.44 (q, J=5.2 Hz, 2H), 3.10 (q, J=6.4 Hz, 2H), 1.62-1.50 (m, 4H). [M+H]⁺: 446.

Example 357: 4-((4-Hydroxybutyl)amino)-N-(7-(2-hydroxyphenyl)-3-oxoisoindolin-4-yl)benzamide

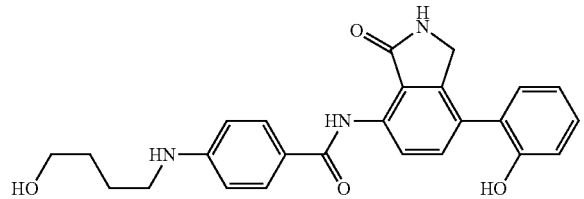 [SMILES: O=C(Nc1ccc(-c2ccccc2O)c2c1C(=O)NC2)c1ccc(NCCCCO)cc1]

¹H NMR (400 MHz, DMSO-d₆) δ 11.40 (s, 1H), 9.73 (br.s, 1H), 8.85 (s, 1H), 8.49 (d, J=8.4 Hz, 1H), 7.73 (d, J=8.4 Hz, 2H), 7.48 (d, J=8.4 Hz, 1H), 7.24-7.19 (m, 2H), 6.96 (d, J=8.0 Hz, 1H), 6.88 (t, J=7.4 Hz, 1H), 6.68 (d, J=8.8 Hz, 2H), 6.48 (t, J=5.2 Hz, 1H), 4.43 (t, J=4.8 Hz, 1H), 4.33 (s, 2H), 3.44 (q, J=5.6 Hz, 2H), 3.10 (q, J=6.0 Hz, 2H), 1.62-1.50 (m, 4H). [M+H]⁺: 432.

Example 358: 4-(Methyl(2-(methylamino)ethyl)amino)-N-(3-oxo-7-phenylisoindolin-4-yl)benzamide

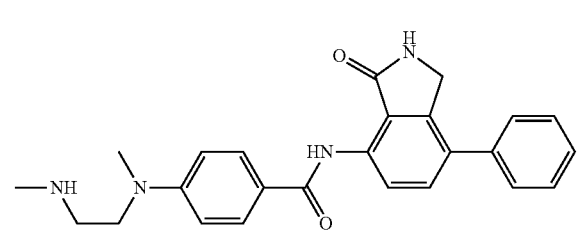 [SMILES: CNCCN(C)c1ccc(C(=O)Nc2ccc(-c3ccccc3)c3c2C(=O)NC3)cc1]

¹H NMR (400 MHz, DMSO-d₆) δ 11.53 (s, 1H), 9.04 (s, 1H), 8.57 (d, J=8.4 Hz, 1H), 7.80 (d, J=8.8 Hz, 2H), 7.67 (d, J=8.4 Hz, 1H), 7.62-7.60 (m, 2H), 7.48 (t, J=7.6 Hz, 2H), 7.39 (t, J=7.4 Hz, 1H), 6.83 (d, J=9.2 Hz, 2H), 4.59 (s, 2H), 3.49 (t, J=6.8 Hz, 2H), 3.02 (s, 3H), 2.65 (t, J=6.6 Hz, 2H), 2.30 (s, 3H). [M+H]⁺: 415.

Example 359: N-(7-(2,3-difluorophenyl)-3-oxoisoindolin-4-yl)-4-((2-morpholinoethyl)amino)benzamide

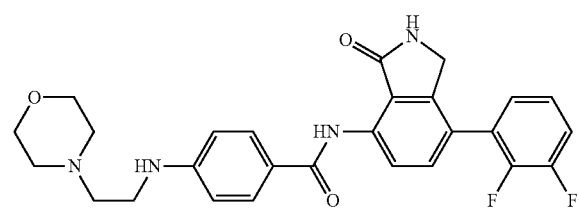 [SMILES: O=C(Nc1ccc(-c2cccc(F)c2F)c2c1C(=O)NC2)c1ccc(NCCN2CCOCC2)cc1]

¹H NMR (400 MHz, DMSO-d₆) δ 11.46 (s, 1H), 9.02 (s, 1H), 8.57 (d, J=8.4 Hz, 1H), 7.74 (d, J=8.8 Hz, 2H), 7.62 (d, J=8.4 Hz, 1H), 7.59 (q, J=8.8 Hz, 1H), 7.40 (t, J=7.4 Hz, 1H), 7.34-7.31 (m, 1H), 6.72 (d, J=8.8 Hz, 2H), 6.38 (t, J=5.6 Hz, 1H), 4.40 (s, 2H), 3.59 (t, J=4.6 Hz, 4H), 3.23 (q, J=6.0 Hz, 2H), 2.55-2.52 (m, 2H), 2.46-2.42 (m, 4H). [M+H]⁺:493.

Example 360: N-(3-oxo-7-phenylisoindolin-4-yl)-4-((2-(piperidin-1-yl)ethyl) amino)benzamide

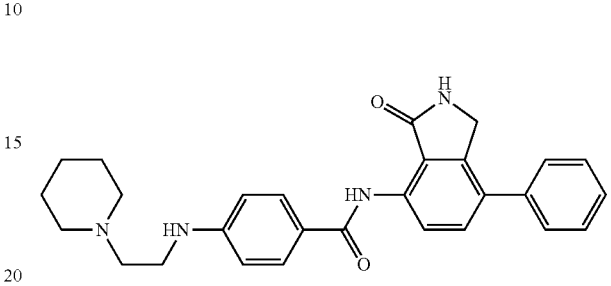

¹H NMR (400 MHz, DMSO-d₆) δ 11.48 (s, 1H), 9.02 (s, 1H), 8.57 (d, J=8.4 Hz, 1H), 7.73 (d, J=8.8 Hz, 2H), 7.67 (d, J=8.4 Hz, 1H), 7.61 (d, J=7.2 Hz, 2H), 7.48 (t, J=7.6 Hz, 2H), 7.39 (t, J=7.2 Hz, 1H), 6.71 (d, J=8.8 Hz, 2H), 6.32 (t, J=5.4 Hz, 1H), 4.59 (s, 2H), 3.21 (q, J=6.0 Hz, 2H), 2.47-2.46 (m, 2H), 2.40-2.37 (m, 4H), 1.54-1.48 (m, 4H), 1.40-1.38 (m, 2H). [M+H]⁺: 455.

Example 361: N-(7-(2-methoxyphenyl)-3-oxoisoindolin-4-yl)-4-((2-(piperidin-1-yl)ethyl)amino)benzamide

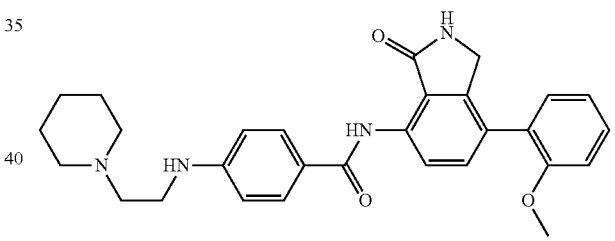

¹H NMR (400 MHz, DMSO-d₆) δ 11.40 (s, 1H), 8.88 (s, 1H), 8.49 (d, J=8.4 Hz, 1H), 7.73 (d, J=8.8 Hz, 2H), 7.46 (d, J=8.4 Hz, 1H), 7.41-7.37 (m, 1H), 7.30 (dd, J=7.6, 1.6 Hz, 1H), 7.13 (d, J=8.0 Hz, 1H), 7.04 (t, J=7.4 Hz, 1H), 6.71 (d, J=8.8 Hz, 2H), 6.31 (t, J=5.2 Hz, 1H), 4.25 (s, 2H), 3.76 (s, 3H), 3.21 (q, J=6.0 Hz, 2H), 2.49-2.46 (m, 2H), 2.40-2.37 (m, 4H), 1.54-1.49 (m, 4H), 1.40-1.38 (m, 2H). [M+H]⁺: 485.

Example 362: 4-((2-(Dimethylamino)ethyl)amino)-N-(3-oxo-7-phenylisoindolin-4-yl)benzamide

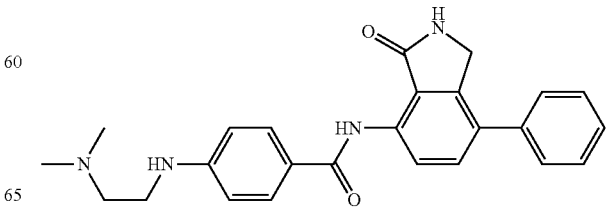

¹H NMR (400 MHz, DMSO-d₆) δ 11.49 (s, 1H), 9.03 (s, 1H), 8.57 (d, J=8.4 Hz, 1H), 7.74 (d, J=8.8 Hz, 2H), 7.67 (d, J=8.4 Hz, 1H), 7.61 (d, J=7.2 Hz, 2H), 7.48 (t, J=7.6 Hz, 2H), 7.39 (t, J=7.4 Hz, 1H), 6.72 (d, J=8.8 Hz, 2H), 6.33 (t, J=5.2 Hz, 1H), 4.59 (s, 2H), 3.21-3.16 (m, 2H), 2.46 (t, J=6.6 Hz, 2H), 2.20 (s, 6H). [M+H]⁺: 415.

Example 363: N-(3-oxo-7-phenylisoindolin-4-yl)-4-((3-(pyrrolidin-1-yl) propyl)amino)benzamide

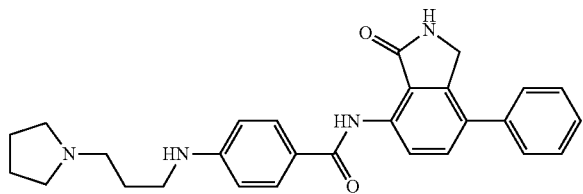 [SMILES: O=C(Nc1ccc(-c2ccccc2)c2c1C(=O)NC2)c1ccc(NCCCN2CCCC2)cc1]

¹H NMR (400 MHz, DMSO-d₆) δ 11.48 (s, 1H), 9.02 (s, 1H), 8.56 (d, J=8.4 Hz, 1H), 7.73 (d, J=8.8 Hz, 2H), 7.67 (d, J=8.8 Hz, 1H), 7.61 (d, J=7.2 Hz, 2H), 7.48 (t, J=7.6 Hz, 2H), 7.39 (t, J=7.2 Hz, 1H), 6.67 (d, J=8.8 Hz, 2H), 6.53 (t, J=5.4 Hz, 1H), 4.58 (s, 2H), 3.14 (q, J=6.8 Hz, 2H), 2.49-2.47 (m, 2H), 2.45-2.42 (m, 4H), 1.71 (quint, J=5.6 Hz, 2H), 1.69-1.67 (m, 4H). [M+H]⁺: 455.

Example 364: N-(7-(2,3-difluorophenyl)-3-oxoisoindolin-4-yl)-4-((2-(pyrrolidin-1-yl)ethyl)amino)benzamide

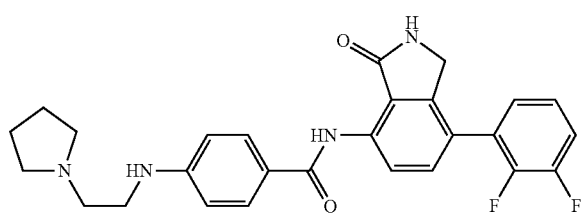 [SMILES: O=C(Nc1ccc(-c2cccc(F)c2F)c2c1C(=O)NC2)c1ccc(NCCN2CCCC2)cc1]

¹H NMR (400 MHz, DMSO-d₆) δ 11.51 (s, 1H), 9.44 (br.s, 1H), 9.04 (s, 1H), 8.57 (d, J=8.4 Hz, 1H), 7.80 (d, J=8.4 Hz, 2H), 7.63 (d, J=8.4 Hz, 1H), 7.51 (q, J=8.8 Hz, 1H), 7.40 (t, J=7.2 Hz, 1H), 7.34-7.29 (m, 1H), 6.79 (d, J=8.8 Hz, 2H), 6.67 (t, J=5.4 Hz, 1H), 4.41 (s, 2H), 3.64-3.60 (m, 2H), 3.56-3.51 (m, 2H), 3.12-3.06 (m, 2H), 2.55-2.52 (m, 2H), 2.08-1.98 (m, 2H), 1.88-1.85 (m, 2H). [M+H]⁺: 477.

Example 365: N-(7-(2,3-difluorophenyl)-3-oxoisoindolin-4-yl)-4-((2-(pyrrolidin-1-yl)ethyl)amino)benzamide hydrochloride

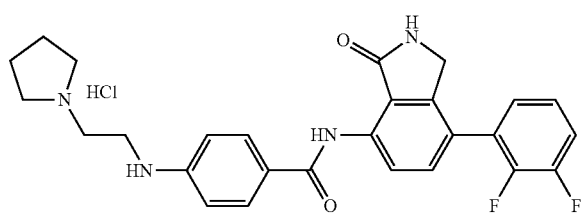 [SMILES: O=C(Nc1ccc(-c2cccc(F)c2F)c2c1C(=O)NC2)c1ccc(NCCN2CCCC2)cc1 ; Cl]

¹H NMR (400 MHz, DMSO-d₆) δ 11.51 (s, 1H), 10.43 (br.s, 1H), 9.06 (s, 1H), 8.57 (d, J=8.8 Hz, 1H), 7.79 (d, J=8.4 Hz, 2H), 7.63 (d, J=8.4 Hz, 1H), 7.46-7.53 (m, 1H), 7.42-7.39 (m, 1H), 7.34-7.29 (m, 1H), 6.81-6.79 (m, 3H), 4.41 (s, 2H), 3.60-3.55 (m, 5H), 3.32 (q, J=6.0 Hz, 2H), 3.04 (d, J=6.0 Hz, 2H), 2.03-1.97 (m, 2H), 1.89-1.86 (m, 2H). [M+H]⁺: 477.

Example 366: N-(7-(2,3-difluorophenyl)-3-oxoisoindolin-4-yl)-4-((3-(pyrrolidin-1-yl)propyl)amino)benzamide hydrochloride

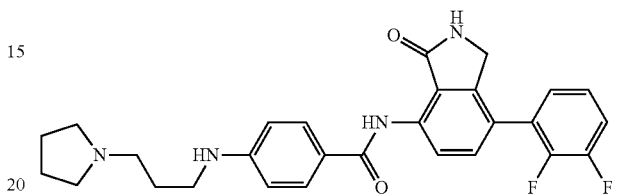

¹H NMR (400 MHz, DMSO-d₆) δ 11.48 (s, 1H), 9.41 (br.s, 1H), 9.03 (s, 1H), 8.56 (d, J=8.4 Hz, 1H), 7.77 (d, J=8.4 Hz, 2H), 7.63 (d, J=8.0 Hz, 1H), 7.53-7.47 (m, 1H), 7.40 (t, J=7.2 Hz, 1H), 7.35-7.29 (m, 1H), 6.72 (d, J=8.8 Hz, 2H), 6.60 (t, J=5.6 Hz, 1H), 4.41 (s, 2H), 3.57-3.54 (m, 2H), 3.23-3.20 (m, 4H), 3.08-3.01 (m, 2H), 2.49-2.45 (m, 2H), 2.10-2.01 (m, 2H), 1.98-1.90 (m, 2H), 1.87-1.85 (m, 2H). [M+H]⁺: 491.

Example 367: N-(7-(2,3-difluorophenyl)-3-oxoisoindolin-4-yl)-4-((2-(dimethylamino)ethyl)amino)benzamide

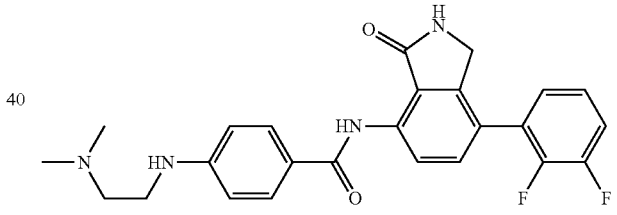

¹H NMR (400 MHz, DMSO-d₆) δ 11.46 (s, 1H), 9.03 (s, 1H), 8.57 (d, J=8.8 Hz, 1H), 7.74 (d, J=8.8 Hz, 2H), 7.62 (d, J=8.4 Hz, 1H), 7.53-7.46 (m, 1H), 7.40 (t, J=6.6 Hz, 1H), 7.35-7.31 (m, 1H), 6.72 (d, J=8.8 Hz, 2H), 6.36 (t, J=5.2 Hz, 1H), 4.40 (s, 2H), 3.19 (q, J=6.0 Hz, 2H), 2.45 (d, J=6.6 Hz, 2H), 2.19 (s, 6H). [M+H]⁺: 451.

Example 368: N-(7-(2,3-difluorophenyl)-3-oxoisoindolin-4-yl)-4-((3-(dimethylamino)propyl)amino)benzamide

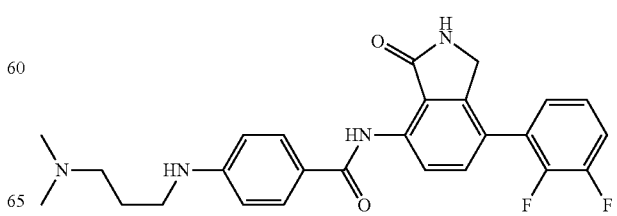

¹H NMR (400 MHz, DMSO-d₆) δ 11.46 (s, 1H), 9.03 (s, 1H), 8.57 (d, J=8.4 Hz, 1H), 7.73 (d, J=8.8 Hz, 2H), 7.62 (d, J=7.6 Hz, 1H), 7.52-7.46 (m, 1H), 7.40 (t, J=6.8 Hz, 1H), 7.34-7.29 (m, 1H), 6.67 (d, J=9.2 Hz, 2H), 6.54 (t, J=5.4 Hz, 1H), 4.40 (s, 2H), 3.13 (q, J=5.6 Hz, 2H), 2.29 (t, J=7.0 Hz, 2H), 2.14 (s, 6H) 1.68 (quint, J=7.0 Hz, 2H). [M+H]⁺: 465.

Example 369: 4-((2-(Azepan-1-yl)ethyl)amino)-N-(3-oxo-7-phenylisoindolin-4-yl)benzamide

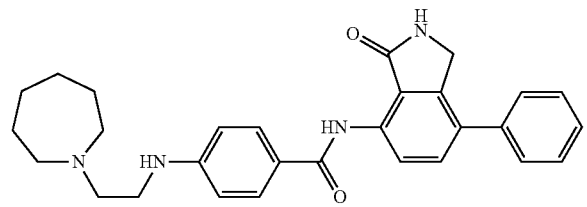 [SMILES: O=C(Nc1ccc(-c2ccccc2)c2c1C(=O)NC2)c1ccc(NCCN2CCCCCC2)cc1]

¹H NMR (400 MHz, DMSO-d₆) δ 11.49 (s, 1H), 9.04 (s, 1H), 8.57 (d, J=8.4 Hz, 1H), 7.73 (d, J=8.8 Hz, 2H), 7.67 (d, J=8.4 Hz, 1H), 7.61 (d, J=7.6 Hz, 2H), 7.48 (t, J=7.6 Hz, 2H), 7.39 (t, J=7.2 Hz, 1H), 6.71 (d, J=8.8 Hz, 2H), 6.29 (t, J=5.6 Hz, 1H), 4.59 (s, 2H), 3.18 (q, J=6.4 Hz, 2H), 2.69-2.56 (m, 7H), 1.58-1.55 (m, 8H). [M+H]⁺: 469.

Example 370: N-(3-oxo-7-phenylisoindolin-4-yl)-4-((3-(piperidin-1-yl) propyl)amino)benzamide

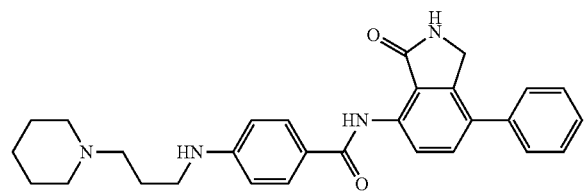 [SMILES: O=C(Nc1ccc(-c2ccccc2)c2c1C(=O)NC2)c1ccc(NCCCN2CCCCC2)cc1]

¹H NMR (400 MHz, DMSO-d₆) δ 11.48 (s, 1H), 9.03 (s, 1H), 8.57 (d, J=8.4 Hz, 1H), 7.73 (d, J=8.8 Hz, 2H), 7.66 (d, J=8.4 Hz, 1H), 7.61 (d, J=7.2 Hz, 2H), 7.48 (t, J=7.6 Hz, 2H), 7.39 (t, J=7.4 Hz, 1H), 6.67 (d, J=8.8 Hz, 2H), 6.57 (t, J=5.4 Hz, 1H), 4.58 (s, 2H), 3.12 (q, J=6.4 Hz, 2H), 2.33 (t, J=6.8 Hz, 2H), 1.70 (quint, J=7.0 Hz, 2H), 1.53-1.46 (m, 4H), 1.39-1.36 (m, 2H). [M+H]⁺: 469.

Example 371: 4-((2-Hydroxyethyl)amino)-N-(3-oxo-7-(thiophen-2-yl) isoindolin-4-yl)benzamide

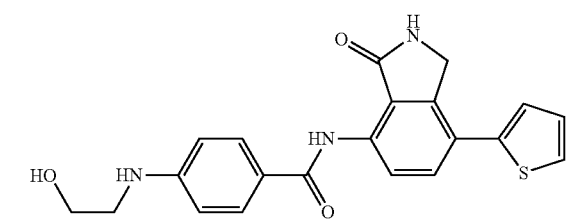 [SMILES: O=C(Nc1ccc(-c2cccs2)c2c1C(=O)NC2)c1ccc(NCCO)cc1]

¹H NMR (400 MHz, DMSO-d₆) δ 11.48 (s, 1H), 9.15 (s, 1H), 8.53 (d, J=8.4 Hz, 1H), 7.86 (d, J=8.8 Hz, 1H), 7.72 (d, J=8.4 Hz, 2H), 7.64 (d, J=5.2 Hz, 1H), 7.46 (d, J=3.6 Hz, 1H), 7.20 (t, J=4.4 Hz, 1H), 6.71 (d, J=8.8 Hz, 2H), 6.49 (t, J=5.4 Hz, 1H), 4.76 (t, J=5.4 Hz, 1H), 4.65 (s, 2H), 3.57 (q, J=6.0 Hz, 2H), 3.19 (q, J=6.0 Hz, 2H). [M+H]⁺: 394.

Example 372: 4-((2-Methoxyethyl)amino)-N-(3-oxo-7-(thiophen-2-yl) isoindolin-4-yl)benzamide

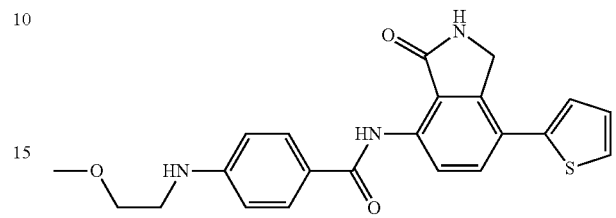

¹H NMR (400 MHz, DMSO-d₆) δ 11.48 (s, 1H), 9.15 (s, 1H), 8.53 (d, J=8.4 Hz, 1H), 7.86 (d, J=8.4 Hz, 1H), 7.72 (d, J=8.8 Hz, 2H), 7.64 (d, J=4.4 Hz, 1H), 7.46 (d, J=3.2 Hz, 1H), 7.20 (dd, J=5.2, 3.6 Hz, 1H), 6.72 (d, J=8.8 Hz, 2H), 6.55 (t, J=5.6 Hz, 1H), 4.65 (s, 2H), 3.51 (t, J=5.6 Hz, 2H), 3.29 (s, 3H), 3.28 (t, J=8.2 Hz, 2H). [M+H]⁺: 408.

Example 373: 4-((2-(Dimethylamino)ethyl)amino)-N-(3-oxo-7-(thiophen-2-yl)isoindolin-4-yl)benzamide

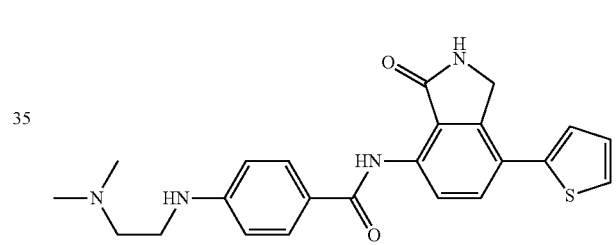

¹H NMR (400 MHz, DMSO-d₆) δ 11.48 (s, 1H), 9.15 (s, 1H), 8.53 (d, J=8.4 Hz, 1H), 7.86 (d, J=8.4 Hz, 1H), 7.72 (d, J=8.8 Hz, 2H), 7.64 (dd, J=4.8, 0.8 Hz, 1H), 7.46 (d, J=2.8 Hz, 1H), 7.20 (dd, J=5.2, 3.6 Hz, 1H), 6.72 (d, J=9.2 Hz, 2H), 6.34 (t, J=5.4 Hz, 1H), 4.65 (s, 2H), 3.18 (q, J=6.0 Hz, 2H), 2.45 (t, J=6.6 Hz, 2H), 2.19 (s, 3H). [M+H]⁺: 421.

Example 374: N-(3-oxo-7-(thiophen-2-yl)isoindolin-4-yl)-4-((2-(piperidin-1-yl)ethyl)amino)benzamide

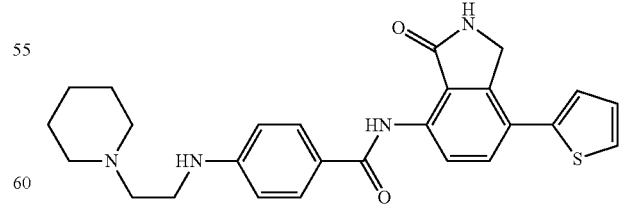

¹H NMR (400 MHz, DMSO-d₆) δ 11.48 (s, 1H), 9.15 (s, 1H), 8.53 (d, J=8.8 Hz, 1H), 7.86 (d, J=8.4 Hz, 1H), 7.72 (d, J=8.8 Hz, 2H), 7.64 (dd, J=4.8, 0.8 Hz, 1H), 7.46 (d, J=2.8 Hz, 1H), 7.20 (dd, J=5.2, 3.6 Hz, 1H), 6.70 (d, J=8.8 Hz, 2H), 6.34 (t, J=5.4 Hz, 1H), 4.65 (s, 2H), 3.20 (q, J=6.0 Hz,

2H), 2.47 (t, J=6.6 Hz, 2H), 2.42-2.37 (m, 4H), 1.53-1.48 (m, 4H), 1.39-1.36 (m, 2H). [M+H]⁺: 461.

Example 375: 4-((2-Morpholinoethyl)amino)-N-(3-oxo-7-(thiophen-2-yl) isoindolin-4-yl) benzamide

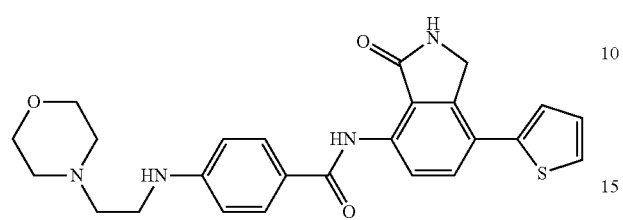

¹H NMR (400 MHz, DMSO-d₆) δ 11.48 (s, 1H), 9.15 (s, 1H), 8.53 (d, J=8.4 Hz, 1H), 7.86 (d, J=8.4 Hz, 1H), 7.73 (d, J=8.8 Hz, 2H), 7.64 (dd, J=5.2, 0.8 Hz, 1H), 7.46 (d, J=3.2 Hz, 1H), 7.20 (dd, J=5.2, 3.6 Hz, 1H), 6.71 (d, J=8.8 Hz, 2H), 6.38 (t, J=5.2 Hz, 1H), 4.65 (s, 2H), 3.59 (t, J=4.4 Hz, 4H), 3.23 (q, J=6.0 Hz, 2H), 2.53-2.50 (m, 2H), 2.46-2.40 (m, 4H). [M+H]⁺: 463.

Example 376: N-(7-(benzo[d]oxazol-7-yl)-3-oxoisoindolin-4-yl)-4-((2-(pyrrolidin-1-yl)ethyl)amino) benzamide

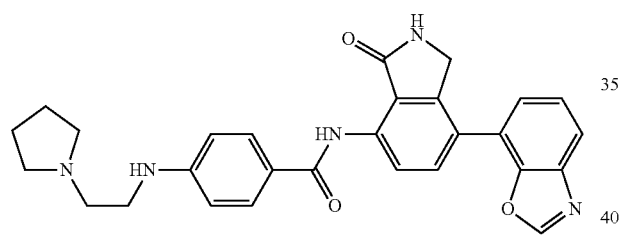

¹H NMR (400 MHz, DMSO-d₆) δ 11.53 (s, 1H), 9.08 (s, 1H), 8.81 (s, 1H), 8.62 (d, J=8.4 Hz, 1H), 7.85 (t, J=7.6 Hz, 2H), 7.75 (d, J=8.8 Hz, 2H), 7.65 (d, J=7.2 Hz, 1H), 7.51 (t, J=7.8 Hz, 1H), 6.72 (d, J=8.8 Hz, 2H), 6.45 (t, J=5.2 Hz, 1H), 4.53 (s, 2H), 3.24 (d, J=6.0 Hz, 2H), 2.66-2.63 (m, 2H), 1.74-1.66 (m, 4H). [M+H]⁺: 482.

Example 377: N-(7-(2-methylbenzo[d]oxazol-7-yl)-3-oxoisoindolin-4-yl)-4-((2-(pyrrolidin-1-yl)ethyl) amino)benzamide

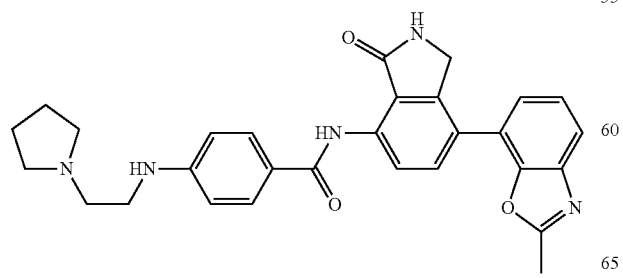

¹H NMR (400 MHz, DMSO-d₆) δ 11.51 (s, 1H), 9.07 (s, 1H), 8.61 (d, J=8.4 Hz, 1H), 7.82 (d, J=8.8 Hz, 1H), 7.75 (d, J=8.8 Hz, 2H), 7.69 (d, J=8.0 Hz, 1H), 7.53 (d, J=6.8 Hz, 1H), 7.43 (t, J=7.8 Hz, 1H), 6.72 (d, J=8.8 Hz, 2H), 6.45 (t, J=5.2 Hz, 1H), 4.51 (s, 2H), 3.23 (d, J=6.4 Hz, 2H), 2.63 (t, J=6.8 Hz, 1H), 2.63 (s, 3H), 1.72-1.67 (m, 4H). [M+H]⁺: 496.

Example 378: 4-((2-(4-Methylpiperazin-1-yl)ethyl)amino)-N-(3-oxo-7-(thiophen-2-yl)isoindolin-4-yl) benzamide

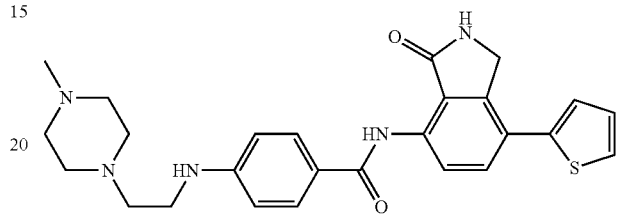

¹H NMR (400 MHz, DMSO-d₆) δ 11.48 (s, 1H), 9.12 (s, 1H), 8.53 (d, J=8.8 Hz, 1H), 7.86 (d, J=8.8 Hz, 1H), 7.73 (d, J=8.8 Hz, 2H), 7.64 (d, J=4.8 Hz, 1H), 7.46 (d, J=3.2 Hz, 1H), 7.20 (dd, J=5.0, 3.8 Hz, 1H), 6.70 (d, J=8.8 Hz, 2H), 6.35 (d, J=5.4 Hz, 1H), 4.65 (s, 2H), 3.21 (q, J=6.4 Hz, 2H), 2.46-2.30 (m, 8H), 2.15 (s, 3H). [M+H]⁺: 476.

Example 379: 4-((2-(4-Methylpiperazin-1-yl)ethyl)amino)-N-(3-oxo-7-phenylisoindolin-4-yl)benzamide

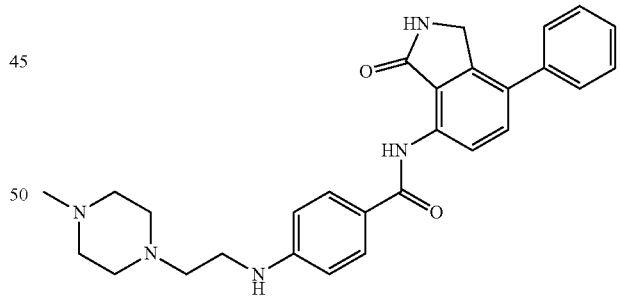

¹H NMR (400 MHz, DMSO-d₆) δ 11.48 (s, 1H), 9.02 (s, 1H), 8.56 (d, J=8.0 Hz, 1H), 7.73 (d, J=8.8 Hz, 2H), 7.66 (d, J=8.4 Hz, 1H), 7.60 (d, J=7.6 Hz, 2H), 7.48 (t, J=7.6 Hz, 2H), 7.39 (t, J=7.4 Hz, 1H), 6.71 (d, J=8.8 Hz, 2H), 6.32 (t, J=5.4 Hz, 1H), 4.58 (s, 2H), 3.21 (q, J=6.4 Hz, 2H), 2.54-2.50 (m, 2H), 2.44 (br.s, 4H), 2.33 (br.s, 4H), 2.15 (s, 3H). [M+H]⁺: 470.

Example 380: 4-((2-Hydroxyethyl)amino)-N-(3-oxo-7-phenylisoindolin-4-yl) benzamide

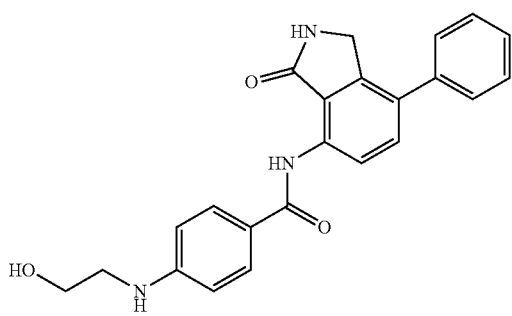 [SMILES: O=C(Nc1ccc(-c2ccccc2)c2c1C(=O)NC2)c1ccc(NCCO)cc1]

¹H NMR (400 MHz, DMSO-d₆) δ 11.48 (s, 1H), 9.02 (s, 1H), 8.57 (d, J=8.4 Hz, 1H), 7.73 (d, J=8.4 Hz, 2H), 7.67 (d, J=8.4 Hz, 1H), 7.61 (d, J=7.6 Hz, 2H), 7.48 (t, J=7.6 Hz, 2H), 7.39 (t, J=7.4 Hz, 1H), 6.71 (d, J=8.8 Hz, 2H), 6.47 (t, J=5.6 Hz, 1H), 4.76 (t, J=5.4 Hz, 1H), 4.59 (s, 2H), 3.58 (q, J=5.6 Hz, 2H), 3.19 (q, J=5.6 Hz, 2H). [M+H]⁺: 388.

Example 381: 4-((3-(Dimethylamino)propyl)amino)-N-(3-oxo-7-phenylisoindolin-4-yl) benzamide

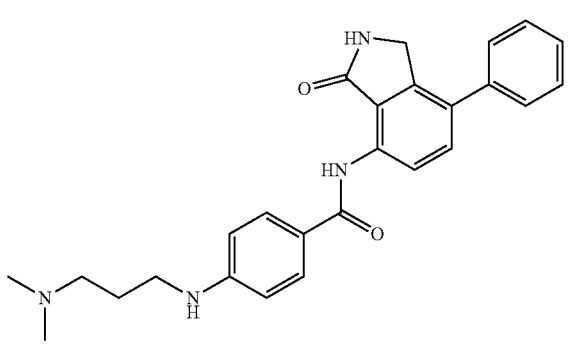 [SMILES: CN(C)CCCNc1ccc(C(=O)Nc2ccc(-c3ccccc3)c3c2C(=O)NC3)cc1]

¹H NMR (400 MHz, DMSO-d₆) δ 11.48 (s, 1H), 9.02 (s, 1H), 8.57 (d, J=8.4 Hz, 1H), 7.73 (d, J=8.8 Hz, 2H), 7.67 (d, J=8.4 Hz, 1H), 7.60 (d, J=7.2 Hz, 2H), 7.48 (t, J=7.6 Hz, 2H), 7.39 (t, J=7.4 Hz, 1H), 6.68 (d, J=8.8 Hz, 2H), 6.52 (t, J=5.4 Hz, 1H), 4.59 (s, 2H), 3.12 (q, J=6.8 Hz, 2H), 2.29 (t, J=7.2 Hz, 2H), 2.14 (s, 6H), 1.69 (qunt, J=6.8 Hz, 2H). [M+H]⁺: 429.

Example 382: 4-((3-Hydroxypropyl)amino)-N-(3-oxo-7-phenylisoindolin-4-yl) benzamide

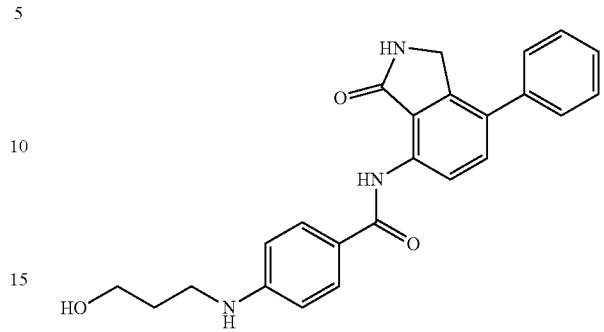

¹H NMR (400 MHz, DMSO-d₆) δ 11.48 (s, 1H), 9.02 (s, 1H), 8.57 (d, J=8.4 Hz, 1H), 7.73 (d, J=8.8 Hz, 2H), 7.67 (d, J=8.8 Hz, 1H), 7.61 (d, J=7.2 Hz, 2H), 7.48 (t, J=7.6 Hz, 2H), 7.40 (t, J=7.4 Hz, 1H), 6.68 (d, J=8.8 Hz, 2H), 6.48 (t, J=5.2 Hz, 1H), 4.58 (s, 2H), 4.52 (t, J=5.0 Hz, 1H), 3.52 (q, J=5.2 Hz, 2H), 3.16 (q, J=6.4 Hz, 2H), 1.72 (qunt, J=6.6 Hz, 2H). [M+H]⁺:402.

Example 383: 4-((4-Hydroxybutyl)amino)-N-(3-oxo-7-phenylisoindolin-4-yl) benzamide

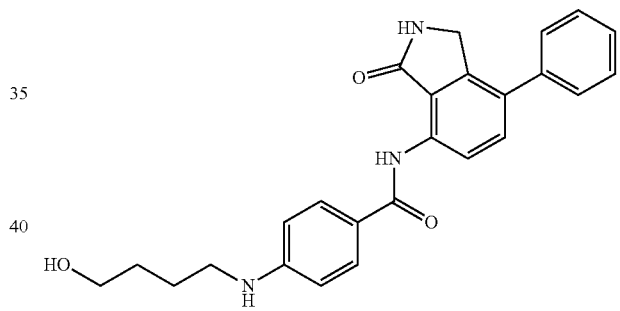

¹H NMR (400 MHz, DMSO-d₆) δ 11.48 (s, 1H), 9.02 (s, 1H), 8.57 (d, J=8.4 Hz, 1H), 7.73 (d, J=8.8 Hz, 2H), 7.67 (d, J=8.4 Hz, 1H), 7.61 (d, J=7.2 Hz, 2H), 7.48 (t, J=7.6 Hz, 2H), 7.39 (t, J=7.4 Hz, 1H), 6.68 (d, J=8.4 Hz, 2H), 6.49 (t, J=5.4 Hz, 1H), 4.58 (s, 2H), 4.44 (t, J=5.0 Hz, 1H), 3.46-3.42 (m, 3H), 3.10 (q, J=6.4 Hz, 2H), 1.62-1.55 (m, 2H), 1.53-1.50 (m, 2H). [M+H]⁺:416.

Example 384: N-(7-(benzofuran-2-yl)-3-oxoisoindolin-4-yl)-4-((2-(pyrrolidin-1-yl)ethyl)amino)benzamide

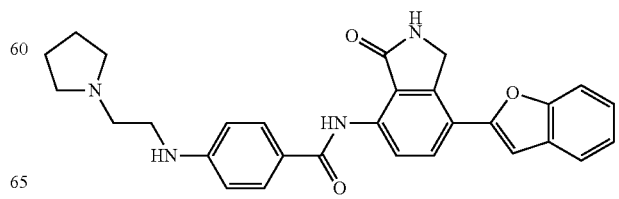

¹H NMR (400 MHz, DMSO-d₆) δ 11.54 (s, 1H), 9.22 (s, 1H), 8.62 (d, J=8.7 Hz, 1H), 8.15 (d, J=8.6 Hz, 1H), 7.74 (d, J=8.7 Hz, 2H), 7.72-7.63 (m, 2H), 7.35 (td, J=8.2, 7.7, 1.5 Hz, 1H), 7.32-7.27 (m, 2H), 6.72 (d, J=8.8 Hz, 2H), 6.45 (t, J=5.5 Hz, 1H), 4.79 (s, 2H), 3.23 (q, J=6.4 Hz, 2H), 2.63 (t, J=6.7 Hz, 2H), 2.49 (s, 4H), 1.70 (p, J=3.0 Hz, 4H); [M+H]⁺: 481.

Example 385: N-(3-oxo-7-(quinolin-6-yl)isoindolin-4-yl)-4-((2-(pyrrolidin-1-yl)ethyl)amino)benzamide

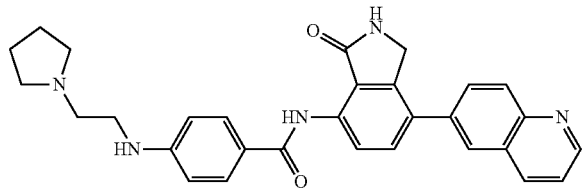 [SMILES: O=C(Nc1ccc(-c2ccc3ncccc3c2)c2c1C(=O)NC2)c1ccc(NCCN2CCCC2)cc1]

¹H NMR (400 MHz, DMSO-d₆) δ 9.12 (s, 1H), 8.94 (dd, J=4.2, 1.7 Hz, 1H), 8.63 (d, J=8.5 Hz, 1H), 8.46 (dd, J=8.5, 1.7 Hz, 1H), 8.25 (d, J=2.0 Hz, 1H), 8.12 (d, J=8.8 Hz, 1H), 8.08-7.99 (m, 2H), 7.85 (d, J=8.5 Hz, 1H), 7.82-7.75 (m, 2H), 7.60 (dd, J=8.3, 4.2 Hz, 1H), 6.77 (d, J=8.6 Hz, 2H), 6.60 (s, 1H), 4.72 (s, 2H), 3.27 (t, J=6.4 Hz, 2H), 2.90 (d, J=33.8 Hz, 4H), 2.72 (s, 2H), 1.81 (d, J=5.8 Hz, 4H); [M+H]⁺: 492.

Example 386: N-(3-oxo-7-(quinolin-5-yl)isoindolin-4-yl)-4-((2-(pyrrolidin-1-yl)ethyl)amino)benzamide

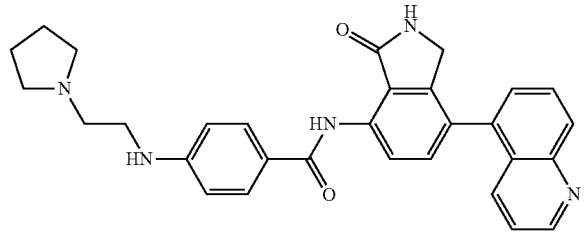 [SMILES: O=C(Nc1ccc(-c2cccc3ncccc23)c2c1C(=O)NC2)c1ccc(NCCN2CCCC2)cc1]

¹H NMR (400 MHz, CDCl₃) δ 11.28 (s, 1H), 8.98 (dd, J=4.2, 1.6 Hz, 1H), 8.86 (d, J=8.4 Hz, 1H), 8.20 (d, J=8.5 Hz, 1H), 7.98 (t, J=8.9 Hz, 3H), 7.81 (dd, J=8.5, 7.1 Hz, 1H), 7.57 (d, J=8.4 Hz, 1H), 7.54 (dd, J=7.1, 1.2 Hz, 1H), 7.39 (dd, J=8.6, 4.2 Hz, 1H), 6.70 (d, J=8.5 Hz, 2H), 6.64 (s, 1H), 4.34-4.02 (m, 2H), 3.29 (q, J=5.6 Hz, 2H), 2.79 (t, J=6.0 Hz, 2H), 2.57 (d, J=5.9 Hz, 4H), 1.87-1.77 (m, 4H); [M+H]⁺: 492.

Example 387: N-(3-oxo-7-(quinolin-4-yl)isoindolin-4-yl)-4-((2-(pyrrolidin-1-yl)ethyl)amino)benzamide

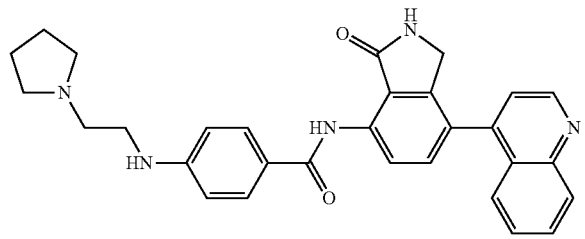 [SMILES: O=C(Nc1ccc(-c2ccnc3ccccc23)c2c1C(=O)NC2)c1ccc(NCCN2CCCC2)cc1]

¹H NMR (400 MHz, CDCl₃) δ 11.30 (s, 1H), 9.00 (d, J=4.4 Hz, 1H), 8.88 (d, J=8.4 Hz, 1H), 8.22 (d, J=8.5 Hz, 1H), 8.00-7.94 (m, 2H), 7.78 (ddd, J=8.4, 6.8, 1.4 Hz, 1H), 7.69 (dd, J=8.6, 1.3 Hz, 1H), 7.61 (d, J=8.4 Hz, 1H), 7.54 (ddd, J=8.2, 6.8, 1.2 Hz, 1H), 7.38 (d, J=4.4 Hz, 1H), 6.74-6.65 (m, 3H), 4.23 (d, J=23.4 Hz, 2H), 3.29 (q, J=5.7 Hz, 2H), 2.79 (t, J=6.0 Hz, 2H), 2.59 (p, J=3.5 Hz, 4H), 1.88-1.76 (m, 4H); [M+H]⁺: 492.

Example 388: 7-(4-Fluorobenzamido)-1-oxoisoindoline-4-carboxylic acid

Scheme 16. Total scheme for compound of Example 388

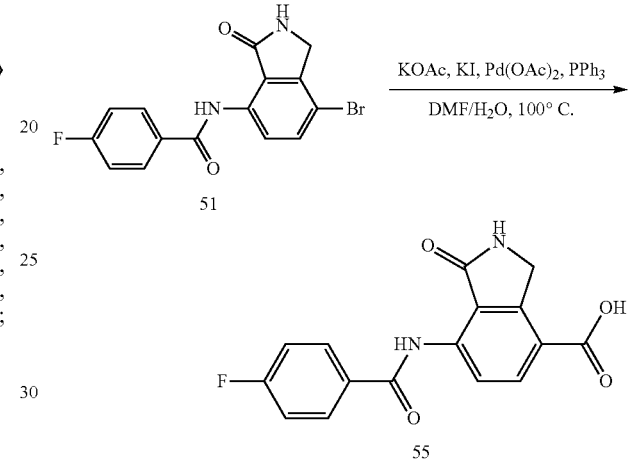

To a suspension solution of compound 51 (5.0 g, 14.3 mmol), KOAc (5.6 g, 57.2 mmol), KI (2.4 g, 14.3 mmol), Pd(OAc)₂ (321 mg, 1.43 mmol) and PPh₃ (750 mg, 2.86 mmol) in DMF (125 mL) and H₂O (7.5 mL) was purged with CO and stirred at 100° C. for 8 hours. The reaction mixture was concentrated in vacuo, added with H₂O (400 mL) and adjusted to pH 8 by adding 1M NaOH solution. The suspension solution was filtered through a Celite pad; the filtrate was washed with EtOAc (100 mL×3); and the aqueous phase was partially concentrated with water and acidified to pH 4 with 10% HCl solution. The precipitate thus obtained was collected to give the title compound 55 (1.6 g) as a white solid.

¹H NMR (400 MHz, DMSO-d₆) δ 13.15 (s, 1H), 11.81 (s, 1H), 9.13 (s, 1H), 8.53-8.51 (d, J=8.6 Hz, 1H), 8.15-8.13 (d, J=8.6 Hz, 1H), 8.05-8.01 (m, 2H), 7.49-7.44 (d, J=8.8 Hz, 2H), 4.64 (s, 2H); [M+H]⁻313.0.

Example 389: 7-(4-Fluorobenzamido)-N-methyl-1-oxoisoindoline-4-carboxamide

Scheme 17. Total scheme for compound of Example 389

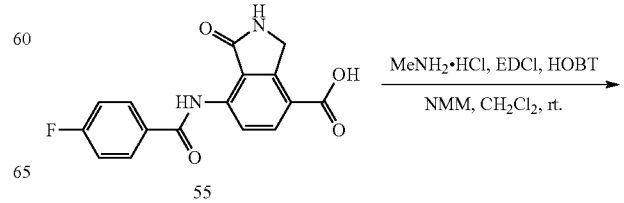

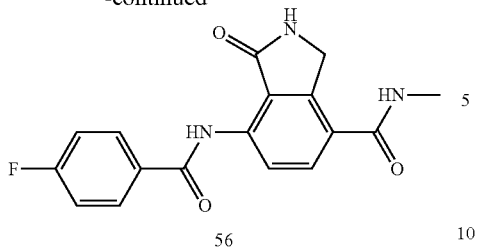

56

To a suspension solution of 7-(4-fluorobenzamido)-1-oxoisoindoline-4-carboxylic acid 55 (100 mg, 0.32 mmol) and MeNH$_2$HCl (33 mg, 0.48 mmol) in CH$_2$Cl$_2$ (1.6 mL) was added EDCI (92 mg, 0.48 mmol), HOBt (86 mg, 0.64 mmol) and NMM (0.1 mL, 0.95 mmol). The resulting mixture was purged with nitrogen, and stirred at room temperature for 12 hours. The reaction mixture was then cooled to room temperature, diluted with EtOAc (100 mL) and water (100 mL), and then filtered. The filtrate was washed with brine (200 mL), and the organic phase was concentrated in vacuo and purified by column chromatography to give the title compound 56 (84.1 mg, 80%).

$^1$H NMR (400 MHz, DMSO-d$_6$) δ 11.77 (s, 1H), 9.09 (s, 1H), 8.51-8.47 (m, 2H), 8.05-8.01 (m, 3H), 7.47 (t, J=8.8 Hz, 2H), 4.66 (s, 2H), 2.79 (d, J=4.4 Hz, 3H). [M+H]$^+$: 328.

The following compounds of Examples 390 to 392 were obtained by using corresponding starting materials and repeating the procedure of Example 389.

Example 390: N-methyl-1-oxo-7-(4-((2-(pyrrolidin-1-yl)ethyl)amino) benzamido)isoindoline-4-carboxamide

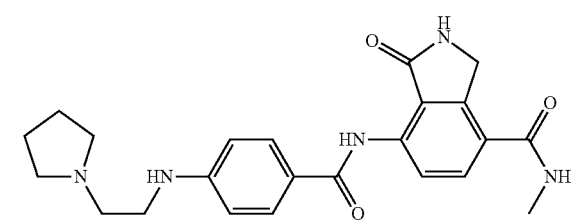 [SMILES: CNC(=O)c1ccc(NC(=O)c2ccc(NCCN3CCCC3)cc2)c2c1CNC2=O]

$^1$H NMR (400 MHz, DMSO-d$_6$) δ 11.54 (s, 1H), 9.01 (s, 1H), 8.50-8.45 (m, 2H), 7.98 (d, J=8.8 Hz, 1H), 7.72 (d, J=8.8 Hz, 2H), 6.71 (d, J=8.8 Hz, 2H), 6.46 (t, J=5.2 Hz, 1H), 4.64 (s, 2H), 3.22 (q, J=6.4 Hz, 2H), 2.78 (d, J=4.4 Hz, 3H), 2.62 (t, J=6.8 Hz, 2H), 2.49-2.47 (m, 4H), 1.71-1.67 (m, 4H). [M+H]$^+$:422.

Example 391: 4-Fluoro-N-(3-oxo-7-(pyrrolidine-1-carbonyl)isoindolin-4-yl) benzamide

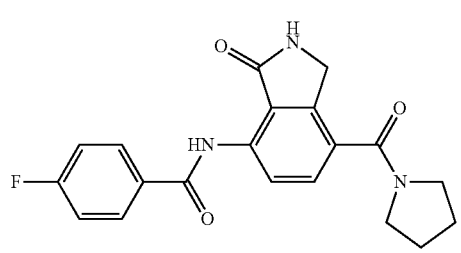 [SMILES: O=C(Nc1ccc(C(=O)N2CCCC2)c2c1C(=O)NC2)c1ccc(F)cc1]

$^1$H NMR (400 MHz, DMSO-d$_6$) δ 11.64 (s, 1H), 9.06 (s, 1H), 8.46 (d, J=8.4 Hz, 1H), 8.04-8.01 (m, 2H), 7.78 (d, J=8.4 Hz, 1H), 7.47 (t, J=8.4 Hz, 2H), 4.48 (s, 2H), 3.48-3.46 (m, 4H), 1.87-1.82 (m, 4H). [M+H]$^+$: 368.

Example 392: N-(3-oxo-7-(pyrrolidine-1-carbonyl)isoindolin-4-yl)-4-((2-(pyrrolidin-1-yl)ethyl)amino)benzamide

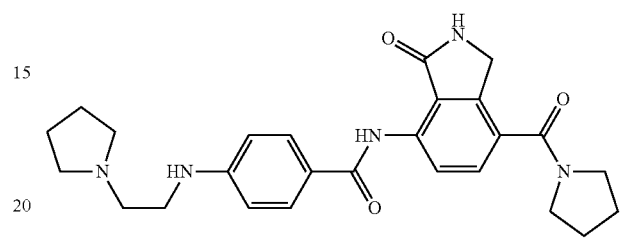

$^1$H NMR (400 MHz, DMSO-d$_6$) δ 11.42 (s, 1H), 8.97 (s, 1H), 8.47 (d, J=8.8 Hz, 1H), 7.73 (dd, J=8.6, 4.2 Hz, 3H), 6.71 (d, J=8.8 Hz, 2H), 6.45 (t, J=5.2 Hz, 1H), 4.46 (s, 2H), 3.48-3.44 (m, 4H), 3.30-3.22 (m, 4H), 2.65-2.63 (m, 2H), 1.86-1.83 (m, 4H), 1.72-1.68 (m, 4H). [M+H]$^+$:462.

Example 393: 4-Fluoro-N-(7-(2-hydroxypropan-2-yl)-3-oxoisoindolin-4-yl) benzamide Scheme 18. Total scheme for compound 58

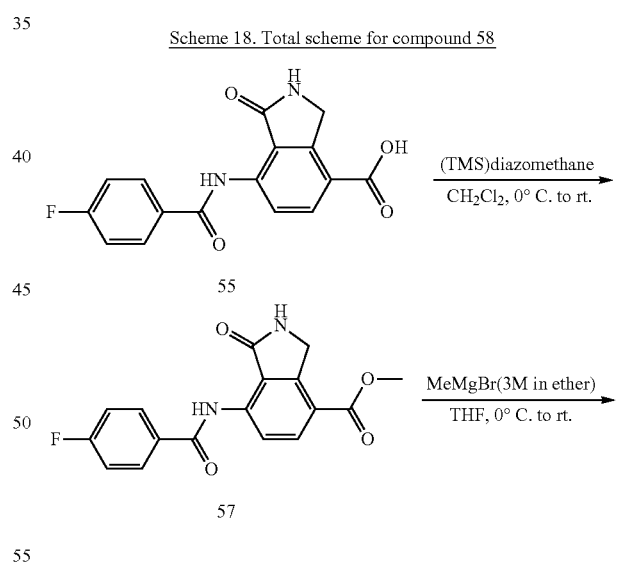

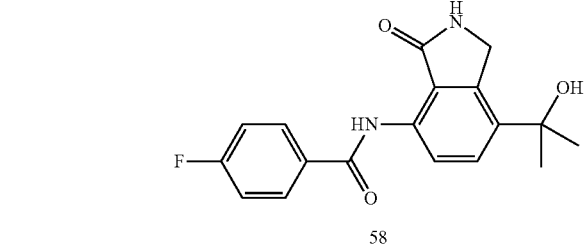

58

Step 1: Preparation of methyl 7-(4-fluorobenzamido)-1-oxoisoindoline-4-carboxylate (57)

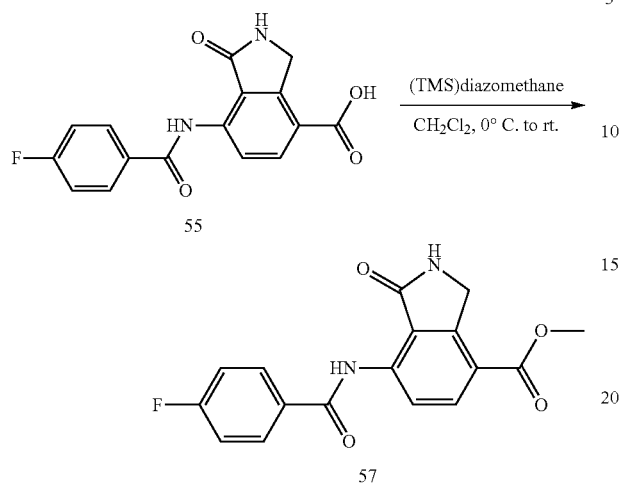

To a suspension solution of 7-(4-fluorobenzamido)-1-oxoisoindoline-4-carboxylic acid 55 (100 mg, 0.32 mmol) in CH$_2$Cl$_2$ (1.6 mL) was added TMS dizaomethane (0.25 mL, 0.48 mmol). The resulting mixture was purged with nitrogen, and stirred at room temperature for 12 hours. The reaction mixture was cooled to room temperature, diluted with EtOAc (100 mL) and water (100 mL), and then filtered. The filtrate was washed with brine (200 mL), and the organic phase was concentrated in vacuo to give the crude product 57 (140 mg) as a solid, which was directly used in the next step without further purification.

$^1$H NMR (400 MHz, DMSO-d$_6$) δ 11.76 (s, 1H), 8.95 (s, 1H), 8.37 (d, J=8.4 Hz, 1H), 8.03-7.99 (m, 2H), 7.53 (d, J=8.4 Hz, 1H), 7.45 (t, J=8.8 Hz, 2H), 5.16 (s, 1H), 4.62 (s, 2H), 1.48 (s, 6H). [M+H]$^+$: 329.

Step 2: Preparation of 4-fluoro-N-(7-(2-hydroxypropan-2-yl)-3-oxoisoindolin-4-yl)benzamide (58)

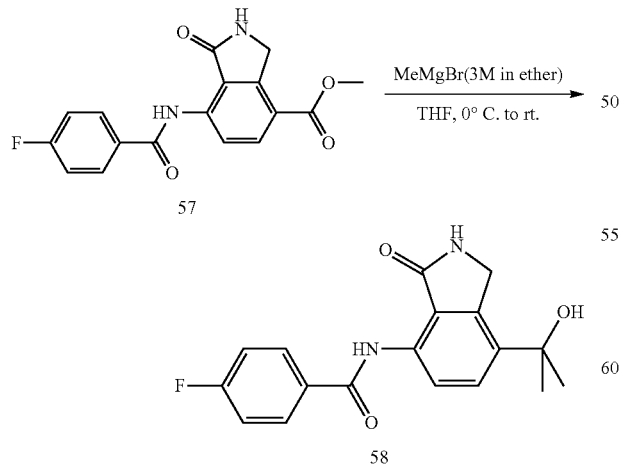

To a suspension solution methyl 7-(4-fluorobenzamido)-1-oxoisoindoline-4-carboxylate 57 (140 mg, 0.32 mmol) in THF (3.2 mL) was added MeMgBr (0.5 mL, 1.60 mmol). The resulting mixture was purged with nitrogen, and stirred at room temperature for 12 hours. The reaction mixture was then cooled to room temperature, diluted with EtOAc (50 mL) and water (50 mL), filtered. The filtrate was washed with brine (50 mL), and the organic phase was concentrated in vacuo and purified by column chromatography to give the title compound 58 (61.8 mg, 59%).

The following compound of Example 394 was obtained by using corresponding starting materials and repeating the procedure of Example 393.

Example 394: N-(7-(2-hydroxypropan-2-yl)-3-oxoisoindolin-4-yl)-4-((2-(pyrrolidin-1-yl)ethyl)amino)benzamide

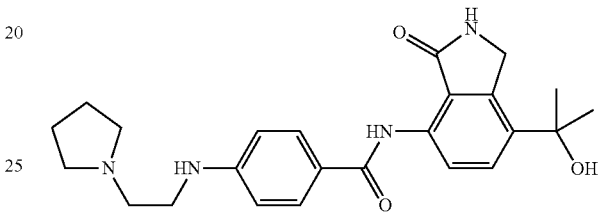

$^1$H NMR (400 MHz, DMSO-d$_6$) δ 11.51 (s, 1H), 8.86 (s, 1H), 8.38 (d, J=8.4 Hz, 1H), 7.70 (d, J=8.8 Hz, 2H), 7.47 (d, J=8.4 Hz, 1H), 6.69 (d, J=8.8 Hz, 2H), 6.37 (t, J=5.4 Hz, 1H), 5.11 (s, 1H), 4.60 (s, 2H), 3.21 (q, J=6.4 Hz, 2H), 2.62 (t, J=6.8 Hz, 2H), 2.49-2.40 (m, 4H), 1.69-1.65 (m, 5H), 1.47 (s, 6H). [M+H]$^+$:423.

Example 395:
N-(7-cyano-3-oxoisoindolin-4-yl)-4-fluorobenzamide

Scheme 19. Preparation of compound of Example 395

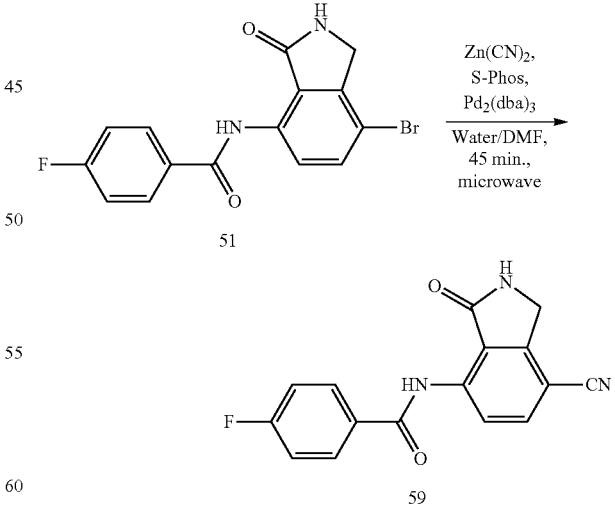

A mixture of N-(7-bromo-3-oxoisoindolin-4-yl)-4-fluorobenzamide 51 (100 mg, 0.29 mmol), S-Phos (12 mg, 0.03 mmol), Zn(CN)$_2$ (38 mg, 0.32 mmol) and Pd$_2$(dba)$_3$ (10 mg, 0.01 mmol) in water/DMF (2 drops/2 mL) was stirred for 45 min at 150° C. under microwave irradiation. The resulting mixture was purified by silica-gel column chromatography (Biotage flash purification system, EtOAc/Hex, KP-Sil) to give the title compound 50 (20 mg, 23%) as a white solid.

$^1$H NMR (400 MHz, DMSO-d$_6$) δ 11.63 (br s, 1H), 9.31 (br s, 1H), 8.55 (d, J=8.4 Hz, 1H), 8.08 (d, J=8.8 Hz, 1H), 8.05-8.02 (m, 2H), 7.51-7.46 (m, 2H), 4.65 (s, 2H); [M+H]$^+$: 296.

Example 396: 4-Fluoro-N-(7-hydroxy-3-oxoisoindolin-4-yl)benzamide

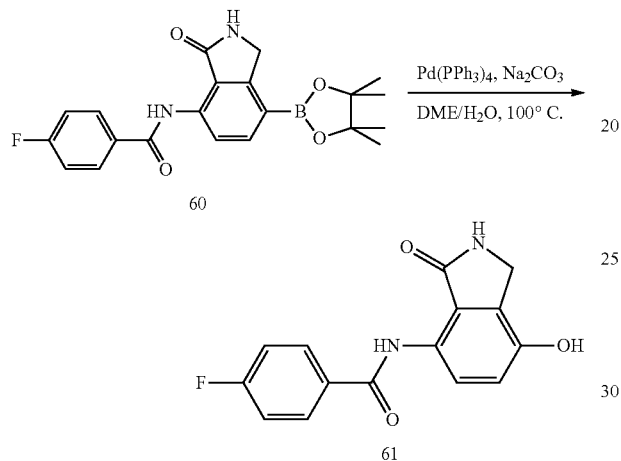

To a suspension solution of 4-fluoro-N-(3-oxo-7-(4,4,5,5-tetramethyl-1,3,2-dioxaborolan-2-yl)isoindolin-4-yl)benzamide 60 (50 mg, 0.126 mmol) and Na$_2$CO$_3$ (27 mg, 0.252 mmol) in DME (0.8 mL) and H$_2$O (0.2 mL) was added Pd(PPh$_3$)$_4$ (15 mg, 0.013 mmol). The resulting mixture was purged with nitrogen, and stirred at 100° C. for 12 hours. The reaction mixture was cooled to room temperature, diluted with EtOAc (100 mL) and water (100 mL), and then filtered. The filtrate was washed with brine (200 mL), and the organic phase was concentrated in vacuo and purified by column chromatography to give the title compound 61 (15 mg, 41%).

$^1$H NMR (400 MHz, DMSO-d$_6$) δ 11.21 (s, 1H), 9.91 (s, 1H), 8.93 (s, 1H), 8.26 (d, J=8.8 Hz, 1H), 7.98 (dd, J=8.8, 5.6 Hz, 2H), 7.44 (t, J=8.8 Hz, 2H), 6.99 (d, J=8.8 Hz, 1H), 4.31 (s, 2H). [M+H]$^+$:287.

Preparation Example 4: Preparation of 3,4-dihydroisoquinolin-1(2H)-one

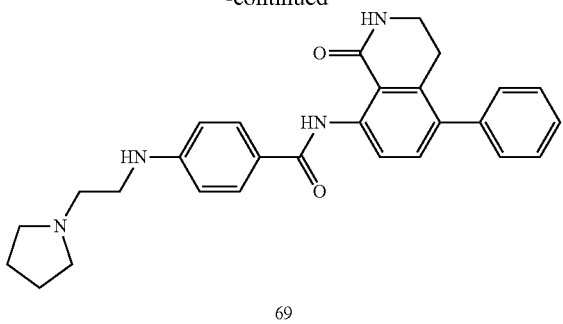

69

Step 1: Preparation of methyl 2-bromopentylcarbamate (63)

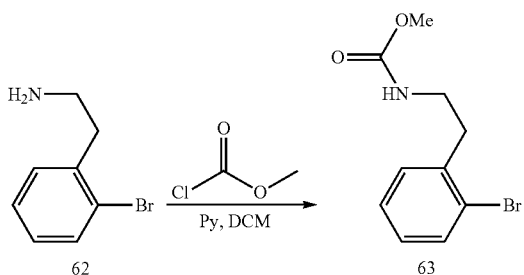

To a stirred solution of 2-(2-bromophenyl)ethanamine (29.0 g, 144.94 mmol) in DCM (400 mL) was added pyridine (17.20 g, 217.41 mmol), which was cooled to 0° C., and then added with methyl carbonochloridate (137.7 g, 144.94 mmol) dropwise over 10 min. The reaction mixture was stirred at room temperature for 3 hours, washed with 1 M HCl (2×200 mL), H$_2$O (200 mL) and brine, dried over Na$_2$SO$_4$, and then concentrated in vacuo to give the intermediate 63 (34.5 g, 133.66 mmol, 92.2%).

Step 2: Preparation of 5-bromo-3,4-dihydroisoquinolin-1(2H)-one (64)

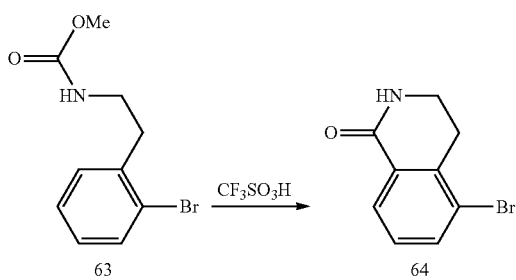

To a single-necked RBF filled with the intermediate 63 (34.5 g, 133.66 mmol, 1.0 eq) was added CF$_3$SO$_3$H (295 mL, 3341.60 mmol, 25 eq). The mixture was heated at 70° C. for 20 hours, and poured into a mixture of water and ice (3 L), adjusted to the pH of about 8 by adding NaHCO$_3$. The mixture was extracted with EtOAc (2×1.5 L), washed with brine, dried over Na$_2$SO$_4$, and concentrated to give the residue, which was purified by chromatography (EtOAc: hexane=1:10~1:1) to give the intermediate 64 (6.6 g, 29.45 mmol, 22.0%).

$^1$H NMR (400 MHz, DMSO-d$_6$) δ 8.09 (br s, 1H), 7.88 (d, J=7.6 Hz, 1H), 7.78 (dd, J=8.0, 0.8 Hz, 1H), 7.31 (t, J=7.8 Hz, 1H), 3.40 (td, J=6.6, 2.8 Hz, 2H), 2.96 (t, J=6.6 Hz, 2H); [M+H]$^+$: 226.

Step 3: Preparation of 5-bromo-8-nitro-3,4-dihydroisoquinolin-1(2H)-one (65)

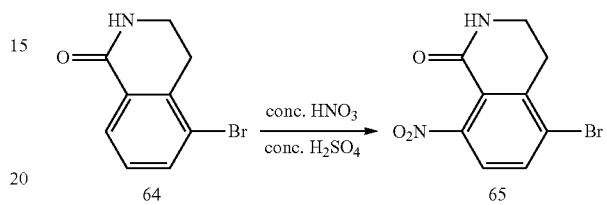

To a solution of the intermediate 64 (6.6 g, 29.19 mmol, 1.0 eq) in conc. H$_2$SO$_4$ (24 mL) was added a mixture solution of conc. HNO$_3$ (2.4 mL) in H$_2$SO$_4$ (24 mL) dropwise at 0~-5° C. over 2 hours. The resulting reaction mixture was stirred at 0~-5° C. for 2 hours. The reaction mixture was poured into ice water (200 mL), filtered, and the filter cake was purified by chromatography (EtOAc: hexane=1:2) to give the intermediate 65 (4.9 g, 18.07 mmol, 61.9%).

$^1$H NMR (400 Hz, DMSO) δ 8.54 (s, 1H), 8.01-7.98 (d, J=8.48 Hz, 1H), 7.64-7.62 (d, J=8.48 Hz, 1H), 3.44-3.43 (m, 2H), 3.02-2.99 (t, J=6.24 Hz, 2H).

Step 4: Preparation of 8-nitro-5-phenyl-3,4-dihydroisoquinolin-1(2H)-one (66)

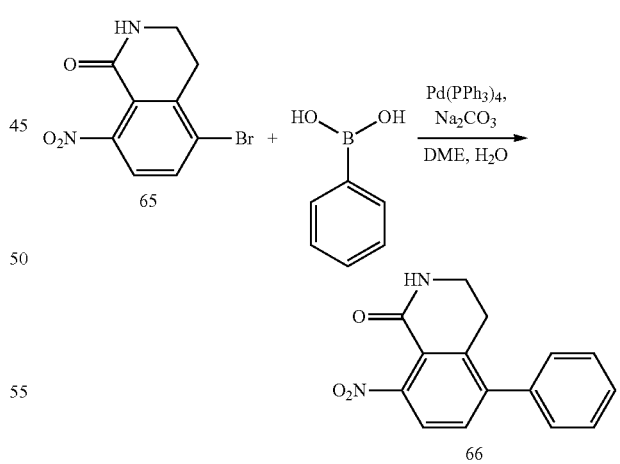

A suspension solution of the intermediate 65 (800 mg, 2.95 mmol, 1.0 eq), phenylboronic acid (540 mg, 4.43 mmol), Pd(PPh$_3$)$_4$ (273 mg, 0.24 mmol, 0.08 eq) and Na$_2$CO$_3$ (625 mg, 5.90 mmol, 2.0 eq) in DME (35 mL) and H$_2$O (9 mL) was degassed with N$_2$ for three times, and then heated at 70° C. for 16 hours. The reaction mixture was cooled to room temperature, added with EtOAc (100 mL) and H$_2$O (100 mL), and concentrated with EtOAc (2×100 mL) The combined organic phase was washed with brine, dried over Na$_2$SO$_4$, and concentrated in vacuo. The residue thus obtained was washed with EtOAc (20 mL), and then dried to give the intermediate 66 (800 mg, 2.98 mmol).

Step 5: Preparation of 8-amino-5-bromo-3,4-dihydroisoquinolin-1(2H)-one (67)

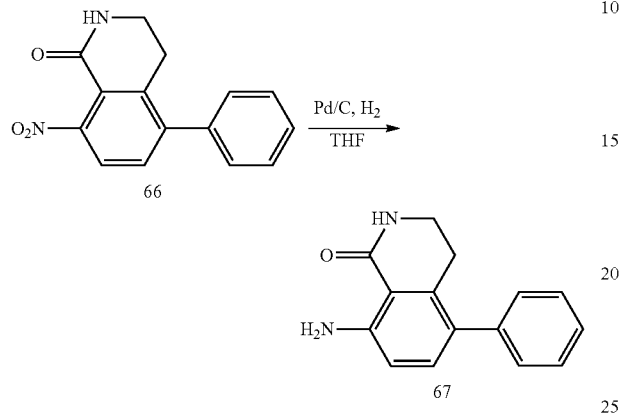

To a stirred solution of the intermediate 66 (800 mg, 2.98 mmol, 1.0 eq) in THF (120 mL) was added 10% Pd/C (200 mg), and the mixture was degassed with H$_2$ three times. The mixture was heated to 40° C. and stirred for 24 hours. The reaction mixture was filtered through a Celite pad, and the filtrate was concentrated to give the intermediate 67 (560 mg, 2.35 mmol, 78.8%).

$^1$H NMR (400 MHz, DMSO-d$_6$) δ 7.72 (br s, 1H), 7.41-7.36 (m, 2H), 7.31-7.25 (m, 3H), 7.07 (d, J=8.4 Hz, 1H), 6.94 (br s, 2H), 6.64 (d, J=8.4 Hz, 1H), 3.17-3.14 (m, 2H), 2.72 (t, J=6.2 Hz, 2H); [M+H]$^+$: 239.

Step 6: Preparation of 4-fluoro-N-(1-oxo-5-phenyl-1,2,3,4-tetrahydroisoquinolin-8-yl)benzamide (68)

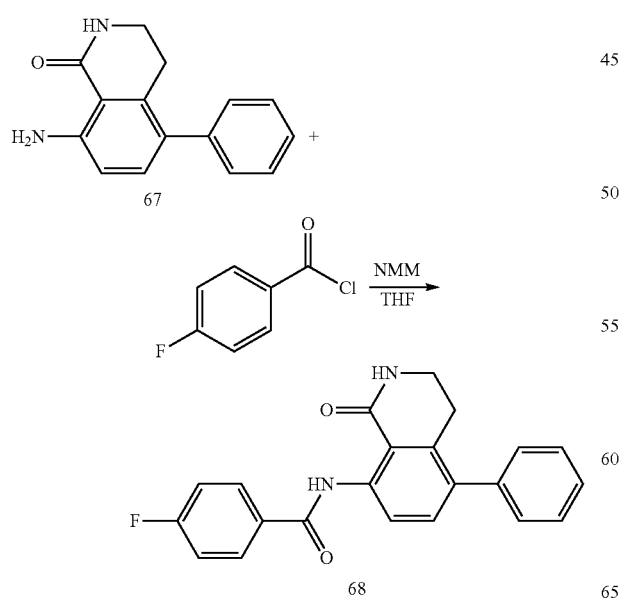

To a solution of the intermediate 67 (560 mg, 2.35 mmol, 1.0 eq) in THF (50 mL) was added NMM (1.4 g, 0.292 mol, 6.0 eq) dropwise at room temperature. The mixture was stirred for 10 min, and then added with 4-fluorobenzoyl chloride (1.1 g, 7.05 mmol, 3.0 eq). The resulting reaction mixture was stirred at 45° C. for 3 hours, concentrated, and added with EtOAc (100 mL) and H$_2$O (50 mL) The organic layer was washed with brine, and concentrated to give the crude product. The crude product was then filtered by chromatography to give the intermediate 68 (600 mg, 1.66 mmol, 70.6%).

The following compounds of Examples 397 to 400 were obtained by using corresponding starting materials and repeating the procedure of Example 396.

Example 397: 4-Acetamido-N-(1-oxo-5-phenyl-1,2,3,4-tetrahydroisoquinolin-8-yl)benzamide

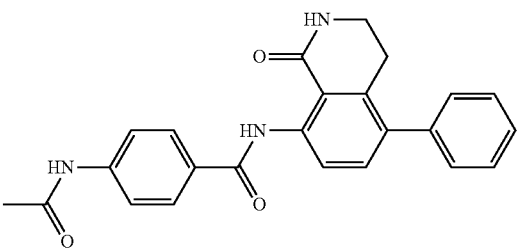 [SMILES: CC(=O)Nc1ccc(C(=O)Nc2ccc(-c3ccccc3)c3c2C(=O)NCC3)cc1]

$^1$H NMR (400 MHz, DMSO-d$_6$) δ 13.49 (br s, 1H), 10.27 (br s, 1H), 8.73 (d, J=8.8 Hz, 1H), 8.54-8.53 (m, 1H), 8.91 (d, J=8.4 Hz, 2H), 7.77 (d, J=8.8 Hz, 2H), 7.50-7.45 (m, 3H), 7.41-7.36 (m, 3H), 3.31-3.25 (m, 2H), 2.87 (t, J=6.4 Hz, 2H), 2.10 (s, 3H); [M+H]$^+$: 400.

Example 398: N-(1-oxo-5-phenyl-1,2,3,4-tetrahydroisoquinolin-8-yl) benzamide

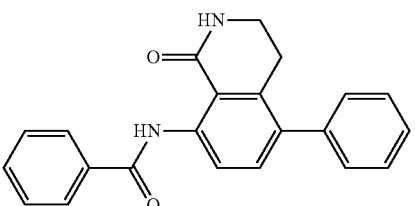

$^1$H NMR (400 MHz, DMSO-d$_6$) δ 13.60 (br s, 1H), 8.75 (d, J=8.4 Hz, 1H), 8.58-8.57 (m, 1H), 7.99-7.96 (m, 2H), 7.67-7.57 (m, 3H), 7.52-7.45 (m, 3H), 7.42-7.37 (m, 3H), 3.29 (td, J=6.4, 2.8 Hz, 2H), 2.87 (t, J=6.4 Hz, 2H); [M+H]$^+$: 343.

Example 399: N-(1-oxo-5-phenyl-1,2,3,4-tetrahydroisoquinolin-8-yl)furan-2-carboxamide

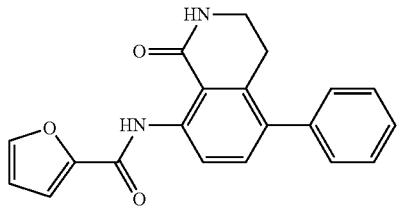 [SMILES: O=C(Nc1ccc(-c2ccccc2)c2c1C(=O)NCC2)c1ccco1]

¹H NMR (400 MHz, DMSO-d₆) δ 13.46 (br s, 1H), 8.64 (d, J=8.8 Hz, 1H), 7.98-7.97 (m, 1H), 7.49-7.44 (m, 3H), 7.41-7.36 (m, 3H), 7.24 (d, J=3.6 Hz, 1H), 6.74-6.72 (m, 1H), 3.31-3.25 (m, 2H), 2.86 (t, J=6.4 Hz, 2H); [M+H]⁺: 333.

Example 400: N-(5-(2,3-dimethoxyphenyl)-1-oxo-1,2,3,4-tetrahydroisoquinolin-8-yl)-4-fluorobenzamide

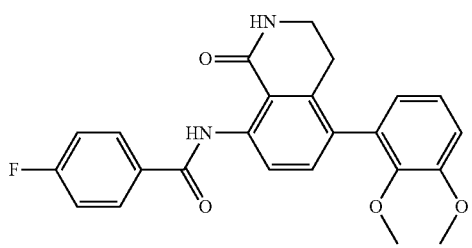 [SMILES: COc1cccc(-c2ccc(NC(=O)c3ccc(F)cc3)c3c2CCNC3=O)c1OC]

¹H NMR (400 MHz, DMSO-d₆) δ 13.62 (br s, 1H), 8.68 (d, J=8.8 Hz, 1H), 8.55 (br s, 1H), 8.05-8.01 (m, 2H), 7.47-7.41 (m, 3H), 7.16-7.09 (m, 2H), 6.78 (dd, J=7.2, 1.6 Hz, 1H), 3.85 (s, 3H), 3.45 (s, 3H), 3.29-3.27 (m, 2H), 2.68-2.60 (m, 2H); [M+H]⁺: 421.

Example 401: N-(1-oxo-5-phenyl-1,2,3,4-tetrahydroisoquinolin-8-yl)-4-((2-(pyrrolidin-1-yl)ethyl)amino)benzamide Scheme 22. Preparation of compound of Example 401

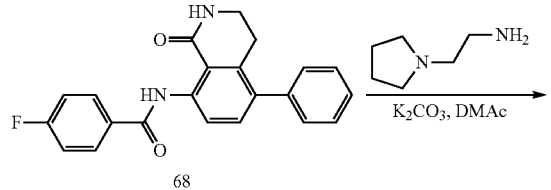

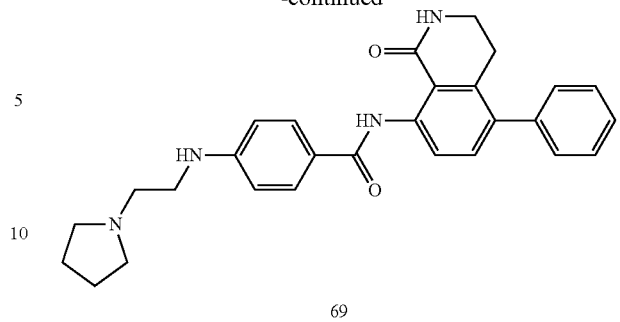

To a solution of the intermediate 68 (600 mg, 1.66 mmol, 1.0 eq) in DMAc (10 mL) was added 2-(pyrrolidin-1-yl)ethanamine (1.90 g, 16.65 mmol, 10.0 eq) and K₂CO₃ (1.15 g, 8.32 mmol, 5.0 eq), and the reaction mixture was stirred at 100° C. for 20 hours. The mixture was cooled to room temperature, and then added with DCM (200 mL) and H₂O (100 mL) The aqueous layer was extracted with DCM (2×200 mL), washed with brine, dried over Na₂SO₄, and concentrated to give the crude product. The crude product was purified by prep-HPLC to give the title compound 69 (140 mg, 0.30 mmol, 18.0%).

¹H NMR (400 MHz, CDCl₃) δ 12.94 (s, 1H), 8.90-8.88 (d, J=8.72 Hz, 1H), 7.95-7.93 (m, 2H), 7.48-7.41 (m, 3H), 7.38-7.34 (m, 1H), 7.31 (m, 2H), 6.67-6.65 (m, 2H), 6.03 (s, 1H), 4.75 (m, 1H), 3.45-3.41 (m, 2H), 3.28-3.23 (m, 2H), 2.98-2.95 (t, J=6.56 Hz, 2H), 2.77-2.74 (t, J=6.12 Hz, 2H), 2.55 (m, 4H), 1.81-1.80 (m, 4H), [M+H⁺]: 455.2.

The following compounds of Examples 402 and 403 were obtained by using corresponding starting materials and repeating the procedure of Example 401.

Example 402: N-(5-(2-methoxyphenyl)-1-oxo-1,2,3,4-tetrahydroisoquinolin-8-yl)-4-((2-(pyrrolidin-1-yl)ethyl)amino)benzamide

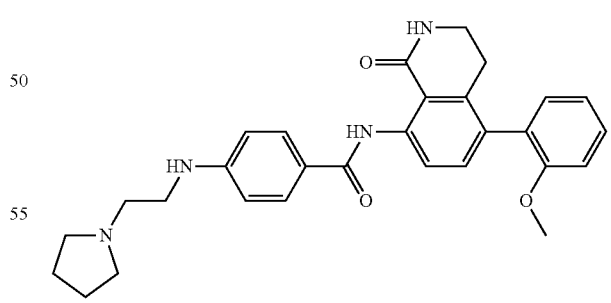

¹H NMR (400 MHz, CDCl₃) δ 12.96 (s, 1H), 8.89-8.86 (d, J=8.68 Hz, 1H), 7.95-7.93 (m, 2H), 7.41-7.35 (m, 2H), 7.19-7.17 (m, 1H), 7.05-7.03 (m, 1H), 6.97-6.95 (d, J=8.20 Hz, 1H), 6.66-6.64 (d, J=8.64 Hz, 2H), 6.01 (s, 1H), 4.75 (m, 1H), 3.77 (s, 1H), 3.44-3.40 (m, 2H), 3.28-3.24 (m, 2H), 2.95-2.87 (m, 1H), 2.77-2.75 (t, J=6.08 Hz, 2H), 2.70-2.63 (m, 1H), 2.55 (m, 4H), 1.80 (m, 4H), M+H⁺485.1.

Example 403: N-(5-bromo-1-oxo-1,2,3,4-tetrahydroisoquinolin-8-yl)-4-((2-(pyrrolidin-1-yl)ethyl)amino)benzamide

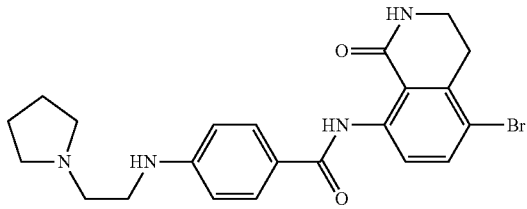 [SMILES: O=C(Nc1ccc(Br)c2c1C(=O)NCC2)c1ccc(NCCN2CCCC2)cc1]

$^1$H NMR (400 MHz, DMSO-d$_6$) δ 13.20 (br s, 1H), 8.63 (d, J=9.2 Hz, 1H), 8.58-8.57 (m, 1H), 7.76 (d, J=9.2 Hz, 1H), 7.70 (d, J=8.8 Hz, 2H), 6.67 (d, J=8.8 Hz, 2H), 6.36 (t, J=5.4 Hz, 1H), 3.40 (td, J=6.6, 2.8 Hz, 2H), 3.20 (q, J=6.4 Hz, 2H), 3.00 (t, J=6.6 Hz, 2H), 2.61 (t, J=6.8 Hz, 2H), 1.70-1.67 (m, 4H); [M+H]$^+$: 457.

Example 404: 4-Fluoro-N-(3-oxo-7-(phenylthio)isoindolin-4-yl)benzamide

Step 1: Preparation of 7-nitro-4-(phenylthio)isoindolin-1-one (71)

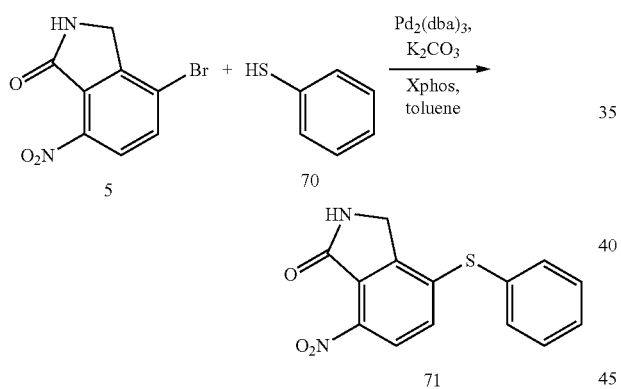

To a stirred solution of benzenethiol (1.43 g, 12.97 mmol, 1.3 eq) in toluene (20 mL) was added K$_2$CO$_3$ (0.97 g, 7.02 mmol, 0.7 eq). The solution was degassed with N$_2$ twice, and stirred at room temperature for 0.5 hour (as a reaction liquid A). Then a suspension solution of 4-bromo-7-nitroisoindolin-1-one 5 (2.57 g, 10.00 mmol, 1.0 eq) in toluene (30 mL) was added with Pd$_2$(dba)$_3$ (0.91 g, 0.99 mmol, 0.1 eq) and Xphos (0.57 g, 1.19 mmol, 0.12 eq), degassed with N$_2$ for twice, stirred at room temperature for 10 min, and then added into the reaction liquid A, followed by stirring them at 100° C. for 20 minutes. The mixture was cooled to room temperature, and then added with EtOAc (50 mL) and H$_2$O (50 mL) The aqueous layer was extracted with EtOAc (2×50 mL), washed with brine, dried over Na$_2$SO$_4$, and concentrated to give the crude product. The crude product was then purified by chromatography to give the intermediate 71 (1.10 g, 3.84 mmol, 38.4%).
$^1$H NMR (400 MHz, DMSO-d$_6$) δ 9.08 (s, 1H), 7.89-7.83 (d, J=8.82 Hz, 1H), 7.56-7.49 (m, 5H), 7.31-7.29 (d, J=8.32 Hz, 1H), 4.34 (s, 2H).

Step 2: Preparation of 7-amino-4-(phenylthio)isoindolin-1-one (72)

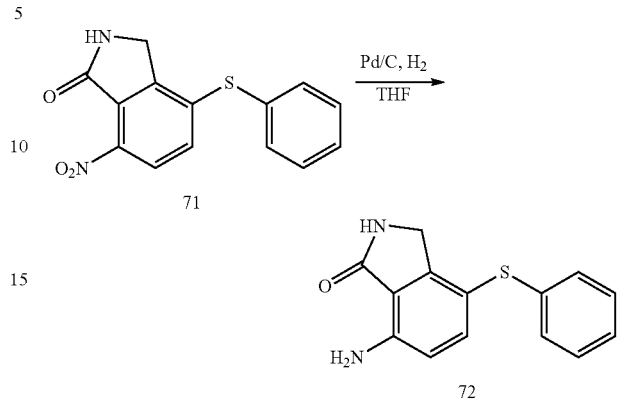

To a stirred solution of the intermediate 71 (1.1 g, 3.84 mmol, 1.0 eq) in THF (190 mL) was added 10% Pd/C (700 mg). The mixture was degassed with H$_2$ three times, heated to 40° C. and stirred for 24 hours, and filtered through a Celite pad. The filtrate was concentrated to give the intermediate 72 (650 mg, 2.53 mmol, 65.8%).
$^1$H NMR (400 MHz, DMSO-d$_6$) δ 8.27 (s, 1H), 7.36-7.34 (d, J=8.36 Hz, 1H/), 7.28-7.24 (t, J=7.60 Hz, 2H), 7.15-7.13 (t, J=7.32 Hz, 1H), 7.04-7.02 (d, J=7.48 Hz, 2H), 6.67-6.6.50 (d, J=8.36 Hz, 1H), 6.47 (s, 2H), 4.08 (s, 2H).

Step 3: Preparation of 4-fluoro-N-(3-oxo-7-(phenylthio)isoindolin-4-yl) benzamide (73)

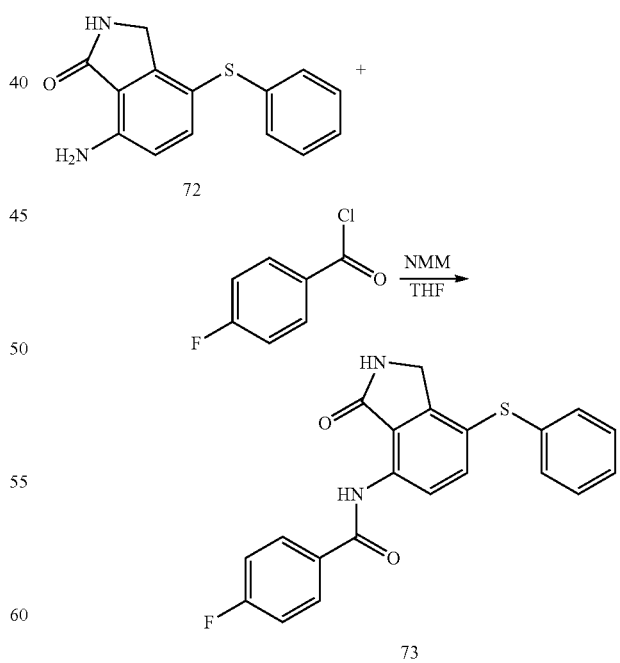

To a solution of the intermediate 72 (650 mg, 2.54 mmol, 1.0 eq) in THF (50 mL) was added NMM (1.5 g, 15.24 mol, 6.0 eq) dropwise at room temperature. The mixture was stirred for 10 min, added with 4-fluorobenzoyl chloride (1.2 g, 7.62 mmol, 3.0 eq), and stirred at 45° C. for 20 hours. The resulting reaction mixture was concentrated and added with EtOAc (100 mL) and H₂O (50 mL) The filtrate was concentrated with EtOAc (100 mL), and the organic layer was washed with brine and concentrated. The filter cake was collected and dried to give the intermediate 73 (700 mg, 1.84 mmol, 72.4%).

Example 405: N-(1-oxo-5-(phenylthio)-1,2,3,4-tetrahydroisoquinolin-8-yl)-4-((2-(pyrrolidin-1-yl)ethyl)amino)benzamide Scheme 23. Preparation of compound of Example 405

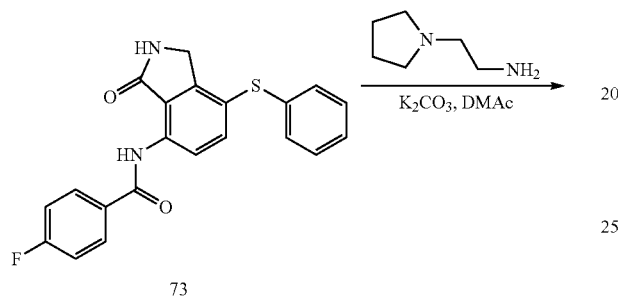

73

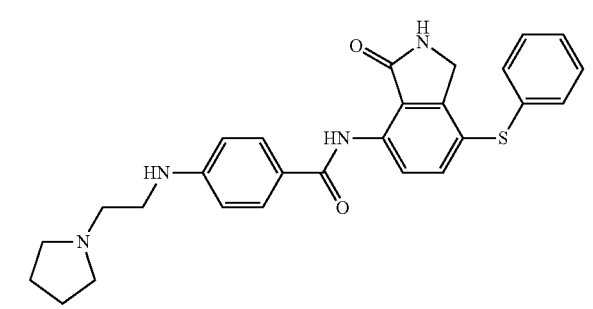

74

To a solution of the intermediate 73 (700 mg, 1.85 mmol, 1.0 eq) in DMAc (10 mL) was added 2-(pyrrolidin-1-yl)ethanamine (2.1 g, 18.50 mmol, 10.0 eq) and K₂CO₃ (1.3 g, 9.25 mmol, 5.0 eq), which was stirred at 100° C. for 20 hour. The resulting mixture was cooled to room temperature, and then added with DCM (200 mL) and H₂O (100 mL) The aqueous layer was extracted with DCM (2×200 mL), washed with brine, dried over Na₂SO₄, and concentrated to crude product, which was purified by prep-HPLC to give the title compound 74 (85 mg, 0.17 mmol, 9.1%).

¹H NMR (400 MHz, CDCl₃) δ 12.90 (s, 1H), 11.15 (s, 1H), 8.69-8.67 (d, J=8.52 Hz, 1H), 7.91-7.89 (d, J=8.64 Hz, 2H), 7.66-7.64 (d, J=8.56 Hz, 2H), 7.20-7.17 (m, 3H), 6.66-6.64 (d, J=8.68 Hz, 1H), 6.64 (s, 1H), 4.29 (s, 2H), 3.91 (s, 2H), 3.69-3.67 (m, 2H), 3.36-3.34 (m, 2H), 2.82 (s, 2H), 2.09-2.05 (m, 4H), M+H⁺455.2.

Example 406: N-(3-oxo-7-(phenylsulfonyl)isoindolin-4-yl)benzamide

Scheme 24. Preparation of compound of Example 406

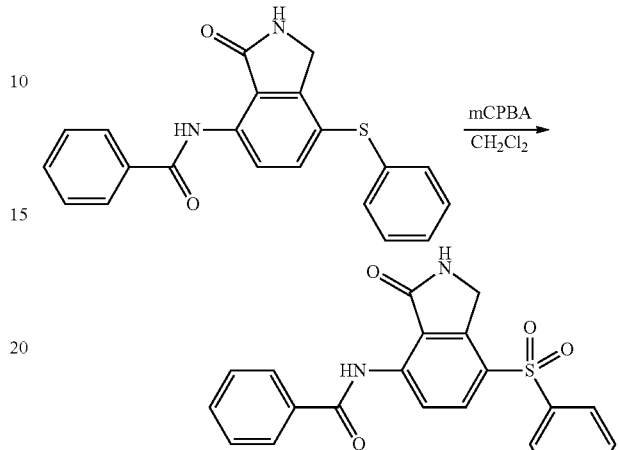

To a solution of N-(3-oxo-7-(phenylthio)isoindolin-4-yl)benzamide 75 (0.1 g, 0.28 mmol, 1.0 eq.) in DCM (3.0 mL) was added mCPBA (0.17 g, 0.7 mmol, 2.5 eq.) at 0° C. The reaction mixture was stirred for 3 hours at room temperature and quenched with 0.5 N aqueous sodium hydrogen carbonate solution (10 mL) The resulting mixture was extracted with EtOAc (10 mL) twice, dried over anhydrous magnesium sulfate, and concentrated. The residue was purified by flash chromatography with EtOAc/n-hexane. The collected residue was triturated in 50% aqueous sodium hydrogen carbonate solution (5 mL) and then filtered to give N-(3-oxo-7-(phenylsulfonyl) isoindolin-4-yl)benzamide 76 (31 mg, 0.08 mmol, 28%) as a white solid.

¹H NMR (400 MHz, DMSO-d₆) δ 11.84 (s, 1H), 9.30 (s, 1H), 8.66 (d, J=8.8 Hz, 1H), 8.18 (d, J=8.6 Hz, 1H), 8.01 (d, J=7.7 Hz, 2H), 7.96 (d, J=7.3 Hz, 2H), 7.72-7.60 (m, 6H), 4.68 (s, 2H); [M+H]⁺: 393.

The following compound of Example 407 was obtained by using corresponding starting materials and repeating the procedure of Example 406.

Example 407:
N-(3-oxo-7-(phenylthio)isoindolin-4-yl)benzamide

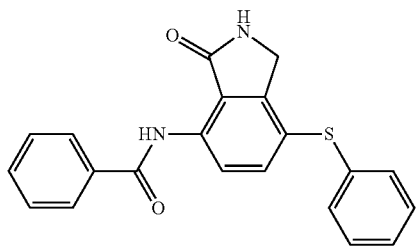 [SMILES: O=C(Nc1ccc(Sc2ccccc2)c2c1C(=O)NC2)c1ccccc1]

¹H NMR (400 MHz, DMSO-d₆) δ 11.55 (s, 1H), 9.05 (s, 1H), 8.52 (d, J=8.7 Hz, 1H), 7.97 (d, J=7.2 Hz, 2H), 7.69-7.60 (m, 5H), 7.34 (d, J=7.7 Hz, 2H), 7.25 (d, J=8.1 Hz, 3H), 4.26 (s, 2H); [M+H]⁺: 361.

Example 408: 4-Fluoro-N-(3-oxo-7-(phenylamino)isoindolin-4-yl)benzamide

Scheme 25. Preparation of compound of Example 408

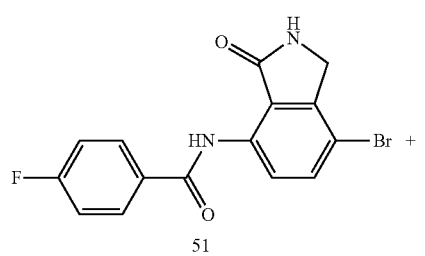

51

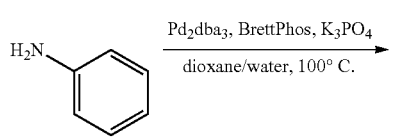

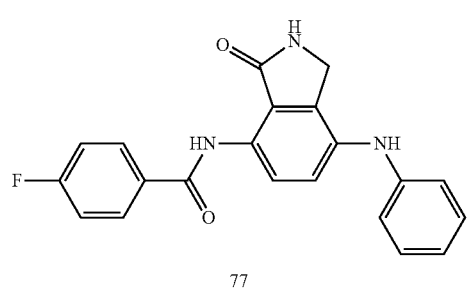

77

A mixture of intermediate 51 (3.0 g, 8.60 mmol, 1.0 eq.), aniline (2.4 g, 25.80 mmol, 3.0 eq.), Pd$_2$dba$_3$ (0.39 g, 5 mol %), BrettPhos (0.46 g, 10 mol %) and K$_3$PO$_4$ (9.1 g, 43.0 mmol, 5.0 eq.) was suspended in a solution of dioxane/water (10:1, 100 mL, 0.1 M). The resulting mixture was stirred at 100° C. for 15 hours and cooled to room temperature. The reaction mixture was diluted in acetone (300 mL) and SMOPEX-234TM (3.0 g), and then added with MgSO$_4$ (20 g). After stirring them for 3 hours, the resultant was filtered through a plug of Celite and concentrated. The residual mixture was triturated in MeOH (30 mL) twice, and filtered to give the precipitate 77 (2.2 g, 6.1 mmol, 71%) as a yellow solid.

$^1$H NMR (400 MHz, DMSO-d$_6$) δ 11.34 (s, 1H), 8.93 (s, 1H), 8.35 (d, J=8.7 Hz, 1H), 8.04-7.96 (m, 2H), 7.91 (s, 1H), 7.44 (q, J=9.0 Hz, 1H), 7.25 (t, J=7.8 Hz, 1H), 7.01 (d, J=7.6 Hz, 1H), 6.85 (t, J=7.3 Hz, 1H), 4.31 (s, 2H); MS (ESI) m/z 362 (M+H)$^+$.

The following compounds of Examples 409 to 437 were obtained by using corresponding starting materials and repeating the procedure of Example 408.

Example 409: N-(3-oxo-7-(phenylamino)isoindolin-4-yl)benzamide

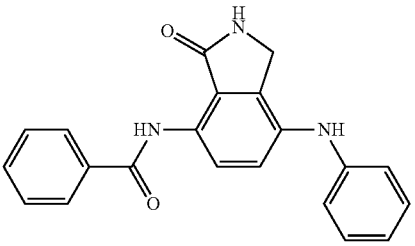 [SMILES: O=C(Nc1ccc(Nc2ccccc2)c2c1C(=O)NC2)c1ccccc1]

$^1$H NMR (400 MHz, DMSO-d$_6$) δ 11.37 (s, 1H), 8.89 (s, 1H), 8.38 (d, J=8.8 Hz, 1H), 7.95 (d, J=7.0 Hz, 2H), 7.88 (s, 1H), 7.65-7.58 (m, 3H), 7.41 (d, J=8.8 Hz, 2H), 7.25 (t, J=7.8 Hz, 2H), 7.01 (d, J=7.8 Hz, 2H), 6.95 (t, J=7.1 Hz, 1H), 4.31 (s, 2H); [M+H]$^+$: 344.

Example 410: N-(7-((2-methoxyphenyl)amino)-3-oxoisoindolin-4-yl) benzamide

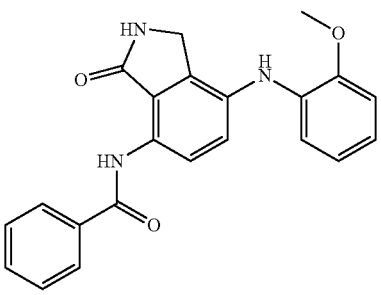 [SMILES: COc1ccccc1Nc1ccc(NC(=O)c2ccccc2)c2c1CNC2=O]

$^1$H NMR (400 MHz, DMSO-d$_6$) δ 11.38 (s, 1H), 8.89 (s, 1H), 8.35 (d, J=8.7 Hz, 1H), 7.94 (d, J=6.9 Hz, 2H), 7.66-7.58 (m, 3H), 7.20 (s, 1H), 7.16 (d, J=8.8 Hz, 1H), 7.02 (d, J=8.0 Hz, 1H), 6.94-6.83 (m, 4H), 4.30 (s, 2H), 3.81 (s, 3H); [M+H]$^+$: 374.

Example 411: N-(3-oxo-7-(o-tolylamino)isoindolin-4-yl)benzamide

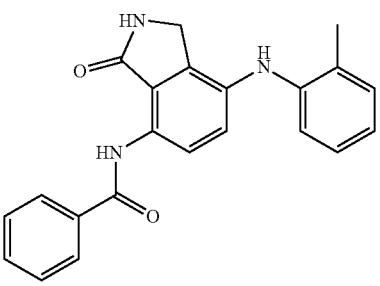 [SMILES: Cc1ccccc1Nc1ccc(NC(=O)c2ccccc2)c2c1CNC2=O]

$^1$H NMR (400 MHz, DMSO-d$_6$) δ 11.35 (s, 1H), 8.88 (s, 1H), 8.33 (d, J=8.6 Hz, 1H), 7.93 (d, J=6.6 Hz, 2H), 7.64-7.59 (m, 3H), 7.28 (s, 1H), 7.21 (d, J=8.4 Hz, 1H), 7.12 (t, J=7.2 Hz, 1H), 6.94 (dd, J=12.2, 9.1 Hz, 3H) 4.20 (s, 2H), 2.20 (s, 3H); [M+H]$^+$: 358.

Example 412: N-(3-oxo-7-(p-tolylamino)isoindolin-4-yl)benzamide

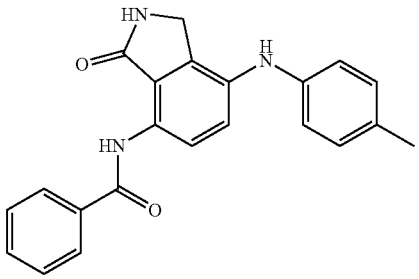 [SMILES: Cc1ccc(Nc2ccc(NC(=O)c3ccccc3)c3c2CNC3=O)cc1]

$^1$H NMR (400 MHz, DMSO-d$_6$) δ 11.35 (s, 1H), 8.91 (s, 1H), 8.35 (d, J=8.6 Hz, 1H), 7.94 (d, J=6.7 Hz, 2H), 7.76 (s, 1H), 7.64-7.58 (m, 3H), 7.33 (d, J=8.8 Hz, 1H), 7.08 (d, J=8.0 Hz, 2H), 6.95 (d, J=8.3 Hz, 2H), 4.29 (s, 2H), 2.24 (s, 3H); [M+H]$^+$: 358.

Example 413: N-(7-((2-fluorophenyl)amino)-3-oxoisoindolin-4-yl)benzamide

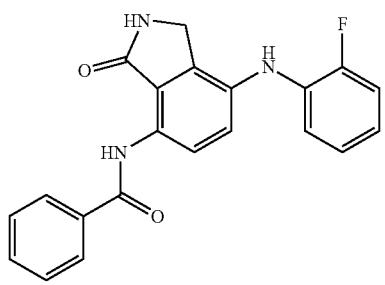 [SMILES: O=C(Nc1ccc(Nc2ccccc2F)c2c1C(=O)NC2)c1ccccc1]

$^1$H NMR (400 MHz, DMSO-d$_6$) δ 11.39 (s, 1H), 8.93 (s, 1H), 8.35 (d, J=8.7 Hz, 1H), 7.95 (d, J=6.8 Hz, 2H), 7.76 (s, 1H), 7.67-7.58 (m, 3H), 7.25-7.16 (m, 2H), 7.11-7.04 (m, 2H), 6.97-6.92 (m, 1H), 4.32 (s, 2H); [M+H]$^+$: 362.

Example 414: N-(7-((4-fluorophenyl)amino)-3-oxoisoindolin-4-yl)benzamide

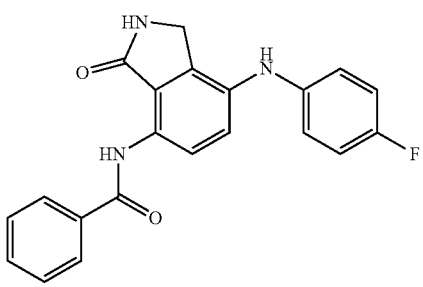 [SMILES: O=C(Nc1ccc(Nc2ccc(F)cc2)c2c1C(=O)NC2)c1ccccc1]

$^1$H NMR (400 MHz, DMSO-d$_6$) δ 11.36 (s, 1H), 8.93 (s, 1H), 8.37 (d, J=8.7 Hz, 1H), 7.94 (d, J=6.7 Hz, 2H), 7.87 (s, 1H), 7.65-7.58 (m, 3H), 7.33 (d, J=8.7 Hz, 1H), 7.12-7.01 (m, 4H), 4.30 (s, 2H); [M+H]$^+$: 362.

Example 415: N-(7-((3-fluorophenyl)amino)-3-oxoisoindolin-4-yl)benzamide

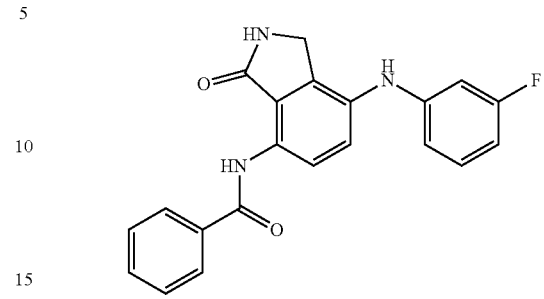

$^1$H NMR (400 MHz, DMSO-d$_6$) δ 11.41 (s, 1H), 8.95 (s, 1H), 8.43 (d, J=8.8 Hz, 1H), 8.17 (s, 1H), 7.95 (d, J=6.8 Hz, 2H), 7.68-7.59 (m, 3H), 7.48 (d, J=8.8 Hz, 1H), 7.24 (q, J=8.0 Hz, 1H), 6.79 (d, J=7.6 Hz, 1H), 6.71 (d, J=11.8 Hz, 1H), 6.60-6.57 (m, 1H), 4.32 (s, 2H); [M+H]$^+$: 362.

Example 416: N-(7-((4-methoxyphenyl)amino)-3-oxoisoindolin-4-yl) benzamide

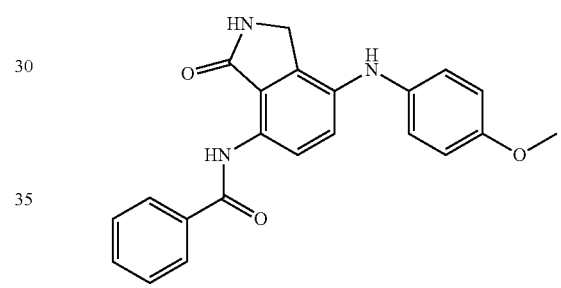

$^1$H NMR (400 MHz, DMSO-d$_6$) δ 11.38 (s, 1H), 8.92 (s, 1H), 8.39 (d, J=8.8 Hz, 1H), 7.93 (dd, J=8.0, 6.4 Hz, 3H), 7.65-7.58 (m, 3H), 7.45 (d, J=8.7 Hz, 1H), 7.14 (t, J=8.1 Hz, 1H), 6.59 (d, J=8.0 Hz, 1H), 6.54 (t, J=2.1 Hz, 1H), 6.43 (dd, J=8.3, 1.8 Hz, 1H), 4.32 (s, 2H), 3.71 (s, 3H); [M+H]$^+$: 374.

Example 417: 4-Methyl-N-(3-oxo-7-(phenylamino)isoindolin-4-yl)benzamide

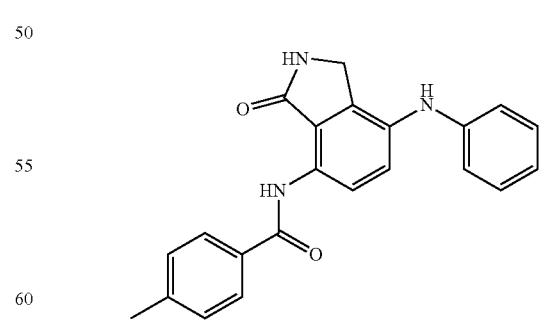

$^1$H NMR (400 MHz, DMSO-d$_6$) δ 11.99 (s, 1H), 8.66 (s, 1H), 8.47 (d, J=8.6 Hz, 1H), 7.86 (s, 1H), 7.72 (d, J=8.6 Hz, 2H), 7.37 (d, J=3.3 Hz, 1H), 7.23 (t, J=8.0 Hz, 2H), 6.97 (d, J=8.0 Hz, 2H), 6.82 (t, J=7.3 Hz, 1H), 6.70 (d, J=8.9 Hz, 2H), 4.29 (s, 2H), 3.25 (s, 3H); [M+H]$^+$: 358.

Example 418: N-(7-((3-chlorophenyl)amino)-3-ox-oisoindolin-4-yl)-4-fluorobenzamide

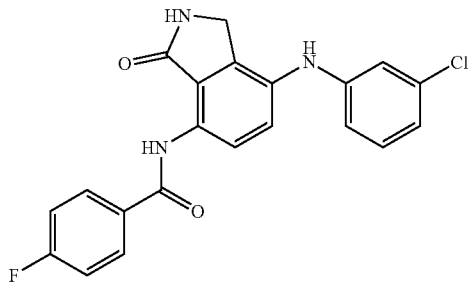 [SMILES: O=C(Nc1ccc(Nc2cccc(Cl)c2)c2c1C(=O)NC2)c1ccc(F)cc1]

MS (ESI) m/z 396 (M+H)$^+$.
$^1$H NMR (400 MHz, DMSO-d$_6$) δ 11.36 (s, 1H), 8.97 (s, 1H), 8.38 (d, J=8.8 Hz, 1H), 8.15 (s, 1H), 8.01-7.97 (m, 2H), 7.46-7.42 (m, 3H), 7.22 (t, J=8.0 Hz, 1H), 6.93-6.89 (m, 2H), 6.83-8.61 (m, 1H), 4.30 (s, 2H); [M+H]$^+$: 396.

Example 419: N-(7-((2-chlorophenyl)amino)-3-ox-oisoindolin-4-yl)-4-fluorobenzamide

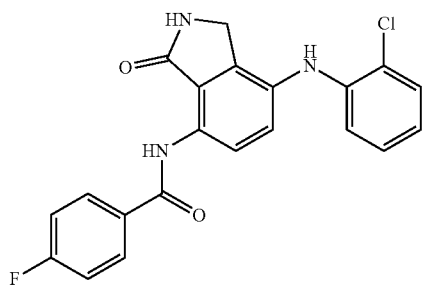 [SMILES: O=C(Nc1ccc(Nc2ccccc2Cl)c2c1C(=O)NC2)c1ccc(F)cc1]

MS (ESI) m/z 396 (M+H)$^+$.
$^1$H NMR (400 MHz, DMSO-d$_6$) δ 11.40 (s, 1H), 8.95 (s, 1H), 8.37 (d, J=8.4 Hz, 1H), 8.02-7.97 (m, 2H), 7.58 (s, 1H), 7.47-7.40 (m, 3H), 7.24 (d, J=8.8 Hz, 1H), 7.20-7.15 (m, 1H), 6.91-6.89 (m, 2H), 4.24 (s, 2H); [M+H]$^+$: 396.

Example 420: 2-Fluoro-N-(3-oxo-7-(phenylamino)isoindolin-4-yl)benzamide

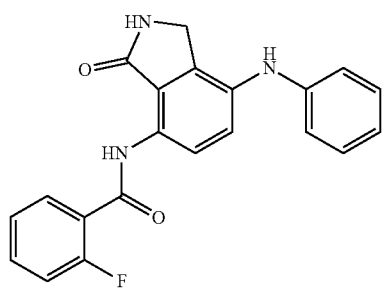 [SMILES: O=C(Nc1ccc(Nc2ccccc2)c2c1C(=O)NC2)c1ccccc1F]

$^1$H NMR (400 MHz, DMSO-d$_6$) δ 11.21 (d, J=6.8 Hz, 1H), 8.83 (s, 1H), 8.44 (d, J=8.7 Hz, 1H), 8.00-7.89 (m, 2H), 7.69-7.62 (m, 1H), 7.47-7.35 (m, 3H), 7.26 (t, J=7.7 Hz, 1H), 7.03 (d, J=7.8 Hz, 1H), 6.86 (t, J=7.2 Hz, 1H), 4.31 (s, 2H); MS (ESI) m/z 362 (M+H)$^+$.

Example 421: 3-Fluoro-N-(3-oxo-7-(phenylamino)isoindolin-4-yl)benzamide

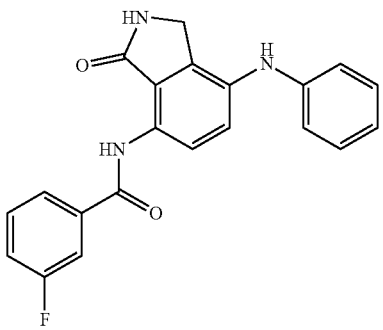 [SMILES: O=C(Nc1ccc(Nc2ccccc2)c2c1C(=O)NC2)c1cccc(F)c1]

$^1$H NMR (400 MHz, DMSO-d$_6$) δ 11.38 (s, 1H), 8.95 (s, 1H), 8.34 (d, J=8.7 Hz, 1H), 7.93 (s, 1H), 7.78 (d, J=7.9 Hz, 1H), 7.79-7.66 (m, 2H), 7.53-7.50 (m, 1H), 7.42 (d, J=8.7 Hz, 1H), 7.26 (t, J=7.9 Hz, 2H), 7.02 (d, J=7.6 Hz, 2H), 6.86 (t, J=7.3 Hz, 1H), 4.32 (s, 2H); MS (ESI) m/z 362 (M+H)$^+$.

Example 422: N-(7-((2,3-dimethoxyphenyl)amino)-3-oxoisoindolin-4-yl)-4-fluorobenzamide

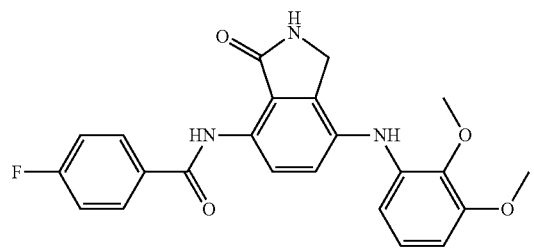 [SMILES: COc1cccc(Nc2ccc(NC(=O)c3ccc(F)cc3)c3c2CNC3=O)c1OC]

$^1$H NMR (400 MHz, DMSO-d$_6$) δ 11.37 (s, 1H), 8.93 (s, 1H), 8.35 (d, J=8.6 Hz, 1H), 8.00 (dd, J=8.8, 5.3 Hz, 2H), 7.45 (t, J=8.8 Hz, 2H), 7.37 (s, 1H), 7.28 (d, J=8.7 Hz, 1H), 6.90 (t, J=8.2 Hz, 1H), 6.58 (d, J=8.4 Hz, 1H), 6.51 (d, J=8.2 Hz, 1H), 4.31 (s, 2H), 3.80 (s, 3H), 3.69 (s, 3H); [M+H]$^+$: 422.

Example 423: N-(7-((3,5-bis(trifluoromethyl)phenyl)amino)-3-oxoisoindolin-4-yl)-4-fluorobenzamide

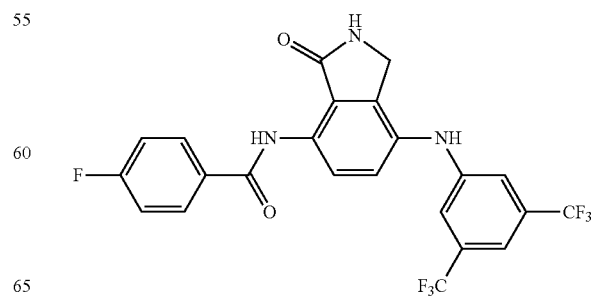

¹H NMR (400 MHz, DMSO-d₆) δ 11.42 (s, 1H), 9.04 (s, 1H), 8.76 (s, 1H), 8.46 (d, J=8.6 Hz, 1H), 8.01 (d, J=5.4 Hz, 2H), 7.58 (d, J=7.4 Hz, 1H), 7.47-7.37 (m, 5H), 4.34 (s, 2H); [M+H]⁺: 498.

Example 424: N-(7-((2,3-dimethylphenyl)amino)-3-oxoisoindolin-4-yl)-4-fluorobenzamide

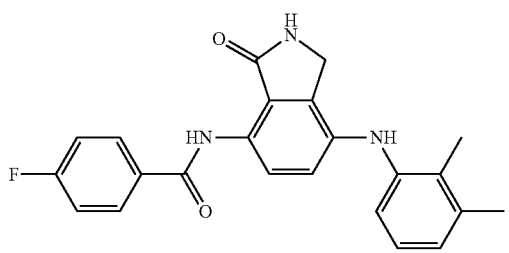 [SMILES: Cc1cccc(Nc2ccc(NC(=O)c3ccc(F)cc3)c3c2CNC3=O)c1C]

¹H NMR (400 MHz, DMSO-d₆) δ 11.30 (s, 1H), 8.90 (s, 1H), 8.25 (d, J=8.7 Hz, 1H), 7.98 (dd, J=8.8, 5.4 Hz, 2H), 7.44 (t, J=8.9 Hz, 3H), 7.36 (s, 1H), 6.91 (d, J=7.5 Hz, 1H), 6.84 (d, J=7.8 Hz, 1H), 6.77 (d, J=8.7 Hz, 1H), 4.21 (s, 2H), 2.27 (s, 3H), 2.08 (s, 3H); [M+H]⁺: 390.

Example 425: 4-Fluoro-N-(7-((2-methoxyphenyl)amino)-3-oxoisoindolin-4-yl)benzamide

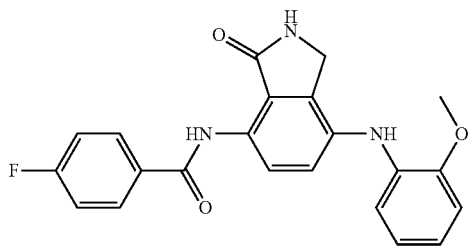 [SMILES: COc1ccccc1Nc1ccc(NC(=O)c2ccc(F)cc2)c2c1CNC2=O]

¹H NMR (400 MHz, DMSO-d₆) δ 11.35 (s, 1H), 8.93 (s, 1H), 8.31 (d, J=8.7 Hz, 1H), 8.0 (dd, J=8.8, 5.4 Hz, 2H), 7.45 (t, J=8.8 Hz, 2H), 7.24 (s, 1H), 7.15 (d, J=8.7 Hz, 1H), 7.02 (d, J=6.8 Hz, 1H), 6.95-6.83 (m, 3H), 4.30 (s, 2H), 3.81 (s, 3H); [M+H]⁺: 392.

Example 426: 4-Fluoro-N-(3-oxo-7-(o-tolylamino)isoindolin-4-yl)benzamide

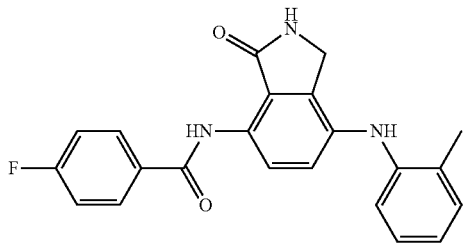 [SMILES: Cc1ccccc1Nc1ccc(NC(=O)c2ccc(F)cc2)c2c1CNC2=O]

¹H NMR (400 MHz, DMSO-d₆) δ 11.34 (s, 1H), 8.92 (s, 1H), 8.30 (d, J=8.7 Hz, 1H), 7.99 (dd, J=8.8, 5.4 Hz, 2H), 7.45 (t, J=8.8 Hz, 3H), 7.30 (s, 1H), 7.21 (d, J=7.1 Hz, 1H), 7.12 (t, J=7.5 Hz, 1H), 6.94 (t, J=8.4 Hz, 3H), 4.21 (s, 2H), 2.20 (s, 3H); [M+H]⁺: 376.

Example 427: 4-Fluoro-N-(3-oxo-7-(pyridin-3-ylamino)isoindolin-4-yl) benzamide

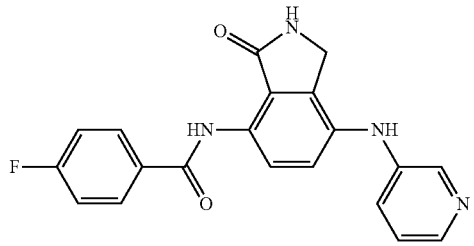 [SMILES: O=C(Nc1ccc(Nc2cccnc2)c2c1C(=O)NC2)c1ccc(F)cc1]

¹H NMR (400 MHz, DMSO-d₆) δ 11.37 (s, 1H), 8.98 (s, 1H), 8.38 (d, J=8.6 Hz, 1H), 8.32 (d, J=2.7 Hz, 1H), 8.13 (s, 1H), 8.05 (dd, J=4.6, 1.3 Hz, 1H), 8.02-7.99 (m, 2H), 7.48-7.43 (m, 3H), 7.38-7.35 (m, 1H), 7.26-7.23 (m, 1H), 4.33 (s, 2H); [M+H]⁺: 363.

Example 428: 4-Fluoro-N-(3-oxo-7-(pyridin-2-ylamino)isoindolin-4-yl) benzamide

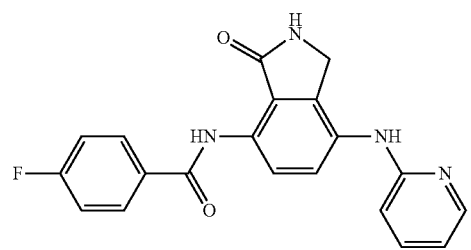 [SMILES: O=C(Nc1ccc(Nc2ccccn2)c2c1C(=O)NC2)c1ccc(F)cc1]

¹H NMR (400 MHz, DMSO-d₆) δ 11.42 (s, 1H), 8.95 (s, 1H), 8.67 (s, 1H), 8.38 (d, J=8.8 Hz, 1H), 8.13 (d, J=3.7 Hz, 1H), 8.06 (d, J=8.7 Hz, 1H), 8.01 (dd, J=8.8, 5.4 Hz, 3H), 7.61-7.57 (m, 1H), 7.45 (t, J=8.8 Hz, 2H), 6.89 (d, J=8.4 Hz, 1H), 6.76 (d, J=6.0 Hz, 1H), 4.40 (s, 2H); [M+H]⁺: 363.

Example 429: 4-Fluoro-N-(3-oxo-7-(pyrazin-2-ylamino)isoindolin-4-yl) benzamide

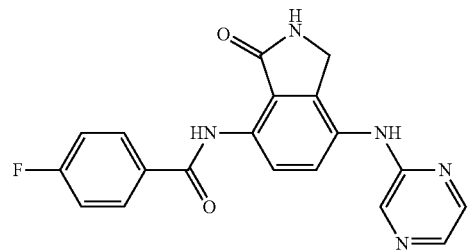 [SMILES: O=C(Nc1ccc(Nc2cnccn2)c2c1C(=O)NC2)c1ccc(F)cc1]

¹H NMR (400 MHz, DMSO-d₆) δ 11.44 (s, 1H), 9.12 (s, 1H), 9.00 (s, 1H), 8.41 (d, J=8.8 Hz, 1H), 8.30 (d, J=1.2 Hz, 1H), 8.12-8.11 (m, 1H), 8.06-8.00 (m, 4H), 7.95 (d, J=2.3 Hz, 1H), 7.46 (t, J=8.8 Hz, 3H), 4.42 (s, 2H); [M+H]⁺: 364.

Example 430: 4-Fluoro-N-(7-(1-methyl-1H-pyrazol-4-yl)amino)-3-oxoisoindolin-4-yl)benzamide

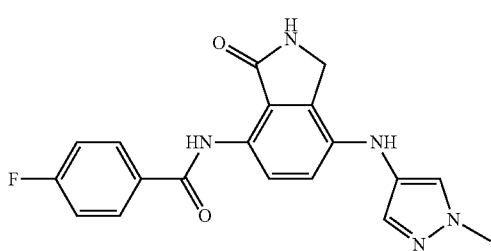 [SMILES: Cn1cc(Nc2ccc(NC(=O)c3ccc(F)cc3)c3c2CNC3=O)cn1]

¹H NMR (400 MHz, DMSO-d₆) δ 11.22 (s, 1H), 8.89 (s, 1H), 8.25 (d, J=8.7 Hz, 1H), 7.99-7.95 (m, 3H), 7.70 (s, 1H), 7.48-7.39 (m, 4H), 7.35 (d, J=6.0 Hz, 2H), 6.97 (d, J=8.7 Hz, 1H), 4.27 (s, 2H), 3.82 (s, 3H); [M+H]⁺: 366.

Example 431: N-(7-((3-methoxyphenyl)amino)-3-oxoisoindolin-4-yl) benzamide

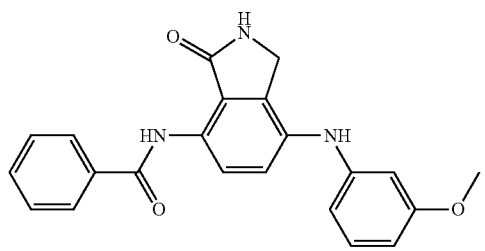 [SMILES: COc1cccc(Nc2ccc(NC(=O)c3ccccc3)c3c2CNC3=O)c1]

¹H NMR (400 MHz, DMSO-d₆) δ 11.38 (s, 1H), 8.92 (s, 1H), 8.39 (d, J=8.8 Hz, 1H), 7.94 (dd, J=8.0, 6.4 Hz, 3H), 7.65-7.58 (m, 3H), 7.45 (d, J=8.7 Hz, 1H), 7.14 (t, J=8.1 Hz, 1H), 6.54 (t, J=2.4 Hz, 1H), 6.43 (dd, J=8.3, 1.8 Hz, 1H), 4.32 (s, 2H), 3.71 (s, 3H); [M+H]⁺: 374.

Example 432: 2-Methoxy-N-(3-oxo-7-(phenylamino)isoindolin-4-yl) benzamide

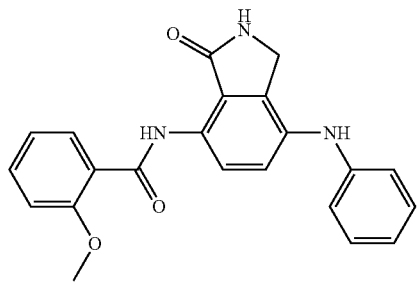 [SMILES: COc1ccccc1C(=O)Nc1ccc(Nc2ccccc2)c2c1C(=O)NC2]

¹H NMR (400 MHz, DMSO-d₆) δ 11.92 (s, 1H), 8.71 (s, 1H), 8.62 (d, J=8.9 Hz, 1H), 8.05 (dd, J=7.8, 1.7 Hz, 1H), 7.84 (s, 1H), 7.60-7.55 (m, 1H), 7.39 (d, J=8.8 Hz, 1H), 7.24 (t, J=7.8 Hz, 1H), 7.12 (t, J=7.5 Hz, 1H), 7.01 (d, J=7.6 Hz, 1H), 6.84 (t, J=7.3 Hz, 1H), 4.28 (s, 2H), 4.05 (s, 3H); [M+H]⁺: 374.

Example 433: 4-Methoxy-N-(3-oxo-7-(phenylamino)isoindolin-4-yl) benzamide

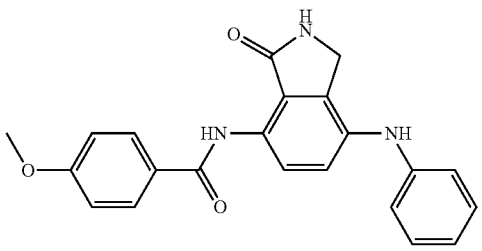 [SMILES: COc1ccc(C(=O)Nc2ccc(Nc3ccccc3)c3c2C(=O)NC3)cc1]

¹H NMR (400 MHz, DMSO-d₆) δ 11.29 (s, 1H), 8.91 (s, 1H), 8.37 (d, J=8.7 Hz, 1H), 7.92-7.88 (m, 3H), 7.40 (d, J=8.8 Hz, 1H), 7.24 (t, J=7.9 Hz, 2H), 7.13 (d, J=8.8 Hz, 2H), 7.00 (d, J=7.6 Hz, 2H), 6.84 (t, J=7.3 Hz, 1H), 4.31 (s, 2H), 3.85 (s, 3H); [M+H]⁺: 374.

Example 434: 3-Methoxy-N-(3-oxo-7-(phenylamino)isoindolin-4-yl) benzamide

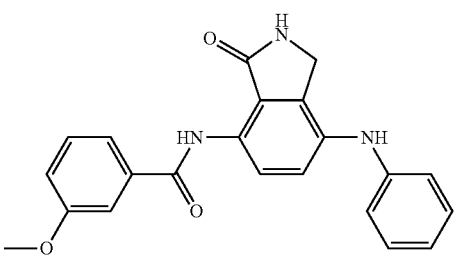 [SMILES: COc1cccc(C(=O)Nc2ccc(Nc3ccccc3)c3c2C(=O)NC3)c1]

¹H NMR (400 MHz, DMSO-d₆) δ 11.37 (s, 1H), 8.92 (s, 1H), 8.36 (d, J=8.7 Hz, 1H), 7.91 (s, 1H), 7.54-7.47 (m, 3H), 7.41 (d, J=8.7 Hz, 1H), 7.27-7.20 (m, 3H), 7.01 (d, J=7.6 Hz, 2H), 6.85 (t, J=7.3 Hz, 1H), 4.31 (s, 2H), 3.85 (s, 3H); [M+H]⁺: 374.

Example 435: 4-Acetamido-N-(3-oxo-7-(phenylamino)isoindolin-4-yl) benzamide

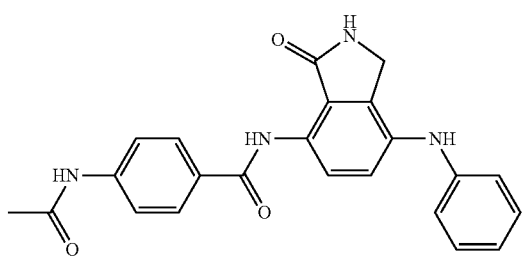 [SMILES: CC(=O)Nc1ccc(C(=O)Nc2ccc(Nc3ccccc3)c3c2C(=O)NC3)cc1]

¹H NMR (400 MHz, DMSO-d₆) δ 11.30 (s, 1H), 10.29 (s, 1H), 8.91 (s, 1H), 8.37 (d, J=8.9 Hz, 1H), 7.88 (d, J=8.1 Hz, 3H), 7.77 (d, J=8.8 Hz, 2H), 7.40 (d, J=9.0 Hz, 1H), 7.24 (d, J=7.9 Hz, 2H), 7.00 (d, J=7.6 Hz, 2H), 6.84 (t, J=7.2 Hz, 1H), 4.31 (s, 2H), 2.09 (s, 3H); [M+H]⁺: 401.

Example 436: N-(3-oxo-7-(m-tolylamino)isoindolin-4-yl)benzamide

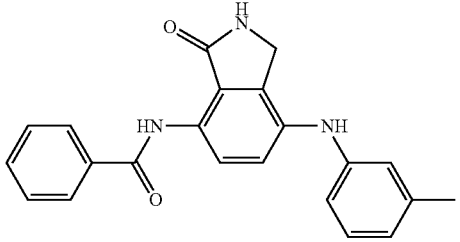 [SMILES: Cc1cccc(Nc2ccc(NC(=O)c3ccccc3)c3c2CNC3=O)c1]

$^1$H NMR (400 MHz, DMSO-d$_6$) δ 11.37 (s, 1H), 8.92 (s, 1H), 8.38 (d, J=8.6 Hz, 1H), 7.94 (d, J=8.3 Hz, 2H), 7.83 (s, 1H), 7.64-7.58 (m, 3H), 7.40 (d, J=8.7 Hz, 1H), 7.13 (t, J=7.6 Hz, 1H), 6.81 (d, J=11.4 Hz, 2H), 6.67 (d, J=8.0 Hz, 1H), 4.30 (s, 2H), 2.25 (s, 3H); [M+H]$^+$: 358.

Example 437: N-(7-(1H-pyrazol-3-yl)amino)-3-oxoisoindolin-4-yl)-4-fluorobenzamide

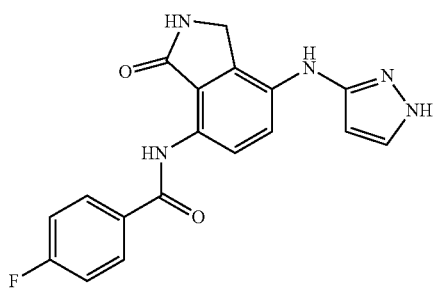 [SMILES: O=C(Nc1ccc(Nc2cc[nH]n2)c2c1C(=O)NC2)c1ccc(F)cc1]

$^1$H NMR (400 MHz, DMSO-d$_6$) δ 12.91 (s, 1H), 10.33 (s, 1H), 7.82 (dd, J=7.6, 1.6 Hz, 1H), 7.76 (d, J=7.4 Hz, 2H), 7.54 (t, J=8.4 Hz, 1H), 7.46 (t, J=7.0 Hz, 2H), 7.36 (d, J=7.2 Hz, 1H), 7.22 (d, J=8.3 Hz, 1H), 7.10 (t, J=7.5 Hz, 1H), 7.04 (br s, 1H), 3.97 (s, 2H); [M+H]$^+$: 352.

Example 438: N-(3-oxo-7-(phenylamino)isoindolin-4-yl)-4-((2-(pyrrolidin-1-yl)ethyl)amino)benzamide Scheme 26. Preparation of compound of Example 438

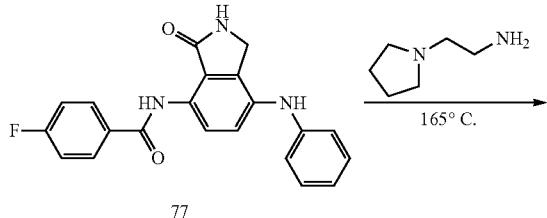

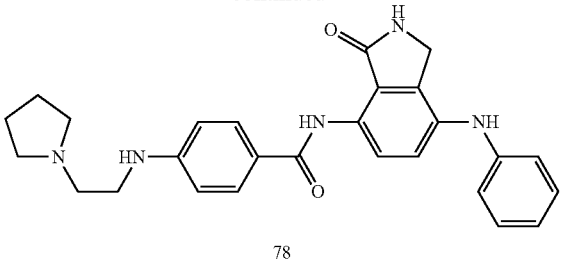

A mixture of the intermediate 77 (0.1 g. 0.27 mmol, 1.0 eq.) and 1-(2-aminoethyl)pyrrolidine (0.14 g, 1.1 mmol, 4.0 eq.) was placed in a sealed tube and stirred at 160° C. for 15 hours. The resulting mixture was cooled to room temperature and diluted in DCM (1 mL) The diluted solution was added into hexane (5 mL) with vigorous stirring. The mixture thus obtained was filtered to give the precipitate 78 (0.12 g, 0.26 mmol, 96%) as a yellow solid.

$^1$H NMR (400 MHz, DMSO-d$_6$) δ 11.13 (s, 1H), 8.87 (s, 1H), 8.38 (d, J=8.8 Hz, 1H), 7.85 (s, 1H), 7.69 (d, J=8.8 Hz, 2H), 7.38 (d, J=8.8 Hz, 1H), 7.23 (d, J=7.8 Hz, 2H), 6.97 (d, J=8.8 Hz, 2H), 6.82 (t, J=7.2 Hz, 1H), 6.69 (d, J=8.8 Hz, 2H), 6.35 (t, J=5.2 Hz, 1H), 4.29 (s, 2H), 3.21 (q, J=6.4 Hz, 2H), 2.62 (t, J=6.8 Hz, 2H), 2.50-2.48 (m, 6H), 1.72-1.68 (m, 4H). [M+H]$^+$: 456.

The following compounds of Examples 439 to 492 were obtained by using corresponding starting materials and repeating the procedure of Example 438.

Example 439: N-(3-oxo-7-(phenylamino)isoindolin-4-yl)-4-((2-(piperidin-1-yl)ethyl)amino)benzamide

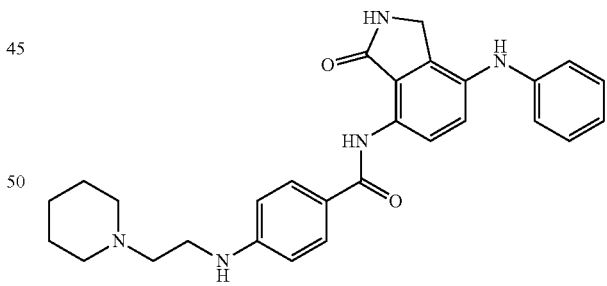

$^1$H NMR (400 MHz, DMSO-d$_6$) δ 11.13 (s, 1H), 8.87 (s, 1H), 8.38 (d, J=8.7 Hz, 1H), 7.85 (s, 1H), 7.69 (d, J=8.3 Hz, 2H), 7.38 (d, J=8.7 Hz, 1H), 7.23 (t, J=7.9 Hz, 2H), 6.97 (d, J=7.7 Hz, 2H), 6.82 (t, J=7.3 Hz, 1H), 6.69 (d, J=8.8 Hz, 2H), 6.27 (t, J=5.3 Hz, 1H), 4.29 (s, 2H), 3.20 (q, J=6.3 Hz, 2H), 2.45-2.33 (m, 6H), 1.58-1.44 (m, 4H), 1.41-1.30 (m, 2H); MS (ESI) m/z 470 (M+H)$^+$.

Example 440: N-(3-oxo-7-(phenylamino)isoindolin-4-yl)-4-((2-(piperidin-1-yl)ethyl)amino)benzamide hydrochloride

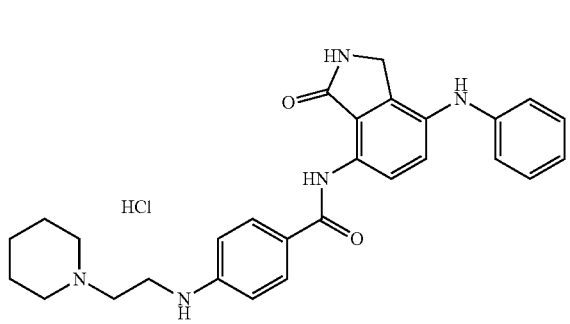 [SMILES: O=C(Nc1ccc(Nc2ccccc2)c2c1C(=O)NC2)c1ccc(NCCN2CCCCC2)cc1 ; Cl]

¹H NMR (400 MHz, DMSO-d₆) δ 11.16 (s, 1H), 9.98 (br s, 1H), 8.88 (s, 1H), 8.36 (d, J=8.8 Hz, 1H), 7.73 (d, J=8.8 Hz, 2H), 7.38 (d, J=8.8 Hz, 1H), 7.22 (t, J=8.0 Hz, 2H), 6.97 (d, J=7.6 Hz, 2H), 6.81 (t, J=7.2 Hz, 1H), 6.76 (d, J=8.4 Hz, 2H), 4.95 (br s, 1H), 4.29 (s, 2H), 3.55 (t, J=6.4 Hz, 2H), 3.50-3.47 (m, 2H), 3.22-3.18 (m, 2H), 2.93-2.90 (m, 2H), 1.78-1.68 (m, 5H), 1.38-1.34 (m, 1H); MS (ESI) m/z 470 (M+H)⁺.

Example 441: 4-((2-(Dimethylamino)ethyl)amino)-N-(3-oxo-7-phenylamino) isoindolin-4-yl)benzamide

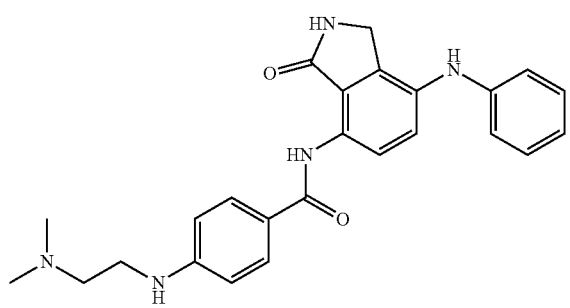 [SMILES: COCCNc1ccc(C(=O)Nc2ccc(Nc3ccccc3)c3c2C(=O)NC3)cc1]

¹H NMR (400 MHz, DMSO-d₆) δ 11.18 (s, 1H), 8.88 (s, 1H), 8.39 (d, J=8.7 Hz, 1H), 7.85 (s, 1H), 7.77 (d, J=8.3 Hz, 2H), 7.39 (d, J=8.8 Hz, 1H), 7.24 (t, J=7.9 Hz, 2H), 6.98 (d, J=7.8 Hz, 2H), 6.86-6.78 (m, 3H), 4.29 (s, 2H), 3.52-3.44 (m, 2H), 3.01 (s, 3H), 2.68-2.59 (m, 2H), 2.30 (s, 3H); MS (ESI) m/z 430 (M+H)⁺.

Example 442: 4-((2-Morpholinoethyl)amino)-N-(3-oxo-7-(phenylamino) isoindolin-4-yl)benzamide

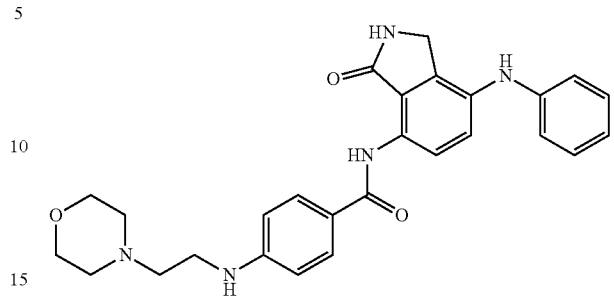

¹H NMR (400 MHz, DMSO-d₆) δ 11.12 (s, 1H), 8.86 (s, 1H), 8.37 (d, J=8.8 Hz, 1H), 7.84 (s, 1H), 7.68 (d, J=8.8 Hz, 2H), 7.37 (d, J=8.8 Hz, 1H), 7.22 (t, J=7.9 Hz, 2H), 6.96 (d, J=7.7 Hz, 2H), 6.80 (t, J=7.3 Hz, 1H), 6.69 (d, J=8.8 Hz, 2H), 6.30 (t, J=5.3 Hz, 1H), 4.28 (s, 2H), 3.62-3.53 (m, 5H), 3.25-3.15 (m, 2H), 2.51-2.40 (m, 5H); MS (ESI) m/z 472 (M+H)⁺.

Example 443: 4-((2-(4-Methylpiperazin-1-yl)ethyl)amino)-N-(3-oxo-7-(phenylamino)isoindolin-4-yl)benzamide

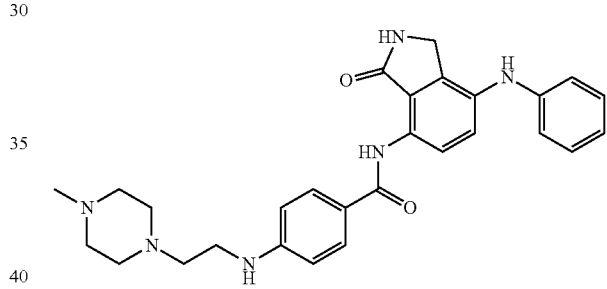

¹H NMR (400 MHz, DMSO-d₆) δ 11.13 (s, 1H), 8.86 (s, 1H), 8.37 (d, J=8.7 Hz, 1H), 7.84 (s, 1H), 7.68 (d, J=8.7 Hz, 2H), 7.38 (d, J=8.7 Hz, 1H), 7.24 (t, J=7.9 Hz, 2H), 6.96 (d, J=7.7 Hz, 2H), 6.82 (t, J=7.3 Hz, 1H), 6.68 (d, J=8.8 Hz, 2H), 6.27 (t, J=5.2 Hz, 1H), 4.28 (s, 2H), 3.25-3.13 (m, 4H), 2.69-2.59 (m, 2H), 2.37-2.17 (m, 6H), 2.13 (s, 3H); MS (ESI) m/z 470 (M+H)⁺.

Example 444: 4-((2-Methoxyethyl)amino)-N-(3-oxo-7-(phenylamino) isoindolin-4-yl)benzamide

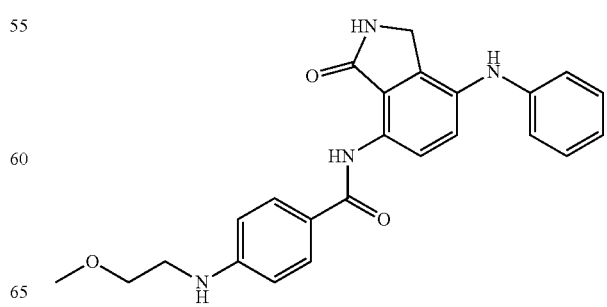

¹H NMR (400 MHz, DMSO-d₆) δ 11.12 (s, 1H), 8.88 (s, 1H), 8.36 (d, J=8.8 Hz, 1H), 7.85 (s, 1H), 7.67 (d, J=8.7 Hz, 2H), 7.36 (d, J=8.7 Hz, 1H), 7.22 (t, J=7.9 Hz, 2H), 6.96 (d, J=7.7 Hz, 2H), 6.81 (t, J=7.3 Hz, 1H), 6.68 (d, J=8.8 Hz, 2H), 6.48 (t, J=5.5 Hz, 1H), 4.28 (s, 2H), 3.49 (t, J=5.5 Hz, 2H), 3.31-3.22 (m, 5H); MS (ESI) m/z 417 (M+H)⁺.

Example 445: N-(7-((3-methoxyphenyl)amino)-3-oxoisoindolin-4-yl)-4-((2-(pyrrolidin-1-yl)ethyl)amino)benzamide

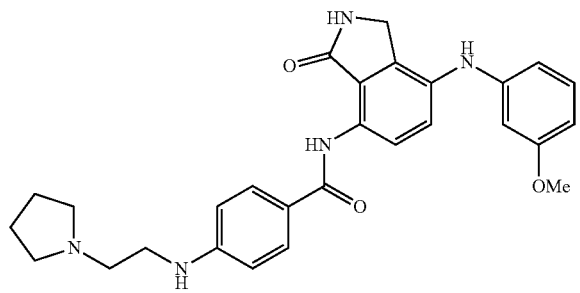 [SMILES: COc1cccc(Nc2ccc(NC(=O)c3ccc(NCCN4CCCC4)cc3)c3c2CNC3=O)c1]

¹H NMR (400 MHz, DMSO-d₆) δ 11.12 (s, 1H), 8.87 (s, 1H), 8.38 (d, J=8.7 Hz, 1H), 7.85 (s, 1H), 7.68 (d, J=8.6 Hz, 2H), 7.39 (d, J=8.7 Hz, 1H), 7.11 (t, J=7.9 Hz, 1H), 6.68 (d, J=8.7 Hz, 3H), 6.53 (d, J=8.1 Hz, 1H), 6.49 (s, 1H), 6.41-6.31 (m, 2H), 4.29 (s, 2H), 3.34 (s, 3H), 3.25-3.14 (m, 3H), 2.63-2.55 (m, 3H), 1.19-1.10 (m, 6H); MS (ESI) m/z 486 (M+H)⁺.

Example 446: N-(7-((3-methoxyphenyl)amino)-3-oxoisoindolin-4-yl)-4-((2-(piperidin-1-yl)ethyl)amino)benzamide

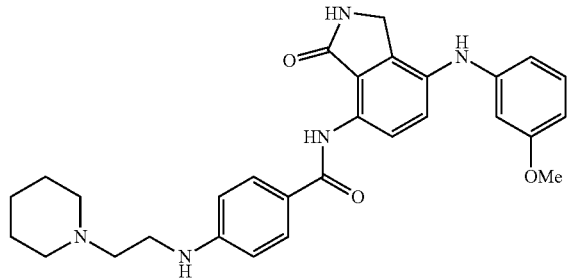 [SMILES: COc1cccc(Nc2ccc(NC(=O)c3ccc(NCCN4CCCCC4)cc3)c3c2CNC3=O)c1]

¹H NMR (400 MHz, DMSO-d₆) δ 11.12 (s, 1H), 8.87 (s, 1H), 8.37 (d, J=8.7 Hz, 1H), 7.86 (s, 1H), 7.68 (d, J=8.7 Hz, 3H), 7.39 (d, J=8.7 Hz, 1H), 7.11 (t, J=7.9 Hz, 1H), 6.68 (d, J=8.7 Hz, 3H), 6.53 (d, J=8.1 Hz, 1H), 6.49 (d, J=2.1 Hz, 1H), 6.41-6.35 (m, 1H), 6.31-6.23 (m, 1H), 4.29 (s, 2H), 3.69 (s, 3H), 3.23-3.14 (m, 3H), 2.41-2.29 (m, 3H), 1.53-1.43 (m, 6H), 1.39-1.25 (m, 3H); MS (ESI) m/z 500 (M+H)⁺.

Example 447: N-(7-((3-methoxyphenyl)amino)-3-oxoisoindolin-4-yl)-4-((3-(pyrrolidin-1-yl)propyl)amino)benzamide

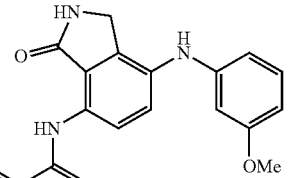

¹H NMR (400 MHz, DMSO-d₆) δ 11.12 (s, 1H), 8.87 (s, 1H), 8.37 (d, J=8.7 Hz, 1H), 7.85 (s, 1H), 7.68 (d, J=8.7 Hz, 2H), 7.39 (d, J=8.7 Hz, 1H), 7.11 (t, J=7.9 Hz, 1H), 6.64 (d, J=8.7 Hz, 3H), 6.53 (d, J=8.1 Hz, 1H), 6.48 (d, J=6.0 Hz, 2H), 6.41-6.31 (m, 1H), 4.28 (s, 2H), 3.71 (s, 3H), 3.15-3.07 (m, 2H), 2.43-2.31 (m, 4H), 1.75-1.59 (m, 8H); MS (ESI) m/z 500 (M+H)⁺.

Example 448: N-(7-(3-methoxyphenyl)amino)-3-oxoisoindolin-4-yl)-4-((3-(piperidin-1-yl)propyl)amino)benzamide

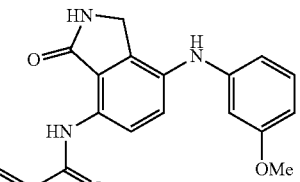

¹H NMR (400 MHz, DMSO-d₆) δ 11.12 (s, 1H), 8.87 (s, 1H), 8.37 (d, J=8.7 Hz, 1H), 7.85 (s, 1H), 7.68 (d, J=8.7 Hz, 3H), 7.40 (d, J=8.8 Hz, 1H), 7.11 (t, J=8.1 Hz, 1H), 6.68 (d, J=8.7 Hz, 3H), 6.64 (d, J=8.8 Hz, 1H), 6.57-6.43 (m, 3H), 6.39 (dd, J=8.1, 2.1 Hz, 1H), 4.29 (s, 2H), 3.69 (s, 3H), 3.15-3.04 (m, 3H), 2.38-2.20 (m, 4H), 1.53-1.43 (m, 6H), 1.39-1.25 (m, 3H); MS (ESI) m/z 514 (M+H)⁺.

Example 449: N-(3-oxo-7-(m-tolylamino)isoindolin-4-yl)-4-((2-(pyrrolidin-1-yl)ethyl)amino)benzamide

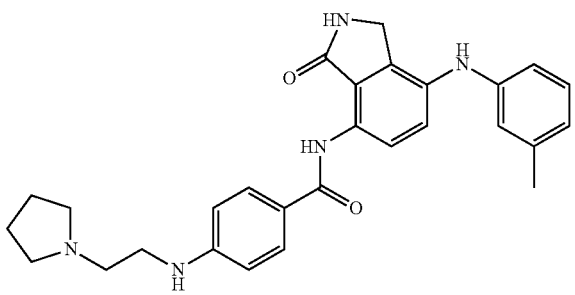 [SMILES: Cc1cccc(Nc2ccc(NC(=O)c3ccc(NCCN4CCCC4)cc3)c3c2CNC3=O)c1]

¹H NMR (400 MHz, DMSO-d₆) δ 11.12 (s, 1H), 8.86 (s, 1H), 8.36 (d, J=8.7 Hz, 1H), 7.77 (s, 1H), 7.67 (d, J=8.6 Hz, 2H), 7.35 (d, J=8.7 Hz, 1H), 7.09 (t, J=7.9 Hz, 1H), 6.75 (d, J=8.7 Hz, 2H), 6.67 (d, J=8.1 Hz, 2H), 6.63 (d, J=7.4 Hz, 1H), 6.35 (t, J=5.3 Hz, 1H), 4.26 (s, 2H), 3.35-3.14 (m, 2H), 2.60 (t, J=6.7 Hz, 2H), 2.22 (s, 3H), 1.71-1.66 (m, 6H); MS (ESI) m/z 470 (M+H)⁺.

Example 450: N-(3-oxo-7-(m-tolylamino)isoindolin-4-yl)-4-((2-(piperidin-1-yl)ethyl)amino)benzamide

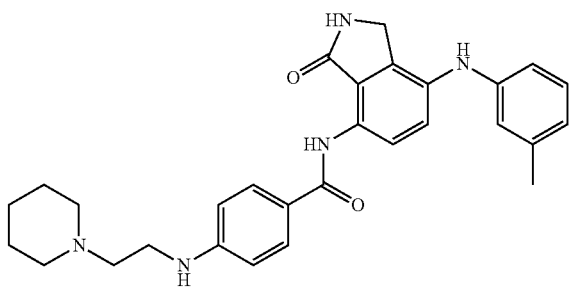 [SMILES: Cc1cccc(Nc2ccc(NC(=O)c3ccc(NCCN4CCCCC4)cc3)c3c2CNC3=O)c1]

¹H NMR (400 MHz, DMSO-d₆) δ 11.12 (s, 1H), 8.86 (s, 1H), 8.36 (d, J=8.7 Hz, 1H), 7.77 (s, 1H), 7.67 (d, J=8.6 Hz, 2H), 7.35 (d, J=8.7 Hz, 1H), 7.09 (t, J=7.9 Hz, 1H), 6.75 (d, J=8.7 Hz, 2H), 6.67 (d, J=8.1 Hz, 2H), 6.62 (d, J=7.4 Hz, 1H), 6.26 (t, J=5.3 Hz, 1H), 4.27 (s, 2H), 3.22-3.14 (m, 2H), 2.51-2.21 (m, 2H), 2.21 (s, 3H), 1.71-1.66 (m, 8H); MS (ESI) m/z 484 (M+H)⁺.

Example 451: N-(3-oxo-7-(m-tolylamino)isoindolin-4-yl)-4-((3-(pyrrolidin-1-yl)propyl)amino)benzamide

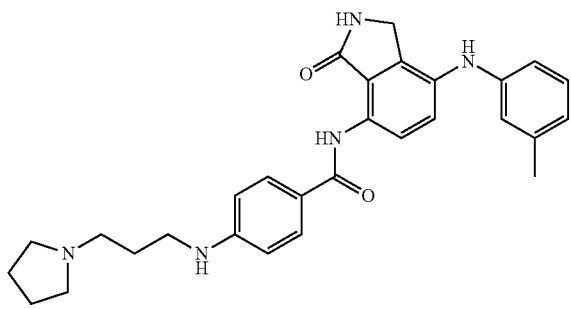 [SMILES: Cc1cccc(Nc2ccc(NC(=O)c3ccc(NCCCN4CCCC4)cc3)c3c2CNC3=O)c1]

¹H NMR (400 MHz, DMSO-d₆) δ 11.11 (s, 1H), 8.86 (s, 1H), 8.36 (d, J=8.7 Hz, 1H), 7.76 (s, 1H), 7.67 (d, J=8.6 Hz, 2H), 7.35 (d, J=8.7 Hz, 1H), 7.09 (t, J=7.9 Hz, 1H), 6.79-6.71 (m, 2H), 6.67-6.59 (m, 4H), 6.48 (t, J=5.3 Hz, 1H), 4.26 (s, 2H), 3.15-3.07 (m, 2H), 2.45-2.37 (m, 2H), 2.22 (s, 3H), 1.79-1.61 (m, 8H); MS (ESI) m/z 484 (M+H)⁺.

Example 452: N-(3-oxo-7-(m-tolylamino)isoindolin-4-yl)-4-((3-(piperidin-1-yl)propyl)amino)benzamide

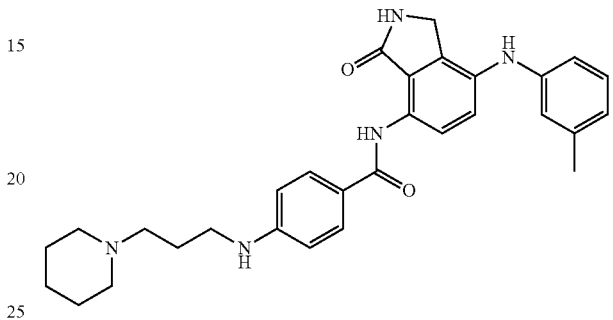

¹H NMR (400 MHz, DMSO-d₆) δ 11.12 (s, 1H), 8.86 (s, 1H), 8.36 (d, J=8.7 Hz, 1H), 7.77 (s, 1H), 7.67 (d, J=8.6 Hz, 2H), 7.35 (d, J=8.7 Hz, 1H), 7.09 (t, J=7.9 Hz, 1H), 6.75 (d, J=8.7 Hz, 2H), 6.67 (d, J=8.1 Hz, 2H), 6.62 (d, J=7.4 Hz, 1H), 6.51 (t, J=5.3 Hz, 1H), 4.26 (s, 2H), 3.15-3.07 (m, 2H), 2.31-2.21 (m, 4H), 2.21 (s, 3H), 1.73-1.66 (m, 2H), 1.53-1.36 (m, 8H); MS (ESI) m/z 498 (M+H)⁺.

Example 453: N-(7-((2-chlorophenyl)amino)-3-oxoisoindolin-4-yl)-4-((2-(pyrrolidin-1-yl)ethyl)amino)benzamide

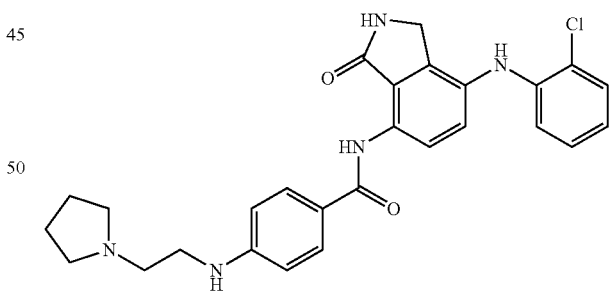

¹H NMR (400 MHz, DMSO-d₆) δ 11.19 (s, 1H), 8.86 (s, 1H), 8.41 (d, J=8.6 Hz, 1H), 7.69 (d, J=8.5 Hz, 2H), 7.47 (s, 1H), 7.39 (d, J=7.7 Hz, 1H), 7.24 (d, J=8.7 Hz, 1H), 7.19-7.13 (m, 1H), 6.87-6.80 (m, 2H), 6.69 (d, J=8.4 Hz, 3H), 6.39-6.31 (m, 1H), 4.22 (s, 2H), 3.25-3.15 (m, 3H), 2.68-2.59 (m, 3H), 1.77-1.61 (m, 5H); MS (ESI) m/z 490 (M+H)⁺.

Example 454: N-(7-((2-chlorophenyl)amino)-3-ox-oisoindolin-4-yl)-4-((2-(piperidin-1-yl)ethyl)amino)benzamide

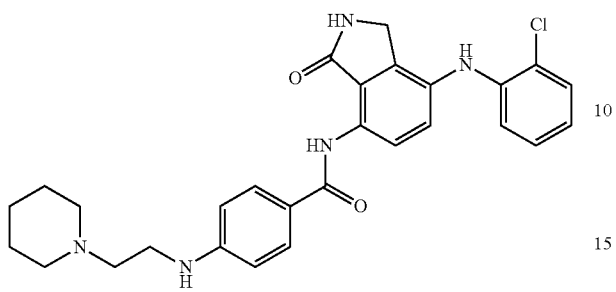

¹H NMR (400 MHz, DMSO-d₆) δ 11.19 (s, 1H), 8.85 (s, 1H), 8.40 (d, J=8.6 Hz, 1H), 7.69 (d, J=8.5 Hz, 2H), 7.47 (s, 1H), 7.39 (d, J=7.7 Hz, 1H), 7.24 (d, J=8.7 Hz, 1H), 7.15 (t, J=7.4 Hz, 1H), 6.87-6.80 (m, 2H), 6.68 (d, J=8.7 Hz, 3H), 6.27 (t, J=5.3 Hz, 1H), 4.22 (s, 2H), 3.22-3.14 (m, 2H), 2.51-2.21 (m, 4H), 1.71-1.66 (m, 8H); MS (ESI) m/z 504 (M+H)⁺.

Example 455: N-(7-((3-chlorophenyl)amino)-3-ox-oisoindolin-4-yl)-4-((2-(pyrrolidin-1-yl)ethyl)amino)benzamide

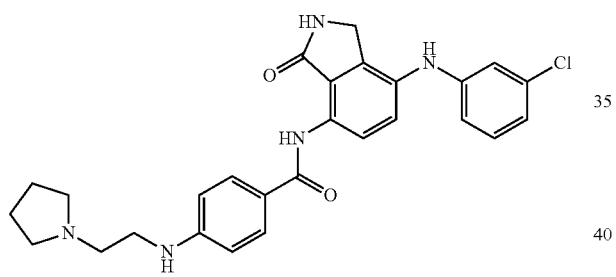

¹H NMR (400 MHz, DMSO-d₆) δ 11.19 (s, 1H), 8.86 (s, 1H), 8.41 (d, J=8.6 Hz, 1H), 8.10 (s, 1H), 7.69 (d, J=8.5 Hz, 3H), 7.47 (s, 1H), 7.40 (d, J=7.7 Hz, 2H), 7.21 (t, J=8.0 Hz, 1H), 6.91-6.75 (m, 3H), 6.38 (t, J=5.2 Hz, 1H), 4.27 (s, 2H), 3.25-3.17 (m, 3H), 2.69-2.59 (m, 3H), 1.77-1.62 (m, 5H); MS (ESI) m/z 490 (M+H)⁺.

Example 456: N-(7-((3-chlorophenyl)amino)-3-ox-oisoindolin-4-yl)-4-((2-(piperidin-1-yl)ethyl)amino)benzamide

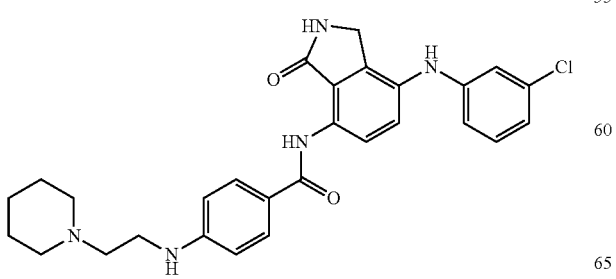

¹H NMR (400 MHz, DMSO-d₆) δ 11.16 (s, 1H), 8.90 (s, 1H), 8.40 (d, J=8.6 Hz, 1H), 8.10 (s, 1H), 7.69 (d, J=8.5 Hz, 2H), 7.41 (d, J=7.7 Hz, 1H), 7.20 (t, J=8.0 Hz, 1H), 6.90-6.71 (m, 3H), 6.68 (d, J=8.3 Hz, 2H), 6.29 (t, J=5.3 Hz, 1H), 4.27 (s, 2H), 3.22-3.14 (m, 2H), 2.51-2.21 (m, 4H), 1.71-1.66 (m, 8H); MS (ESI) m/z 504 (M+H)⁺.

Example 457: N-(7-((3-chlorophenyl)amino)-3-ox-oisoindolin-4-yl)-4-((3-(pyrrolidin-1-yl)propyl)amino)benzamide

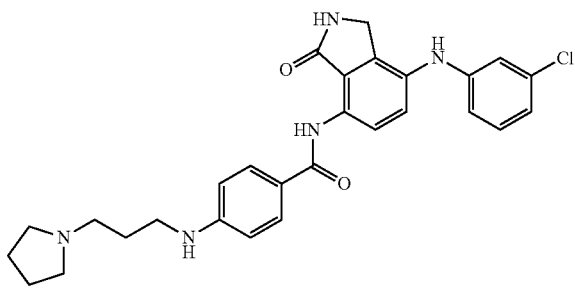 [SMILES: O=C(Nc1ccc(Nc2cccc(Cl)c2)c2c1C(=O)NC2)c1ccc(NCCCN2CCCC2)cc1]

¹H NMR (400 MHz, DMSO-d₆) δ 11.15 (s, 1H), 8.88 (s, 1H), 8.41 (d, J=8.6 Hz, 1H), 8.08 (s, 1H), 7.69 (d, J=8.5 Hz, 2H), 7.40 (d, J=8.6 Hz, 1H), 7.19 (t, J=8.0 Hz, 1H), 6.91-6.74 (m, 3H), 6.65 (d, J=7.2 Hz, 3H), 6.49-6.43 (m, 1H), 4.27 (s, 2H), 3.25-3.17 (m, 3H), 2.69-2.59 (m, 3H), 1.77-1.62 (m, 7H); MS (ESI) m/z 504 (M+H)⁺.

Example 458: N-(7-((3-chlorophenyl)amino)-3-ox-oisoindolin-4-yl)-4-((3-(piperidin-1-yl)propyl)amino)benzamide

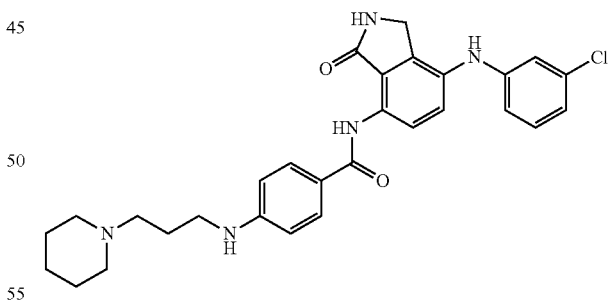

¹H NMR (400 MHz, DMSO-d₆) δ 11.15 (s, 1H), 8.88 (s, 1H), 8.40 (d, J=8.6 Hz, 1H), 8.10 (s, 1H), 7.67 (d, J=8.5 Hz, 2H), 7.41 (d, J=8.6 Hz, 1H), 7.19 (t, J=8.0 Hz, 1H), 6.93-6.77 (m, 4H), 6.66 (d, J=7.2 Hz, 3H), 6.50-6.41 (m, 1H), 4.27 (s, 2H), 3.25-3.12 (m, 2H), 2.55-2.24 (m, 4H), 1.81-1.66 (m, 8H); MS (ESI) m/z 518 (M+H)⁺.

Example 459: N-(3-oxo-7-(phenylamino)isoindolin-4-yl)-4-((3-(2-oxopyrrolidin-1-yl)propyl)amino)benzamide

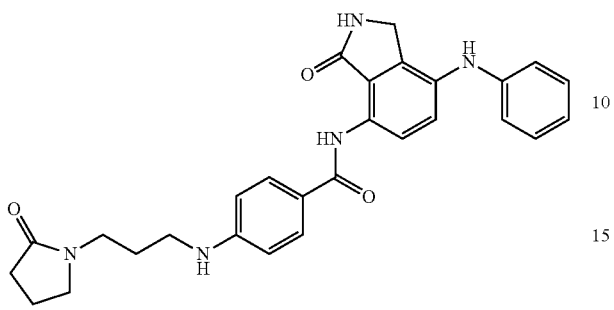

¹H NMR (400 MHz, DMSO-d₆) δ 11.12 (s, 1H), 8.87 (s, 1H), 8.37 (d, J=8.7 Hz, 1H), 7.84 (s, 1H), 7.69 (d, J=8.7 Hz, 2H), 7.37 (d, J=8.7 Hz, 1H), 7.22 (t, J=7.7 Hz, 2H), 6.95 (d, J=7.6 Hz, 3H), 6.80 (t, J=7.3 Hz, 1H), 6.55 (d, J=8.7 Hz, 2H), 6.43 (t, J=5.4 Hz, 1H), 4.28 (s, 2H), 3.31-3.05 (m, 3H), 2.15-2.07 (m, 3H), 1.94-1.73 (m, 6H); MS (ESI) m/z 484 (M+H)⁺.

Example 460: 4-((3-(Dimethylamino)propyl)amino)-N-(3-oxo-7-(phenylamino)isoindolin-4-yl)benzamide

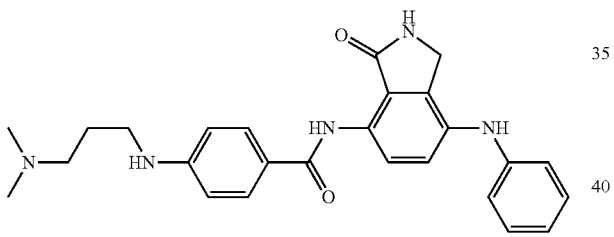

¹H NMR (400 MHz, DMSO-d₆) δ 11.13 (s, 1H), 8.87 (s, 1H), 8.38 (d, J=8.6 Hz, 1H), 7.84 (s, 1H), 7.69 (d, J=8.7 Hz, 2H), 7.38 (d, J=8.7 Hz, 1H), 7.23 (t, J=7.8 Hz, 2H), 6.97 (d, J=7.7 Hz, 2H), 6.82 (t, J=7.4 Hz, 1H), 6.66 (d, J=8.8 Hz, 2H), 6.46 (t, J=8.4 Hz, 1H), 4.29 (s, 2H), 3.11 (q, J=6.5 Hz, 2H), 2.29 (t, J=6.9 Hz, 2H), 2.14 (s, 6H), 1.68 (quint, J=6.9 Hz, 2H); [M+H]⁺: 444.

Example 461: 4-((3-Morpholinopropyl)amino)-N-(3-oxo-7-(phenylamino) isoindolin-4-yl)benzamide

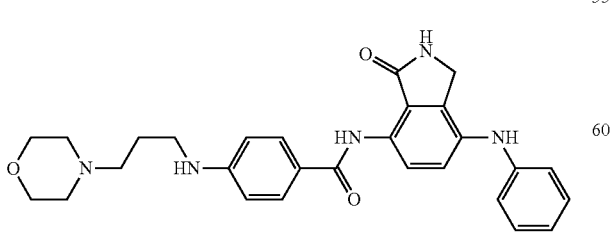

¹H NMR (400 MHz, DMSO-d₆) δ 11.13 (s, 1H), 8.87 (s, 1H), 8.38 (d, J=8.7 Hz, 1H), 7.85 (s, 1H), 7.69 (d, J=8.8 Hz, 2H), 7.38 (d, J=8.8 Hz, 1H), 7.23 (t, J=7.8 Hz, 2H), 6.97 (d, J=7.8 Hz, 2H), 6.82 (t, J=7.3 Hz, 1H), 6.66 (d, J=8.8 Hz, 3H), 6.48 (t, J=8.4 Hz, 1H), 4.29 (s, 2H), 3.59-3.55 (m, 5H), 3.13 (q, J=6.4 Hz, 2H), 2.38-2.31 (m, 5H), 1.73 (quint, J=6.9 Hz, 2H); [M+H]⁺: 486.

Example 462: N-(3-oxo-7-(phenylamino)isoindolin-4-yl)-4-((3-(pyrrolidin-1-yl)propyl)amino)benzamide

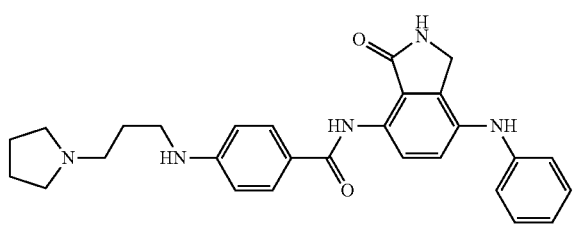 [SMILES: O=C(Nc1ccc(Nc2ccccc2)c2c1C(=O)NC2)c1ccc(NCCCN2CCCC2)cc1]

¹H NMR (400 MHz, DMSO-d₆) δ 11.13 (s, 1H), 8.87 (s, 1H), 8.38 (d, J=8.9 Hz, 1H), 7.85 (s, 1H), 7.69 (d, J=8.7 Hz, 2H), 7.38 (d, J=8.8 Hz, 1H), 7.23 (t, J=7.9 Hz, 2H), 6.97 (d, J=8.4 Hz, 2H), 6.82 (t, J=7.4 Hz, 1H), 6.66 (d, J=8.6 Hz, 3H), 6.49 (t, J=8.4 Hz, 1H), 4.29 (s, 2H), 3.14-3.09 (m, 3H), 2.42-2.38 (m, 6H), 1.68-1.66 (m, 7H); [M+H]⁺: 486.

Example 463: 4-((3-(4-Methylpiperazin-1-yl)propyl)amino)-N-(3-oxo-7-(phenylamino)isoindolin-4-yl)benzamide

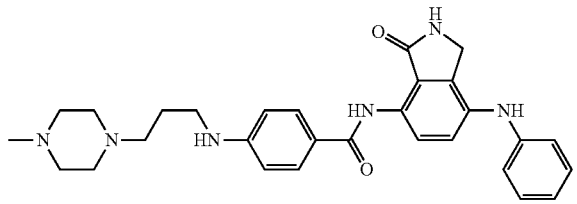 [SMILES: CN1CCN(CCCNc2ccc(C(=O)Nc3ccc(Nc4ccccc4)c4c3C(=O)NC4)cc2)CC1]

¹H NMR (400 MHz, DMSO-d₆) δ 11.13 (s, 1H), 8.87 (s, 1H), 8.38 (d, J=8.6 Hz, 1H), 7.85 (s, 1H), 7.69 (d, J=8.2 Hz, 2H), 7.38 (d, J=8.7 Hz, 1H), 7.23 (t, J=7.5 Hz, 2H), 6.97 (d, J=7.8 Hz, 2H), 6.82 (t, J=7.2 Hz, 1H), 6.66 (d, J=8.7 Hz, 2H), 6.48 (t, J=8.4 Hz, 1H), 4.29 (s, 2H), 3.12-3.11 (m, 3H), 2.36-2.32 (m, 5H), 2.15-2.14 (m, 6H), 1.71-1.68 (m, 3H); [M+H]⁺: 499.

Example 464: 4-((3-Hydroxypropyl)amino)-N-(3-oxo-7-(phenylamino) isoindolin-4-yl)benzamide

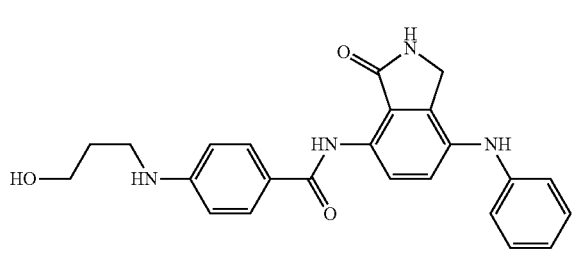 [SMILES: O=C(Nc1ccc(Nc2ccccc2)c2c1C(=O)NC2)c1ccc(NCCCO)cc1]

¹H NMR (400 MHz, DMSO-d₆) δ 11.13 (s, 1H), 8.87 (s, 1H), 8.38 (d, J=8.7 Hz, 1H), 7.84 (s, 1H), 7.69 (d, J=8.7 Hz,

2H), 7.38 (d, J=8.7 Hz, 1H), 7.23 (t, J=7.9 Hz, 2H), 6.97 (d, J=7.7 Hz, 2H), 6.82 (t, J=7.3 Hz, 1H), 6.66 (d, J=8.8 Hz, 1H), 6.43 (t, J=5.0 Hz, 1H), 4.52 (t, J=5.0 Hz, 1H), 4.29 (s, 2H), 3.51 (q, J=6.0 Hz, 2H), 3.15 (q, J=6.7 Hz, 2H), 1.71 (quint, J=6.6 Hz, 2H); [M+H]⁺: 417.

Example 465: N-(7-((3,5-bis(trifluoromethyl)phenyl)amino)-3-oxoisoindolin-4-yl)-4-((2-(pyrrolidin-1-yl)ethyl)amino)benzamide

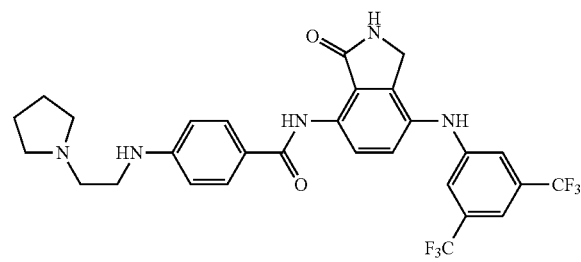 [SMILES: O=C(Nc1ccc(Nc2cc(C(F)(F)F)cc(C(F)(F)F)c2)c2c1C(=O)NC2)c1ccc(NCCN2CCCC2)cc1]

¹H NMR (400 MHz, DMSO-d₆) δ 11.21 (s, 1H), 8.96 (s, 1H), 8.71 (s, 1H), 8.48 (d, J=8.6 Hz, 1H), 7.71 (d, J=8.8 Hz, 2H), 7.52 (d, J=8.7 Hz, 1H), 7.35 (d, J=7.3 Hz, 3H), 6.70 (d, J=8.7 Hz, 2H), 6.41 (t, J=5.3 Hz, 1H), 4.31 (s, 2H), 3.22 (q, J=6.3 Hz, 2H), 2.62 (t, J=6.7 Hz, 2H), 1.69 (br s, 4H); [M+H]⁺ 592.

Example 466: N-(7-((3,5-bis(trifluoromethyl)phenyl)amino)-3-oxoisoindolin-4-yl)-4-((3-(pyrrolidin-1-yl)propyl)amino)benzamide

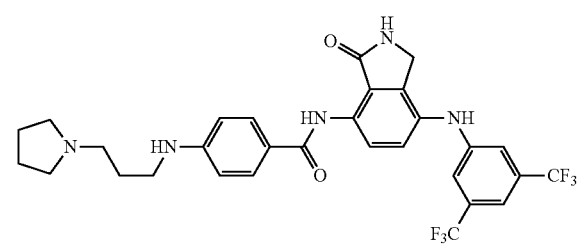 [SMILES: O=C(Nc1ccc(Nc2cc(C(F)(F)F)cc(C(F)(F)F)c2)c2c1C(=O)NC2)c1ccc(NCCCN2CCCC2)cc1]

¹H NMR (400 MHz, DMSO-d₆) δ 11.21 (s, 1H), 8.96 (s, 1H), 8.71 (s, 1H), 8.49 (d, J=7.3 Hz, 1H), 7.71 (d, J=7.3 Hz, 2H), 7.53 (d, J=8.2 Hz, 1H), 7.35 (d, J=8.9 Hz, 3H), 6.66 (d, J=8.7 Hz, 2H), 6.54 (br s, 1H), 4.31 (s, 2H), 3.13 (q, J=6.3 Hz, 2H), 2.43 (m, 8H), 1.69 (br s, 4H); [M+H]⁺: 606.

Example 467: N-(7-((3,5-bis(trifluoromethyl)phenyl)amino)-3-oxoisoindolin-4-yl)-4-((2-(piperidin-1-yl)ethyl)amino)benzamide

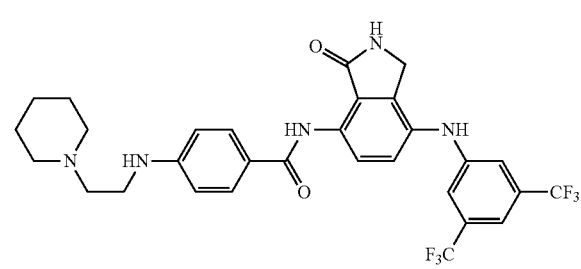 [SMILES: O=C(Nc1ccc(Nc2cc(C(F)(F)F)cc(C(F)(F)F)c2)c2c1C(=O)NC2)c1ccc(NCCN2CCCCC2)cc1]

¹H NMR (400 MHz, DMSO-d₆) δ 11.21 (s, 1H), 8.96 (s, 1H), 8.71 (s, 1H), 8.48 (d, J=8.7 Hz, 1H), 7.71 (d, J=8.8 Hz, 2H), 7.53 (d, J=8.8 Hz, 1H), 7.35 (d, J=7.2 Hz, 3H), 6.70 (d, J=8.9 Hz, 2H), 6.33 (t, J=5.3 Hz, 1H), 4.31 (s, 2H), 3.20 (q, J=6.1 Hz, 2H), 2.47-2.45 (m, 2H), 2.39 (br s, 4H), 1.51 (quint, J=5.5 Hz, 4H), 1.40-1.38 (m, 2H); [M+H]⁺: 606.

Example 468: N-(7-((3,5-bis(trifluoromethyl)phenyl)amino)-3-oxoisoindolin-4-yl)-4-((3-(piperidin-1-yl)propyl)amino)benzamide

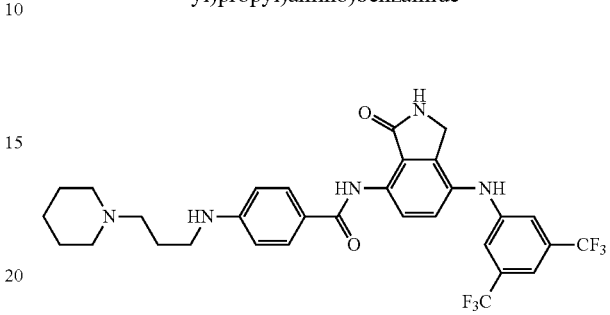

¹H NMR (400 MHz, DMSO-d₆) δ 11.21 (s, 1H), 8.96 (s, 1H), 8.70 (s, 1H), 8.48 (d, J=8.7 Hz, 1H), 7.70 (d, J=8.8 Hz, 2H), 7.52 (d, J=8.7 Hz, 1H), 7.35 (d, J=8.0 Hz, 3H), 6.66 (d, J=8.8 Hz, 2H), 6.56 (t, J=5.2 Hz, 1H), 4.31 (s, 2H), 3.12 (q, J=6.6 Hz, 2H), 2.32 (t, J=6.8 Hz, 5H), 1.69 (quint, J=7.0 Hz, 2H), 1.53-1.45 (m, 5H), 1.38-1.35 (m, 2H); [M+H]⁺: 620.

Example 469: N-(7-((2,3-dimethylphenyl)amino)-3-oxoisoindolin-4-yl)-4-((2-(pyrrolidin-1-yl)ethyl)amino)benzamide

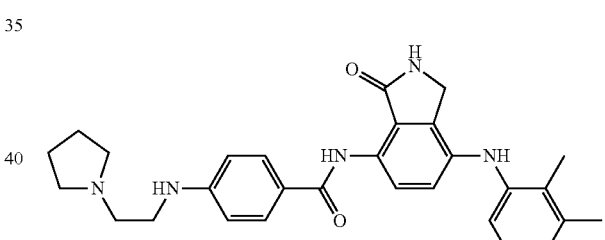

¹H NMR (400 MHz, DMSO-d₆) δ 11.09 (s, 1H), 8.82 (s, 1H), 8.29 (d, J=8.6 Hz, 1H), 7.67 (d, J=8.7 Hz, 2H), 7.23 (s, 1H), 7.01 (d, J=7.7 Hz, 1H), 6.87 (d, J=7.8 Hz, 1H), 6.79 (d, J=8.7 Hz, 2H), 6.73-6.67 (m, 3H), 6.33 (t, J=5.2 Hz, 1H), 4.19 (s, 2H), 3.21 (q, J=6.6 Hz, 4H), 2.61 (t, J=6.6 Hz, 2H), 2.26 (s, 3H), 2.08 (s, 3H), 1.69 (br s, 4H); [M+H]⁺: 484.

Example 470: N-(7-((2,3-dimethylphenyl)amino)-3-oxoisoindolin-4-yl)-4-((3-(pyrrolidin-1-yl)propyl)amino)benzamide

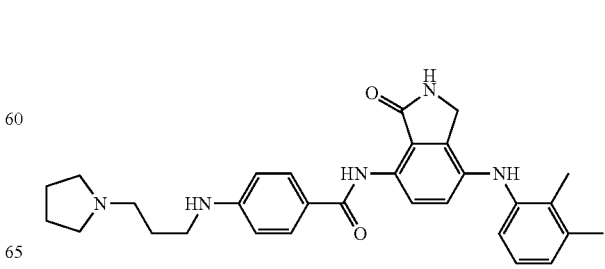

¹H NMR (400 MHz, DMSO-d₆) δ 11.08 (s, 1H), 8.82 (s, 1H), 8.29 (d, J=8.7 Hz, 1H), 7.67 (d, J=8.7 Hz, 2H), 7.23 (s, 1H), 7.01 (d, J=7.7 Hz, 1H), 6.87 (d, J=7.6 Hz, 1H), 6.79 (d, J=8.7 Hz, 2H), 6.69-6.63 (m, 3H), 6.46 (t, J=5.8 Hz, 1H), 4.19 (s, 2H), 3.12 (q, J=6.7 Hz, 2H), 2.47-2.42 (m, 6H), 2.26 (s, 3H), 2.08 (s, 3H), 1.74-1.68 (m, 6H); [M+H]⁺: 498.

Example 471: N-(7-((2,3-dimethylphenyl)amino)-3-oxoisoindolin-4-yl)-4-((2-(piperidin-1-yl)ethyl)amino)benzamide

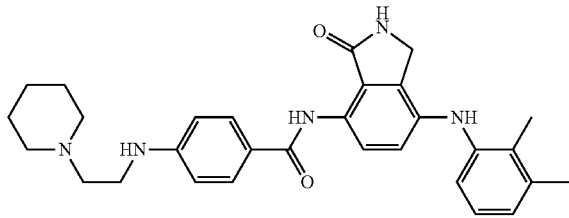 [SMILES: Cc1cccc(Nc2ccc(NC(=O)c3ccc(NCCN4CCCCC4)cc3)c3c2CNC3=O)c1C]

¹H NMR (400 MHz, DMSO-d₆) δ 11.08 (s, 1H), 8.82 (s, 1H), 8.29 (d, J=8.8 Hz, 1H), 7.67 (d, J=8.8 Hz, 2H), 7.23 (s, 1H), 7.01 (d, J=7.9 Hz, 1H), 6.85 (d, J=5.6 Hz, 1H), 6.79 (d, J=8.8 Hz, 2H), 6.72-6.67 (m, 3H), 6.25 (t, J=5.4 Hz, 1H), 4.19 (s, 2H), 3.19 (q, J=6.6 Hz, 2H), 2.47-2.43 (m, 2H), 2.38 (br s, 4H), 2.26 (s, 3H), 2.08 (s, 3H), 1.52-1.48 (m, 4H), 1.38 (br s, 2H); [M+H]⁺: 498.

Example 472: N-(7-((2,3-dimethylphenyl)amino)-3-oxoisoindolin-4-yl)-4-((3-(piperidin-1-yl)propyl)amino)benzamide

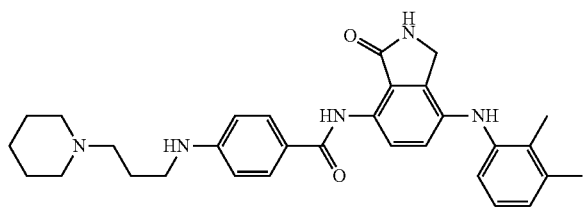 [SMILES: Cc1cccc(Nc2ccc(NC(=O)c3ccc(NCCCN4CCCCC4)cc3)c3c2CNC3=O)c1C]

¹H NMR (400 MHz, DMSO-d₆) δ 11.08 (s, 1H), 8.82 (s, 1H), 8.29 (d, J=8.8 Hz, 1H), 7.67 (d, J=8.7 Hz, 2H), 7.23 (s, 1H), 7.01 (d, J=7.7 Hz, 1H), 6.86 (d, J=7.5 Hz, 1H), 6.79 (d, J=8.8 Hz, 2H), 6.69-6.63 (m, 3H), 6.49 (t, J=5.0 Hz, 1H), 4.19 (s, 2H), 3.11 (q, J=6.4 Hz, 2H), 2.32-2.28 (m, 5H), 2.26 (s, 3H), 2.08 (s, 3H), 1.69 (t, J=6.8 Hz, 2H), 1.51-1.49 (m, 5H), 1.38 (br s, 2H); [M+H]⁺ 512.

Example 473: N-(3-oxo-7-(o-tolylamino)isoindolin-4-yl)-4-((2-(pyrrolidin-1-yl)ethyl)amino)benzamide

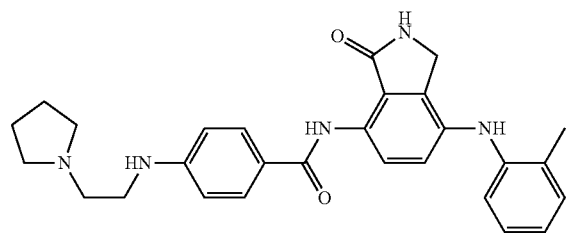 [SMILES: Cc1ccccc1Nc1ccc(NC(=O)c2ccc(NCCN3CCCC3)cc2)c2c1CNC2=O]

¹H NMR (400 MHz, DMSO-d₆) δ 11.12 (s, 1H), 8.83 (s, 1H), 8.34 (d, J=8.6 Hz, 1H), 7.69 (d, J=8.8 Hz, 2H), 7.21-7.18 (m, 2H), 7.09 (t, J=7.4 Hz, 1H), 6.97 (d, J=8.7 Hz, 1H), 6.87 (t, J=7.4 Hz, 2H), 6.69 (d, J=8.8 Hz, 2H), 6.34 (t, J=5.4 Hz, 1H), 4.18 (s, 2H), 3.21 (q, J=6.5 Hz, 2H), 2.62 (t, J=6.7 Hz, 2H), 2.20 (s, 3H), 1.69-1.68 (m, 8H); [M+H]⁺: 470.

Example 474: N-(7-((2-methoxyphenyl)amino)-3-oxoisoindolin-4-yl)-4-((2-(pyrrolidin-1-yl)ethyl)amino)benzamide

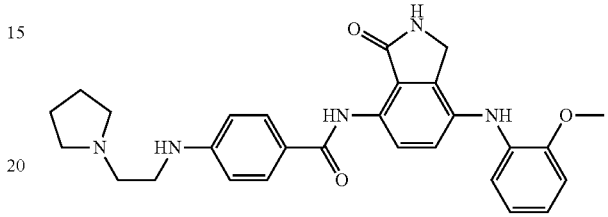

¹H NMR (400 MHz, DMSO-d₆) δ 11.14 (s, 1H), 8.84 (s, 1H), 8.35 (d, J=9.0 Hz, 1H), 7.17 (d, J=8.7 Hz, 1H), 7.12 (s, 1H), 7.00 (d, J=7.4 Hz, 1H), 6.88-6.82 (m, 3H), 6.69 (d, J=8.8 Hz, 2H), 6.35 (t, J=7.4 Hz, 1H), 4.28 (s, 2H), 3.82 (s, 3H), 3.21 (q, J=6.3 Hz, 2H), 2.62 (t, J=6.3 Hz, 3H), 1.70 (br s, 7H); [M+H]⁺: 486.

Example 475: N-(7-((2-methoxyphenyl)amino)-3-oxoisoindolin-4-yl)-4-((3-(pyrrolidin-1-yl)propyl)amino)benzamide

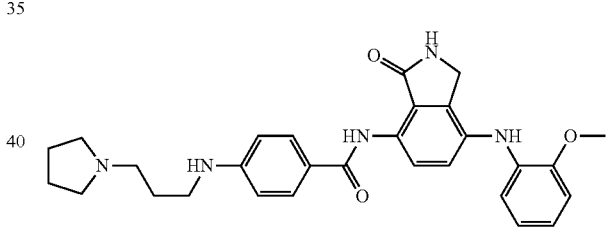

¹H NMR (400 MHz, DMSO-d₆) δ 11.14 (s, 1H), 8.84 (s, 1H), 8.35 (d, J=8.7 Hz, 1H), 7.69 (d, J=8.7 Hz, 3H), 7.17 (d, J=8.7 Hz, 1H), 7.12 (s, 1H), 7.00 (d, J=7.8 Hz, 1H), 6.88-6.82 (m, 3H), 6.65 (d, J=8.8 Hz, 3H), 6.48 (t, J=5.1 Hz, 1H), 4.28 (s, 2H), 3.82 (s, 3H), 3.13 (q, J=6.7 Hz, 2H), 2.47-2.45 (m, 2H), 2.42 (br s, 4H), 1.47-1.70 (m, 2H), 1.68-1.67 (m, 4H); [M+H]⁺ 500.

Example 476: N-(3-oxo-7-(o-tolylamino)isoindolin-4-yl)-4-((3-(pyrrolidin-1-yl)propyl)amino)benzamide

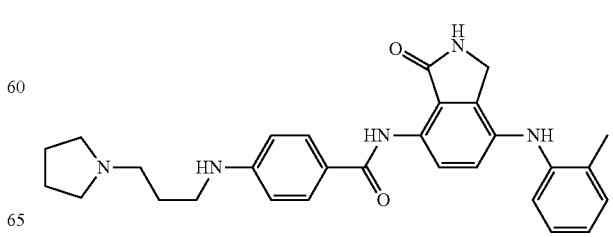

¹H NMR (400 MHz, DMSO-d₆) δ 11.12 (s, 1H), 8.83 (s, 1H), 8.34 (d, J=8.7 Hz, 1H), 7.68 (d, J=8.9 Hz, 3H), 7.19 (d, J=5.6 Hz, 2H), 7.09 (d, J=8.1 Hz, 1H), 6.97 (d, J=8.6 Hz, 1H), 6.91-6.85 (m, 2H), 6.65 (d, J=8.9 Hz, 4H), 6.47 (t, J=5.5 Hz, 1H), 4.18 (s, 2H), 3.13 (q, J=5.5 Hz, 2H), 2.47-2.42 (m, 2H), 2.38 (br s, 5H), 2.20 (s, 3H), 1.68-1.67 (m, 5H); [M+H]⁺: 484.

Example 477: N-(7-((2-methoxyphenyl)amino)-3-oxoisoindolin-4-yl)-4-((2-(piperidin-1-yl)ethyl)amino)benzamide

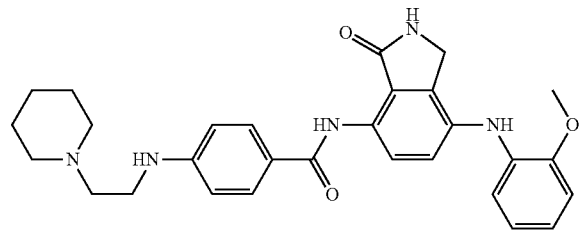 [SMILES: COc1ccccc1Nc1ccc(NC(=O)c2ccc(NCCN3CCCCC3)cc2)c2c1CNC2=O]

¹H NMR (400 MHz, DMSO-d₆) δ 11.14 (s, 1H), 8.84 (s, 1H), 8.35 (d, J=8.8 Hz, 1H), 7.69 (d, J=8.8 Hz, 2H), 7.17 (d, J=8.8 Hz, 1H), 7.12 (s, 1H), 7.00 (d, J=7.8 Hz, 1H), 6.88-6.82 (m, 3H), 6.69 (d, J=8.8 Hz, 2H), 6.27 (t, J=5.3 Hz, 1H), 4.28 (s, 2H), 3.82 (s, 3H), 3.20 (q, J=6.3 Hz, 2H), 2.47-2.45 (m, 2H), 2.33 (br s, 4H), 1.50 (q, J=5.4 Hz, 4H), 1.38 (br s, 2H); [M+H]⁺ 500.

Example 478: N-(7-((2-methoxyphenyl)amino)-3-oxoisoindolin-4-yl)-4-((3-(piperidin-1-yl)propyl)amino)benzamide

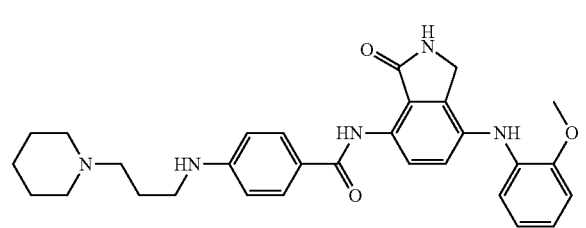 [SMILES: COc1ccccc1Nc1ccc(NC(=O)c2ccc(NCCCN3CCCCC3)cc2)c2c1CNC2=O]

¹H NMR (400 MHz, DMSO-d₆) δ 11.14 (s, 1H), 8.84 (s, 1H), 8.35 (d, J=8.8 Hz, 1H), 7.69 (d, J=8.8 Hz, 2H), 7.17 (d, J=8.8 Hz, 1H), 7.12 (s, 1H), 7.00 (d, J=7.8 Hz, 1H), 6.88-6.82 (m, 3H), 6.65 (d, J=8.8 Hz, 2H), 6.51 (t, J=5.5 Hz, 1H), 4.28 (s, 2H), 3.82 (s, 3H), 3.11 (q, J=6.4 Hz, 2H), 2.34-2.31 (m, 5H), 1.69 (quint, J=6.9 Hz, 2H), 1.51-1.49 (m, 5H), 1.38 (br s, 2H); [M+H]⁺ 514.

Example 479: N-(3-oxo-7-(phenylamino)isoindolin-4-yl)-4-((3-(piperidin-1-yl)propyl)amino)benzamide

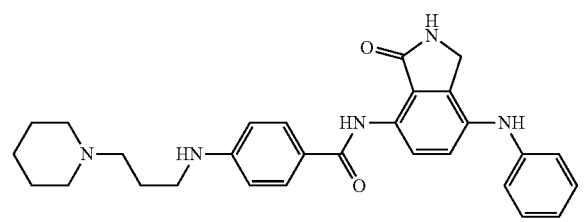 [SMILES: O=C(Nc1ccc(Nc2ccccc2)c2c1C(=O)NC2)c1ccc(NCCCN2CCCCC2)cc1]

¹H NMR (400 MHz, DMSO-d₆) δ 11.13 (s, 1H), 8.88 (s, 1H), 8.38 (d, J=8.7 Hz, 1H), 7.84 (s, 1H), 7.69 (d, J=8.8 Hz, 2H), 7.38 (d, J=8.8 Hz, 1H), 7.23 (d, J=7.9 Hz, 2H), 6.97 (d, J=7.7 Hz, 2H), 6.82 (t, J=7.3 Hz, 1H), 6.66 (d, J=8.8 Hz, 2H), 6.51 (t, J=5.4 Hz, 1H), 4.29 (s, 2H), 3.11 (q, J=6.5 Hz, 2H), 2.34-2.31 (m, 5H), 1.69 (quint, J=6.9 Hz, 2H), 1.53-1.47 (m, 5H), 1.39-1.38 (m, 2H); [M+H]⁺: 484.

Example 480: N-(3-oxo-7-(phenylamino)isoindolin-4-yl)-4-((3-(piperidin-1-yl)propyl)amino)benzamide hydrochloride

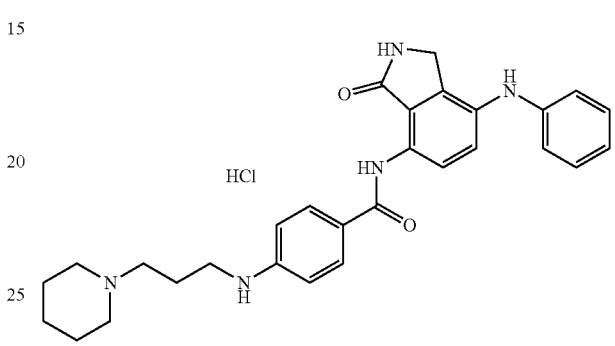

¹H NMR (400 MHz, DMSO-d₆) δ 11.15 (s, 1H), 9.21 (br s, 1H), 8.67 (s, 1H), 8.37 (d, J=8.6 Hz, 1H), 7.86 (s, 1H), 7.72 (d, J=8.6 Hz, 2H), 7.37 (d, J=3.3 Hz, 1H), 7.23 (t, J=8.0 Hz, 2H), 6.97 (d, J=8.0 Hz, 2H), 6.82 (t, J=7.3 Hz, 1H), 6.70 (d, J=8.9 Hz, 2H), 6.55 (br s, 1H), 4.29 (s, 2H), 3.44-3.37 (m, 2H), 3.20-3.18 (m, 2H), 3311-3.90 (m, 2H), 2.86 (q, J=11.5 Hz, 2H), 1.95-1.90 (m, 2H), 1.82-1.79 (m, 2H), 1.70-1.63 (m, 3H); [M+H]⁺: 484.

Example 481: 4-((2-Aminoethyl)amino)-N-(3-oxo-7-(phenylamino) isoindolin-4-yl)benzamide

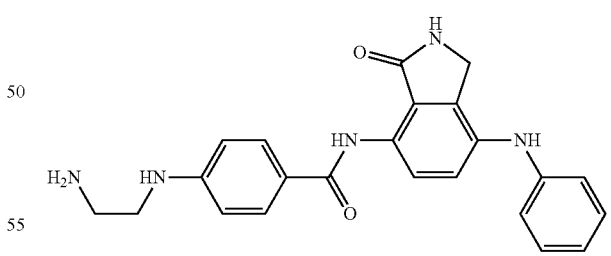

¹H NMR (400 MHz, DMSO-d₆) δ 11.13 (s, 1H), 8.87 (s, 1H), 8.38 (d, J=8.4 Hz, 1H), 7.84 (s, 1H), 7.69 (d, J=8.5 Hz, 2H), 7.38 (d, J=8.7 Hz, 1H), 7.23 (d, J=8.1 Hz, 2H), 6.97 (d, J=7.6 Hz, 2H), 6.82 (t, J=7.5 Hz, 1H), 6.68 (d, J=8.3 Hz, 2H), 6.43 (t, J=5.8 Hz, 1H), 4.29 (s, 2H), 3.09 (q, J=5.1 Hz, 2H), 2.73 (t, J=6.3 Hz, 2H); [M+H]⁺: 402.

Example 482: N-(3-oxo-7-(o-tolylamino)isoindolin-4-yl)-4-((2-(piperidin-1-yl)ethyl)amino)benzamide Example 485: 4-((2-Acetamidoethyl)amino)-N-(3-oxo-7-(phenylamino) isoindolin-4-yl)benzamide

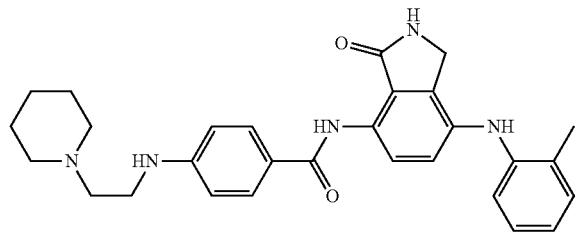 [SMILES: Cc1ccccc1Nc1ccc(NC(=O)c2ccc(NCCN3CCCCC3)cc2)c2c1CNC2=O]

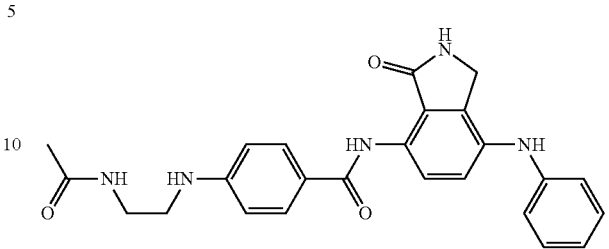

¹H NMR (400 MHz, DMSO-d₆) δ 11.12 (s, 1H), 8.82 (s, 1H), 8.34 (d, J=8.6 Hz, 1H), 7.68 (d, J=8.8 Hz, 2H), 7.19 (d, J=7.0 Hz, 2H), 7.09 (t, J=7.3 Hz, 1H), 6.97 (d, J=8.8 Hz, 2H), 6.91-6.85 (m, 2H), 6.68 (d, J=8.8 Hz, 3H), 6.25 (t, J=5.3 Hz, 1H), 4.18 (s, 2H), 3.19 (q, J=6.4 Hz, 2H), 2.45-2.35 (m, 5H), 2.32 (s, 3H), 1.52-1.48 (m, 5H), 1.38 (br s, 2H); [M+H]⁺: 484.

¹H NMR (400 MHz, DMSO-d₆) δ 11.14 (s, 1H), 8.87 (s, 1H), 8.38 (d, J=8.7 Hz, 1H), 7.84 (s, 1H), 7.70 (d, J=8.8 Hz, 2H), 7.38 (d, J=8.8 Hz, 1H), 7.23 (t, J=7.9 Hz, 2H), 6.97 (d, J=7.6 Hz, 2H), 6.82 (t, J=7.3 Hz, 1H), 6.69 (d, J=8.9 Hz, 2H), 6.49 (t, J=5.2 Hz, 1H), 4.29 (s, 2H), 3.22-3.16 (m, 4H), 1.82 (s, 3H); [M+H]⁺: 444.

Example 483: N-(3-oxo-7-(o-tolylamino)isoindolin-4-yl)-4-((3-(piperidin-1-yl)propyl)amino)benzamide Example 486: 4-((3-Aminopropyl)amino)-N-(3-oxo-7-(phenylamino) isoindolin-4-yl)benzamide

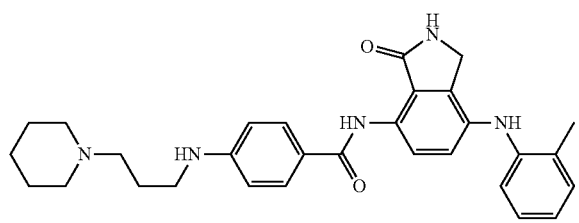 [SMILES: Cc1ccccc1Nc1ccc(NC(=O)c2ccc(NCCCN3CCCCC3)cc2)c2c1CNC2=O]

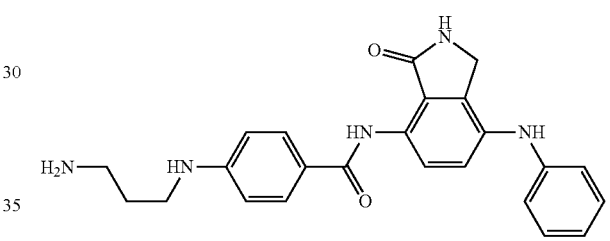

¹H NMR (400 MHz, DMSO-d₆) δ 11.12 (s, 1H), 8.82 (s, 1H), 8.34 (d, J=8.8 Hz, 1H), 7.68 (d, J=8.8 Hz, 2H), 7.18 (d, J=7.3 Hz, 2H), 7.09 (t, J=7.4 Hz, 1H), 6.97 (d, J=8.7 Hz, 1H), 6.91-6.87 (m, 2H), 6.65 (d, J=8.9 Hz, 4H), 6.50 (t, J=5.3 Hz, 1H), 4.18 (s, 2H), 3.11 (q, J=6.2 Hz, 2H), 2.32-2.31 (m, 5H), 2.22 (s, 3H), 1.71-1.68 (2, 5H), 1.53-1.46 (m, 5H), 1.38 (br s, 2H); [M+H]⁺: 498.

¹H NMR (400 MHz, DMSO-d₆) δ 11.13 (s, 1H), 8.87 (s, 1H), 8.38 (d, J=8.7 Hz, 1H), 7.84 (s, 1H), 7.69 (d, J=8.9 Hz, 3H), 7.38 (d, J=8.7 Hz, 1H), 7.23 (t, J=7.8 Hz, 3H), 6.97 (d, J=7.7 Hz, 2H), 6.82 (t, J=7.2 Hz, 1H), 6.66 (d, J=8.9 Hz, 4H), 4.29 (s, 2H), 3.42-3.33 (m, 2H), 3.29-3.26 (m, 2H), 3.15-3.13 (m, 2H); [M+H]⁺: 416.

Example 484: 4-((4-Hydroxybutyl)amino)-N-(3-oxo-7-(phenylamino) isoindolin-4-yl)benzamide Example 487: 4-((2-Hydroxyethyl)amino)-N-(3-oxo-7-(phenylamino) isoindolin-4-yl)benzamide

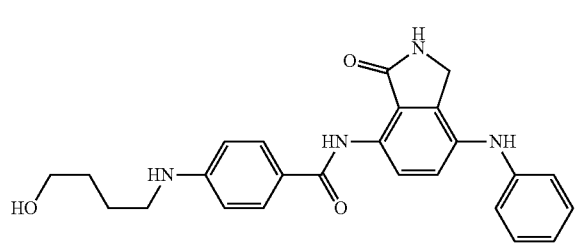 [SMILES: O=C(Nc1ccc(Nc2ccccc2)c2c1C(=O)NC2)c1ccc(NCCCCO)cc1]

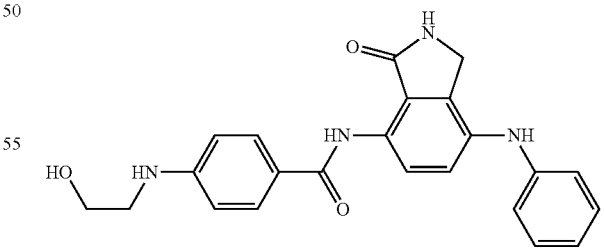

¹H NMR (400 MHz, DMSO-d₆) δ 11.12 (s, 1H), 8.86 (s, 1H), 8.38 (d, J=8.7 Hz, 1H), 7.84 (s, 1H), 7.69 (d, J=8.7 Hz, 3H), 7.44 (d, J=7.0 Hz, 1H), 7.22 (t, J=7.9 Hz, 3H), 6.97 (d, J=7.7 Hz, 2H), 6.83-6.79 (m, 1H), 6.66 (d, J=8.8 Hz, 3H), 6.47-6.43 (m, 1H), 4.43 (t, J=5.1 Hz, 1H), 4.29 (s, 2H), 3.43 (q, J=6.1 Hz, 2H), 3.09 (q, J=6.2 Hz, 2H), 1.61-1.50 (m, 4H); [M+H]⁺: 431.

¹H NMR (400 MHz, DMSO-d₆) δ 11.12 (s, 1H), 8.85 (s, 1H), 8.37 (d, J=8.5 Hz, 1H), 7.83 (s, 1H), 7.69 (d, J=8.4 Hz, 2H), 7.38 (d, J=8.8 Hz, 1H), 7.23 (t, J=7.9 Hz, 2H), 6.97 (d, J=7.8 Hz, 2H), 6.82 (t, J=7.2 Hz, 1H), 6.69 (d, J=8.8 Hz, 2H), 6.39 (d, J=5.9 Hz, 1H), 4.76 (t, J=5.5 Hz, 1H), 4.29 (s, 2H), 3.57 (q, J=5.6 Hz, 2H), 3.18 (q, J=5.32 Hz, 2H); [M+H]⁺: 403.

Example 488: 4-((2-Hydroxy-3-(piperidin-1-yl)propyl)amino)-N-(3-oxo-7-(phenylamino)isoindolin-4-yl)benzamide

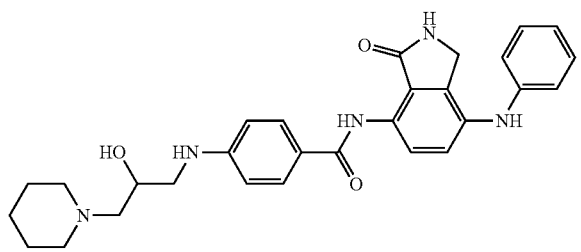 [SMILES: O=C(Nc1ccc(Nc2ccccc2)c2c1C(=O)NC2)c1ccc(NCC(O)CN2CCCCC2)cc1]

$^1$H NMR (400 MHz, DMSO-d$_6$) δ 11.13 (s, 1H), 8.86 (s, 1H), 8.38 (d, J=8.8 Hz, 1H), 7.83 (s, 1H), 7.68 (d, J=8.8 Hz, 2H), 7.38 (d, J=8.4 Hz, 1H), 7.23 (t, J=8.0 Hz, 2H), 6.97 (d, J=7.6 Hz, 2H), 6.82 (t, J=7.2 Hz, 1H), 6.71 (d, J=8.8 Hz, 2H), 6.44 (t, J=5.6 Hz, 1H), 4.68 (d, J=4.8 Hz, 1H), 4.29 (s, 2H), 3.79-3.76 (m, 1H), 3.26-3.20 (m, 1H), 3.06-3.00 (m, 1H), 2.39-2.28 (m, 6H), 1.52-1.48 (m, 4H), 1.39-1.37 (m, 2H). [M+H]$^+$ 500.

Example 489: (S)-4-((2-hydroxy-3-(piperidin-1-yl)propyl)amino)-N-(3-oxo-7-(phenylamino)isoindolin-4-yl)benzamide

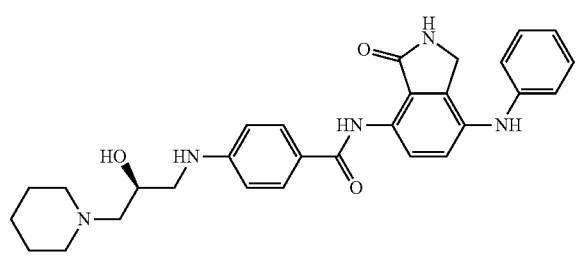 [SMILES: O=C(Nc1ccc(Nc2ccccc2)c2c1C(=O)NC2)c1ccc(NC[C@H](O)CN2CCCCC2)cc1]

$^1$H NMR (400 MHz, DMSO-d$_6$) δ 11.13 (s, 1H), 8.86 (s, 1H), 8.38 (d, J=8.8 Hz, 1H), 7.83 (s, 1H), 7.68 (d, J=8.8 Hz, 2H), 7.38 (d, J=8.4 Hz, 1H), 7.23 (t, J=8.0 Hz, 2H), 6.97 (d, J=7.6 Hz, 2H), 6.82 (t, J=7.2 Hz, 1H), 6.71 (d, J=8.8 Hz, 2H), 6.44 (t, J=5.6 Hz, 1H), 4.68 (d, J=4.8 Hz, 1H), 4.29 (s, 2H), 3.79-3.76 (m, 1H), 3.26-3.20 (m, 1H), 3.06-3.00 (m, 1H), 2.39-2.28 (m, 6H), 1.52-1.48 (m, 4H), 1.39-1.37 (m, 2H). [M+H]$^+$ 500.

Example 490: (R)-4-((2-hydroxy-3-(piperidin-1-yl)propyl)amino)-N-(3-oxo-7-(phenylamino)isoindolin-4-yl)benzamide

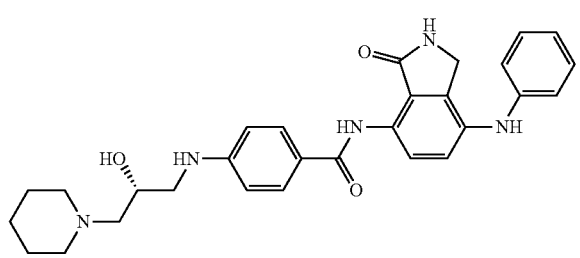 [SMILES: O=C(Nc1ccc(Nc2ccccc2)c2c1C(=O)NC2)c1ccc(NC[C@@H](O)CN2CCCCC2)cc1]

$^1$H NMR (400 MHz, DMSO-d$_6$) δ 11.13 (s, 1H), 8.86 (s, 1H), 8.38 (d, J=8.8 Hz, 1H), 7.83 (s, 1H), 7.68 (d, J=8.8 Hz, 2H), 7.38 (d, J=8.4 Hz, 1H), 7.23 (t, J=8.0 Hz, 2H), 6.97 (d, J=7.6 Hz, 2H), 6.82 (t, J=7.2 Hz, 1H), 6.71 (d, J=8.8 Hz, 2H), 6.44 (t, J=5.6 Hz, 1H), 4.68 (d, J=4.8 Hz, 1H), 4.29 (s, 2H), 3.79-3.76 (m, 1H), 3.26-3.20 (m, 1H), 3.06-3.00 (m, 1H), 2.39-2.28 (m, 6H), 1.52-1.48 (m, 4H), 1.39-1.37 (m, 2H). [M+H]$^+$ 500.

Example 491: 4-(4-Aminopiperidin-1-yl)-N-(3-oxo-7-(phenylamino) isoindolin-4-yl)benzamide

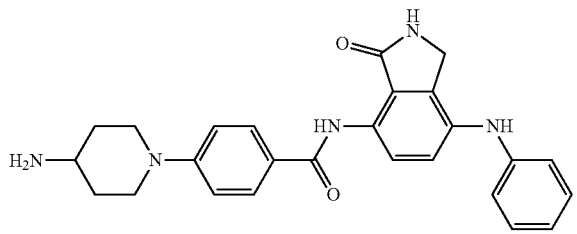 [SMILES: NC1CCN(c2ccc(C(=O)Nc3ccc(Nc4ccccc4)c4c3C(=O)NC4)cc2)CC1]

$^1$H NMR (400 MHz, DMSO-d$_6$) δ 11.19 (s, 1H), 8.88 (s, 1H), 8.38 (d, J=8.8 Hz, 1H), 7.86 (s, 1H), 7.77 (d, J=9.2 Hz, 2H), 7.38 (d, J=8.8 Hz, 1H), 7.23 (t, J=8.0 Hz, 2H), 7.04 (d, J=9.2 Hz, 2H), 6.98 (d, J=7.6 Hz, 2H), 6.82 (t, J=7.4 Hz, 1H), 4.29 (s, 2H), 3.84 (d, J=13.2 Hz, 2H), 2.92-2.86 (m, 2H), 2.81-2.76 (m, 1H), 1.79-1.74 (m, 2H), 1.31-1.23 (m, 2H). [M+H]$^+$: 442.

Example 492: 4-((2-(Azepan-1-yl)ethyl)amino)-N-(3-oxo-7-(phenylamino) isoindolin-4-yl)benzamide

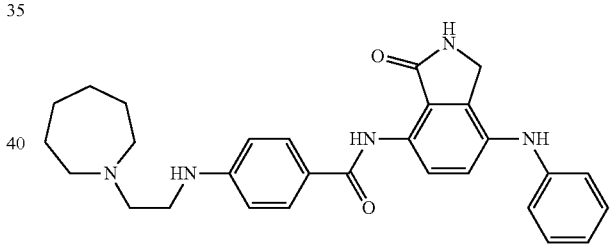

$^1$H NMR (400 MHz, DMSO-d$_6$) δ 11.13 (s, 1H), 8.87 (s, 1H), 8.37 (d, J=8.8 Hz, 1H), 7.85 (s, 1H), 7.69 (d, J=8.4 Hz, 2H), 7.38 (d, J=8.8 Hz, 1H), 7.23 (t, J=7.8 Hz, 2H), 6.97 (d, J=7.6 Hz, 2H), 6.82 (d, J=7.4 Hz, 1H), 6.69 (d, J=8.8 Hz, 2H), 6.23 (t, J=5.6 Hz, 1H), 4.29 (s, 2H), 3.17 (q, J=6.4 Hz, 2H), 2.68-2.64 (m, 6H), 1.58-1.55 (m, 8H). [M+H]$^+$: 484.

Experimental Example

Inhibition Activities on TNIK, IKKε and TBK1

Inhibition activities on TNIK, IKKε and TBK1 were evaluated using the compounds of Examples 1 to 492.

The inhibition activities on TNIK, IKKε and TBK1 were measured by a luminometer, TNIK/IKKε/TBK1 Kinase Enzyme System (Promega, Ca# V4158; Invitrogen, PR8031B, Promega, Ca# V3991) and ADP-Glo Kinase Assay using ADP-Glo™ Kinase Analysis Kit (Promega, Ca# V9101) and a kinase reaction buffer [40 mM Tris(pH 7.5), 20 mM MgCl2, 0.1 mg/mL BSA] in accordance with the manufacturer's protocol.

The results of the inhibition activities of the compounds of Examples 1 to 492 against TNIK, IKKε and TBK1 are shown in Table 1 below.

TABLE 1

| Example | Name | TNIK (μM) | TBK1 (μM) | IKKε (μM) |
|---|---|---|---|---|
| 1 | N-(7-(2-ethylphenyl)-3-oxoisoindolin-4-yl)benzamide | 3.1 | | |
| 2 | N-(7-(3-isopropylphenyl)-3-oxoisoindolin-4-yl)benzamide | >20 | | |
| 3 | N-(7-(4-(tert-butyl)phenyl)-3-oxoisoindolin-4-yl)benzamide | >20 | | |
| 4 | N-(3-oxo-7-(2-(trifluoromethoxy)phenyl)isoindolin-4-yl)benzamide | 3 | | |
| 5 | N-(3-oxo-7-(3-(trifluoromethoxy)phenyl)isoindolin-4-yl)benzamide | >20 | | |
| 6 | N-(7-(2-isopropoxyphenyl)-3-oxoisoindolin-4-yl)benzamide | >20 | | |
| 7 | N-(7-(3-isopropoxyphenyl)-3-oxoisoindolin-4-yl)benzamide | >20 | | |
| 8 | methyl 2-(7-benzamido-1-oxoisoindolin-4-yl)benzoate | >20 | | |
| 9 | methyl 3-(7-benzamido-1-oxoisoindolin-4-yl)benzoate | >20 | | |
| 10 | methyl 4-(7-benzamido-1-oxoisoindolin-4-yl)benzoate | Insoluble | | |
| 11 | N-(7-(2-acetylphenyl)-3-oxoisoindolin-4-yl)benzamide | 9.5 | | |
| 12 | N-(7-(3-acetylphenyl)-3-oxoisoindolin-4-yl)benzamide | >20 | | |
| 13 | N-(7-(4-acetylphenyl)-3-oxoisoindolin-4-yl)benzamide | Insoluble | | |
| 14 | N-(7-(2-(methylthio)phenyl)-3-oxoisoindolin-4-yl)benzamide | 1.1 | | |
| 15 | N-(7-(2,4-difluorophenyl)-3-oxoisoindolin-4-yl)benzamide | >20 | | |
| 16 | N-(7-(2,3-dimethylphenyl)-3-oxoisoindolin-4-yl)benzamide | 1.3 | | |
| 17 | N-(7-(2,3-dichlorophenyl)-3-oxoisoindolin-4-yl)benzamide | 1 | | |
| 18 | N-(7-(2,4-dichlorophenyl)-3-oxoisoindolin-4-yl)benzamide | >20 | | |
| 19 | N-(7-(2,5-dichlorophenyl)-3-oxoisoindolin-4-yl)benzamide | Insoluble | | |
| 20 | N-(7-(3,4-dichlorophenyl)-3-oxoisoindolin-4-yl)benzamide | >20 | | |
| 21 | N-(7-(3,5-dichlorophenyl)-3-oxoisoindolin-4-yl)benzamide | >20 | | |
| 22 | N-(7-(4-fluoro-2-methoxyphenyl)-3-oxoisoindolin-4-yl)benzamide | Insoluble | | |
| 23 | N-(7-(2-chloro-3-fluorophenyl)-3-oxoisoindolin-4-yl)benzamide | 8.9 | | |
| 24 | N-(7-(2-fluoro-3-methoxyphenyl)-3-oxoisoindolin-4-yl)benzamide | >20 | | |
| 25 | N-(3-oxo-7-(2,3,4-trimethoxyphenyl)isoindolin-4-yl)benzamide | Insoluble | | |
| 26 | N-(7-(3,4-dimethylphenyl)-3-oxoisoindolin-4-yl)benzamide | 3.8 | | |
| 27 | N-(7-(3,5-dimethylphenyl)-3-oxoisoindolin-4-yl)benzamide | 3 | | |
| 28 | N-(7-(2,6-dimethylphenyl)-3-oxoisoindolin-4-yl)benzamide | 1.7 | | |
| 29 | N-(7-ethyl-3-oxoisoindolin-4-yl)benzamide | 1.8 | | |
| 30 | N-(7-(3,5-difluorophenyl)-3-oxoisoindolin-4-yl)benzamide | >20 | | |
| 31 | N-(7-(2,5-dimethylphenyl)-3-oxoisoindolin-4-yl)benzamide | 1.6 | | |
| 32 | N-(7-(2,5-difluorophenyl)-3-oxoisoindolin-4-yl)benzamide | 1 | | |
| 33 | N-(7-(3,4-difluorophenyl)-3-oxoisoindolin-4-yl)benzamide | 3.7 | | |
| 34 | N-(7-(2,3-difluorophenyl)-3-oxoisoindolin-4-yl)benzamide | 0.54 | | |
| 35 | N-(7-butyl-3-oxoisoindolin-4-yl)benzamide | 8.6 | | |
| 36 | 4-fluoro-N-(3-oxo-7-propylisoindolin-4-yl)benzamide | >20 | | |
| 37 | N-(7-methyl-3-oxoisoindolin-4-yl)benzamide | 6.1 | | |
| 38 | N-(7-(2,4-dimethylphenyl)-3-oxoisoindolin-4-yl)benzamide | 1.7 | | |
| 39 | N-(7-(4-ethylphenyl)-3-oxoisoindolin-4-yl)benzamide | 6.1 | | |
| 40 | N-(7-(4-isopropoxyphenyl)-3-oxoisoindolin-4-yl)benzamide | >20 | | |
| 41 | N-(7-(4-(methylthio)phenyl)-3-oxoisoindolin-4-yl)benzamide | 1.2 | | |
| 42 | N-(7-(3-ethylphenyl)-3-oxoisoindolin-4-yl)benzamide | 3.7 | | |
| 43 | N-(3-oxo-7-(2-propoxyphenyl)isoindolin-4-yl)benzamide | >20 | | |
| 44 | N-(3-oxo-7-(3-propoxyphenyl)isoindolin-4-yl)benzamide | >20 | | |
| 45 | N-(7-(2-butoxyphenyl)-3-oxoisoindolin-4-yl)benzamide | >20 | | |
| 46 | N-(7-(3-butoxyphenyl)-3-oxoisoindolin-4-yl)benzamide | >20 | | |
| 47 | N-(7-(2-(methylsulfonyl)phenyl)-3-oxoisoindolin-4-yl)benzamide | >20 | | |
| 48 | N-(7-(3-fluoro-2-methoxyphenyl)-3-oxoisoindolin-4-yl)benzamide | 0.49 | | |
| 49 | N-(7-(4-chloro-2-methoxyphenyl)-3-oxoisoindolin-4-yl)benzamide | >20 | | |
| 50 | N-(7-(3-chloro-2-fluorophenyl)-3-oxoisoindolin-4-yl)benzamide | >20 | | |
| 51 | N-(3-oxo-7-(thiazol-5-yl)isoindolin-4-yl)benzamide | 0.44 | | |
| 52 | N-(3-oxo-7-(thiazol-4-yl)isoindolin-4-yl)benzamide | 2.80 | | |
| 53 | N-(3-oxo-7-(thiazol-2-yl)isoindolin-4-yl)benzamide | 2.34 | | |
| 54 | N-(7-(1H-imidazol-4-yl)-3-oxoisoindolin-4-yl)benzamide | 3.82 | | |
| 55 | N-(3-oxo-7-(1H-pyrazol-4-yl)isoindolin-4-yl)benzamide | 4.62 | | |
| 56 | N-(7-(1-methyl-1H-imidazol-5-yl)-3-oxoisoindolin-4-yl)benzamide | 2.21 | | |
| 57 | N-(7-(1-methyl-1H-pyrazol-4-yl)-3-oxoisoindolin-4-yl)benzamide | 2.17 | | |
| 58 | N-(3-oxo-7-(1H-1,2,4-triazol-5-yl)isoindolin-4-yl)benzamide | 2.67 | | |
| 59 | N-(7-(1-methyl-1H-1,2,4-triazol-5-yl)-3-oxoisoindolin-4-yl)benzamide | >20 | | |
| 60 | 7-amino-4-(4-methoxyphenyl)isoindolin-1-one | >20 | | |
| 61 | 7-amino-4-(4-fluorophenyl)isoindolin-1-one | Insoluble | | |
| 62 | 7-amino-4-(4-chlorophenyl)isoindolin-1-one | >20 | | |
| 63 | 7-amino-4-(p-tolyl)isoindolin-1-one | >20 | | |
| 64 | 4-(4-acetylphenyl)-7-aminoisoindolin-1-one | >20 | | |
| 65 | 7-amino-4-(pyridin-4-yl)isoindolin-1-one | >20 | | |
| 66 | 7-amino-4-(2,6-dichloropyrimidin-4-yl)isoindolin-1-one | | | |
| 67 | 7-amino-4-(2-chloropyrimidin-4-yl)isoindolin-1-one | | | |
| 68 | 7-amino-4-(2-((3-methoxyphenyl)amino)pyridin-4-yl)isoindolin-1-one | | 1.24 | 2.64 |
| 69 | 7-amino-4-(4-((3-methoxyphenyl)amino)pyridin-2-yl)isoindolin-1-one | | >10 | |
| 70 | 7-amino-4-(2-((3-methoxyphenyl)amino)pyrimidin-4-yl)isoindolin-1-one | | 0.051 | 0.051 |
| 71 | 7-amino-4-(2-((1-methyl-1H-pyrazol-4-yl)amino)pyrimidin-4-yl)isoindolin-1-one | | 0.15 | 0.16 |
| 72 | 7-amino-4-(2-(phenylamino)pyrimidin-4-yl)isoindolin-1-one | | 0.09 | 0.28 |
| 73 | 7-amino-4-(2-((3-fluorophenyl)amino)pyrimidin-4-yl)isoindolin-1-one | | 0.035 | 0.35 |
| 74 | 7-amino-4-(2-((4-fluorophenyl)amino)pyrimidin-4-yl)isoindolin-1-one | | 0.043 | 0.56 |
| 75 | 7-amino-4-(2-((4-methoxyphenyl)amino)pyrimidin-4-yl)isoindolin-1-one | | 0.11 | 0.36 |
| 76 | N-(4-((4-(7-amino-1-oxoisoindolin-4-yl)pyrimidin-2-yl)amino)phenyl)acetamide | | 0.1 | 0.35 |
| 77 | N-(3-((4-(7-amino-1-oxoisoindolin-4-yl)pyrimidin-2-yl)amino)phenyl)acetamide | | 0.027 | 0.2 |

TABLE 1-continued

| Example | Name | TNIK (μM) | TBK1 (μM) | IKKε (μM) |
|---|---|---|---|---|
| 78 | 7-amino-4-(6-((3-methoxyphenyl)amino)pyrimidin-4-yl)isoindolin-1-one | | 0.19 | 1.39 |
| 79 | 7-amino-4-(5-phenyl-1H-pyrrolo[2,3-b]pyridin-3-yl)isoindolin-1-one | | 0.64 | 10 |
| 80 | 7-amino-4-(1H-pyrrolo[2,3-b]pyridin-4-yl)isoindolin-1-one | | 9.23 | >10 |
| 81 | 7-amino-4-(2-(4-methylpiperazin-1-yl)pyrimidin-4-yl)isoindolin-1-one | | >10 | >10 |
| 82 | 7-amino-4-(2-morpholinopyrimidin-4-yl)isoindolin-1-one | | >10 | >10 |
| 83 | 7-amino-4-(2-(p-tolylamino)pyrimidin-4-yl)isoindolin-1-one | | 0.38 | 0.87 |
| 84 | 7-amino-4-(2-(m-tolylamino)pyrimidin-4-yl)isoindolin-1-one | | 0.2 | 0.44 |
| 85 | N-(4-(3-(7-amino-1-oxoisoindolin-4-yl)-1H-pyrrolo[2,3-b]pyridin-5-yl)phenyl)acetamide | | 0.072 | 0.16 |
| 86 | 7-amino-4-(5-(5-(morpholinomethyl)thiophen-2-yl)-1H-pyrrolo[2,3-b]pyridin-3-yl)isoindolin-1-one | | 0.032 | 0.056 |
| 87 | 2-methyl-N-(3-oxo-7-phenylisoindolin-4-yl)benzamide | 14.6 | | |
| 88 | 3-methyl-N-(3-oxo-7-phenylisoindolin-4-yl)benzamide | 2.8 | | |
| 89 | 4-methyl-N-(3-oxo-7-phenylisoindolin-4-yl)benzamide | 0.77 | | |
| 90 | 3-chloro-N-(3-oxo-7-phenylisoindolin-4-yl)benzamide | >20 | | |
| 91 | 2,4-difluoro-N-(3-oxo-7-phenylisoindolin-4-yl)benzamide | >20 | | |
| 92 | 3,4-difluoro-N-(3-oxo-7-phenylisoindolin-4-yl)benzamide | >20 | | |
| 93 | 3,4-dimethyl-N-(3-oxo-7-phenylisoindolin-4-yl)benzamide | 1.1 | | |
| 94 | 2-(dimethylamino)-N-(3-oxo-7-phenylisoindolin-4-yl)benzamide | >20 | | |
| 95 | 3-(dimethylamino)-N-(3-oxo-7-phenylisoindolin-4-yl)benzamide | Insoluble | | |
| 96 | 2-(methylthio)-N-(3-oxo-7-phenylisoindolin-4-yl)benzamide | 7 | | |
| 97 | 3-(methylthio)-N-(3-oxo-7-phenylisoindolin-4-yl)benzamide | >20 | | |
| 98 | 2-(methylsulfonyl)-N-(3-oxo-7-phenylisoindolin-4-yl)benzamide | 10.5 | | |
| 99 | 3-(methylsulfonyl)-N-(3-oxo-7-phenylisoindolin-4-yl)benzamide | 4.3 | | |
| 100 | 4-(methylsulfonyl)-N-(3-oxo-7-phenylisoindolin-4-yl)benzamide | >20 | | |
| 101 | 2,4-dimethoxy-N-(3-oxo-7-phenylisoindolin-4-yl)benzamide | >20 | | |
| 102 | 3,4-dimethoxy-N-(3-oxo-7-phenylisoindolin-4-yl)benzamide | Insoluble | | |
| 103 | 2,4-dichloro-N-(3-oxo-7-phenylisoindolin-4-yl)benzamide | >20 | | |
| 104 | 3,4-dichloro-N-(3-oxo-7-phenylisoindolin-4-yl)benzamide | Insoluble | | |
| 105 | 2,4-dimethyl-N-(3-oxo-7-phenylisoindolin-4-yl)benzamide | >20 | | |
| 106 | 2-acetamido-N-(3-oxo-7-phenylisoindolin-4-yl)benzamide | >20 | | |
| 107 | 3-acetamido-N-(3-oxo-7-phenylisoindolin-4-yl)benzamide | 0.48 | | |
| 108 | 4-(methylamino)-N-(3-oxo-7-phenylisoindolin-4-yl)benzamide | 0.78 | | |
| 109 | 3-methyl-N-(3-oxo-7-phenylisoindolin-4-yl)thiophene-2-carboxamide | >20 | | |
| 110 | 4-methyl-N-(3-oxo-7-phenylisoindolin-4-yl)thiophene-2-carboxamide | >20 | | |
| 111 | 5-methyl-N-(3-oxo-7-phenylisoindolin-4-yl)thiophene-2-carboxamide | 0.54 | | |
| 112 | N-(3-oxo-7-(o-tolyl)isoindolin-4-yl)benzamide | 2.2 | | |
| 113 | N-(3-oxo-7-(m-tolyl)isoindolin-4-yl)benzamide | 1.7 | | |
| 114 | N-(3-oxo-7-(2-(trifluoromethyl)phenyl)isoindolin-4-yl)benzamide | >20 | | |
| 115 | N-(3-oxo-7-(3-(trifluoromethyl)phenyl)isoindolin-4-yl)benzamide | >20 | | |
| 116 | 4-acetamido-N-(3-oxo-7-phenylisoindolin-4-yl)benzamide | 0.13 | | |
| 117 | N-(3-oxo-7-phenylisoindolin-4-yl)benzamide | 2.32 | | |
| 118 | N-(7-(4-methoxyphenyl)-3-oxoisoindolin-4-yl)benzamide | >20 | | |
| 119 | 4-nitro-N-(3-oxo-7-phenylisoindolin-4-yl)benzamide | Insoluble | | |
| 120 | 4-acetamido-N-(7-(4-methoxyphenyl)-3-oxoisoindolin-4-yl)benzamide | >20 | | |
| 121 | 4-methoxy-N-(3-oxo-7-phenylisoindolin-4-yl)benzamide | 3.4 | | |
| 122 | 4-fluoro-N-(3-oxo-7-phenylisoindolin-4-yl)benzamide | 2.2 | | |
| 123 | N-(7-(4-fluorophenyl)-3-oxoisoindolin-4-yl)-4-methoxybenzamide | 7.0 | | |
| 124 | 4-acetamido-N-(7-(4-fluorophenyl)-3-oxoisoindolin-4-yl)benzamide | 0.17 | | |
| 125 | N-(3-oxo-7-(thiophen-2-yl)isoindolin-4-yl)benzamide | 1.4 | | |
| 126 | N-(7-(furan-2-yl)-3-oxoisoindolin-4-yl)benzamide | 0.6 | | |
| 127 | N-(3-oxo-7-(pyridin-4-yl)isoindolin-4-yl)benzamide | Insoluble | | |
| 128 | N-(3-oxo-7-(pyridin-4-yl)isoindolin-4-yl)benzamide hydrochloride | >20 | | |
| 129 | 2-methoxy-N-(3-oxo-7-phenylisoindolin-4-yl)benzamide | >20 | | |
| 130 | 3-fluoro-N-(3-oxo-7-phenylisoindolin-4-yl)benzamide | >20 | | |
| 131 | 4-(methylthio)-N-(3-oxo-7-phenylisoindolin-4-yl)benzamide | 2.3 | | |
| 132 | N-(3-oxo-7-(4-propoxyphenyl)isoindolin-4-yl)benzamide | >20 | | |
| 133 | N-(7-(4-isopropylphenyl)-3-oxoisoindolin-4-yl)benzamide | >20 | | |
| 134 | N-(7-(2,3-dimethoxyphenyl)-3-oxoisoindolin-4-yl)furan-2-carboxamide | 0.054 | | |
| 135 | N-(7-(2,3-dimethoxyphenyl)-3-oxoisoindolin-4-yl)-4-fluorobenzamide | 0.14 | | |
| 136 | N-(7-(2,3-dimethoxyphenyl)-3-oxoisoindolin-4-yl)thiophene-2-carboxamide | 0.068 | | |
| 137 | 4-fluoro-2-methyl-N-(3-oxo-7-phenylisoindolin-4-yl)benzamide | >20 | | |
| 138 | 4-acetamido-N-(7-(2-methoxyphenyl)-3-oxoisoindolin-4-yl)benzamide | 0.2 | | |
| 139 | 4-(dimethylamino)-N-(3-oxo-7-phenylisoindolin-4-yl)benzamide | 1.8 | | |
| 140 | 4-acetamido-N-(7-(furan-2-yl)-3-oxoisoindolin-4-yl)benzamide | 0.3 | | |
| 141 | 4-fluoro-N-(7-(2-methoxyphenyl)-3-oxoisoindolin-4-yl)benzamide | 1.6 | | |
| 142 | 2-fluoro-N-(3-oxo-7-phenylisoindolin-4-yl)benzamide | 0.95 | | |
| 143 | 4-chloro-N-(3-oxo-7-phenylisoindolin-4-yl)benzamide | 1.1 | | |
| 144 | N-(7-(2-methoxyphenyl)-3-oxoisoindolin-4-yl)benzamide | 0.7 | | |
| 145 | N-(7-(3-methoxyphenyl)-3-oxoisoindolin-4-yl)benzamide | 1.3 | | |
| 146 | N-(3-oxo-7-(thiophen-3-yl)isoindolin-4-yl)benzamide | >20 | | |
| 147 | N-(7-(3-cyanophenyl)-3-oxoisoindolin-4-yl)benzamide | >20 | | |
| 148 | N-(7-(3-(dimethylamino)phenyl)-3-oxoisoindolin-4-yl)benzamide | 7.4 | | |
| 149 | N-(7-(2-fluorophenyl)-3-oxoisoindolin-4-yl)benzamide | 3.8 | | |
| 150 | N-(7-(furan-3-yl)-3-oxoisoindolin-4-yl)benzamide | 2.7 | | |
| 151 | N-(7-(3-fluorophenyl)-3-oxoisoindolin-4-yl)benzamide | 1.5 | | |
| 152 | N-(3-oxo-7-(pyridin-3-yl)isoindolin-4-yl)benzamide | >20 | | |
| 153 | N-(3-oxo-7-(pyridin-3-yl)isoindolin-4-yl)benzamide hydrochloride | | | |
| 154 | N-(3-oxo-7-(pyrimidin-5-yl)isoindolin-4-yl)benzamide | >20 | | |

TABLE 1-continued

| Example | Name | TNIK (μM) | TBK1 (μM) | IKKε (μM) |
|---|---|---|---|---|
| 155 | 3-chloro-N-(3-oxo-7-phenylisoindolin-4-yl)thiophene-2-carboxamide | 2.29 | | |
| 156 | 5-bromo-N-(3-oxo-7-phenylisoindolin-4-yl)thiophene-2-carboxamide | 2.86 | | |
| 157 | 3-bromo-N-(3-oxo-7-phenylisoindolin-4-yl)thiophene-2-carboxamide | 3.40 | | |
| 158 | 4-fluoro-N-(7-(furan-2-yl)-3-oxoisoindolin-4-yl)benzamide | 1.27 | | |
| 159 | N-(3-oxo-7-phenylisoindolin-4-yl)pentanamide | 1.8 | | |
| 160 | N-(3-oxo-7-phenylisoindolin-4-yl)acetamide | 1.1 | | |
| 161 | N-(7-(2-chloropyrimidin-4-yl)-3-oxoisoindolin-4-yl)acetamide | | | |
| 162 | N-(7-(2-((3-methoxyphenyl)amino)pyrimidin-4-yl)-3-oxoisoindolin-4-yl)acetamide | | 0.1 | 0.63 |
| 163 | N-(7-(2-((3-fluorophenyl)amino)pyrimidin-4-yl)-3-oxoisoindolin-4-yl)acetamide | | 4 | >10 |
| 164 | N-(3-oxo-7-(2-(m-tolylamino)pyrimidin-4-yl)isoindolin-4-yl)acetamide | | 0.35 | 0.83 |
| 165 | N-(3-oxo-7-(2-(p-tolylamino)pyrimidin-4-yl)isoindolin-4-yl)acetamide | | >10 | >10 |
| 166 | N-(7-(2-((3-methoxyphenyl)amino)pyrimidin-4-yl)-3-oxoisoindolin-4-yl)propionamide | | 0.094 | >10 |
| 167 | N-(7-(4-(methylsulfonyl)phenyl)-3-oxoisoindolin-4-yl)benzamide | 9.8 | | |
| 168 | N-(7-(3-(methylsulfonyl)phenyl)-3-oxoisoindolin-4-yl)benzamide | >20 | | |
| 169 | N-(7-(3-acetamidophenyl)-3-oxoisoindolin-4-yl)benzamide | 4.2 | | |
| 170 | 5-chloro-N-(3-oxo-7-phenylisoindolin-4-yl)thiophene-2-carboxamide | 3.52 | | |
| 171 | N-(7-(2,3-dimethoxyphenyl)-3-oxoisoindolin-4-yl)benzamide | 0.057 | | |
| 172 | N-(7-(3,5-dimethoxyphenyl)-3-oxoisoindolin-4-yl)benzamide | >20 | | |
| 173 | N-(7-cyclopropyl-3-oxoisoindolin-4-yl)benzamide | 0.75 | | |
| 174 | N-(7-(2-chlorophenyl)-3-oxoisoindolin-4-yl)benzamide | >20 | | |
| 175 | N-(7-(2,4-dimethoxyphenyl)-3-oxoisoindolin-4-yl)benzamide | 3 | | |
| 176 | N-(7-(3,4-dimethoxyphenyl)-3-oxoisoindolin-4-yl)benzamide | >20 | | |
| 177 | N-(7-(3-ethoxyphenyl)-3-oxoisoindolin-4-yl)benzamide | 8.1 | | |
| 178 | N-(7-(2,5-dimethoxyphenyl)-3-oxoisoindolin-4-yl)benzamide | >20 | | |
| 179 | N-(7-(4-chlorophenyl)-3-oxoisoindolin-4-yl)benzamide | >20 | | |
| 180 | N-(7-(3-chlorophenyl)-3-oxoisoindolin-4-yl)benzamide | 13.7 | | |
| 181 | N-(7-(4-ethoxyphenyl)-3-oxoisoindolin-4-yl)benzamide | >20 | | |
| 182 | N-(7-(2-ethoxyphenyl)-3-oxoisoindolin-4-yl)benzamide | 2.8 | | |
| 183 | N-(7-(2-cyanophenyl)-3-oxoisoindolin-4-yl)benzamide | 1.7 | | |
| 184 | N-(7-(4-butoxyphenyl)-3-oxoisoindolin-4-yl)benzamide | >20 | | |
| 185 | N-(7-(2-(dimethylamino)phenyl)-3-oxoisoindolin-4-yl)benzamide | 2.8 | | |
| 186 | N-(3-oxo-7-(4-(trifluoromethoxy)phenyl)isoindolin-4-yl)benzamide | >20 | | |
| 187 | N-(7-(2,6-dimethoxyphenyl)-3-oxoisoindolin-4-yl)benzamide | 2.2 | | |
| 188 | N-(3-oxo-7-(4-propylphenyl)isoindolin-4-yl)benzamide | >20 | | |
| 189 | N-(7-(2,3-dihydroxyphenyl)-3-oxoisoindolin-4-yl)-4-fluorobenzamide | Insoluble | | |
| 190 | 4-fluoro-N-(7-(2-hydroxy-3-methoxyphenyl)-3-oxoisoindolin-4-yl)benzamide | 0.52 | | |
| 191 | 4-fluoro-N-(3-oxo-7-(thiophen-2-yl)isoindolin-4-yl)benzamide | 13.34 | | |
| 192 | 5-methyl-N-(3-oxo-7-phenylisoindolin-4-yl)furan-2-carboxamide | 0.73 | | |
| 193 | N-(benzo[d]oxazol-7-yl)-3-oxoisoindolin-4-yl)-4-fluorobenzamide | 1.45 | | |
| 194 | 4-fluoro-N-(7-(2-methylbenzo[d]oxazol-7-yl)-3-oxoisoindolin-4-yl)benzamide | Insoluble | | |
| 195 | N-(3-oxo-7-(5-(pyrrolidin-1-ylmethyl)thiophen-2-yl)isoindolin-4-yl)benzamide | >20 | | |
| 196 | N-(3-oxo-7-(5-(piperidin-1-ylmethyl)thiophen-2-yl)isoindolin-4-yl)benzamide | 17.7 | | |
| 197 | N-(7-(5-(morpholinomethyl)thiophen-2-yl)-3-oxoisoindolin-4-yl)benzamide | >20 | | |
| 198 | tert-butyl 4-((5-(7-benzamido-1-oxoisoindolin-4-yl)thiophen-2-yl)methyl)piperazine-1-carboxylate | >20 | | |
| 199 | N-(7-(6-fluoropyridin-3-yl)-3-oxoisoindolin-4-yl)benzamide | Insoluble | | |
| 200 | N-(7-(6-methoxypyridin-3-yl)-3-oxoisoindolin-4-yl)benzamide | Insoluble | | |
| 201 | 2-chloro-N-(3-oxo-7-phenylisoindolin-4-yl)benzamide | 15.2 | | |
| 202 | 3-methoxy-N-(3-oxo-7-phenylisoindolin-4-yl)benzamide | >20 | | |
| 203 | N-(3-oxo-7-phenylisoindolin-4-yl)thiophene-2-carboxamide | 0.35 | | |
| 204 | N-(7-(4-acetylphenyl)-3-oxoisoindolin-4-yl)-4-methoxybenzamide | >20 | | |
| 205 | N-(7-(4-fluorophenyl)-3-oxoisoindolin-4-yl)benzamide | >20 | | |
| 206 | N-(7-(4-(dimethylamino)phenyl)-3-oxoisoindolin-4-yl)benzamide | 4.8 | | |
| 207 | N-(7-(4-cyanophenyl)-3-oxoisoindolin-4-yl)benzamide | >20 | | |
| 208 | 4-cyano-N-(3-oxo-7-phenylisoindolin-4-yl)benzamide | >20 | | |
| 209 | N-(3-oxo-7-(p-tolyl)isoindolin-4-yl)benzamide | 2.8 | | |
| 210 | N-(3-oxo-7-(4-(trifluoromethyl)phenyl)isoindolin-4-yl)benzamide | >20 | | |
| 211 | N-(3-oxo-7-phenylisoindolin-4-yl)isonicotinamide | 0.7 | | |
| 212 | N-(3-oxo-7-phenylisoindolin-4-yl)furan-2-carboxamide | 0.3 | | |
| 213 | N-(3-oxo-7-phenylisoindolin-4-yl)nicotinamide | 0.6 | | |
| 214 | 4-fluoro-N-(3-oxo-7-(quinolin-6-yl)isoindolin-4-yl)benzamide | >20 | | |
| 215 | 4-fluoro-N-(3-oxo-7-(quinolin-5-yl)isoindolin-4-yl)benzamide | 0.24 | | |
| 216 | 4-fluoro-N-(3-oxo-7-(quinolin-4-yl)isoindolin-4-yl)benzamide | 0.16 | | |
| 217 | N-(7-(1H-indol-7-yl)-3-oxoisoindolin-4-yl)-4-fluorobenzamide | 2.95 | | |
| 218 | N-(7-(1H-benzo[d]imidazol-4-yl)-3-oxoisoindolin-4-yl)-4-fluorobenzamide | 0.59 | | |
| 219 | N-(7-benzyl-3-oxoisoindolin-4-yl)-4-fluorobenzamide | 13.9 | | |
| 220 | (R)-tert-butyl 2-((3-oxo-7-phenylisoindolin-4-yl)carbamoyl)pyrrolidine-1-carboxylate | N/A | | |
| 221 | (R)-N-(3-oxo-7-phenylisoindolin-4-yl)pyrrolidine-2-carboxamide | N/A | | |
| 222 | 3-amino-N-(2-methyl-3-oxo-7-phenylisoindolin-4-yl)benzamide | N/A | | |
| 223 | 2-amino-N-(2-methyl-3-oxo-7-phenylisoindolin-4-yl)benzamide | N/A | | |
| 224 | N-(7-(2,3-dimethoxyphenyl)-2-(furan-2-carbonyl)-3-oxoisoindolin-4-yl)furan-2-carboxamide | 1 | | |
| 225 | N-(7-(2,3-dimethoxyphenyl)-3-oxo-2-(thiophene-2-carbonyl)isoindolin-4-yl)thiophene-2-carboxamide | >20 | | |
| 226 | 1-(4-fluorophenyl)-3-(3-oxo-7-phenylisoindolin-4-yl)urea | 2.5 | | |
| 227 | 1-(3-oxo-7-phenylisoindolin-4-yl)-3-phenylurea | 1.2 | | |
| 228 | 1-(4-cyanophenyl)-3-(3-oxo-7-phenylisoindolin-4-yl)urea | >20 | | |
| 229 | 1-butyl-3-(3-oxo-7-phenylisoindolin-4-yl)urea | 1.1 | | |
| 230 | 1-(4-methoxyphenyl)-3-(3-oxo-7-phenylisoindolin-4-yl)urea | 0.9 | | |
| 231 | 1-cyclohexyl-3-(3-oxo-7-phenylisoindolin-4-yl)urea | >20 | | |

TABLE 1-continued

| Example | Name | TNIK (μM) | TBK1 (μM) | IKKε (μM) |
|---|---|---|---|---|
| 232 | 1-(3-oxo-7-phenylisoindolin-4-yl)-3-(p-tolyl)urea | 2.1 | | |
| 233 | 1-(2-methoxyphenyl)-3-(3-oxo-7-phenylisoindolin-4-yl)urea | 16.7 | | |
| 234 | 1-isopropyl-3-(3-oxo-7-phenylisoindolin-4-yl)urea | 1.9 | | |
| 235 | 1-(4-nitrophenyl)-3-(3-oxo-7-phenylisoindolin-4-yl)urea | 4.6 | | |
| 236 | 1-ethyl-3-(3-oxo-7-phenylisoindolin-4-yl)urea | 0.58 | | |
| 237 | 1-(4-acetylphenyl)-3-(3-oxo-7-phenylisoindolin-4-yl)urea | 4.9 | | |
| 238 | 1-(3-oxo-7-phenylisoindolin-4-yl)-3-(o-tolyl)urea | >20 | | |
| 239 | 1-cyclopentyl-3-(3-oxo-7-phenylisoindolin-4-yl)urea | >20 | | |
| 240 | 1-(3-fluorophenyl)-3-(3-oxo-7-phenylisoindolin-4-yl)urea | 2.4 | | |
| 241 | 1-(3-(methylthio)phenyl)-3-(3-oxo-7-phenylisoindolin-4-yl)urea | 2.7 | | |
| 242 | 1-(2-fluorophenyl)-3-(3-oxo-7-phenylisoindolin-4-yl)urea | 2.3 | | |
| 243 | 1-(4-chlorophenyl)-3-(3-oxo-7-phenylisoindolin-4-yl)urea | 3.9 | | |
| 244 | 1-(7-(4-methoxyphenyl)-3-oxoisoindolin-4-yl)-3-phenylurea | 4.02 | | |
| 245 | 1-(7-(4-fluorophenyl)-3-oxoisoindolin-4-yl)-3-phenylurea | 6.5 | | |
| 246 | 7-amino-N-cyclohexyl-1-oxo-4-phenylisoindolin-2-carboxamide | >20 | | |
| 247 | 1-(3-oxo-7-phenylisoindolin-4-yl)-3-phenylthiourea | >20 | | |
| 248 | phenyl (3-oxo-7-phenylisoindolin-4-yl)carbamate | >20 | | |
| 249 | N-(3-oxo-7-phenylisoindolin-4-yl)benzenesulfonamide | >20 | | |
| 250 | N-(3-oxo-7-phenylisoindolin-4-yl)methanesulfonamide | 21.0 | | |
| 251 | 4-fluoro-N-(3-oxo-7-phenylisoindolin-4-yl)benzenesulfonamide | >20 | | |
| 252 | 4-methoxy-N-(3-oxo-7-phenylisoindolin-4-yl)benzenesulfonamide | >20 | | |
| 253 | 7-((2-chloroethyl)amino)-4-phenylisoindolin-1-one | 2.6 | | |
| 254 | 3-((3-oxo-7-phenylisoindolin-4-yl)amino)propanenitrile | 5.6 | | |
| 255 | 7-((2-(dimethylamino)ethyl)amino)-4-phenylisoindolin-1-one | >20 | | |
| 256 | 7-((2-hydroxyethyl)amino)-4-phenylisoindolin-1-one | 4.9 | | |
| 257 | 2-(2-((3-oxo-7-phenylisoindolin-4-yl)amino)ethyl)isoindolin-1,3-dione | Insoluble | | |
| 258 | 7-((2-(4-methylpiperazin-1-yl)ethyl)amino)-4-phenylisoindolin-1-one | >20 | | |
| 259 | 4-phenyl-7((2-(piperidin-1-yl)ethyl)amino)isoindolin-1-one | >20 | | |
| 260 | 7-((2-morpholinoethyl)amino)-4-phenylisoindolin-1-one | >20 | | |
| 261 | 7-((2-(methylamino)ethyl)amino)-4-phenylisoindolin-1-one | >20 | | |
| 262 | 4-phenyl-7-((2-(pyrrolidin-1-yl)ethyl)amino)isoindolin-1-one | >20 | | |
| 263 | 7-(benzylamino)-4-phenylisoindolin-1-one | >20 | | |
| 264 | 2-(3-((3-oxo-7-phenylisoindolin-4-yl)amino)propyl)isoindolin-1,3-dione | Insoluble | | |
| 265 | 4-(pyridin-4-yl)-7-(pyrrolidin-1-yl)isoindolin-1-one | | | |
| 266 | 7-(dimethylamino)-4-(2-((3-methoxyphenyl)amino)pyrimidin-4-yl)isoindolin-1-one | | 0.75 | 1.96 |
| 267 | 7-(dimethylamino)-4-(2-((3-fluorophenyl)amino)pyrimidin-4-yl)isoindohn-1-one | | 3.98 | 5.51 |
| 268 | 7-(butylamino)-4-(2-((3-methoxyphenyl)amino)pyrimidin-4-yll)isomdohn-1-one | | 0.32 | 0.88 |
| 269 | 7-(butyl(methyl)amino)-4-(2-((3-methoxyphenyl)amino)pyrimidin-4-yl)isoindolin-1-one | | 2.55 | 5.97 |
| 270 | 7-(butyl(methyl)amino)-4-(2-((3-methoxyphenyl)amino)pyrimidin-4-yl)-2-methylisoindolin-1-one | | >10 | >10 |
| 271 | 4-amino-7-phenylisoindolin-1,3-dione | 2.5 | | |
| 272 | 4-amino-7-(2-methoxyphenyl)isoindolin-1,3-dione | 10.9 | | |
| 273 | 4-amino-7-(2,3-dimethoxyphenyl)isoindolin-1,3-dione | Insoluble | | |
| 274 | 4-amino-7-(furan-2-yl)isoindolin-1,3-dione | 3.6 | | |
| 275 | 4-amino-7-(thiophen-2-yl)isoindolin-1,3-dione | 1.1 | | |
| 276 | N-(1,3-dioxo-7-phenylisoindolin-4-yl)benzamide | 1.1 | | |
| 277 | N-(7-(2-methoxyphenyl)-1,3-dioxoisoindolin-4-yl)benzamide | 0.65 | | |
| 278 | N-(7-(2,3-dimethoxyphenyl)-1,3-dioxoisoindolin-4-yl)benzamide | 0.41 | | |
| 279 | 4-fluoro-N-(3-oxo-7-phenyl-2,3-dihydro-1H-pyrrolo[3,4-c]pyridin-4-yl)benzamide | >20 | | |
| 280 | N-(7-(2,3-dimethoxyphenyl)-3-oxoisoindolin-4-yl)-4-((3-(pyrrolidin-1-yl)propyl)amino)benzamide | 0.073 | | |
| 281 | N-(7-bromo-3-oxoisoindolin-4-yl)-4-((2-(dimethylamino)ethyl)amino)benzamide | 2.42 | | |
| 282 | N-(7-bromo-3-oxoisoindolin-4-yl)-4-((3-(piperidin-1-yl)propyl)amino)benzamide | 1.40 | | |
| 283 | N-(7-bromo-3-oxoisoindolin-4-yl)-4-((2-(pyrrolidin-1-yl)ethyl)amino)benzamide | 1.76 | | |
| 284 | N-(7-bromo-3-oxoisoindolin-4-yl)-4-((2-(piperidin-1-yl)ethyl)amino)benzamide | 1.55 | | |
| 285 | 4-((2-(azep an-1-yl)ethyl)amino)-N-(7-bromo-3-oxoisoindolin-4-yl)benzamide | 1.13 | | |
| 286 | N-(7-bromo-3-oxoisoindolin-4-yl)-4-((3-(dimethylamino)propyl)amino)benzamide | 1.48 | | |
| 287 | N-(7-(furan-2-yl)-3-oxoisoindolin-4-yl)-44(2-((2-1-yl)ethyl)amino)benzamide | 0.66 | | |
| 288 | N-(7-(furan-2-yl)-3-oxoisoindolin-4-yl)-4-((2-methoxyethyl)amino)benzamide | 0.45 | | |
| 289 | N-(7-(furan-2-yl)-3-oxoisoindolin-4-yl)-4-((2-(piperidin-1-yl)ethyl)amino)benzamide | 0.36 | | |
| 290 | N-(7-(furan-2-yl)-3-oxoisoindolin-4-yl)-4-((2-morpholinoethyl)amino)benzamide | 0.18 | | |
| 291 | 4-((2-(dimethylamino)ethyl)amino)-N-(7-(furan-2-yl)-3-oxoisoindolin-4-yl)benzamide | 0.54 | | |
| 292 | N-(7-(furan-2-yl)-3-oxoisoindolin-4-yl)-4-((2-hydroxyethyl)amino)benzamide | 0.47 | | |
| 293 | 4-((2-(azepan-1-yl)ethyl)amino)-N-(7-(furan-2-yl)-3-oxoisoindolin-4-yl)benzamide | 0.48 | | |
| 294 | N-(7-(furan-2-yl)-3-oxoisoindolin-4-yl)-4-((2-(4-methylpiperazin-1-yl)ethyl)amino)benzamide | 0.23 | | |
| 295 | N-(7-(furan-2-yl)-3-oxoisoindolin-4-yl)-4-((3-(4-methylpiperazin-1-yl)propyl)amino)benzamide | 0.52 | | |
| 296 | N-(7-(2,3-dimethoxyphenyl)-3-oxoisoindolin-4-yl)-4-((3-morpholinopropyl)amino)benzamide | 0.085 | | |
| 297 | N-(7-(2,3-dimethoxyphenyl)-3-oxoisoindolin-4-yl)-4-((2-morpholinoethyl)amino)benzamide | 0.075 | | |
| 298 | N-(7-(2,3-dimethoxyphenyl)-3-oxoisoindolin-4-yl)-4-((2-(piperidin-1-yl)ethyl)amino)benzamide | 0.078 | | |
| 299 | N-(7-(2,3-dimethoxyphenyl)-3-oxoisoindolin-4-yl)-4-((2-(pyrrolidin-1-yl)ethyl)amino)benzamide | 0.05 | | |
| 300 | N-(7-(2,3-dimethoxyphenyl)-3-oxoisoindolin-4-yl)-4-((2-methoxyethyl)amino)benzamide | 0.11 | | |
| 301 | N-(7-(2,3-dimethoxyphenyl)-3-oxoisoindolin-4-yl)-4-((2-(dimethylamino)ethyl)amino)benzamide | 0.10 | | |
| 302 | N-(7-(2-methoxyphenyl)-3-oxoisoindolin-4-yl)-4-((3-(pyrrolidin-1-yl)propyl)amino)benzamide | 0.16 | | |
| 303 | N-(7-(2-methoxyphenyl)-3-oxoisoindolin-4-yl)-4-((2-(pyrrolidin-1-yl)ethyl)amino)benzamide hydrochloride | 0.30 | | |
| 304 | N-(7-(2,3-dimethoxyphenyl)-3-oxoisoindolin-4-yl)-4-((2-(pyrrolidin-1-yl)ethyl)amino)benzamide hydrochloride | 0.073 | | |
| 305 | 4-((2-(dimethylamino)ethyl)amino)-N-(7-(2-methoxyphenyl)-3-oxoisoindolin-4-yl)benzamide | 0.20 | | |
| 306 | N-(7-(2,3-dimethoxyphenyl)-3-oxoisoindolin-4-yl)-4-((3-(dimethylamino)propyl)amino)benzamide | 0.074 | | |

TABLE 1-continued

| Example | Name | TNIK (μM) | TBK1 (μM) | IKKε (μM) |
|---|---|---|---|---|
| 307 | N-(7-(2-methoxyphenyl)-3-oxoisoindolin-4-yl)-4-((3-(piperidin-1-yl)propyl)amino)benzamide | 0.19 | | |
| 308. | N-(7-(2,3-dimethoxyphenyl)-3-oxoisoindolin-4-yl)-4-((3-(piperidin-1-yl)propyl)amino)benzamide | 0.053 | | |
| 309 | 2-methyl-N-(3-oxo-7-phenylisoindolin-4-yl)-4-((2-(pyrrolidin-1-yl)ethyl)amino)benzamide | 4.82 | | |
| 310 | 4-((3-methoxypropyl)amino)-N-(7-(2-methoxypyridin-3-yl)-3-oxoisoindolin-4-yl)benzamide | 0.39 | | |
| 311 | N-(7-(2,3-dimethoxyphenyl)-3-oxoisoindolin-4-yl)-4-((2-hydroxyethyl)amino)benzamide | 0.052 | | |
| 312 | N-(7-(2,3-dimethoxyphenyl)-3-oxoisoindolin-4-yl)-4-morpholinobenzamide | 0.73 | | |
| 313 | N-(7-(3-fluoro-2-methoxyphenyl)-3-oxoisoindolin-4-yl)-4-((2-(pyrrolidin-1-yl)ethyl)amino)benzamide | 0.45 | | |
| 314 | N-(7-(2,3-dimethoxyphenyl)-3-oxoisoindolin-4-yl)-4-((2-(4-methylpiperazin-1-yl)ethyl)amino)benzamide | 0.086 | | |
| 315 | 4-((2-aminoethyl)amino)-N-(7-(2,3-dimethoxyphenyl)-3-oxoisoindolin-4-yl)benzamide | 0.037 | | |
| 316 | N-(7-(2,3-dimethoxyphenyl)-3-oxoisoindolin-4-yl)-4-((3-(4-methylpiperazin-1-yl)propyl)amino)benzamide | 0.057 | | |
| 317 | N-(3-oxo-7-phenylisoindolin-4-yl)-4-((2-(pyrrolidin-1-yl)ethyl)amino)benzamide | 0.36 | | |
| 318 | N-(7-(2-methoxyphenyl)-3-oxoisoindolin-4-yl)-4-((2-(pyrrolidin-1-yl)ethyl)amino)benzamide | 0.26 | | |
| 319 | 4-(4-methylpiperazin-1-yl)-N-(3-oxo-7-phenylisoindolin-4-yl)benzamide | 2.7 | | |
| 320 | 4-morpholino-N-(3-oxo-7-phenylisoindolin-4-yl)benzamide | 8.8 | | |
| 321 | 4-((2-methoxyethyl)amino)-N-(3-oxo-7-phenylisoindolin-4-yl)benzamide | 0.5 | | |
| 322 | 4-((2-morpholinoethyl)amino)-N-(3-oxo-7-phenylisoindolin-4-yl)benzamide | 0.34 | | |
| 323 | N-(7-(2-methoxyphenyl)-3-oxoisoindolin-4-yl)-4-morpholinobenzamide | 0.37 | | |
| 324 | 4-((2-methoxyethyl)amino)-N-(7-(2-methoxyphenyl)-3-oxoisoindolin-4-yl)benzamide | 0.3 | | |
| 325 | N-(7-(2-methoxyphenyl)-3-oxoisoindolin-4-yl)-4-(4-methylpiperazin-1-yl)benzamide | 0.37 | | |
| 326 | N-(7-(2-methoxyphenyl)-3-oxoisoindolin-4-yl)-4-((2-morpholinoethyl)amino)benzamide | 0.093 | | |
| 327 | 4-((3-morpholinopropyl)amino)-N-(3-oxo-7-phenylisoindolin-4-yl)benzamide | 0.7 | | |
| 328 | N-(7-(2-methoxyphenyl)-3-oxoisoindolin-4-yl)-4-((3-morpholinopropyl)amino)benzamide | 0.4 | | |
| 329 | 4-((3-(4-methylpiperazin-1-yl)propyl)amino)-N-(3-oxo-7-phenylisoindolin-4-yl)benzamide | 0.44 | | |
| 330 | N-(7-(2-methoxyphenyl)-3-oxoisoindolin-4-yl)-4-((3-(4-methylpiperazin-1-yl)propyl)amino)benzamide | 0.51 | | |
| 331 | 4-((3-methoxypropyl)amino)-N-(3-oxo-7-phenylisoindolin-4-yl)benzamide | 0.79 | | |
| 332 | N-(7-(2-methoxyphenyl)-3-oxoisoindolin-4-yl)-4-((3-methoxypropyl)amino)benzamide | 0.51 | | |
| 333 | N-(3-oxo-7-phenylisoindolin-4-yl)-4-((thiophen-2-ylmethyl)amino)benzamide | 1.6 | | |
| 334 | N-(7-(2-methoxyphenyl)-3-oxoisoindolin-4-yl)-4-((thiophen-2-ylmethyl)amino)benzamide | 0.41 | | |
| 335 | 4-((3-(dimethylamino)propyl)amino)-N-(7-(furan-2-yl)-3-oxoisoindolin-4-yl)benzamide | 0.43 | | |
| 336 | N-(7-(furan-2-yl)-3-oxoisoindolin-4-yl)-4-((3-methoxypropyl)amino)benzamide | 0.98 | | |
| 337 | N-(7-(furan-2-yl)-3-oxoisoindolin-4-yl)-4-((3-morpholinopropyl)amino)benzamide | 0.56 | | |
| 338 | N-(7-(furan-2-yl)-3-oxoisoindolin-4-yl)-4-((3-(piperidin-1-yl)propyl)amino)benzamide | 0.37 | | |
| 339 | N-(7-(furan-2-yl)-3-oxoisoindolin-4-yl)-44(3-((3-1-yl)propyl)amino)benzamide | 0.31 | | |
| 340 | 4-(4-aminopiperidin-1-yl)-N-(3-oxo-7-phenylisoindolin-4-yl)benzamide | 0.68 | | |
| 341 | N-(7-(benzo[d]oxazol-7-yl)-3-oxoisoindolin-4-yl)-4-((2-(dimethylamino)ethyl)amino)benzamide | 0.038 | | |
| 342 | N-(7-(benzo[d]oxazol-7-yl)-3-oxoisoindolin-4-yl)-4-((2-(piperidin-1-yl)ethyl)amino)benzamide | 0.043 | | |
| 343 | N-(7-(benzo[d]oxazol-7-yl)-3-oxoisoindolin-4-yl)-4-((3-(piperidin-1-yl)propyl)amino)benzamide | 0.042 | | |
| 344 | 4-((2-(azepan-1-yl)ethyl)amino)-N-(7-(benzo[d]oxazol-7-yl)-3-oxoisoindolin-4-yl)benzamide | 0.061 | | |
| 345 | 4-(2-morpholinoethoxy)-N-(3-oxo-7-phenylisoindolin-4-yl)benzamide | 1.14 | | |
| 346 | N-(3-oxoisoindolin-4-yl)-4-((2-(pyrrolidin-1-yl)ethyl)amino)benzamide | 6.17 | | |
| 347 | N-(7-(2,3-dimethoxyphenyl)-3-oxoisoindolin-4-yl)-4-(2-morpholinoethoxy)benzamide | 0.20 | | |
| 348 | N-(7-(3-amino-2-hydroxyphenyl)-3-oxoisoindolin-4-yl)-4-((2-morpholinoethyl)amino)benzamide | 3.18 | | |
| 349 | 4-((2-(azepan-1-yl)ethyl)amino)-N-(7-(2-methoxyphenyl)-3-oxoisoindolin-4-yl)benzamide | 0.24 | | |
| 350 | 4-((2-(azepan-1-yl)ethyl)amino)-N-(7-(2,3-dimethoxyphenyl)-3-oxoisoindolin-4-yl)benzamide | 0.061 | | |
| 351 | 4-((3-(dimethylamino)propyl)amino)-N-(7-(2-hydroxyphenyl)-3-oxoisoindolin-4-yl)benzamide | 0.96 | | |
| 352 | 4-((2-hydroxyethyl)amino)-N-(7-(2-methoxyphenyl)-3-oxoisoindolin-4-yl)benzamide | 0.084 | | |
| 353 | 4-((2-hydroxyethyl)amino)-N-(7-(2-hydroxyphenyl)-3-oxoisoindolin-4-yl)benzamide | 0.37 | | |
| 354 | 4-((3-hydroxypropyl)amino)-N-(7-(2-methoxyphenyl)-3-oxoisoindolin-4-yl)benzamide | 0.22 | | |
| 355 | N-(7-(2-hydroxyphenyl)-3-oxoisoindolin-4-yl)-4-((3-hydroxypropyl)amino)benzamide | 0.59 | | |
| 356 | 4-((4-hydroxybutyl)amino)-N-(7-(2-methoxyphenyl)-3-oxoisoindolin-4-yl)benzamide | 0.25 | | |
| 357 | 4-((4-hydroxybutyl)amino)-N-(7-(2-hydroxyphenyl)-3-oxoisoindolin-4-yl)benzamide | 0.64 | | |
| 358 | 4-(methyl(2-(methylamino)ethyl)amino)-N-(3-oxo-7-phenylisoindolin-4-yl)benzamide | 1.1 | | |
| 359 | N-(7-(2,3-difluorophenyl)-3-oxoisoindolin-4-yl)-4-((2-morpholinoethyl)amino)benzamide | 0.17 | | |
| 360 | N-(3-oxo-7-phenylisoindolin-4-yl)-4-((2-(piperidin-1-yl)ethyl)amino)benzamide | 0.32 | | |
| 361 | N-(7-(2-methoxyphenyl)-3-oxoisoindolin-4-yl)-4-((2-(piperidin-1-yl)ethyl)amino)benzamide | 0.17 | | |
| 362 | 4-((2-(dimethylamino)ethyl)amino)-N-(3-oxo-7-phenylisoindolin-4-yl)benzamide | 0.49 | | |
| 363 | N-(3-oxo-7-phenylisoindolin-4-yl)-4-((3-(pyrrolidin-1-yl)propyl)amino)benzamide | 0.33 | | |
| 364 | N-(7-(2,3-difluorophenyl)-3-oxoisoindolin-4-yl)-4-((2-(pyrrolidin-1-yl)ethyl)amino)benzamide | 0.18 | | |
| 365 | N-(7-(2,3-difluorophenyl)-3-oxoisoindolin-4-yl)-4-((2-(pyrrolidin-1-yl)ethyl)amino)benzamide hydrochloride | 0.17 | | |
| 366 | N-(7-(2,3-difluorophenyl)-3-oxoisoindolin-4-yl)-4-((3-(pyrrolidin-1-yl)propyl)amino)benzamide hydrochloride | 0.17 | | |
| 367 | N-(7-(2,3-difluorophenyl)-3-oxoisoindolin-4-yl)-4-((2-(dimethylamino)ethyl)amino)benzamide | 0.28 | | |
| 368 | N-(7-(2,3-difluorophenyl)-3-oxoisoindolin-4-yl)-4-((3-(dimethylamino)propyl)amino)benzamide | Insoluble | | |
| 369 | 4-((2-(azepan-1-yl)ethyl)amino)-N-(3-oxo-7-phenylisoindolin-4-yl)benzamide | 0.56 | | |
| 370 | N-(3-oxo-7-phenylisoindolin-4-yl)-4-(3-(piperidin-1-yl)propyl)amino)benzamide | 0.51 | | |
| 371 | 4-((2-hydroxyethyl)amino)-N-(3-oxo-7-(thiophen-2-yl)isoindolin-4-yl)benzamide | Insoluble | | |
| 372 | 4-((2-methoxyethyl)amino)-N-(3-oxo-7-(thiophen-2-yl)isoindolin-4-yl)benzamide | 1.36 | | |
| 373 | 4-((2-(dimethylamino)ethyl)amino)-N-(3-oxo-7-(thiophen-2-yl)isoindolin-4-yl)benzamide | 0.40 | | |
| 374 | N-(3-oxo-7-(thiophen-2-yl)isoindolin-4-yl)-4-((2-(piperidin-1-yl)ethyl)amino)benzamide | 0.48 | | |
| 375 | 4-((2-morpholinoethyl)amino)-N-(3-oxo-7-(thiophen-2-yl)isoindolin-4-yl)benzamide | 0.54 | | |
| 376 | N-(7-(benzo[d]oxazol-7-yl)-3-oxoisoindolin-4-yl)-4-((2-(pyrrolidin-1-yl)ethyl)amino)benzamide | 0.072 | | |
| 377 | N-(7-(2-methylbenzo[d]oxazol-7-yl)-3-oxoisoindolin-4-yl)-4-((2-(pyrrolidin-1-yl)ethyl)amino)benzamide | 0.36 | | |
| 378 | 4-((2-(4-methylpiperazin-1-yl)ethyl)amino)-N-(3-oxo-7-(thiophen-2-yl)isoindolin-4-yl)benzamide | 0.13 | | |
| 379 | 4-((2-(4-methylpiperazin-1-yl)ethyl)amino)-N-(3-oxo-7-phenylisoindolin-4-yl)benzamide | 0.35 | | |
| 380 | 4-((2-hydroxyethyl)amino)-N-(3-oxo-7-phenylisoindolin-4-yl)benzamide | 0.23 | | |

TABLE 1-continued

| Example | Name | TNIK (μM) | TBK1 (μM) | IKKε (μM) |
|---|---|---|---|---|
| 381 | 4-((3-(dimethylamino)propyl)amino)-N-(3-oxo-7-phenylisoindolin-4-yl)benzamide | 0.31 | | |
| 382 | 4-((3-hydroxypropyl)amino)-N-(3-oxo-7-phenylisoindolin-4-yl)benzamide | 0.33 | | |
| 383 | 4-((4-hydroxybutyl)amino)-N-(3-oxo-7-phenylisoindolin-4-yl)benzamide | 0.38 | | |
| 384 | N-(7-(benzofuran-2-yl)-3-oxoisoindolin-4-yl)-4-((2-(pyrrolidin-1-yl)ethyl)amino)benzamide | 1.11 | | |
| 385 | N-(3-oxo-7-(quinolin-6-yl)isoindolin-4-yl)-4-((2-(pyrrolidin-1-yl)ethyl)amino)benzamide | 0.78 | | |
| 386 | N-(3-oxo-7-(quinolin-5-yl)isoindolin-4-yl)-4-((2-(pyrrolidin-1-yl)ethyl)amino)benzamide | 0.099 | | |
| 387 | N-(3-oxo-7-(quinolin-4-yl)isoindolin-4-yl)-4-((2-(pyrrolidin-1-yl)ethyl)amino)benzamide | 0.033 | | |
| 388 | 7-(4-fluorobenzamido)-1-oxoisoindoline-4-carboxylic acid | 3.89 | | |
| 389 | 7-(4-fluorobenzamido)-N-methyl-1-oxoisoindoline-4-carboxamide | >20 | | |
| 390 | N-methyl-1-oxo-7-(4-((2-(pyrrolidin-1-yl)ethyl)amino)benzamido)isoindoline-4-carboxamide | 3.87 | | |
| 391 | 4-fluoro-N-(3-oxo-7-(pyrrolidine-1-carbonyl)isoindolin-4-yl)benzamide | >20 | | |
| 392 | N-(3-oxo-7-(pyrrolidine-1-carbonyl)isoindolin-4-yl)-4-((2-(pyrrolidin-1-yl)ethyl)amino)benzamide | >20 | | |
| 393 | 4-fluoro-N-(7-(2-hydroxypropan-2-yl)-3-oxoisoindolin-4-yl)benzamide | 2.57 | | |
| 394 | N-(7-(2-hydroxypropan-2-yl)-3-oxoisoindolin-4-yl)-4-((2-(pyrrolidin-1-yl)ethyl)amino)benzamide | 5.44 | | |
| 395 | N-(7-cyano-3-oxoisoindolin-4-yl)-4-fluorobenzamide | | | |
| 396 | 4-fluoro-N-(7-hydroxy-3-oxoisoindolin-4-yl)benzamide | 1.29 | | |
| 397 | 4-acetamido-N-(1-oxo-5-phenyl-1,2,3,4-tetrahydroisoquinolin-8-yl)benzamide | 5.4 | | |
| 398 | N-(1-oxo-5-phenyl-1,2,3,4-tetrahydroisoquinolin-8-yl)benzamide | 3.3 | | |
| 399 | N-(1-oxo-5-phenyl-1,2,3,4-tetrahydroisoquinolin-8-yl)furan-2-carboxamide | 1.8 | | |
| 400 | N-(5-(2,3-dimethoxyphenyl)-1-oxo-1,2,3,4-tetrahydroisoquinolin-8-yl)-4-fluorobenzamide | 8.18 | | |
| 401 | N-(1-oxo-5-phenyl-1,2,3,4-tetrahydroisoquinolin-8-yl)-4-((2-(pyrrolidin-1-yl)ethyl)amino)benzamide | 2.15 | | |
| 402 | N-(5-(2-methoxyphenyl)-1-oxo-1,2,3,4-tetrahydroisoquinolin-8-yl)-4-((2-(pyrrolidin-1-yl)ethyl)amino)benzamide | 2.38 | | |
| 403 | N-(5-bromo-1-oxo-1,2,3,4-tetrahydroisoquinolin-8-yl)-4-((2-(pyrrolidin-1-yl)ethyl)amino)benzamide | 9.82 | | |
| 404 | 4-fluoro-N-(3-oxo-7-(phenylthio)isoindolin-4-yl)benzamide | >20 | | |
| 405 | N-(1-oxo-5-(phenylthio)-1,2,3,4-tetrahydroisoquinolin-8-yl)-4-((2-(pyrrolidin-1-yl)ethyl)amino)benzamide | 0.57 | | |
| 406 | N-(3-oxo-7-(phenylsulfonyl)isoindolin-4-yl)benzamide | >20 | | |
| 407 | N-(3-oxo-7-(phenylthio)isoindolin-4-yl)benzamide | 2.3 | | |
| 408 | 4-fluoro-N-(3-oxo-7-(phenylamino)isoindolin-4-yl)benzamide | 0.28 | | |
| 409 | N-(3-oxo-7-(phenylamino)isoindolin-4-yl)benzamide | 0.32 | | |
| 410 | N-(7-((2-methoxyphenyl)amino)-3-oxoisoindolin-4-yl)benzamide | 0.45 | | |
| 411 | N-(3-oxo-7-(o-tolylamino)isoindolin-4-yl)benzamide | >20 | | |
| 412 | N-(3-oxo-7-(p-tolylamino)isoindolin-4-yl)benzamide | 4.1 | | |
| 413 | N-(7-((2-fluorophenyl)amino)-3-oxoisoindolin-4-yl)benzamide | 0.5 | | |
| 414 | N-(7-((4-fluorophenyl)amino)-3-oxoisoindolin-4-yl)benzamide | 0.55 | | |
| 415 | N-(7-((3-fluorophenyl)amino)-3-oxoisoindolin-4-yl)benzamide | 1.7 | | |
| 416 | N-(7-((4-methoxyphenyl)amino)-3-oxoisoindolin-4-yl)benzamide | 3.7 | | |
| 417 | 4-methyl-N-(3-oxo-7-(phenylamino)isoindolin-4-yl)benzamide | 0.5 | | |
| 418 | N-(7-((3-chlorophenyl)amino)-3-oxoisoindolin-4-yl)-4-fluorobenzamide | 1.17 | | |
| 419 | N-(7-((2-chlorophenyl)amino)-3-oxoisoindolin-4-yl)-4-fluorobenzamide | 2.11 | | |
| 420 | 2-fluoro-N-(3-oxo-7-(phenylamino)isoindolin-4-yl)benzamide | 0.79 | | |
| 421 | 3-fluoro-N-(3-oxo-7-(phenylamino)isoindolin-4-yl)benzamide | 0.82 | | |
| 422 | N-(7-((2,3-dimethoxyphenyl)amino)-3-oxoisoindolin-4-yl)-4-fluorobenzamide | 1.18 | | |
| 423 | N-(7-((3,5-bis(trifluoromethyl)phenyl)amino)-3-oxoisoindolin-4-yl)-4-fluorobenzamide | >20 | | |
| 424 | N-(7-((2,3-dimethylphenyl)amino)-3-oxoisoindolin-4-yl)-4-fluorobenzamide | 1.35 | | |
| 425 | 4-fluoro-N-(7-((2-methoxyphenyl)-3-oxoisoindolin-4-yl)benzamide | 0.84 | | |
| 426 | 4-fluoro-N-(3-oxo-7-(o-tolylamino)isoindolin-4-yl)benzamide | 1.26 | | |
| 427 | 4-fluoro-N-(3-oxo-7-(pyridin-3-ylamino)isoindolin-4-yl)benzamide | 0.62 | | |
| 428 | 4-fluoro-N-(3-oxo-7-(pyridin-2-ylamino)isoindolin-4-yl)benzamide | Insoluble | | |
| 429 | 4-fluoro-N-(3-oxo-7-(pyrazin-2-ylamino)isoindolin-4-yl)benzamide | 0.53 | | |
| 430 | 4-fluoro-N-(7-((1-methyl-1H-pyrazol-4-yl)amino)-3-oxoisoindolin-4-yl)benzamide | 6.47 | | |
| 431 | N-(7-((3-methoxyphenyl)amino)-3-oxoisoindolin-4-yl)benzamide | 0.94 | | |
| 432 | 2-methoxy-N-(3-oxo-7-(phenylamino)isoindolin-4-yl)benzamide | 12.2 | | |
| 433 | 4-methoxy-N-(3-oxo-7-(phenylamino)isoindolin-4-yl)benzamide | 0.4 | | |
| 434 | 3-methoxy-N-(3-oxo-7-(phenylamino)isoindolin-4-yl)benzamide | 0.67 | | |
| 435 | 4-acetamido-N-(3-oxo-7-(phenylamino)isoindolin-4-yl)benzamide | 0.21 | | |
| 436 | N-(3-oxo-7-(m-tolylamino)isoindolin-4-yl)benzamide | 0.59 | | |
| 437 | N-(7-((1H-pyrazol-3-yl)amino)-3-oxoisoindolin-4-yl)-4-fluorobenzamide | 2.9 | | |
| 438 | N-(3-oxo-7-(phenylamino)isoindolin-4-yl)-4-((2-(pyrrolidin-1-yl)ethyl)amino)benzamide | 0.16 | | |
| 439 | N-(3-oxo-7-(phenylamino)isoindolin-4-yl)-4-((2-(piperidin-1-yl)ethyl)amino)benzamide | 0.15 | | |
| 440 | N-(3-oxo-7-(phenylamino)isoindolin-4-yl)-4-((2-(piperidin-1-yl)ethyl)amino)benzamide hydrochloride | — | | |
| 441 | 4-((2-(dimethylamino)ethyl)amino)-N-(3-oxo-7-(phenylamino)isoindolin-4-yl)benzamide | 0.24 | | |
| 442 | 4-((2-morpholinoethyl)amino)-N-(3-oxo-7-(phenylamino)isoindolin-4-yl)benzamide | 0.15 | | |
| 443 | 4-((2-(4-methylpiperazin-1-yl)ethyl)amino)-N-(3-oxo-7-(phenylamino)isoindolin-4-yl)benzamide | 0.12 | | |
| 444 | 4-((2-methoxyethyl)amino)-N-(3-oxo-7-(phenylamino)isoindolin-4-yl)benzamide | 0.11 | | |
| 445 | N-(7-((3-methoxyphenyl)amino)-3-oxoisoindolin-4-yl)-4-((2-(pyrrolidin-1-yl)ethyl)amino)benzamide | 0.55 | | |
| 446 | N-(7-((3-methoxyphenyl)amino)-3-oxoisoindolin-4-yl)-4-((2-(piperidin-1-yl)ethyl)amino)benzamide | 0.63 | | |
| 447 | N-(7-((3-methoxyphenyl)amino)-3-oxoisoindolin-4-yl)-4-((3-(pyrrolidin-1-yl)propyl)amino)benzamide | 0.55 | | |
| 448 | N-(7-((3-methoxyphenyl)amino)-3-oxoisoindolin-4-yl)-4-((3-(piperidin-1-yl)propyl)amino)benzamide | 0.62 | | |
| 449 | N-(3-oxo-7-(m-tolylamino)isoindolin-4-yl)-4-((2-(pyrrolidin-1-yl)ethyl)amino)benzamide | 0.59 | | |
| 450 | N-(3-oxo-7-(m-tolylamino)isoindolin-4-yl)-4-((2-(piperidin-1-yl)ethyl)amino)benzamide | 0.58 | | |
| 451 | N-(3-oxo-7-(m-tolylamino)isoindolin-4-yl)-4-((3-(pyrrolidin-1-yl)propyl)amino)benzamide | 0.48 | | |
| 452 | N-(3-oxo-7-(m-tolylamino)isoindolin-4-yl)-4-((3-(piperidin-1-yl)propyl)amino)benzamide | 0.44 | | |
| 453 | N-(7-((2-chlorophenyl)amino)-3-oxoisoindolin-4-yl)-4-((2-(pyrrolidin-1-yl)ethyl)amino)benzamide | 0.51 | | |
| 454 | N-(7-((2-chlorophenyl)amino)-3-oxoisoindolin-4-yl)-4-((2-(piperidin-1-yl)ethyl)amino)benzamide | 0.53 | | |
| 455 | N-(7-((3-chlorophenyl)amino)-3-oxoisoindolin-4-yl)-4-((2-(pyrrolidin-1-yl)ethyl)amino)benzamide | 0.20 | | |
| 456 | N-(7-((3-chlorophenyl)amino)-3-oxoisoindolin-4-yl)-4-((2-(piperidin-1-yl)ethyl)amino)benzamide | 0.34 | | |

TABLE 1-continued

| Example | Name | TNIK (μM) | TBK1 (μM) | IKKε (μM) |
|---|---|---|---|---|
| 457 | N-(7-((3-chlorophenyl)amino)-3-oxoisoindolin-4-yl)-4-((3-(pyrrolidin-1-yl)propyl)amino)benzamide | 0.15 | | |
| 458 | N-(7-((3-chlorophenyl)amino)-3-oxoisoindolin-4-yl)-4-((3-(piperidin-1-yl)propyl)amino)benzamide | 0.24 | | |
| 459 | N-(3-oxo-7-(phenylamino)isoindolin-4-yl)-4-((3-(2-oxopyrrolidin-1-yl)propyl)amino)benzamide | 0.21 | | |
| 460 | 4-((3-(dimethylamino)propyl)amino)-N-(3-oxo-7-(phenylamino)isoindolin-4-yl)benzamide | 0.14 | | |
| 461 | 4-((3-morpholinopropyl)amino)-N-(3-oxo-7-(phenylamino)isoindolin-4-yl)benzamide | 0.38 | | |
| 462 | N-(3-oxo-7-(phenylamino)isoindolin-4-yl)-4-((3-(pyrrolidin-1-yl)propyl)amino)benzamide | 0.29 | | |
| 463 | 4-((3-(4-methylpiperazin-1-yl)propyl)amino)-N-(3-oxo-7-(phenylamino)isoindolin-4-yl)benzamide | 0.37 | | |
| 464 | 4-((3-hydroxypropyl)amino)-N-(3-oxo-7-(phenylamino)isoindolin-4-yl)benzamide | 0.074 | | |
| 465 | N-(7-((3,5-bis(trifluoromethyl)phenyl)amino)-3-oxoisoindolin-4-yl)-4-((2-(pyrrolidin-1-yl)ethyl)amino)benzamide | >20 | | |
| 466 | N-(7-((3,5-bis(trifluoromethyl)phenyl)amino)-3-oxoisoindolin-4-yl)-4-((3-(pyrrolidin-1-yl)propyl)amino)benzamide | 14 | | |
| 467 | N-(7-((3,5-bis(trifluoromethyl)phenyl)amino)-3-oxoisoindolin-4-yl)-4-((2-(piperidin-1-yl)ethyl)amino)benzamide | >20 | | |
| 468 | N-(7-((3,5-bis(trifluoromethyl)phenyl)amino)-3-oxoisoindolin-4-yl)-4-((3-(piperidin-1-yl)propyl)amino)benzamide | 17.11 | | |
| 469 | N-(7-((2,3-dimethylphenyl)amino)-3-oxoisoindolin-4-yl)-4-((2-(pyrrolidin-1-yl)ethyl)amino)benzamide | 0.37 | | |
| 470 | N-(7-((2,3-dimethylphenyl)amino)-3-oxoisoindolin-4-yl)-4-((3-(pyrrolidin-1-yl)propyl)amino)benzamide | 0.47 | | |
| 471 | N-(7-((2,3-dimethylphenyl)amino)-3-oxoisoindolin-4-yl)-4-((2-(piperidin-1-yl)ethyl)amino)benzamide | 0.61 | | |
| 472 | N-(7-((2,3-dimethylphenyl)amino)-3-oxoisoindolin-4-yl)-4-((3-(piperidin-1-yl)propyl)amino)benzamide | 0.41 | | |
| 473 | N-(3-oxo-7-(o-tolylamino)isoindolin-4-yl)-4-((2-(pyrrolidin-1-yl)ethyl)amino)benzamide | 0.43 | | |
| 474 | N-(7-((2-methoxyphenyl)amino)-3-oxoisoindolin-4-yl)-4-((2-(pyrrolidin-1-yl)ethyl)amino)benzamide | 0.44 | | |
| 475 | N-(7-((2-methoxyphenyl)amino)-3-oxoisoindolin-4-yl)-4-((3-(pyrrolidin-1-yl)propyl)amino)benzamide | 0.47 | | |
| 476 | N-(3-oxo-7-(o-tolylamino)isoindolin-4-yl)-4-((3-(pyrrolidin-1-yl)propyl)amino)benzamide | 0.50 | | |
| 477 | N-(7-((2-methoxyphenyl)amino)-3-oxoisoindolin-4-yl)-4-((2-(piperidin-1-yl)ethyl)amino)benzamide | 0.42 | | |
| 478 | N-(7-((2-methoxyphenyl)amino)-3-oxoisoindolin-4-yl)-4-((3-(piperidin-1-yl)propyl)amino)benzamide | 0.49 | | |
| 479 | N-(3-oxo-7-(phenylamino)isoindolin-4-yl)-4-((3-(piperidin-1-yl)propyl)amino)benzamide | 0.11 | | |
| 480 | N-(3-oxo-7-(phenylamino)isoindolin-4-yl)-4-((3-(piperidin-1-yl)propyl)amino)benzamide hydrochloride | 0.22 | | |
| 481 | 4-((2-aminoethyl)amino)-N-(3-oxo-7-(phenylamino)isoindolin-4-yl)benzamide | 0.20 | | |
| 482 | N-(3-oxo-7-(o-tolylamino)isoindolin-4-yl)-4-((2-(piperidin-1-yl)ethyl)amino)benzamide | 0.42 | | |
| 483 | N-(3-oxo-7-(o-tolylamino)isoindolin-4-yl)-4-((3-(piperidin-1-yl)propyl)amino)benzamide | 0.25 | | |
| 484 | 4-((4-hydroxybutyl)amino)-N-(3-oxo-7-(phenylamino)isoindolin-4-yl)benzamide | 0.29 | | |
| 485 | 4-((2-acetamidoethyl)amino)-N-(3-oxo-7-(phenylamino)isoindolin-4-yl)benzamide | 0.10 | | |
| 486 | 4-((3-aminopropyl)amino)-N-(3-oxo-7-(phenylamino)isoindolin-4-yl)benzamide | 0.2 | | |
| 487 | 4-((2-hydroxyethyl)amino)-N-(3-oxo-7-(phenylamino)isoindolin-4-yl)benzamide | 0.097 | | |
| 488 | 4-((2-hydroxy-3-(piperidin-1-yl)propyl)amino)-N-(3-oxo-7-(phenylamino)isoindolin-4-yl)benzamide | 0.093 | | |
| 489 | (S)-4-((2-hydroxy-3-(piperidin-1-yl)propyl)amino)-N-(3-oxo-7-(phenylamino)isoindolin-4-yl)benzamide | 0.087 | | |
| 490 | (R)-4-((2-hydroxy-3-(piperidin-1-yl)propyl)amino)-N-(3-oxo-7-(phenylamino)isoindolin-4-yl)benzamide | 0.14 | | |
| 491 | 4-(4-aminopiperidin-1-yl)-N-(3-oxo-7-(phenylamino)isoindolin-4-yl)benzamide | 0.11 | | |
| 492 | 4-((2-(azepan-1-yl)ethyl)amino)-N-(3-oxo-7-(phenylamino)isoindolin-4-yl)benzamide | 0.18 | | |

What is claimed is:

1. A compound of formula (I) or a pharmaceutically acceptable salt thereof:

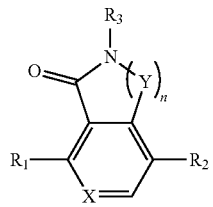

wherein,
X is CH;
Y is $CH_2$;
n is 1;
$R_1$ is —NH—C(=O)—$R_4$;
$R_2$ is $C_{6-14}$ aryl, 5- to 10-membered heteroaryl, or —NH—$R_{17}$; and
$R_3$ is H or $C_{1-7}$ alkyl;
$R_4$ is $C_{1-7}$ alkyl, $C_{6-14}$ aryl, or 5- to 10-membered heteroaryl; and
$R_{17}$ is $C_{6-14}$ aryl or 5- to 10-membered heteroaryl;
wherein said $C_{6-14}$ aryl or 5- to 10-membered heteroaryl is optionally substituted with one or more substituents selected from the group consisting of $C_{1-7}$ alkyl; —$OCF_3$; $C_{1-7}$ alkoxy; ($C_{1-7}$ alkoxy)carbonyl; ($C_{1-7}$ alkyl)carbonyl; $C_{6-14}$ aryl; ($C_{1-7}$ alkyl)thio; halogen; ($C_{1-7}$ alkyl)sulfonyl; —NH—$R_{20}$—$R_{21}$; —N($CH_3$)—$R_{20}$—$R_{21}$; 5- to 10-membered heteroaryl; heterocycloalkyl unsubstituted or substituted with $C_{1-7}$ alkyl or amino; ($C_{1-7}$ alkylcarbonylamino)($C_{6-14}$ aryl); (heterocycloalkyl)-($C_{1-7}$ alkyl)-(5- to 10-membered heteroaryl); —$CF_3$; cyano; ($C_{1-7}$ alkyl)amino; nitro; oxo; (heterocycloalkyl)-($C_{1-7}$ alkoxy); (di$C_{1-7}$ alkyl)amino; ($C_{1-7}$ alkyl)carbonylamino; hydroxy; (heterocycloalkyl)-($C_{1-7}$ alkyl); (tertbutoxycarbonyl)-(heterocycloalkyl)-($C_{1-7}$ alkyl); benzyl; and amino, wherein $R_{20}$ is $C_{6-14}$ aryl, 5- to 10-membered heteroaryl or $C_{1-7}$ alkyl which is unsubstituted or substituted with hydroxy; and $R_{21}$ is 5- to 10-membered heteroaryl or heterocycloalkyl which is unsubstituted or substituted with H, hydroxy, halogen, amino, $C_{1-7}$ alkyl, (di$C_{1-7}$ alkyl)amino, $C_{1-7}$ alkylcarbonylamino, $C_{1-7}$ alkoxy, methyl or oxo;
wherein said 5- to 10-membered heteroaryl is a mono or bicyclic heteroaryl comprising one to three heteroatoms selected from the group consisting of O, N, and S and
wherein said heterocycloalkyl is selected from the group consisting of pyrrolidinyl, piperidinyl, morpholino, azepanyl and piperazinyl.

2. The compound of claim 1, wherein $R_4$ is $C_{1-4}$ alkyl, substituted or unsubstituted phenyl, substituted or unsubstituted thiophenyl, substituted or unsubstituted furanyl, or substituted or unsubstituted pyridinyl.

3. The compound of claim 2, wherein said phenyl, thiophenyl, furanyl, or pyridinyl is substituted with one or more substituents selected from the group consisting of fluoro, chloro, bromo, nitro, cyano, amino, tertbutyloxycarbonyl, methyl, methylthio, methylsulfonyl, methoxy, acetamido, methylpiperazinyl, aminopiperidinyl, morpholino, morpholinoethoxy, methylamino, dimethylamino, dimethylaminoethylamino, dimethylaminopropylamino, aminoethylamino, hydroxyethylamino, hydroxypropylamino, hydroxybutylamino, methoxyethylamino, methoxypropylamino, methyl(2-(methylamino)ethyl)amino, acetamidoethylamino, pyrrolidinylethylamino, pyrrolidinylpropylamino, piperidinylethylamino, piperidinylpropylamino, azepanylethylamino, morpholinoethylamino, morpholinopropylamino, methylpiperazinylethylamino, methylpiperazinylpropylamino, thiophenylmethylamino, oxopyrrolidinylpropylamino, and (2-hydroxy-3-(piperidinyl)propyl)amino.

4. The compound of claim 1, wherein $R_2$ is substituted or unsubstituted phenyl, thiazolyl, pyrazolyl, imidazolyl, triazolyl, pyridinyl, 1H-pyrrolo[2,3-b]pyridinyl, pyrimidinyl, thiophenyl, furanyl, benzo[d]oxazol-7-yl, quinolinyl, indolyl, benzo[d]imidazolyl or benzofuranyl.

5. The compound of claim 1, wherein $R_2$ is selected from the group consisting of thiazolyl; pyrazolyl; methylpyrazolyl; imidazolyl; methylimidazolyl; triazolyl; methyltriazolyl; pyridinyl; chloropyridinyl; fluoropyridinyl; methoxyphenylaminopyridinyl; methoxypyridinyl; phenyl-1H-pyrrolo[2,3-b]pyridinyl; 1H-pyrrolo[2,3-b]pyridinyl; acetamidophenyl-1H-pyrrolo[2,3-b]pyridinyl; morpholinomethylthiophenyl-1H-pyrrolo[2,3-b]pyridinyl; pyrimidinyl; dichloropyrimidinyl; methoxyphenylaminopyrimidinyl; methylpyrazolylaminopyrimidinyl; phenylaminopyrimidinyl; fluorophenylaminopyrimidinyl; acetamidophenylaminopyrimidinyl; methylpiperazinylpyrimidinyl; morpholinopyrimidinyl; tolylaminopyrimidinyl; chloropyrimidinyl; thiophenyl; pyrrolidinylmethylthiophenyl; piperidinylmethylthiophenyl; morpholinomethylthiophenyl; tertbutyloxycarbonylpiperazinylmethylthiophenyl; furanyl; benzo[d]oxazol-7-yl; methyl-benzo[d]oxazol-7-yl; quinolinyl; indolyl; benzo[d]imidazolyl; and benzofuranyl.

6. The compound of claim 1, wherein $R_3$ is methyl.

7. The compound of claim 1, which is selected from the group consisting of:
(1) N-(7-(2-ethylphenyl)-3-oxoisoindolin-4-yl)benzamide;
(2) N-(7-(3-isopropylphenyl)-3-oxoisoindolin-4-yl)benzamide;
(3) N-(7-(4-(tert-butyl)phenyl)-3-oxoisoindolin-4-yl)benzamide;
(4) N-(3-oxo-7-(2-(trifluoromethoxy)phenyl)isoindolin-4-yl)benzamide;
(5) N-(3-oxo-7-(3-(trifluoromethoxy)phenyl)isoindolin-4-yl)benzamide;
(6) N-(7-(2-isopropoxyphenyl)-3-oxoisoindolin-4-yl)benzamide;
(7) N-(7-(3-isopropoxyphenyl)-3-oxoisoindolin-4-yl)benzamide;
(8) methyl 2-(7-benzamido-1-oxoisoindolin-4-yl)benzoate;
(9) methyl 3-(7-benzamido-1-oxoisoindolin-4-yl)benzoate;
(10) methyl 4-(7-benzamido-1-oxoisoindolin-4-yl)benzoate;
(11) N-(7-(2-acetylphenyl)-3-oxoisoindolin-4-yl)benzamide;
(12) N-(7-(3-acetylphenyl)-3-oxoisoindolin-4-yl)benzamide;
(13) N-(7-(4-acetylphenyl)-3-oxoisoindolin-4-yl)benzamide;
(14) N-(7-(2-(methylthio)phenyl)-3-oxoisoindolin-4-yl)benzamide;
(15) N-(7-(2,4-difluorophenyl)-3-oxoisoindolin-4-yl)benzamide;
(16) N-(7-(2,3-dimethylphenyl)-3-oxoisoindolin-4-yl)benzamide;
(17) N-(7-(2,3-dichlorophenyl)-3-oxoisoindolin-4-yl)benzamide;
(18) N-(7-(2,4-dichlorophenyl)-3-oxoisoindolin-4-yl)benzamide;
(19) N-(7-(2,5-dichlorophenyl)-3-oxoisoindolin-4-yl)benzamide;
(20) N-(7-(3,4-dichlorophenyl)-3-oxoisoindolin-4-yl)benzamide;
(21) N-(7-(3,5-dichlorophenyl)-3-oxoisoindolin-4-yl)benzamide;
(22) N-(7-(4-fluoro-2-methoxyphenyl)-3-oxoisoindolin-4-yl)benzamide;
(23) N-(7-(2-chloro-3-fluorophenyl)-3-oxoisoindolin-4-yl)benzamide;
(24) N-(7-(2-fluoro-3-methoxyphenyl)-3-oxoisoindolin-4-yl)benzamide;
(25) N-(3-oxo-7-(2,3,4-trimethoxyphenyl)isoindolin-4-yl)benzamide;
(26) N-(7-(3,4-dimethylphenyl)-3-oxoisoindolin-4-yl)benzamide;
(27) N-(7-(3,5-dimethylphenyl)-3-oxoisoindolin-4-yl)benzamide;
(28) N-(7-(2,6-dimethylphenyl)-3-oxoisoindolin-4-yl)benzamide;
(30) N-(7-(3,5-difluorophenyl)-3-oxoisoindolin-4-yl)benzamide;
(31) N-(7-(2,5-dimethylphenyl)-3-oxoisoindolin-4-yl)benzamide;
(32) N-(7-(2,5-difluorophenyl)-3-oxoisoindolin-4-yl)benzamide;
(33) N-(7-(3,4-difluorophenyl)-3-oxoisoindolin-4-yl)benzamide;
(34) N-(7-(2,3-difluorophenyl)-3-oxoisoindolin-4-yl)benzamide;
(38) N-(7-(2,4-dimethylphenyl)-3-oxoisoindolin-4-yl)benzamide;
(39) N-(7-(4-ethylphenyl)-3-oxoisoindolin-4-yl)benzamide;
(40) N-(7-(4-isopropoxyphenyl)-3-oxoisoindolin-4-yl)benzamide;
(41) N-(7-(4-(methylthio)phenyl)-3-oxoisoindolin-4-yl)benzamide;
(42) N-(7-(3-ethylphenyl)-3-oxoisoindolin-4-yl)benzamide;
(43) N-(3-oxo-7-(2-propoxyphenyl)isoindolin-4-yl)benzamide;
(44) N-(3-oxo-7-(3-propoxyphenyl)isoindolin-4-yl)benzamide;
(45) N-(7-(2-butoxyphenyl)-3-oxoisoindolin-4-yl)benzamide;
(46) N-(7-(3-butoxyphenyl)-3-oxoisoindolin-4-yl)benzamide;
(47) N-(7-(2-(methylsulfonyl)phenyl)-3-oxoisoindolin-4-yl)benzamide;

(48) N-(7-(3-fluoro-2-methoxyphenyl)-3-oxoisoindolin-4-yl)benzamide;
(49) N-(7-(4-chloro-2-methoxyphenyl)-3-oxoisoindolin-4-yl)benzamide;
(50) N-(7-(3-chloro-2-fluorophenyl)-3-oxoisoindolin-4-yl)benzamide;
(51) N-(3-oxo-7-(thiazol-5-yl)isoindolin-4-yl)benzamide;
(52) N-(3-oxo-7-(thiazol-4-yl)isoindolin-4-yl)benzamide;
(53) N-(3-oxo-7-(thiazol-2-yl)isoindolin-4-yl)benzamide;
(54) N-(7-(1H-imidazol-4-yl)-3-oxoisoindolin-4-yl)benzamide;
(55) N-(3-oxo-7-(1H-pyrazol-4-yl)isoindolin-4-yl)benzamide;
(56) N-(7-(1-methyl-1H-imidazol-5-yl)-3-oxoisoindolin-4-yl)benzamide;
(57) N-(7-(1-methyl-1H-pyrazol-4-yl)-3-oxoisoindolin-4-yl)benzamide;
(58) N-(3-oxo-7-(1H-1,2,4-triazol-5-yl)isoindolin-4-yl)benzamide;
(59) N-(7-(1-methyl-1H-1,2,4-triazol-5-yl)-3-oxoisoindolin-4-yl)benzamide;
(88) 3-methyl-N-(3-oxo-7-phenylisoindolin-4-yl)benzamide;
(89) 4-methyl-N-(3-oxo-7-phenylisoindolin-4-yl)benzamide;
(90) 3-chloro-N-(3-oxo-7-phenylisoindolin-4-yl)benzamide;
(91) 2,4-difluoro-N-(3-oxo-7-phenylisoindolin-4-yl)benzamide;
(92) 3,4-difluoro-N-(3-oxo-7-phenylisoindolin-4-yl)benzamide;
(93) 3,4-dimethyl-N-(3-oxo-7-phenylisoindolin-4-yl)benzamide;
(94) 2-(dimethylamino)-N-(3-oxo-7-phenylisoindolin-4-yl)benzamide;
(95) 3-(dimethylamino)-N-(3-oxo-7-phenylisoindolin-4-yl)benzamide;
(96) 2-(methylthio)-N-(3-oxo-7-phenylisoindolin-4-yl)benzamide;
(97) 3-(methylthio)-N-(3-oxo-7-phenylisoindolin-4-yl)benzamide;
(98) 2-(methylsulfonyl)-N-(3-oxo-7-phenylisoindolin-4-yl)benzamide;
(99) 3-(methylsulfonyl)-N-(3-oxo-7-phenylisoindolin-4-yl)benzamide;
(100) 4-(methylsulfonyl)-N-(3-oxo-7-phenylisoindolin-4-yl)benzamide;
(101) 2,4-dimethoxy-N-(3-oxo-7-phenylisoindolin-4-yl)benzamide;
(102) 3,4-dimethoxy-N-(3-oxo-7-phenylisoindolin-4-yl)benzamide;
(103) 2,4-dichloro-N-(3-oxo-7-phenylisoindolin-4-yl)benzamide;
(104) 3,4-dichloro-N-(3-oxo-7-phenylisoindolin-4-yl)benzamide;
(105) 2,4-dimethyl-N-(3-oxo-7-phenylisoindolin-4-yl)benzamide;
(106) 2-acetamido-N-(3-oxo-7-phenylisoindolin-4-yl)benzamide;
(107) 3-acetamido-N-(3-oxo-7-phenylisoindolin-4-yl)benzamide;
(108) 4-(methylamino)-N-(3-oxo-7-phenylisoindolin-4-yl)benzamide;
(109) 3-methyl-N-(3-oxo-7-phenylisoindolin-4-yl)thiophene-2-carboxamide;
(110) 4-methyl-N-(3-oxo-7-phenylisoindolin-4-yl)thiophene-2-carboxamide;
(111) 5-methyl-N-(3-oxo-7-phenylisoindolin-4-yl)thiophene-2-carboxamide;
(112) N-(3-oxo-7-(o-tolyl)isoindolin-4-yl)benzamide;
(113) N-(3-oxo-7-(m-tolyl)isoindolin-4-yl)benzamide;
(114) N-(3-oxo-7-(2-(trifluoromethyl)phenyl)isoindolin-4-yl)benzamide;
(115) N-(3-oxo-7-(3-(trifluoromethyl)phenyl)isoindolin-4-yl)benzamide;
(116) 4-acetamido-N-(3-oxo-7-phenylisoindolin-4-yl)benzamide;
(117) N-(3-oxo-7-phenylisoindolin-4-yl)benzamide;
(118) N-(7-(4-methoxyphenyl)-3-oxoisoindolin-4-yl)benzamide;
(119) 4-nitro-N-(3-oxo-7-phenylisoindolin-4-yl)benzamide;
(120) 4-acetamido-N-(7-(4-methoxyphenyl)-3-oxoisoindolin-4-yl)benzamide;
(121) 4-methoxy-N-(3-oxo-7-phenylisoindolin-4-yl)benzamide;
(122) 4-fluoro-N-(3-oxo-7-phenylisoindolin-4-yl)benzamide;
(123) N-(7-(4-fluorophenyl)-3-oxoisoindolin-4-yl)-4-methoxybenzamide;
(124) 4-acetamido-N-(7-(4-fluorophenyl)-3-oxoisoindolin-4-yl)benzamide;
(125) N-(3-oxo-7-(thiophen-2-yl)isoindolin-4-yl)benzamide;
(126) N-(7-(furan-2-yl)-3-oxoisoindolin-4-yl)benzamide;
(127) N-(3-oxo-7-(pyridin-4-yl)isoindolin-4-yl)benzamide;
(128) N-(3-oxo-7-(pyridin-4-yl)isoindolin-4-yl)benzamide hydrochloride;
(129) 2-methoxy-N-(3-oxo-7-phenylisoindolin-4-yl)benzamide;
(130) 3-fluoro-N-(3-oxo-7-phenylisoindolin-4-yl)benzamide;
(131) 4-(methylthio)-N-(3-oxo-7-phenylisoindolin-4-yl)benzamide;
(132) N-(3-oxo-7-(4-propoxyphenyl)isoindolin-4-yl)benzamide;
(133) N-(7-(4-isopropylphenyl)-3-oxoisoindolin-4-yl)benzamide;
(134) N-(7-(2,3-dimethoxyphenyl)-3-oxoisoindolin-4-yl)furan-2-carboxamide;
(135) N-(7-(2,3-dimethoxyphenyl)-3-oxoisoindolin-4-yl)-4-fluorobenzamide;
(136) N-(7-(2,3-dimethoxyphenyl)-3-oxoisoindolin-4-yl)thiophene-2-carboxamide;
(137) 4-fluoro-2-methyl-N-(3-oxo-7-phenylisoindolin-4-yl)benzamide;
(138) 4-acetamido-N-(7-(2-methoxyphenyl)-3-oxoisoindolin-4-yl)benzamide;
(139) 4-(dimethylamino)-N-(3-oxo-7-phenylisoindolin-4-yl)benzamide;
(140) 4-acetamido-N-(7-(furan-2-yl)-3-oxoisoindolin-4-yl)benzamide;
(141) 4-fluoro-N-(7-(2-methoxyphenyl)-3-oxoisoindolin-4-yl)benzamide;
(142) 2-fluoro-N-(3-oxo-7-phenylisoindolin-4-yl)benzamide;
(143) 4-chloro-N-(3-oxo-7-phenylisoindolin-4-yl)benzamide;
(144) N-(7-(2-methoxyphenyl)-3-oxoisoindolin-4-yl)benzamide;
(145) N-(7-(3-methoxyphenyl)-3-oxoisoindolin-4-yl)benzamide;

(146) N-(3-oxo-7-(thiophen-3-yl)isoindolin-4-yl)benzamide;
(147) N-(7-(3-cyanophenyl)-3-oxoisoindolin-4-yl)benzamide;
(148) N-(7-(3-(dimethylamino)phenyl)-3-oxoisoindolin-4-yl)benzamide;
(149) N-(7-(2-fluorophenyl)-3-oxoisoindolin-4-yl)benzamide;
(150) N-(7-(furan-3-yl)-3-oxoisoindolin-4-yl)benzamide;
(151) N-(7-(3-fluorophenyl)-3-oxoisoindolin-4-yl)benzamide;
(152) N-(3-oxo-7-(pyridin-3-yl)isoindolin-4-yl)benzamide;
(153) N-(3-oxo-7-(pyridin-3-yl)isoindolin-4-yl)benzamide hydrochloride;
(154) N-(3-oxo-7-(pyrimidin-5-yl)isoindolin-4-yl)benzamide;
(155) 3-chloro-N-(3-oxo-7-phenylisoindolin-4-yl)thiophene-2-carboxamide;
(156) 5-bromo-N-(3-oxo-7-phenylisoindolin-4-yl)thiophene-2-carboxamide;
(157) 3-bromo-N-(3-oxo-7-phenylisoindolin-4-yl)thiophene-2-carboxamide;
(158) 4-fluoro-N-(7-(furan-2-yl)-3-oxoisoindolin-4-yl)benzamide;
(159) N-(3-oxo-7-phenylisoindolin-4-yl)pentanamide;
(160) N-(3-oxo-7-phenylisoindolin-4-yl)acetamide;
(161) N-(7-(2-chloropyrimidin-4-yl)-3-oxoisoindolin-4-yl)acetamide;
(162) N-(7-(2-((3-methoxyphenyl)amino)pyrimidin-4-yl)-3-oxoisoindolin-4-yl)acetamide;
(163) N-(7-(2-((3-fluorophenyl)amino)pyrimidin-4-yl)-3-oxoisoindolin-4-yl)acetamide;
(164) N-(3-oxo-7-(2-(m-tolylamino)pyrimidin-4-yl)isoindolin-4-yl)acetamide;
(165) N-(3-oxo-7-(2-(p-tolylamino)pyrimidin-4-yl)isoindolin-4-yl)acetamide;
(166) N-(7-(2-((3-methoxyphenyl)amino)pyrimidin-4-yl)-3-oxoisoindolin-4-yl)propionamide;
(167) N-(7-(4-(methylsulfonyl)phenyl)-3-oxoisoindolin-4-yl)benzamide;
(168) N-(7-(3-(methylsulfonyl)phenyl)-3-oxoisoindolin-4-yl)benzamide;
(169) N-(7-(3-acetamidophenyl)-3-oxoisoindolin-4-yl)benzamide;
(170) 5-chloro-N-(3-oxo-7-phenylisoindolin-4-yl)thiophene-2-carboxamide;
(171) N-(7-(2,3-dimethoxyphenyl)-3-oxoisoindolin-4-yl)benzamide;
(172) N-(7-(3,5-dimethoxyphenyl)-3-oxoisoindolin-4-yl)benzamide;
(174) N-(7-(2-chlorophenyl)-3-oxoisoindolin-4-yl)benzamide;
(175) N-(7-(2,4-dimethoxyphenyl)-3-oxoisoindolin-4-yl)benzamide;
(176) N-(7-(3,4-dimethoxyphenyl)-3-oxoisoindolin-4-yl)benzamide;
(177) N-(7-(3-ethoxyphenyl)-3-oxoisoindolin-4-yl)benzamide;
(178) N-(7-(2,5-dimethoxyphenyl)-3-oxoisoindolin-4-yl)benzamide;
(179) N-(7-(4-chlorophenyl)-3-oxoisoindolin-4-yl)benzamide;
(180) N-(7-(3-chlorophenyl)-3-oxoisoindolin-4-yl)benzamide;
(181) N-(7-(4-ethoxyphenyl)-3-oxoisoindolin-4-yl)benzamide;
(182) N-(7-(2-ethoxyphenyl)-3-oxoisoindolin-4-yl)benzamide;
(183) N-(7-(2-cyanophenyl)-3-oxoisoindolin-4-yl)benzamide;
(184) N-(7-(4-butoxyphenyl)-3-oxoisoindolin-4-yl)benzamide;
(185) N-(7-(2-(dimethylamino)phenyl)-3-oxoisoindolin-4-yl)benzamide;
(186) N-(3-oxo-7-(4-(trifluoromethoxy)phenyl)isoindolin-4-yl)benzamide;
(187) N-(7-(2,6-dimethoxyphenyl)-3-oxoisoindolin-4-yl)benzamide;
(188) N-(3-oxo-7-(4-propylphenyl)isoindolin-4-yl)benzamide;
(189) N-(7-(2,3-dihydroxyphenyl)-3-oxoisoindolin-4-yl)-4-fluorobenzamide;
(190) 4-fluoro-N-(7-(2-hydroxy-3-methoxyphenyl)-3-oxoisoindolin-4-yl)benzamide;
(191) 4-fluoro-N-(3-oxo-7-(thiophen-2-yl)isoindolin-4-yl)benzamide;
(192) 5-methyl-N-(3-oxo-7-phenylisoindolin-4-yl)furan-2-carboxamide;
(193) N-(7-(benzo[d]oxazol-7-yl)-3-oxoisoindolin-4-yl)-4-fluorobenzamide;
(194) 4-fluoro-N-(7-(2-methylbenzo[d]oxazol-7-yl)-3-oxoisoindolin-4-yl)benzamide;
(195) N-(3-oxo-7-(5-(pyrrolidin-1-ylmethyl)thiophen-2-yl)isoindolin-4-yl)benzamide;
(196) N-(3-oxo-7-(5-(piperidin-1-ylmethyl)thiophen-2-yl)isoindolin-4-yl)benzamide;
(197) N-(7-(5-(morpholinomethyl)thiophen-2-yl)-3-oxoisoindolin-4-yl)benzamide;
(198) tert-butyl 4-((5-(7-benzamido-1-oxoisoindolin-4-yl)thiophen-2-yl)methyl)piperazine-1-carboxylate;
(199) N-(7-(6-fluoropyridin-3-yl)-3-oxoisoindolin-4-yl)benzamide;
(200) N-(7-(6-methoxypyridin-3-yl)-3-oxoisoindolin-4-yl)benzamide;
(201) 2-chloro-N-(3-oxo-7-phenylisoindolin-4-yl)benzamide;
(202) 3-methoxy-N-(3-oxo-7-phenylisoindolin-4-yl)benzamide;
(203) N-(3-oxo-7-phenylisoindolin-4-yl)thiophene-2-carboxamide;
(204) N-(7-(4-acetylphenyl)-3-oxoisoindolin-4-yl)-4-methoxybenzamide;
(205) N-(7-(4-fluorophenyl)-3-oxoisoindolin-4-yl)benzamide;
(206) N-(7-(4-(dimethylamino)phenyl)-3-oxoisoindolin-4-yl)benzamide;
(207) N-(7-(4-cyanophenyl)-3-oxoisoindolin-4-yl)benzamide;
(208) 4-cyano-N-(3-oxo-7-phenylisoindolin-4-yl)benzamide;
(209) N-(3-oxo-7-(p-tolyl)isoindolin-4-yl)benzamide;
(210) N-(3-oxo-7-(4-(trifluoromethyl)phenyl)isoindolin-4-yl)benzamide;
(211) N-(3-oxo-7-phenylisoindolin-4-yl)isonicotinamide;
(212) N-(3-oxo-7-phenylisoindolin-4-yl)furan-2-carboxamide;
(213) N-(3-oxo-7-phenylisoindolin-4-yl)nicotinamide;
(214) 4-fluoro-N-(3-oxo-7-(quinolin-6-yl)isoindolin-4-yl)benzamide;
(215) 4-fluoro-N-(3-oxo-7-(quinolin-5-yl)isoindolin-4-yl)benzamide;
(216) 4-fluoro-N-(3-oxo-7-(quinolin-4-yl)isoindolin-4-yl)benzamide;

(217) N-(7-(1H-indol-7-yl)-3-oxoisoindolin-4-yl)-4-fluorobenzamide;
(218) N-(7-(1H-benzo[d]imidazol-4-yl)-3-oxoisoindolin-4-yl)-4-fluorobenzamide;
(219) N-(7-benzyl-3-oxoisoindolin-4-yl)-4-fluorobenzamide;
(220) (R)-tert-butyl 2-((3-oxo-7-phenylisoindolin-4-yl)carbamoyl)pyrrolidine-1-carboxylate;
(221) (R)—N-(3-oxo-7-phenylisoindolin-4-yl)pyrrolidine-2-carboxamide;
(222) 3-amino-N-(2-methyl-3-oxo-7-phenylisoindolin-4-yl)benzamide;
(223) 2-amino-N-(2-methyl-3-oxo-7-phenylisoindolin-4-yl)benzamide;
(224) N-(7-(2,3-dimethoxyphenyl)-2-(furan-2-carbonyl)-3-oxoisoindolin-4-yl)furan-2-carboxamide;
(225) N-(7-(2,3-dimethoxyphenyl)-3-oxo-2-(thiophene-2-carbonyl)isoindolin-4-yl)thiophene-2-carboxamide;
(280) N-(7-(2,3-dimethoxyphenyl)-3-oxoisoindolin-4-yl)-4-((3-(pyrrolidin-1-yl)propyl)amino)benzamide;
(287) N-(7-(furan-2-yl)-3-oxoisoindolin-4-yl)-4-((2-(pyrrolidin-1-yl)ethyl)amino)benzamide;
(288) N-(7-(furan-2-yl)-3-oxoisoindolin-4-yl)-4-((2-methoxyethyl)amino)benzamide;
(289) N-(7-(furan-2-yl)-3-oxoisoindolin-4-yl)-4-((2-(piperidin-1-yl)ethyl)amino)benzamide;
(290) N-(7-(furan-2-yl)-3-oxoisoindolin-4-yl)-4-((2-morpholinoethyl)amino)benzamide;
(291) 4-((2-(dimethylamino)ethyl)amino)-N-(7-(furan-2-yl)-3-oxoisoindolin-4-yl)benzamide;
(292) N-(7-(furan-2-yl)-3-oxoisoindolin-4-yl)-4-((2-hydroxyethyl)amino)benzamide;
(293) 4-((2-(azepan-1-yl)ethyl)amino)-N-(7-(furan-2-yl)-3-oxoisoindolin-4-yl)benzamide;
(294) N-(7-(furan-2-yl)-3-oxoisoindolin-4-yl)-4-((2-(4-methylpiperazin-1-yl)ethyl)amino)benzamide;
(295) N-(7-(furan-2-yl)-3-oxoisoindolin-4-yl)-4-((3-(4-methylpiperazin-1-yl)propyl)amino)benzamide;
(296) N-(7-(2,3-dimethoxyphenyl)-3-oxoisoindolin-4-yl)-4-((3-morpholinopropyl)amino)benzamide;
(297) N-(7-(2,3-dimethoxyphenyl)-3-oxoisoindolin-4-yl)-4-((2-morpholinoethyl)amino)benzamide;
(298) N-(7-(2,3-dimethoxyphenyl)-3-oxoisoindolin-4-yl)-4-((2-(piperidin-1-yl)ethyl)amino)benzamide;
(299) N-(7-(2,3-dimethoxyphenyl)-3-oxoisoindolin-4-yl)-4-((2-(pyrrolidin-1-yl)ethyl)amino)benzamide;
(300) N-(7-(2,3-dimethoxyphenyl)-3-oxoisoindolin-4-yl)-4-((2-methoxyethyl)amino)benzamide;
(301) N-(7-(2,3-dimethoxyphenyl)-3-oxoisoindolin-4-yl)-4-((2-(dimethylamino)ethyl)amino)benzamide;
(302) N-(7-(2-methoxyphenyl)-3-oxoisoindolin-4-yl)-4-((3-(pyrrolidin-1-yl)propyl)amino)benzamide;
(303) N-(7-(2-methoxyphenyl)-3-oxoisoindolin-4-yl)-4-((2-(pyrrolidin-1-yl)ethyl)amino)benzamide hydrochloride;
(304) N-(7-(2,3-dimethoxyphenyl)-3-oxoisoindolin-4-yl)-4-((2-(pyrrolidin-1-yl)ethyl)amino)benzamide hydrochloride;
(305) 4-((2-(dimethylamino)ethyl)amino)-N-(7-(2-methoxyphenyl)-3-oxoisoindolin-4-yl)benzamide;
(306) N-(7-(2,3-dimethoxyphenyl)-3-oxoisoindolin-4-yl)-4-((3-(dimethylamino)propyl)amino)benzamide;
(307) N-(7-(2-methoxyphenyl)-3-oxoisoindolin-4-yl)-4-((3-(piperidin-1-yl)propyl)amino)benzamide;
(308) N-(7-(2,3-dimethoxyphenyl)-3-oxoisoindolin-4-yl)-4-((3-(piperidin-1-yl)propyl)amino)benzamide;
(309) 2-methyl-N-(3-oxo-7-phenylisoindolin-4-yl)-4-((2-(pyrrolidin-1-yl)ethyl)amino)benzamide;
(310) 4-((3-methoxypropyl)amino)-N-(7-(2-methoxypyridin-3-yl)-3-oxoisoindolin-4-yl)benzamide;
(311) N-(7-(2,3-dimethoxyphenyl)-3-oxoisoindolin-4-yl)-4-((2-hydroxyethyl)amino)benzamide;
(312) N-(7-(2,3-dimethoxyphenyl)-3-oxoisoindolin-4-yl)-4-morpholinobenzamide;
(313) N-(7-(3-fluoro-2-methoxyphenyl)-3-oxoisoindolin-4-yl)-4-((2-(pyrrolidin-1-yl)ethyl)amino)benzamide;
(314) N-(7-(2,3-dimethoxyphenyl)-3-oxoisoindolin-4-yl)-4-((2-(4-methylpiperazin-1-yl)ethyl)amino)benzamide;
(315) 4-((2-aminoethyl)amino)-N-(7-(2,3-dimethoxyphenyl)-3-oxoisoindolin-4-yl)benzamide;
(316) N-(7-(2,3-dimethoxyphenyl)-3-oxoisoindolin-4-yl)-4-((3-(4-methylpiperazin-1-yl)propyl)amino)benzamide;
(317) N-(3-oxo-7-phenylisoindolin-4-yl)-4-((2-(pyrrolidin-1-yl)ethyl)amino)benzamide;
(318) N-(7-(2-methoxyphenyl)-3-oxoisoindolin-4-yl)-4-((2-(pyrrolidin-1-yl)ethyl)amino)benzamide;
(319) 4-(4-methylpiperazin-1-yl)-N-(3-oxo-7-phenylisoindolin-4-yl)benzamide;
(320) 4-morpholino-N-(3-oxo-7-phenylisoindolin-4-yl)benzamide;
(321) 4-((2-methoxyethyl)amino)-N-(3-oxo-7-phenylisoindolin-4-yl)benzamide;
(322) 4-((2-morpholinoethyl)amino)-N-(3-oxo-7-phenylisoindolin-4-yl)benzamide;
(323) N-(7-(2-methoxyphenyl)-3-oxoisoindolin-4-yl)-4-morpholinobenzamide;
(324) 4-((2-methoxyethyl)amino)-N-(7-(2-methoxyphenyl)-3-oxoisoindolin-4-yl)benzamide;
(325) N-(7-(2-methoxyphenyl)-3-oxoisoindolin-4-yl)-4-(4-methylpiperazin-1-yl)benzamide;
(326) N-(7-(2-methoxyphenyl)-3-oxoisoindolin-4-yl)-4-((2-morpholinoethyl)amino)benzamide;
(327) 4-((3-morpholinopropyl)amino)-N-(3-oxo-7-phenylisoindolin-4-yl)benzamide;
(328) N-(7-(2-methoxyphenyl)-3-oxoisoindolin-4-yl)-4-((3-morpholinopropyl)amino)benzamide;
(329) 4-((3-(4-methylpiperazin-1-yl)propyl)amino)-N-(3-oxo-7-phenylisoindolin-4-yl)benzamide;
(330) N-(7-(2-methoxyphenyl)-3-oxoisoindolin-4-yl)-4-((3-(4-methylpiperazin-1-yl)propyl)amino)benzamide;
(331) 4-((3-methoxypropyl)amino)-N-(3-oxo-7-phenylisoindolin-4-yl)benzamide;
(332) N-(7-(2-methoxyphenyl)-3-oxoisoindolin-4-yl)-4-((3-methoxypropyl)amino)benzamide;
(333) N-(3-oxo-7-phenylisoindolin-4-yl)-4-((thiophen-2-ylmethyl)amino)benzamide;
(334) N-(7-(2-methoxyphenyl)-3-oxoisoindolin-4-yl)-4-((thiophen-2-ylmethyl)amino)benzamide;
(335) 4-((3-(dimethylamino)propyl)amino)-N-(7-(furan-2-yl)-3-oxoisoindolin-4-yl)benzamide;
(336) N-(7-(furan-2-yl)-3-oxoisoindolin-4-yl)-4-((3-methoxypropyl)amino)benzamide;
(337) N-(7-(furan-2-yl)-3-oxoisoindolin-4-yl)-4-((3-morpholinopropyl)amino)benzamide;
(338) N-(7-(furan-2-yl)-3-oxoisoindolin-4-yl)-4-((3-(piperidin-1-yl)propyl)amino)benzamide;
(339) N-(7-(furan-2-yl)-3-oxoisoindolin-4-yl)-4-((3-(pyrrolidin-1-yl)propyl)amino)benzamide;
(340) 4-(4-aminopiperidin-1-yl)-N-(3-oxo-7-phenylisoindolin-4-yl)benzamide;

(341) N-(7-(benzo[d]oxazol-7-yl)-3-oxoisoindolin-4-yl)-44(2-(dimethylamino)ethyl)amino)benzamide;
(342) N-(7-(benzo[d]oxazol-7-yl)-3-oxoisoindolin-4-yl)-4-((2-(piperidin-1-yl)ethyl)amino)benzamide;
(343) N-(7-(benzo[d]oxazol-7-yl)-3-oxoisoindolin-4-yl)-4-((3-(piperidin-1-yl)propyl)amino)benzamide;
(344) 4-((2-(azepan-1-yl)ethyl)amino)-N-(7-(benzo[d]oxazol-7-yl)-3-oxoisoindolin-4-yl)benzamide;
(345) 4-(2-morpholinoethoxy)-N-(3-oxo-7-phenylisoindolin-4-yl)benzamide;
(346) N-(3-oxoisoindolin-4-yl)-4-((2-(pyrrolidin-1-yl)ethyl)amino)benzamide;
(347) N-(7-(2,3-dimethoxyphenyl)-3-oxoisoindolin-4-yl)-4-(2-morpholinoethoxy)benzamide;
(348) N-(7-(3-amino-2-hydroxyphenyl)-3-oxoisoindolin-4-yl)-4-((2-morpholinoethyl)amino)benzamide;
(349) 4-((2-(azepan-1-yl)ethyl)amino)-N-(7-(2-methoxyphenyl)-3-oxoisoindolin-4-yl)benzamide;
(350) 4-((2-(azepan-1-yl)ethyl)amino)-N-(7-(2,3-dimethoxyphenyl)-3-oxoisoindolin-4-yl)benzamide;
(351) 4-((3-(dimethylamino)propyl)amino)-N-(7-(2-hydroxyphenyl)-3-oxoisoindolin-4-yl)benzamide;
(352) 4-((2-hydroxyethyl)amino)-N-(7-(2-methoxyphenyl)-3-oxoisoindolin-4-yl)benzamide;
(353) 4-((2-hydroxyethyl)amino)-N-(7-(2-hydroxyphenyl)-3-oxoisoindolin-4-yl)benzamide;
(354) 4-((3-hydroxypropyl)amino)-N-(7-(2-methoxyphenyl)-3-oxoisoindolin-4-yl)benzamide;
(355) N-(7-(2-hydroxyphenyl)-3-oxoisoindolin-4-yl)-4-((3-hydroxypropyl)amino)benzamide;
(356) 4-((4-hydroxybutyl)amino)-N-(7-(2-methoxyphenyl)-3-oxoisoindolin-4-yl)benzamide;
(357) 4-((4-hydroxybutyl)amino)-N-(7-(2-hydroxyphenyl)-3-oxoisoindolin-4-yl)benzamide;
(358) 4-(methyl(2-(methylamino)ethyl)amino)-N-(3-oxo-7-phenylisoindolin-4-yl)benzamide;
(359) N-(7-(2,3-difluorophenyl)-3-oxoisoindolin-4-yl)-4-((2-morpholinoethyl)amino)benzamide;
(360) N-(3-oxo-7-phenylisoindolin-4-yl)-4-((2-(piperidin-1-yl)ethyl)amino)benzamide;
(361) N-(7-(2-methoxyphenyl)-3-oxoisoindolin-4-yl)-4-((2-(piperidin-1-yl)ethyl)amino)benzamide;
(362) 4-((2-(dimethylamino)ethyl)amino)-N-(3-oxo-7-phenylisoindolin-4-yl)benzamide;
(363) N-(3-oxo-7-phenylisoindolin-4-yl)-4-((3-(pyrrolidin-1-yl)propyl)amino)benzamide;
(364) N-(7-(2,3-difluorophenyl)-3-oxoisoindolin-4-yl)-4-((2-(pyrrolidin-1-yl)ethyl)amino)benzamide;
(365) N-(7-(2,3-difluorophenyl)-3-oxoisoindolin-4-yl)-4-((2-(pyrrolidin-1-yl)ethyl)amino)benzamide hydrochloride;
(366) N-(7-(2,3-difluorophenyl)-3-oxoisoindolin-4-yl)-4-((3-(pyrrolidin-1-yl)propyl)amino)benzamide hydrochloride;
(367) N-(7-(2,3-difluorophenyl)-3-oxoisoindolin-4-yl)-4-((2-(dimethylamino)ethyl)amino)benzamide;
(368) N-(7-(2,3-difluorophenyl)-3-oxoisoindolin-4-yl)-4-((3-(dimethylamino)propyl)amino)benzamide;
(369) 4-((2-(azepan-1-yl)ethyl)amino)-N-(3-oxo-7-phenylisoindolin-4-yl)benzamide;
(370) N-(3-oxo-7-phenylisoindolin-4-yl)-4-((3-(piperidin-1-yl)propyl)amino)benzamide;
(371) 4-((2-hydroxyethyl)amino)-N-(3-oxo-7-(thiophen-2-yl)isoindolin-4-yl)benzamide;
(372) 4-((2-methoxyethyl)amino)-N-(3-oxo-7-(thiophen-2-yl)isoindolin-4-yl)benzamide;
(373) 4-((2-(dimethylamino)ethyl)amino)-N-(3-oxo-7-(thiophen-2-yl)isoindolin-4-yl)benzamide;
(374) N-(3-oxo-7-(thiophen-2-yl)isoindolin-4-yl)-4-((2-(piperidin-1-yl)ethyl)amino)benzamide;
(375) 4-((2-morpholinoethyl)amino)-N-(3-oxo-7-(thiophen-2-yl)isoindolin-4-yl)benzamide;
(376) N-(7-(benzo[d]oxazol-7-yl)-3-oxoisoindolin-4-yl)-4-((2-(pyrrolidin-1-yl)ethyl)amino)benzamide;
(377) N-(7-(2-methylbenzo[d]oxazol-7-yl)-3-oxoisoindolin-4-yl)-4-((2-(pyrrolidin-1-yl)ethyl)amino)benzamide;
(378) 4-((2-(4-methylpiperazin-1-yl)ethyl)amino)-N-(3-oxo-7-(thiophen-2-yl)isoindolin-4-yl)benzamide;
(379) 4-((2-(4-methylpiperazin-1-yl)ethyl)amino)-N-(3-oxo-7-phenylisoindolin-4-yl)benzamide;
(380) 4-((2-hydroxyethyl)amino)-N-(3-oxo-7-phenylisoindolin-4-yl)benzamide;
(381) 4-((3-(dimethylamino)propyl)amino)-N-(3-oxo-7-phenylisoindolin-4-yl)benzamide;
(382) 4-((3-hydroxypropyl)amino)-N-(3-oxo-7-phenylisoindolin-4-yl)benzamide;
(383) 4-((4-hydroxybutyl)amino)-N-(3-oxo-7-phenylisoindolin-4-yl)benzamide;
(384) N-(7-(benzofuran-2-yl)-3-oxoisoindolin-4-yl)-4-((2-(pyrrolidin-1-yl)ethyl)amino)benzamide;
(385) N-(3-oxo-7-(quinolin-6-yl)isoindolin-4-yl)-4-((2-(pyrrolidin-1-yl)ethyl)amino)benzamide;
(386) N-(3-oxo-7-(quinolin-5-yl)isoindolin-4-yl)-4-((2-(pyrrolidin-1-yl)ethyl)amino)benzamide;
(387) N-(3-oxo-7-(quinolin-4-yl)isoindolin-4-yl)-4-((2-(pyrrolidin-1-yl)ethyl)amino)benzamide;
(408) 4-fluoro-N-(3-oxo-7-(phenylamino)isoindolin-4-yl)benzamide;
(409) N-(3-oxo-7-(phenylamino)isoindolin-4-yl)benzamide;
(410) N-(7-((2-methoxyphenyl)amino)-3-oxoisoindolin-4-yl)benzamide;
(411) N-(3-oxo-7-(o-tolylamino)isoindolin-4-yl)benzamide;
(412) N-(3-oxo-7-(p-tolylamino)isoindolin-4-yl)benzamide;
(413) N-(7-((2-fluorophenyl)amino)-3-oxoisoindolin-4-yl)benzamide;
(414) N-(7-((4-fluorophenyl)amino)-3-oxoisoindolin-4-yl)benzamide;
(415) N-(7-((3-fluorophenyl)amino)-3-oxoisoindolin-4-yl)benzamide;
(416) N-(7-((4-methoxyphenyl)amino)-3-oxoisoindolin-4-yl)benzamide;
(417) 4-methyl-N-(3-oxo-7-(phenylamino)isoindolin-4-yl)benzamide;
(418) N-(7-((3-chlorophenyl)amino)-3-oxoisoindolin-4-yl)-4-fluorobenzamide;
(419) N-(7-((2-chlorophenyl)amino)-3-oxoisoindolin-4-yl)-4-fluorobenzamide;
(420) 2-fluoro-N-(3-oxo-7-(phenylamino)isoindolin-4-yl)benzamide;
(421) 3-fluoro-N-(3-oxo-7-(phenylamino)isoindolin-4-yl)benzamide;
(422) N-(7-((2,3-dimethoxyphenyl)amino)-3-oxoisoindolin-4-yl)-4-fluorobenzamide;
(423) N-(7-((3,5-bis(trifluoromethyl)phenyl)amino)-3-oxoisoindolin-4-yl)-4-fluorobenzamide;
(424) N-(7-((2,3-dimethylphenyl)amino)-3-oxoisoindolin-4-yl)-4-fluorobenzamide;
(425) 4-fluoro-N-(7-((2-methoxyphenyl)amino)-3-oxoisoindolin-4-yl)benzamide;

(426) 4-fluoro-N-(3-oxo-7-(o-tolylamino)isoindolin-4-yl)benzamide;
(427) 4-fluoro-N-(3-oxo-7-(pyridin-3-ylamino)isoindolin-4-yl)benzamide;
(428) 4-fluoro-N-(3-oxo-7-(pyridin-2-ylamino)isoindolin-4-yl)benzamide;
(429) 4-fluoro-N-(3-oxo-7-(pyrazin-2-ylamino)isoindolin-4-yl)benzamide;
(430) 4-fluoro-N-(7-((l-methyl-1H-pyrazol-4-yl)amino)-3-oxoisoindolin-4-yl)benzamide;
(431) N-(7-((3-methoxyphenyl)amino)-3-oxoisoindolin-4-yl)benzamide;
(432) 2-methoxy-N-(3-oxo-7-(phenylamino)isoindolin-4-yl)benzamide;
(433) 4-methoxy-N-(3-oxo-7-(phenylamino)isoindolin-4-yl)benzamide;
(434) 3-methoxy-N-(3-oxo-7-(phenylamino)isoindolin-4-yl)benzamide;
(435) 4-acetamido-N-(3-oxo-7-(phenylamino)isoindolin-4-yl)benzamide;
(436) N-(3-oxo-7-(m-tolylamino)isoindolin-4-yl)benzamide;
(437) N-(7-((1H-pyrazol-3-yl)amino)-3-oxoisoindolin-4-yl)-4-fluorobenzamide;
(438) N-(3-oxo-7-(phenylamino)isoindolin-4-yl)-4-((2-(pyrrolidin-1-yl)ethyl)amino)benzamide;
(439) N-(3-oxo-7-(phenylamino)isoindolin-4-yl)-4-((2-(piperidin-1-yl)ethyl)amino)benzamide;
(440) N-(3-oxo-7-(phenylamino)isoindolin-4-yl)-4-((2-(piperidin-1-yl)ethyl)amino)benzamide hydrochloride;
(441) 4-((2-(dimethylamino)ethyl)amino)-N-(3-oxo-7-(phenylamino)isoindolin-4-yl)benzamide;
(442) 4-((2-morpholinoethyl)amino)-N-(3-oxo-7-(phenylamino)isoindolin-4-yl)benzamide;
(443) 4-((2-(4-methylpiperazin-1-yl)ethyl)amino)-N-(3-oxo-7-(phenylamino)isoindolin-4-yl)benzamide;
(444) 4-((2-methoxyethyl)amino)-N-(3-oxo-7-(phenylamino)isoindolin-4-yl)benzamide;
(445) N-(7-((3-methoxyphenyl)amino)-3-oxoisoindolin-4-yl)-4-((2-(pyrrolidin-1-yl)ethyl)amino)benzamide;
(446) N-(7-((3-methoxyphenyl)amino)-3-oxoisoindolin-4-yl)-4-((2-(piperidin-1-yl)ethyl)amino)benzamide;
(447) N-(7-((3-methoxyphenyl)amino)-3-oxoisoindolin-4-yl)-4-((3-(pyrrolidin-1-yl)propyl)amino)benzamide;
(448) N-(7-((3-methoxyphenyl)amino)-3-oxoisoindolin-4-yl)-4-((3-(piperidin-1-yl)propyl)amino)benzamide;
(449) N-(3-oxo-7-(m-tolylamino)isoindolin-4-yl)-4-((2-(pyrrolidin-1-yl)ethyl)amino)benzamide;
(450) N-(3-oxo-7-(m-tolylamino)isoindolin-4-yl)-4-((2-(piperidin-1-yl)ethyl)amino)benzamide;
(451) N-(3-oxo-7-(m-tolylamino)isoindolin-4-yl)-4-((3-(pyrrolidin-1-yl)propyl)amino)benzamide;
(452) N-(3-oxo-7-(m-tolylamino)isoindolin-4-yl)-4-((3-(piperidin-1-yl)propyl)amino)benzamide;
(453) N-(7-((2-chlorophenyl)amino)-3-oxoisoindolin-4-yl)-4-((2-(pyrrolidin-1-yl)ethyl)amino)benzamide;
(454) N-(7-((2-chlorophenyl)amino)-3-oxoisoindolin-4-yl)-4-((2-(piperidin-1-yl)ethyl)amino)benzamide;
(455) N-(7-((3-chlorophenyl)amino)-3-oxoisoindolin-4-yl)-4-((2-(pyrrolidin-1-yl)ethyl)amino)benzamide;
(456) N-(7-((3-chlorophenyl)amino)-3-oxoisoindolin-4-yl)-4-((2-(piperidin-1-yl)ethyl)amino)benzamide;
(457) N-(7-((3-chlorophenyl)amino)-3-oxoisoindolin-4-yl)-4-((3-(pyrrolidin-1-yl)propyl)amino)benzamide;
(458) N-(7-((3-chlorophenyl)amino)-3-oxoisoindolin-4-yl)-4-((3-(piperidin-1-yl)propyl)amino)benzamide;
(459) N-(3-oxo-7-(phenylamino)isoindolin-4-yl)-4-((3-(2-oxopyrrolidin-1-yl)propyl)amino)benzamide;
(460) 4-((3-(dimethylamino)propyl)amino)-N-(3-oxo-7-(phenylamino)isoindolin-4-yl)benzamide;
(461) 4-((3-morpholinopropyl)amino)-N-(3-oxo-7-(phenylamino)isoindolin-4-yl)benzamide;
(462) N-(3-oxo-7-(phenylamino)isoindolin-4-yl)-4-((3-(pyrrolidin-1-yl)propyl)amino)benzamide;
(463) 4-((3-(4-methylpiperazin-1-yl)propyl)amino)-N-(3-oxo-7-(phenylamino)isoindolin-4-yl)benzamide;
(464) 4-((3-hydroxypropyl)amino)-N-(3-oxo-7-(phenylamino)isoindolin-4-yl)benzamide;
(465) N-(7-((3,5-bis(trifluoromethyl)phenyl)amino)-3-oxoisoindolin-4-yl)-4-((2-(pyrrolidin-1-yl)ethyl)amino)benzamide;
(466) N-(7-((3,5-bis(trifluoromethyl)phenyl)amino)-3-oxoisoindolin-4-yl)-4-((3-(pyrrolidin-1-yl)propyl)amino)benzamide;
(467) N-(7-((3,5-bis(trifluoromethyl)phenyl)amino)-3-oxoisoindolin-4-yl)-4-((2-(piperidin-1-yl)ethyl)amino)benzamide;
(468) N-(7-((3,5-bis(trifluoromethyl)phenyl)amino)-3-oxoisoindolin-4-yl)-4-((3-(piperidin-1-yl)propyl)amino)benzamide;
(469) N-(7-((2,3-dimethylphenyl)amino)-3-oxoisoindolin-4-yl)-4-((2-(pyrrolidin-1-yl)ethyl)amino)benzamide;
(470) N-(7-((2,3-dimethylphenyl)amino)-3-oxoisoindolin-4-yl)-4-((3-(pyrrolidin-1-yl)propyl)amino)benzamide;
(471) N-(7-((2,3-dimethylphenyl)amino)-3-oxoisoindolin-4-yl)-4-((2-(piperidin-1-yl)ethyl)amino)benzamide;
(472) N-(7-((2,3-dimethylphenyl)amino)-3-oxoisoindolin-4-yl)-4-((3-(piperidin-1-yl)propyl)amino)benzamide;
(473) N-(3-oxo-7-(o-tolylamino)isoindolin-4-yl)-4-((2-(pyrrolidin-1-yl)ethyl)amino)benzamide;
(474) N-(7-((2-methoxyphenyl)amino)-3-oxoisoindolin-4-yl)-4-((2-(pyrrolidin-1-yl)ethyl)amino)benzamide;
(475) N-(7-((2-methoxyphenyl)amino)-3-oxoisoindolin-4-yl)-4-((3-(pyrrolidin-1-yl)propyl)amino)benzamide;
(476) N-(3-oxo-7-(o-tolylamino)isoindolin-4-yl)-4-((3-(pyrrolidin-1-yl)propyl)amino)benzamide;
(477) N-(7-((2-methoxyphenyl)amino)-3-oxoisoindolin-4-yl)-4-((2-(piperidin-1-yl)ethyl)amino)benzamide;
(478) N-(7-((2-methoxyphenyl)amino)-3-oxoisoindolin-4-yl)-4-((3-(piperidin-1-yl)propyl)amino)benzamide;
(479) N-(3-oxo-7-(phenylamino)isoindolin-4-yl)-4-((3-(piperidin-1-yl)propyl)amino)benzamide;
(480) N-(3-oxo-7-(phenylamino)isoindolin-4-yl)-4-((3-(piperidin-1-yl)propyl)amino)benzamide hydrochloride;
(481) 4-((2-aminoethyl)amino)-N-(3-oxo-7-(phenylamino)isoindolin-4-yl)benzamide;
(482) N-(3-oxo-7-(o-tolylamino)isoindolin-4-yl)-4-((2-(piperidin-1-yl)ethyl)amino)benzamide;
(483) N-(3-oxo-7-(o-tolylamino)isoindolin-4-yl)-4-((3-(piperidin-1-yl)propyl)amino)benzamide;
(484) 4-((4-hydroxybutyl)amino)-N-(3-oxo-7-(phenylamino)isoindolin-4-yl)benzamide;
(485) 4-((2-acetamidoethyl)amino)-N-(3-oxo-7-(phenylamino)isoindolin-4-yl)benzamide;
(486) 4-((3-aminopropyl)amino)-N-(3-oxo-7-(phenylamino)isoindolin-4-yl)benzamide;
(487) 4-((2-hydroxyethyl)amino)-N-(3-oxo-7-(phenylamino)isoindolin-4-yl)benzamide;

(488) 4-((2-hydroxy-3-(piperidin-1-yl)propyl)amino)-N-(3-oxo-7-(phenylamino)isoindolin-4-yl)benzamide;
(489) (S)-4-((2-hydroxy-3-(piperidin-1-yl)propyl)amino)-N-(3-oxo-7-(phenylamino)isoindolin-4-yl)benzamide;
(490) (R)-4-((2-hydroxy-3-(piperidin-1-yl)propyl)amino)-N-(3-oxo-7-(phenylamino)isoindolin-4-yl)benzamide;
(491) 4-(4-aminopiperidin-1-yl)-N-(3-oxo-7-(phenylamino)isoindolin-4-yl)benzamide;
(492) 4-((2-(azepan-1-yl)ethyl)amino)-N-(3-oxo-7-(phenylamino)isoindolin-4-yl)benzamide, and
a pharmaceutically acceptable salt thereof.

8. A pharmaceutical composition, which comprises the compound according to claim 1 and one or more pharmaceutically acceptable additives.

9. A pharmaceutical composition, which comprises the compound according to claim 2 and one or more pharmaceutically acceptable additives.

10. A pharmaceutical composition, which comprises the compound according to claim 3 and one or more pharmaceutically acceptable additives.

11. A pharmaceutical composition, which comprises the compound according to claim 4 and one or more pharmaceutically acceptable additives.

12. A pharmaceutical composition, which comprises the compound according to claim 5 and one or more pharmaceutically acceptable additives.

13. A pharmaceutical composition, which comprises the compound according to claim 6 and one or more pharmaceutically acceptable additives.

14. A pharmaceutical composition, which comprises the compound according to claim 7 and one or more pharmaceutically acceptable additives.

* * * * *